(12) United States Patent
Keaney et al.

(10) Patent No.: US 11,926,619 B2
(45) Date of Patent: Mar. 12, 2024

(54) CERTAIN PLADIENOLIDE COMPOUNDS AND METHODS OF USE

(71) Applicant: EISAI R&D MANAGEMENT CO., LTD., Tokyo (JP)

(72) Inventors: Gregg F. Keaney, Lexington, MA (US); John Wang, Andover, MA (US); Baudouin Gerard, Belmont, MA (US); Kenzo Arai, Ibaraki (JP); Xiang Liu, Winchester, MA (US); Guo Zhu Zheng, Lexington, MA (US); Kazunobu Kira, Ibaraki (JP); Lisa A. Marcaurelle, Arlington, MA (US); Marta Nevalainen, Weymouth, MA (US); Ming-Hong Hao, Quincy, MA (US); Morgan Welzel O'Shea, Arlington, MA (US); Parcharee Tivitmahaisoon, Boston, MA (US); Sudeep Prajapati, Somerville, MA (US); Tuoping Luo, Newton, MA (US); Nicholas C. Gearhart, Durango, CO (US); Jason T. Lowe, East Bridgewater, MA (US); Yoshihiko Kotake, Ibaraki (JP); Satoshi Nagao, Ibaraki (JP); Regina Mikie Kanada Sonobe, Ibaraki (JP); Masayuki Miyano, Ibaraki (JP); Norio Murai, Ibaraki (JP); Andrew Cook, Stow, MA (US); Shelby Ellery, Boston, MA (US); Atsushi Endo, Andover, MA (US); James Palacino, Wellesley, MA (US); Dominic Reynolds, Stoneham, MA (US)

(73) Assignee: Eisai R&D Management Co., Ltd., Tokyo (JP)

( * ) Notice: Subject to any disclaimer, the term of this patent is extended or adjusted under 35 U.S.C. 154(b) by 85 days.

(21) Appl. No.: 17/045,952

(22) PCT Filed: Apr. 8, 2019

(86) PCT No.: PCT/US2019/026313
§ 371 (c)(1),
(2) Date: Oct. 7, 2020

(87) PCT Pub. No.: WO2019/199667
PCT Pub. Date: Oct. 17, 2019

(65) Prior Publication Data
US 2021/0163456 A1    Jun. 3, 2021

Related U.S. Application Data

(60) Provisional application No. 62/814,843, filed on Mar. 6, 2019, provisional application No. 62/814,838, filed on Mar. 6, 2019, provisional application No. 62/679,653, filed on Jun. 1, 2018, provisional application No. 62/655,021, filed on Apr. 9, 2018.

(51) Int. Cl.

| | | |
|---|---|---|
| C07D 407/12 | (2006.01) | |
| A61K 31/365 | (2006.01) | |
| A61K 31/4427 | (2006.01) | |
| A61K 31/497 | (2006.01) | |
| A61K 45/06 | (2006.01) | |
| A61P 35/00 | (2006.01) | |
| C07D 313/00 | (2006.01) | |

(Continued)

(52) U.S. Cl.
CPC .......... C07D 407/06 (2013.01); A61K 45/06 (2013.01); A61P 35/00 (2018.01); C07D 313/00 (2013.01); C07D 405/12 (2013.01); C07D 405/14 (2013.01); C07D 413/12 (2013.01); C07D 417/12 (2013.01); C07D 487/08 (2013.01); C07D 487/10 (2013.01); C07D 491/107 (2013.01)

(58) Field of Classification Search
CPC .... C07D 31/00; C07D 407/12; C07D 407/14; A61K 31/497; A61K 31/4427; A61K 31/365; A61P 35/00
See application file for complete search history.

(56) References Cited

U.S. PATENT DOCUMENTS

| | | | | |
|---|---|---|---|---|
| 7,026,352 B1 * | 4/2006 | Mizui | ............ | A61P 35/04 514/218 |
| 2005/0245514 A1 | 11/2005 | Kotake et al. | | |

(Continued)

FOREIGN PATENT DOCUMENTS

| | | |
|---|---|---|
| EP | 1 508 570 A1 | 2/2005 |
| EP | 1 712 642 A1 | 10/2006 |

(Continued)

OTHER PUBLICATIONS

International Search Report and Written Opinion for PCT/US2019/026313 dated Oct. 9, 2019 (21 pages).

*Primary Examiner* — Bruck Kifle
(74) *Attorney, Agent, or Firm* — Finnegan, Henderson, Farabow, Garrett & Dunner, LLP

(57) ABSTRACT

The present disclosure provides novel pladienolide compounds, pharmaceutical compositions containing such compounds, and methods for using the compounds as therapeutic agents. These compounds may be useful in the treatment of cancers, particularly cancers in which agents that target the spliceosome and mutations therein are known to be useful. Also provided herein are methods of treating cancers by administering at least one compound disclosed herein and at least one additional therapy.

18 Claims, No Drawings
Specification includes a Sequence Listing.

(51) Int. Cl.
*C07D 405/12* (2006.01)
*C07D 405/14* (2006.01)
*C07D 407/06* (2006.01)
*C07D 407/14* (2006.01)
*C07D 413/12* (2006.01)
*C07D 417/12* (2006.01)
*C07D 487/08* (2006.01)
*C07D 487/10* (2006.01)
*C07D 491/107* (2006.01)

(56) References Cited

U.S. PATENT DOCUMENTS

| | | |
|---|---|---|
| 2006/0079572 A1 | 4/2006 | Mizui et al. |
| 2006/0235002 A1 | 10/2006 | Nagai et al. |
| 2008/0214564 A1 | 9/2008 | Ishihara et al. |
| 2014/0275010 A1 | 9/2014 | Zheng et al. |

FOREIGN PATENT DOCUMENTS

| | | |
|---|---|---|
| EP | 2 168 961 A1 | 3/2010 |
| WO | 2002/060890 A1 | 8/2002 |
| WO | WO 2007/110704 A2 | 10/2007 |
| WO | WO 2007/110705 A2 | 10/2007 |
| WO | 2008/020584 A1 | 2/2008 |
| WO | WO 2013/148324 A1 | 10/2013 |
| WO | WO 2015/175594 A1 | 11/2015 |
| WO | 2017/040526 A2 | 3/2017 |
| WO | WO 2017/087667 A1 | 5/2017 |
| WO | 2019/232433 A2 | 12/2019 |

\* cited by examiner

SEQUENCE LISTING

```
<160> NUMBER OF SEQ ID NOS: 58

<210> SEQ ID NO 1
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ser Pro Thr Leu Pro Pro Arg Ser Leu
1               5

<210> SEQ ID NO 2
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

His Pro Ser Ile Lys Arg Gly Leu Ser Ser Leu
1               5                   10
```

```
<210> SEQ ID NO 3
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Leu Leu Leu Pro His His Val Leu
1               5

<210> SEQ ID NO 4
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Arg Thr Ala Pro Gly Val Arg Pro Pro Phe
1               5                   10

<210> SEQ ID NO 5
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Arg Pro Gln Lys Ser Ile Gln Ala Leu
1               5

<210> SEQ ID NO 6
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Ala Pro Ala Pro Pro Pro Leu Pro Ala
1               5

<210> SEQ ID NO 7
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Arg Pro Arg Pro Ser Phe Pro Val Ser Leu
1               5                   10

<210> SEQ ID NO 8
<211> LENGTH: 10
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Pro Lys His Gly Asp Gly Phe Ser Leu
1               5                   10

<210> SEQ ID NO 9
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Gly Pro Ala Pro Gly Lys Thr Gly Leu
1               5

<210> SEQ ID NO 10
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Glu Ala Ala Arg Lys Gly Asn Ser Leu
1               5

<210> SEQ ID NO 11
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Arg Ile Lys Glu Lys Ile Glu Glu Leu
1               5

<210> SEQ ID NO 12
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Glu Ile Lys Lys Arg Phe Arg Gln Phe
1               5

<210> SEQ ID NO 13
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 13

His Glu Ser Ala Ala Met Ala Glu Thr
1               5

<210> SEQ ID NO 14
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

Ala Leu Lys Leu Lys Gln Val Gly Val
1               5

<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Asp Leu Lys Lys Arg His Ile Thr Phe
1               5

<210> SEQ ID NO 16
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Asp Val Lys Arg Asn Asp Ile Ala Met
1               5

<210> SEQ ID NO 17
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Ile Pro Ser Asp His Ile Leu Thr Pro Ala
1               5                   10

<210> SEQ ID NO 18
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18
```

-continued

```
Thr Val Phe Ser Thr Ser Ser Leu Lys
1               5

<210> SEQ ID NO 19
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Ile Thr Ser Cys Leu Leu Asn Phe
1               5

<210> SEQ ID NO 20
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Arg Ala Ser Pro Val Arg Gly Gln Leu
1               5

<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Val Val Arg Lys Pro Val Ile Ala Leu
1               5

<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Leu Leu Ser Glu Lys Lys Lys Ile Ser
1               5

<210> SEQ ID NO 23
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Ala Pro Ala Ser Lys Pro Arg Pro Arg Leu
1               5                   10
```

```
<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Arg Tyr Gly Gln Leu Ser Glu Lys Phe
1               5

<210> SEQ ID NO 25
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 25

Val Tyr Ile Ser Asn Val Ser Lys Leu
1               5

<210> SEQ ID NO 26
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 26

Leu Pro Thr Lys Glu Thr Pro Ser Phe
1               5

<210> SEQ ID NO 27
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 27

Gly Glu Ala Pro Pro Pro Pro Pro Ala
1               5

<210> SEQ ID NO 28
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 28

Leu Glu Glu Ile Ser Lys Gln Glu Ile
1               5

<210> SEQ ID NO 29
<211> LENGTH: 9
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ile Tyr Asn His Ile Thr Val Lys Ile
1               5

<210> SEQ ID NO 30
<211> LENGTH: 160
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Val Asp Leu Glu Pro Thr Val Ile Gly Glu Leu Thr Ser Val Thr Gln
1               5                   10                  15

Val Arg Ser Gln Gly Ala Gly Thr Gly Gly Leu Ser Trp Gly Gly Ser
            20                  25                  30

Ala Gly His Ser Pro Thr Leu Pro Arg Ser Leu Ser Leu Leu Leu
        35                  40                  45

Leu Pro His His Val Leu Gln Met Lys Phe Ala Leu Ala Leu Thr Ala
50                  55                  60

Ser Ser Ser Thr Leu Ser Asn Ser Ser Gln Ala Arg Lys Met Leu Pro
65                  70                  75                  80

Ile Thr Met Pro Glu Gly Thr Thr Pro Leu Ala Arg Arg Ser Leu Thr
                85                  90                  95

Ser Cys Trp Thr Glu Phe Ala Ser Trp Leu Thr Ser Ala Pro Val Phe
            100                 105                 110

Arg Ala Ser Trp Phe Ser Thr Ala Leu Val Gly Glu Leu Val Leu Gly
        115                 120                 125

Ser Pro Arg Cys Ser Trp Asn Val Ser Gln Leu Ile Met Ala Arg Ser
    130                 135                 140

Pro Ser Trp Ser Ser Pro Phe Thr Arg Arg Pro Arg Phe Pro Gln Leu
145                 150                 155                 160

<210> SEQ ID NO 31
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Ala Pro Pro Arg Ser His Pro Ser Ile Lys Arg Gly Leu Ser Ser Leu
1               5                   10                  15

<210> SEQ ID NO 32
<211> LENGTH: 28
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32
```

```
Met Val Arg Arg Ala Arg Trp Pro Gly Gly Arg Gly Glu Ala Arg Lys
1               5                   10                  15

Ala Pro Arg Thr Ala Pro Gly Val Arg Pro Pro Phe
                20                  25
```

<210> SEQ ID NO 33
<211> LENGTH: 199
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

```
Trp Val Asn Cys Leu Phe Val Ser Gly Arg Ala Ala Gly Gly Gly
1               5                   10                  15

Gly Gly Gly Ala Val Pro Pro Tyr Leu Glu Leu Ala Gly Pro Pro Phe
                20                  25                  30

Leu Leu Leu Thr Leu Ile Arg Ile Gly Leu Gly Arg Arg Ser Gly Arg
            35                  40                  45

Ala Gly Gly Arg Ala Gly Thr Gln Cys Gly Gly Glu Arg Gly Pro Gly
        50                  55                  60

Phe Ala Ala Phe Arg Pro Leu Arg Pro Phe Arg Arg Leu Arg Val Cys
65                  70                  75                  80

Ala Val Cys Val Arg Gly Ser Ala Leu Gly Arg Ser Val Gly Leu Pro
                85                  90                  95

Arg Gly Gly Ala Ala Gly Ala Pro Phe Ser Ser Pro Ala Pro His
                100                 105                 110

Pro Arg Arg Val Leu Cys Arg Cys Leu Leu Phe Leu Phe Phe Ser Cys
            115                 120                 125

His Asp Arg Arg Gly Asp Ser Gln Pro Tyr Gln Val Pro Ala Glu Ala
        130                 135                 140

Gly Val Glu Gly Leu Glu Gly Ala Gly Gly Arg Glu Gly Leu Leu
145                 150                 155                 160

Leu Glu Arg Arg Pro Gln Lys Ser Ile Gln Ala Leu Arg Cys Asn Thr
                165                 170                 175

Ser Glu Thr Ser Thr Ala Asp Pro Leu Lys Ile Pro Gly Leu Val Pro
                180                 185                 190

Leu Ala Leu Ser Ser Lys Val
            195
```

<210> SEQ ID NO 34
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

```
Met Pro Leu Pro Val Gln Val Phe Asn Leu Gln Val Thr Ser Arg Gly
1               5                   10                  15

Arg Pro Gly Pro Pro Arg Pro Arg Ala Pro Arg His Trp Gly Arg Ala
                20                  25                  30

Glu Val Glu Gln Gly Arg Gly Ala Cys Ala Arg Ser Arg Ser Gly Thr
            35                  40                  45
```

-continued

```
Leu Arg Ala Gly Pro Pro Arg Ala Ala Arg Val Gly Gly Cys Arg Ala
        50                  55                  60
Glu Gly Ala Ser Pro Pro Trp Leu Arg Ala Ala Ile Gly Gly Arg Arg
 65                  70                  75                  80
Ala Ala Pro Ala Pro Pro Leu Pro Ala Ala His Gly Arg Gly Ser
                 85                  90                  95
Arg Pro Pro Arg Arg
            100

<210> SEQ ID NO 35
<211> LENGTH: 162
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Gln Pro Ala Gln Pro Arg Thr Gly Ala Pro Ala Arg Arg Pro Arg Pro
 1               5                  10                  15
Arg Pro Ser Phe Pro Val Ser Leu Arg Ser Ala Ala Pro Pro Thr Gly
             20                  25                  30
Thr Ala Gly Gly Thr Gly Arg Phe Val Leu Arg Pro Gly Glu Ser Gly
         35                  40                  45
Ala Gly Gly Gly Asp Ala Trp Asp Thr Gly Leu Gln Ala Arg Arg
     50                  55                  60
Gly Thr Ala Ala Gly Thr Ser Gly Ala Pro Asn Arg Ser Gln Leu Ser
 65                  70                  75                  80
Ser Leu Thr Phe Pro Ala Gln Leu Arg Arg Ile Gly Val Ser Gly Arg
                 85                  90                  95
Lys Pro Gly Ala Gly Arg Leu Gly Pro Gly Ser Arg Thr Cys Ala
            100                 105                 110
Pro Arg Cys Leu Pro Arg Ala Arg Arg Gly Pro Gly Ala His Pro Arg
        115                 120                 125
Gly Gly Arg Cys Pro Pro Ala Glu Thr Ala Leu Phe Arg Glu Ala Glu
    130                 135                 140
Glu Gly Thr Gln Lys Tyr Ser Leu Pro Ser Asp Pro Ala Gly Gln Ala
145                 150                 155                 160
Ala Phe

<210> SEQ ID NO 36
<211> LENGTH: 39
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Phe Arg Leu His Thr Gly Pro Val Ser Pro Val Gly Arg Arg Gln
 1               5                  10                  15
Met Gly Arg Pro Lys His Gly Asp Gly Phe Ser Leu Gln Val Cys Ser
             20                  25                  30
Phe Ile Met Glu Gln Asn Gly
         35

<210> SEQ ID NO 37
```

```
<211> LENGTH: 71
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gly Val Val Glu Ile Thr Gly Glu Pro Pro Cys Ser Cys Arg Gly Glu
1               5                   10                  15

Glu Glu Ala Ser Arg Ala Gly Arg Ala Gly Gly Val Arg Leu Lys Arg
            20                  25                  30

Gly Ser Arg Gly Pro Gly Glu Leu Asn Val Gly Pro Ala Pro Gly Lys
        35                  40                  45

Thr Gly Leu Leu Ile Pro Leu Leu Arg Asn Trp Glu Cys Gly Ser Leu
    50                  55                  60

Leu Arg Ala Leu Ser Ala Leu
65                  70

<210> SEQ ID NO 38
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 38

Lys Met Gly Phe Pro Glu Ala Ala Arg Lys Gly Asn Ser Leu
1               5                   10

<210> SEQ ID NO 39
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 39

Leu Glu Ala Arg Ile Lys Glu Lys Ile Glu Glu Leu Gln Gln Ala Leu
1               5                   10                  15

Ile

<210> SEQ ID NO 40
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 40

Glu Ile Lys Lys Arg Phe Arg Gln Phe Lys Gln Ala Val Tyr Lys Gln
1               5                   10                  15

<210> SEQ ID NO 41
<211> LENGTH: 16
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 41

Ala His Glu Ser Ala Ala Met Ala Glu Thr Leu Gln His Val Pro Ser
1               5                   10                  15

<210> SEQ ID NO 42
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Asn Arg Pro Ser Val Gln Ala Ala Leu Lys Leu Lys Gln Val Gly Val
1               5                   10                  15

<210> SEQ ID NO 43
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Lys Thr Asp Asp Leu Lys Lys Arg His Ile Thr Phe Thr Leu Gly Cys
1               5                   10                  15

Gly Ile Cys

<210> SEQ ID NO 44
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Met Lys Leu Asp Glu Asp Val Lys Arg Asn Asp Ile Ala Met Ala Ile
1               5                   10                  15

<210> SEQ ID NO 45
<211> LENGTH: 26
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 45

Asn Ser Ile Ser Gln Ile Pro Ser Asp His Ile Leu Thr Pro Ala Leu
1               5                   10                  15

Phe Ile Thr Phe Met Thr Ile Leu Asp Leu
            20                  25

<210> SEQ ID NO 46
<211> LENGTH: 24
<212> TYPE: PRT
<213> ORGANISM: Artificial Sequence
<220> FEATURE:
```

```
<221> NAME/KEY: source
<223> OTHER INFORMATION: /note="Description of Artificial Sequence:
      Synthetic peptide"

<400> SEQUENCE: 46

Thr Val Phe Ser Thr Ser Ser Leu Lys Leu Asn Gln Pro Gln Lys Tyr
1               5                   10                  15

Leu Lys Met Lys Ser Trp Pro Cys
            20

<210> SEQ ID NO 47
<211> LENGTH: 24
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 47

Ala Glu Glu Asp Arg Arg Lys Lys Val Ile Thr Ser Cys Leu Leu Asn
1               5                   10                  15

Phe Asn Leu Ser Lys Ala Gln Ser
            20

<210> SEQ ID NO 48
<211> LENGTH: 34
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 48

Arg Ser Phe Ser Thr Ser Ala Gln Val Gly Gln Thr Arg Gly Gly Leu
1               5                   10                  15

Gln Ala Glu Ala Pro Arg Pro Gly Pro Arg Ala Ser Pro Val Arg Gly
            20                  25                  30

Gln Leu

<210> SEQ ID NO 49
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Arg Gly Tyr Val Val Arg Lys Pro Val Ile Ala Leu Ser Val Lys Ile
1               5                   10                  15

<210> SEQ ID NO 50
<211> LENGTH: 86
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Val Asp Met Asp Phe Gly Thr Gly Gly Gln Gly Ala Gly Pro Val Gly
1               5                   10                  15
```

```
Arg Gly Lys Asp Trp Ser Cys Thr Leu Ala Val His Leu Leu Ser Glu
            20                  25                  30

Lys Lys Lys Ile Ser Phe Ser Gln Ile Asp Arg Ala Trp Gly Gly Ser
        35                  40                  45

Gln Gly Thr Val Leu Asp Lys Trp Gly Pro Val Val Ser Glu Leu
    50                  55                  60

His Pro Ser Ala Lys Glu Val Ser Val Gly Arg Asn Ser Val Glu Ser
65                  70                  75                  80

Leu Met Thr Trp Ala Ser
                85

<210> SEQ ID NO 51
<211> LENGTH: 66
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Glu Lys Gly Ser His Glu Glu Val Arg Val Pro Ala Leu Ser Trp
1               5                   10                  15

Gly Arg Pro Arg Ala Pro Ala Pro Ala Ser Lys Pro Arg Pro Arg Leu
            20                  25                  30

Asp Leu Asn Cys Leu Trp Leu Arg Pro Gln Pro Ile Phe Leu Trp Lys
        35                  40                  45

Leu Arg Pro Arg Pro Val Pro Ala Ala Thr Pro Leu Thr Gly Pro Leu
    50                  55                  60

Pro Leu
65

<210> SEQ ID NO 52
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

Arg Tyr Gly Gln Leu Ser Glu Lys Phe Asn Arg Arg Lys Val Met Asp
1               5                   10                  15

Ser

<210> SEQ ID NO 53
<211> LENGTH: 15
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

Met Val Tyr Ile Ser Asn Val Ser Lys Leu Cys Phe Ser Lys Met
1               5                   10                  15

<210> SEQ ID NO 54
<211> LENGTH: 48
<212> TYPE: PRT
```

```
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Asn Thr Leu Pro Thr Lys Glu Thr Pro Ser Phe Leu Leu Asn Pro His
1               5                   10                  15

Thr Ser Trp Val Pro Arg Pro His Arg Glu Ala Pro Arg Leu Arg Val
            20                  25                  30

Gly Val Ala Ala Pro Leu Gln Arg Pro Leu Pro Ala Leu His Ser His
        35                  40                  45

<210> SEQ ID NO 55
<211> LENGTH: 58
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Phe Gly Asp Ile Tyr Leu Gly Glu Ala Pro Pro Pro Pro Ala Ala
1               5                   10                  15

Arg Arg Pro Gly Pro Cys Gly Cys Gln Asp Gln Ala Arg Ser Arg Lys
            20                  25                  30

Glu Val Val Ala Pro Ala Gly Ser Pro Arg Lys Ser Arg His Arg Arg
        35                  40                  45

Ile Val Ala Arg Thr Gln Arg Pro Leu Gly
    50                  55

<210> SEQ ID NO 56
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 56

Gly Ser Ala Ser Asp Leu Leu Glu Glu Ile Ser Lys Gln Glu Ile Ser
1               5                   10                  15

Phe

<210> SEQ ID NO 57
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 57

Gln Leu Ile Tyr Asn His Ile Thr Val Lys Ile Asn Leu Gln Gly Asp
1               5                   10                  15

<210> SEQ ID NO 58
<211> LENGTH: 4
<212> TYPE: PRT
<213> ORGANISM: Unknown
<220> FEATURE:
```

```
<221> NAME/KEY: source
<223> OTHER INFORMATION: /note="Description of Unknown:
      DEAH box helicase 9 (DHX9) peptide"

<400> SEQUENCE: 58

Asp Glu Ala His
1
```

CERTAIN PLADIENOLIDE COMPOUNDS AND METHODS OF USE

The present application is a national stage filing under 35 U.S.C. § 371 of International Application No. PCT/US2019/026313, filed on Apr. 8, 2019, which claims the benefit of priority to U.S. Provisional Application No. 62/655,021 filed Apr. 9, 2018; U.S. Provisional Application No. 62/679,653 filed Jun. 1, 2018; U.S. Provisional Application No. 62/814,838 filed Mar. 6, 2019; and U.S. Provisional Application No. 62/814,843 filed Mar. 6, 2019, all of which are incorporated herein by reference.

Disclosed herein are novel organic compounds and pharmaceutical compositions containing such compounds. These compounds are useful in the treatment of cancer, particularly cancers in which agents that target the spliceosome and mutations therein are known to be useful. These compounds are also useful in the treatment of cancer when administered in combination with at least one additional therapy.

In eukaryote organisms, newly synthesized messenger RNAs typically have multiple introns, which are excised to provide the mature mRNA. The spliceosome is a multisubunit complex that accomplishes this task. The spliceosome consists of five small nuclear RNAs (snRNAs; U1-6) in combination with a variety of proteins.

Mutations in the splicing factor 3B subunit 1 (SF3B1) of the spliceosome exist in a number of cancers and comprise a target for anticancer agents. Compounds isolated from the bacteria *Streptomyces platensis* (Sakai, Takashi; Sameshima, Tomohiro; Matsufuji, Motoko; Kawamura, Naoto; Dobashi, Kazuyuki; Mizui, Yoshiharu. Pladienolides, New Substances from Culture of *Streptomyces platensis* Mer-11107. I. Taxonomy, Fermentation, Isolation and Screening. *The Journal of Antibiotics*. 2004, Vol. 57, No. 3.), termed pladienolides and discovered while screening for inhibitors of the vascular endothelial growth factor (VEGF) promoter, inhibit expression of a reporter gene controlled by human VEGF promoter, which inhibition is known to be a useful mechanism of action for anticancer agents.

These compounds also inhibit proliferation of U251 human glioma cells in vitro. The most potent of these compounds, Pladienolide B, inhibits VEGF-promoted gene expression with an $IC_{50}$ of 1.8 nM, and inhibits glioma cell proliferation with an $IC_{50}$ of 3.5 nM. The structure of pladienolide B is known, (Sakai, Takashi; Sameshima, Tomohiro; Matsufuji, Motoko; Kawamura, Naoto; Dobashi, Kazuyuki; Mizui, Yoshiharu. Pladienolides, New Substances from Culture of *Streptomyces platensis* Mer-11107. II. Physico-chemical Properties and Structure Elucidation. *The Journal of Antibiotics*. Vol. 57, No. 3. (2004)) and pladienolide B is known to target the SF3b spliceosome to inhibit splicing and alter the pattern of gene expression (Kotake et al., "Splicing factor SF3b as a target of the antitumor natural product pladienolide", Nature Chemical Biology 2007, 3, 570-575).

Certain pladienolide B analogs are, likewise, known: WO 2002/060890; WO 2004/011459; WO 2004/011661; WO 2004/050890; WO 2005/052152; WO 2006/009276; WO 2008/126918; and WO 2015/175594. For example, a pladienolide compound, (8E,12E,14E)-7-((4-Cycoheptylpiperazin-1-yl)carbonyl)oxy-3,6,16,21-tetrahydroxy-6,10,12,16,20-pentamethyl-18,19-epoxytricosa-8,12,14-trien-11-olide, also known as E7107, is a semisynthetic derivative of the natural product pladienolide D, and the results of its Phase I study have been reported. As another example, the pladienolide pyridine compound (2S,3S,6S,7R,10R,E)-7,10-dihydroxy-3,7-dimethyl-12-oxo-2-4R,2E,4E)-6-(pyridin-2-yl)hepta-2,4-dien-2-yl)oxacyclododec-4-en-6-yl 4-methylpiperazine-1-carboxylate (also named "(2S,3S,4E,6S,7R,10R)-7,10-dihydroxy-3,7-dimethyl-12-oxo-2-((2E,4E,6R)-6-(pyridin-2-yl)hepta-2,4-dien-2-yl)oxacyclododec-4-en-6-yl 4-methylpiperazine-1-carboxylate"), also known as H3B-8800, has received orphan drug designation for the treatment of certain hematological cancers.

However, additional agents useful in the treatment of cancer, particularly cancers in which agents that target the spliceosome and mutations therein are known to be useful, are needed.

Immune checkpoint blockade (ICB) has recently proven to be a paradigm shift for the treatment of several different cancer types. However, not all patients demonstrate robust/durable responses to ICB. See, e.g., Zappasodi, R. et al. Emerging Concepts for Immune Checkpoint Blockade-Based Combination Therapies. *Cancer Cell* 33, 581-598, doi:10.1016/j.ccell.2018.03.005 (2018); and Wolchok, J. D. et al. Overall Survival with Combined Nivolumab and Ipilimumab in Advanced Melanoma. *N Engl J Med* 377, 1345-1356, doi:10.1056/NEJMoa1709684 (2017). Therefore, there also exists a need to discover complementary therapeutic agents to administer in combination with ICB or any other therapy to improve and/or maximize patient response.

Disclosed herein are compounds of Formula I:

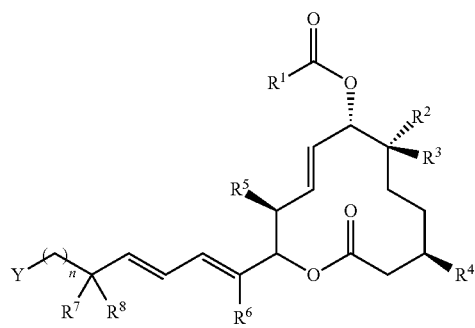

and pharmaceutically acceptable salts thereof,
wherein:
n is chosen from 0, 1, 2 and 3;
$R^1$ is chosen from $C_1$-$C_6$ alkyl groups, $C_3$-$C_8$ cycloalkyl groups, —$NR^9R^{10}$ groups,

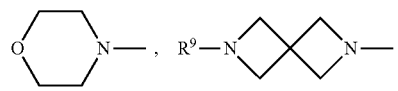

groups,

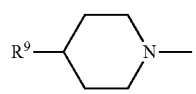

groups,

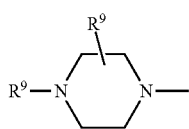

groups,

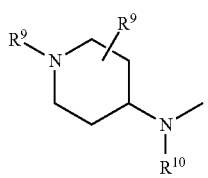

groups,

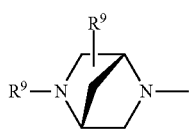

groups,

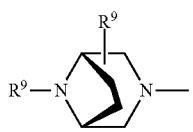

groups

groups, and

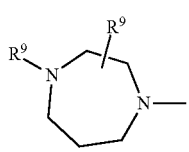

groups;

$R^9$ is chosen from hydrogen, —$NR^{11}R^{12}$ groups, $C_1$-$C_6$ alkyl groups, —($C_1$-$C_6$ alkyl)-$CO_2H$ groups, $C_3$-$C_8$ cycloalkyl groups, and $C_3$-$C_8$ heterocyclyl groups, wherein the $C_3$-$C_8$ cycloalkyl groups and $C_3$-$C_8$ heterocyclyl groups may be unsubstituted or substituted from 1-3 times with a group independently chosen from $C_1$-$C_6$ alkyl groups, —($C_1$-$C_6$ alkyl)-$CO_2H$ groups, hydroxy, halogen groups, and $C_1$-$C_6$ alkoxy groups;

$R^{10}$ is chosen from hydrogen and $C_1$-$C_6$ alkyl groups;

one of either $R^2$ or $R^3$ is chosen from hydrogen and $C_1$-$C_6$ alkyl groups, and the other is chosen from hydrogen, —$OR^{10}$, —$OC(O)R^{10}$, —$OC(O)R^1$, and $C_1$-$C_6$ alkyl groups;

$R^4$ is hydrogen or hydroxy;

$R^5$ and $R^6$ are each independently chosen from $C_1$-$C_6$ alkyl groups;

$R^7$ and $R^8$ are each independently chosen from hydrogen, hydroxy, $C_1$-$C_6$ alkoxy groups, and $C_1$-$C_6$ alkyl groups; and Y is chosen from phenyl, thiophenyl, triazolyl, pyridinyl, pyrimidinyl, pyridazinyl, and pyrazinyl, wherein Y may be unsubstituted or substituted from 1-3 times with a group independently chosen from hydroxyl, oxo groups, $C_1$-$C_6$ alkyl groups, $C_3$-$C_5$ cycloalkyl groups, hydroxy $C_1$-$C_6$ alkyl groups, $C_1$-$C_6$ alkoxy groups, methoxy $C_1$-$C_6$ alkyl groups, —$NR^{11}R^{12}$ groups,

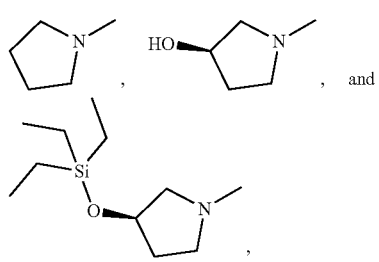

wherein $R^{11}$ and $R^{12}$ are each independently chosen from hydrogen and $C_1$-$C_6$ alkyl groups.

Also disclosed herein are compounds of Formula II:

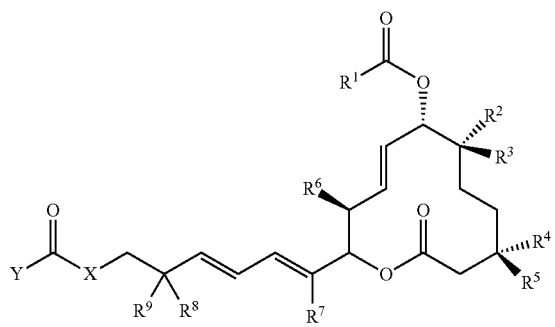

II and pharmaceutically acceptable salts thereof, wherein:

X is chosen from O, NR' groups, and $CH_2$, wherein R' is chosen from hydrogen and $C_1$-$C_6$ alkyl groups;

$R^1$ is chosen from methyl, $NR^{11}R^{12}$ groups,

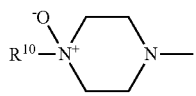

groups, and

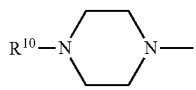

groups, $R^{10}$ is chosen from $C_1$-$C_6$ alkyl groups, $C_3$-$C_8$ cycloalkyl groups, and halo-$C_1$-$C_6$ alkyl groups, wherein the $C_3$-$C_8$ cycloalkyl groups may be unsubstituted or substituted from 1-3 times with a group independently chosen from $C_1$-$C_6$ alkyl groups, hydroxy, halogen groups, and $C_1$-$C_6$ alkoxy groups;

$R^{11}$ and $R^{12}$ are each independently chosen from $C_1$-$C_6$ alkyl groups;

one of either $R^2$ or $R^3$ is hydrogen or $C_1$-$C_6$ alkyl groups, and the other is chosen from hydrogen, hydroxy and $C_1$-$C_6$ alkyl groups;

one of either $R^4$ or $R^5$ is hydrogen, and the other is chosen from hydrogen, hydroxy, and

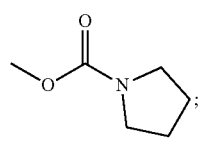

$R^6$ and $R^7$ are each independently chosen from $C_1$-$C_6$ alkyl groups;

$R^8$ and $R^9$ are each independently chosen from hydrogen and $C_1$-$C_6$ alkyl groups; or $R^8$ and $R^9$ are taken together to form a cyclopropyl ring; and Y is chosen from $C_1$-$C_6$ alkyl groups, $C_3$-$C_8$ cycloalkyl groups, methoxy, and —$NR^{13}R^{14}$ groups, wherein $R^{13}$ and $R^{14}$ are each independently chosen from hydrogen, $C_1$-$C_6$ alkyl groups, and methoxy $C_1$-$C_6$ alkyl groups; or $R^{13}$ and $R^{14}$ may be taken together with the N to form a group chosen from

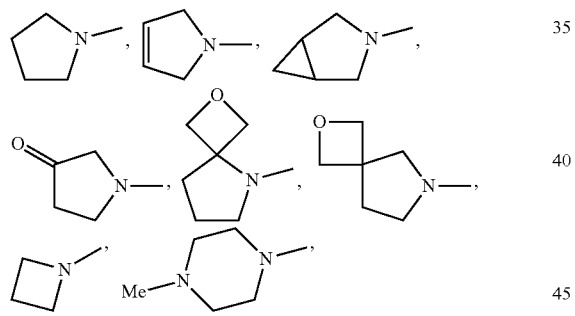

a morpholine, a piperidine, a thiazolidine, an indole, an indoline, and an isoindoline ring;

wherein Y may be unsubstituted or substituted from 1-3 times with a group independently chosen from $C_1$-$C_6$ alkyl groups, hydroxy, hydroxy $C_1$-$C_6$ alkyl groups, methoxy, methoxy $C_1$-$C_6$ alkyl groups, halo, halo $C_1$-$C_6$ alkyl groups, —$C(O)NH_2$, —NHCOO—$C_1$-$C_6$ alkyl groups, —COOH,

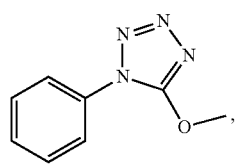

and —$NR^{15}R^{16}$ groups, wherein $R^{15}$ and $R^{16}$ are each independently chosen from hydrogen and $C_1$-$C_6$ alkyl groups.

Also disclosed herein are compounds of Formula III:

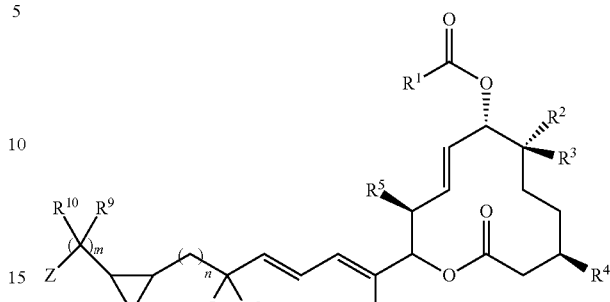

III and pharmaceutically acceptable salts thereof, wherein:

n is chosen from 0, 1, 2 and 3;

m is chosen from 1, 2, and 3;

$R^1$ is chosen from $C_1$-$C_6$ alkyl groups, $C_3$-$C_8$ cycloalkyl groups, —$NR^{11}R^{12}$ groups,

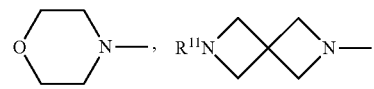

groups,

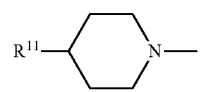

groups,

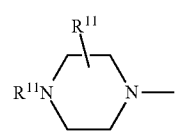

groups,

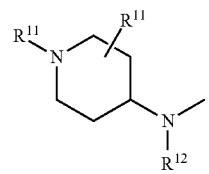

groups,

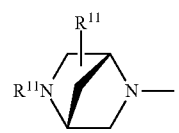

groups,

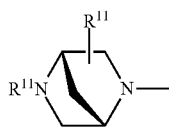

groups,

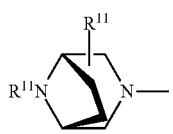

groups,

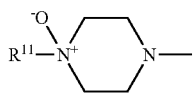

groups, and

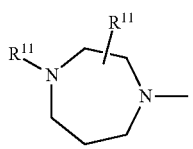

groups;

$R^{11}$ is chosen from hydrogen, —$NR^{16}R^{17}$ groups, $C_1$-$C_6$ alkyl groups, $C_3$-$C_8$ cycloalkyl groups, —($C_1$-$C_6$ alkyl)-$CO_2H$ groups, —($C_1$-$C_6$ alkyl)-$CO_2R^{12}$ groups, —($C_1$-$C_6$ alkyl)-$NR^{16}R^{17}$ groups, and $C_3$-$C_8$ heterocyclyl groups, wherein the —$NR^{11}R^{12}$ groups, $C_1$-$C_6$ alkyl groups, $C_3$-$C_8$ cycloalkyl groups, and $C_3$-$C_8$ heterocyclyl groups may be unsubstituted or substituted from 1-3 times with a group independently chosen from $C_1$-$C_6$ alkyl groups, —($C_1$-$C_6$ alkyl)-$CO_2H$ groups, hydroxy, halogen groups, and $C_1$-$C_6$ alkoxy groups;

$R^{12}$ is chosen from hydrogen and $C_1$-$C_6$ alkyl groups;

one of either $R^2$ or $R^3$ is chosen from hydrogen and $C_1$-$C_6$ alkyl groups, and the other is chosen from hydrogen, —$OR^{10}$, —$PC(O)R^{10}$, —$OC(O)R^1$ and $C_1$-$C_6$ alkyl groups;

$R^4$ is chosen from hydrogen and hydroxy;

$R^5$ and $R^6$ are each independently chosen from $C_1$-$C_6$ alkyl groups;

$R^7$ and $R^8$ are each independently chosen from hydrogen, hydroxy, $C_1$-$C_6$ alkoxy groups, and $C_1$-$C_6$ alkyl groups; and $R^9$ and $R^{10}$ are each independently chosen from hydrogen, $C_1$-$C_6$ alkyl groups, hydroxy, and $C_1$-$C_6$ alkoxy groups; or, one of $R^9$ or $R^{10}$ is oxo and the other is absent;

Z is chosen from $C_1$-$C_6$ alkyl groups, —C(O)—$C_1$-$C_6$ alkyl groups, —$OR^{13}$, and —$NR^{14}R^{15}$ groups, wherein $R^{13}$ is chosen from hydrogen, $C_1$-$C_6$ alkyl groups, and —C(O)—$C_1$-$C_6$ alkyl groups, wherein $R^{14}$ and $R^{15}$ are each independently chosen from hydrogen, $C_1$-$C_6$ alkyl groups, and methoxy $C_1$-$C_6$ alkyl groups; or $R^{14}$ and $R^{15}$ may be taken together with the N to form a group chosen from

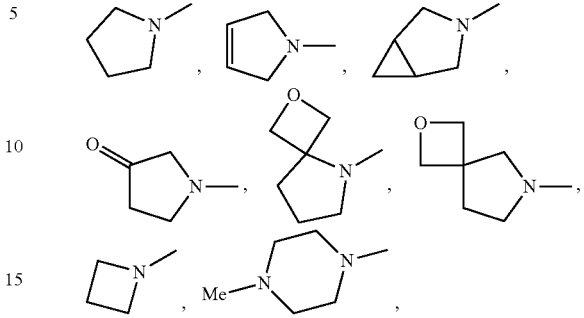

a morpholine, a piperidine, a thiazolidine, an indole, an indoline, and an isoindoline ring;

wherein Z may be unsubstituted or substituted from 1-3 times with a group independently chosen from $C_1$-$C_6$ alkyl groups, $C_3$-$C_5$ cycloalkyl groups, hydroxy $C_1$-$C_6$ alkyl groups, $C_1$-$C_6$ alkoxy groups, methoxy $C_1$-$C_6$ alkyl groups, —$NR^{16}R^{17}$ groups,

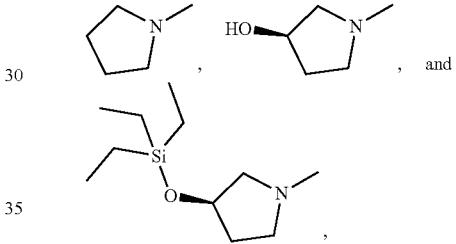

wherein $R^{16}$ and $R^{17}$ are each independently chosen from hydrogen and $C_1$-$C_6$ alkyl groups.

Also disclosed herein are pharmaceutical compositions comprising at least one compound chosen from compounds of Formula I, compounds of Formula II, compounds of Formula III, and pharmaceutically acceptable salts of any of the foregoing. In some embodiments, the pharmaceutical compositions further comprise at least one pharmaceutically acceptable carriers.

Also disclosed herein are methods of treating a subject with cancer comprising administering to the subject a therapeutically acceptable amount of at least one compound of Formula I, at least one compound of Formula II, at least one compound of Formula III, and/or a pharmaceutically acceptable salt of any of the foregoing. In some embodiments, the cancer may be chosen from myelodysplastic syndrome, chronic lymphocytic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and/or lung cancer. In some embodiments, the cancer is chosen from cancers that test positive for one or more mutations in the Splicing factor 3B subunit 1 (SF3B1) gene or protein. In some embodiments, the cancer is chosen from cancers that test positive for one or more mutations in a spliceosome gene or protein, such as those listed in Table 1. In some embodiments, administration of at least one compound of Formula I, at least one compound of Formula II, at least one compound of Formula III, and/or a pharmaceutically acceptable salt of any of the foregoing, induces at least one neoantigen and/or a T-cell response.

Also disclosed herein are uses of at least one compound chosen from compounds of Formula I, compounds of Formula II, compounds of Formula III, and pharmaceutically acceptable salts of any of the foregoing in a method of therapeutic treatment, e.g., treatment for a cancer. In some embodiments, the cancer may be chosen from myelodysplastic syndrome, chronic lymphocytic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and/or lung cancer. In some embodiments, the cancer is chosen from cancers that test positive for one or more mutations in the Splicing factor 3B subunit 1 (SF3B1) gene or protein. In some embodiments, the cancer is chosen from cancers that test positive for one or more mutations in a spliceosome gene or protein, such as those listed in Table 1. In some embodiments, administration of at least one compound of Formula I, at least one compound of Formula II, at least one compound of Formula III, and/or a pharmaceutically acceptable salt of any of the foregoing, induces at least one neoantigen and/or a T-cell response.

Also disclosed herein are uses of at least one compound chosen from compounds of Formula I, compounds of Formula II, compounds of Formula III, and pharmaceutically acceptable salts of any of the foregoing, in the preparation of a medicament. In some embodiments, the medicament is useful for the treatment of cancer. In some embodiments, the cancer may be chosen from myelodysplastic syndrome, chronic lymphocytic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and/or lung cancer. In some embodiments, the cancer is chosen from cancers that test positive for one or more mutations in the Splicing factor 3B subunit 1 (SF3B1) gene or protein. In some embodiments, the cancer is chosen from cancers that test positive for one or more mutations in a spliceosome gene or protein, such as those listed in Table 1. In some embodiments, administration of at least one compound of Formula I, at least one compound of Formula II, at least one compound of Formula III, and/or a pharmaceutically acceptable salt of any of the foregoing, induces at least one neoantigen and/or a T-cell response.

Also disclosed herein are uses of at least one compound chosen from compounds of Formula I, compounds of Formula II, compounds of Formula III, and pharmaceutically acceptable salts of any of the foregoing to target the spliceosome, e.g., subunit 1 of the SF3B spliceosome. As used herein, the following definitions shall apply unless otherwise indicated.

Also disclosed herein are methods of inducing at least one neoantigen, comprising contacting a neoplastic cell with a therapeutically effective amount at least one compound chosen from compounds of Formula I, compounds of Formula II, compounds of Formula III, and pharmaceutically acceptable salts of any of the foregoing. In some embodiments, such contact may induce production of at least one neoantigen.

Also disclosed herein are methods of inducing at least one neoantigen and/or a T-cell response in a subject having or suspected of having a neoplastic disorder, comprising administering to the subject a therapeutically effective amount of at least one compound chosen from compounds of Formula I, compounds of Formula II, compounds of Formula III, and pharmaceutically acceptable salts of any of the foregoing.

Also disclosed herein are methods of treating a subject having or suspect of having a neoplastic disorder. In some embodiments, the method comprises administering to the subject a therapeutically effective amount of at least one compound chosen from compounds of Formula I, compounds of Formula II, compounds of Formula III, and pharmaceutically acceptable salts of any of the foregoing, wherein administration may result in inducing at least one neoantigen and/or a T-cell response. In some embodiments, the method may also comprise detecting one or more neoantigens and/or a T-cell response in the subject after administration of at least one compound chosen from compounds of Formula I, compounds of Formula II, compounds of Formula III, and pharmaceutically acceptable salts of any of the foregoing. In some embodiments, the method may also comprise continuing administration of at least one compound chosen from compounds of Formula I, compounds of Formula II, compounds of Formula III, and pharmaceutically acceptable salts of any of the foregoing, if one or more neoantigens and/or a T-cell response is detected.

Also provided herein are methods of treating a subject having or suspected of having a neoplastic disorder, comprising administering to the subject a therapeutically effective amount of at least one compound chosen from at least one compound chosen from compounds of Formula I, compounds of Formula II, compounds of Formula III, and pharmaceutically acceptable salts of any of the foregoing.

Also provided herein are neoantigen vaccines comprising at least one neoantigen peptide. In some embodiments, the at least one neoantigen peptide comprises a modified or novel neoantigen sequence induced by contacting a neoplastic cell with a therapeutically effective amount of at least one compound chosen from compounds of Formula I, compounds of Formula II, compounds of Formula III, and pharmaceutically acceptable salts of any of the foregoing.

The methods and uses provided herein, in some embodiments, may further comprise administering at least one additional therapy. In some embodiments, the methods and uses provided herein may result in lower systemic toxicity and/or improved tolerance.

Also disclosed herein is a method of treating cancer in a subject in need thereof, comprising administering at least one compound chosen from compounds of Formula I, compounds of Formula II, compounds of Formula III, and pharmaceutically acceptable salts of any of the foregoing, and at least one additional therapy. Also disclosed herein is a method of treating a subject having or suspected of having a neoplastic disorder comprising administering at least one compound chosen from compounds of Formula I, compounds of Formula II, compounds of Formula III, and pharmaceutically acceptable salts of any of the foregoing, and at least one additional therapy.

As described herein, compounds disclosure may be substituted with one or more substituents, such as those illustrated generally herein, or as exemplified by particular classes, subclasses, and species of the disclosure. In general, the term "substituted" refers to the replacement of hydrogen radicals in a given structure with the radical of a specified substituent. Unless otherwise indicated, a substituted group may have a substituent at each substitutable position of the group, and when more than one position in any given structure may be substituted with more than one substituent chosen from a specified group, the substituent may be either the same or different at every position. Combinations of substituents envisioned by this disclosure are those that result in the formation of stable or chemically feasible compounds.

"Stable" refers to compounds that are not substantially altered chemically and/or physically when subjected to conditions to allow for their production, detection, and their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

"Isomers" refers to compounds having the same number and kind of atoms, and hence the same molecular weight, but differing with respect to the arrangement or configuration of the atoms. "Stereoisomers" refers to compounds that have the same atomic connectivity but different arrangements of their atoms in space. "Diastereoisomers" or "diastereomers" refers to stereoisomers that are not enantiomers. "Enantiomers" refers to stereoisomers that are non-superimposable mirror images of one another.

Enantiomers taught herein may include "enantiomerically pure" isomers that comprise substantially a single enantiomer, for example, greater than or equal to 90%, 92%, 95%, 98%, or 99%, or equal to 100% of a single enantiomer, at a particular asymmetric center or centers. An "asymmetric center" or "chiral center" refers to a tetrahedral carbon atom that comprises four different substituents.

"Stereomerically pure" as used herein means a compound or composition thereof that comprises one stereoisomer of a compound and is substantially free of other stereoisomers of that compound. For example, a stereomerically pure composition of a compound having one chiral center will be substantially free of the opposite enantiomer of the compound. In some embodiments, a stereomerically pure composition of a compound having two chiral centers will be substantially free of diastereomers, and substantially free of the opposite enantiomer, of the compound. In some embodiments, a stereomerically pure compound comprises greater than about 80% by weight of one stereoisomer of the compound and less than about 20% by weight of the other stereoisomers of the compound, such as greater than about 90% by weight of one stereoisomer of the compound and less than about 10% by weight of the other stereoisomers of the compound, further such as greater than about 95% by weight of one stereoisomer of the compound and less than about 5% by weight of the other stereoisomers of the compound, and further such as greater than about 97% by weight of one stereoisomer of the compound and less than about 3% by weight of the other stereoisomers of the compound. See, e.g., U.S. Pat. No. 7,189,715.

"R" and "S" as terms describing isomers are descriptors of the stereochemical configuration at an asymmetrically substituted carbon atom. The designation of an asymmetrically substituted carbon atom as "R" or "S" is done by application of the Cahn-Ingold-Prelog priority rules, as are well known to those skilled in the art, and described in the International Union of Pure and Applied Chemistry (IUPAC) Rules for the Nomenclature of Organic Chemistry. Section E, Stereochemistry.

"Amine oxide" or "amine-N-oxide" or "N-oxide" is a chemical compound that contains the functional group $R^3N^+$—$P^-$, an N—O bond with three additional hydrogen and/or hydrocarbon sidechains attached to N. Sometimes it is written as $R^3N \rightarrow O$.

"Ar" or "aryl" refer to an aromatic carbocyclic moiety having one or more closed rings. Examples include, without limitation, phenyl, naphthyl, anthracenyl, phenanthracenyl, biphenyl, and pyrenyl.

"Heteroaryl" refers to a cyclic moiety having one or more closed rings, with one or more heteroatoms (oxygen, nitrogen or sulfur) in at least one of the rings, wherein at least one of the rings is aromatic, and wherein the ring or rings may independently be fused, and/or bridged. Examples include without limitation phenyl, thiophenyl, triazolyl, pyridinyl, pyrimidinyl, pyridazinyl, and pyrazinyl.

"Alkyl" or "alkyl group," as used herein, means a straight-chain (i.e., unbranched), branched, or cyclic hydrocarbon chain that is completely saturated. In some embodiments, alkyl groups contain 1-8 carbon atoms. In some embodiments, alkyl groups contain 1-6 carbon atoms ("$C_1$-$C_6$ alkyl groups"). In some embodiments, alkyl groups contain 1-3 carbon atoms. In still other embodiments, alkyl groups contain 2-3 carbon atoms, and in some embodiments, alkyl groups contain 1-2 carbon atoms. In some embodiments, the term "alkyl" or "alkyl group" refers to a cycloalkyl group, also known as carbocycle. Non-limiting examples of alkyl groups include methyl, ethyl, propyl, isopropyl, butyl, cyclopropyl, and cyclohexyl.

"Alkoxy", as used herein, refers to an alkyl group, as previously defined, attached to the principal carbon chain through an oxygen ("alkoxy") atom.

"Haloalkyl" refers to an alkyl group substituted with one or more halo atoms (F, Cl, Br, I). For example, "fluoromethyl" refers to a methyl group substituted with one or more fluoro atoms (e.g., monofluoromethyl, difluoromethyl, or trifluoromethyl).

"Heteroatom" refers to O, S or N.

"Heterocyclyl" or "heterocyclic" as used herein, means a monocyclic heterocycle, a bicyclic heterocycle, or a tricyclic heterocycle containing at least one heteroatom in the ring.

The monocyclic heterocycle is a 3-, 4-, 5-, 6-, 7, or 8-membered ring containing at least one heteroatom independently chosen from O, N, and S. In some embodiments, the heterocycle is a 3- or 4-membered ring containing one heteroatom chosen from O, N and S. In some embodiments, the heterocycle is a 5-membered ring containing zero or one double bond and one, two or three heteroatoms chosen from O, N and S. In some embodiments, the heterocycle is a 6-, 7-, or 8-membered ring containing zero, one or two double bonds and one, two or three heteroatoms chosen from O, N and S. Representative examples of monocyclic heterocycle include, but are not limited to, azetidinyl, azepanyl, aziridinyl, diazepanyl, 1,3-dioxanyl, 1,3-dioxolanyl, dihydropyranyl (including 3,4-dihydro-2H-pyran-6-yl), 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydropyranyl (including tetrahydro-2H-pyran-4-yl), tetrahydrothienyl, thiadiazolinyl, thiadiazolidinyl, thiazolinyl, thiazolidinyl, thiomorpholinyl, 1,1-dioxidothiomorpholinyl (thiomorpholine sulfone), thiopyranyl, and trithianyl.

The bicyclic heterocycles of the present disclosure include a monocyclic heterocycle fused to an aryl group, or a monocyclic heterocycle fused to a monocyclic cycloalkyl, or a monocyclic heterocycle fused to a monocyclic cycloalkenyl, or a monocyclic heterocycle fused to a monocyclic heterocycle. Examples of bicyclic heterocycles include, but are not limited to, 3,4-dihydro-2H-pyranyl, 1,3-benzodioxolyl, 1,3-benzodithiolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl.

In some embodiments, the bicyclic heterocycle is a spiro heterocycle. As known in the art, a "spiro" heterocycle is a bicyclic moiety with rings connected through just one atom. The connecting atom is also called the spiro atom and most often is a quaternary atom such as carbon or nitrogen. Spiro compounds may be designated with the infix spiro followed by square brackets containing the number of atoms in the smaller ring and the number of atoms in the larger ring excluding the spiroatom itself; the numbers being separated by a dot. A non-limiting example of such compounds is 2,6-diazaspiro[3.3]heptane.

The tricyclic heterocycle is a bicyclic heterocycle fused to an aryl group, a bicyclic heterocycle fused to a monocyclic cycloalkyl, a bicyclic heterocycle fused to a monocyclic cycloalkenyl, or a bicyclic heterocycle fused to a monocyclic heterocycle. Representative examples of tricyclic heterocycles include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycle groups of the present disclosure are connected to the parent molecular moiety through any substitutable carbon atom or any substitutable nitrogen, oxygen or sulfur atom contained within the groups and may contain one or two alkylene bridges of 1, 2, 3, or 4 carbon atoms, each linking two non-adjacent carbon atoms of the groups. Examples of such "bridged" heterocycle groups include, but are not limited to, oxatricyclo[3.3.1.1$^{3,7}$]decyl (including 2-oxatricyclo [3.3.1.1$^{3,7}$]decyl), 2,4-dioxabicyclo[4.2.1]nonyl, oxabicyclo[2.2.1]heptyl (including 2-oxabicyclo[2.2.1]heptyl) and 2,5-diazabicyclo[2.2.1]heptane.

In the above heteroaryl and heterocycles the nitrogen or sulfur atoms can be optionally oxidized to various oxidation states. In a specific example, the group $S(O)_{0-2}$ refers to —S-(sulfide), —S(O)-(sulfoxide), and —SO$_2$-(sulfone) respectively. For convenience, nitrogens, particularly but not exclusively, those defined as annular aromatic nitrogens, are meant to include those corresponding N-oxide forms. Thus, for a compound of the disclosure having, for example, a pyridyl ring; the corresponding pyridyl-N-oxide is meant to be included as another compound of the disclosure.

"Treatment," "treat," or "treating" cancer refers to reversing (e.g., overcoming a differentiation blockage of the cells), alleviating (e.g., alleviating one or more symptoms, such as fatigue from anemia, low blood counts, etc.), and/or delaying the progression of (e.g., delaying the progression of the condition such as transformation to AML) a cancer as described herein.

"Subject", as used herein, means an animal subject, such as a mammalian subject, and particularly human beings.

The term "antibody" is used in the broadest sense to refer to an immunoglobulin molecule that recognizes and specifically binds to a target, such as a protein, polypeptide, carbohydrate, polynucleotide, lipid, or combinations of the foregoing through at least one antigen recognition site within the variable region of the immunoglobulin molecule. The heavy chain of an antibody is composed of a heavy chain variable domain ($V_H$) and a heavy chain constant region ($C_H$). The light chain is composed of a light chain variable domain ($V_L$) and a light chain constant domain ($C_L$). For the purposes of this application, the mature heavy chain and light chain variable domains each comprise three complementarity determining regions (CDR1, CDR2 and CDR3) within four framework regions (FR1, FR2, FR3, and FR4) arranged from N-terminus to C-terminus: FR1, CDR1, FR2, CDR2, FR3, CDR3, and FR4. An "antibody" can be naturally occurring or man-made, such as monoclonal antibodies produced by conventional hybridoma technology. The term "antibody" includes full-length monoclonal antibodies and full-length polyclonal antibodies, as well as antibody fragments such as Fab, Fab', F(ab')$_2$, Fv, and single chain antibodies. An antibody can be any one of the five major classes of immunoglobulins: IgA, IgD, IgE, IgG, and IgM, or subclasses thereof (e.g., isotypes IgG1, IgG2, IgG3, IgG4). The term further encompasses human antibodies, chimeric antibodies, humanized antibodies and any modified immunoglobulin molecule containing an antigen recognition site, so long as it demonstrates the desired biological activity (e.g., binds the target antigen, internalizes within a target-antigen expressing cell).

"Pharmaceutically acceptable carrier" as used herein refers to a nontoxic carrier, adjuvant, or vehicle that does not destroy the pharmacological activity of the compound with which it is formulated. Pharmaceutically acceptable carriers, adjuvants or vehicles that may be used in the compositions of this disclosure include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, cyclodextrins, sodium carboxymethylcellulose, polyacrylates, waxes, polyethylene-polyoxypropylene-block polymers, polyethylene glycol and wool fat.

A "pharmaceutically acceptable salt" is a salt that retains the desired biological activity of the parent compound and does not impart undesired toxicological effects. Examples of such salts are: (a) acid addition salts formed with inorganic acids, for example, hydrochloric acid, hydrobromic acid, sulfuric acid, phosphoric acid, nitric acid and the like; and salts formed with organic acids, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (b) salts formed from elemental anions such as chlorine, bromine, and iodine. See, e.g., Haynes et al., "Commentary: Occurrence of Pharmaceutically Acceptable Anions and Cations in the Cambridge Structural Database," J. Pharmaceutical Sciences, vol. 94, no. 10 (2005), and Berge et al., "Pharmaceutical Salts", J. Pharmaceutical Sciences, vol. 66, no. 1 (1977), which are incorporated by reference herein.

Unless indicated otherwise, nomenclature used to describe chemical groups or moieties as used herein follow the convention where, reading the name from left to right, the point of attachment to the rest of the molecule is at the right-hand side of the name. For example, the group "($C_{1-3}$ alkoxy)$C_{1-3}$ alkyl," is attached to the rest of the molecule at the alkyl end. Further examples include methoxyethyl, where the point of attachment is at the ethyl end, and methylamino, where the point of attachment is at the amine end.

Unless indicated otherwise, where a chemical group is described by its chemical formula or structure having a terminal bond moiety indicated by "—", it will be understood that the "—" represents the point of attachment.

Unless otherwise stated, compounds depicted herein include all enantiomeric, diastereomeric, and geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. Unless otherwise stated, all tautomeric forms of the compounds of the disclosure are within the scope of the disclosure. Additionally, unless otherwise stated, structures depicted herein include compounds that differ only by the presence of one or more isotopically enriched atoms. For example, compounds having the formulae disclosed herein except for the replacement of hydrogen by deuterium or tritium, or the replacement of a carbon by a $^{13}C$- or $^{14}C$-enriched carbon are within the scope of this disclosure. Such compounds may be useful, for example, as analytical tools or probes in biological assays.

Provided herein according to some embodiments are compounds of Formula I:

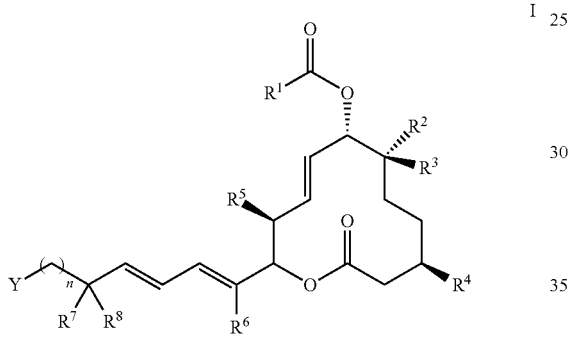

I and pharmaceutically acceptable salts thereof,
wherein:
n is chosen from 0, 1, 2 or 3;
$R^1$ is chosen from $C_1$-$C_6$ alkyl groups, $C_3$-$C_8$ cycloalkyl groups, —$NR^9R^{10}$ groups,

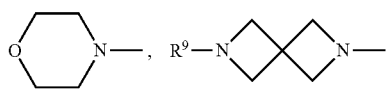

groups,

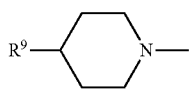

groups,

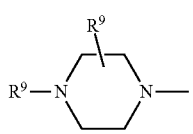

groups,

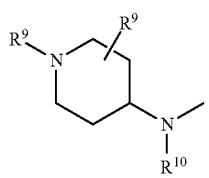

groups,

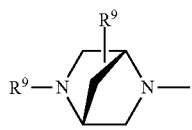

groups,

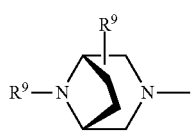

groups,

groups, and

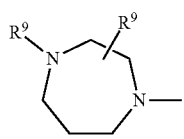

groups;
$R^9$ is chosen from hydrogen, —$NR^{11}R^{12}$ groups, $C_1$-$C_6$ alkyl groups, —($C_1$-$C_6$ alkyl)-$CO_2H$ groups, $C_3$-$C_8$ cycloalkyl groups, and $C_3$-$C_8$ heterocyclyl groups, wherein the —$NR^{11}R^{12}$ groups, $C_1$-$C_6$ alkyl groups, $C_3$-$C_8$ cycloalkyl groups, and $C_3$-$C_8$ heterocyclyl groups may be unsubstituted or substituted from 1-3 times with a group independently chosen from $C_1$-$C_6$ alkyl groups, —($C_1$-$C_6$ alkyl)-$CO_2H$ groups, hydroxy, halogen groups, and $C_1$-$C_6$ alkoxy groups;
$R^{10}$ is chosen from hydrogen and $C_1$-$C_6$ alkyl groups;
one of either $R^2$ or $R^3$ is chosen from hydrogen and $C_1$-$C_6$ alkyl groups, and the other is chosen from hydrogen, —$OR^{10}$, —OC(O)$R^{10}$, —OC(O)$R^1$, and $C_1$-$C_6$ alkyl groups;
$R^4$ is chosen from hydrogen and hydroxy;
$R^5$ and $R^6$ are each independently chosen from $C_1$-$C_6$ alkyl groups;
$R^7$ and $R^8$ are each independently chosen from hydrogen, hydroxy, $C_1$-$C_6$ alkoxy groups, and $C_1$-$C_6$ alkyl groups; and
Y is chosen from phenyl, thiophenyl, triazolyl, pyridinyl, pyrimidinyl, pyridazinyl, and pyrazinyl, wherein Y may be unsubstituted or substituted from 1-3 times with groups independently chosen from oxo groups, $C_1$-$C_6$ alkyl groups, $C_3$-$C_5$ cycloalkyl groups, hydroxy $C_1$-$C_6$ alkyl groups, $C_1$-$C_6$ alkoxy groups, methoxy $C_1$-$C_6$ alkyl groups, —$NR^{11}R^{12}$ groups,

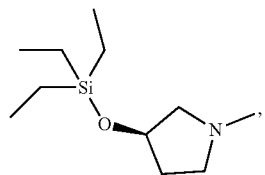

wherein $R^{11}$ and $R^{12}$ are each independently chosen from hydrogen and $C_1$-$C_6$ alkyl groups.

In some embodiments, in Formula I, Y is

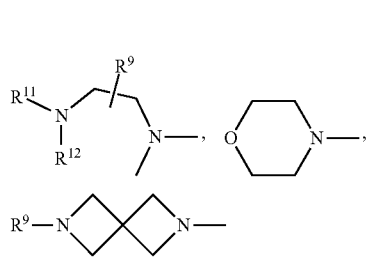

In some embodiments, in Formula I, Y is chosen from optionally substituted phenyl groups.

In some embodiments, in Formula I, $R^1$ is chosen from methyl,

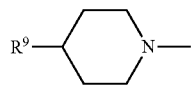

groups,

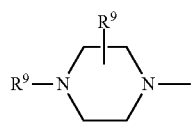

groups,

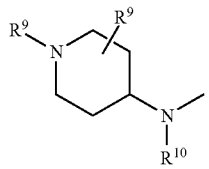

groups,

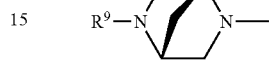

groups,

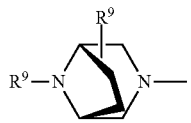

groups,

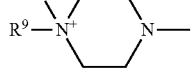

groups,

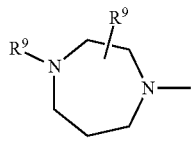

groups, and groups, wherein $R^9$, $R^{10}$, $R^{11}$, and $R^{12}$ are defined as above.

Also provided herein are compounds of Formula II:

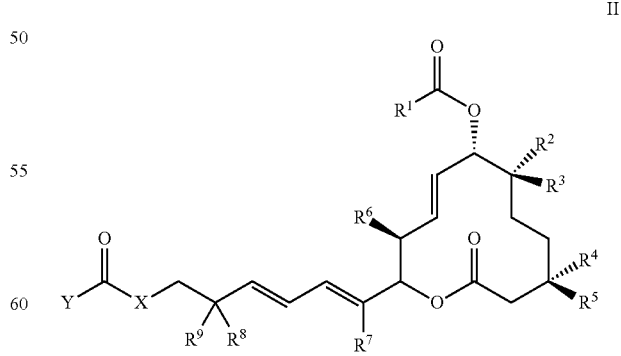

II and pharmaceutically acceptable salts thereof, wherein:
X is chosen from O, NR' groups, and $CH_2$, wherein R' is chosen from hydrogen and $C_1$-$C_6$ alkyl groups;

$R^1$ is chosen from methyl, $NR^{11}R^{12}$ groups,

groups, and

groups;

$R^{10}$ is chosen from $C_1$-$C_6$ alkyl groups, $C_3$-$C_8$ cycloalkyl groups, and halo $C_1$-$C_6$ alkyl groups, wherein the $C_3$-$C_8$ cycloalkyl groups may be unsubstituted or substituted from 1-3 times with a group independently chosen from $C_1$-$C_6$ alkyl groups, hydroxy, halogen groups, and $C_1$-$C_6$ alkoxy groups;

$R^{11}$ and $R^{12}$ are each independently chosen from $C_1$-$C_6$ alkyl groups;

one of either $R^2$ or $R^3$ is chosen from hydrogen and $C_1$-$C_6$ alkyl groups, and the other is chosen from hydrogen, hydroxy and $C_1$-$C_6$ alkyl groups;

one of either $R^4$ or $R^5$ is hydrogen, and the other is chosen from hydrogen, hydroxy, and

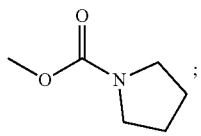

$R^6$ and $R^7$ are each independently chosen from $C_1$-$C_6$ alkyl groups;

$R^8$ and $R^9$ are each independently chosen from hydrogen and $C_1$-$C_6$ alkyl groups; or $R^8$ and $R^9$ are taken together to form a cyclopropyl ring; and Y is chosen from $C_1$-$C_6$ alkyl groups, $C_3$-$C_8$ cycloalkyl groups, methoxy, and $-NR^{13}R^{14}$ groups, wherein $R^{13}$ and $R^{14}$ are each independently chosen from hydrogen, $C_1$-$C_6$ alkyl groups, and methoxy $C_1$-$C_6$ alkyl groups; or $R^{13}$ and $R^{14}$ may be taken together with the N to form a group chosen from

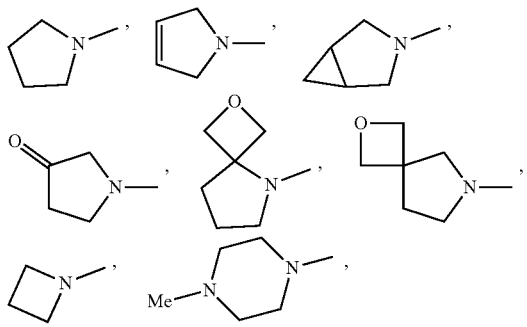

a morpholine, a piperidine, a thiazolidine, an indole, an indoline, and an isoindoline ring;

wherein Y may be unsubstituted or substituted from 1-3 times with a group independently chosen from $C_1$-$C_6$ alkyl groups, hydroxy, hydroxy $C_1$-$C_6$ alkyl groups, methoxy, methoxy $C_1$-$C_6$ alkyl groups, halo, halo $C_1$-$C_6$ alkyl groups, $-C(O)NH_2$, $-NHCOO-C_1$-$C_6$ alkyl groups, $-COOH$,

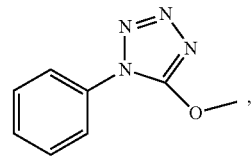

and $-NR^{15}R^{16}$ groups, wherein $R^{15}$ and $R^{16}$ are each independently chosen from hydrogen and $C_1$-$C_6$ alkyl groups.

Also disclosed herein are compounds of Formula III:

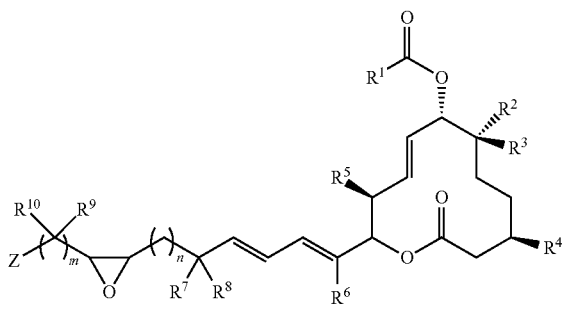

III and pharmaceutically acceptable salts thereof, wherein:

n is chosen from 0, 1 and 2;

m is chosen from 1, 2, and 3;

$R^1$ is chosen from $C_1$-$C_6$ alkyl groups, $C_3$-$C_8$ cycloalkyl groups, $-NR^{11}R^{12}$ groups,

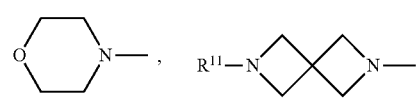

groups,

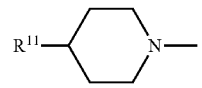

groups,

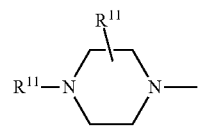

groups,

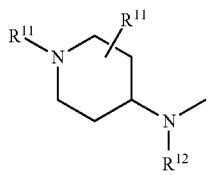

groups,

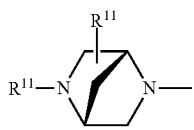

groups,

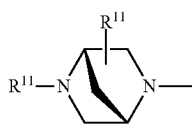

groups,

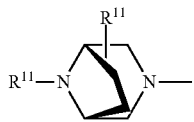

groups,

groups, and

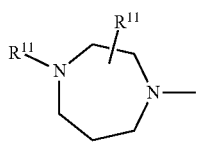

groups, $R^{11}$ is chosen from hydrogen, —$NR^{16}R^{17}$ groups, $C_1$-$C_6$ alkyl groups, —($C_1$-$C_6$ alkyl)-$CO_2H$ groups, —($C_1$-$C_6$ alkyl)-$CO_2R^{12}$ groups, —($C_1$-$C_6$ alkyl)-$NR^{16}R^{17}$ groups, $C_3$-$C_8$ cycloalkyl groups, and $C_3$-$C_8$ heterocyclyl groups, wherein the —$NR^{16}R^{17}$ groups, $C_1$-$C_6$ alkyl groups, $C_3$-$C_8$ cycloalkyl groups and $C_3$-$C_8$ heterocyclyl groups may be unsubstituted or substituted from 1-3 times with a group independently chosen from $C_1$-$C_6$ alkyl groups, —($C_1$-$C_6$ alkyl)-$CO_2H$ groups, hydroxy, halogen groups, and $C_1$-$C_6$ alkoxy groups;

$R^{12}$ is chosen from hydrogen and $C_1$-$C_6$ alkyl groups;
one of either $R^2$ or $R^3$ is chosen from hydrogen and $C_1$-$C_6$ alkyl groups, and the other is chosen from hydrogen, —$OR^{10}$, —$OC(O)R^{10}$, —$OC(O)R^1$, and $C_1$-$C_6$ alkyl groups;
$R^4$ is hydrogen or hydroxy;
$R^5$ and $R^6$ are each independently chosen from $C_1$-$C_6$ alkyl groups;
$R^7$ and $R^8$ are each independently chosen from hydrogen, hydroxy, $C_1$-$C_6$ alkoxy groups, and $C_1$-$C_6$ alkyl groups; and
$R^9$ and $R^{10}$ are each independently chosen from hydrogen, $C_1$-$C_6$ alkyl groups, hydroxy, and $C_1$-$C_6$ alkoxy groups; or, one of $R^9$ or $R^{10}$ is oxo and the other is absent;
Z is chosen from $C_1$-$C_6$ alkyl groups, —C(O)—$C_1$-$C_6$ alkyl groups, —$OR^{13}$, and —$NR^{14}R^{15}$ groups,
wherein $R^{13}$ is chosen from hydrogen, $C_1$-$C_6$ alkyl groups, and —C(O)—$C_1$-$C_6$ alkyl groups,
wherein $R^{14}$ and $R^{15}$ are each independently chosen from hydrogen, $C_1$-$C_6$ alkyl groups, and methoxy $C_1$-$C_6$ alkyl groups; or $R^{14}$ and $R^{15}$ may be taken together with the N to form a group chosen from

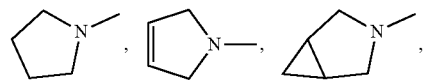

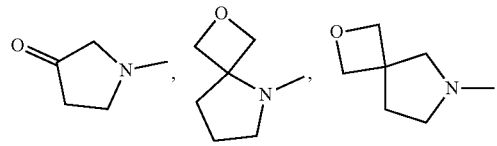

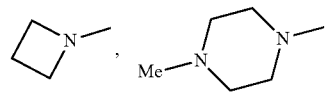

a morpholine, a piperidine, a thiazolidine, an indole, an indoline, and an isoindoline ring;
wherein Z may be unsubstituted or substituted from 1-3 times with a group independently chosen from $C_1$-$C_6$ alkyl groups, $C_3$-$C_5$ cycloalkyl groups, hydroxy $C_1$-$C_6$ alkyl groups, $C_1$-$C_6$ alkoxy groups, methoxy $C_1$-$C_6$ alkyl groups, —$NR^{16}R^{17}$ groups,

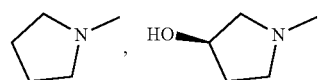

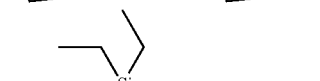

and

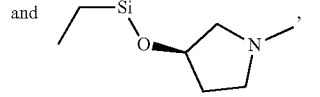

wherein $R^{16}$ and $R^{17}$ are each independently chosen from hydrogen and $C_1$-$C_6$ alkyl groups.
In some embodiments, in Formula III, $R^1$ is chosen from methyl,

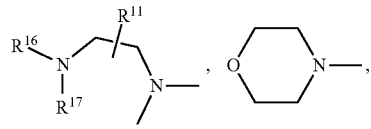

groups,
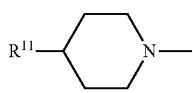
groups,
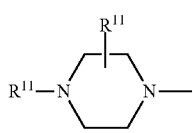
groups,
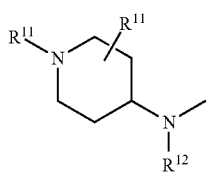
groups,
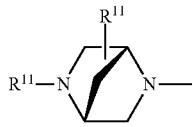
groups,
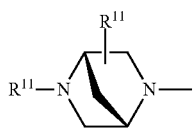
groups,
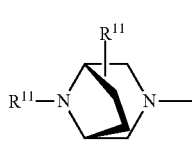
groups,
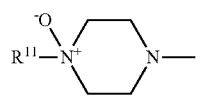
groups, and
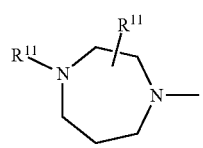
groups, wherein $R^{11}$, $R^{12}$, $R^{16}$, $R^{17}$ are defined as above.
Also disclosed herein are compounds chosen from:
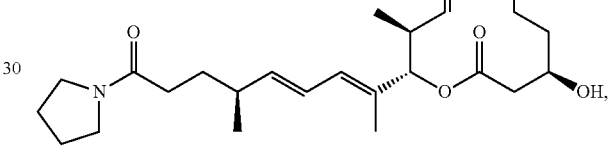
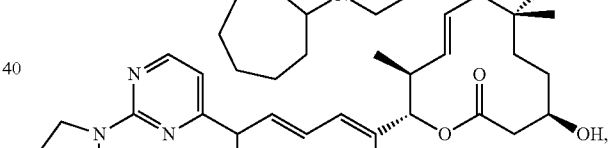
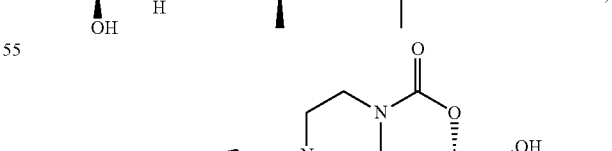
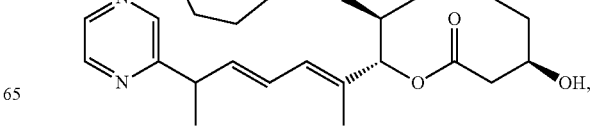

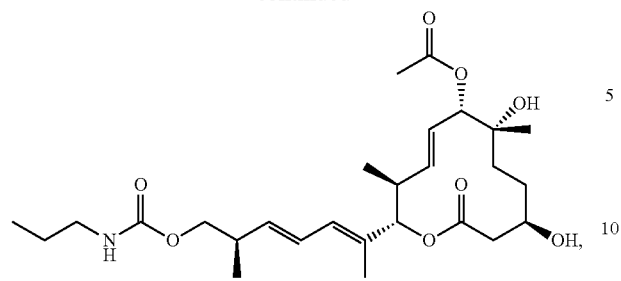
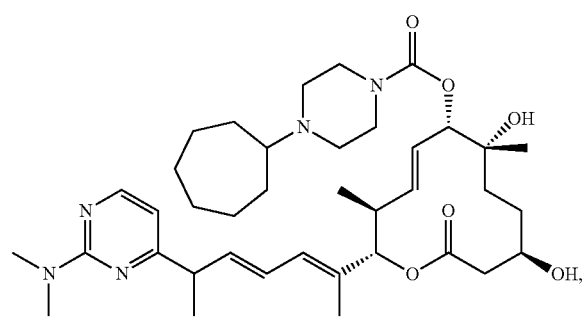
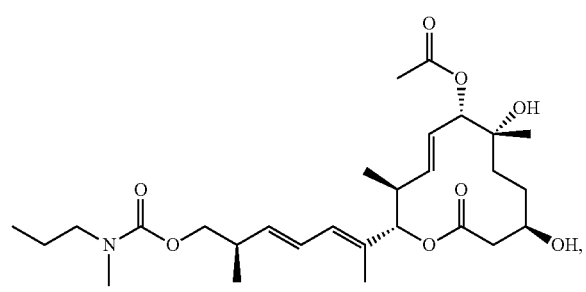
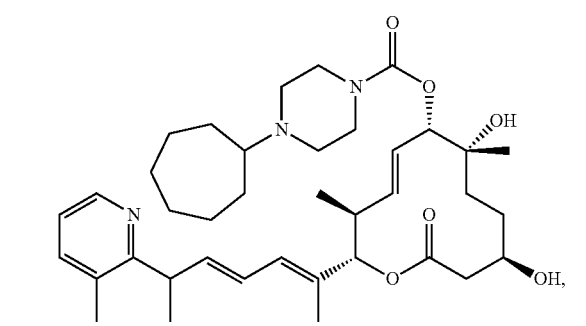
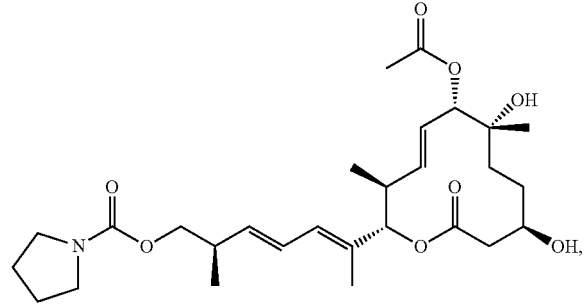
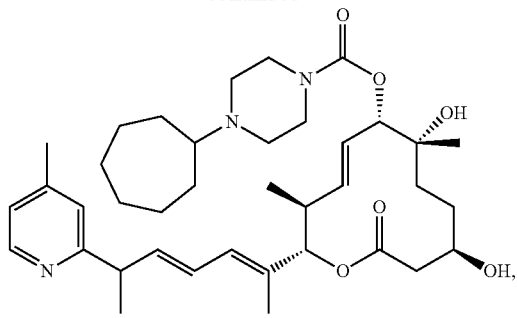
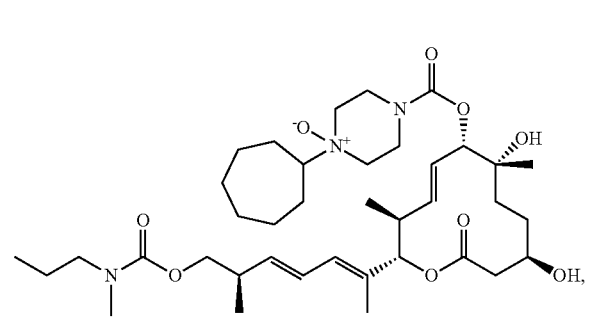
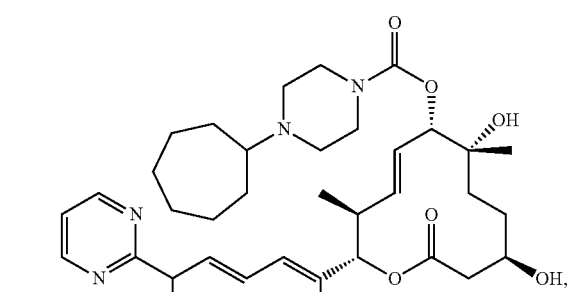
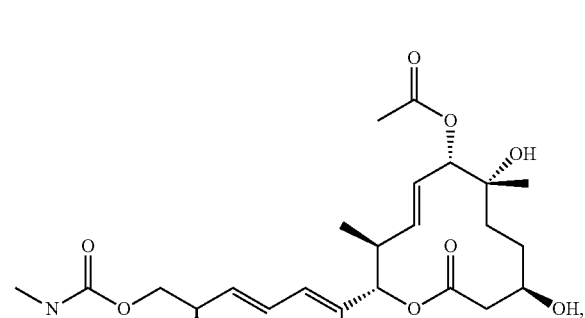
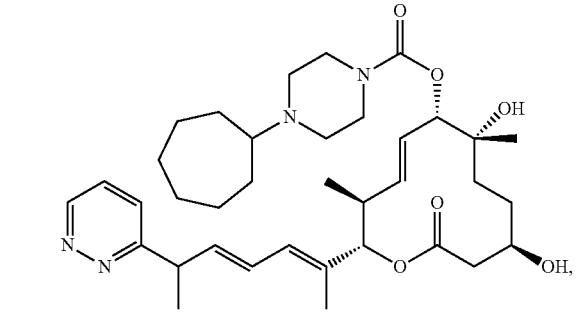

27
-continued
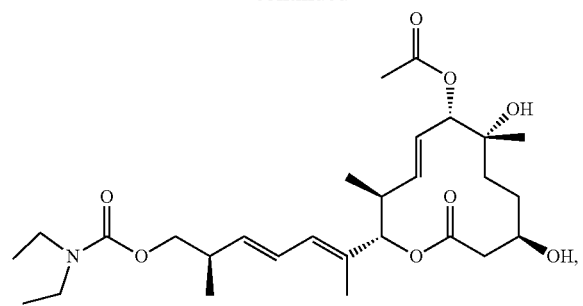
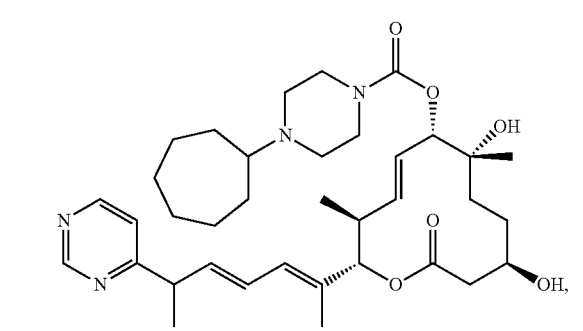
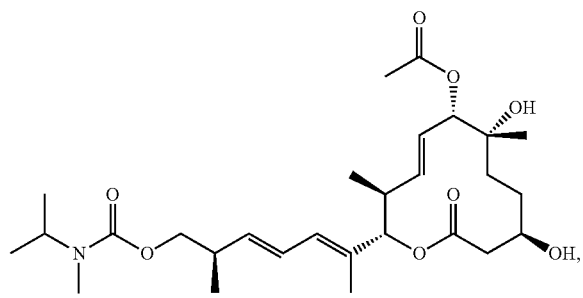
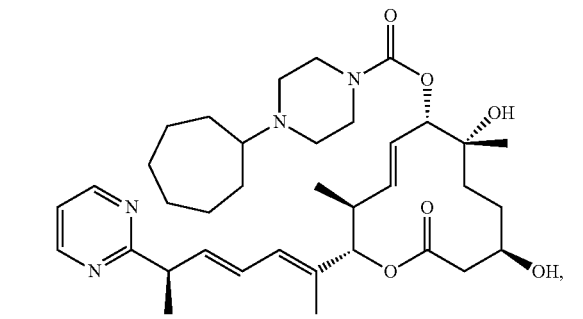
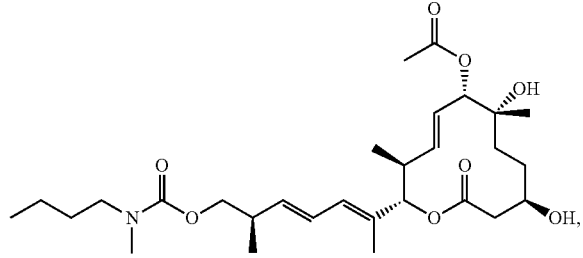
28
-continued
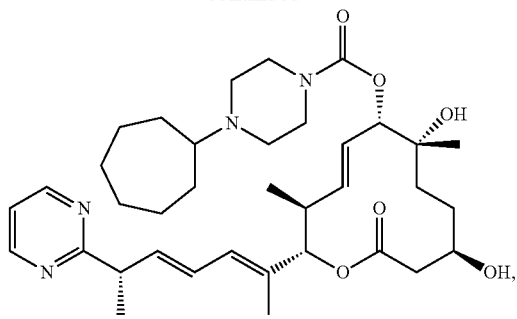
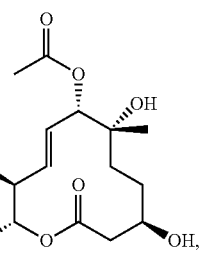
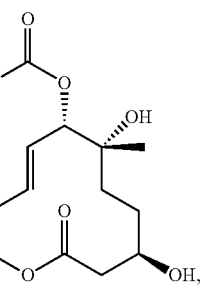
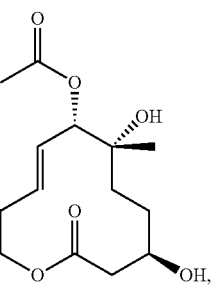
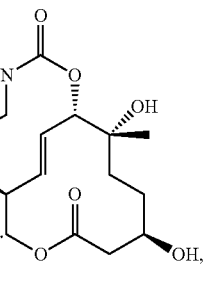

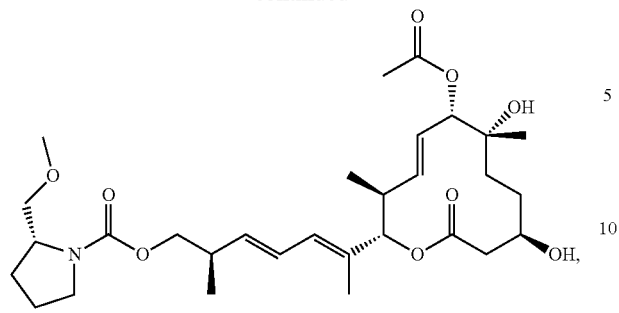
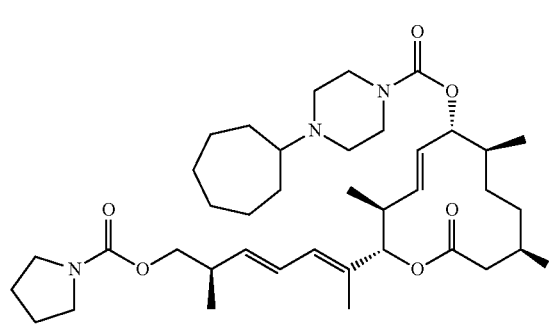
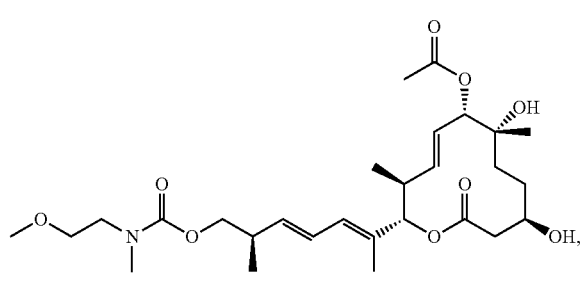
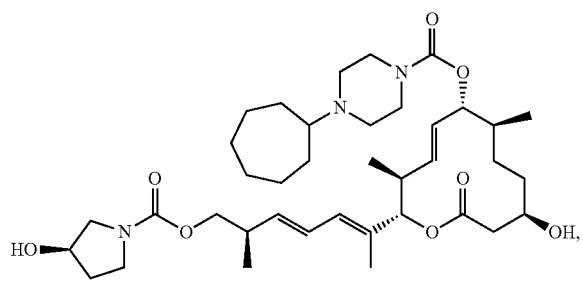
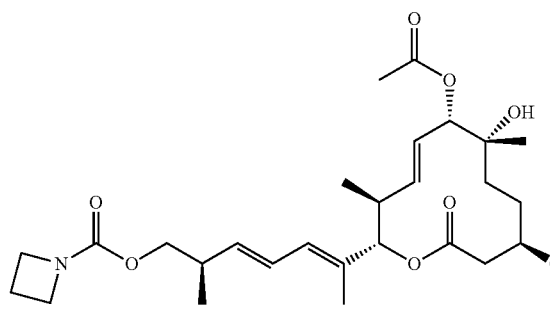
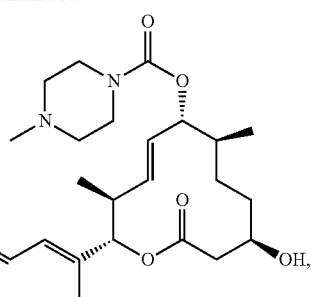
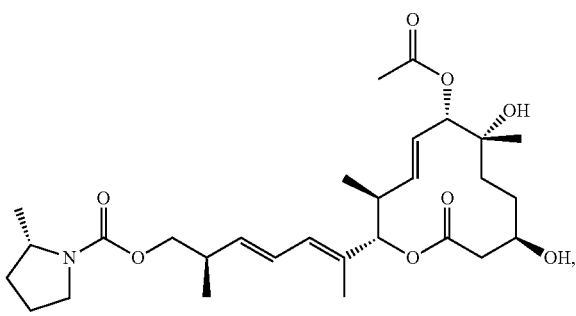
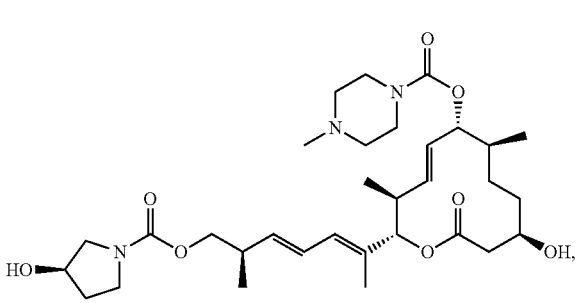
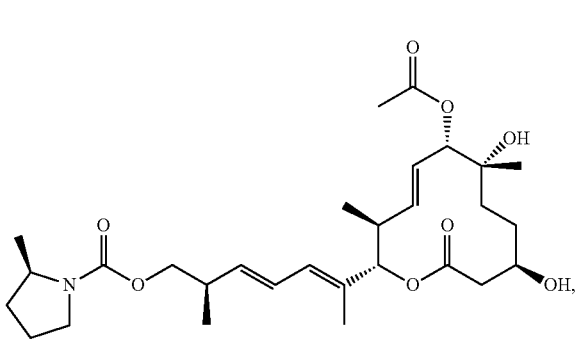
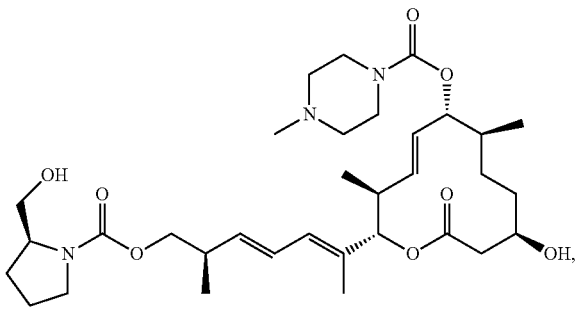

31
-continued
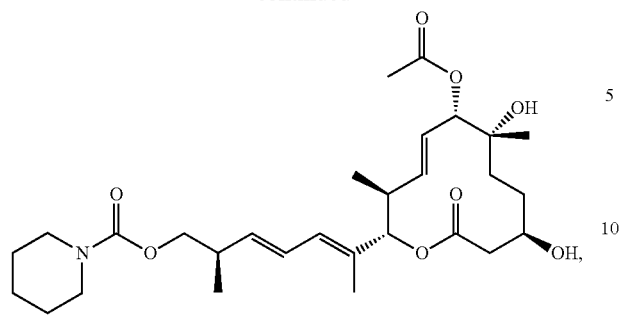
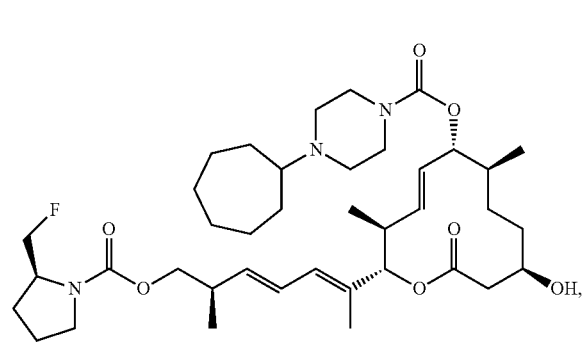
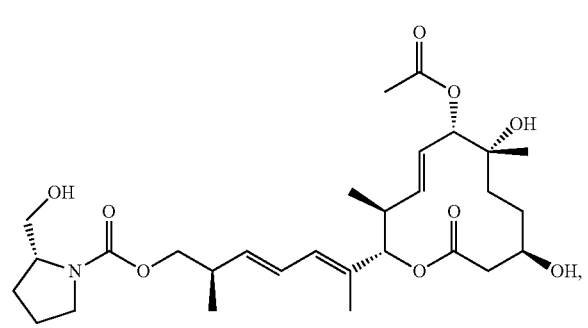
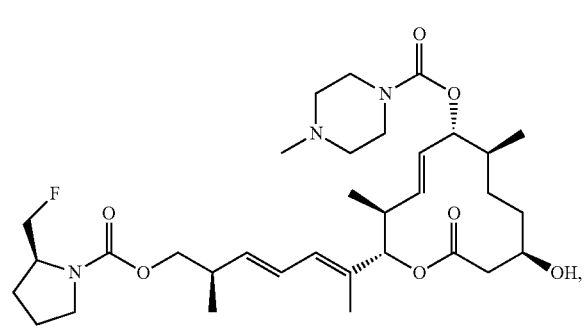
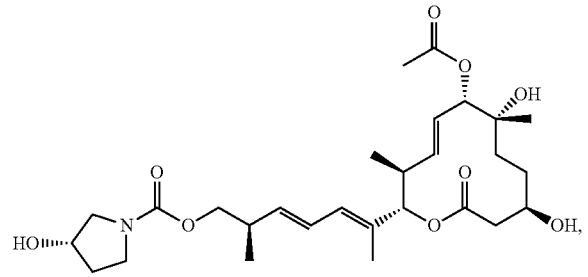
32
-continued
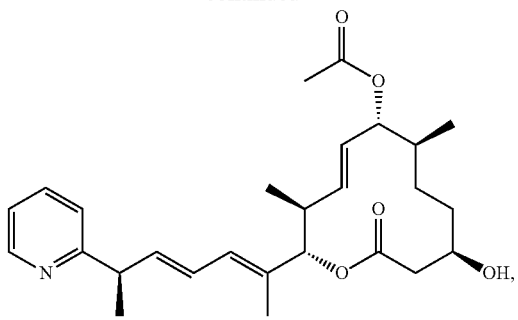
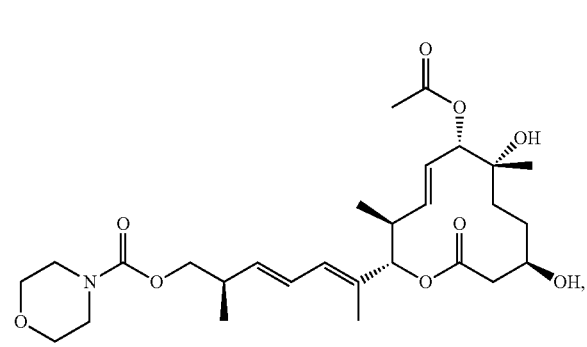
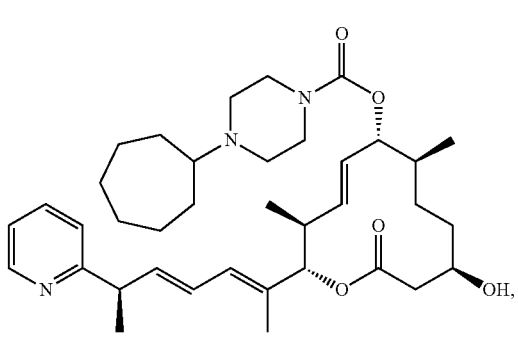
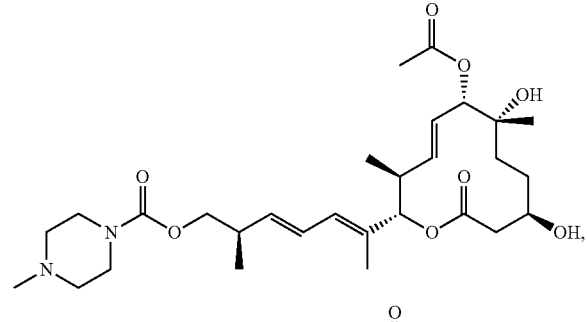
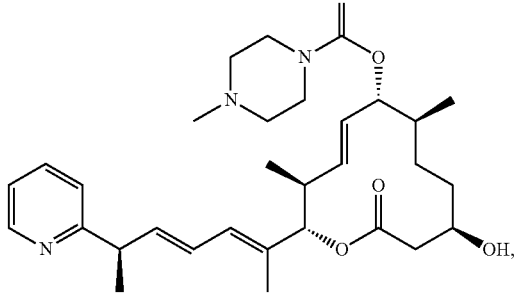

33
-continued
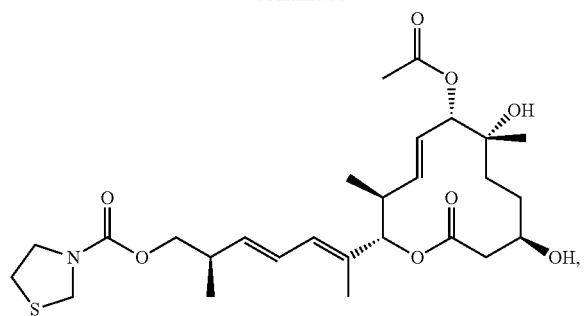
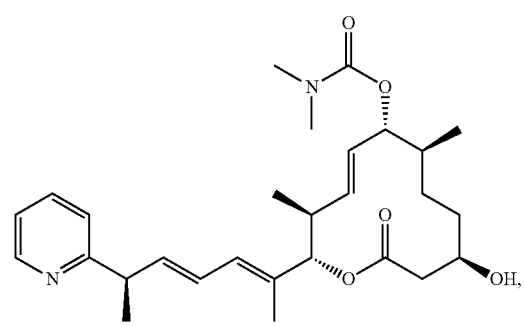
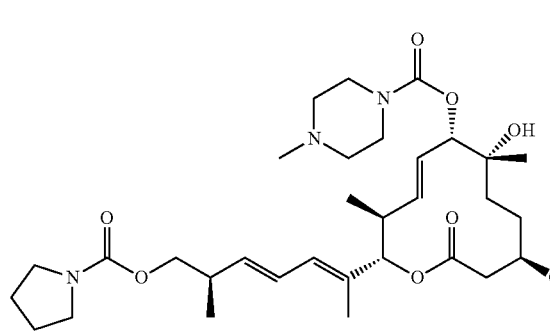
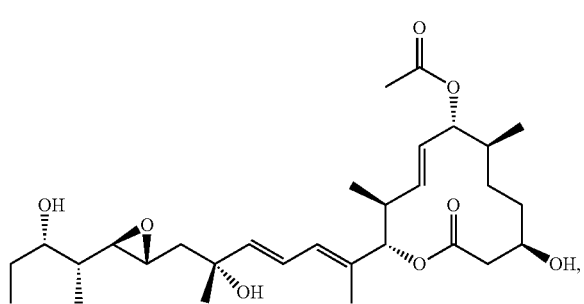
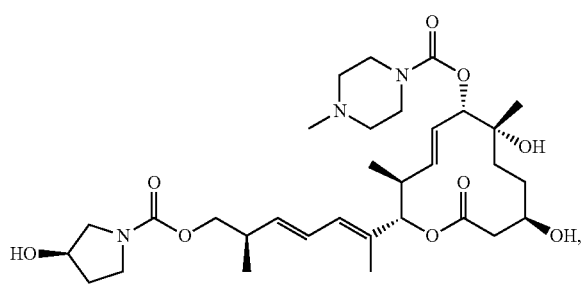
34
-continued
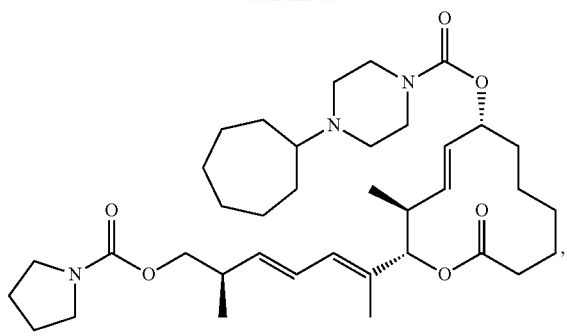
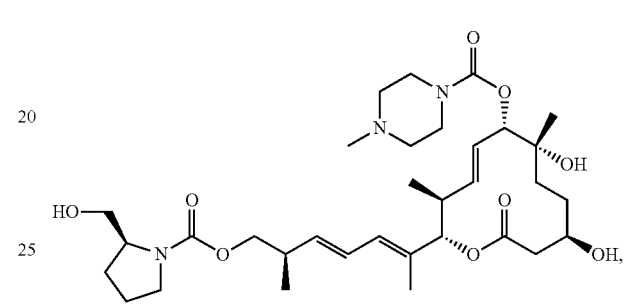
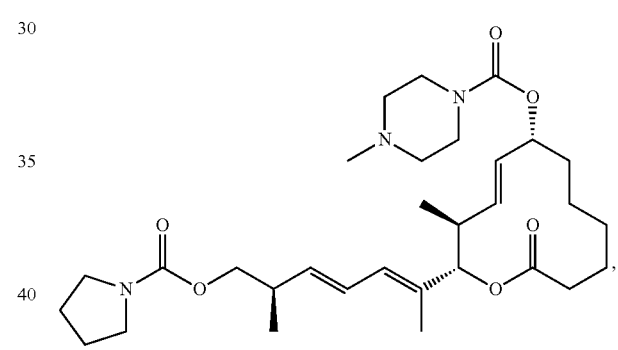
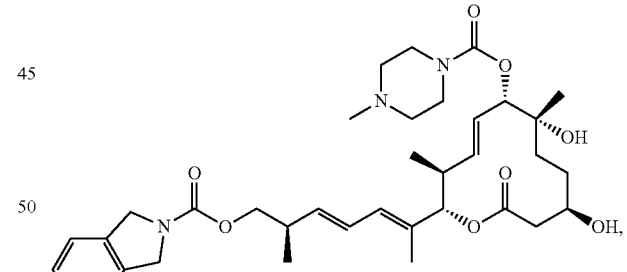
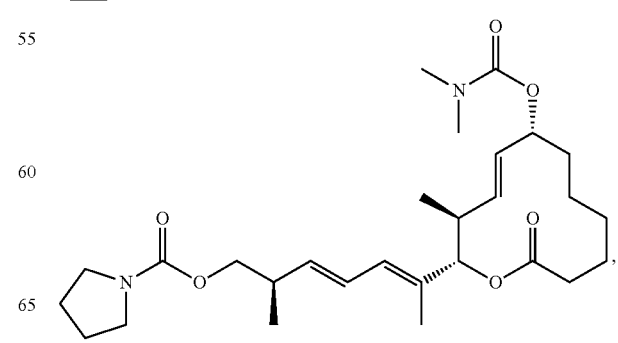

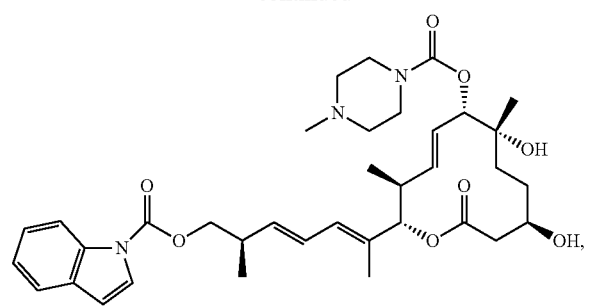
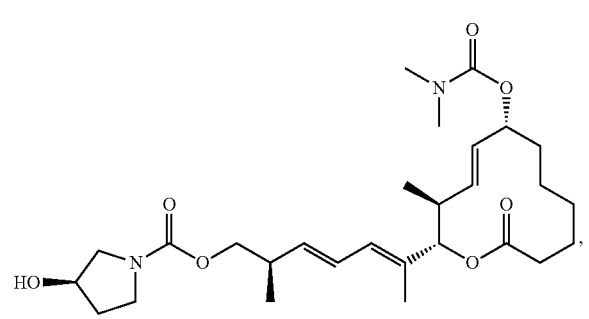
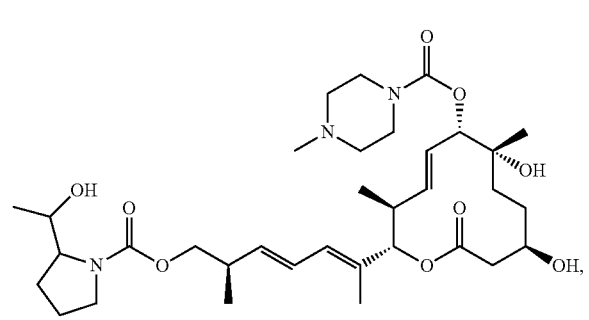
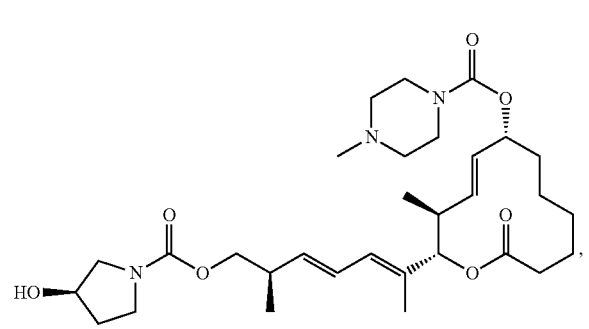
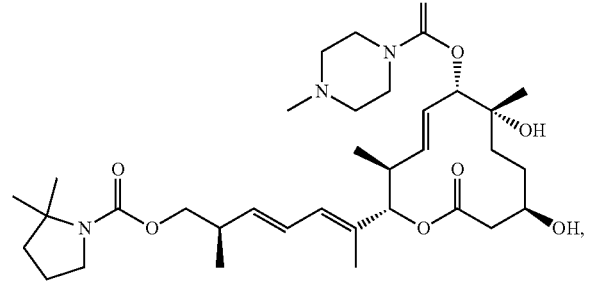
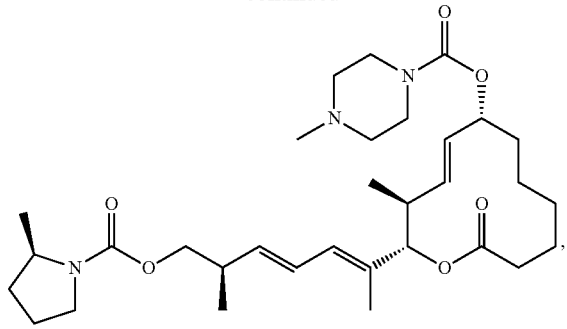
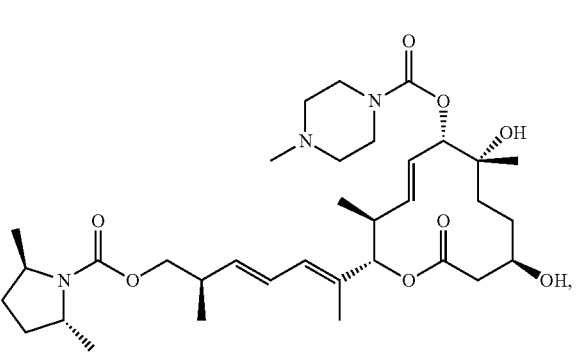
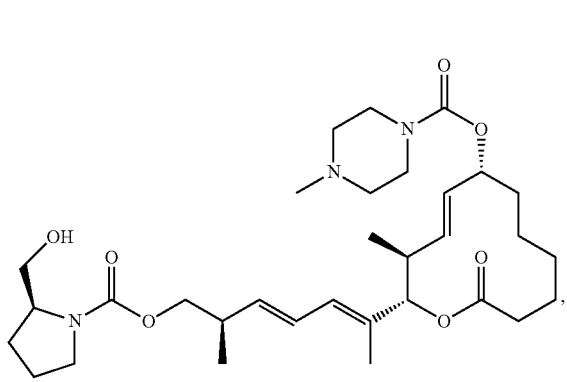
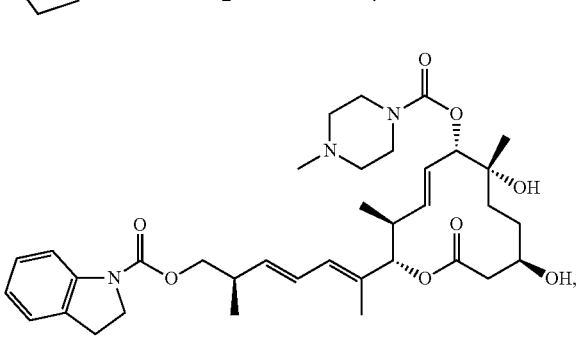

37
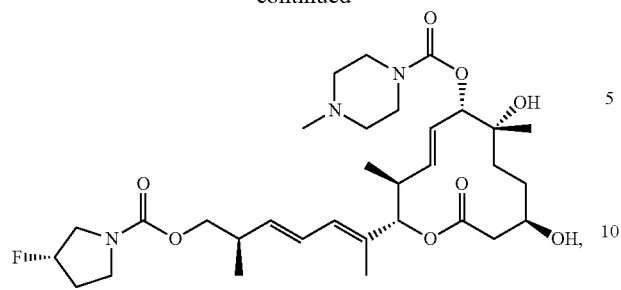

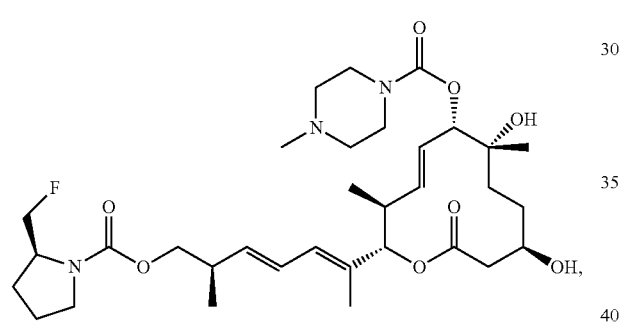
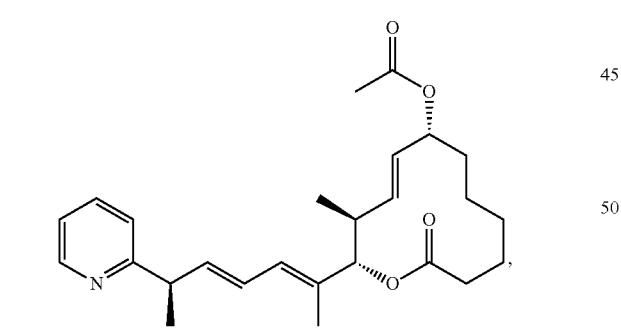
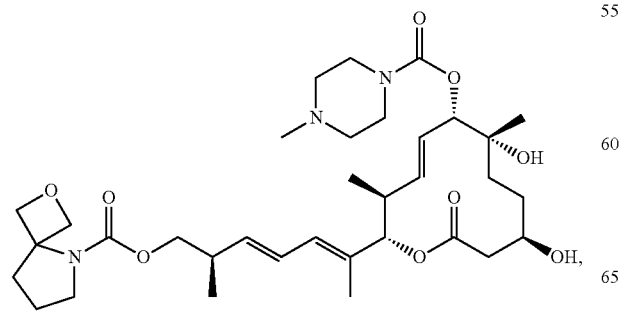
38
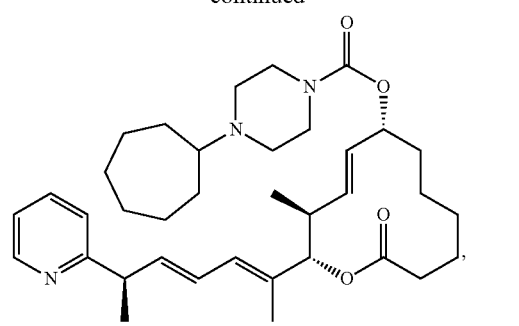
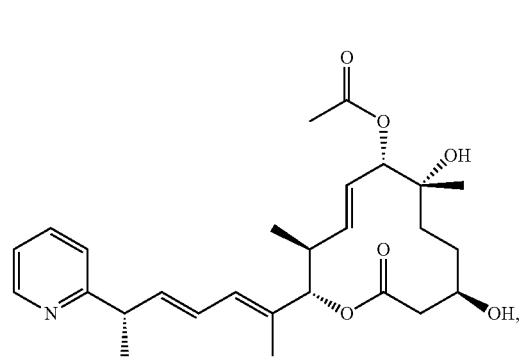
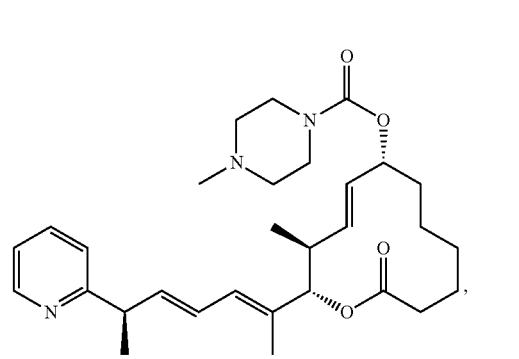
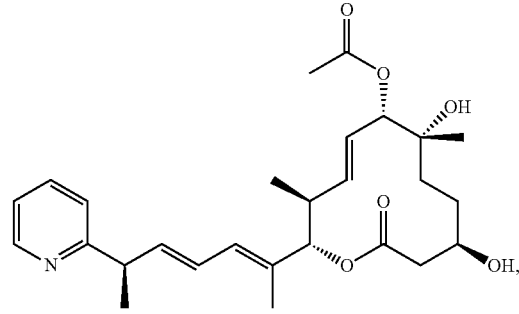
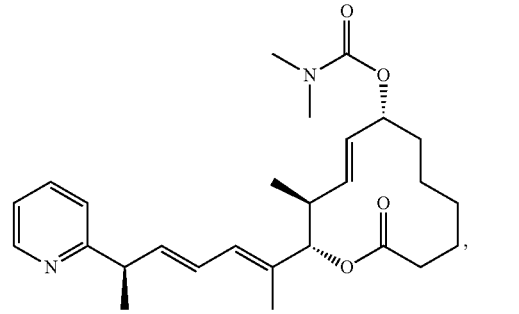

39
-continued
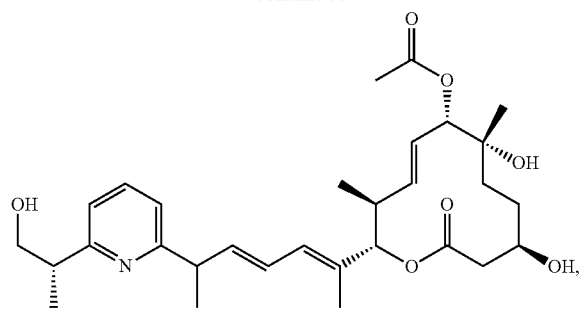
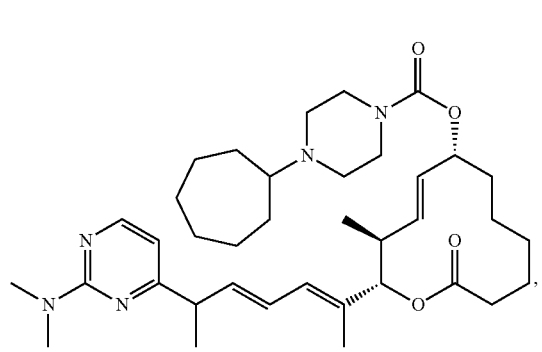
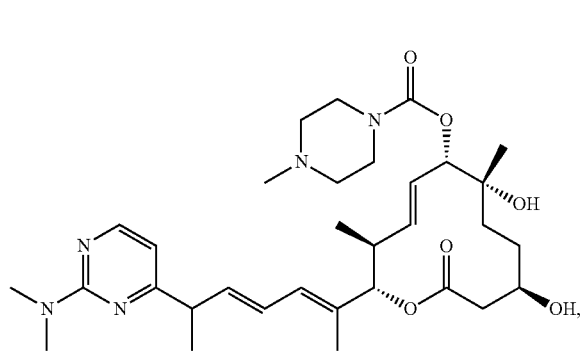
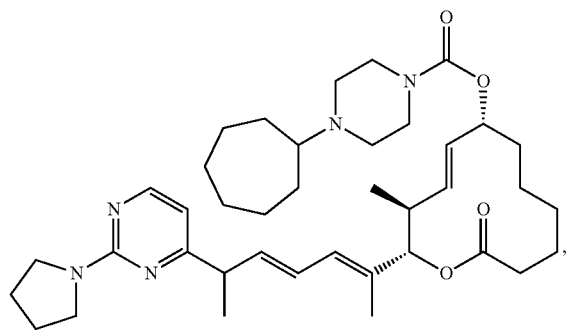
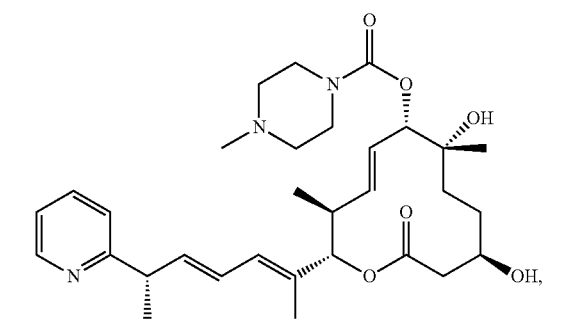
40
-continued
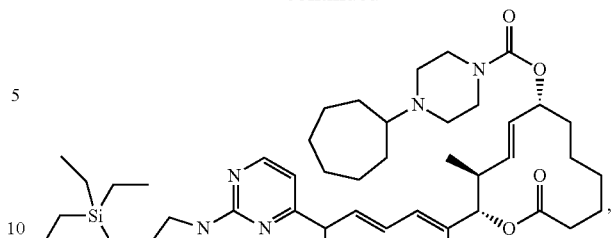
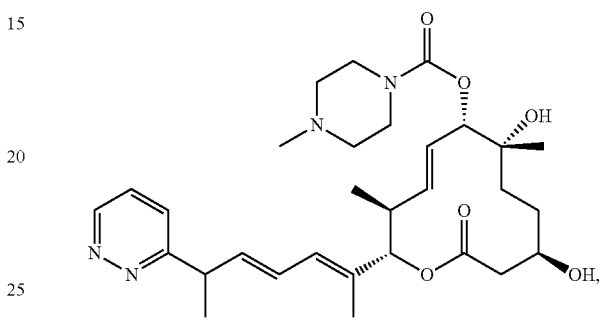
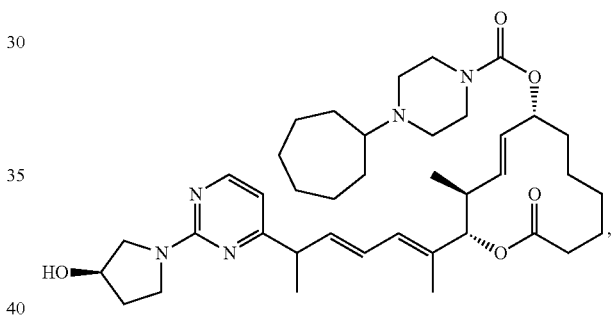
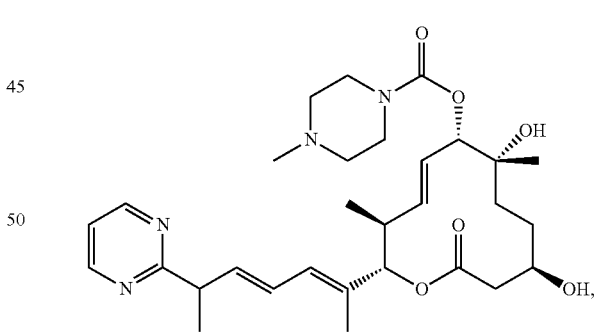
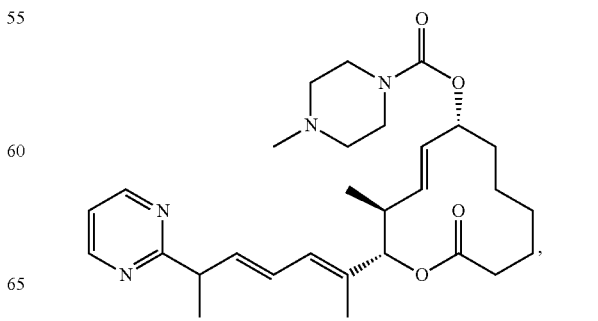

41
-continued
42
-continued
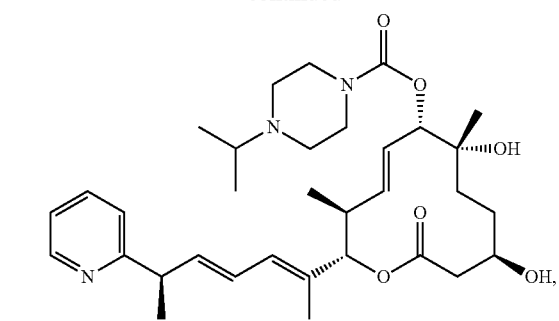
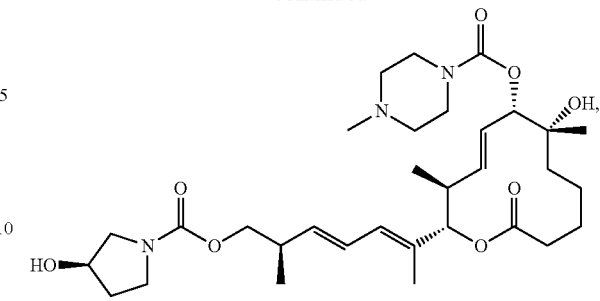

-continued
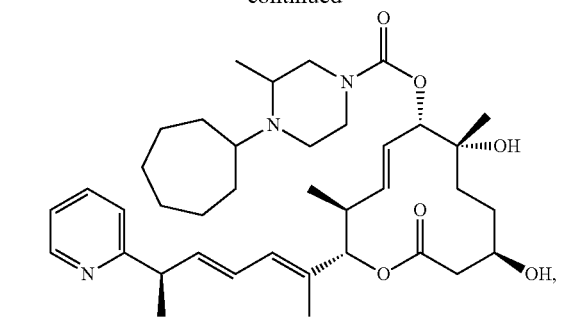
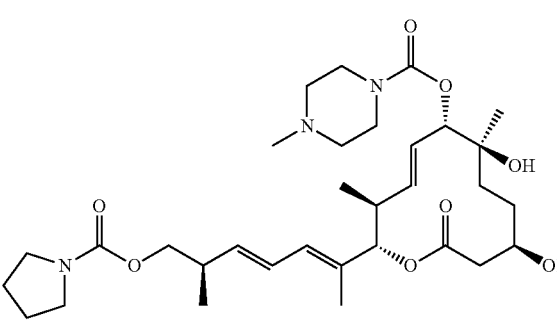
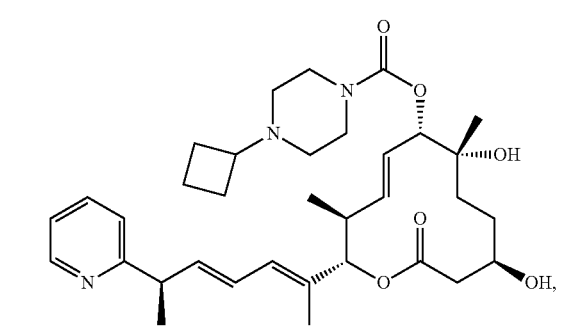
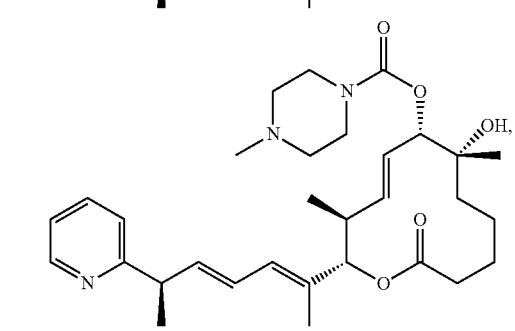
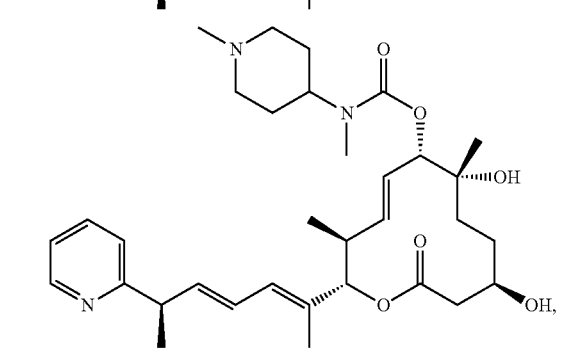
-continued
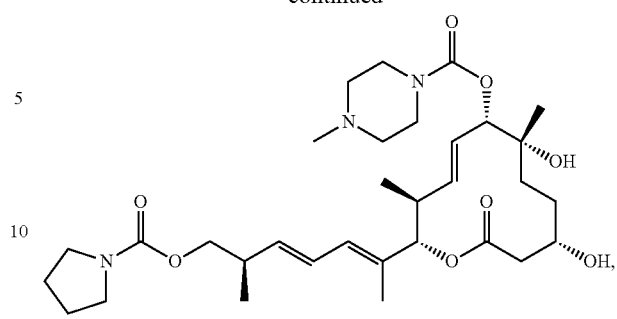
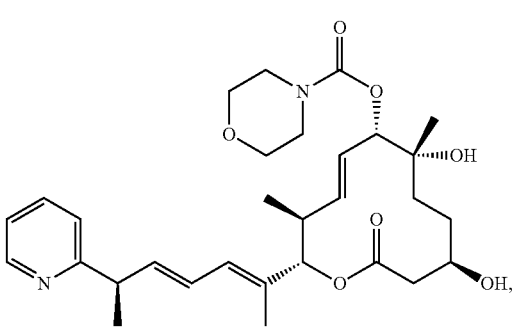
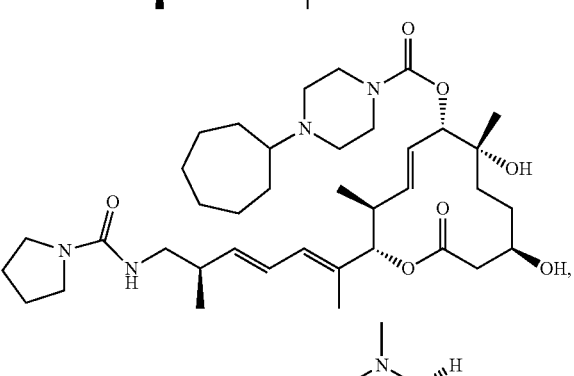
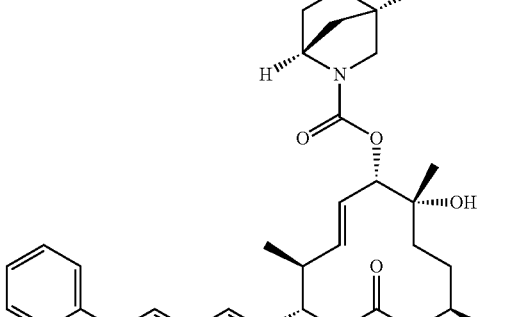
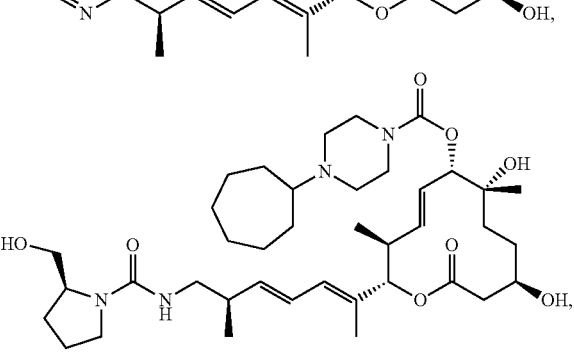

45
-continued
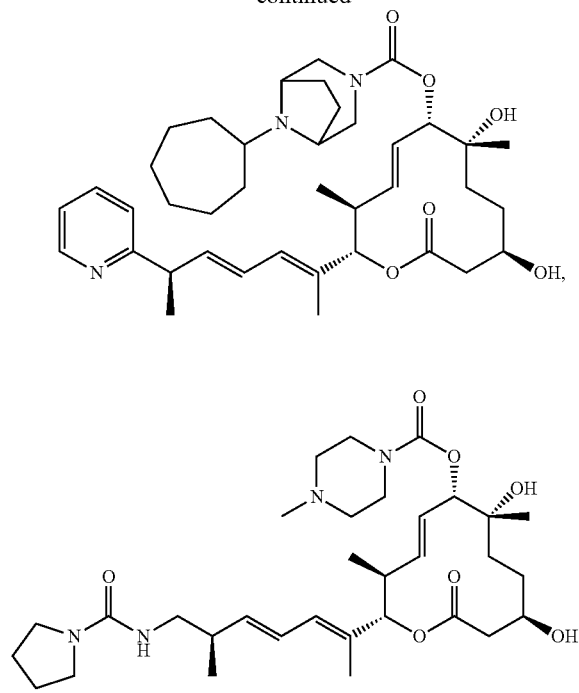
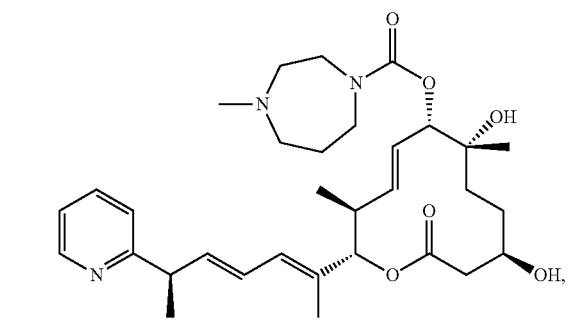
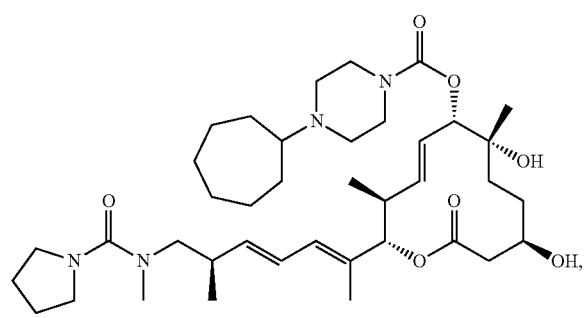
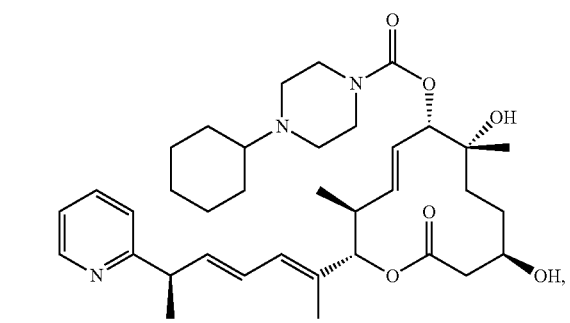
46
-continued
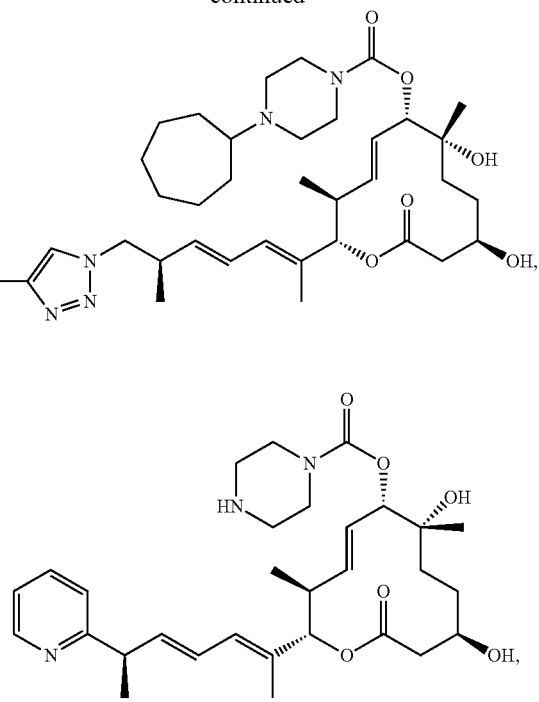
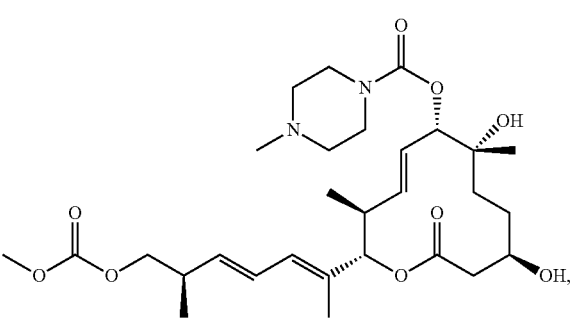
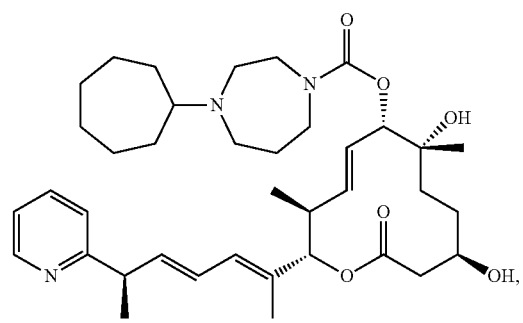
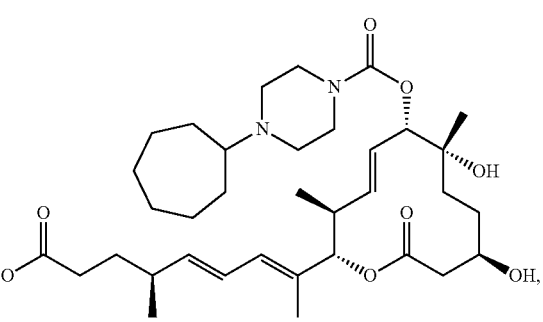

47
-continued
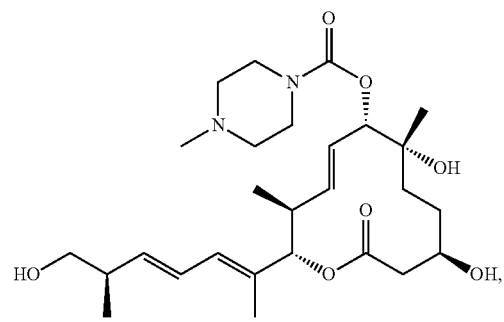
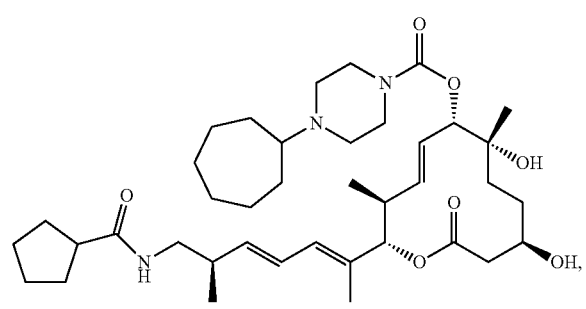
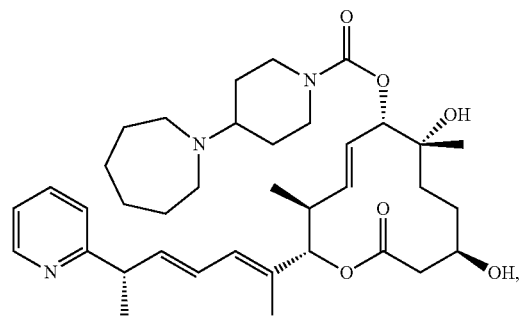
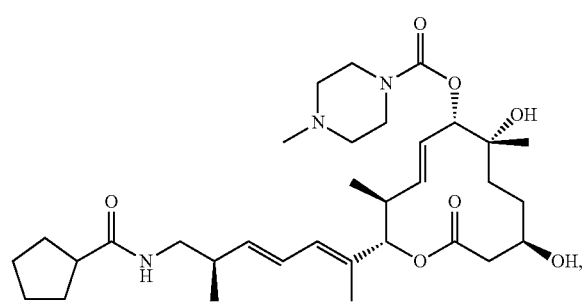
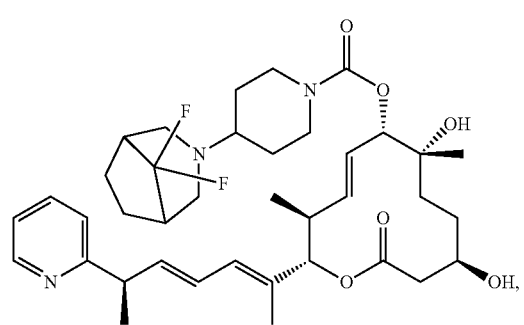
48
-continued
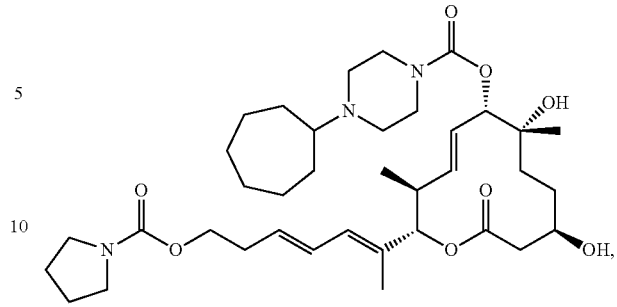
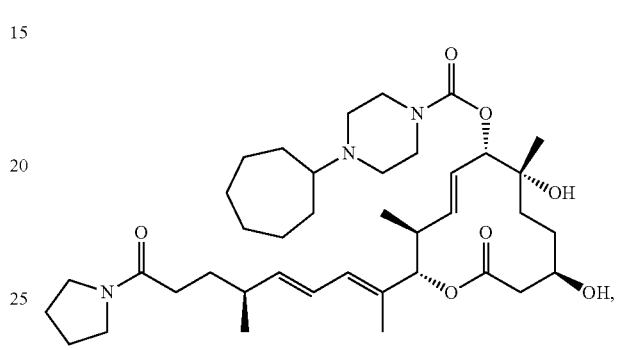
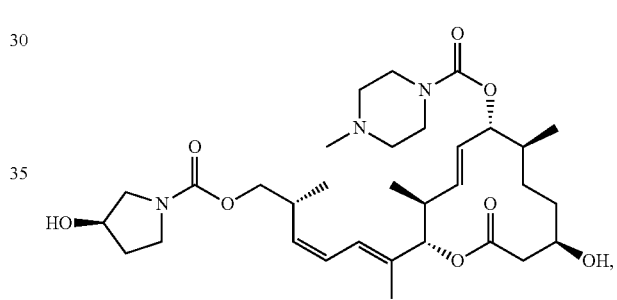
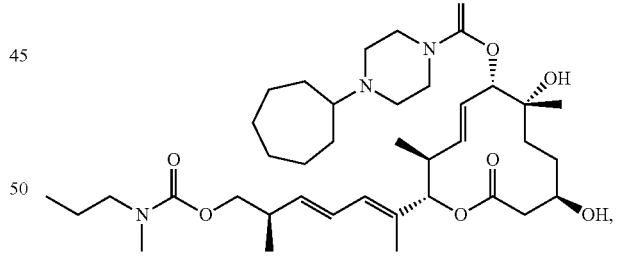
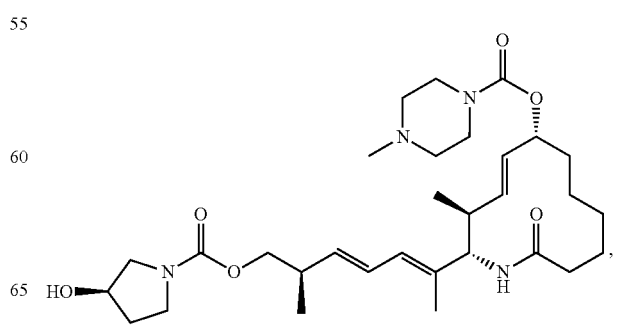

49
-continued
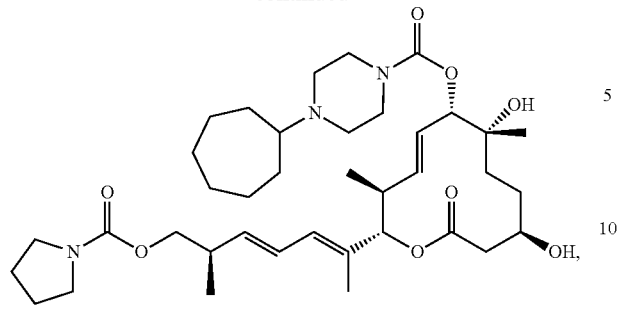
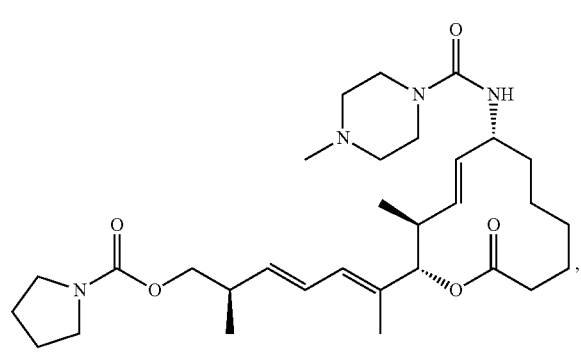
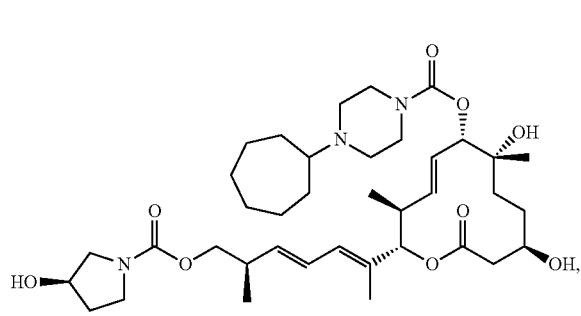
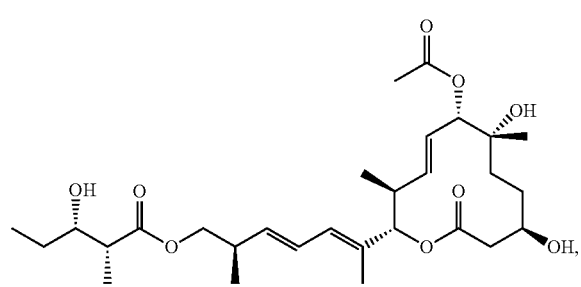
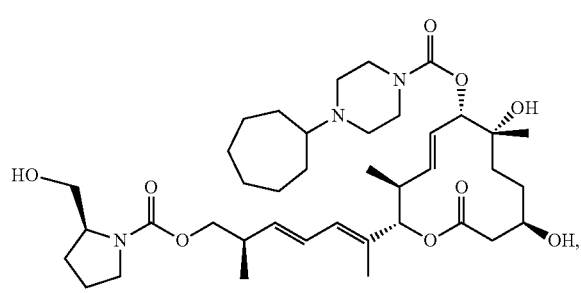
50
-continued
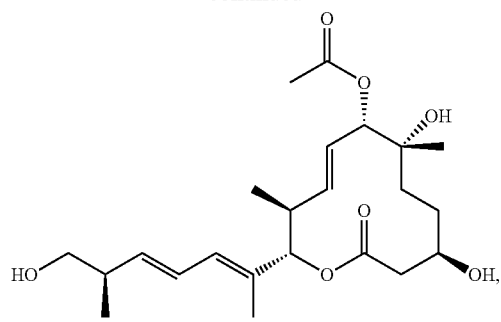
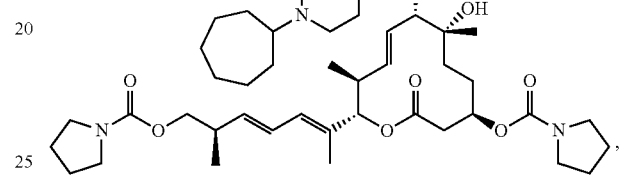
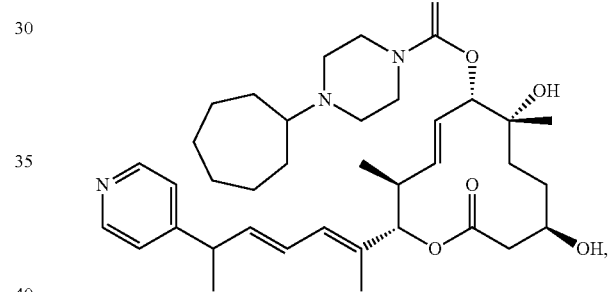
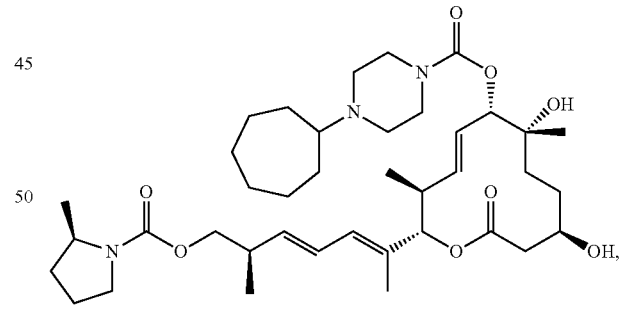
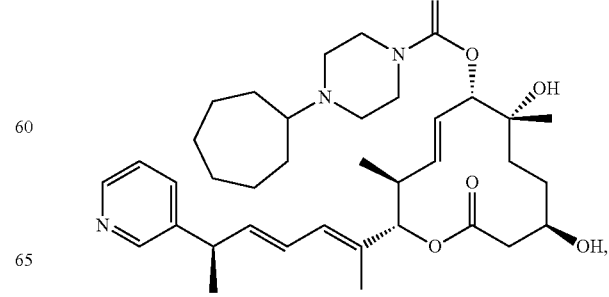

51
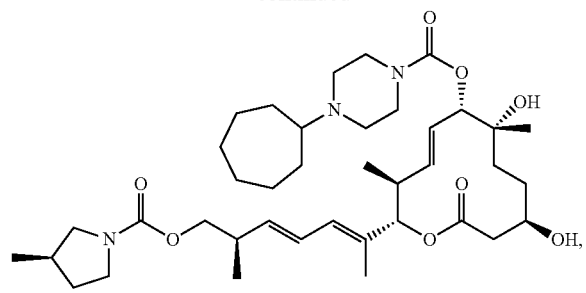
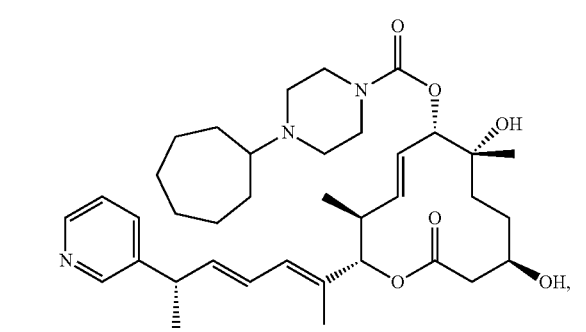
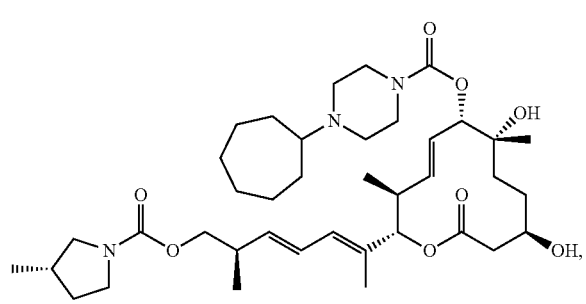
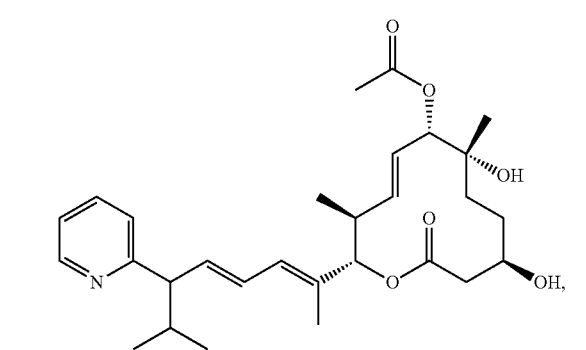
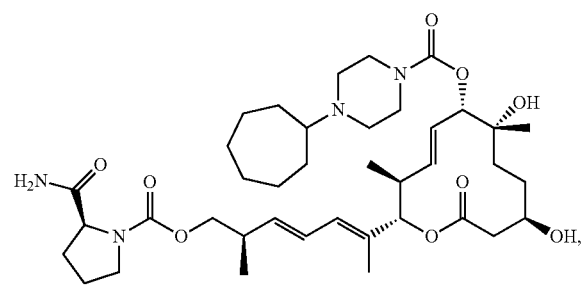
52
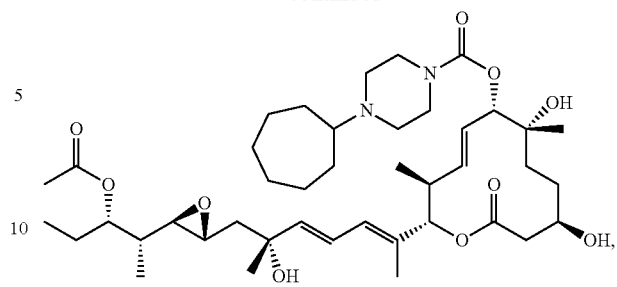
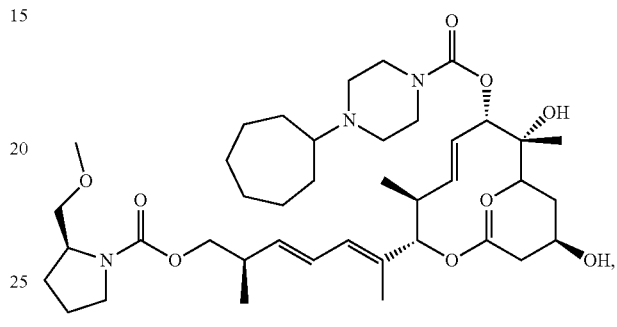
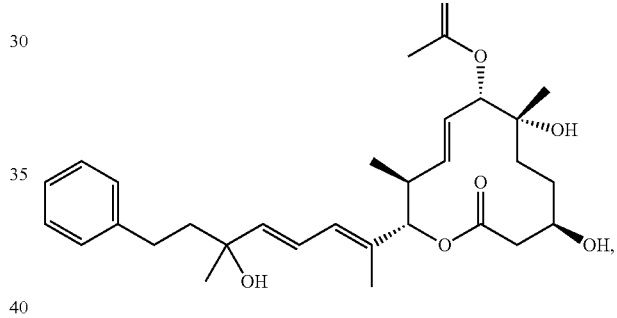
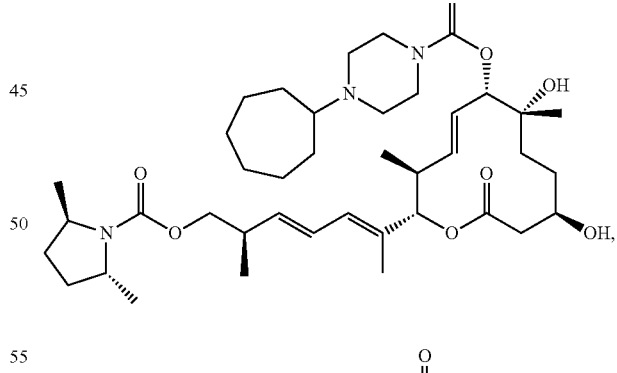
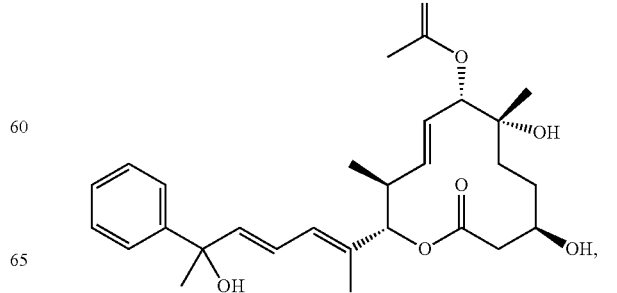

53
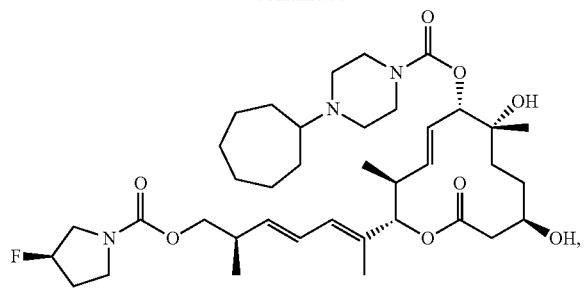
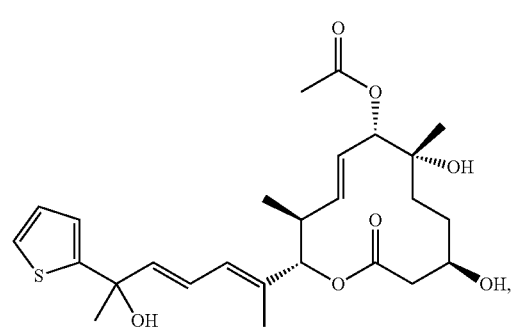
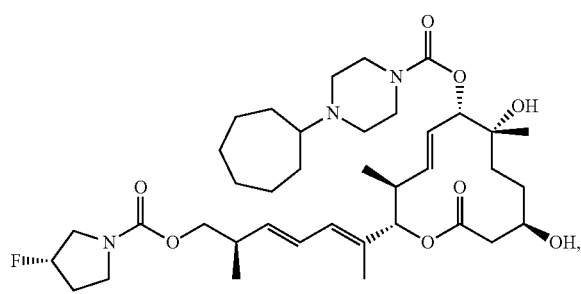
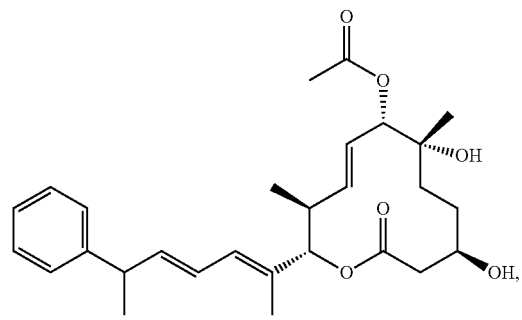
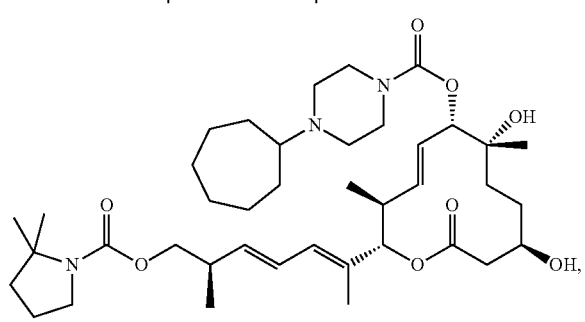
54
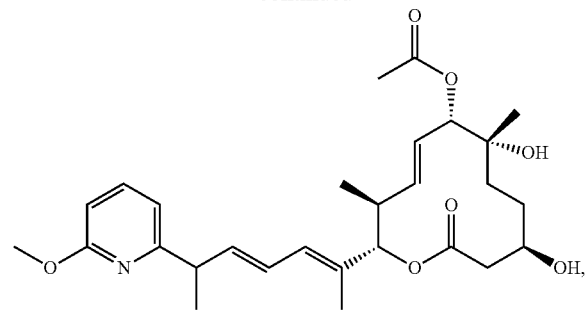
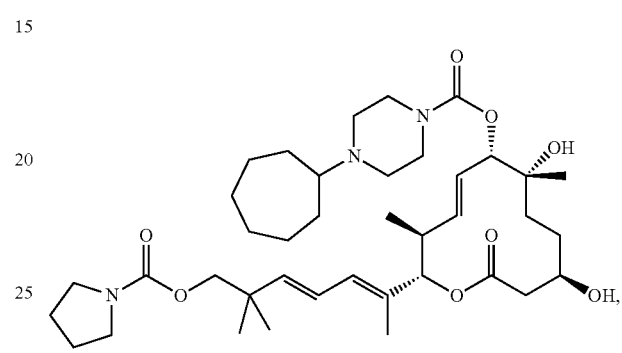
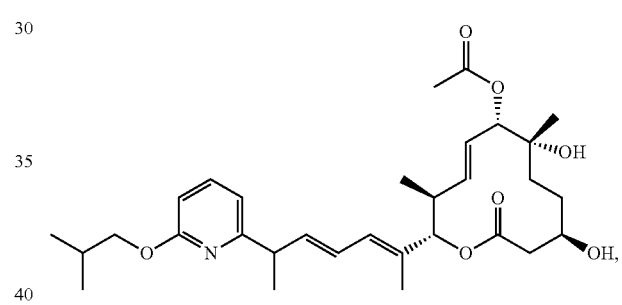
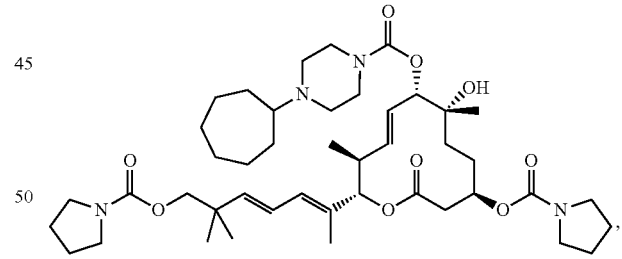
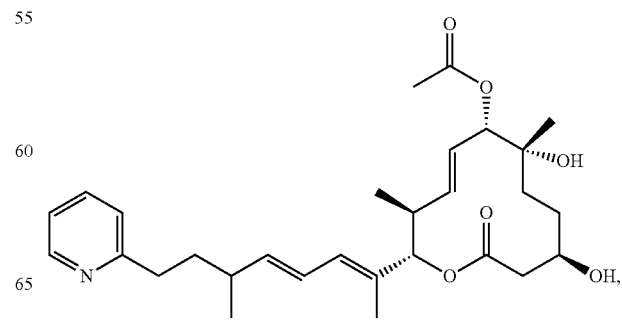

55 -continued
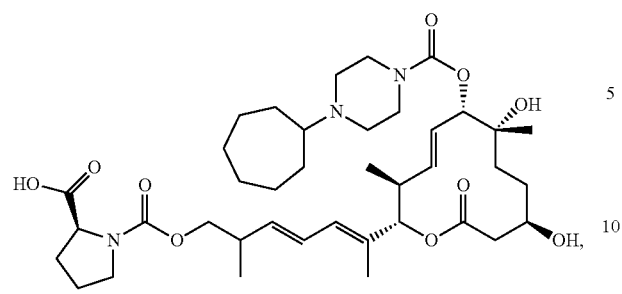
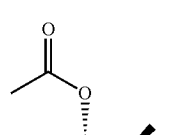
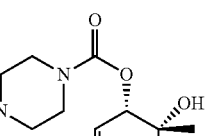
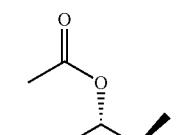
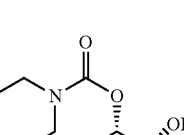
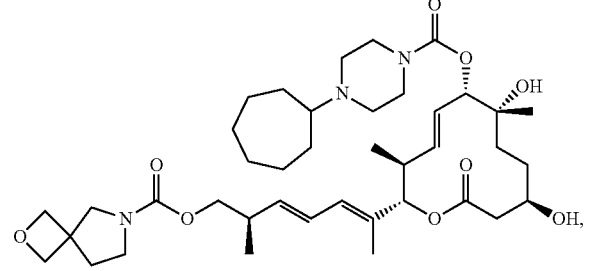
56 -continued
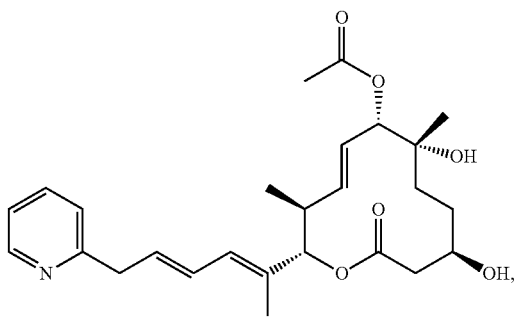
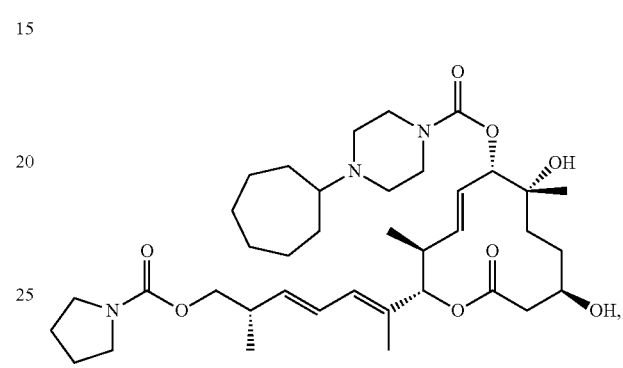
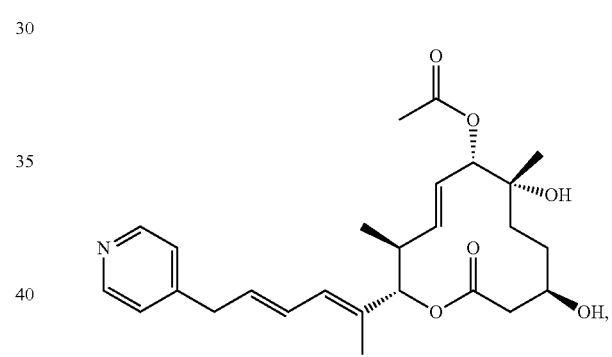
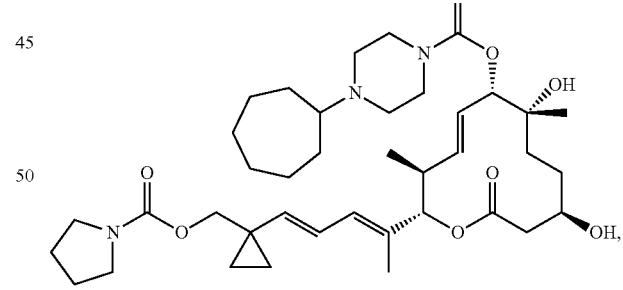
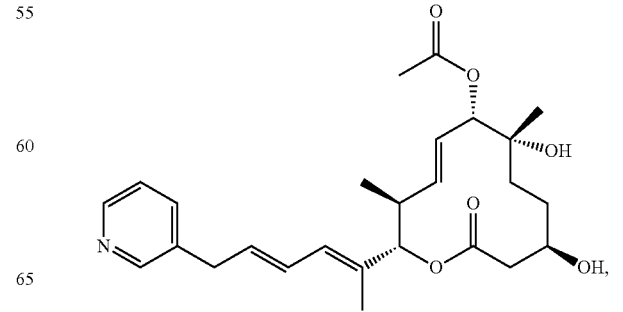
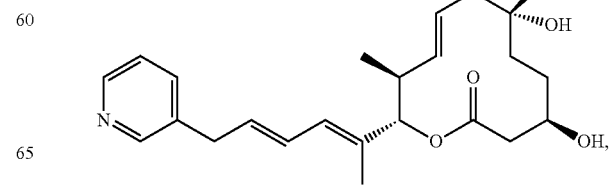

57
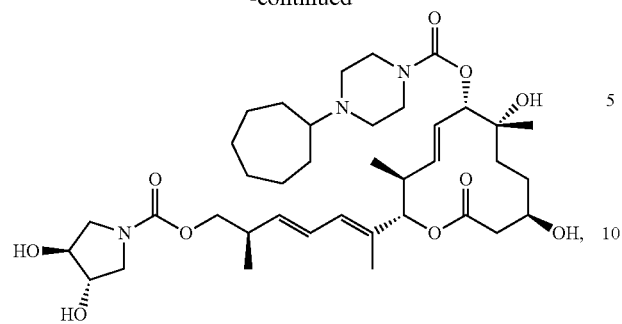
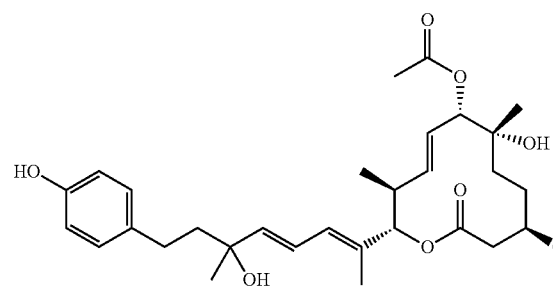
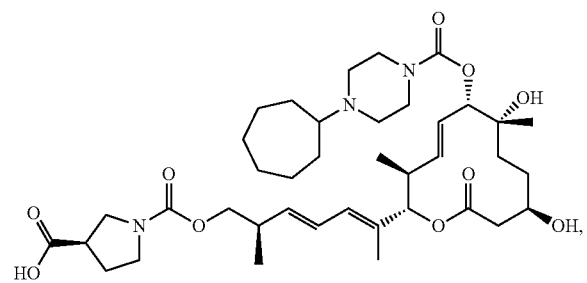
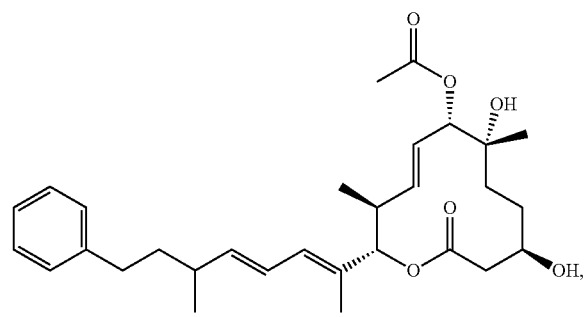
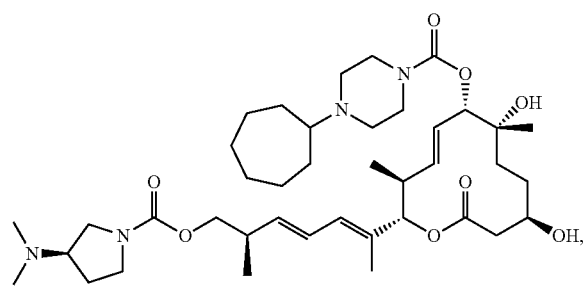
58
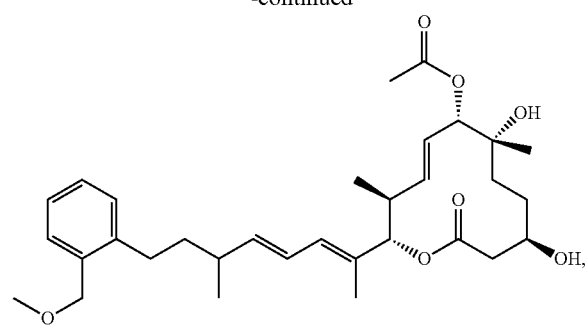
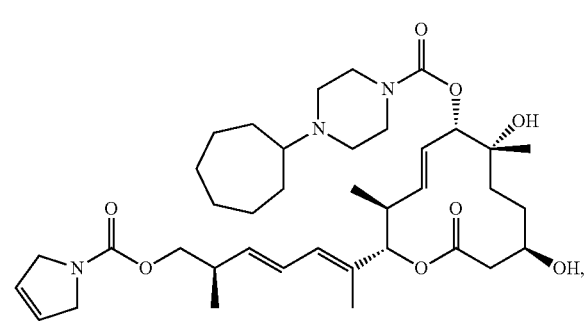
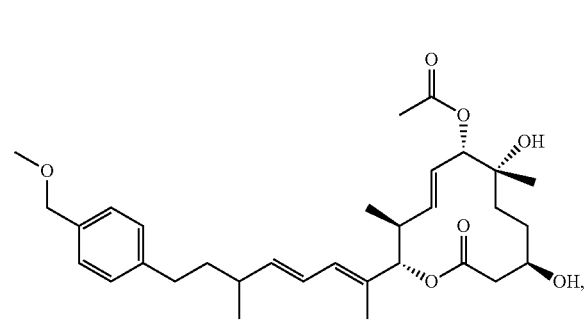
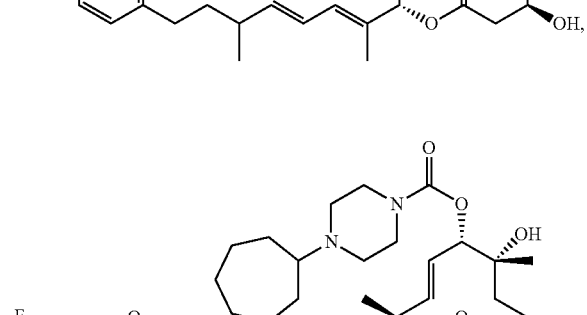
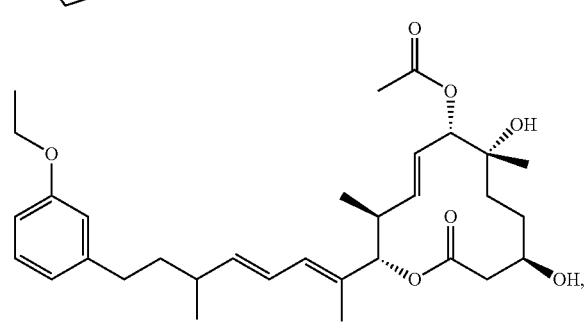

-continued
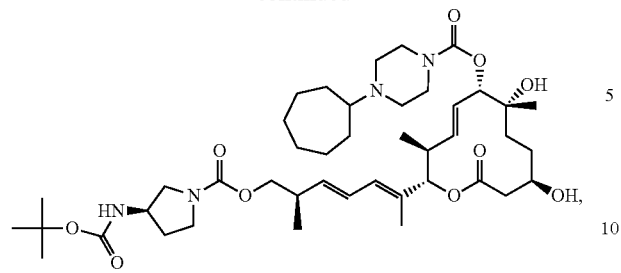
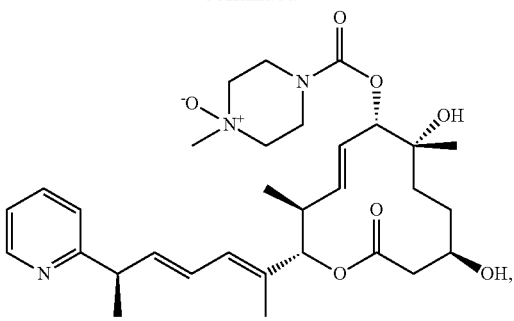
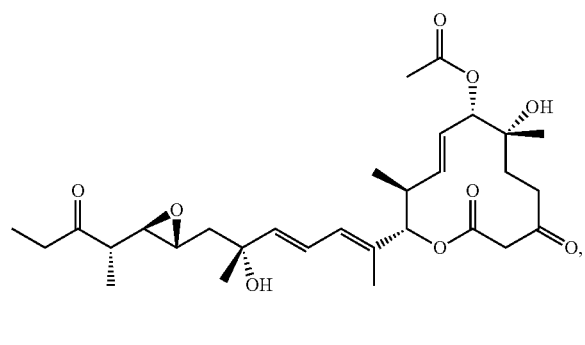
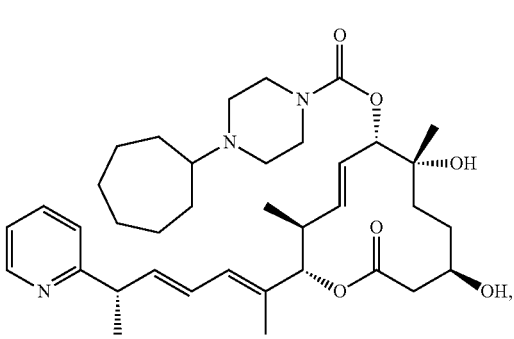
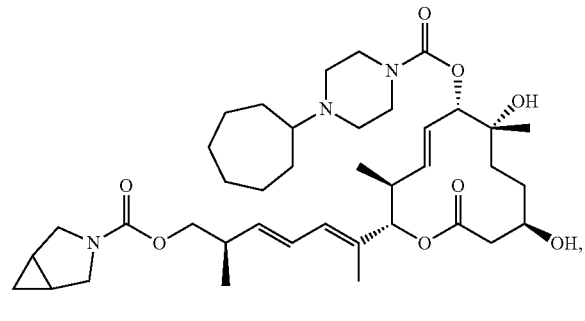
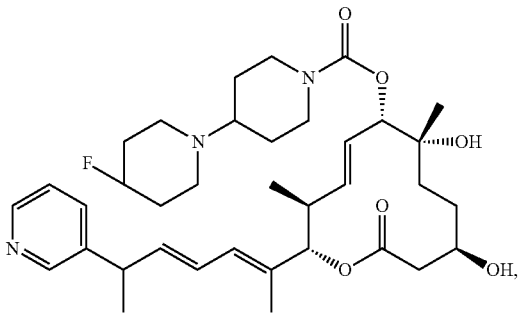
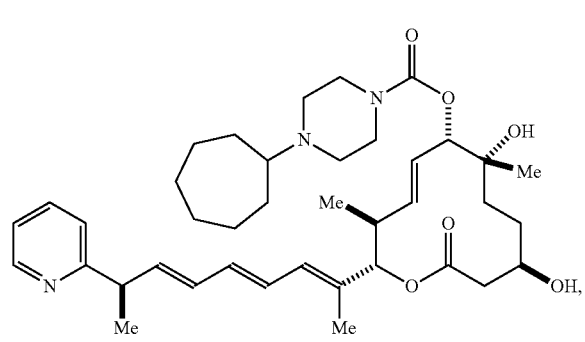
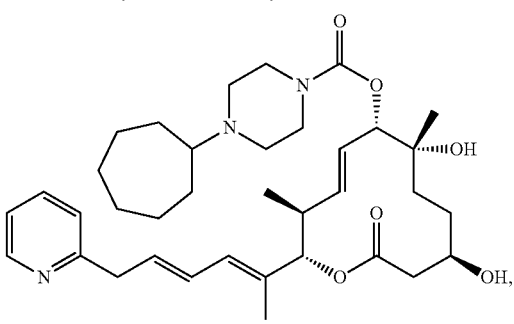
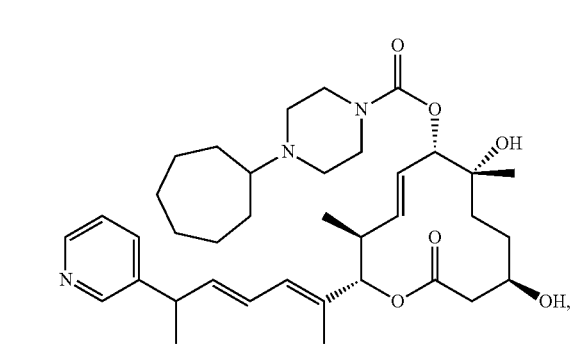
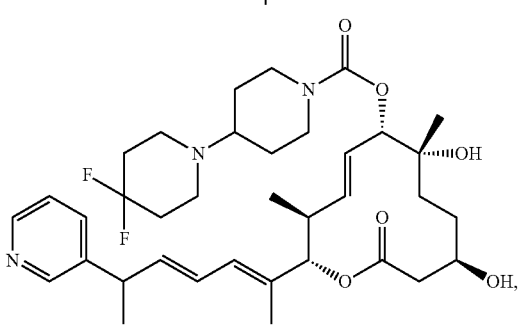

61
-continued
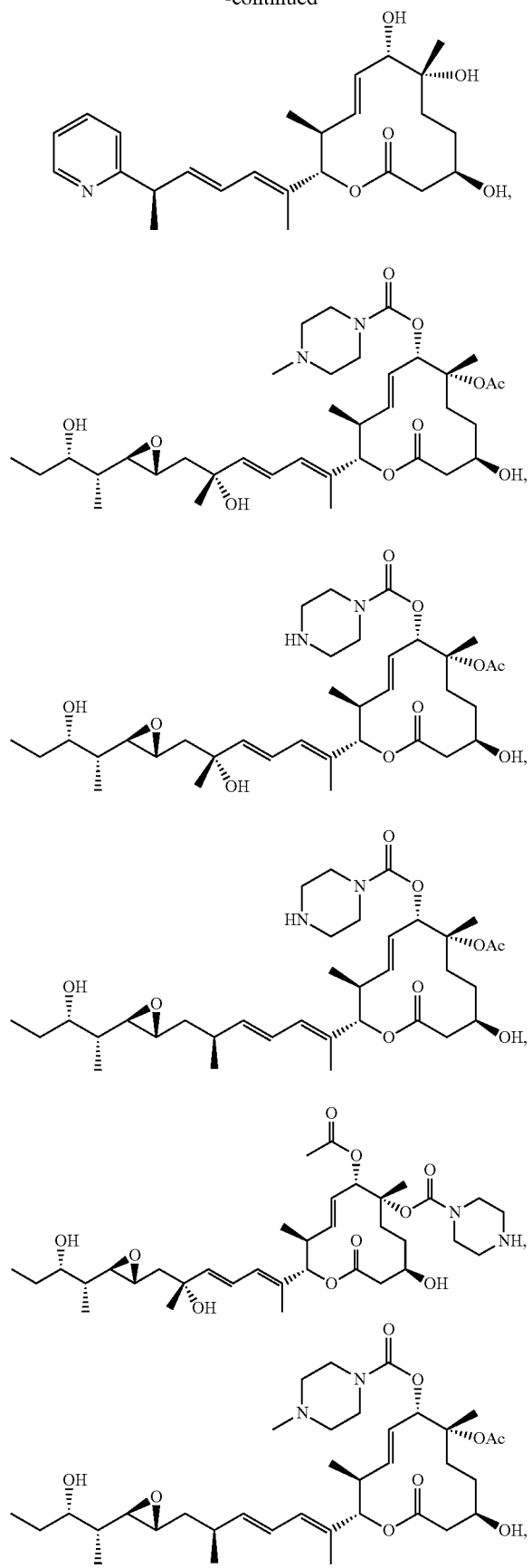
62
-continued
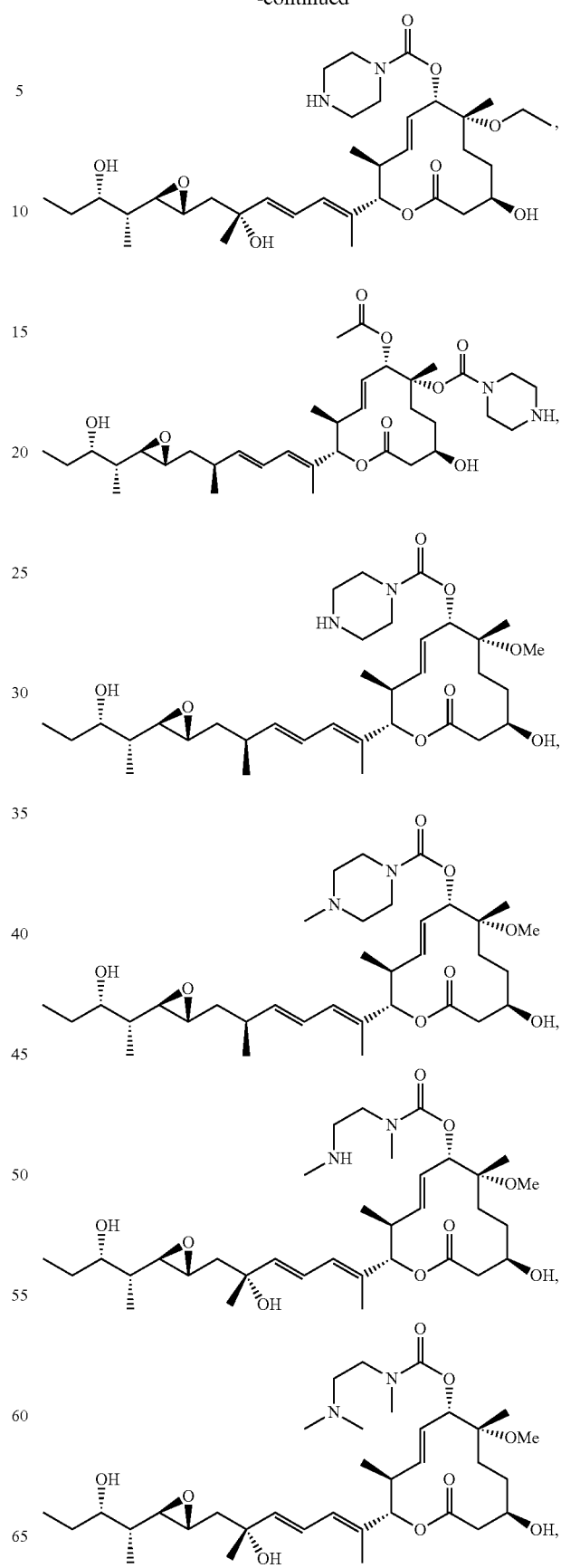

63
-continued

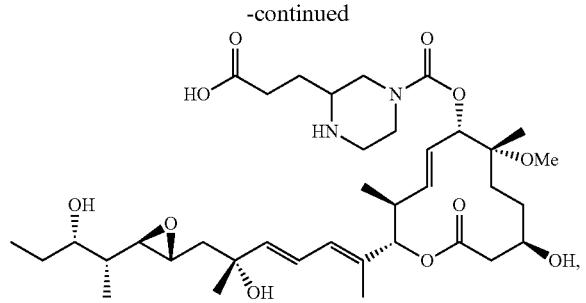

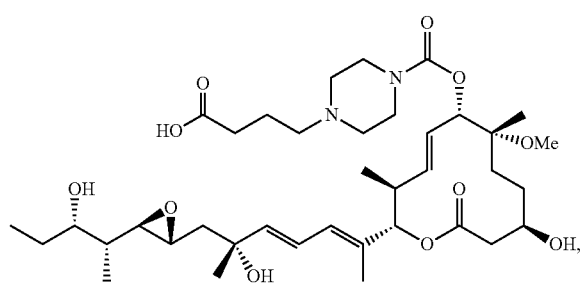

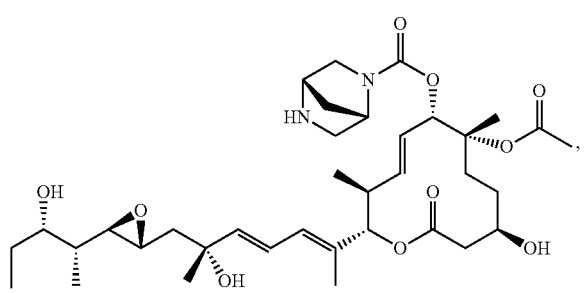

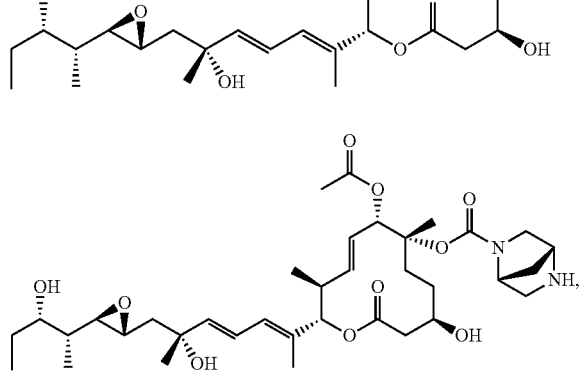

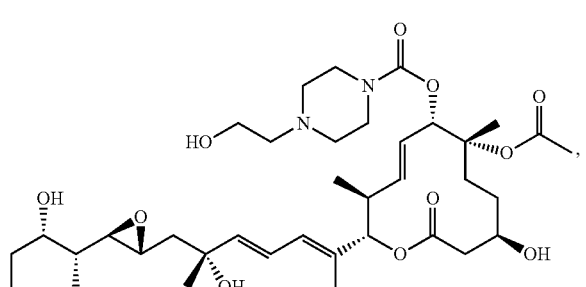

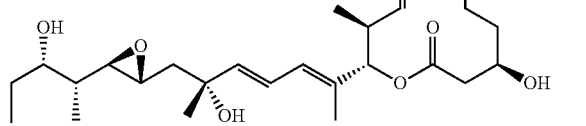

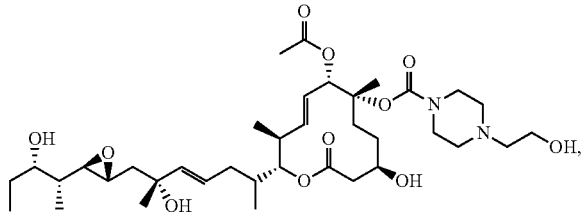

64
-continued

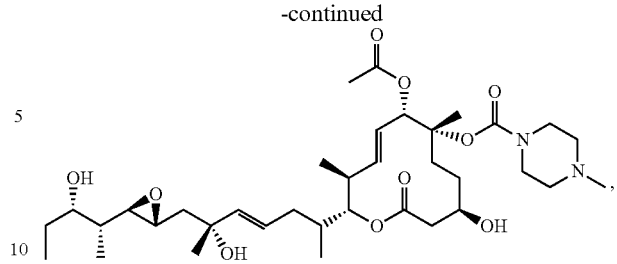

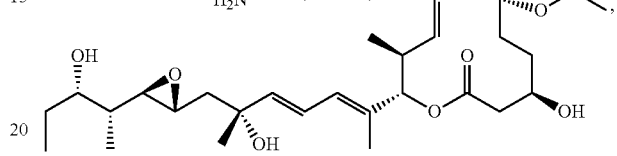

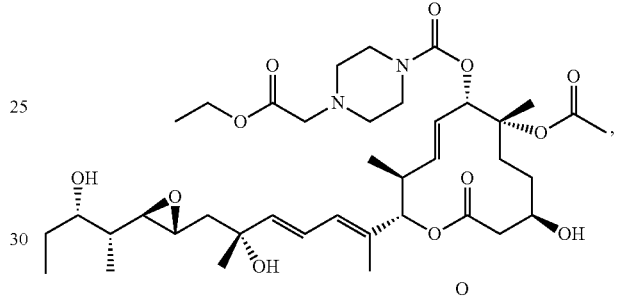

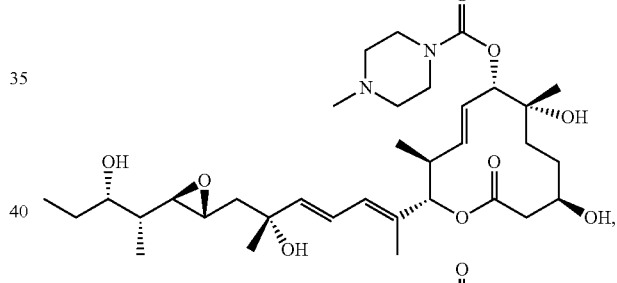

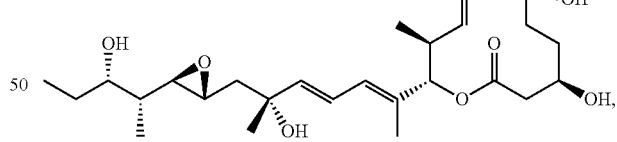

and pharmaceutically acceptable salts thereof.

Also disclosed herein are compounds chosen from:

[(2S,3S,4E,6S,7S,10S)-7,10-dihydroxy-3,7-dimethyl-2-[(2E,4E,6S)-6-methyl-9-oxo-9-pyrrolidin-1-ylona-2,4-dien-2-yl]-12-oxo-1-oxacyclododec-4-en-6-yl]4-methylpiperazine-1-carboxylate;

[(2S,3S,4E,6S,7S,10S)-7,10-dihydroxy-2-[(2E,4E,6S)-7-[[(2R,3R)-3-hydroxypentan-2-yl]carbamoyloxy]-6-methylhepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E,6S)-6-methyl-7-(propylcarbamoyloxy)hepta-2,4-dien-2-yl]-12-oxo-1-oxacyclododec-4-en-6-yl] acetate;

[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclodec-4-en-6-yl] acetate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] pyrrolidine-1-carboxylate;

[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclodec-4-en-6-yl] 4-cycloheptyl-4-oxidopiperazin-4-ium-1-carboxylate;

[(2S,3S,4E,6S,7S,10S)-2-[(2E,4E,6R)-7-(dimethylcarbamoyloxy)-6-methylhepta-2,4-dien-2-yl]-7,10-dihydroxy-3,7-dimethyl-12-oxo-1-oxacyclodec-4-en-6-yl] acetate;

[(2S,3S,4E,6S,7S,10S)-2-[(2E,4E,6S)-7-(diethylcarbamoyloxy)-6-methylhepta-2,4-dien-2-yl]-7,10-dihydroxy-3,7-dimethyl-12-oxo-1-oxacyclodec-4-en-6-yl] acetate;

[(2S,3S,4E,6S,7S,10S)-7,10-dihydroxy-3,7-dimethyl-2-[(2E,4E,6 S)-6-methyl-7-[methyl(propan-2-yl)carbamoyl]oxyhepta-2,4-dien-2-yl]-12-oxo-1-oxacyclodec-4-en-6-yl] acetate;

[(2S,3S,4E,6S,7S,10S)-2-[(2E,4E,6S)-7-[butyl(methyl)carbamoyl]oxy-6-methylhepta-2,4-dien-2-yl]-7,10-dihydroxy-3,7-dimethyl-12-oxo-1-oxacyclodec-4-en-6-yl] acetate;

[(2S,3S,4E,6S,7S,10S)-2-[(2E,4E,6S)-7-[butan-2-yl(methyl)carbamoyl]oxy-6-methylhepta-2,4-dien-2-yl]-7,10-dihydroxy-3,7-dimethyl-12-oxo-1-oxacyclodec-4-en-6-yl] acetate;

[(2S,3S,4E,6S,7S,10S)-2-[(2E,4E,6R)-7-carbamoyloxy-6-methylhepta-2,4-dien-2-yl]-7,10-dihydroxy-3,7-dimethyl-12-oxo-1-oxacyclodec-4-en-6-yl] acetate;

[(2S,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] (2R)-2-(methoxymethyl)pyrrolidine-1-carboxylate;

[(2S,3S,4E,6S,7S,10S)-7,10-dihydroxy-2-[(2E,4E,6S)-7-[2-(methoxyethylmethyl)carbamoyl]oxy-6-methylhepta-2,4-dien-2-yl]-3,7-dimethyl-12-oxo-1-oxacyclodec-4-en-6-yl] acetate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] azetidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] (2S)-2-methylpyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] (2S)-2-methylpyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] piperidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] (2R)-2-(hydroxymethyl)pyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] (3R)-3-hydroxypyrrolidine-1-carboxylate;

[(2R,3E,5E)-6-[(2S,3S,4E,6S,7 S,10S)-6-acetyloxy-7,10-dihydroxy-3,7-dimethyl-12-oxo-1-oxacyclodec-4-en-2-yl]-2-methylhepta-3,5-dienyl] morpholine-4-carboxylate;

[(2R,3E,5E)-6-[(2S,3S,4E,6S,7S,10S)-6-acetyloxy-7,10-dihydroxy-3,7-dimethyl-12-oxo-1-oxacyclodec-4-en-2-yl]-2-methylhepta-3,5-dienyl] 4-methylpiperazine-1-carboxylate; 3-thiazolidinecarboxylic acid [(2R,3E,5E)-6-[(2R,3S,4E,6R,7R,10R)-6-acetyloxy-7,10-dihydroxy-3,7-dimethyl-12-oxo-1-oxacyclodec-4-en-2-yl]-2-methylhepta-3,5-dienyl] ester;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclodec-4-en-6-yl] 4-methylpiperazine-1-carboxylate;

[(2S,3S,4E,6S,7S,10S)-7,10-dihydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclodec-4-en-6-yl] 4-methylpiperazine-1-carboxylate;

[(2S,3S,4E,6S,7S,10S)-7,10-dihydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclodec-4-en-6-yl] 4-methylpiperazine-1-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclodec-4-en-2-yl]-2-methylhepta-3,5-dienyl]1,3-dihydroisoindole-2-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclodec-4-en-2-yl]-2-methylhepta-3,5-dienyl] indole-1-carboxylate;

[(2S,3S,4E,6S,7S,10S)-7,10-dihydroxy-2-[(2E,4E,6S)-7-[2-(1-hydroxyethyl)pyrrolidine-1-carbonyl]oxy-6-methylhepta-2,4-dien-2-yl]-3,7-dimethyl-12-oxo-1-oxacyclodec-4-en-6-yl] 4-methylpiperazine-1-carboxylate;

[(2S,3S,4E,6S,7S,10S)-2-[(2E,4E,6R)-7-(2,2-dimethylpyrrolidine-1-carbonyl)oxy-6-methylhepta-2,4-dien-2-yl]-7,10-dihydroxy-3,7-dimethyl-12-oxo-1-oxacyclodec-4-en-6-yl] 4-methylpiperazine-1-carboxylate;

[(2S,3S,4E,6S,7S,10S)-2-[(2E,4E,6R)-7-[(2S,5S)-2,5-dimethylpyrrolidine-1-carbonyl]oxy-6-methylhepta-2,4-dien-2-yl]-7,10-dihydroxy-3,7-dimethyl-12-oxo-1-oxacyclodec-4-en-6-yl] 4-methylpiperazine-1-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclodec-4-en-2-yl]-2-methylhepta-3,5-dienyl] 2,3-dihydroindole-1-carboxylate;

[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclodec-4-en-6-yl] 4-methylpiperazine-1-carboxylate;

[(2S,3S,4E,6S,7S,10S)-2-[(2E,4E,6R)-7-[(2R)-2-(fluoromethyl)pyrrolidine-1-carbonyl]oxy-6-methylhepta-2,4-dien-2-yl]-7,10-dihydroxy-3,7-dimethyl-12-oxo-1-oxacyclodec-4-en-6-yl] 4-methylpiperazine-1-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclodec-4-en-2-yl]-2-methylhepta-3,5-dienyl] 2-oxa-5-azaspiro[3.4]octane-5-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclodec-4-en-6-yl] acetate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclodec-4-en-6-yl] acetate;

[(2S,3S,4E,6S,7S,10S)-7,10-dihydroxy-2-[(2E,4E)-6-[6-[(2R)-1-hydroxypropan-2-yl]pyridin-2-yl]hepta-2,4-dien-2-yl]-3,7-dimethyl-12-oxo-1-oxacyclodec-4-en-6-yl] acetate;

[(2S,3S,4E,6S,7S,10S)-2-[(2E,4E)-6-[2-(dimethylamino)pyrimidin-4-yl]hepta-2,4-dien-2-yl]-7,10-dihydroxy-3,7-dimethyl-12-oxo-1-oxacyclodec-4-en-6-yl] 4-methylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacydodec-4-en-6-yl] 4-methylpiperazine-1-carboxylate;

[(2S,3S,4E,6S,7S,10S)-7,10-dihydroxy-3,7-dimethyl-12-oxo-2-[(2E,4E)-6-pyridazin-3-ylhepta-2,4-dien-2-yl]-1-oxacydodec-4-en-6-yl] 4-methylpiperazine-1-carboxylate;

[(2S,3S,4E,6S,7S,10S)-7,10-dihydroxy-3,7-dimethyl-12-oxo-2-[(2E,4E)-6-pyrimidin-2-ylhepta-2,4-dien-2-yl]-1-oxacydodec-4-en-6-yl] 4-methylpiperazine-1-carboxylate;

[(2R,3R,4E,6S,7R,10S)-7,10-dihydroxy-3,7-dimethyl-12-oxo-2-[(2E,4E,6R)-6-pyridin-2-ylhepta-2,4-dien-2-yl]-1-oxacyclodec-4-en-6-yl] 4-propan-2-ylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-tert-butylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacydodec-4-en-6-yl] 4-cyclopentylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(oxan-4-yl)piperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 6-cycloheptyl-2,6-diazaspiro[3.3]heptane-2-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacydodec-4-en-6-yl] 4-cycloheptyl-3-methylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cyclobutylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] N-methyl-N-(1-methylpiperidin-4-yl)carbamate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] morpholine-4-carboxylate;

[(2R,3R,4E,6S,7R,10S)-7,10-dihydroxy-3,7-dimethyl-12-oxo-2-[(2E,4E,6R)-6-pyridin-2-ylhepta-2,4-dien-2-yl]-1-oxacyclododec-4-en-6-yl] (1S,4R)-5-methyl-2,5-diazabicyclo[2.2.1]heptane-2-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 8-cycloheptyl-3,8-diazabicyclo[3.2.1]octane-3-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methyl-1,4-diazepane-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cyclohexylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] piperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptyl-1,4-diazepane-1-carboxylate;

[(2S,3S,4E,6S,7S,10S)-7,10-dihydroxy-2-[(2E,4E,6R)-7-hydroxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(azepan-1-yl)piperidine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(8,8-difluoro-3-azabicyclo[3.2.1]octan-3-yl)piperidine-1-carboxylate;

[(2S,3S,4E,6S,7S,10S)-7,10-dihydroxy-3,7-dimethyl-2-[(2E,4E,6S)-6-methyl-9-oxo-9-pyrrolidin-1-ylnona-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10R)-7-hydroxy-3,7-dimethyl-2-[(2E,4E,6R)-6-methyl-7-(pyrrolidine-1-carbonyloxy)hepta-2,4-dien-2-yl]-12-oxo-10-(pyrrolidine-1-carbonyloxy)-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(2S)-2-methylpyrrolidine-1-carbonyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(3R)-3-methylpyrrolidine-1-carbonyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(3R)-3-methylpyrrolidine-1-carbonyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-2-[(2E,4E,6R)-7-[(2R)-2-carbamoylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6S)-7-[(2R)-2-(methoxymethyl)pyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(2S,5S)-2,5-dimethylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(2,2-dimethylpyrrolidine-1-carbonyl)oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6R,7R,10R)-2-[(2E,4E)-6,6-dimethyl-7-(pyrrolidine-1-carbonyloxy)hepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6R,7R,10S)-2-[(2E,4E)-6,6-dimethyl-7-(pyrrolidine-1-carbonyloxy)hepta-2,4-dien-2-yl]-7-hydroxy-3,7-dimethyl-12-oxo-10-(pyrrolidine-1-carbonyloxy)-1-oxacyclododec-4-en-6-yl] 4-cycloheptylpiperazine-1-carboxylate;

(2R)-1-[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-2-en-2-yl]-2-methylhepta-3,5-dienoxy]carbonylpyrrolidine-2-carboxylic acid;

[(2S,3S,4E,6S,7S,10S)-7,10-dihydroxy-3,7-dimethyl-2-[(2E,4E,6R)-6-methyl-7-(3-oxopyrrolidine-1-carbonyl)oxyhepta-2,4-dien-2-yl]-12-oxo-1-oxacyclododec-4-en-6-yl]4-cycloheptylpiperazine-1-carboxylate;

[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-2-en-2-yl]-2-methylhepta-3,5-dienyl]2-oxa-7-azaspiro[3.4]octane-7-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6R,7R,10R)-7,10-dihydroxy-3,7-dimethyl-12-oxo-2-[(2E,4E)-5-[1-(pyrrolidine-1-carbonyloxymethyl)cyclopropyl]penta-2,4-dien-2-yl]-1-oxacyclododec-4-en-6-yl] 4-cycloheptylpiperazine-1-carboxylate;

[(2S,3S,4E,6S,7S,10S)-2-[(2E,4E,6R)-7-[(3S,4R)-3,4-dihydroxypyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

(3S)-1-[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-2-en-2-yl]-2-methylhepta-3,5-dienoxy]carbonylpyrrolidine-3-carboxylic acid;

[(2S,3S,4E,6S,7S,10S)-2-[(2E,4E,6R)-7-[(3S)-3-(dimethylamino)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(2,5-dihydropyrrole-1-carbonyloxy)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(2R)-2-(fluoromethyl)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(3S)-3-[(2-methylpropan-2-yl)oxycarbonylamino]pyrrolidine-1-carbonyl]oxyhepta-2,4-dien-2-yl]-12-oxo-1-oxacyclododec-4-en-6-yl] 4-cycloheptylpiperazine-1-carboxylate;

[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienyl]3-azabicyclo[3.1.0]hexane-3-carboxylate;

[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate;

[(2S,3S,4E,6R,7R,10R)-7,10-dihydroxy-3,7-dimethyl-12-oxo-2-[(2E,4E)-6-pyridin-2-ylhexa-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-(2-pyrrolidin-1-ylpyrimidin-4-yl)hepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyrazin-2-ylhepta-2,4-dien-2-yl]-1-oxacyclododec-4-en-6-yl] 4-cycloheptylpiperazine-1-carboxylate;

[(2S,3S,4E,6S,7S,10S)-2-[(2E,4E)-6-[2-(dimethylamino)pyrimidin-4-yl]hepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(3-methylpyridin-2-yl)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(4-methylpyridin-2-yl)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyrimidin-2-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyridazin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyrimidin-4-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyrimidin-2-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyrimidin-2-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(4-methylpyrimidin-2-yl)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-(6-pyrrolidin-1-ylpyridin-2-yl)hepta-2,4-dien-2-yl]-1-oxacyclododec-4-en-6-yl] 4-cycloheptylpiperazine-1-carboxylate;

[(2S,3S,4E,6R,7R,10S)-10-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6R,7R,10S)-10-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6R,7R,10S)-10-hydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6R,7R,10S)-2-[(2E,4E,6R)-7-[(2R)-2-(fluoromethyl)pyrrolidine-1-carbonyl]oxy-6-methylhepta-2,4-dien-2-yl]-10-hydroxy-3,7-dimethyl-12-oxo-1-oxacyclododec-4-en-6-yl] 4-cycloheptylpiperazine-1-carboxylate;

[(2S,3S,4E,6R,7R,10S)-2-[(2E,4E,6R)-7-[(2R)-2-(fluoromethyl)pyrrolidine-1-carbonyl]oxy-6-methylhepta-2,4-dien-2-yl]-10-hydroxy-3,7-dimethyl-12-oxo-1-oxacyclododec-4-en-6-yl] 4-methylpiperazine-1-carboxylate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] acetate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] N,N-dimethylcarbamate;

[(2S,3S,4E,6R,7R,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] acetate;

[(2S,3S,4E,6R)-3-methyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6R)-3-methyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2R,3E,5E)-6-[(2S,3S,4E,6R)-6-(dimethylcarbamoyloxy)-3-methyl-12-oxo-1-oxacyclododec-4-en-2-yl]-2-methylhepta-3,5-dienyl] pyrrolidine-1-carboxylate;

[(2R,3E,5E)-6-[(2S,3S,4E,6R)-6-(dimethylcarbamoyloxy)-3-methyl-12-oxo-1-oxacyclododec-4-en-2-yl]-2-methylhepta-3,5-dienyl] (3R)-3-hydroxypyrrolidine-1-carboxylate;

[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-oxacyclododec-4-en-6-yl] 4-methylpiperazine-1-carboxylate;

[(2S,3S,4E,6R)-3-methyl-2-[(2E,4E,6R)-6-methyl-7-[(2S)-2-methylpyrrolidine-1-carbonyl]oxyhepta-2,4-dien-2-yl]-12-oxo-1-oxacyclododec-4-en-6-yl] 4-methylpiperazine-1-carboxylate;

[(2S,3S,4E,6R)-2-[(2E,4E,6R)-7-[(2R)-2-(hydroxymethyl)pyrrolidine-1-carbonyl]oxy-6-methylhepta-2,4-dien-2-yl]-3-methyl-12-oxo-1-oxacyclododec-4-en-6-yl] 4-methylpiperazine-1-carboxylate;

[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-oxacyclododec-4-en-6-yl] 4-cycloheptylpiperazine-1-carboxylate;

[(2S,3S,4E,6R)-2-[(2E,4E,6R)-7-[(2R)-2-(hydroxymethyl)pyrrolidine-1-carbonyl]oxy-6-methylhepta-2,4-dien-2-yl]-3-methyl-12-oxo-1-oxacyclododec-4-en-6-yl] 4-(2,2,2-trifluoroethyl)piperazine-1-carboxylate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] acetate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] 4-methylpiperazine-1-carboxylate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] N,N-dimethylcarbamate;

[(2S,3S,4E,6R)-2-[(2E,4E)-6-[2-(dimethylamino)pyrimidin-4-yl]hepta-2,4-dien-2-yl]-3-methyl-12-oxo-1-oxacyclododec-4-en-6-yl] 4-cycloheptylpiperazine-1-carboxylate;

[(2S,3S,4E,6R)-3-methyl-12-oxo-2-[(2E,4E)-6-(2-pyrrolidin-1-ylpyrimidin-4-yl)hepta-2,4-dien-2-yl]-1-oxacyclododec-4-en-6-yl] 4-cycloheptylpiperazine-1-carboxylate;

[(2S,3S,4E,6R)-3-methyl-12-oxo-2-[(2E,4E)-6-[2-[(3S)-3-triethylsilyloxypyrrolidin-1-yl]pyrimidin-4-yl]hepta-2,4-dien-2-yl]-1-oxacyclododec-4-en-6-yl] 4-cycloheptylpiperazine-1-carboxylate;

[(2S,3S,4E,6R)-2-[(2E,4E)-6-[2-[(3R)-3-hydroxypyrrolidin-1-yl]pyrimidin-4-yl]hepta-2,4-dien-2-yl]-3-methyl-12-oxo-1-oxacyclododec-4-en-6-yl] 4-cycloheptylpiperazine-1-carboxylate;

[(2S,3S,4E,6R)-3-methyl-12-oxo-2-[(2E,4E)-6-pyrimidin-2-ylhepta-2,4-dien-2-yl]-1-oxacyclododec-4-en-6-yl] 4-methylpiperazine-1-carboxylate;

[(2S,3S,4E,6S,7S)-7-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6S,7S)-7-hydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S)-7-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S)-7-hydroxy-3,7-dimethyl-2-[(2E,4E,6R)-6-methyl-7-[(3S)-3-(1-phenyltetrazol-5)oxypyrrolidine-1-carbonyl]oxyhepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6S,7S)-7-hydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonylamino)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-[[(2R)-2-(hydroxymethyl)pyrrolidine-1-carbonyl]amino]-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonylamino)hepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-[methyl(pyrrolidine-1-carbonyl)amino]hepta-2,4-dien-2-yl]-12-oxo-1-oxacyclododec-4-en-6-yl] 4-cycloheptylpiperazine-1-carboxylate;

[(2S,3S,4E,6S,7S,10S)-2-[(2E,4E,6R)-7-(4-cyclopropyltriazol-1-yl)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6S)-7-methoxycarbonyloxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-7,10-dihydroxy-2-[(2E,4E,6R)-9-methoxy-6-methyl-9-oxonona-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(cyclopentanecarbonylamino)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(cyclopentanecarbonylamino)-6-methylhepta-2,4-dien-2-yl]-7,10-dihydroxy-3,7-dimethyl-12-oxo-1-oxacyclododec-4-en-6-yl] 4-methylpiperazine-1-carboxylate;

4-cycloheptyl-1-piperazinecarboxylic acid [(2R,3S,4E,6R,7R,10R)-7,10-dihydroxy-3,7-dimethyl-12-oxo-2-[(2E,4E)-7-[oxo(1-pyrrolidinyl)methoxy]hepta-2,4-dien-2-yl]-1-oxacyclododec-4-en-6-yl] ester;

[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-azacyclododec-4-en-6-yl] 4-methylpiperazine-1-carboxylate;

[(2R,3E,5E)-2-methyl-6-[(2S,3S,4E,6R)-3-methyl-6-[(4-methylpiperazine-1-carbonyl)amino]-12-oxo-1-oxacyclododec-4-en-2-yl]hepta-3,5-dienyl] pyrrolidine-1-carboxylate;

[(2S,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R,3R)-3-hydroxy-2-methylpentanoate;

[(2S,3S,4E,6S,7S,10S)-7,10-dihydroxy-2-[(2E,4E,6R)-7-hydroxy-6-methylhepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-12-oxo-2-[(2E,4E)-6-pyridin-4-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-7-methyl-6-pyridin-2-ylocta-2,4-dien-2-yl]-12-oxo-1-oxacyclododec-4-en-6-yl] acetate;

[(2S,3S,4E,6S,7S,10S)-2-[(2E,4E,6S)-7-[(2R,3R)-3-[(2R,3R)-3-acetyloxypentan-2-yl]oxiran-2-yl]-6-hydroxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6R,7R,10R)-7,10-dihydroxy-2-[(2E,4E)-6-hydroxy-6-methyl-8-phenylocta-2,4-dien-2-yl]-3,7-dimethyl-12-oxo-1-oxacyclododec-4-en-6-yl] acetate;

[(2S,3S,4E,6R,7R,10R)-7,10-dihydroxy-2-[(2E,4E)-6-hydroxy-6-phenylhepta-2,4-dien-2-yl]-3,7-dimethyl-12-oxo-1-oxacyclododec-4-en-6-yl] acetate;

[(2S,3S,4E,6R,7R,10R)-7,10-dihydroxy-2-[(2E,4E)-6-hydroxy-6-thiophen-2-ylhepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-12-oxo-2-[(2E,4E)-6-phenylhepta-2,4-dien-2-yl]-1-oxacyclododec-4-en-6-yl] acetate;

[(2S,3S,4E,6S,7S,10S)-7,10-dihydroxy-2-[(2E,4E)-6-(6-methoxypyridin-2-yl)hepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E)-6-[6-(2-methylpropoxy)pyridin-2-yl]hepta-2,4-dien-2-yl]-12-oxo-1-oxacyclododec-4-en-6-yl] acetate;

[(2S,3S,4E,6S,7S,10S)-7,10-dihydroxy-3,7-dimethyl-2-[(2E,4E)-6-methyl-8-pyridin-2-ylocta-2,4-dien-2-yl]-12-oxo-1-oxacyclododec-4-en-6-yl] acetate;

[(2S,3S,4E,6S,7S,10S)-7,10-dihydroxy-3,7-dimethyl-2-[(2E,4E)-6-methyl-7-pyridin-2-ylhepta-2,4-dien-2-yl]-12-oxo-1-oxacyclododec-4-en-6-yl] acetate;

[(2S,3S,4E,6R,7R,10R)-7,10-dihydroxy-2-[(2E,4E,6R)-6-hydroxy-6-methyl-8-phenylocta-2,4-dien-2-yl]-3,7-dimethyl-12-oxo-1-oxacyclododec-4-en-6-yl] acetate;

[(2S,3S,4E,6R,7R,10R)-7,10-dihydroxy-3,7-dimethyl-12-oxo-2-[(2E,4E)-6-pyridin-2-ylhexa-2,4-dien-2-yl]-1-oxacyclododec-4-en-6-yl] acetate;

[(2S,3S,4E,6R,7R,10R)-7,10-dihydroxy-3,7-dimethyl-12-oxo-2-[(2E,4E)-6-pyridin-3-ylhexa-2,4-dien-2-yl]-1-oxacyclododec-4-en-6-yl] acetate;

[(2S,3S,4E,6R,7R,10R)-7,10-dihydroxy-3,7-dimethyl-12-oxo-2-[(2E,4E)-6-pyridin-4-ylhexa-2,4-dien-2-yl]-1-oxacyclododec-4-en-6-yl] acetate;

[(2S,3S,4E,6R,7R,10R)-7,10-dihydroxy-2-[(2E,4E)-6-hydroxy-8-(4-hydroxyphenyl)-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E)-6-methyl-8-phenylocta-2,4-dien-2-yl]-12-oxo-1-oxacyclododec-4-en-6-yl] acetate;

[(2S,3S,4E,6S,7S,10S)-7,10-dihydroxy-2-[(2E,4E)-8-[2-(methoxymethyl)phenyl]-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-2-[(2E,4E)-8-[4-(methoxymethyl)phenyl]-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-2-[(2E,4E)-8-[3-(methoxymethyl)phenyl]-6-methylocta-2,4-dien-2-yl]-3,7-dimethyl-12-oxo-1-oxacyclododec-4-en-6-yl] acetate;

[(2S,3S,4E,6S,7S)-7-hydroxy-2-[(2E,4E,6S)-6-hydroxy-6-methyl-7-[(2R,3R)-3-[(2S)-3-oxopentan-2-yl]oxiran-2-yl]hepta-2,4-dien-2-yl]-3,7-dimethyl-10,12-dioxo-1-oxacyclododec-4-en-6-yl] acetate;

[(2S,3S,4E,6S,7S,10S)-7,10-dihydroxy-3,7-dimethyl-12-oxo-2-[(2E,4E,6E,8S)-8-pyridin-2-ylnona-2,4,6-trien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methyl-4-oxidopiperazin-4-ium-1-carboxylate;

[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-(4-fluoropiperidin-1-yl)piperidine-1-carboxylate;

[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-(4,4-difluoropiperidin-1-yl)piperidine-1-carboxylate;

(4S,7S,8S,9E,11S,12S)-4,7,8-trihydroxy-7,11-dimethyl-12-[(2E,4E,6S)-6-pyridin-2-ylhepta-2,4-dien-2-yl]-1-oxacyclododec-9-en-2-one;

[(2S,3S,4E,6S,7S,10S)-7-acetyloxy-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] piperazine-1-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate;

(2S,3S,6S,7R,10R,E)-7-acetoxy-10-hydroxy-2-((S,2E,4E)-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate;

[(2S,3S,4E,6S,7S,10S)-6-acetyloxy-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-7-yl] piperazine-1-carboxylate;

[(2S,3S,4E,6S,7S,10S)-7-acetyloxy-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] piperazine-1-carboxylate;

[(2S,3S,4E,6S,7R,10R)-7-ethoxy-10-hydroxy-2-[(2E,4E,6R)-6-hydroxy-7-[(2R,3R)-3-[(2S,3S)-3-hydroxypentan-2-yl]oxiran-2-yl]-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-6-acetyloxy-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-7-yl] piperazine-1-carboxylate;

[(2S,3S,4E,6S,7S,10S)-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] piperazine-1-carboxylate;

[(2 S,3S,4E,6S,7S,10S)-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] 4-methylpiperazine-1-carboxylate;

[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] N-methyl-N-[2-(methylamino)ethyl]carbamate;

[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] N-methyl-N-[2-(dimethylamino)ethyl]carbamate;

3-[4-[[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl]oxycarbonyl]piperazin-2-yl]propanoic acid;

4-[4-[[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl]oxycarbonyl]piperazin-1-yl]butanoic acid;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl (1S,4S)-2,5-diazabicyclo[2.2.1]heptane-2-carboxylate;

(2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl 2,5-diazabicyclo[2.2.1]heptane-2-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-propylpiperazine-1-carboxylate;

(2R,3 S,6S,7R,10R,E)-6-acetoxy-10-hydroxy-2-((2S,6R,E)-6-hydroxy-7-((2R,3R)-3-((2R,3S)-3-hydroxypentan-2-yl)oxiran-2-yl)-6-methylhept-4-en-2-yl)-3,7-dimethyl-12-oxooxacyclododec-4-en-7-yl 4-(2-hydroxyethyl)piperazine-1-carboxylate;

(2S,3S,6S,7R,10R,E)-6-acetoxy-10-hydroxy-2-((R,2E,4E)-6-hydroxy-7-((2R,3R)-3-((2R,3S)-3-hydroxypentan-2-yl)

oxiran-2-yl)-6-methylhepta-2,4-dien-2-yl)-3,7-dimethyl-12-oxooxacyclododec-4-en-7-yl 4-methylpiperazine-1-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-ethoxy-2-oxoethyl)piperazine-1-carboxylate;

(2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl4-methylpiperazine-1-carboxylate;

(2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate; and pharmaceutically acceptable salts thereof.

Disclosed herein are compositions comprising at least one compound of the present disclosure (e.g., compounds of Formulas I, II, and III) and/or pharmaceutically acceptable salts thereof and at least one pharmaceutically acceptable carrier. The at least one pharmaceutically acceptable carrier may be chosen according to the particular route of administration for which the composition is intended.

The pharmaceutical compositions of the present disclosure may be formulated for parenteral, oral, inhalation spray, topical, rectal, nasal, buccal, vaginal or implanted reservoir administration, etc. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered intravenously, orally, subcutaneously, or via intramuscular administration. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

Any bland fixed oil may be employed including synthetic mono- or di-glycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms, may also be used for the purposes of formulation.

For oral administration, a compound of the present disclosure (e.g., Formulas I, II, or III) and/or a pharmaceutically acceptable salt thereof may be provided in an acceptable oral dosage form, including, but not limited to, capsules, tablets, aqueous suspensions or solutions. In the case of tablets for oral use, carriers commonly used include lactose and corn starch. Lubricating agents, such as magnesium stearate, may also be added. For oral administration in a capsule form, useful diluents include lactose and dried cornstarch. When aqueous suspensions are required for oral use, the active ingredient may be combined with an emulsifying and/or suspending agent. If desired, certain sweetening, flavoring or coloring agents may also be added.

Compounds and compositions of the present disclosure may be used to treat various types of cancers, including those responsive to agents that target the spliceosome, including SF3B1. As noted above, the anti-tumor activity of pladienolide B is reported as being connected to its targeting of the SF3b complex, inhibiting splicing and altering the pattern of gene expression (Kotake et al., "Splicing factor SF3b as a target of the antitumor natural product pladienolide," Nature Chemical Biology 2007, 3, 570-575). Mutations in the Splicing factor 3B subunit 1 (SF3B1) protein are known to be implicated in a number of cancers, such as hematologic malignancies and solid tumors. Scott et al., "Acquired mutations that affect pre-mRNA splicing in hematologic malignancies and solid tumors," JNCI 105, 20, 1540-1549.

Accordingly, the compounds (e.g., compounds of Formulas I, II, and III and pharmaceutically acceptable salts of the foregoing) and compositions of the present disclosure may be used to treat hematological malignancies, such as, for example, cancers of the blood (leukemia) and cancers of the lymph nodes (lymphomas). Leukemias include acute lymphoblastic leukemia (ALL), acute myleogenous leukemia (AML), chronic lymphocytic leukemia (CLL), chronic myelogenous leukemia (CML), chronic myelomonocytic leukemia (CMML), acute monocytic leukemia (AMoL), etc. Lymphomas include Hodgkin's lymphoma and non-Hodgkin's lymphoma. Other hematologic malignancies may include myelodysplastic syndrome (MDS).

Solid tumors include carcinomas such as adenocarcinoma, e.g., breast cancer, pancreatic cancer, prostate cancer, colon or colorectal cancer, lung cancer, gastric cancer, cervical cancer, endometrial cancer, ovarian cancer, cholangiocarcinoma, glioma, melanoma, etc.

The compounds (e.g., compounds of Formulas I, II, and III) and pharmaceutically acceptable salts thereof and compositions of the present disclosure may also be used to treat cancers that may be responsive to agents that target a spliceosome gene or protein other than SF3B1. The following are non-limiting examples of cancers responsive to agents that target the spliceosome. Thus, compounds of the present disclosure may be administered to subjects to treat a variety of such cancers or conditions, particularly patients or subjects afflicted with:

a) Myelodysplastic syndrome (MDS): See, e.g., "SF3B1 mutations in myelodysplastic syndromes: clinical associations and prognostic implications," Damm F. et al. Leukemia, 2011, 1-4; "Frequent pathway mutations in splicing machinery in myelodysplasia," Yoshida K. et al, Nature, 2011, 478, 64-69; "Clinical significance of SF3B1 mutations in myelodysplastic syndromes and myelodysplastic/myeloproliferative neoplasms," Malcovati L. et al., Blood, 2011, 118, 24, 6239-6246; "Mutations in the spliceosome machinery, a novel and ubiquitous pathway in leukemogenesis," Makishima et al, Blood, 2012, 119, 3203-3210; "Somatic SF3B1 mutation in myelodysplasia with ring sideroblasts," Pappaemannuil, E. et al, New England J. Med. 2011, DOI 10.1056/NEJMoa1103283.

b) Chronic lymphocytic leukemia (CLL): See, e.g., "Defects in the spliceosomal machinery: a new pathway of leukaemogenesis," Maciejewski, J. P., Padgett, R. A., Br. J. Haematology, 2012, 1-9; "Mutations in the SF3B1 splicing factor in chronic lymphocytic leukemia: associations with progression and fludarabine-refractoriness," Rossi et al, Blood, 2011, 118, 6904-6908; "Exome sequencing identifies recurrent mutations of the splicing factor SF3B1 gene in chronic lymphocytic leukemia," Quesada et al, Nature Genetics, 2011, 44, 47-52.

c) Chronic myelomonocytic leukemia (CMML): See, e.g., Yoshida et al, Nature 2011; "Spliceosomal gene mutations are frequent events in the diverse mutational spectrum of chronic myelomonocytic leukemia but largely absent in juvenile myelomonocytic leukemia," Kar S. A. et al, Haematologia, 2012, DOI: 10.3324/haematol.2012.064048.

d) Acute myeloid leukemia (AML): See, e.g., Malcovati et al., Blood 2011; Yoshida et al, Nature 2011.

e) Breast cancer: See, e.g., "Whole genome analysis informs breast cancer response to aromatase inhibition," Ellis et al, Nature, 2012, 486, 353-360.

f) Uveal melanoma: See, e.g., "SF3B1 mutations are associated with alternative splicing in uveal melanoma", Furney et al, Cancer Disc. 2013, 10, 1122-1129.

g) Endometrial cancer: See, e.g., Tefferi et al., "Myelodysplastic syndromes." N Engl J Med. 2009; 361:1872-85.

h) Gastric cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

i) Ovarian cancer: See, e.g., Int J Cancer. 2013 July; 133(1):260-5, "Mutational analysis of splicing machinery genes SF3B1, U2AF1 and SRSF2 in myelodysplasia and other common tumors." Je et al.

j) Biliary Tract cancers such as Cholangiocarcinoma and Pancreatic cancer: See, e.g., Biankin et al., "Pancreatic cancer genomes reveal aberrations in axon guidance pathway genes," Nature 2012, 491, 399-405.

k) Lung cancer: See, e.g., "Exome sequencing identifies recurrent mutations of the splicing factor SF3B1 gene in chronic lymphocytic leukemia," Quesada et al., Nature Genetics 44, 47-52 (2012); Scott et al., "Acquired mutations that affect pre-mRNA splicing in hematologic malignancies and solid tumors," JNCI 105, 20, 1540-1549.

In addition, the Catalogue of somatic mutations in cancer (COSMIC) (Wellcome Trust Sanger Institute, Genome Research Limited, England) reports SF3B1 mutations have been found in various types of cancer samples.

A compound of the present disclosure (e.g., a compound of Formulas I, II, or III) may be administered to a subject in a treatment effective or therapeutically effective amount. The amount of a compound of the present disclosure that may be combined with a carrier material to produce a composition in a single dosage form will vary depending upon the subject treated and the particular route of administration. In some embodiments, a dose of 0.01 mg/kg-100 mg/kg body weight/day of the at least one compound disclosed herein is administered. In some embodiments, the dose is from from 0.01 mg to 50 mg of the at least one compound disclosed herein. In some embodiments, 0.1 mg to 25 mg of the at least one compound disclosed herein is provided. In some embodiments, 5 mg to 40 mg of the at least compound disclosed herein is provided.

One of ordinary skill will understand that a specific dosage and treatment regimen for a particular patient will depend upon a variety of factors, including the activity of the specific compound employed, the age, body weight, general health, sex, diet, time of administration, rate of excretion, drug combination, the judgment of the treating physician, and the severity of the particular disease being treated. The amount of the the at least one compound disclosed herein will also depend upon the particular compound/salt being used.

In some embodiments, the cancer is tested for and/or is positive for one or more mutations in the Splicing factor 3B subunit 1 (SF3B1) gene or protein, wherein the presence of the mutation(s) ("positive") indicates the subject's cancer is responsive to a method of treatment comprising administration of the at least one compound disclosed herein targeting this protein and/or the spliceosome. Examples of such spliceosome genes include, but are not limited to, those presented in Table 1

TABLE 1

Spliceosome genes and potential diseases affected

| Spliceosome gene | Disease(s) |
|---|---|
| Splicing factor 3B subunit 1 (SF3B1) | see listings above |
| U2 small nuclear RNA auxiliary factor 1 (U2AF1) | MDS, AML, CMML, LUAD, UCEC |
| | CMML, MDS, PMF, AML |
| Serine/arginine-rich splicing factor 2 (SRSF2) | MDS |
| Zinc finger (CCCH type), RNA-binding motif and serine/arginine rich 2 (ZRSR2) | Retinitis Pigmentosa |
| Pre-mRNA-processing-splicing factor 8 (PRPF8) | Myeloid neoplasms |
| U2 Small Nuclear RNA Auxiliary Factor 2 (U2AF2) | MDS, PRAD, COAD |
| Splicing Factor 1 (SF1) | myeloid neoplasms, OV, COAD |
| Splicing factor 3a subunit 1 (SF3A1) | MDS |
| PRP40 pre-mRNA processing factor 40 homolog B (PRPF40B) | LUAD |
| RNA Binding Motif Protein 10 (RBM10) | COAD |
| Poly(rC) binding protein 1 (PCBP1) | SKCM |
| Crooked neck pre-mRNA splicing factor 1 (CRNKL1) | LUSC |
| DEAH (Asp-Glu-Ala-His) box helicase 9 (DHX9) | STAD |
| Peptidyl-prolyl cis-trans isomerase-like 2 (PPIL2) | SKCM |
| RNA binding motif protein 22 (RBM22) | LUAD |
| Small nuclear ribonucleoprotein Sm D3 (SNRPD3) | GBM, LGG |
| Probable ATP-dependent RNA helicase DDX5 (DDX5) | LUAD |
| Pre-mRNA-splicing factor ATP-dependent RNA helicase DHX15 (DHX15) | DLBCL |
| Polyadenylate-binding protein 1 (PABPC1) | myeloid neoplasms |

Key:
MDS = Myelodysplastic syndrome
AML = Acute Myeloid Leukemia
CMML = chronic myelomonocytic leukemia
LUAD = Lung adenocarcinoma
UCEC = Uterine Corpus Endometrial Carcinoma
PMF = Progressive Massive Fibrosis
PRAD = Prostate adenocarcinoma
COAD = Colon adenocarcinoma
OV = Ovarian serous cystadenocarcinoma
SKCM = Skin Cutaneous Melanoma
LUSC = Lung squamous cell carcinoma
STAD = Stomach adenocarcinoma
GBM = Glioblastoma multiforme
LGG = Brain Lower Grade Glioma
DLBCL = Diffuse Large B-Cell Lymphoma In some embodiments, the subject's cancer may be responsive to a method of treatment comprising administration of a compound targeting this protein and/or the spliceosome even in the absence of such mutations in a spliceosome gene or protein.

Screening or testing for the mutations may be carried out by any known means, for example, genotyping, phenotyping, etc., by way of nucleic acid amplification, electrophoresis, microarrays, blot, functional assays, immunoassays, etc. Methods of screening may include, for example, collecting a biological sample from said subject containing the cancerous cells/tissue.

In some embodiments, a subject having cancer as described herein can be treated with at least one compound chosen from compounds of Formula I, compounds of Formula II, compounds of Formula III, and pharmaceutically acceptable salts of any of the foregoing, and at least one additional therapy.

In some embodiments, the at least one additional therapy comprises a cytokine or cytokine analog therapy, e.g., any cytokine or cytokine analog therapy disclosed herein. Cytokines are a broad category of small proteins shown to be involved in autocrine signaling, paracrine signaling, and/or endocrine signaling as immunomodulating agents. Exemplary cytokines are disclosed herein, and include chemokines, interferons, interleukins, lymphokines, and tumor necrosis factors. As used herein, the term "cytokine" refers to a polypeptide secreted from a cell that influences the function of other cells to mediate an immune response, and the term "cytokine therapy" refers to the administration and/or induction of secretion of such a peptide. In some embodiments, the cytokine is a recombinant cytokine or an analog thereof. In some embodiments, the cytokine is a cytokine analog. The terms "cytokine analog" and "cytokine analog therapy" refer to a modified cytokine, wherein one or more amino acid residues of a native cytokine have been substituted with other natural or unnatural amino acid residues and/or wherein one or more natural or unnatural amino acid residues have been added to a native cytokine. In some embodiments, a cytokine or cytokine analog therapy comprises administering at least one cytokine or cytokine analog to a patient in need of such treatment.

In some embodiments, the at least one additional therapy comprises one or more engineered tumor-targeting T-cells (e.g., CAR-T or other cell-based therapy), e.g., any CAR-T therapy disclosed herein. The terms "CAR-T" and "CAR-T therapy" are used interchangeably to refer to a CAR-modified cell or cell population (e.g., a T-cell or T-cell population). In some embodiments, a chimeric T-cell receptor (CAR) can be engineered using antigen recognition sequences such that when the CAR is expressed on a cell (e.g., a T-cell), the CAR and/or cell is reactive with the target antigen. For instance, in some embodiments, a CAR may be engineered by first identifying antibodies that recognize a cell-surface expressed antigen protein domain. The antigen recognition sequences of such antibodies can then be fused to a T-cell receptor domain for selective targeting and activation. In some embodiments, the CAR sequences are cloned into patient-derived T-cell populations and expanded using currently available protocols. In some embodiments, the engineered T-cells are then transfused back into the patient's circulation, before, simultaneously with, or following treatment with at least one compound chosen from compounds of Formula I, compounds of Formula II, compounds of Formula III, and pharmaceutically acceptable salts of any of the foregoing. After treatment with the at least one compound and/or pharmaceutically acceptable salt, in some embodiments, the tumor cells may begin to present an antigen, e.g., an antigen targeted by the engineered T-cell population. In some embodiments, the engineered T-cell population can engage with and kill antigen presenting tumor cells.

In some embodiments, the at least one additional therapy comprises a checkpoint inhibitor therapy, e.g., any checkpoint inhibitor therapy disclosed herein. Immune checkpoints are inhibitory pathways that slow down or stop immune reactions and prevent excessive tissue damage from uncontrolled activity of immune cells. As used herein, the terms "checkpoint inhibitor" and "checkpoint inhibitor therapy" are used interchangeably to refer to any therapeutic agent, including any small molecule chemical compound, antibody, nucleic acid molecule, or polypeptide, or any fragments thereof, that inhibits one or more of the inhibitory pathways, thereby allowing more extensive immune activity. In some embodiments, a checkpoint inhibitor therapy comprises administering at least one checkpoint inhibitor to a patient in need of such treatment.

In some embodiments, the at least one additional therapy comprises a neoantigen vaccine. In some embodiments, treatment comprises administering at least one compound chosen from compounds of Formula I, compounds of Formula II, compounds of Formula III, and pharmaceutically acceptable salts of any of the foregoing and administering a neoantigen vaccine. In some embodiments, the neoantigen vaccine comprises a tumor neoantigen and/or a neoantigen induced by the at least one compound chosen from compounds of Formula I, compounds of Formula II, compounds of Formula III, and pharmaceutically acceptable salts of any of the foregoing. In some embodiments, treatment further comprises administering a checkpoint inhibitor therapy. In some embodiments, the checkpoint inhibitor therapy is targeted at PD1/PDL1, CTLA4, OX40, CD40, LAG3, TIM3, GITR, and/or MR. In some embodiments, the checkpoint inhibitor therapy is targeted at PD1/PDL1 (e.g., an anti-PD1 antibody or an anti-PDL1 antibody). In some embodiments, the checkpoint inhibitor therapy is targeted at CTLA4 (e.g., an anti-CTLA4 antibody). In some embodiments, treatment comprises administering a combination therapy comprising a neoantigen vaccine after first (i) administering at least one compound chosen from compounds of Formula I, compounds of Formula II, compounds of Formula III, and pharmaceutically acceptable salts of any of the foregoing; and (ii) detecting the presence of a neoantigen (e.g., a neoantigen from the neoantigen vaccine). In some embodiments, neoantigen expression is monitored during the course of treatment. In some embodiments, treatment is discontinued if neoantigens are not detected.

Also disclosed herein, in some embodiments, are methods of treating a patient by inducing neoantigens in tumor cells that can be targeted by the patient's immune system for clearance. Without being bound by theory, in some embodiments, administering at least one compound chosen from compounds of Formula I, compounds of Formula II, compounds of Formula III, and pharmaceutically acceptable salts of any of the foregoing, may produce neoantigens that induce an immune response, induce a double-stranded RNA immune response, e.g., as a result of re-expressed intron-resident endogenous retroviruses, and/or produce neoantigens that induce immunogenic cell death.

As used herein, the term "neoantigen" refers to any antigen to which the immune system has not previously been exposed that arises from one or more tumor-specific mutations and/or from exposing a tumor to at least one compound chosen from at least one compound chosen from compounds of Formula I, compounds of Formula II, compounds of Formula III, and pharmaceutically acceptable salts of any of the foregoing. Tumor-specific mutations can include missense mutations, frameshifts, translocations, and mRNA splicing variants, as well as mutations that influence post-translational processing, such as phosphorylation and glycosylation. These exemplary mutations, in some embodiments, can be derived from non-synonymous coding changes and/or mutations that alter mRNA processing (e.g., splicing). All of these exemplary mutations, in some embodiments, can result in molecular changes that can be discriminated by an appropriate T-cell receptor. In some embodiments, an exemplary neoantigen is a neoantigen induced by delivery of at least one compound chosen from compounds of Formula I, compounds of Formula II, compounds of Formula III, and pharmaceutically acceptable salts of any of the foregoing. In some embodiments, delivery of at least one compound chosen from compounds of Formula I, compounds of Formula II, compounds of Formula III, and pharmaceutically acceptable salts of any of the foregoing can induce novel mRNA splicing that results in the translation of proteins containing one or more novel peptide domains to which the immune system has not previously been exposed. In some embodiments, tumor-specific mutations may be mRNA splicing variants resulting from delivery or administration of at least one compound chosen from compounds of Formula I, compounds of Formula II, compounds of Formula III, and pharmaceutically acceptable salts of any of the foregoing.

Without being bound by theory, in some embodiments, the delivery of at least one compound chosen from compounds of Formula I, compounds of Formula II, compounds of Formula III, and pharmaceutically acceptable salts of any of the foregoing may induce novel mRNA splicing (e.g., exon skipping, intron retention) that results in the alteration of the open reading frames and/or coding sequences of various genes. In some embodiments, these altered genes are translated into proteins containing one or more novel peptide domains recognized by the immune system as foreign. In some embodiments, the one or more novel peptide domains do not exist in the proteins or in any other part of the human proteome in the absence of compound treatment. In some embodiments, the proteins containing the one or more novel peptide domains can be degraded by the proteasome to create novel peptide fragments that act as substrates for the immunopeptide presentation machinery, e.g., via MHC presentation. In some embodiments, the novel peptide fragments representing neoantigens can be presented in the MHC1-bound peptidome, e.g., on tumor cells.

In some embodiments, the delivery of at least one compound chosen from compounds of Formula I, compounds of Formula II, compounds of Formula III, and pharmaceutically acceptable salts of any of the foregoing may lead to one or more tumor cell-intrinsic events (e.g., cell growth arrest). In some embodiments, the tumor cell-intrinsic event(s) may lead to (1) enhanced engagement by phagocytic cells (Bracci et al. (2014) Cell Death Differ. 21(1):15-25); (2) the transport of novel peptide fragments to a tumor draining lymph node to engage with antigen-presenting cells; (3) antigen-presenting cells processing novel peptide fragments from a phagocytosed tumor cell and presenting the fragments as neoantigens to circulating naïve T-cell populations; (4) novel peptide fragments interacting with T-cells expressing receptors that recognize the fragments as neoantigens; (5) maturation and activation of effector T-cell responses (e.g., CD4+ and/or CD8+ T-cells; and/or (6) engagement of T-cells with additional tumor cells exposed to the compound treatment and presenting novel peptide fragments representing neoantigens on their surface MHC1 complexes. In some embodiments, the tumor cell-intrinsic event(s) may result, either directly or indirectly, in T-cell engagement of effector function and/or killing of neoantigen-presenting tumor cells.

Also, without being bound by theory, in some embodiments, the delivery of at least one compound chosen from compounds of Formula I, compounds of Formula II, compounds of Formula III, and pharmaceutically acceptable salts of any of the foregoing may cause the re-expression of intron-resident endogenous retroviruses, leading to a double-stranded RNA immune response.

Further, without being bound by theory, in some embodiments, the delivery of at least one compound chosen from compounds of Formula I, compounds of Formula II, compounds of Formula III, and pharmaceutically acceptable salts of any of the foregoing may lead to immunogenic cell death triggered by compound-induced release of mutationally-derived neoantigens. In some embodiments, the delivery of at least one compound chosen from compounds of Formula I, compounds of Formula II, compounds of Formula III, and pharmaceutically acceptable salts of any of the foregoing may induce a double-stranded RNA immune response. In some embodiments, the double-stranded RNA immune response can result from the re-expression of intron-resident endogenous retroviruses. In some embodiments, the double-stranded RNA immune response can result in tumor cell death. In some embodiments, the delivery of at least one compound chosen from compounds of Formula I, compounds of Formula II, compounds of Formula III, and pharmaceutically acceptable salts of any of the foregoing may induce immunogenic cell death. In some embodiments, the immunogenic cell death can result from release of mutational-derived neoantigens and/or a host immune response against tumor cells.

Accordingly, in some embodiments, methods of treatment are disclosed comprising inducing neoantigens by administering at least one compound chosen from compounds of Formula I, compounds of Formula II, compounds of Formula III, and pharmaceutically acceptable salts of any of the foregoing. In some embodiments, the method comprises administering a reduced dosage of the at least one compound chosen from compounds of Formula I, compounds of Formula II, compounds of Formula III, and pharmaceutically acceptable salts of any of the foregoing than would be needed absent the induction of neoantigens. In some embodiments, the method comprises administering one or more initial induction doses to produce neoantigens and induce an immune response (e.g., converting naïve T-cells to memory cells), followed by a reduced dosage or administration frequency (i.e., because of the combinatorial effect of the at least one compound chosen from compounds of Formula I, compounds of Formula II, compounds of Formula III, and pharmaceutically acceptable salts of any of the foregoing and of immune targeting of the neoantigens). In some embodiments, treatment can comprise a combination of administering the at least one compound chosen from compounds of Formula I, compounds of Formula II, compounds of Formula III, and pharmaceutically acceptable salts of any of the foregoing to induce a neoantigen-based immune response and at least one additional therapy (e.g., a second anti-cancer therapy). For example, in some embodiments, treatment can comprise a combination of administering the at least one compound chosen from compounds of Formula I, compounds of Formula II, compounds of Formula III, and pharmaceutically acceptable salts of any of the foregoing to induce a neoantigen-based immune response and one or more checkpoint inhibitors. In some embodiments, treatment can comprise a combination of administering the at least one compound chosen from compounds of Formula I, compounds of Formula II, compounds of Formula III, and pharmaceutically acceptable salts of any of the foregoing to induce a neoantigen-based immune response and one or more cytokines or cytokine analogs. In some embodiments, treatment can comprise a combination of administering the at least one compound chosen from compounds of Formula I, compounds of Formula II, compounds of Formula III, and pharmaceutically acceptable salts of any of the foregoing to induce a neoantigen-based immune response and one or more neoantigen vaccines. In some other embodiments, treatment can comprise a combination of administering the at least one compound chosen from compounds of Formula I, compounds of Formula II, compounds of Formula III, and pharmaceutically acceptable salts of any of the foregoing to induce a neoantigen-based immune response and one or more engineered tumor-targeting T-cells (e.g., CAR-T).

In some embodiments, neoantigens can be used to monitor the effectiveness of treatment with at least one compound chosen from compounds of Formula I, compounds of Formula II, compounds of Formula III, and pharmaceutically acceptable salts of any of the foregoing. For instance, after administration of at least one compound chosen from compounds of Formula I, compounds of Formula II, compounds of Formula III, and pharmaceutically acceptable salts of any of the foregoing, a patient sample (e.g., a tumor biopsy) can be obtained and screened for neoantigens or for identifiers of an immune or inflammatory response. Further treatment can be provided, e.g., at reduced dosage, if a neoantigen and/or immune response is detected.

In some embodiments, methods of treatment are disclosed comprising inducing a double-stranded RNA immune response by administering at least one compound chosen from compounds of Formula I, compounds of Formula II, compounds of Formula III, and pharmaceutically acceptable salts of any of the foregoing.

In some embodiments, methods of treatment are disclosed comprising inducing immunogenic cell death by administering at least one compound chosen from compounds of Formula I, compounds of Formula II, compounds of Formula III, and pharmaceutically acceptable salts of any of the foregoing.

In some embodiments, administration of at least one compound chosen from compounds of Formula I, compounds of Formula II, compounds of Formula III, and pharmaceutically acceptable salts of any of the foregoing can be combined with any known anti-cancer therapy. Examples of current immune activating strategies available for oncology treatment include, but are not limited to, treatment with immune checkpoint inhibitor (ICI) molecules, treatment with cytokines or cytokine analogs, vaccination with tumor-associated vaccines, and engineering tumor-targeting T-cells (e.g., expansion of tumor-infiltrating lymphocytes or CAR-T). These technologies are predominantly focused on enhancing or inducing an immune response to already existing tumor antigens (either mutations or aberrant expression of cell-surface proteins). One or more of these strategies may involve one or more mutations that are capable of inducing an antigenic T-cell response. For example, patient responses to checkpoint inhibition may correlate with non-synonymous mutational burden. In addition, cancer vaccine approaches may be used that rely on pre-existing mutations and the antigenicity of these mutations.

Compounds of Formula I, compounds of Formula II, compounds of Formula III, and pharmaceutically acceptable salts of any of the foregoing may induce broad-ranging changes in the transcriptome that occur in multiple lineages. Translation of these mRNA changes may produce robust and reproducible protein changes that produce MHC1-bound neopeptides with high affinity across multiple HLA isotypes. Without being bound by theory, due to the large number of changes to the transcriptome and proteome, treatment with at least one compound chosen from compounds of Formula I, compounds of Formula II, compounds of Formula III, and pharmaceutically acceptable salts of any of the foregoing may enrich the number of potentially reactive neoantigens for enhanced engagement of the adaptive immune response.

In some embodiments, the present disclosure provides a method of inducing at least one neoantigen by contacting a neoplastic cell with a therapeutically effective amount of at least one compound chosen from compounds of Formula I, compounds of Formula II, compounds of Formula III, and pharmaceutically acceptable salts of any of the foregoing. In some embodiments, the present disclosure provides a method of inducing a double-stranded RNA immune response by contacting a neoplastic cell with a therapeutically effective amount of at least one compound chosen from compounds of Formula I, compounds of Formula II, compounds of Formula III, and pharmaceutically acceptable salts of any of the foregoing. In some embodiments, the present disclosure provides a method of inducing immunogenic cell death by contacting a neoplastic cell with a therapeutically effective amount of at least one compound chosen from compounds of Formula I, compounds of Formula II, compounds of Formula III, and pharmaceutically acceptable salts of any of the foregoing.

In some embodiments, the neoplastic cell is present in an in vitro cell culture. In some embodiments, the neoplastic cell is obtained from a subject. In some embodiments, the neoplastic cell is present in a subject. In some embodiments, the neoplastic cell is derived from a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer (e.g., HER2-positive breast cancer), gastric cancer (e.g., gastric adenocarcinoma), prostate cancer, ovarian cancer, lung cancer (e.g., lung adenocarcinoma), uterine cancer (e.g., uterine serous endometrial carcinoma), salivary duct carcinoma, melanoma, colon cancer, and esophageal cancer. In some embodiments, the solid tumor is chosen from HER2-positive breast cancer, gastric adenocarcinoma, and prostate cancer.

In some embodiments, the present disclosure further provides a method of inducing at least one neoantigen and/or a T-cell response in a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing. Also provided herein, in some embodiments, is a method of treating a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing, wherein administration of the at least one compound chosen from compounds of Formula I, compounds of Formula II, compounds of Formula III, and pharmaceutically acceptable salts of any of the foregoing induces at least one neoantigen and/or a T-cell response.

In various other embodiments, the present disclosure provides a method of inducing a double-stranded RNA immune response in a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing. Also provided herein, in some embodiments, is a method of treating a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing, wherein administration of the at least one compound chosen from compounds of Formula I, compounds of Formula II, compounds of Formula III, and pharmaceutically acceptable salts of any of the foregoing induces a double-stranded RNA immune response.

In still other embodiments, the present disclosure provides a method of inducing immunogenic cell death in a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing. Further provided herein, in some embodiments, is a method of treating a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing comprising at least one compound chosen from compounds of Formula I, compounds of Formula II, compounds of Formula III, and pharmaceutically acceptable salts of any of the foregoing, wherein administration of the at least one compound chosen from compounds of Formula I, compounds of Formula II, compounds of Formula III, and pharmaceutically acceptable salts of any of the foregoing induces immunogenic cell death.

In some embodiments, the present disclosure further provides a method of treating a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing, wherein administration of the at least one compound chosen from compounds of Formula I, compounds of Formula II, compounds of Formula III, and pharmaceutically acceptable salts of any of the foregoing induces immunogenic cell death, in combination with one or more additional therapies comprising a second agent.

In some embodiments of the therapeutic methods described herein, the amount of the at least one compound chosen from compounds of Formula I, compounds of Formula II, compounds of Formula III, and pharmaceutically acceptable salts of any of the foregoing, or second agent administered is reduced due to induction of at least one neoantigen and/or a T-cell response, as compared to a standard dosage of the at least one compound chosen from compounds of Formula I, compounds of Formula II, compounds of Formula III, and pharmaceutically acceptable salts of any of the foregoing, or second agent. In some embodiments, the administered amount of the at least one compound chosen from compounds of Formula I, compounds of Formula II, compounds of Formula III, and pharmaceutically acceptable salts of any of the foregoing, or second agent is reduced by 10%, 15%, 20%, 25%, 30%, 35%, 40%, 45%, 50%, 75%, or 90%, as compared to a standard dosage of the at least one compound chosen from compounds of Formula I, compounds of Formula II, compounds of Formula III, and pharmaceutically acceptable salts of any of the foregoing, or second agent. In some embodiments, the at least one compound chosen from compounds of Formula I, compounds of Formula II, compounds of Formula III, and pharmaceutically acceptable salts of any of the foregoing, or second agent is administered at least 10%, 15%, 20%, 25%, 30%, 35%, 40%, 45%, 50%, 75%, or 90% less frequently, as compared to a standard dosing regimen of the at least one compound chosen from compounds of Formula I, compounds of Formula II, compounds of Formula III, and pharmaceutically acceptable salts of any of the foregoing, or second agent. In some embodiments, the administered amount and/or dosage of the at least one compound chosen from compounds of Formula I, compounds of Formula II, compounds of Formula III, and pharmaceutically acceptable salts of any of the foregoing, or second agent results in lower systemic toxicity and/or improved tolerance.

As used herein, the term "standard dosage" or "standard dosing regimen" refers to any usual or routine dosing regimen for a therapeutic agent, e.g., a regimen proposed by the manufacturer, approved by regulatory authorities, or otherwise tested in human subjects to meet the average patient's needs. In some embodiments, the therapeutic agent is at least one compound chosen from compounds of Formula I, compounds of Formula II, compounds of Formula III, and pharmaceutically acceptable salts of any of the foregoing with anti-cancer activity.

For instance, a standard dosing regimen for trastuzumab, an exemplary anti-HER2 antibody, may be 8 mg/kg administered intravenously over 90 min (week 1) followed by 6 mg/kg administered intravenously over 30-90 min every 3 weeks (week 4 through the end of the therapy cycle) (Herceptin® (trastuzumab) FDA Label Supplement, 2017).

As another example, a standard dosing regimen for ipilimumab, an exemplary anti-CTLA4 checkpoint inhibitor antibody, may be 3 mg/kg administered intravenously over 90 min every 3 weeks for 4 doses (Yervoy® (ipilimumab) FDA Label Supplement, 2018). Another standard dosing regimen for ipilimumab may be 10 mg/kg administered intravenously over 90 min every 3 weeks for 4 doses, followed by 10 mg/kg every 12 weeks for up to 3 years (Yervoy® (ipilimumab) FDA Label Supplement, 2018).

As another example, a standard dosing regimen for nivolumab, an exemplary anti-PD1 checkpoint inhibitor antibody, may be 3 mg/kg administered intravenously over 60 min every 2 weeks (Opdivo® (nivolumab) FDA Label, 2015).

As another example, a standard dosing regimen for atezolizumab, an exemplary anti-PDL1 checkpoint inhibitor antibody, may be 1200 mg administered intravenously over 60 min every 3 weeks (Tecentriq® (atezolizumab) FDA Label Supplement, 2018).

As yet another example, a standard dosing regimen for T-DM1, an exemplary anti-HER2 antibody-drug conjugate, may be 3.6 mg/kg administered intravenously over 90 min every 3 weeks (Kadcyla® (T-DM1) FDA Label Supplement, 2016).

In some embodiments, the methods described herein may further comprise administering at least one additional therapy (e.g., a checkpoint inhibitor, a neoantigen vaccine, a cytokine or cytokine analog, CAR-T, etc.). In some embodiments, the amount of the at least one compound chosen from compounds of Formula I, compounds of Formula II, compounds of Formula III, and pharmaceutically acceptable salts of any of the foregoing, and/or the at least one additional therapy administered is reduced due to induction of at least one neoantigen and/or a T-cell response, as compared to a standard dosage of the at least one compound chosen from compounds of Formula I, compounds of Formula II, compounds of Formula III, and pharmaceutically acceptable salts of any of the foregoing, and/or the at least one additional therapy. In some embodiments, the amount of the at least one compound chosen from compounds of Formula I, compounds of Formula II, compounds of Formula III, and pharmaceutically acceptable salts of any of the foregoing, and/or the at least one additional therapy administered is reduced due to induction of a double-stranded RNA immune response, as compared to a standard dosage of the at least one compound chosen from compounds of Formula I, compounds of Formula II, compounds of Formula III, and pharmaceutically acceptable salts of any of the foregoing, and/or the at least one additional therapy. In some embodiments, the amount of the at least one compound chosen from compounds of Formula I, compounds of Formula II, compounds of Formula III, and pharmaceutically acceptable salts of any of the foregoing, and/or the at least one additional therapy administered is reduced due to induction of immunogenic cell death, as compared to a standard dosage of the at least one compound chosen from at least one compound chosen from compounds of Formula I, compounds of Formula II, compounds of Formula III, and pharmaceutically acceptable salts of any of the foregoing, and/or the at least one additional therapy. In some embodiments, the administered amount of the at least one compound chosen from compounds of Formula I, compounds of Formula II, compounds of Formula III, and pharmaceutically acceptable salts of any of the foregoing, and/or the at least one additional therapy is reduced by 10%, 15%, 20%, 25%, 30%, 35%, 40%, 45%, 50%, 75%, or 90%, as compared to a standard dosage of the at least one compound chosen from compounds of Formula I, compounds of Formula II, compounds of Formula III, and pharmaceutically acceptable salts of any of the foregoing, and/or the at least one additional therapy. In some embodiments, the at least one compound chosen from compounds of Formula I, compounds of Formula II, compounds of Formula III, and pharmaceutically acceptable salts of any of the foregoing, and/or the at least one additional therapy is administered at least 10%, 15%, 20%, 25%, 30%, 35%, 40%, 45%, 50%, 75%, or 90% less frequently, as compared to a standard dosing regimen of the at least one compound chosen from compounds of Formula I, compounds of Formula II, compounds of Formula III, and pharmaceutically acceptable salts of any of the foregoing, and/or the at least one additional therapy. In some embodiments, the administered amount and/or dosage of the at least one compound chosen from compounds of Formula I, compounds of Formula II, compounds of Formula III, and pharmaceutically acceptable salts of any of the foregoing, and/or the at least one additional therapy results in lower systemic toxicity and/or improved tolerance.

In some embodiments, administration of the at least one compound chosen from compounds of Formula I, compounds of Formula II, compounds of Formula III, and pharmaceutically acceptable salts of any of the foregoing is initiated before administration of the at least one additional therapy. In other embodiments, administration of the at least one compound chosen from compounds of Formula I, compounds of Formula II, compounds of Formula III, and pharmaceutically acceptable salts of any of the foregoing is initiated after administration of the at least one additional therapy. In still other embodiments, administration of the at least one compound chosen from compounds of Formula I, compounds of Formula II, compounds of Formula III, and pharmaceutically acceptable salts of any of the foregoing is initiated concurrently with administration of the at least one additional therapy.

In some embodiments, administration of the at least one compound chosen from compounds of Formula I, compounds of Formula II, compounds of Formula III, and pharmaceutically acceptable salts of any of the foregoing is repeated at least once after initial administration. In some embodiments, the amount of the at least one compound chosen from compounds of Formula I, compounds of Formula II, compounds of Formula III, and pharmaceutically acceptable salts of any of the foregoing used for repeated administration is reduced as compared to the amount used for initial administration. In some embodiments, the amount of the at least one compound chosen from compounds of Formula I, compounds of Formula II, compounds of Formula III, and pharmaceutically acceptable salts of any of the foregoing used for repeated administration is reduced as compared to a standard dosage of the at least one compound chosen from compounds of Formula I, compounds of Formula II, compounds of Formula III, and pharmaceutically acceptable salts of any of the foregoing. In some embodiments, the amount of the at least one compound chosen from compounds of Formula I, compounds of Formula II, compounds of Formula III, and pharmaceutically acceptable salts of any of the foregoing used for repeated administration is reduced by 10%, 15%, 20%, 25%, 30%, 35%, 40%, 45%, 50%, 75%, or 90%, as compared to a standard dosage or initial dosage of the at least one compound chosen from compounds of Formula I, compounds of Formula II, compounds of Formula III, and pharmaceutically acceptable salts of any of the foregoing.

In some embodiments, administration of the at least one additional therapy is repeated at least once after initial administration. In some embodiments, the amount of the at least one additional therapy used for repeated administration is reduced as compared to the amount used for initial administration. In some embodiments, the amount of the at least one additional therapy used for repeated administration is reduced as compared to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, as compared to a standard dosage or initial dosage of the at least one additional therapy.

In some embodiments, repeated administration of the at least one compound chosen from compounds of Formula I, compounds of Formula II, compounds of Formula III, and pharmaceutically acceptable salts of any of the foregoing is concurrent with repeated administration of the at least one additional therapy. In some embodiments, administration of the at least one compound chosen from compounds of Formula I, compounds of Formula II, compounds of Formula III, and pharmaceutically acceptable salts of any of the foregoing is sequential or staggered with repeated administration of the at least one additional therapy.

In some embodiments, the at least one additional therapy comprises administering a checkpoint inhibitor, e.g., any checkpoint inhibitor disclosed herein. In some embodiments, the subject is intolerant, non-responsive, or poorly responsive to the checkpoint inhibitor when administered alone. In some embodiments, the checkpoint inhibitor is targeted at PD1/PDL1, CTLA4, OX40, CD40, LAG3, TIM3, GITR, and/or MR. In some embodiments, the checkpoint inhibitor is targeted at CTLA4, OX40, CD40, and/or GITR. In some embodiments, the checkpoint inhibitor is an antibody having inhibitory or agonist activity to its target. In some embodiments, a checkpoint inhibitor is targeted with an inhibitory antibody or other similar inhibitory molecule. In other embodiments, a checkpoint inhibitor is targeted with an agonist antibody or other similar agonist molecule.

In some other embodiments, the at least one additional therapy comprises administering a neoantigen vaccine, e.g., any neoantigen vaccine disclosed herein. In some embodiments, the at least one compound chosen from compounds of Formula I, compounds of Formula II, compounds of Formula III, and pharmaceutically acceptable salts of any of the foregoing is administered before administration of the neoantigen vaccine. In some embodiments, the at least one compound chosen from compounds of Formula I, compounds of Formula II, compounds of Formula III, and pharmaceutically acceptable salts of any of the foregoing is administered after administration of the neoantigen vaccine. In some embodiments, the at least one compound chosen from compounds of Formula I, compounds of Formula II, compounds of Formula III, and pharmaceutically acceptable salts of any of the foregoing is administered concurrently with administration of the neoantigen vaccine. In some embodiments, administration of the at least one compound chosen from compounds of Formula I, compounds of Formula II, compounds of Formula III, and pharmaceutically acceptable salts of any of the foregoing is repeated at least once after initial administration. In some embodiments, the amount of the at least one compound chosen from compounds of Formula I, compounds of Formula II, compounds of Formula III, and pharmaceutically acceptable salts of any of the foregoing used for repeated administration is reduced as compared to the amount used for initial administration.

In some embodiments, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length. In some embodiments, the at least one neoantigen peptide comprises one or more than one neoantigen sequence.

In some embodiments, the neoantigen sequence and/or antigenic portion ranges from about 10 to about 50 amino acids in length. In some embodiments, the at least one neoantigen peptide ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 13).

The term "antigenic portion" or "antigenic fragment" of a neoantigen sequence, as used herein, refers to one or more fragments of a neoantigen sequence that retain the ability to induce a T-cell response (e.g., antigen-specific expansion and/or maturation of effector T-cell population(s)). An antigenic portion, in some embodiments, may also retain the ability to be internalized, processed, and/or presented by antigen-presenting cells (e.g., dendritic cells). In some embodiments, an antigenic portion also retains T-cell priming function. In some embodiments, an antigenic portion of a neoantigen sequence ranges from about 10 to about 50 amino acids in length. In some embodiments, an antigenic portion of a neoantigen sequence ranges from about 10 to about 35 amino acids in length. In some embodiments, an antigenic portion of a neoantigen sequence ranges from about 15 to about 25 amino acids in length. In some embodiments, an antigenic portion of a neoantigen sequence ranges from about 10 to about 20 amino acids in length. In some embodiments, an antigenic portion of a neoantigen sequence (e.g., an antigenic portion of any one of SEQ ID NOs: 30-57), or its encoding mRNA, is formulated as a neoantigen vaccine.

An exemplary embodiment of an antigenic portion is the region(s) flanking amino acids 45-53 of SEQ ID NO: 30. Another exemplary embodiment of an antigenic portion is the region(s) flanking amino acids 82-90 of SEQ ID NO: 30. In some embodiments, the antigenic portion is capable of binding to at least one HLA allele expressed in a subject (e.g., HLA-A*02:01). In some other embodiments, the antigenic portion is capable of binding to at least one HLA allele expressed in at least 10%, at least 15%, at least 20%, at least 25%, at least 30%, at least 35%, at least 40%, or at least 45% of subjects in a population of subjects suffering from a neoplastic disorder. In some embodiments, the antigenic portion is capable of eliciting a T-cell response against a tumor present in at least 1%, at least 5%, or at least 10% of a population of subjects suffering from a neoplastic disorder.

In some embodiments, an antigenic portion does not exclusively overlap or consist of a canonical peptide sequence. The term "canonical peptide sequence," as used herein, refers to any contiguous peptide sequence present in the human proteome in the absence of contact with at least one compound chosen from compounds of Formula I, compounds of Formula II, compounds of Formula III, and pharmaceutically acceptable salts of any of the foregoing (e.g., in the absence of contact with at least one compound chosen from compounds of Formula I, compounds of Formula II, compounds of Formula III, and pharmaceutically acceptable salts of any of the foregoing), and/or to which the immune has previously been exposed. In some embodiments, the canonical peptide sequence is derived from and/or encoded by the canonical transcript open reading frame. Exemplary canonical peptide sequences are underlined in Table 13.

In some embodiments, when at least one compound chosen from compounds of Formula I, compounds of Formula II, compounds of Formula III, and pharmaceutically acceptable salts of any of the foregoing is administered, a canonical peptide sequence may be derived from and/or encoded by the immediate 5' in-frame 24 nucleotides preceding an aberrant splicing event induced by the at least one compound chosen from compounds of Formula I, compounds of Formula II, compounds of Formula III, and pharmaceutically acceptable salts of any of the foregoing. Thus, in some embodiments, the canonical peptide sequence comprises or consists of the 8 amino acids immediately N-terminal to the neoantigen sequence induced by the at least one compound chosen from compounds of Formula I, compounds of Formula II, compounds of Formula III, and pharmaceutically acceptable salts of any of the foregoing. In some embodiments, when a 5' exon sequence terminates with a terminal nucleotide of a codon, the canonical peptide sequence terminates at the end of the exon. In some other embodiments, when a 5' exon sequence terminates with one or two of the three nucleotides of a codon, the canonical peptide sequence is derived from and/or encoded by the 24 nucleotides preceding the incomplete codon. In some embodiments, mRNA sequences 3' of the aberrant splicing event may be translated in the same open reading frame derived from the 5' exon until reaching a stop codon, whereupon translation may terminate. In some embodiments, when the aberrant splicing event (e.g., exon skipping) results in a conservation of the canonical transcript open reading frame, the C-terminal sequence may be translated for an additional 24 nucleotides, encoding 8 C-terminal amino acids. In this context, in some embodiments, only the region across the aberrant exon junction may encode a neoantigen sequence. In some embodiments, when the open reading frame is shifted (e.g., intron retention), the complete C-terminal sequence (encoded by the 3' mRNA) may encode a neoantigen sequence.

In some embodiments, an antigenic portion of a neoantigen sequence is chosen by comparing the neoantigen sequence to the canonical peptide sequence; and selecting a portion of the neoantigen sequence that does not exclusively overlap, consist of, and/or align with the canonical peptide sequence. An antigenic portion of a neoantigen sequence, in some embodiments, can be screened for antigenicity and/or T-cell priming function in the same manner as are full-length neoantigen sequences (e.g., the neoantigen sequence from which the antigenic portion is derived). In some embodiments, an antigenic portion of a neoantigen sequence is evaluated for antigenicity and/or T-cell priming function using a T-cell priming assay, such as the exemplary T-cell priming experiments described herein.

In some embodiments, the neoantigen sequence is a neoantigen sequence specific to the subject. In some embodiments, the neoantigen sequence is a personalized neoantigen vaccine for the subject. In some embodiments, the neoantigen sequence used to create a personalized neoantigen vaccine for a subject is capable of binding to at least one HLA allele expressed in the subject. In some embodiments, a personalized neoantigen vaccine is selected by identifying neoantigens expressed in a subject's tumor, e.g., after administration of at least one compound chosen from compounds of Formula I, compounds of Formula II, compounds of Formula III, and pharmaceutically acceptable salts of any of the foregoing, and selecting a vaccine comprising a neoantigen sequence observed in the patient's tumor.

The term "personalized" when used to describe a neoantigen vaccine refers to a vaccine created by identifying one or more neoantigens produced in a patient, preferably one identified in the patient after an exposure to at least one compound chosen from compounds of Formula I, compounds of Formula II, compounds of Formula III, and pharmaceutically acceptable salts of any of the foregoing, and then using one or more of those neoantigens as the basis of the vaccine for the same patient. Accordingly, in some embodiments, a patient is given at least one compound chosen from compounds of Formula I, compounds of Formula II, compounds of Formula III, and pharmaceutically acceptable salts of any of the foregoing and screened for neoantigens produced by the treatment. In some embodiments, the selected neoantigen vaccine comprises a neoantigen peptide or mRNA disclosed herein and confirmed to be present in the patient after exposure to the at least one compound chosen from compounds of Formula I, compounds of Formula II, compounds of Formula III, and pharmaceutically acceptable salts of any of the foregoing. In some embodiments, the at least one compound chosen from compounds of Formula I, compounds of Formula II, compounds of Formula III, and pharmaceutically acceptable salts of any of the foregoing and/or peptide or mRNA vaccine may be administered to the patient once or repeatedly. Subsequently, in some embodiments, one or more of those neoantigens are used to create a personalized vaccine that is given to the patient. In some embodiments, the one or more neoantigens used to create a personalized vaccine possess binding affinity for one or more patient-specific HLA alleles. In some embodiments, the patient expresses one or more MHC1 alleles that bind to the one or more neoantigens. The prediction of whether a given neoantigen will bind to a specific MHC1 allele can be determined using any computational prediction method known in the art. Exemplary computational prediction methods are disclosed, e.g., in Meydan et al. (2013) BMC Bioinformatics 14 (Suppl. 2):513, which is incorporated herein by reference for such methods.

In some other embodiments, the neoantigen sequence is a universal neoantigen sequence. In some embodiments, the neoantigen sequence is a universal neoantigen vaccine.

The term "universal" when used to describe a neoantigen vaccine refers to a vaccine having a peptide or mRNA sequence that is based on common or known neoantigen(s) observed by sequencing neoantigens produced in multiple patients and/or patient tissue samples, preferably after an exposure to at least one compound chosen from compounds of Formula I, compounds of Formula II, compounds of Formula III, and pharmaceutically acceptable salts of any of the foregoing. The peptide or mRNA sequence used in the vaccine need not be present in every patient but rather be observed in at least several patients or patient tissue samples. In some embodiments, the at least one compound chosen from compounds of Formula I, compounds of Formula II, compounds of Formula III, and pharmaceutically acceptable salts of any of the foregoing and/or peptide or mRNA vaccine may be administered to the patient once or repeatedly. Subsequently, in some embodiments, that peptide or mRNA sequence is used for vaccinating further patients. In some embodiments, a patient is given at least one compound chosen from compounds of Formula I, compounds of Formula II, compounds of Formula III, and pharmaceutically acceptable salts of any of the foregoing, and then given a peptide or mRNA vaccine of known neoantigen to enhance immune response to the neoantigens produced by the at least one compound chosen from compounds of Formula I, compounds of Formula II, compounds of Formula III, and pharmaceutically acceptable salts of any of the foregoing. In some embodiments, a patient is given a universal peptide or mRNA vaccine and then given at least one compound chosen from compounds of Formula I, compounds of Formula II, compounds of Formula III, and pharmaceutically acceptable salts of any of the foregoing. In some embodiments, the neoantigen sequence (or sequences) used to create a universal neoantigen vaccine is selected based on overall MHC1 allele frequency in a given patient population (Maiers et al. (2007) Hum. Immunol. 68(9):779-88).

In some embodiments, the neoantigen (e.g., a universal neoantigen) sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide, or its encoding mRNA, induced in the subject by administering a therapeutically effective amount of the at least one compound chosen from compounds of Formula I, compounds of Formula II, compounds of Formula III, and pharmaceutically acceptable salts of any of the foregoing. In some embodiments, the at least one neoantigen peptide comprises a neoantigen sequence induced by contacting a neoplastic cell with a therapeutically effective amount of the at least one compound chosen from compounds of Formula I, compounds of Formula II, compounds of Formula III, and pharmaceutically acceptable salts of any of the foregoing. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide and a pharmaceutically acceptable carrier (e.g., any of the exemplary carriers described herein). In some embodiments, the at least one neoantigen peptide is linked to the pharmaceutically acceptable carrier. In some embodiments, the pharmaceutically acceptable carrier is chosen from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen peptide and the pharmaceutically acceptable carrier are covalently attached via a linker. In some embodiments, the neoantigen peptide and the pharmaceutically acceptable carrier are expressed as a fusion protein. In some embodiments, the neoantigen vaccine comprises at least one neoantigen peptide and a pharmaceutically acceptable diluent. In some embodiments, the neoantigen vaccine comprises at least one neoantigen peptide and a pharmaceutically acceptable adjuvant.

In some embodiments, the neoantigen vaccine comprises at least one neoantigen mRNA. In some embodiments, the at least one neoantigen mRNA encodes one or more than one neoantigen sequence.

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing the protein sequence of at least one neoantigen. In some embodiments, the neoantigen sequence has been identified by sequencing at least one mRNA encoding a neoantigen induced in the subject by administering a therapeutically effective amount of the at least one compound chosen from compounds of Formula I, compounds of Formula II, compounds of Formula III, and pharmaceutically acceptable salts of any of the foregoing. In some embodiments, the at least one neoantigen mRNA encodes a neoantigen sequence induced by contacting a neoplastic cell with a therapeutically effective amount of the at least one compound chosen from compounds of Formula I, compounds of Formula II, compounds of Formula III, and pharmaceutically acceptable salts of any of the foregoing. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier (e.g., any of the exemplary carriers described herein). In some embodiments, the at least one neoantigen mRNA is linked to the pharmaceutically acceptable carrier. In some embodiments, the pharmaceutically acceptable carrier is chosen from a peptide, a serum albumin, a keyhole limpet hemocyanin, an immunoglobulin, a thyroglobulin, an ovalbumin, a toxoid or an attenuated toxoid derivative, a cytokine, and a chemokine. In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant. In some embodiments, the neoantigen mRNA is encapsulated by an encapsulating agent. In some embodiments, the encapsulating agent is a liposome. In some embodiments, the encapsulating agent is a nanoparticle.

In some embodiments, the at least one additional therapy comprises administering a cytokine or cytokine analog, e.g., any cytokine or cytokine analog disclosed herein. In some embodiments, the subject is intolerant, non-responsive, or poorly responsive to the cytokine or cytokine analog when administered alone. In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of at least one compound chosen from compounds of Formula I, compounds of Formula II, compounds of Formula III, and pharmaceutically acceptable salts of any of the foregoing due to the induction and presentation of neoantigens.

In some embodiments, the at least one additional therapy comprises administering engineered tumor-targeting T-cells (i.e., CAR-T), e.g., any CAR-T therapy disclosed herein.

In some embodiments, the methods described herein may further comprise detecting one or more neoantigens and/or a T-cell response in the subject after administration of the at least one compound chosen from compounds of Formula I, compounds of Formula II, compounds of Formula III, and pharmaceutically acceptable salts of any of the foregoing, and, optionally, continuing administration of the at least one compound chosen from compounds of Formula I, compounds of Formula II, compounds of Formula III, and pharmaceutically acceptable salts of any of the foregoing if one or more neoantigens and/or a T-cell response is detected. In some embodiments, detecting one or more neoantigens and/or a T-cell response in the subject indicates efficacy of treatment with the at least one compound chosen from compounds of Formula I, compounds of Formula II, compounds of Formula III, and pharmaceutically acceptable salts of any of the foregoing. In some embodiments, treatment with the additional therapy, along with the at least one compound chosen from compounds of Formula I, compounds of Formula II, compounds of Formula III, and pharmaceutically acceptable salts of any of the foregoing, is continued if one or more neoantigens and/or a T-cell response is detected. In some embodiments, treatment is continued at a reduced dosage and/or frequency if one or more neoantigens and/or a T-cell response is detected.

In some embodiments, the methods described herein may further comprise detecting a double-stranded RNA immune response in the subject after administration of the at least one compound chosen from compounds of Formula I, compounds of Formula II, compounds of Formula III, and pharmaceutically acceptable salts of any of the foregoing, and, optionally, continuing administration of the at least one compound chosen from compounds of Formula I, compounds of Formula II, compounds of Formula III, and pharmaceutically acceptable salts of any of the foregoing if a double-stranded RNA immune response is detected. In some embodiments, detecting a double-stranded RNA immune response in the subject indicates efficacy of treatment with the at least one compound chosen from compounds of Formula I, compounds of Formula II, compounds of Formula III, and pharmaceutically acceptable salts of any of the foregoing. In some embodiments, treatment with the additional therapy, along with the at least one compound chosen from compounds of Formula I, compounds of Formula II, compounds of Formula III, and pharmaceutically acceptable salts of any of the foregoing, is continued if a double-stranded RNA immune response is detected. In some embodiments, treatment is continued at a reduced dosage and/or frequency if a double-stranded RNA immune response is detected.

In some embodiments, the methods described herein may further comprise detecting immunogenic cell death in the subject after administration of the at least one compound chosen from compounds of Formula I, compounds of Formula II, compounds of Formula III, and pharmaceutically acceptable salts of any of the foregoing, and, optionally, continuing administration of the at least one compound chosen from compounds of Formula I, compounds of Formula II, compounds of Formula III, and pharmaceutically acceptable salts of any of the foregoing if immunogenic cell death is detected. In some embodiments, detecting immunogenic cell death in the subject indicates efficacy of treatment with the at least one compound chosen from compounds of Formula I, compounds of Formula II, compounds of Formula III, and pharmaceutically acceptable salts of any of the foregoing. In some embodiments, treatment with the additional therapy, along with the at least one compound chosen from compounds of Formula I, compounds of Formula II, compounds of Formula III, and pharmaceutically acceptable salts of any of the foregoing, is continued if immunogenic cell death is detected. In some embodiments, treatment is continued at a reduced dosage and/or frequency if immunogenic cell death is detected.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer, gastric cancer, prostate cancer, ovarian cancer, lung cancer, uterine cancer, salivary duct carcinoma, melanoma, colon cancer, and esophageal cancer. In some embodiments, the solid tumor is chosen from HER2-positive breast cancer, gastric adenocarcinoma, and prostate cancer.

In some embodiments, the present disclosure further provides a method of treating a subject having or suspected of having a neoplastic disorder, comprising: (a) administering to the subject a therapeutically effective amount of at least one compound chosen from compounds of Formula I, compounds of Formula II, compounds of Formula III, and pharmaceutically acceptable salts of any of the foregoing, wherein administration of the at least one compound chosen from compounds of Formula I, compounds of Formula II, compounds of Formula III, and pharmaceutically acceptable salts of any of the foregoing induces at least one neoantigen and/or a T-cell response; (b) detecting one or more neoantigens and/or a T-cell response in the subject after administration of the at least one compound chosen from compounds of Formula I, compounds of Formula II, compounds of Formula III, and pharmaceutically acceptable salts of any of the foregoing; and (c) continuing administration of the at least one compound chosen from compounds of Formula I, compounds of Formula II, compounds of Formula III, and pharmaceutically acceptable salts of any of the foregoing if one or more neoantigens and/or a T-cell response is detected. In some embodiments, detecting one or more neoantigens and/or a T-cell response in the subject indicates efficacy of treatment with the at least one compound chosen from compounds of Formula I, compounds of Formula II, compounds of Formula III, and pharmaceutically acceptable salts of any of the foregoing. In some embodiments, the one or more neoantigens comprise an amino acid sequence of any one of SEQ ID NOs: 1-29. In some embodiments, the one or more neoantigens comprise an amino acid sequence of SEQ ID NO: 1. In some embodiments, the one or more neoantigens comprise an amino acid sequence of SEQ ID NO: 3. In some embodiments, the one or more neoantigens comprise an amino acid sequence of any one of SEQ ID NOs: 10-13.

In some embodiments, a patient having a cancer as described herein can be treated with a combination of at least one compound chosen from compounds of Formula I, compounds of Formula II, compounds of Formula III, and pharmaceutically acceptable salts of any of the foregoing and a checkpoint inhibitor therapy.

Treatment of patients with immune checkpoint inhibition has been shown to have robust efficacy in certain clinical indications. Recently, the FDA approved use of a checkpoint inhibitor in patients with tumors exhibiting high microsatellite instability, agnostic to the tissue lineage. This approval was based, in part, on the observation that response rates correlate positively with mutational burden (Rizvi et al. (2015) Science 348(6230):124-8; Hellmann et al. (2018) Cancer Cell 33(5):853-861). Estimates from the literature vary in absolute numbers and by lineage, but generally support that above a threshold of ~150-250 mutations, the probability of response rises. Analysis of TCGA data shows that a large percentage of adult-onset tumor lineages have comparatively low non-synonymous mutational burden (Vogelstein et al. (2013) Science 339:1549-58). Most lineages have median non-synonymous mutational rates of ~30-80 per patient, well below the thresholds for improved odds of response to checkpoint inhibitors.

For instance, HER2-positive breast cancer has been shown to have a median of ~60 non-synonymous mutations present per patient sample. However, the threshold for checkpoint inhibitor treatment efficacy, as mentioned above, is estimated to be in the range of ~150-250 non-synonymous mutations, i.e., patients above this threshold are more likely to show complete remission, partial remission, and/or stable disease, whereas patients below this threshold are more likely to exhibit progressive disease. Strategies to enhance the apparent number of non-synonymous mutations and/or neoantigens being presented on tumor cells are therefore desirable, and may enhance the overall probability of responses, e.g., to checkpoint inhibitor therapies. As cytokines (and analogs thereof) act via a similar mechanism of action, such strategies may also enhance the overall probability of response to cytokine-based therapies.

Current response rates in HER2-positive breast cancer are ~15-25% (CTI NCT02129556). In some embodiments disclosed herein, treatment with at least one compound chosen from compounds of Formula I, compounds of Formula II, compounds of Formula III, and pharmaceutically acceptable salts of any of the foregoing in combination with a checkpoint inhibitor and/or cytokine therapy may improve such response rates. In some embodiments, treatment with a therapeutically effective amount of at least one compound chosen from compounds of Formula I, compounds of Formula II, compounds of Formula III, and pharmaceutically acceptable salts of any of the foregoing, in combination with a checkpoint inhibitor and/or cytokine therapy may apply to any adult-onset tumor, particularly those in which the median non-synonymous mutational rate is below the estimated ~150 mutations threshold. In some embodiments, exemplary cancer types suitable for treatment with a therapeutically effective amount of at least one compound chosen from compounds of Formula I, compounds of Formula II, compounds of Formula III, and pharmaceutically acceptable salts of any of the foregoing, alone or in combination with an additional therapy (e.g., a checkpoint inhibitor therapy, a cytokine therapy) include but are not limited to esophageal cancer, non-Hodgkin's lymphoma, colorectal cancer, head and neck cancer, gastric cancer, endometrial cancer, pancreatic adenocarcinoma, ovarian cancer, prostate cancer, hepatocellular cancer, glioblastoma, breast cancer (e.g., HER2-positive breast cancer), lung cancer (e.g., non-small cell lung cancer), chronic lymphocytic leukemia, and acute myeloid leukemia. Other exemplary suitable cancer types are identified, e.g., in Vogelstein et al. (2013) Science 339:1549-58, which is incorporated herein by reference in its entirety.

As many checkpoint inhibitor therapies are based on chronic expression of tumor-associated antigens, regular treatment boosts are required for efficacy and for "re-boosting" reactive T-cell populations. The inducible nature of at least one compound chosen from compounds of Formula I, compounds of Formula II, compounds of Formula III, and pharmaceutically acceptable salts of any of the foregoing, derived neoantigens described herein provide for therapeutic dosing regimens that may be designed to enhance the immune response of neoantigen-reactive T-cells, while limiting T-cell exhaustion often caused by chronic antigen stimulation. For instance, in some embodiments, an initial dose of at least one compound chosen from compounds of Formula I, compounds of Formula II, compounds of Formula III, and pharmaceutically acceptable salts of any of the foregoing, is administered to a subject to trigger aberrant splicing and production of neoantigen peptides. After a period of time to allow for protein production and antigen presentation, in some embodiments, the subject is then administered an initial dose of a checkpoint inhibitor to boost and/or enhance effector T-cell priming and expansion. In some embodiments, the wait period between doses of at least one compound chosen from compounds of Formula I, compounds of Formula II, compounds of Formula III, and pharmaceutically acceptable salts of any of the foregoing, and checkpoint inhibitor is about 2, about 3, about 4, about 5, about 6, or about 7 days. In some embodiments, the wait period is between about 3 days and about 5 days.

In some embodiments, the checkpoint inhibitor is targeted at CTLA4, OX40, CD40, and/or GITR. In some embodiments, the combination therapeutic benefit of a therapeutically effective amount of at least one compound chosen from compounds of Formula I, compounds of Formula II, compounds of Formula III, and pharmaceutically acceptable salts of any of the foregoing, and a checkpoint inhibitor may be additive or superadditive.

In some embodiments, administration of the therapeutically effective amount of at least one compound chosen from compounds of Formula I, compounds of Formula II, compounds of Formula III, and pharmaceutically acceptable salts of any of the foregoing is initiated before administration of the checkpoint inhibitor.

In some embodiments, administration of the therapeutically effective amount of at least one compound chosen from compounds of Formula I, compounds of Formula II, compounds of Formula III, and pharmaceutically acceptable salts of any of the foregoing thereof is initiated after administration of the checkpoint inhibitor.

In some embodiments, administration of the therapeutically effective amount of at least one compound chosen from compounds of Formula I, compounds of Formula II, compounds of Formula III, and pharmaceutically acceptable salts of any of the foregoing is initiated concurrently with administration of the checkpoint inhibitor, e.g., in a single formulated product or separate formulated products administered in a single procedure.

In some embodiments, after a period to allow for T-cell priming and expansion, the subject is then administered a second or subsequent dose of at least one compound chosen from compounds of Formula I, compounds of Formula II, compounds of Formula III, and pharmaceutically acceptable salts of any of the foregoing, to trigger re-presentation of neoantigen peptides. In some embodiments, the wait period between an initial dose of a checkpoint inhibitor and a second or subsequent dose of a therapeutically effective amount of at least one compound chosen from compounds of Formula I, compounds of Formula II, compounds of Formula III, and pharmaceutically acceptable salts of any of the foregoing, is about 2, about 3, about 4, or about 5 weeks. In some embodiments, the wait period is about 3 weeks. Following a second or subsequent dose of at least one compound chosen from compounds of Formula I, compounds of Formula II, compounds of Formula III, and pharmaceutically acceptable salts of any of the foregoing, in some embodiments, the immune system may engage with the neoantigen-presenting tumor cells and/or elicit tumor cell killing. In some embodiments, the subject is then administered a second or subsequent dose of the checkpoint inhibitor to further expand the memory effector T-cell population, after allowing for secondary T-cell priming and expansion.

In some embodiments, the wait period between an initial dose of a therapeutically effective amount of at least one compound chosen from compounds of Formula I, compounds of Formula II, compounds of Formula III, and pharmaceutically acceptable salts of any of the foregoing and a second or subsequent dose of a checkpoint inhibitor is about 2, about 3, about 4, or about 5 weeks. In some embodiments, the wait period is about 3 weeks.

In some embodiments, dosing of a therapeutically effective amount of at least one compound chosen from compounds of Formula I, compounds of Formula II, compounds of Formula III, and pharmaceutically acceptable salts of any of the foregoing, following this exemplary initial treatment regimen can be pulsatile, i.e., a therapeutically effective amount of at least one compound chosen from compounds of Formula I, compounds of Formula II, compounds of Formula III, and pharmaceutically acceptable salts of any of the foregoing, may be dosed at prolonged intervals (e.g., about every 4 weeks, about every 5 weeks, about every 6 weeks) to allow for antigen presentation, T-cell engagement and/or tumor cell killing, and/or recovery of the memory T-cell population. At later timepoints, in some embodiments, a therapeutically effective amount of at least one compound chosen from compounds of Formula I, compounds of Formula II, compounds of Formula III, and pharmaceutically acceptable salts of any of the foregoing, treatment may be combined with one or more checkpoint inhibitors targeted to restore effector functionality to exhausted T-cell populations. For example, in some embodiments, at later timepoints, the at least one compound chosen from compounds of Formula I, compounds of Formula II, compounds of Formula III, and pharmaceutically acceptable salts of any of the foregoing, treatment may be combined with one or more checkpoint inhibitors targeted at PD1/PDL1, LAG3, and/or TIM3. In some embodiments, the pulsed nature of neoantigen presentation and priming may allow a checkpoint inhibitor and/or at least one compound chosen from compounds of Formula I, compounds of Formula II, compounds of Formula III, and pharmaceutically acceptable salts of any of the foregoing, to be administered less frequently and/or at lower doses. In some embodiments, the pulsed nature of neoantigen presentation may provide one or more treatment benefits for a checkpoint inhibitor (e.g., an anti-CTLA4 antibody such as ipilimumab), relative to the checkpoint inhibitor when administered without concurrent administration of a therapeutically effective amount of at least one compound chosen from compounds of Formula I, compounds of Formula II, compounds of Formula III, and pharmaceutically acceptable salts of any of the foregoing, for example, by lowering the potential risk of adverse reactions often observed with the checkpoint inhibitor's standard dosing regimen. In certain embodiments, the checkpoint inhibitor is an inhibitor of the cytotoxic T-lymphocyte-associated antigen (CTLA4) pathway. CTLA4, also known as CD152, is a protein receptor that downregulates immune responses. CTLA4 is constitutively expressed in regulatory T-cells, but only upregulated in conventional T-cells after activation. As used herein, the term "CTLA4 inhibitor" is meant to refer to any inhibitor of CTLA4 and/or the CTLA4 pathway. Exemplary CTLA4 inhibitors include but are not limited to anti-CTLA4 antibodies. CTLA4 blocking antibodies for use in humans were developed based on the pre-clinical activity seen in mouse models of anti-tumor immunity. Exemplary anti-CTLA4 antibodies include but are not limited to ipilimumab (MDX-010) and tremelimumab (CP-675,206), both of which are fully human. Ipilimumab is an IgG1 with a plasma half-life of approximately 12-14 days; tremelimumab is an IgG2 with a plasma half-life of approximately 22 days. See, e.g., Phan et al. (2003) Proc Natl Acad Sci USA. 100:8372-7; Ribas et al. (2005) J Clin Oncol. 23:8968-77; Weber et al. (2008) J Clin Oncol. 26:5950-6. In some embodiments, the anti-CTLA4 antibody is ipilimumab.

In certain embodiments, the checkpoint inhibitor is an inhibitor of the programmed death-1 (PD1) pathway. The programmed cell death 1 (PD1) pathway represents a major immune control switch which may be engaged by tumor cells to overcome active T-cell immune surveillance. The ligands for PD1 (PDL1 and PDL2) are constitutively expressed or can be induced in various tumors. High expression of PDL1 on tumor cells (and to a lesser extent of PDL2) has been found to correlate with poor prognosis and survival in various other solid tumor types. Furthermore, PD1 has been suggested to regulate tumor-specific T-cell expansion in patients with malignant melanoma. These observations suggest that the PD1/PDL1 pathway plays a critical role in the tumor immune evasion and may be considered an attractive target for therapeutic intervention. As used herein, the term "PD1 inhibitor" is meant to refer to any inhibitor of PD1 and/or the PD1 pathway. Exemplary PD1 inhibitors include but are not limited to anti-PD1 and anti-PDL1 antibodies. In certain embodiments, the checkpoint inhibitor is an anti-PD1 antibody. Exemplary anti-PD1 antibodies include but are not limited to nivolumab and pembrolizumab (MK-3475). Nivolumab, for example, is a fully human immunoglobulin G4 (IgG4) PD1 immune checkpoint inhibitor antibody that disrupts the interaction of the PD1 receptor with its ligands PDL1 and PDL2, thereby inhibiting the cellular immune response (Guo et al. (2017) J Cancer 8(3):410-6). In some embodiments, the anti-PD1 antibody is nivolumab. Pembrolizumab, for example, is a potent and highly-selective humanized mAb of the IgG4/kappa isotype designed to directly block the interaction between PD1 and its ligands, PDL1 and PDL2. Pembrolizumab strongly enhances T lymphocyte immune responses in cultured blood cells from healthy human donors, cancer patients, and primates. Pembrolizumab has also been reported to modulate the level of interleukin-2 (IL-2), tumor necrosis factor alpha (TNFα), interferon gamma (IFNγ), and other cytokines. Exemplary anti-PDL1 antibodies include but are not limited to atezolizumab, avelumab, and durvalumab. Atezolizumab, for example, is an IgG1 humanized mAb that is reported to block the PD1/PDL1 interaction, by targeting the expressed PDL1 on numerous kinds of malignant cells. This blockage of the PD1/PDL1 pathway may stimulate the immune defense mechanisms against tumors (Abdin et al. (2018) Cancers (Basel) 10(2):32). In some embodiments, the anti-PDL1 antibody is atezolizumab.

In certain embodiments, the checkpoint inhibitor is targeted at PD1/PDL1, CTLA4, OX40, CD40, LAG3, TIM3, GITR, and/or MR. In certain embodiments, the checkpoint inhibitor is targeted at CTLA4, OX40, CD40, and/or GITR. In certain embodiments, a checkpoint inhibitor is targeted with an inhibitory antibody or other similar inhibitory molecule (e.g., an inhibitory anti-CTLA4 or anti-PD1/PDL1 antibody). In certain other embodiments, a checkpoint inhibitor is targeted with an agonist for the target; examples of this class include the stimulatory targets OX40, CD40, and/or GITR. In some embodiments, the checkpoint inhibitor targeted at OX40, CD40, and/or GITR is an agonist antibody. Agonist antibodies directed against OX40 may have a dual role, inhibiting regulatory T-cell suppression, while enhancing effector T-cell functions. Agonist anti-GITR antibodies have also been shown to make effector T-cells more resistant to the inhibition induced by regulatory T-cells (Karaki et al. (2016) Vaccines (Basel) 4(4):37). Likewise, agonist CD40 antibodies demonstrate T-cell-dependent anti-tumor activity. Activation of CD40 on dendritic cells increases cross-presentation of tumor antigens and consequently the number of activated tumor-directed effector T-cells (Ellmark et al. (2015) Oncoimmunol. 4(7): e1011484).

In certain embodiments, the checkpoint inhibitor is targeted at CTLA4 (e.g., an anti-CTLA4 antibody). In certain embodiments, targeting CTLA4 facilitates priming and activation of naïve T-cells. In certain embodiments, the checkpoint inhibitor is targeted at OX40 (e.g., an anti-OX40 antibody). In certain embodiments, targeting OX40 enhances expansion of effector T-cells. In certain embodiments, the checkpoint inhibitor is targeted at CD40 (e.g., an anti-CD40 antibody). In certain embodiments, targeting CD40 inhibits "tolerogenic" priming of T-cells and/or formation of regulatory T-cells. In certain embodiments, the checkpoint inhibitor is targeted at GITR (e.g., an anti-GITR antibody). In certain embodiments, targeting GITR inhibits activity of regulatory T-cells. In certain embodiments, the benefit of combination therapy (e.g., the effect on at least one symptom or the risk/rate of disease progression) with a therapeutically effective amount of at least one compound chosen from compounds of Formula I, compounds of Formula II, compounds of Formula III, and pharmaceutically acceptable salts of any of the foregoing, and a CTLA4-, OX40-, CD40-, and/or GITR-targeted agent is additive. In some embodiments, the benefit of combination therapy with a therapeutically effective amount of at least one compound chosen from compounds of Formula I, compounds of Formula II, compounds of Formula III, and pharmaceutically acceptable salts of any of the foregoing, and a CTLA4-, OX40-, CD40-, and/or GITR-targeted agent is superadditive (i.e., synergistic).

Checkpoint inhibitor treatment strategies are based on the hypothesis that treatment facilitates and/or enhances priming of T-cell responses to weakly or poorly antigenic tumors (e.g., CTLA4) or that treatment restores and/or reinvigorates T-cells that respond to tumor antigens, but have become "exhausted" due to the chronic nature of the antigen presentation (e.g., PD1, PDL1) (Chen and Mellman (2013) Immunity 39(1):1-10). Examples of suitable checkpoint inhibition therapies and agents, e.g., anti-PD1, anti-PDL1, or anti-CTLA4 antibodies, are known in the art. See, e.g., WO 2001/014424 WO 2013/173223, WO 2016/007235.

Combining these primed T-cell responses following checkpoint inhibitor therapy with treatment to induce neoantigens in tumor cells (e.g., by administration of a therapeutically effective amount of at least one compound chosen from compounds of Formula I, compounds of Formula II, compounds of Formula III, and pharmaceutically acceptable salts of any of the foregoing) to which the primer immune system can react may provide beneficial synergy. As compounds chosen from compounds of Formula I, compounds of Formula II, compounds of Formula III, and pharmaceutically acceptable salts of any of the foregoing derived neoantigens have not yet been presented for T-cell priming, combination with a CTLA4 inhibitor may be particularly beneficial. In some embodiments, treatment comprises administering a therapeutically effective amount of at least one compound chosen from compounds of Formula I, compounds of Formula II, compounds of Formula III, and pharmaceutically acceptable salts of any of the foregoing, to induce the production of neoantigens, followed before, concurrently, or thereafter by an initial administration of a CTLA4 inhibitor to stimulate CD8 T-cell priming. In some embodiments, additional administrations of a CTLA4 inhibitor are provided to the patient, e.g., to further stimulate priming and/or activation of neoantigen-reactive CD8 populations. In some embodiments, additional administrations of a therapeutically effective amount of at least one compound chosen from compounds of Formula I, compounds of Formula II, compounds of Formula III, and pharmaceutically acceptable salts of any of the foregoing, can be given to the patient to increase neoantigen presentation by the tumor. Repeat administrations of a therapeutically effective amount of at least one compound chosen from compounds of Formula I, compounds of Formula II, compounds of Formula III, and pharmaceutically acceptable salts of any of the foregoing, and checkpoint inhibitor therapy can occur concurrently or in staggered intervals. In some embodiments, treatment further comprises administering a PD1/PDL1 inhibitor co-treatment, e.g., to restore effector function of exhausted neoantigen-targeted T-cells within the tumor microenvironment.

The terms "combination" or "combination therapy," as used herein, refer to the administration of a therapeutically effective amount of at least one compound chosen from compounds of Formula I, compounds of Formula II, compounds of Formula III, and pharmaceutically acceptable salts of any of the foregoing, together with an additional agent or therapy (e.g., a checkpoint inhibitor, a cytokine or cytokine analog, a neoantigen vaccine, CAR-T), as part of a treatment regimen intended to provide a beneficial (i.e., additive or synergistic) effect from the co-action of one or more of the administered agents. In some embodiments, the combination may also include one or more additional agents, including but not limited to chemotherapeutic agents, anti-angiogenesis agents, and agents that reduce immune-suppression (e.g., a second checkpoint inhibitor). The beneficial effect of the combination includes, but is not limited to, pharmacokinetic or pharmacodynamic co-action resulting from the combination of therapeutic agents. Administration of these therapeutic agents in combination typically is carried out over a defined time period (for example, minutes, hours, days, or weeks, depending upon the combination selected).

Administered "in combination" or "co-administration," as used herein, means that two or more different treatments are delivered to a subject during the subject's affliction with a medical condition (e.g., cancer or a neoplastic disorder), in any order. For example, in some embodiments, the two or more treatments are delivered after the subject has been diagnosed with a disease or disorder, and before the disease or disorder has been cured or eliminated, or when a subject is identified as being at risk but before the subject has developed symptoms of the disease. In some embodiments, the delivery of one treatment is still occurring when the delivery of the second treatment begins, so that there is overlap. In some embodiments, the first and second treatment are initiated at the same time. These types of delivery are sometimes referred to herein as "simultaneous," "concurrent," or "concomitant" delivery. In other embodiments, the delivery of one treatment ends before delivery of the second treatment begins. This type of delivery is sometimes referred to herein as "successive" or "sequential" delivery.

In some embodiments, the two treatments (e.g., at least one compound chosen from compounds of Formula I, compounds of Formula II, compounds of Formula III, and pharmaceutically acceptable salts of any of the foregoing, and a checkpoint inhibitor) are comprised in the same composition. Such compositions may be administered in any appropriate form and by any suitable route. In other embodiments, the two treatments (e.g., at least one compound chosen from compounds of Formula I, compounds of Formula II, compounds of Formula III, and pharmaceutically acceptable salts of any of the foregoing, and a checkpoint inhibitor) are administered in separate compositions, in any appropriate form and by any suitable route. For example, in some embodiments, a composition comprising a therapeutically effective amount of at least one compound chosen from compounds of Formula I, compounds of Formula II, compounds of Formula III, and pharmaceutically acceptable salts of any of the foregoing, and a composition comprising a checkpoint inhibitor may be administered concurrently or sequentially, in any order at different points in time; in either case, they should be administered sufficiently close in time so as to provide the desired therapeutic or prophylactic effect.

In embodiments of either simultaneous or sequential delivery, treatment may be more effective because of combined administration. In some embodiments, the first treatment is more effective, e.g., an equivalent effect is seen with less of the first treatment (e.g., with a lower dose), than would be seen if the first treatment were administered in the absence of the second treatment. In some embodiments, the first treatment is more effective such that the reduction in a symptom, or other parameter associated with the disease or disorder, is greater than what would be observed with the first treatment delivered in the absence of the second treatment. In other embodiments, an analogous situation is observed with the second treatment. In some embodiments, the benefit of combination therapy (e.g., the effect on at least one symptom or the risk/rate of disease progression) is additive. In some embodiments, the benefit of combination therapy is superadditive.

In some embodiments, the present disclosure provides a method of treating cancer in a subject in need thereof and/or a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing; and at least one additional therapy (e.g., a checkpoint inhibitor therapy, a cytokine or cytokine analog, a neoantigen vaccine, CAR-T). In some embodiments, administration of at least one compound chosen from compounds of Formula I, compounds of Formula II, compounds of Formula III, and pharmaceutically acceptable salts of any of the foregoing, induces at least one neoantigen and/or a T-cell response. In some embodiments, administration of a therapeutically effective amount of at least one compound chosen from compounds of Formula I, compounds of Formula II, compounds of Formula III, and pharmaceutically acceptable salts of any of the foregoing, induces a double-stranded RNA immune response. In some embodiments, administration of a therapeutically effective amount of at least one compound chosen from compounds of Formula I, compounds of Formula II, compounds of Formula III, and pharmaceutically acceptable salts of any of the foregoing, induces immunogenic cell death. In some embodiments, the at least one additional therapy may comprise at least one, at least two, at least three, at least four, or at least five additional therapies. For example, in some embodiments, a therapeutically effective amount of at least one compound chosen from compounds of Formula I, compounds of Formula II, compounds of Formula III, and pharmaceutically acceptable salts of any of the foregoing, may be administered in combination with two checkpoint therapies, i.e., using two different checkpoint inhibitors. In some embodiments, at least one compound chosen from compounds of Formula I, compounds of Formula II, compounds of Formula III, and pharmaceutically acceptable salts of any of the foregoing, may be administered in combination with a checkpoint inhibitor therapy and a neoantigen vaccine.

In some embodiments of combination therapy, the administered amount of the at least one compound chosen from compounds of Formula I, compounds of Formula II, compounds of Formula III, and pharmaceutically acceptable salts of any of the foregoing, and/or the at least one additional therapy is reduced by 10%, 15%, 20%, 25%, 30%, 35%, 40%, 45%, 50%, 75%, or 90%, relative to a standard dosage of at least one compound chosen from compounds of Formula I, compounds of Formula II, compounds of Formula III, and pharmaceutically acceptable salts of any of the foregoing, and/or the at least one additional therapy. In some embodiments, the at least one compound chosen from compounds of Formula I, compounds of Formula II, compounds of Formula III, and pharmaceutically acceptable salts of any of the foregoing, and/or the at least one additional therapy is administered at least 10%, 15%, 20%, 25%, 30%, 35%, 40%, 45%, 50%, 75%, or 90% less frequently, relative to a standard dosing regimen of the at least one compound chosen from compounds of Formula I, compounds of Formula II, compounds of Formula III, and pharmaceutically acceptable salts of any of the foregoing, and/or the at least one additional therapy. In some embodiments, the administered amount and/or dosage of the at least one compound chosen from compounds of Formula I, compounds of Formula II, compounds of Formula III, and pharmaceutically acceptable salts of any of the foregoing, and/or the at least one additional therapy results in lower systemic toxicity and/or improved tolerance.

In some embodiments, administration of a therapeutically effective amount of at least one compound chosen from compounds of Formula I, compounds of Formula II, compounds of Formula III, and pharmaceutically acceptable salts of any of the foregoing, is initiated before administration of the at least one additional therapy. In some embodiments, administration of a therapeutically effective amount of at least one compound chosen from compounds of Formula I, compounds of Formula II, compounds of Formula III, and pharmaceutically acceptable salts of any of the foregoing, is initiated after administration of the at least one additional therapy. In some embodiments, administration of a therapeutically effective amount of at least one compound chosen from compounds of Formula I, compounds of Formula II, compounds of Formula III, and pharmaceutically acceptable salts of any of the foregoing, is initiated concurrently with administration of the at least one additional therapy.

In some embodiments, administration of a therapeutically effective amount of at least one compound chosen from compounds of Formula I, compounds of Formula II, compounds of Formula III, and pharmaceutically acceptable salts of any of the foregoing, is repeated at least once after initial administration. In some embodiments, the amount of the at least one compound chosen from compounds of Formula I, compounds of Formula II, compounds of Formula III, and pharmaceutically acceptable salts of any of the foregoing, used for repeated administration is reduced relative to the amount used for initial administration. In some embodiments, the amount of the at least one compound chosen from compounds of Formula I, compounds of Formula II, compounds of Formula III, and pharmaceutically acceptable salts of any of the foregoing, used for repeated administration is reduced relative to a standard dosage of the at least one compound chosen from compounds of Formula I, compounds of Formula II, compounds of Formula III, and pharmaceutically acceptable salts of any of the foregoing. In some embodiments, the amount of the at least one compound chosen from compounds of Formula I, compounds of Formula II, compounds of Formula III, and pharmaceutically acceptable salts of any of the foregoing, used for repeated administration is reduced by 10%, 15%, 20%, 25%, 30%, 35%, 40%, 45%, 50%, 75%, or 90%, relative to a standard dosage of the at least one compound chosen from compounds of Formula I, compounds of Formula II, compounds of Formula III, and pharmaceutically acceptable salts of any of the foregoing.

In some embodiments, administration of the at least one additional therapy is repeated at least once after initial administration. In some embodiments, the amount of the at least one additional therapy used for repeated administration is reduced relative to the amount used for initial administration. In some embodiments, the amount of the at least one additional therapy used for repeated administration is reduced relative to a standard dosage of the at least one additional therapy. In some embodiments, the amount of the at least one additional therapy used for repeated administration is reduced by 10%, 15%, 20%, 25%, 30%, 35%, 40%, 45%, 50%, 75%, or 90%, relative to a standard dosage of the at least one additional therapy.

In some embodiments, repeated administration of a therapeutically effective amount of at least one compound chosen from compounds of Formula I, compounds of Formula II, compounds of Formula III, and pharmaceutically acceptable salts of any of the foregoing, is concurrent with repeated administration of the at least one additional therapy. In some embodiments, repeated administration of a therapeutically effective amount of at least one compound chosen from compounds of Formula I, compounds of Formula II, compounds of Formula III, and pharmaceutically acceptable salts of any of the foregoing, is sequential or staggered with repeated administration of the at least one additional therapy.

In some embodiments, the present disclosure provides a method of treating cancer in a subject in need thereof and/or a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing; and a checkpoint inhibitor therapy. In some embodiments, the checkpoint inhibitor therapy comprises administering at least one checkpoint inhibitor. In some embodiments, the subject is intolerant, non-responsive, or poorly responsive to the at least one checkpoint inhibitor when administered alone. In some embodiments, a subject may be considered non-responsive or poorly responsive to the at least one checkpoint inhibitor as determined using, e.g., the immune-related Response Criteria (irRC) and/or the immune-related Response Evaluation Criteria in Solid Tumors (irRECIST). See, e.g., Wolchok et al. (2009) Clin Cancer Res. 15(23):7412-20; Bohnsack et al. "Adaptation of the Immune-Related Response Criteria:irRECIST" (Abstract 4958) ESMO 2014. Exemplary criteria may include those used in the art to define when tumors in cancer patients improve ("respond"), remain the same ("stabilize"), or worsen ("progress") during treatment, when the treatment being evaluated is an immune-oncology drug (e.g., a checkpoint inhibitor). In some embodiments, a subject may be considered intolerant to the at least one checkpoint inhibitor if the subject presents with one or more than one adverse (grade 2+) event identified for the respective checkpoint inhibitor (e.g., ipilimumab). In some embodiments, for example, a subject may be considered intolerant to ipilimumab treatment if the subject presents with one or more adverse events chosen from enterocolitis, hepatitis, dermatitis (including toxic epidermal necrolysis), neuropathy, and endocrinopathy (Yervoy® (ipilimumab) FDA Label Supplement, 2018).

In some embodiments, the checkpoint inhibitor is targeted at PD1/PDL1, CTLA4, OX40, CD40, LAG3, TIM3, GITR, and/or MR. In some embodiments, the checkpoint inhibitor is targeted at CTLA4, OX40, CD40, and/or GITR. In some embodiments, the checkpoint inhibitor is targeted with an inhibitory antibody or other similar inhibitory molecule. In some other embodiments, the checkpoint inhibitor is targeted with an agonist antibody or other similar agonist molecule. In some embodiments, the checkpoint inhibitor comprises a cytotoxic T-lymphocyte-associated antigen 4 pathway (CTLA4) inhibitor. In some embodiments, the CTLA4 inhibitor is an anti-CTLA4 antibody. In some embodiments, the anti-CTLA4 antibody is ipilimumab. In some embodiments, the checkpoint inhibitor comprises a programmed death-1 pathway (PD1) inhibitor. In some embodiments, the PD1 inhibitor is an anti-PD1 antibody. In some embodiments, the anti-PD1 antibody is nivolumab. In some embodiments, the PD1 inhibitor is an anti-PDL1 antibody. In some embodiments, the anti-PDL1 antibody is atezolizumab. In some embodiments, the checkpoint inhibitor comprises a CTLA4 inhibitor and a PD1 inhibitor. In some embodiments, the checkpoint inhibitor is targeted at OX40. In some embodiments, the checkpoint inhibitor is targeted at CD40. In some embodiments, the checkpoint inhibitor is targeted at GITR. In some embodiments, the benefit of combination therapy (e.g., the effect on at least one symptom or the risk/rate of disease progression) with a therapeutically effective amount of at least one compound chosen from compounds of Formula I, compounds of Formula II, compounds of Formula III, and pharmaceutically acceptable salts of any of the foregoing, and a checkpoint inhibitor (e.g., a CTLA4-, PD1/PDL1-, OX40-, CD40-, and/or GITR-targeted antibody or molecule) is additive. In some embodiments, the benefit of combination therapy with a therapeutically effective amount of at least one compound chosen from compounds of Formula I, compounds of Formula II, compounds of Formula III, and pharmaceutically acceptable salts of any of the foregoing, and a checkpoint inhibitor (e.g., a CTLA4-, PD1/PDL1, OX40-, CD40-, and/or GITR-targeted antibody or molecule) is superadditive (i.e., synergistic).

In some embodiments, the present disclosure provides a method of treating cancer in a subject in need thereof and/or a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing; and a cytokine or cytokine analog therapy. In some embodiments, the cytokine or cytokine analog therapy comprises administering at least one cytokine or cytokine analog. In some embodiments, the subject is intolerant, non-responsive, or poorly responsive to the at least one cytokine or cytokine analog when administered alone.

In some embodiments, the cytokine or cytokine analog comprises a T-cell enhancer. In some embodiments, the cytokine or cytokine analog comprises IL-2, IL-10, IL-12, IL-15, IFNγ, and/or TNFα. In some embodiments, the cytokine or cytokine analog comprises IL-2, IL-10, IL-12, and/or IL-15. In some embodiments, administering the cytokine or cytokine analog enhances T-cell priming following administration of a therapeutically effective amount of at least one compound chosen from compounds of Formula I, compounds of Formula II, compounds of Formula III, and pharmaceutically acceptable salts of any of the foregoing, due to induction and presentation of neoantigens.

In some embodiments, the cytokine or cytokine analog comprises IL-2. In some embodiments, IL-2 boosts signals to effector cells promoting their expansion (Rosenberg (2014) J Immunol. 192(12):5451-8). In some embodiments, the cytokine or cytokine analog comprises IL-10. In some embodiments, IL-10 boosts CD8+ T-cell priming and activation (Mumm et al. (2011) Cancer Cell 20(6):781-96). In some embodiments, the cytokine or cytokine analog comprises IL-12. In some embodiments, IL-12 links the innate and adaptive immune responses to boost antigen-specific priming and targeting (Tugues et al. (2015) Cell Death Differ. 22(2):237-46). In some embodiments, the cytokine or cytokine analog comprises IL-15. In some embodiments, IL-15 boosts T-effector (CD8) cell priming and/or activation. In some embodiments, the cytokine or cytokine analog comprises IFNγ. In some embodiments, IFNγ supplements T-effector cell secretion of IFNγ. In some embodiments, the cytokine or cytokine analog comprises TNFα. In some embodiments, TNFα supplements T-effector cell secretion of TNFα.

In some embodiments, an initial dose of a therapeutically effective amount of at least one compound chosen from compounds of Formula I, compounds of Formula II, compounds of Formula III, and pharmaceutically acceptable salts of any of the foregoing, is administered to a subject to trigger aberrant splicing and production of neoantigen peptides. After a period of time to allow for protein production and antigen presentation, in some embodiments, the subject is then administered an initial dose of a cytokine or cytokine analog to boost and/or enhance effector T-cell priming and expansion. In some embodiments, the wait period between doses of the at least one compound chosen from compounds of Formula I, compounds of Formula II, compounds of Formula III, and pharmaceutically acceptable salts of any of the foregoing, and cytokine or cytokine analog is about 2, about 3, about 4, about 5, about 6, or about 7 days. In some embodiments, the wait period is between about 3 days and about 5 days. In some embodiments, the cytokine or cytokine analog is IL-2, IL-10, IL-12, IL-15, IFNγ, and/or TNFα. In some embodiments, the combination therapeutic benefit of the at least one compound chosen from compounds of Formula I, compounds of Formula II, compounds of Formula III, and pharmaceutically acceptable salts of any of the foregoing, and a cytokine or cytokine analog may be additive or superadditive.

In some embodiments, after a period to allow for T-cell priming and expansion, the subject is then administered a second or subsequent dose of a therapeutically effective amount of at least one compound chosen from compounds of Formula I, compounds of Formula II, compounds of Formula III, and pharmaceutically acceptable salts of any of the foregoing, to trigger re-presentation of neoantigen peptides. In some embodiments, the wait period between an initial dose of a cytokine or cytokine analog and a second or subsequent dose of a therapeutically effective amount of at least one compound chosen from compounds of Formula I, compounds of Formula II, compounds of Formula III, and pharmaceutically acceptable salts of any of the foregoing, is about 2, about 3, about 4, or about 5 weeks. In some embodiments, the wait period is about 3 weeks. In some embodiments, subsequent doses of the cytokine or cytokine analog may be administered, e.g., interspersed between subsequent doses of a therapeutically effective amount of at least one compound chosen from compounds of Formula I, compounds of Formula II, compounds of Formula III, and pharmaceutically acceptable salts of any of the foregoing. Following a second or subsequent dose of a therapeutically effective amount of at least one compound chosen from compounds of Formula I, compounds of Formula II, compounds of Formula III, and pharmaceutically acceptable salts of any of the foregoing, in some embodiments, the immune system may engage with the neoantigen-presenting tumor cells and/or elicit tumor cell killing. In some embodiments, dosing of a therapeutically effective amount of at least one compound chosen from compounds of Formula I, compounds of Formula II, compounds of Formula III, and pharmaceutically acceptable salts of any of the foregoing, following this exemplary initial treatment regimen can be pulsatile, i.e., the at least one compound chosen from compounds of Formula I, compounds of Formula II, compounds of Formula III, and pharmaceutically acceptable salts of any of the foregoing, may be dosed at prolonged intervals (e.g., about every 4 weeks, about every 5 weeks, about every 6 weeks) to allow for antigen presentation, T-cell engagement and/or tumor cell killing, and/or recovery of the memory T-cell population.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer, gastric cancer, prostate cancer, ovarian cancer, lung cancer, uterine cancer, salivary duct carcinoma, melanoma, colon cancer, and esophageal cancer. In some embodiments, the solid tumor is chosen from HER2-positive breast cancer, gastric adenocarcinoma, and prostate cancer.

In some embodiments, the subject is in need of a method of treating cancer. In some embodiments, the cancer is a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer, gastric cancer, prostate cancer, ovarian cancer, lung cancer, uterine cancer, salivary duct carcinoma, melanoma, colon cancer, and esophageal cancer. In some embodiments, the solid tumor is chosen from HER2-positive breast cancer, gastric adenocarcinoma, and prostate cancer.

In some embodiments, a patient having a cancer as described herein can be treated with a combination of at least one compound chosen from compounds of Formula I, compounds of Formula II, compounds of Formula III, and pharmaceutically acceptable salts of any of the foregoing and a neoantigen vaccine. Without being bound by theory, vaccines, used alone or in combination with immune checkpoint inhibitor (ICI) molecules, have shown promise in early trials (Ott et al. (2017) Nature 547(7662):217-21; Sahin et al. (2017) Nature 547(7662):222-6), but generally require sequencing of patient tumor mutations (Ott et al. (2017)

Nature 547(7662):217-21; Aldous and Dong (2018) Bioorg. Med. Chem. 26(10):2842-9). As such, vaccines are often dependent on sufficient numbers of non-synonymous mutations that are antigenic. In general, tumors with very low mutation burden provide few candidate antigens, and those with rapid growth provide limited time to identify and produce patient-specific vaccines.

To date, attempts to develop vaccines that would be broadly immunogenic across a large percentage of patients have focused on proteins that are either frequently mutated, ectopically overexpressed, or amplified, and/or that exist as "self" proteins within the organism. In addition, these proteins are often expressed in immunologically restricted tissues (e.g., neuronal markers expressed in neuroendocrine tumor types), while others may be normally expressed during embryogenesis (e.g., oncofetal antigens). Thus, utility of vaccines using such proteins as antigens is often limited to specific tumor lineages or subsets where one or more of the antigens are presented. Vaccine utility would also need to be confirmed by sequencing of patient tumor samples, which can be time-consuming.

Moreover, if these antigens exist as "self" proteins, the immune system would likely be primed to recognize these as "self" and thus, not respond. Or, alternatively, if the immune system is able to mount an effector response to these antigens, it may lead to on-target side effects in tissues where the antigen may be expressed. In both of these cases, one of the key challenges is that most antigenic peptides are derived from "passenger" genes (i.e., genes that are mutated or amplified in the course of tumorigenesis, but that do not play a critical role in the continued survival or proliferation of the tumor itself). As such, these genes may be silenced without significant consequence to the tumor progression, and thus would allow a tumor to "escape" an immune response against these antigens. Without wishing to be bound by theory, this mechanism may play a role in tumor evolution, where random mutations that are strongly antigenic are often "selected against" by the tumor during the early stages of tumorigenesis (Dunn et al. (2004) Annu. Rev. Immunol. 22:329-60).

In addition, certain evidence also indicates that chronic antigen presentation and immune stimulation may lead to immune cell anergy and exhaustion (Pardoll (2012) Nat. Rev. Cancer 12(4):252-64). These phenotypes underlie the therapeutic rationale behind current ICI treatments, as ICI has been shown to either repress the exhausted immune cell phenotype (α-PD1/PD-L1) or to facilitate additional immune cell responses (α-CTLA4). Notably, with α-CTLA4 therapy, a certain subset of patients have been reported to exhibit severe immune-related adverse events that may be ascribed to the promotion of T-cell activation and a break of the immune tolerance mechanisms that restrain self-reactive immune responses.

Both of these approaches (i.e., triggering or enhancing de novo immune responses to neoantigens or derepressing the anergy or exhaustion of existing immune responses) are linked to a chronic immune activation. As such, these approaches are sensitive to anergy, editing, and other tumor-mediated mechanisms designed to suppress immune engagement.

In contrast, treatment with at least one compound chosen from compounds of Formula I, compounds of Formula II, compounds of Formula III, and pharmaceutically acceptable salts of any of the foregoing may induce an immune response to novel sequences representing neoantigens. In some embodiments, presentation of neoantigens provides the adaptive immune system with more divergent targets with which to engage and activate. In some embodiments, the ability of at least one compound chosen from compounds of Formula I, compounds of Formula II, compounds of Formula III, and pharmaceutically acceptable salts of any of the foregoing to acutely induce alternative splicing and the resulting neoantigens may reduce the risk of immune system fatigue due to chronic exposure to mutation-driven neoantigens and/or limit the ability of tumor cells to adapt to evade therapy. In some embodiments, administering at least one compound chosen from compounds of Formula I, compounds of Formula II, compounds of Formula III, and pharmaceutically acceptable salts of any of the foregoing in combination with a neoantigen vaccine enhances the immune response to the neoantigens produced by the at least one compound chosen from compounds of Formula I, compounds of Formula II, compounds of Formula III, and pharmaceutically acceptable salts of any of the foregoing. In some embodiments, the at least one compound chosen from compounds of Formula I, compounds of Formula II, compounds of Formula III, and pharmaceutically acceptable salts of any of the foregoing is administered before, during, or after vaccination. In some embodiments, the at least one compound chosen from compounds of Formula I, compounds of Formula II, compounds of Formula III, and pharmaceutically acceptable salts of any of the foregoing and/or vaccine may be administered once or more than once during the course of treatment. In some embodiments, the vaccine is administered once and the at least one compound chosen from compounds of Formula I, compounds of Formula II, compounds of Formula III, and pharmaceutically acceptable salts of any of the foregoing is administered more than once during the course of treatment. In some embodiments, the vaccine is administered once and then one or more boosters are administered during the course of treatment.

As used herein, the term "neoantigen vaccine" refers to a pooled sample of one or more immunogenic neoantigen peptides or mRNAs, for example at least two, at least three, at least four, at least five, or more neoantigen peptides. The term "vaccine" refers to a composition for generating immunity for the prophylaxis and/or treatment of a disease (e.g., a neoplastic disorder, e.g., a hematological malignancy or solid tumor). Accordingly, vaccines are medicaments which comprise immunogenic agents and are intended to be used in humans or animals for generating specific immune defenses and protective substances after vaccination. A neoantigen vaccine can additionally include a pharmaceutically acceptable carrier, diluent, excipient, and/or adjuvant.

As used herein, the term "immunogenic" refers to any agent or composition that can elicit an immune response, e.g., a T-cell response. The immune response can be antibody- or cell-mediated, or both.

In some embodiments, a patient is given at least one compound chosen from compounds of Formula I, compounds of Formula II, compounds of Formula III, and pharmaceutically acceptable salts of any of the foregoing and then given a peptide or mRNA vaccine of known neoantigen to enhance immune response to the neoantigens produced by the at least one compound chosen from compounds of Formula I, compounds of Formula II, compounds of Formula III, and pharmaceutically acceptable salts of any of the foregoing. In some other embodiments, a patient is given at least one compound chosen from compounds of Formula I, compounds of Formula II, compounds of Formula III, and pharmaceutically acceptable salts of any of the foregoing and screened for neoantigens produced by the treatment. Subsequently, one or more of those neoantigens are used to create a personalized vaccine that is given to the patient. In either of these embodiments, the at least one compound chosen from compounds of Formula I, compounds of Formula II, compounds of Formula III, and pharmaceutically acceptable salts of any of the foregoing and/or peptide or mRNA vaccine may be administered to the patient once or repeatedly.

In some embodiments, a suitable neoantigen for a vaccine can be identified by screening a panel of transcripts with altered splicing and robust expression from one or more tissue samples in a patient (e.g., from a tumor biopsy). In some embodiments, variant protein sequences are identified in the screened sample based on translation across the aberrantly spliced mRNA junction while retaining portions of the protein sequence (up to 12 amino acids) flanking the junction-spanning amino acid changes. In some embodiments, these junction-spanning peptide fragments are scanned for high affinity binding to MHC1 alleles, e.g., using a tool such as NetMHC1 (Nielsen et al. (2003) Protein Sci 12(5):1007-17; Andreatta and Neilsen (2016) Bioinformatics 32(4):511-7). These results allow for filtering of the neopeptides to those that are predicted high affinity binders for a unique patient HLA allele makeup as well as assembly of pools of neopeptides predicted to be broadly binding to HLA alleles that are present with high frequencies in different populations (Maiers et al. (2007) Hum Immunol 68(9):779-88). In some embodiments, the identified neopeptides are then formulated as a vaccine, e.g., by conjugation to a suitable carrier or adjuvant (Ott et al. (2017) Nature 547(7662):217-21), or for delivery as an mRNA (Sahin et al. (2017) Nature 547(7662):222-6).

In some embodiments, the selected neoantigen is based on a screen of an individual patent's tumor response to the at least one compound chosen from compounds of Formula I, compounds of Formula II, compounds of Formula III, and pharmaceutically acceptable salts of any of the foregoing to identify one or more neoantigens resulting from treatment to use in subsequent vaccination. In other embodiments, a neoantigen is chosen, e.g., based on screening a panel of samples from different patients to identify common neoantigens produced by the at least one compound chosen from compounds of Formula I, compounds of Formula II, compounds of Formula III, and pharmaceutically acceptable salts of any of the foregoing and then used as a universal vaccine for future patients.

Without being bound by theory, in some embodiments, use of a universal neoantigen vaccine would avoid the need to sequence and analyze the unique mutation status of each patient's tumor because the chosen neoantigens are not dependent on tumor mutation but rather mimic a neoantigen produced by at least one compound chosen from compounds of Formula I, compounds of Formula II, compounds of Formula III, and pharmaceutically acceptable salts of any of the foregoing and generally recognized by the body as foreign. In addition, in some embodiments, use of a neoantigen vaccine may be particularly effective since a patient's tumor cells may be more likely to mutate away from producing one or more neoantigens that are dependent on tumor mutation, as compared to those that mimic a neoantigen produced by at least one compound chosen from compounds of Formula I, compounds of Formula II, compounds of Formula III, and pharmaceutically acceptable salts of any of the foregoing. This may allow for the formulation of a bulk vaccine that would be broadly immunogenic across a large percentage of patients, expediting the initiation of a treatment regime. Patients may be vaccinated according to the schedules outlined herein and, prior to following completion of the vaccination, could be further treated with at least one compound chosen from compounds of Formula I, compounds of Formula II, compounds of Formula III, and pharmaceutically acceptable salts of any of the foregoing, e.g., to induce expression of the neoantigen peptides. In some embodiments, patients may be administered at least one compound chosen from compounds of Formula I, compounds of Formula II, compounds of Formula III, and pharmaceutically acceptable salts of any of the foregoing before, at the same time as, or after vaccination. In some embodiments, patients are administered at least one compound chosen from compounds of Formula I, compounds of Formula II, compounds of Formula III, and pharmaceutically acceptable salts of any of the foregoing, screened for one or more neoantigens found in a panel of universal neoantigens, and vaccinated with a universal neoantigen vaccine comprising at least one universal neoantigen identified in the subject. In some embodiments, patients may be administered at least one compound chosen from compounds of Formula I, compounds of Formula II, compounds of Formula III, and pharmaceutically acceptable salts of any of the foregoing once or more than once after vaccination. The at least one compound chosen from compounds of Formula I, compounds of Formula II, compounds of Formula III, and pharmaceutically acceptable salts of any of the foregoing and/or the vaccine may be administered once or more than once during the course of treatment.

In some embodiments, a vaccine may comprise one or more than one neoantigen peptide or mRNA. In some embodiments, a vaccine may comprise one or more than one long neoantigen peptide. Such "long" neoantigen peptides, in some embodiments, undergo efficient internalization, processing, and cross-presentation in professional antigen-presenting cells such as dendritic cells. Similarly, long vaccine peptides have been shown, in other contexts, to induce cytotoxic T-cells in humans (Melief and van der Burg (2008) Nat Rev Cancer 8(5):351-60). In some embodiments, a neoantigen peptide is extended to comprise the neoantigen peptide sequence itself in addition to flanking amino acid sequences. In some embodiments, the extended peptide sequence facilitates the uptake of protein by antigen-presenting cells, e.g., dendritic cells. In some embodiments, the extended peptide sequence enables efficient antigen presentation and T-cell priming in models with different HLA isotypes. In some embodiments, a longer neoantigen peptide and/or extended peptide sequence exhibits increased uptake by antigen-presenting cells (e.g., dendritic cells), increased antigen presentation, and/or increased T-cell priming, as compared to a shorter neoantigen peptide and/or shorter peptide sequence (e.g., a peptide sequence less than about 10 or less than about 5 amino acids in length). In some embodiments, a long neoantigen peptide ranges from about 5 to about 50 amino acids in length. In some embodiments, a long neoantigen peptide ranges from about 10 to about 50 amino acids in length. In some embodiments, the at least one neoantigen peptide ranges from about 10 to about 35 amino acids in length. In some embodiments, a long neoantigen peptide ranges from about 15 to about 25 amino acids in length.

In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 13).

Amino acid sequences of exemplary long neoantigen peptides are set forth in Table 13.

These exemplary neoantigen peptides are generated after administration of ADCs containing pladienolide splicing modulators, however, given the similar mechanism of action (i.e., similar mechanisms of splicing modulation), similar neoantigen peptides may be produced by compounds chosen from compounds of Formula I, compounds of Formula II, compounds of Formula III, and pharmaceutically acceptable salts of any of the foregoing.

TABLE 12

Neopeptides

| Neopeptide | SEQ ID NO | Junction (HG19) | Gene | Event type | Observed in |
|---|---|---|---|---|---|
| 1 SPTLPPRSL | 1 | chr12: 49663470-49663610: + | TUBA1C | Intron retention | H1568 |
| 2 HPSIKRGLSSL | 2 | chr12: 42729776-42781257: + | PPHLN1 | Exon skipping | H1568 |
| 3 LLLPHHVL | 3 | chr12: 49663470-49663610: + | TUBA1C | Intron retention | H1568 |
| 4 RTAPGVRPPF | 4 | chr14: 35182767-35183743: − | CFL2 | Intron retention | H1568 |
| 5 RPQKSIQAL | 5 | chr10: 28822963-28823162: + | WAC | Intron retention | H1568 |
| 6 APAPPPLPA | 6 | chr17: 80009840-80011149: + | GPS1 | Intron retention | H1568 |
| 7 RPRPSFPVSL | 7 | chr7: 55087058-55134942: + | EGFR | Intron retention | H1568 |
| 8 RPKHGDGFSL | 8 | chr11: 57472287-57472444: − | MED19 | Intron retention | H1568 |
| 9 GPAPGKTGL | 9 | chr7: 75932393-75933118: + | HSBP1 | Intron retention | H1568 |
| 10 EAARKGNSL | 10 | chr1: 53480715-53504588: + | SCP2 | Exon skipping | H1568 |
| 11 RIKEKIEEL | 11 | chr9: 72897499-72912881: + | SMC5 | Exon skipping | H1568 |
| 12 EIKKRFRQF | 12 | chr1: 28531860-28541450: − | DNAJC8 | Exon skipping | H1568 |
| 13 HESAAMAET | 13 | chr11: 102272937-102323254: − | TMEM123 | Exon skipping | HCC1954 |
| 14 ALKLKQVGV | 14 | chr1: 153610924-153617539: + | CHTOP | Exon skipping | H1568 |
| 15 DLKKRHITF | 15 | chr13: 41323417-41331008: − | MRPS31 | Exon skipping | H1568 |
| 16 DVKRNDIAM | 16 | chr1: 41213277-41218822: + | NFYC | Exon skipping | H1568 |
| 17 IPSDHILTPA | 17 | chr6: 149718900-149720239: + | TAB2 | Exon skipping | H1568 |
| 18 TVFSTSSLK | 18 | chr11: 61197654-61213412: + | SDHAF2 | Exon skipping | H1568 |
| 19 ITSCLLNF | 19 | chr5: 137892555-137893090: − | HSPA9 | Intron retention | H1568 |
| 20 RASPVRGQL | 20 | chr7: 75677544-75677893: + | MDH2 | Intron retention | H1568 |
| 21 VVRKPVIAL | 21 | chr1: 36923582-36929406: − | MRPS15 | Exon skipping | H1568 |
| 22 LLSEKKKIS | 22 | chr6: 31750622-31750872: − | VARS | Intron retention | H1568 |

TABLE 12-continued

Neopeptides

| Neopeptide | SEQ ID NO | Junction (HG19) | Gene | Event type | Observed in |
|---|---|---|---|---|---|
| 23 APASKPRPRL | 23 | chr19: 3573798-3574380: + | HMG20B | Intron retention | H1568 |
| 24 RYGQLSEKF | 24 | chr19: 33076813-33078158: + | PDCD5 | Exon skipping | HCC1954 |
| 25 VYISNVSKL | 25 | chr3: 53920961-53925796: − | SELK | Exon skipping | HCC1954 |
| 26 LPTKETPSF | 26 | chr2: 85133241-85133394: + | TMSB10 | Alt 3'ss | HCC1954 |
| 27 GEAPPPPPA | 27 | chr17: 80223672-80231181: − | CSNK1D | Intron retention | HCC1954 |
| 28 LEEISKQEI | 28 | chr17: 27804724-27807385: + | TAOK1 | Exon skipping | HCC1954 |
| 29 IYNHITVKI | 29 | chr4: 2886393-2896308: + | ADD1 | Exon skipping | HCC1954 |

The protein sequences of the twenty nine neopeptides listed in Table 12 can be extended. The extended protein sequence incorporates both the neopeptide sequence itself in addition to flanking amino acid sequences. The extended protein sequence better facilitates the uptake of protein by dendritic cells and enables antigen presentation and T-cell priming in models with different HLA isotypes. Amino acid sequences of the twenty nine extended neopeptides are set forth in Table 13.

TABLE 13

Amino acid sequences of extended neopeptides

| Gene | SEQ ID NO | Extended neopeptide amino acid sequence* |
|---|---|---|
| TUBA1C | 30 | VDLEPTVIGELTSVTQVRSQGAGTGGLSWGGSAGHSPTLPPRSLSLLLLPHHVLQMKFALALTASSSTLNSSQARKMLPITMPEGTTPLARRSLTSCWTEFASWLTSAPVFRASWFSTALVGELVLGSPRCSWNVSQLIMARSPSWSSPFTRRPRFPQL |
| PPHLN1 | 31 | APPRSHPSIKRGLSSL |
| CFL2 | 32 | MVRRARWPGGRGEARKAPRTAPGVRPPF |
| WAC | 33 | WVNCLFVSGRAAAGGGGGAVPPYLELAGPPFLLLTLIRIGLGRRSGRAGGRAGTQCGGERGPGFAAFRPLRPFRRLRVCAVCVRGSALGRSVGLPRGGAAGAPFSSSPAPHPRRVLCRCLLFLFFSCHDRRGDSQPYQVPAEAGVEGLEGAGGGREGLLLERRPQKSIQALRCNTSETSTADPLKIPGLVPLALSSKV |
| GPS1 | 34 | MPLPVQVFNLQVTSRGRPGPPRPRAPRHWGRAEVEQRGRGACARSRSGTLRAGPPRAARVGGCRAEGASPPWLRAAIGGRRAAPAPPPLPAAHGRGSRPPRR |
| EGFR | 35 | QPAQPRTGAPARRPRPRPSFPVSLRSAAPPTGTAGGTGRFVLRPGESGAGGGGDAWDTGLQARRGTAAGTSGAPNRSQLSSLTFPAQLRRIGVSGRKPGAGGRLGPGSRTCAPRCLPRARRGPGAHPRGGRCPPAETALFREAEEGTQKYSLPSDPAGQAAF |
| MED19 | 36 | FRLHTGPVSPVGGRRQMGRPKHGDGFSLQVCSFIMEQNG |
| HSBP1 | 37 | GVVEITGEPPCSCRGEEEASRAGRAGGVRLKRGSRGPGELNVGPAPGKTGLLIPLLRNWECGSLLRALSAL |
| SCP2 | 38 | KMGFPEAARKGNSL |
| SMC5 | 39 | LEARIKEKIEELQQALI |
| DNAJC8 | 40 | EIKKRFRQFKQAVYKQ |
| TMEM123 | 41 | AHESAAMAETLQHVPS |
| CHTOP | 42 | NRPSVQAALKLKQVGV |
| MRPS31 | 43 | KTDDLKKRHITFTLGCGIC |
| NFYC | 44 | MKLDEDVKRNDIAMAI |
| TAB2 | 45 | NSISQIPSDHILTPALFITFMTILDL |
| SDHAF2 | 46 | TVFSTSSLKLNQPQKYLKMKSWPC |
| HSPA9 | 47 | AEEDRRKKVITSCLLNFNLSKAQS |
| MDH2 | 48 | RSFSTSAQVGQTRGGLQAEAPRPGPRASPVRGQL |
| MRPS15 | 49 | RGYVVRKPVIALSVKI |
| VARS | 50 | VDMDFGTGQGAGPVGRGKDWSCTLAVHLLSEKKISFSQIDRAWGGSQGTVLDKWGPGVVSELHPSAKEVSVGRNSVESLMTWAS |

TABLE 13-continued

Amino acid sequences of extended neopeptides

| Gene | SEQ ID NO | Extended neopeptide amino acid sequence* |
|---|---|---|
| HMG20B | 51 | EKGSHEEEVRVPALSWGRPRAPAPAS KPRPRLDLNCLWLRPQPIFLWKLRPR PVPAATPLTGPLPL |
| PDCD5 | 52 | RYGQLSEKFNRRKVMDS |
| SELK | 53 | MVYISNVSKLCFSKM |
| TMSB10 | 54 | NTLPTKETPSFLLNPHTSWVPRPHRE APRLRVGVAAPLQRPLPALHSH |
| CSNK1D | 55 | FGDIYLGEAPPPPPAARRPGPCGCQD QARSRKEVVAPAGSPRKSRHRRIVAR TQRPLG |
| TAOK1 | 56 | GSASDLLEEISKQEISF |
| ADD1 | 57 | QLIYNHITVKINLQGD |

*Underline indicates amino acids derived from the canonical transcript reading open frame (i.e., the canonical peptide sequence).

As used herein, a neoantigen peptide or mRNA vaccine encompasses using a fragment of a neoantigen peptide or its encoding mRNA, so long as that fragment retains immunogenic potential.

In some embodiments, a neoantigen vaccine comprises at least one neoantigen peptide. In some embodiments, a neoantigen vaccine comprises at least 2, at least 3, at least 4, at least 5, at least 6, at least 7, at least 8, at least 9, at least 10, at least 12, at least 15, or at least 20 neoantigen peptides. In some embodiments, the neoantigen peptide(s) range from about 5 to about 50 amino acids in length. In some embodiments, the neoantigen peptide(s) range from about 10 to about 50 amino acids in length. In some embodiments, the at least one neoantigen peptide ranges from about 10 to about 35 amino acids in length. In some embodiments, the neoantigen peptide(s) range from about 15 to about 25 amino acids in length.

In some embodiments, the present disclosure provides a method of treating a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing; and a neoantigen vaccine. A neoantigen vaccine may be, e.g., a peptide or mRNA neoantigen vaccine. In some embodiments, the at least one compound chosen from compounds of Formula I, compounds of Formula II, compounds of Formula III, and pharmaceutically acceptable salts of any of the foregoing is administered before administration of the neoantigen vaccine. In some embodiments, the at least one compound chosen from compounds of Formula I, compounds of Formula II, compounds of Formula III, and pharmaceutically acceptable salts of any of the foregoing is administered after administration of the neoantigen vaccine. In some embodiments, the at least one compound chosen from compounds of Formula I, compounds of Formula II, compounds of Formula III, and pharmaceutically acceptable salts of any of the foregoing is administered concurrently with administration of the neoantigen vaccine. In some embodiments, administration of the at least one compound chosen from compounds of Formula I, compounds of Formula II, compounds of Formula III, and pharmaceutically acceptable salts of any of the foregoing is repeated at least once after initial administration. In some embodiments, the amount of the at least one compound chosen from compounds of Formula I, compounds of Formula II, compounds of Formula III, and pharmaceutically acceptable salts of any of the foregoing used for repeated administration is reduced as compared to the amount used for initial administration.

In some embodiments, the present disclosure further provides a combination comprising at least one compound chosen from compounds of Formula I, compounds of Formula II, compounds of Formula III, and pharmaceutically acceptable salts of any of the foregoing; and a neoantigen vaccine (e.g., a universal neoantigen vaccine) for use in treating a subject having or suspected of having a neoplastic disorder. In some embodiments, the neoantigen vaccine is a peptide or mRNA neoantigen vaccine. In some embodiments, the combination further comprises at least one additional therapy. In some embodiments, the at least one additional therapy comprises at least one, at least two, at least three, at least four, or at least five additional therapies.

In some embodiments, the present disclosure further provides a method of treating a subject having or suspected of having a neoplastic disorder by (a) administering to the subject a therapeutically effective amount of at least one compound chosen from compounds of Formula I, compounds of Formula II, compounds of Formula III, and pharmaceutically acceptable salts of any of the foregoing; (b) detecting one or more neoantigens in the subject after administration of the at least one compound chosen from compounds of Formula I, compounds of Formula II, compounds of Formula III, and pharmaceutically acceptable salts of any of the foregoing; (c) comparing the one or more neoantigens to a panel of universal neoantigens; and (d) administering to the subject a universal neoantigen vaccine comprising at least one universal neoantigen present in the subject. In some embodiments, the universal neoantigen vaccine is administered alone or in combination with at least one additional therapy. In some embodiments, the at least one additional therapy comprises at least one, at least two, at least three, at least four, or at least five additional therapies.

In some embodiments, the at least one additional therapy comprises repeated administration of the at least one compound chosen from compounds of Formula I, compounds of Formula II, compounds of Formula III, and pharmaceutically acceptable salts of any of the foregoing. In some embodiments, repeated administration of the at least one compound chosen from compounds of Formula I, compounds of Formula II, compounds of Formula III, and pharmaceutically acceptable salts of any of the foregoing is initiated before administration of the universal neoantigen vaccine. In some embodiments, repeated of the at least one compound chosen from compounds of Formula I, compounds of Formula II, compounds of Formula III, and pharmaceutically acceptable salts of any of the foregoing is initiated after administration of the universal neoantigen vaccine. In some embodiments, repeated administration of the at least one compound chosen from compounds of Formula I, compounds of Formula II, compounds of Formula III, and pharmaceutically acceptable salts of any of the foregoing is initiated concurrently with administration of the universal neoantigen vaccine. In some embodiments, the amount of the at least one compound chosen from compounds of Formula I, compounds of Formula II, compounds of Formula III, and pharmaceutically acceptable salts of any of the foregoing used for repeated administration is reduced as compared to the amount used for initial administration. In some embodiments, the amount of the at least one compound chosen from compounds of Formula I, compounds of Formula II, compounds of Formula III, and pharmaceutically acceptable salts of any of the foregoing used for the initial and/or repeated administration is reduced as compared to a standard dosage of the at least one compound chosen from compounds of Formula I, compounds of Formula II, compounds of Formula III, and pharmaceutically acceptable salts of any of the foregoing when used without a vaccine treatment. In some embodiments, the amount of the at least one compound chosen from compounds of Formula I, compounds of Formula II, compounds of Formula III, and pharmaceutically acceptable salts of any of the foregoing used for initial and/or repeated administration is reduced by 10%, 15%, 20%, 25%, 30%, 35%, 40%, 45%, 50%, 75%, or 90%, as compared to a standard dosage of the at least one compound chosen from compounds of Formula I, compounds of Formula II, compounds of Formula III, and pharmaceutically acceptable salts of any of the foregoing.

In some embodiments, the at least one additional therapy comprises administering a checkpoint inhibitor (e.g., any of the exemplary checkpoint inhibitors described herein). In some embodiments, administration of the checkpoint inhibitor is initiated before administration of the universal neoantigen vaccine and/or repeated administration of the at least one compound chosen from compounds of Formula I, compounds of Formula II, compounds of Formula III, and pharmaceutically acceptable salts of any of the foregoing. In some embodiments, administration of the checkpoint inhibitor is initiated after administration of the universal neoantigen vaccine and/or repeated of the at least one compound chosen from compounds of Formula I, compounds of Formula II, compounds of Formula III, and pharmaceutically acceptable salts of any of the foregoing. In some embodiments, administration of the checkpoint inhibitor is initiated concurrently with administration of the universal neoantigen vaccine and/or repeated administration of the at least one compound chosen from compounds of Formula I, compounds of Formula II, compounds of Formula III, and pharmaceutically acceptable salts of any of the foregoing. In some embodiments, administration of the checkpoint inhibitor is repeated at least once after initial administration. In some embodiments, the amount of the checkpoint inhibitor used for repeated administration is reduced as compared to the amount used for initial administration. In some embodiments, the amount of the checkpoint inhibitor used for repeated administration is reduced as compared to a standard dosage of the checkpoint inhibitor. In some embodiments, the amount of the checkpoint inhibitor used for repeated administration is reduced by 10%, 15%, 20%, 25%, 30%, 35%, 40%, 45%, 50%, 75%, or 90%, as compared to a standard dosage of the checkpoint inhibitor. In some embodiments, the subject is intolerant, non-responsive, or poorly responsive to the checkpoint inhibitor when administered alone.

Also provided herein, in some embodiments, are neoantigen vaccines comprising at least one neoantigen peptide or at least one neoantigen mRNA. In some embodiments, a neoantigen vaccine comprises at least one neoantigen peptide. In some other embodiments, a neoantigen vaccine comprises at least one neoantigen mRNA.

Also provided herein, in some embodiments, are kits comprising at least one compound chosen from compounds of Formula I, compounds of Formula II, compounds of Formula III, and pharmaceutically acceptable salts of any of the foregoing; and a neoantigen vaccine (e.g., a universal neoantigen vaccine). In some embodiments, the neoantigen vaccine is a peptide or mRNA neoantigen vaccine. In some embodiments, the kit further comprises one or more additional components, including but not limited to: instructions for use; other agents, e.g., one or more additional therapeutic agents; devices, containers, or other materials for preparing the at least one compound chosen from compounds of Formula I, compounds of Formula II, compounds of Formula III, and pharmaceutically acceptable salts of any of the foregoing, and/or neoantigen vaccine for therapeutic administration; pharmaceutically acceptable carriers; and devices, containers, or other materials for administering the at least one compound chosen from compounds of Formula I, compounds of Formula II, compounds of Formula III, and pharmaceutically acceptable salts of any of the foregoing, and/or neoantigen vaccine to a patient. Instructions for use can include guidance for therapeutic applications including suggested dosages and/or modes of administration, e.g., in a patient having or suspected of having a neoplastic disorder. In some embodiments, the kit further contains instructions for therapeutic use, e.g., use of the at least one compound chosen from compounds of Formula I, compounds of Formula II, compounds of Formula III, and pharmaceutically acceptable salts of any of the foregoing, and the neoantigen vaccine to treat or prevent a neoplastic disorder in a patient. In some embodiments, the kit further contains at least one additional therapeutic agent (e.g., for administering together with the at least one compound chosen from compounds of Formula I, compounds of Formula II, compounds of Formula III, and pharmaceutically acceptable salts of any of the foregoing, and the neoantigen vaccine, e.g., a checkpoint inhibitor). In some embodiments, the at least one compound chosen from compounds of Formula I, compounds of Formula II, compounds of Formula III, and pharmaceutically acceptable salts of any of the foregoing, and/or neoantigen vaccine is formulated as a pharmaceutical composition.

In some embodiments of the methods and compositions disclosed herein, the neoantigen vaccine comprises at least one neoantigen peptide. In some embodiments, the at least one neoantigen peptide ranges from about 10 to about 50 amino acids in length. In some embodiments, the at least one neoantigen peptide ranges from about 10 to about 35 amino acids in length. In some embodiments, the at least one neoantigen peptide ranges from about 15 to about 25 amino acids in length.

In some embodiments, the at least one neoantigen peptide comprises one or more than one neoantigen sequence disclosed herein.

In some embodiments, the neoantigen sequence and/or antigenic portion ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 13).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen peptide induced in the subject by administering a therapeutically effective amount of the at least one compound chosen from compounds of Formula I, compounds of Formula II, compounds of Formula III, and pharmaceutically acceptable salts of any of the foregoing. In some embodiments, the at least one neoantigen peptide comprises a neoantigen sequence induced by contacting a neoplastic cell with a therapeutically effective amount of the at least one compound chosen from compounds of Formula I, compounds of Formula II, compounds of Formula III, and pharmaceutically acceptable salts of any of the foregoing. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen peptide or mRNA and a pharmaceutically acceptable carrier. In some embodiments, a neoantigen peptide or mRNA can be linked to a suitable carrier to help elicit an immune response. Exemplary carriers for linking to immunogenic agents (e.g., a neoantigen peptide or mRNA) include serum albumins, keyhole limpet hemocyanin, immunoglobulin molecules, thyroglobulin, ovalbumin, tetanus toxoid, or a toxoid from other pathogenic bacteria, such as diphtheria, E. coli, cholera, or H. pylori, or an attenuated toxin derivative. Other carriers for stimulating or enhancing an immune response include cytokines such as IL-1, IL-1α and β peptides, IL-2, γINF, IL-10, GM-CSF, and chemokines, such as M1P1α and β and RANTES. Immunogenic agents can also be linked to peptides that enhance transport across tissues, as described, e.g., in WO 97/17613 and WO 97/17614. In some embodiments, the pharmaceutically acceptable carrier is chosen from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen peptide or mRNA may be linked to the pharmaceutically acceptable carrier. Immunogenic agents can be linked to carriers by chemical crosslinking. Techniques for linking an immunogenic peptide to a carrier include the formation of disulfide linkages using N-succinimidyl-3-(2-pyridyl-thio) propionate (SPDP) and succinimidyl 4-(N-maleimidomethyl)cyclohexane-1-carboxylate (SMCC) (if the peptide lacks a sulfhydryl group, this can be provided by addition of a cysteine residue). These reagents create a disulfide linkage between themselves and peptide cysteine resides on one protein and an amide linkage through the epsilon-amino on a lysine, or other free amino group in other amino acids. A variety of such disulfide/amide-forming agents are described in Jansen et al. ((1982) Immun Rev. 62:185). Other bifunctional coupling agents form a thioether rather than a disulfide linkage. Many of these thioether-forming agents are commercially available and include reactive esters of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt. In some embodiments, the neoantigen peptide and the pharmaceutically acceptable carrier are covalently attached via a linker.

Neoantigen and other such immunogenic peptides can also be expressed as fusion proteins with carriers. The immunogenic peptide can be linked at the amino terminus, the carboxyl terminus, or at a site anywhere within the peptide (internally) to the carrier. In some embodiments, multiple repeats of the immunogenic peptide can be present in the fusion protein. In some embodiments, the neoantigen peptide and the pharmaceutically acceptable carrier are expressed as a fusion protein.

In some embodiments, the neoantigen vaccine comprises at least one neoantigen peptide or its encoding mRNA and a pharmaceutically acceptable diluent. In some embodiments, the neoantigen vaccine comprises at least one neoantigen peptide or its encoding mRNA and a pharmaceutically acceptable adjuvant (e.g., an adjuvant as described herein).

In some embodiments of the methods and compositions disclosed herein, the neoantigen vaccine comprises at least one neoantigen mRNA. In some embodiments, the at least one neoantigen mRNA encodes one or more than one neoantigen sequence.

In some embodiments, the neoantigen sequence and/or antigenic portion ranges from about 10 to about 50 amino acids in length. In some embodiments, the at least one neoantigen peptide ranges from about 10 to about 35 amino acids in length. In some embodiments, the neoantigen sequence and/or antigenic portion ranges from about 15 to about 25 amino acids in length. In some embodiments, the neoantigen sequence and/or antigenic portion ranges from about 10 to about 20 amino acids in length. In some embodiments, the neoantigen sequence and/or antigenic portion does not exclusively overlap or consist of the canonical peptide sequence (e.g., any of the exemplary canonical peptide sequences underlined in Table 13).

In some embodiments, the neoantigen sequence is a neoantigen sequence specific to the subject. In some embodiments, the neoantigen sequence is a personalized neoantigen vaccine for the subject. In some embodiments, the neoantigen sequence is capable of binding to at least one HLA allele expressed in the subject.

In some other embodiments, the neoantigen sequence is a universal neoantigen sequence. In some embodiments, the neoantigen sequence is a universal neoantigen vaccine. In some embodiments, the neoantigen sequence is capable of binding to at least one HLA allele expressed in at least 10%, at least 15%, at least 20%, at least 25%, at least 30%, at least 35%, at least 40%, or at least 45% of subjects in a population of subjects suffering from the neoplastic disorder. In some embodiments, the neoantigen sequence is capable of eliciting a T-cell response against a tumor present in at least 1%, at least 5%, or at least 10% of a population of subjects suffering from the neoplastic disorder.

In some embodiments, the neoantigen sequence has been identified by sequencing at least one neoantigen mRNA induced in the subject by administering a therapeutically effective amount of the at least one compound chosen from compounds of Formula I, compounds of Formula II, compounds of Formula III, and pharmaceutically acceptable salts of any of the foregoing. In some embodiments, the at least one neoantigen mRNA encodes a neoantigen sequence induced by contacting a neoplastic cell with a therapeutically effective amount of the at least one compound chosen from compounds of Formula I, compounds of Formula II, compounds of Formula III, and pharmaceutically acceptable salts of any of the foregoing. In some embodiments, the neoplastic cell is present in an in vitro cell culture. In some embodiments, the neoplastic cell is obtained from the subject. In some embodiments, the neoplastic cell is present in the subject.

In some embodiments, the neoantigen vaccine comprises at least one neoantigen mRNA and a pharmaceutically acceptable carrier. In some embodiments, the at least one neoantigen mRNA is linked to the pharmaceutically acceptable carrier. In some embodiments, the pharmaceutically acceptable carrier is chosen from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, the neoantigen vaccine comprises at least one neoantigen mRNA and a pharmaceutically acceptable diluent. In some embodiments, the neoantigen vaccine comprises at least one neoantigen mRNA and a pharmaceutically acceptable adjuvant (e.g., an adjuvant as described herein).

In some embodiments, the neoantigen mRNA is encapsulated by an encapsulating agent. In some embodiments, the encapsulating agent protects the neoantigen mRNA from degradation and improves vaccine delivery (McNamara et al. (2015) J Immunol Res. 2015:794528). In some embodiments, the encapsulating agent is a liposome. In some embodiments, the liposome is a cationic liposome such as N-[1-(2,3-dioleoloxy)propyl]-N,N,N-trimethyl ammonium chloride 1 (DOTAP). In some embodiments, the encapsulating agent is a nanoparticle. In some embodiments, the nanoparticle protects the neoantigen mRNA from nuclease degradation and/or enhances cell uptake and/or delivery efficiency. In some embodiments, the nanoparticle may be engineered to be fully degradable. In some embodiments, the nanoparticle is a biodegradable core-shell structured nanoparticle with a pH responsive poly-(b-amino ester) (PBAE) core enveloped by a phospholipid shell (Su et al. (2011) Mol Pharm. 8(3):774-87). In some embodiments, such nanoparticles are particularly efficient in delivering mRNA in vivo and eliciting an anti-tumor immune response.

In some embodiments, the subject has a non-synonymous mutational burden of about 150 mutations or less. In some embodiments, the subject has a non-synonymous mutational burden of about 100 mutations or less. In some embodiments, the subject has a non-synonymous mutational burden of about 50 mutations or less. In some embodiments, the subject has or is suspected of having a neoplastic disorder, e.g., a hematological malignancy or a solid tumor. In some embodiments, the hematological malignancy is chosen from a B-cell malignancy, a leukemia, a lymphoma, and a myeloma. In some embodiments, the hematological malignancy is chosen from acute myeloid leukemia and multiple myeloma. In some embodiments, the solid tumor is chosen from breast cancer, gastric cancer, prostate cancer, ovarian cancer, lung cancer, uterine cancer, salivary duct carcinoma, melanoma, colon cancer, and esophageal cancer. In some embodiments, the solid tumor is chosen from HER2-positive breast cancer, gastric adenocarcinoma, and prostate cancer.

As used herein, "adjuvant" refers to a substance that is capable of increasing, amplifying, or modulating an immune response to an accompanying immunogenic agent, e.g., a neoantigen peptide or mRNA. In certain embodiments, a neoantigen of the present disclosure can be administered in combination with adjuvants, i.e., substances that do not themselves cause adaptive immune responses, but amplify or modulate the response to an accompanying neoantigen. A variety of adjuvants can be used in combination with the disclosed neoantigens, in order to elicit an immune response. In some embodiments, the adjuvant(s) are chosen to augment the intrinsic response to the neoantigen without causing conformational changes in the neoantigen that would affect the qualitative form of the response. In some embodiments, the adjuvant(s) are chosen to enhance T-effector (e.g., CD8) cell priming and/or activation.

In certain embodiments, the adjuvant is an aluminum salt (alum), such as aluminum hydroxide, aluminum phosphate, and aluminum sulphate. Such adjuvants can be used with or without other specific immunostimulating agents, such as 3 de-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2'dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP)), or other bacterial cell wall components. Other adjuvants are oil-in-water emulsions and include (a) MF59 (WO 90/14837), containing 5% Squalene, 0.5% Tween 80, and 0.5% Span 85 (optionally containing various amounts of MTP-PE) formulated into submicron particles using a microfluidizer such as Model 110Y microfluidizer (Microfluidics), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (c) Ribi™ adjuvant system (RAS), (Ribi ImmunoChem) containing 2% squalene, 0.2% Tween 80, and one or more bacterial cell wall components from the group consisting of monophosphoryllipid A (MPL), trehalose dimycolate (TDM), and cell wall skeleton (CWS), for example MPL-FCWS (Detox™). In some embodiments, the adjuvant is a saponin, such as Stimulon™ (QS21) or particles generated therefrom such as ISCOMs (immunostimulating complexes) and ISCOMATRIX. Other adjuvants include Complete Freund's Adjuvant (CFA) and Incomplete Freund's Adjuvant (IFA), cytokines, such as interleukins (IL-1, IL-2, and IL-12), macrophage colony stimulating factor (M-CSF), and tumor necrosis factor (TNF).

An adjuvant can be administered with an immunogenic agent (e.g., a neoantigen peptide or mRNA) as a single composition, or can be administered before, concurrent with, or after administration of the immunogenic agent. In some embodiments, the immunogenic agent and adjuvant can be packaged and supplied in the same vial or can be packaged in separate vials and mixed before use. In some embodiments, the immunogenic agent and adjuvant can be packaged with a label, indicating the intended therapeutic application. In some embodiments, if the immunogenic agent and adjuvant are packaged separately, the packaging can include instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al. (1998) Adv Drug Deliv Rev. 32:173-186) alone or optionally in combination with any of alum, QS21, and MPL and all combinations thereof are suitable for human administration.

In some embodiments, the present disclosure further provides methods of screening for and identifying at least one neoantigen. More specifically, in some embodiments, the present disclosure provides a method of identifying at least one neoantigen by (a) contacting a neoplastic cell with a therapeutically effective amount of at least one compound chosen from compounds of Formula I, compounds of Formula II, compounds of Formula III, and pharmaceutically acceptable salts of any of the foregoing; (b) detecting at least one alternatively-spliced mRNA transcript after contacting the neoplastic cell with the at least one compound chosen from compounds of Formula I, compounds of Formula II, compounds of Formula III, and pharmaceutically acceptable salts of any of the foregoing; (c) predicting translation of the at least one alternatively-spliced mRNA transcript into at least one peptide; and (d) comparing the at least one peptide to a reference proteome, wherein at least one neoantigen is identified if the at least one peptide does not match any peptides in the reference proteome. In some embodiments, the method further comprises contacting one or more additional neoplastic cells to identify at least one universal neoantigen. In some embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In various other embodiments, the present disclosure provides a method of identifying at least one neoantigen by (a) contacting a neoplastic cell with a therapeutically effective amount of at least one compound chosen from compounds of Formula I, compounds of Formula II, compounds of Formula III, and pharmaceutically acceptable salts of any of the foregoing; (b) detecting at least one peptide comprising a potential neoantigen sequence after contacting the neoplastic cell with the at least one compound chosen from compounds of Formula I, compounds of Formula II, compounds of Formula III, and pharmaceutically acceptable salts of any of the foregoing; and (c) comparing the at least one peptide to a reference proteome, wherein at least one neoantigen is identified if the at least one peptide does not match any peptides in the reference proteome. In some embodiments, the method further comprises contacting one or more additional neoplastic cells to identify at least one universal neoantigen. In some embodiments, the method is repeated on one or more additional neoplastic cells or samples (e.g., a tissue biopsy) to confirm suitable neoantigens (e.g., for use in a neoantigen vaccine) and/or to identify one or more universal neoantigens.

In some embodiments of the neoantigen identification methods described herein, detecting at least one alternatively-spliced mRNA transcript comprises RNAseq. In some embodiments, predicting translation of the at least one alternatively-spliced mRNA transcript comprises quantifying the change in percent spliced in (dPSI) value for the at least one transcript. In some embodiments, predicting translation of the at least one alternatively-spliced mRNA transcript comprises RiboSeq and/or ribosomal profiling.

In some embodiments of the neoantigen identification methods described herein, the methods further comprise evaluating the at least one peptide for predicted major histocompatibility complex (MHC) binding. In some embodiments, predicted MHC binding is determined by measuring raw affinity predicted binding strength of the at least one peptide. In some embodiments, a raw affinity predicted binding strength of about 500 nM or higher indicates MHC binding. In some embodiments, predicted MHC binding is determined by identifying a distribution of predicted binding strengths for a series of random peptides; and comparing predicted binding strength of the at least one peptide to the distribution. In some embodiments, a predicted binding strength in the top 2% of the distribution indicates weak MHC binding. In some embodiments, a predicted binding strength in the top 0.5% of the distribution indicates strong MHC binding.

In some embodiments of the neoantigen identification methods described herein, the neoplastic cell is present in an in vitro cell culture. In some embodiments, the neoplastic cell is obtained from the subject. In some embodiments, the neoplastic cell is present in the subject.

Also provided herein, in some embodiments, are methods of making a neoantigen vaccine by (a) identifying at least one neoantigen (e.g., at least one neoantigen peptide or its encoding mRNA) using any of the exemplary identification methods disclosed herein; and (b) formulating the at least one neoantigen together with a pharmaceutically acceptable carrier, diluent, or adjuvant (e.g., any of the pharmaceutically acceptable carriers, diluents, or adjuvants described herein).

In some embodiments, the at least one neoantigen and/or antigenic portion ranges from about 10 to about 50 amino acids in length. In some embodiments, the at least one neoantigen peptide ranges from about 10 to about 35 amino acids in length. In some embodiments, the at least one neoantigen and/or antigenic portion ranges from about 15 to about 25 amino acids in length. In some embodiments, the at least one neoantigen and/or antigenic portion ranges from about 10 to about 20 amino acids in length. In some embodiments, the at least one neoantigen and/or antigenic portion does not exclusively overlap or consist of the canonical peptide sequence (e.g., any of the exemplary canonical peptide sequences underlined in Table 13).

In some embodiments, the at least one neoantigen used in the vaccine is linked to the pharmaceutically acceptable carrier. In some embodiments, the pharmaceutically acceptable carrier is chosen from a peptide, a serum albumin, a keyhole limpet hemocyanin, an immunoglobulin, a thyroglobulin, an ovalbumin, a toxoid or an attenuated toxoid derivative, a cytokine, and a chemokine.

In some embodiments, a patient having a cancer as described herein can be treated with a combination of at least one compound chosen from compounds of Formula I, compounds of Formula II, compounds of Formula III, and pharmaceutically acceptable salts of any of the foregoing and one or more engineered tumor-targeting T-cells (i.e., CAR-T). Thus, in some embodiments, the present disclosure provides a method of treating a subject having or suspected of having a neoplastic disorder by administering to the subject a therapeutically effective amount of at least one compound chosen from compounds of Formula I, compounds of Formula II, compounds of Formula III, and pharmaceutically acceptable salts of any of the foregoing; and engineered tumor-targeting T-cells (i.e., CAR-T). In some embodiments, a chimeric T-cell receptor can be engineered using antigen recognition sequences that are reactive with an identified neoantigen.

For instance, in some embodiments, in order to target changes in the extracellular domains of cell surface proteins induced by at least one compound chosen from compounds of Formula I, compounds of Formula II, compounds of Formula III, and pharmaceutically acceptable salts of any of the foregoing, a chimeric antigen-reactive T-cell receptor (CAR) may be engineered by first identifying antibodies that recognize a cell surface-expressed neoantigen protein domain. The antigen recognition sequences of such antibodies can then be fused to a T-cell receptor domain for selective targeting and activation.

In various other embodiments, a strategy integrating the antigen presentation machinery of tumor cells together with neoantigens derived from at least one compound chosen from compounds of Formula I, compounds of Formula II, compounds of Formula III, and pharmaceutically acceptable salts of any of the foregoing is employed. In some embodiments, cells containing known and frequently represented HLA alleles (e.g., HLA-A*02:01) can be treated with at least one compound chosen from compounds of Formula I, compounds of Formula II, compounds of Formula III, and pharmaceutically acceptable salts of any of the foregoing and MHC1-bound neoantigens are identified by ligandomics. In some embodiments, these peptides can be used to prime and/or expand T-cells from healthy donors expressing the same HLA allele. Such T-cells, in some embodiments, can be isolated and the T-cell receptor (TCR) α and β chains sequenced to identify the cognate antigen recognition/variable regions. In some embodiments, a cognate CAR can then be engineered.

In some embodiments, the CAR sequences are cloned into patient-derived T-cell populations and expanded using currently available protocols. In some embodiments, the engineered T-cells are then transfused back into the patient's circulation, before, simultaneously with, or following treatment with at least one compound chosen from compounds of Formula I, compounds of Formula II, compounds of Formula III, and pharmaceutically acceptable salts of any of the foregoing. After treatment with the at least one compound chosen from compounds of Formula I, compounds of Formula II, compounds of Formula III, and pharmaceutically acceptable salts of any of the foregoing, in some embodiments, the tumor cells may begin to present an antigen, e.g., an antigen targeted by the engineered T-cell population. In some embodiments, the engineered T-cell population can engage with and kill antigen presenting tumor cells.

In order that the disclosure described herein may be more fully understood, the following examples are set forth. It should be understood that these examples are for illustrative purposes only and are not to be construed as limiting this disclosure in any manner.

EXAMPLES 1-205

General: Microwave heating was done using a Biotage Emrys Liberator or Initiator microwave. Column chromatography was carried out using an Isco Rf200d. Solvent removal was carried out using either a BUchi rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using a Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimentals for preparing compounds of the present disclosure are set forth below. In certain cases, a particular compound is described by way of example. However, it will be appreciated that in each case a series of compounds of the present disclosure were prepared in accordance with the schemes and experimentals described below.

The following abbreviations are used herein:
COMU: (1-Cyano-2-ethoxy-2-oxoethylidenaminooxy)dimethylamino-morpholino-carbenium hexafluorophosphate
DMAP: 4-(Dimethylamino)pyridine
DMP: Dess Martin Periodinane
EDC: N-(3-Dimethylaminopropyl)-N'-ethylcarbodiimide
KHMDS: Potassium bis(trimethylsilyl)amide
LCMS: Liquid chromatography—mass spectrometry
$Pd_2(dba)_3$: Tris(dibenzylideneacetone)dipalladium(0)
TBAF: Tetrabutylammonium fluoride
TBSCl: tert-Butyldimethylsilyl chloride
TBSOTf: tert-Butyldimethylsilyl trifluoromethanesulfonate
TESCl: Chlorotriethylsilane
THF: Tetrahy drofuran
TLC: Thin-layer chromatography
pTsOH: p-Toluenesulfonic acid
PPTS: Pyridinium p-toluenesulfonate Materials: The following compounds are commercially available and/or can be prepared in a number of ways well known to one skilled in the art of organic synthesis. More specifically, disclosed compounds can be prepared using the reactions and techniques described herein. In the description of the synthetic methods described below, it is to be understood that all proposed reaction conditions, including choice of solvent, reaction atmosphere, reaction temperature, duration of the experiment, and workup procedures, can be chosen to be the conditions standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

LCMS information: Mobile phases: A (0.1% formic acid in $H_2O$) and B (0.1% formic acid in acetonitrile). Gradient: B 5%→95% in 1.8 minutes. Column: Acquity BEH C18 column (1.7 um, 2.1×50 mm).

U.S. Pat. Nos. 7,884,128 and 7,816,401, both entitled: Process for Total Synthesis of Pladienolide B and Pladienolide D, describe methods known in the art for synthesis of Pladienolide B and D. Synthesis of Pladienolide B and D may also be performed using methods known in the art and described in Kanada et al., "Total Synthesis of the Potent Antitumor Macrolides Pladienolide B and D," *Angew. Chem. Int. Ed.* 46:4350-4355 (2007). Kanada et al. and PCT application publication WO 2003/099813, entitled: Novel Physiologically Active Substances, describe methods known in the art for the synthesis of E7107 (Compound 45 of WO '813) from Pladienolide D (11107D of WO '813). A corresponding U.S. Pat. No. 7,550,503 to Kotake et al.

Exemplified Synthesis of Compounds
Compounds 1-60 (Table I) were prepared by the method of Scheme 1.
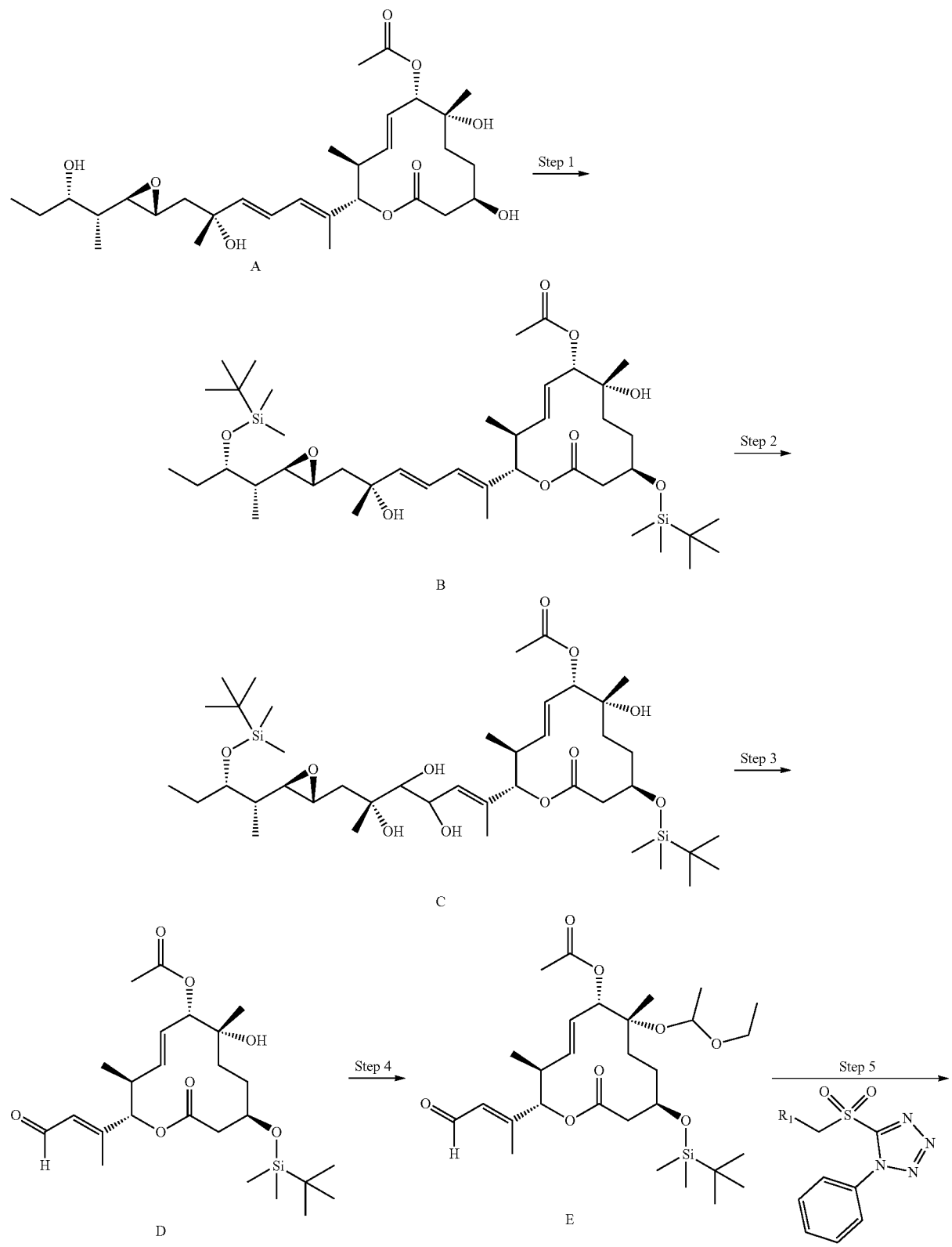

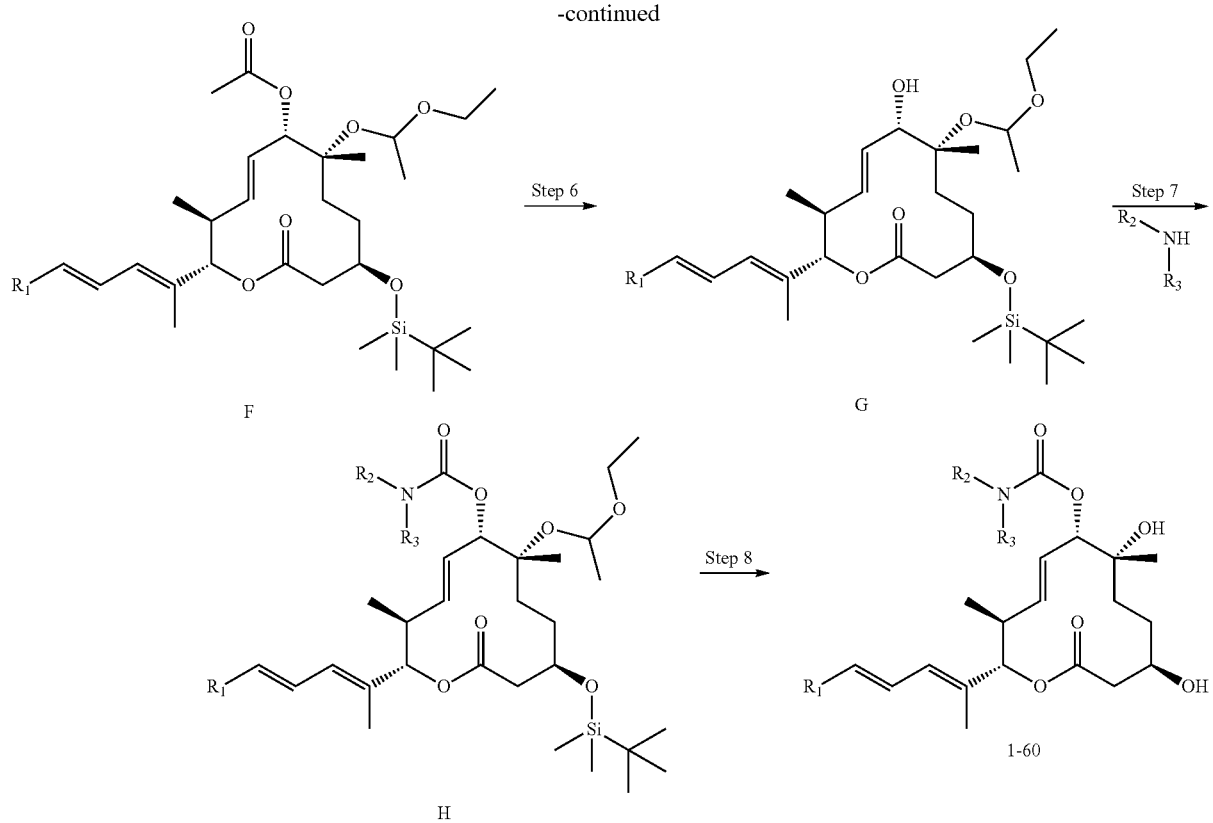

General Protocol for the Synthesis of Compounds 1-60:

Step 1: A solution of pladienolide D (A, 5.3 g, 9.7 mmol, 1.0 equiv.) under nitrogen in DMF (80 mL, 0.1M) at 0° C. was treated with imidazole (4.6 g, 67.8 mmol, 7.0 equiv.) and TBSCl (7.3 g, 48.4 mmol, 5.0 equiv.). The reaction was allowed to warm to room temperature and stirred for 20 hours, or until the reaction was determined to be complete by LCMS or TLC. The reaction was extracted with ethyl acetate and the organic layer was washed with brine, dried over sodium sulfate, filtered, and concentrated in vacuo. The resulting oil was purified by silica gel column chromatography (hexanes/ethyl acetate as eluant) to afford the desired product (B, 7.5 g, 9.6 mmol, 99%).

Step 2: To a solution of olefin B (7.6 g, 9.7 mmol, 1.0 equiv.) in degassed THF:H$_2$O (210 mL:21 mL, 0.01M) under nitrogen at 0° C. was added osmium tetroxide (24.4 mL, 1.9 mmol, 0.2 equiv., 2.5% solution in tert-butanol) followed by N-methylmorpholine N-oxide (2.3 g, 19.5 mmol, 2.0 equiv.). The reaction was allowed to warm to room temperature and stirred for 13 hours, or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (C, 6.8 g, 8.3 mmol, 86%).

Step 3: To a solution of diol C (7.9 g, 9.7 mmol, 1.0 equiv.) in benzene (350 mL, 0.03M) under nitrogen at room temperature was added lead tetraacetate (8.6 g, 19.4 mmol, 2.0 equiv.). The reaction was stirred for 30 minutes, or until the reaction was determined to be complete by LCMS or TLC. The reaction was concentrated and purified by silica gel column chromatography (hexane/ethyl acetate as eluent) to afford the desired product (D, 2.5 g, 5.26 mmol, 54%).

Step 4: To a solution of aldehyde D (1.4 g, 2.9 mmol, 1.0 equiv.) in THF (9.5 mL, 0.5M) was added ethoxyethene (11.1 mL, 40.0 equiv.) and pyridinium p-toluenesulfonate (0.07 g, 0.3 mmol, 0.1 equiv.) at room temperature. The reaction was stirred for 24 hours, or until the reaction was determined to be complete by LCMS or TLC. The reaction was quenched with sodium bicarbonate and diluted with ethyl acetate. The ethyl acetate was washed with water, brine, dried over magnesium sulfate, filtered, and concentrated in vacuo. The resulting oil was purified by silica gel column chromatography (hexane/ethyl acetate as eluent) to afford the desired product (E, 1.2 g, 2.2 mmol, 75%).

Step 5: To a solution of corresponding sulfone (1.5 equiv.) in THF (0.02M) under nitrogen at −78° C. was added KHMDS (1.5 equiv.) dropwise and the reaction was stirred for 20 minutes. Then aldehyde E (1.0 equiv.) in THF was added dropwise. The reaction was stirred at −78° C. for 90 minutes and then allowed to warm to −20° C. for 1 hour. The reaction was quenched with ammonium chloride, diluted with ethyl acetate, and warmed to room temperature. The organic layer was washed with water, brine, dried over magnesium sulfate, filtered, and concentrated in vacuo. The resulting oil was purified by silica gel column chromatography (hexane/ethyl acetate as eluent) to afford the desired product (F).

Step 6: To a solution of acetate F (1.0 equiv.) in methanol (0.1M) at room temperature was added potassium carbonate (1.1 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting oil (G) was advanced into the next step without additional purification.

Step 7: To a solution of alcohol (G) (1.0 equiv.) in dichloromethane (0.1M) at room temperature was added N,N-dimethylaminopyridine (0.5 equiv.) followed by 4-nitrophenyl chloroformate (2.0 equiv.). The reaction was stirred at room temperature for three hours. Next, the corresponding amine (3.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluant) to afford the desired product (H).

Step 8: To a solution of silyl ether (H, 1.0 equiv.) in methanol (0.1M) at room temperature was added p-methoxytoluenesulfonic acid (3.0 equiv.). The reaction was stirred for 3 hours, or until the reaction was determined to be complete by LCMS or TLC. The reaction was quenched with sodium bicarbonate, diluted with ethyl acetate, washed with water and brine, dried over magnesium sulfate, filtered, and concentrated in vacuo. The resulting oil was purified by silica gel column chromatography (hexane/ethyl acetate as eluant) to afford the desired product (1-59).

Exemplified Protocol for the Synthesis of compound 46

Steps 1-4 as above.

Step 5: To a solution of (S)-2-(1-((1-phenyl-1H-tetrazol-5-yl)sulfonyl)propan-2-yl)pyridine (233.0 mg, 0.7 mmol, 1.4 equiv.) in THF (2.5 mL, 0.2M) under nitrogen at −78° C. was added KHMDS (1.5 mL, 0.75 mmol, 1.5 equiv.) dropwise and the reaction was stirred for 20 minutes. Then aldehyde E (280.0 mg, 0.5 mmol, 1.0 equiv.) in THF (0.5 mL) was added dropwise. The reaction was stirred at −78° C. for 90 minutes and then allowed to warm to −20° C. over 1 hour. The reaction was quenched with ammonium chloride, diluted with ethyl acetate, and warmed to room temperature. The organic layer was washed with water, brine, dried over magnesium sulfate, filtered, and concentrated in vacuo. The resulting oil was purified by silica gel column chromatography (hexane/ethyl acetate as eluant) to afford the desired Julia product (F, 180 mg, 0.3 mmol, 54%).

Step 6: To a solution of acetate F (250.0 mg, 0.4 mmol, 1.0 equiv.) in methanol (3 mL, 0.1M) at room temperature was added potassium carbonate (58.0 mg, 0.4 mmol, 1.1 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting foamy solid (G, 235 mg, 0.4 mmol, 100%) was advanced into the next step without additional purification.

Step 7: To a solution of alcohol G (22.0 mg, 0.04 mmol, 1.0 equiv.) in dichloromethane (0.5 mL, 0.1M) at room temperature was added N,N-dimethylaminopyridine (2.1 mg, 0.02 mmol, 0.5 equiv.) followed by 4-nitrophenyl chloroformate (14.4 mg, 0.08 mmol, 2.0 equiv.). The reaction was stirred at room temperature for three hours. Next, 1-(tetrahydro-2H-pyran-4-yl)piperazine (20.4 mg, 0.12 mmol, 3.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluant) to afford the desired product (H, 26.0 mg, 0.03 mmol, 80%).

Step 8: To a solution of silyl ether (H, 26.0 mg, 0.03 mmol, 1.0 equiv.) in methanol (0.3 mL, 0.1M) at room temperature was added p-methoxytoluenesulfonic acid (17.0 mg, 0.09 mmol, 3.0 equiv.). The reaction was stirred for 3 hours, or until the reaction was determined to be complete by LCMS or TLC. The reaction was quenched with sodium bicarbonate, diluted with ethyl acetate, washed with water, brine, dried over magnesium sulfate, filtered, and concentrated in vacuo. The resulting oil was purified by silica gel column chromatography (hexane/ethyl acetate as eluant) to afford the desired product (compound 46, 16.3 mg, 0.025 mmol, 85%). $^1$H NMR (400 MHz, CHLOROFORM-d) δ:8.48 (ddd, J=4.9, 1.9, 1.0 Hz, 1H), 7.54 (td, J=7.7, 1.9 Hz, 1H), 7.09 (d, J=8.0 Hz, 1H), 7.05 (t, J=6.1 Hz, 1H), 6.15-6.34 (m, 1H), 6.04 (d, J=10.8 Hz, 1H), 5.93 (dd, J=15.1, 7.5 Hz, 1H), 5.48-5.67 (m, 2H), 5.08 (d, J=10.5 Hz, 1H), 4.94 (d, J=9.5 Hz, 1H), 3.95 (dd, J=11.3, 3.8 Hz, 2H), 3.53-3.76 (m, 2H), 3.37-3.49 (m, 5H), 3.22-3.37 (m, 2H), 2.35-2.57 (m, 7H), 1.88 (s, 1H), 1.44-1.70 (m, 11H), 1.14-1.39 (m, 8H), 0.72-0.89 (m, 3H), MS (ES+)=626.6[M+H].

TABLE 1

Structures and analytical data for Compounds 1-60

| Structure, Compound #, and Chemical Name | $^1$H NMR data | LCMS data (ES+) |
|---|---|---|
| 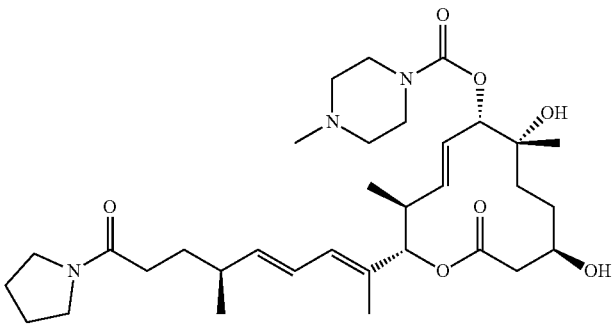 [SMILES: C/C(=C\C=C\[C@@H](C)CCC(=O)N1CCCC1)[C@H]1OC(=O)C[C@H](O)CC[C@@](C)(O)[C@@H](OC(=O)N2CCN(C)CC2)/C=C/[C@@H]1C]<br>1<br>[(2S,3S,4E,6S,7S,10S)-7,10-dihydroxy-3,7-dimethyl-2-[(2E,4E,6S)-6-methyl-9-oxo-9-pyrrolidin-1-ylnona-2,4-dien-2-yl]-12-oxo-1-oxacyclododec-4-en-6-yl] 4-methylpiperazine-1-carboxylate | $^1$H NMR (400 MHz, METHANOL-d4) δ: 0.91 (d, J = 6.78 Hz, 3 H) 1.07 (d, J = 6.65 Hz, 3 H) 1.23 (s, 3 H) 1.30-1.43 (m, 4 H) 1.55-1.79 (m, 7H) 1.84-2.01 (m, 4 H) 2.28-2.34 (m, 5 H) 2.42 (t, J = 4.96 Hz, 4 H) 2.51-2.66 (m, 3 H) 3.41 (td, J = 6.87, 1.94 Hz, 2 H) 3.48 (t, J = 6.78 Hz, 2 H) 3.51-3.86 (m, 4 H) 4.96 (d, J = 9.66 Hz, 1 H) 5.07 (d, J = 10.67 Hz, 1 H) 5.55-5.68 (m, 2 H) 5.74 (dd, J = 15.18 9.66 Hz, 1 H) 6.12 (d, J = 10.79 Hz, 1 H) 6.29 (dt, J = 14.81, 10.54 Hz, 1 H) | 604.3 |

TABLE 1-continued

Structures and analytical data for Compounds 1-60

| Structure, Compound #, and Chemical Name | ¹H NMR data | LCMS data (ES+) |
|---|---|---|
| 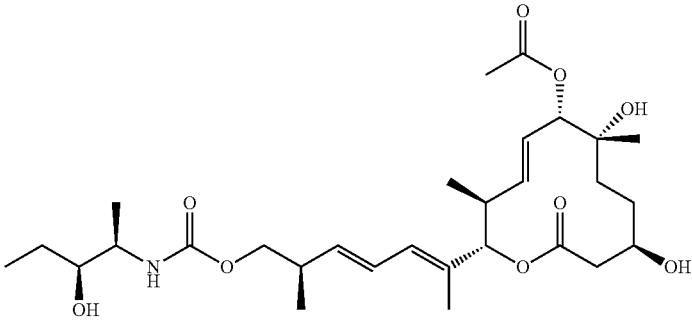 [SMILES: CC[C@H](O)[C@@H](C)NC(=O)OC[C@H](C)/C=C/C=C(\C)[C@H]1OC(=O)C[C@H](O)CC[C@@](C)(O)[C@@H](OC(C)=O)/C=C/[C@@H]1C]<br>2<br>[(2S,3S,4E,6S,7S,10S)-7,10-dihydroxy-2-[(2E,4E,6S)-7-[[(2R,3R)-3-hydroxypentan-2-yl]carbamoyloxy]-6-methylhepta-2,4-dien-2-yl]-3,7-dimethyl-12-oxo-1-oxacyclododec-4-en-6-yl] acetate | ¹H NMR (400 MHz, METHANOL-d4) δ: 0.73-0.91 (m, 5 H) 0.92-1.04 (m, 5 H) 1.07-1.33 (m, 5 H) 1.37-1.59 (m, 3 H) 1.60-1.71 (m, 2 H) 1.80 (s, 1 H) 1.86-2.07 (m, 2 H) 2.24-2.52 (m, 3 H) 2.89-3.09 (m, 1 H) 3.34-3.50 (m, 1 H) 3.52-3.62 (m, 1H) 3.64-3.75 (m, 1 H) 3.76-4.03 (m, 2 H) 4.83 (s, 1 H) 4.87-5.04 (m, 1 H) 5.24-5.53 (m, 2 H) 5.53-5.69 (m, 1 H) 5.99 (d, J = 11.04 Hz, 1 H) 6.24 (dd, J = 15.18, 10.92 Hz, 1 H) | 534.3 |
| 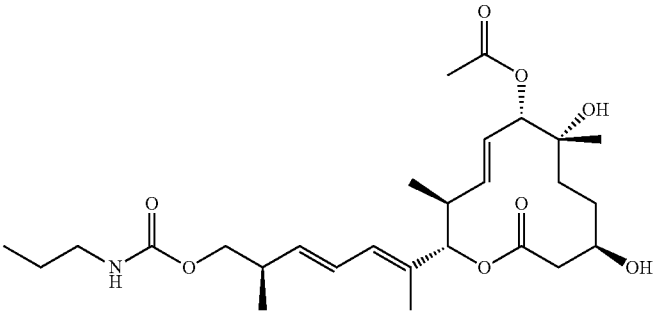 [SMILES: CCCNC(=O)OC[C@H](C)/C=C/C=C(\C)[C@H]1OC(=O)C[C@H](O)CC[C@@](C)(O)[C@@H](OC(C)=O)/C=C/[C@@H]1C]<br>3<br>[(2S,3S,4E,6S,7S,10S)-7,10-dihydroxy-3,7-dimethyl-2-[(2E,4E,6S)-6-methyl-7-(propylcarbamoyloxy)hepta-2,4-dien-2-yl]-12-oxo-1-oxacyclododec-4-en-6-yl] acetate | ¹H NMR (400 MHz, METHANOL-d4) δ: 0.87-0.97 (m, 3 H) 0.97-1.15 (m, 5 H) 1.21 (s, 1 H) 1.29-1.40 (m, 1 H) 1.46-1.70 (m, 5 H) 1.72-1.77 (m, 1 H) 1.82 (s, 1 H) 2.08 (s, 1 H) 2.18 (s, 1 H) 2.35-2.63 (m, 3 H) 3.05 (t, J = 7.03 Hz, 2 H) 3.14-3.27 (m, 3 H) 3.50 (dd, J = 3.26, 1.51 Hz, 1 H) 3.62-3.79 (m, 3 H) 3.79-4.08 (m, 3 H) 4.96 (br. s., 1 H) 5.07 (d, J = 9.79 Hz, 1 H) 5.38-5.52 (m, 1 H) 5.54-5.72 (m, 2 H) 5.97 (dd, J = 17.07, 10.79 Hz, 1 H) 6.21-6.49 (m, 1 H) 8.57 (s, 1 H) | |
| 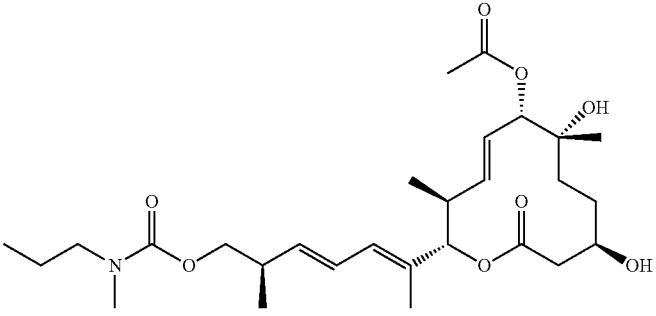<br>4<br>[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] acetate | ¹H NMR (400 MHz, METHANOL-d4) δ: 0.90 (d, J = 6.53 Hz, 6 H) 1.01-1.15 (m, 3 H) 1.21 (s, 3 H) 1.29-1.47 (m, 2 H) 1.50-1.71 (m, 4 H) 1.77 (d, J = 1.00 Hz, 3 H) 2.04-2.09 (m, 3 H) 2.18 (s, 1 H) 2.39 (s, 1 H) 2.48-2.68 (m, 4 H) 2.89 (s, 3 H) 3.15 (s, 1 H) 3.19-3.29 (m, 2 H) 3.31-3.50 (s, 1 H) 3.69 (s, 1 H) 3.74-3.88 (m, 1 H) 3.89-4.15 (m, 2 H) 5.07 (d, J = 9.79 Hz, 2 H) 5.51-5.64 (m, 1 H) 5.64-5.76 (m, 2 H) 6.09-6.19 (m, 1 H) 6.37 (ddd, J = 15.12, 10.85, 0.88 Hz, 1 H) 7.25 (dd, J = 8.28, 1.00 Hz, 1 H) 7.73 (d, J = 8.03 Hz, 1 H) | |

TABLE 1-continued

Structures and analytical data for Compounds 1-60

| Structure, Compound #, and Chemical Name | ¹H NMR data | LCMS data (ES+) |
|---|---|---|
| 5<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] pyrrolidine-1-carboxylate | ¹H NMR (400 MHz, METHANOL-d4) δ: 0.90 (d, J = 6.78 Hz, 3 H) 1.09 (d, J = 6.78 Hz, 3 H) 1.21 (s, 3 H) 1.34-1.46 (m, 2 H) 1.54-1.67 (m, 2 H) 1.77 (d, J = 0.88 Hz, 3 H) 1.82-1.95 (m, 4 H) 2.08 (s, 3 H) 2.49-2.70 (m, 4 H) 3.34-3.39 (m, 4 H) 3.75-3.87 (m, 1 H) 3.98 (dd, J = 6.78, 1.38 Hz, 2 H) 5.07 (d, J = 9.91 Hz, 2 H) 5.59 (dd, J = 15.18 9.79 Hz, 1 H) 5.65-5.76 (m, 2 H) 6.12 (d, J = 10.79 Hz, 1 H) 6.37 (ddd, J = 15.15, 10.82, 1.00 Hz, 1 H) | 522.4 |
| 6<br>[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] 4-cycloheptyl-4-oxidopiperazin-4-ium-1-carboxylate | ¹H NMR (400 MHz, METHANOL-d4) δ: 0.60-1.79 (m, 15 H) 2.05-2.35 (m, 5 H) 2.43 (d, J = 3.26 Hz, 6 H) 2.78 (s, 3 H) 2.86-3.00 (m, 3 H) 3.44-3.62 (m, 4 H) 3.64-3.75 (m, 2 H) 3.76-4.05 (m, 6 H) 4.37-4.56 (m, 3 H) 4.95 (d, J = 10.79 Hz, 1 H) 5.41-5.79 (m, 3H) 6.00 (d, J = 10.79 Hz, 1 H) 6.13-6.39 (m, 1 H) | |
| 7<br>[(2S,3S,4E,6S,7S,10S)-2-[(2E,4E,6R)-7-(dimethylcarbamoyloxy)-6-methylhepta-2,4-dien-2-yl]-7,10-dihydroxy-3,7-dimethyl-12-oxo-1-oxacyclododec-4-en-6-yl] acetate | ¹H NMR (400 MHz, METHANOL-d4) δ: 0.90 (d, J = 6.65 Hz, 3 H) 1.09 (d, J = 6.78 Hz, 3 H) 1.21 (s, 3 H) 1.31-1.47 (m, 2 H) 1.62 (dd, J = 15.25, 8.34 Hz, 2 H) 1.75-1.78 (m, 3 H) 2.08 (s, 3 H) 2.51-2.66 (m, 4 H) 2.91 (s, 6 H) 3.81 (br. s., 1 H) 3.97 (dd, J = 6.65, 1.76 Hz, 2 H) 45.07 (d, J = 9.91 Hz, 2 H) 5.51-5.75 (m, 3 H) 6.12 (d, J = 10.92 Hz, 1 H) 6.37 (ddd, J = 15.18, 10.79, 1.00 Hz, 1 H) | 518.4 |

TABLE 1-continued

Structures and analytical data for Compounds 1-60

| Structure, Compound #, and Chemical Name | $^1$H NMR data | LCMS data (ES+) |
|---|---|---|
| 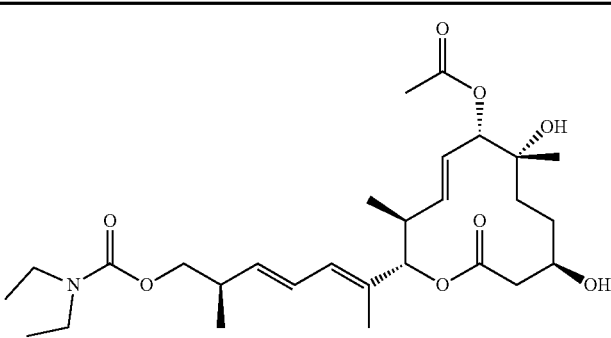<br>8<br>[(2S,3S,4E,6S,7S,10S)-2-[(2E,4E,6S)-7-(diethylcarbamoyloxy)-6-methylhepta-2,4-dien-2-yl]-7,10-dihydroxy-3,7-dimethyl-12-oxo-1-oxacyclododec-4-en-6-yl] acetate | $^1$H NMR (400 MHz, METHANOL-d4) δ: 0.89 (d, J = 6.78 Hz, 3 H) 1.06-1.15 (m, 9 H) 1.21 (s, 3 H) 1.28-1.45 (m, 2 H) 1.54-1.70 (m, 2 H) 1.74-1.78 (m, 3 H) 2.08 (s, 3 H) 2.51-2.68 (m, 4 H) 3.76-3.87 (m, 1 H) 3.93-4.03 (m, 2 H) 5.06 (d, J = 9.79 Hz, 2 H) 5.55-5.75 (m, 3 H) 6.12 (d, J = 10.79 Hz, 1 H) 6.37 (ddd, J = 15.12, 10.85, 0.88 Hz, 1 H) | 546.4 |
| 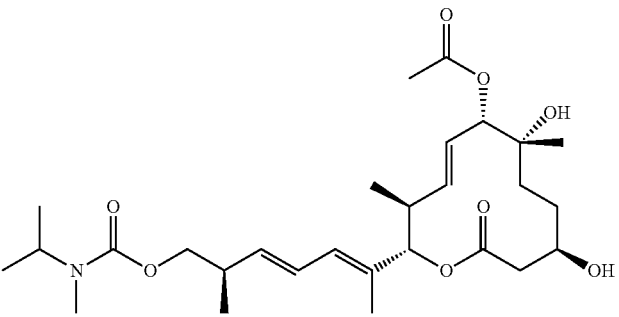 [SMILES: CC(=O)O[C@H]1/C=C/[C@H](C)[C@@H](/C(C)=C/C=C/[C@@H](C)COC(=O)N(C)C(C)C)OC(=O)C[C@H](O)CC[C@@]1(C)O]<br>9<br>[(2S,3S,4E,6S,7S,10S)-7,10-dihydroxy-3,7-dimethyl-2-[(2E,4E,6S)-6-methyl-7-[methyl(propan-2-yl)carbamoyl]oxyhepta-2,4-dien-2-yl]-12-oxo-1-oxacyclododec-4-en-6-yl] acetate | $^1$H NMR (400 MHz, METHANOL-d4) δ: 0.89 (d, J = 6.65 Hz, 3 H) 1.08 (d, J = 6.78 Hz, 3 H) 1.13 (d, J = 6.78 Hz, 6 H) 1.21 (s, 3 H) 1.29-1.45 (m, 2 H) 1.54-1.71 (m, 2 H) 1.75-1.78 (m, 3 H) 2.08 (s, 3 H) 2.51-2.67 (m, 4 H) 2.76 (s, 3 H) 3.77-3.83 (m, 1 H) 3.98 (d, J = 7.03 Hz, 2 H) 4.33 (br. s., 1 H) 5.06 (d, J = 9.91 Hz, 2 H) 5.55-5.63 (m, 1 H) 5.65-5.75 (m, 2 H) 6.12 (d, J = 10.92 Hz, 1 H) 6.37 (ddd, J = 15.12, 10.85, 0.88 Hz, 1 H) | 546.5 |
| 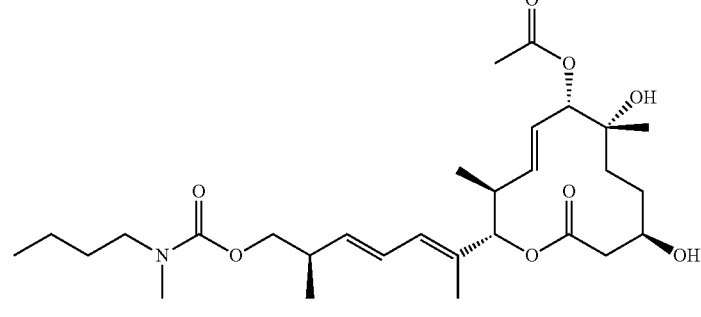<br>10<br>[(2S,3S,4E,6S,7S,10S)-2-[(2E,4E,6S)-7-[butyl(methyl)carbamoyl]oxy-6-methylhepta-2,4-dien-2-yl]-7,10-dihydroxy-3,7-dimethyl-12-oxo-1-oxacyclododec-4-en-6-yl] acetate | $^1$H NMR (400 MHz, METHANOL-d4) δ: 0.87-0.98 (m, 6 H) 1.09 (d, J = 6.90 Hz, 3 H) 1.16-1.22 (m, 3 H) 1.32 (br. s., 2 H) 1.38 (d, J = 9.91 Hz, 2 H) 1.49-1.68 (m, 4 H) 1.75-1.78 (m, 3 H) 2.08 (s, 3 H) 2.52-2.66 (m, 4 H) 2.89 (s, 3 H) 3.28-3.37 (m, 18 H) 3.80 (d, J = 6.15 Hz, 1 H) 3.98 (d, J = 7.03 Hz, 2 H) 4.87 (s, 72 H) 5.05-5.09 (m, 2 H) 5.55-5.62 (m, 1 H) 5.66-5.75 (m, 2 H) 6.12 (d, J = 10.79 Hz, 1 H) 6.33-6.40 (m, 1 H) | 560.5 |

TABLE 1-continued

Structures and analytical data for Compounds 1-60

| Structure, Compound #, and Chemical Name | ¹H NMR data | LCMS data (ES+) |
|---|---|---|
| 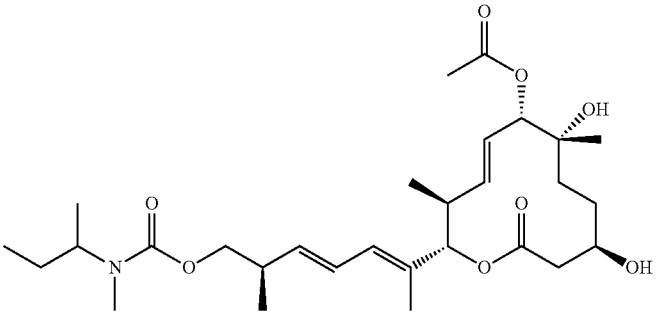 [SMILES: CCC(C)N(C)C(=O)OC[C@H](C)/C=C/C=C(\C)[C@H]1OC(=O)C[C@H](O)CC[C@@](C)(O)[C@@H](OC(C)=O)/C=C/[C@@H]1C]<br>11<br>[(2S,3S,4E,6S,7S,10S)-2-[(2E,4E,6S)-7-[butan-2-yl(methyl)carbamoyl]oxy-6-methylhepta-2,4-dien-2-yl]-7,10-dihydroxy-3,7-dimethyl-12-oxo-1-oxacyclododec-4-en-6-yl] acetate | ¹H NMR (400 MHz, METHANOL-d4) δ: 0.77-0.98 (m, 9 H) 1.01-1.18 (m, 7 H) 1.20-1.34 (m, 10 H) 1.34-1.53 (m, 5 H) 1.58-1.66 (m, 2 H) 1.76 (s, 3 H) 2.06-2.09 (m, 3 H) 2.50-2.68 (m, 5 H) 2.73 (s, 3 H) 3.94-4.07 (m, 3 H) 5.06 (d, J = 9.79 Hz, 2 H) 5.53-5.64 (m, 1 H) 5.65-5.75 (m, 2 H) 6.12 (d, J = 10.04 Hz, 1 H) 6.37 (dd, J = 15.18, 10.79 Hz, 1 H) | 560.5 |
| 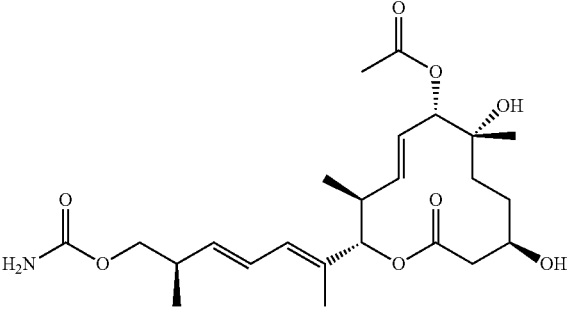 [SMILES: CC(=O)O[C@H]1/C=C/[C@H](C)[C@@H](/C(C)=C/C=C/[C@@H](C)COC(N)=O)OC(=O)C[C@H](O)CC[C@@]1(C)O]<br>12<br>[(2S,3S,4E,6S,7S,10S)-2-[(2E,4E,6R)-7-carbamoyloxy-6-methylhepta-2,4-dien-2-yl]-7,10-dihydroxy-3,7-dimethyl-12-oxo-1-oxacyclododec-4-en-6-yl] acetate | ¹H NMR (400 MHz, METHANOL-d4) δ: 0.90 (d, J = 6.78 Hz, 3 H) 1.08 (d, J = 6.78 Hz, 3 H) 1.21 (s, 3 H) 1.23-1.30 (m, 2 H) 1.31 (s, 4 H) 1.34-1.49 (m, 3 H) 1.62 (dd, J = 15.62, 8.22 Hz, 2 H) 1.75-1.79 (m, 2 H) 2.03-2.09 (m, 3 H) 2.51-2.65 (m, 3 H) 3.15 (s, 1 H) 3.81 (d, J = 3.76 Hz, 1 H) 3.87-3.98 (m, 1 H) 4.59 (s, 4 H) 4.97 (s, 1 H) 5.07 (d, J = 9.79 Hz, 2 H) 5.57 (dd, J = 15.18, 9.79 Hz, 1 H) 5.67-5.77 (m, 2 H) 6.11 (d, J = 10.79 Hz, 1 H) 6.37 (ddd, J = 15.15, 10.82, 1.00 Hz, 1 H) | 490.3 |
| 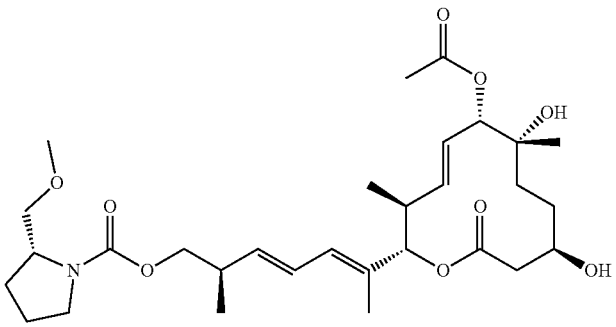 [SMILES: COC[C@H]1CCCN1C(=O)OC[C@H](C)/C=C/C=C(\C)[C@H]1OC(=O)C[C@H](O)CC[C@@](C)(O)[C@@H](OC(C)=O)/C=C/[C@@H]1C]<br>13<br>[(2S,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R)-2-(methoxymethyl)pyrrolidine-1-carboxylate | ¹H NMR (400 MHz, METHANOL-d4) δ: 0.78 (d, J = 6.65 Hz, 3 H) 0.80-0.91 (m, 1 H) 0.95 (d, J = 6.78 Hz, 3 H) 1.09 (s, 3 H) 1.17-1.30 (m, 2 H) 1.40-1.59 (m, 2 H) 1.63-1.73 (m, 4 H) 1.78-1.87 (m, 3 H) 1.96 (s, 3 H) 2.38-2.55 (m, 4 H) 3.19-3.27 (m, 10 H) 3.28-3.41 (m, 1 H) 3.64-3.75 (m, 1 H) 3.79-3.90 (m, 2 H) 4.46 (s, 1 H) 4.74 (s, 25 H) 4.94 (d, J = 9.66 Hz, 2 H) 5.46 (dd, J = 15.18, 9.79 Hz, 1 H) 5.54-5.64 (m, 2 H) 6.01 (d, J = 10.92 Hz, 1 H) 6.19-6.31 (m, 1 H) | 566.5 |

TABLE 1-continued

Structures and analytical data for Compounds 1-60

| Structure, Compound #, and Chemical Name | ¹H NMR data | LCMS data (ES+) |
|---|---|---|
| 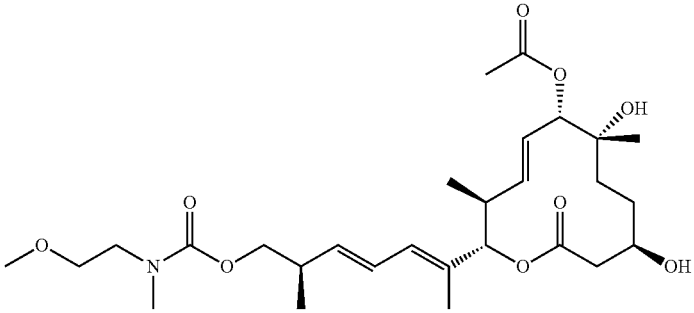<br>14<br>[(2S,3S,4E,6S,7S,10S)-7,10-dihydroxy-2-[(2E,4E,6S)-7-[2-methoxyethyl(methyl)carbamoyl]oxy-6-methylhepta-2,4-dien-2-yl]-3,7-dimethyl-12-oxo-1-oxacyclododec-4-en-6-yl] acetate | ¹H NMR (400 MHz, METHANOL-d4) δ: 0.90 (d, J = 6.78 Hz, 3 H) 1.09 (d, J = 6.90 Hz, 3 H) 1.21 (s, 2 H) 1.48-1.71 (m, 2 H) 1.77 (s, 3 H) 2.08 (s, 3 H) 2.48-2.70 (m, 4 H) 2.95 (s, 3 H) 3.38-3.58 (m, 4 H) 3.69-4.06 (m, 3 H) 5.01-5.16 (m, 2 H) 5.59 (dd, J = 15.43, 9.79 Hz, 1 H) 5.69 (s, 2 H) 6.12 (d, J = 10.29 Hz, 1 H) 6.38 (dd, J = 15.43, 11.04 Hz, 1 H) | 562.3 |
| 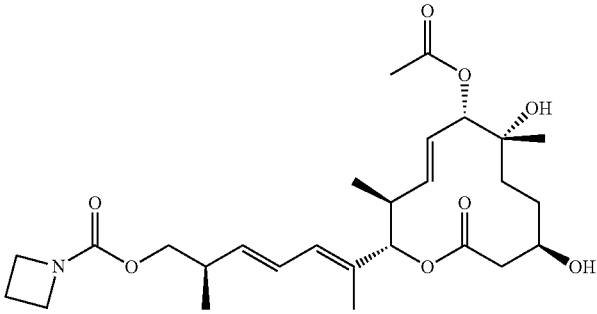 [SMILES: CC(=O)O[C@H]1/C=C/[C@H](C)[C@@H](/C(C)=C/C=C/[C@@H](C)COC(=O)N2CCC2)OC(=O)C[C@H](O)CC[C@@]1(C)O]<br>15<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] azetidine-1-carboxylate | ¹H NMR (400 MHz, METHANOL-d4) δ: 0.91 (d, J = 6.02 Hz, 3 H) 1.07 (d, J = 6.78 Hz, 3 H) 1.21 (s, 3 H) 1.34-1.47 (m, 2 H) 1.48-1.49 (m, 1 H) 1.51-1.73 (m, 2 H) 1.78 (d, J = 1.00 Hz, 3 H) 2.08 (s, 3 H) 2.19-2.34 (m, 2 H) 2.46-2.66 (m, 3 H) 3.37 (s, 3 H) 3.74-4.07 (m, 6 H) 5.07 (d, J = 9.79 Hz, 2 H) 5.49-5.80 (m, 3 H) 6.12 (d, J = 10.67 Hz, 1 H) 6.36 (ddd, J = 15.06, 10.67, 1.25 Hz, 1 H) | |
| 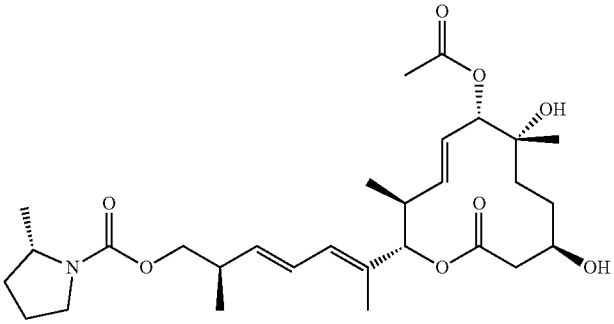 [SMILES: CC(=O)O[C@H]1/C=C/[C@H](C)[C@@H](/C(C)=C/C=C/[C@@H](C)COC(=O)N2CCC[C@@H]2C)OC(=O)C[C@H](O)CC[C@@]1(C)O]<br>16<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2S)-2-methylpyrrolidine-1-carboxylate | ¹H NMR (400 MHz, METHANOL-d4) δ: 0.89 (d, J = 6.78 Hz, 3 H) 1.09 (d, J = 6.78 Hz, 3 H) 1.18 (d, J = 6.27 Hz, 3 H) 1.21 (s, 3 H) 1.28-1.48 (m, 3 H) 1.53-1.69 (m, 3 H) 1.76 (d, J = 1.00 Hz, 3 H) 1.79-2.06 (m, 3 H) 2.08 (s, 3 H) 2.55 (br. s., 4 H) 3.36-3.45 (m, 1 H) 3.73-4.11 (m, 4 H) 5.06 (m, J = 9.54 Hz, 2 H) 5.58 (dd, J = 15.31, 9.79 Hz, 1 H) 5.65-5.77 (m, 2 H) 6.13 (d, J = 9.79 Hz, 1 H) 6.37 (dd, J = 15.81, 10.54 Hz, 1 H) | 536.4 |

TABLE 1-continued

Structures and analytical data for Compounds 1-60

| Structure, Compound #, and Chemical Name | ¹H NMR data | LCMS data (ES+) |
|---|---|---|
| 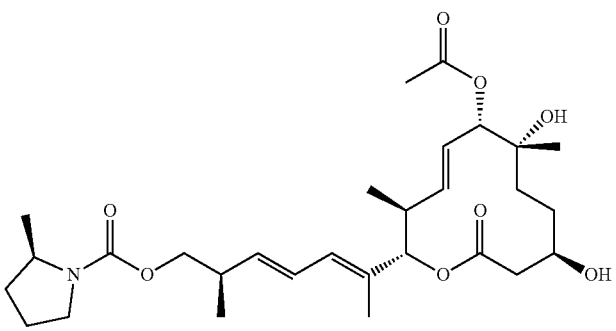 [SMILES: CC(=O)O[C@H]1/C=C/[C@H](C)[C@@H](/C(C)=C/C=C/[C@@H](C)COC(=O)N2CCC[C@H]2C)OC(=O)C[C@H](O)CC[C@@]1(C)O]<br>17<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2S)-2-methylpyrrolidine-1-carboxylate | ¹H NMR (400 MHz, METHANOL-d4) δ: 0.77 (d, J = 6.65 Hz, 3 H) 0.97 (d, J = 6.90 Hz, 3 H) 1.01-1.14 (m, 6 H) 1.19-1.32 (m, 2 H) 1.39-1.57 (m, 3 H) 1.64 (s, 3 H) 1.96 (s, 3 H) 2.36-2.61 (m, 4 H) 3.24-3.34 (m, 2 H) 3.60-3.74 (m, 1 H) 3.74-3.94 (m, 3 H) 4.86-5.00 (m, 2 H) 5.46 (dd, J = 15.18, 9.79 Hz, 1 H) 5.56 (m, 2 H) 5.98 (d, J = 9.91 Hz, 1 H) 6.25 (dd, J = 16.06, 10.54 Hz, 1 H) | 536.3 |
| 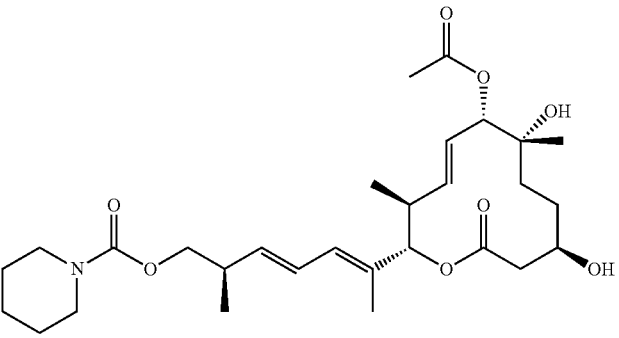 [SMILES: CC(=O)O[C@H]1/C=C/[C@H](C)[C@@H](/C(C)=C/C=C/[C@@H](C)COC(=O)N2CCCCC2)OC(=O)C[C@H](O)CC[C@@]1(C)O]<br>18<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] piperidine-1-carboxylate | ¹H NMR (400 MHz, METHANOL-d4) δ: 0.00-0.00 (m, 1 H) 0.90 (d, J = 6.78 Hz, 3 H) 1.08 (d, J = 6.78 Hz, 3 H) 1.21 (s, 3 H) 1.29-1.70 (m, 12 H) 1.77 (d, J = 1.00 Hz, 3 H) 2.08 (s, 3 H) 2.46-2.71 (m, 4 H) 3.37-3.47 (m, 4 H) 3.73-3.86 (m, 1 H) 3.92-4.03 (m, 2 H) 5.05 (m, 2 H) 5.59 (dd, J = 15.18, 9.79 Hz, 1 H) 5.64-5.77 (m, 2 H) 6.12 (dd, J = 10.79, 1.00 Hz, 1 H) 6.37 (ddd, J = 15.12, 10.85, 0.88 Hz, 1 H) | |
| 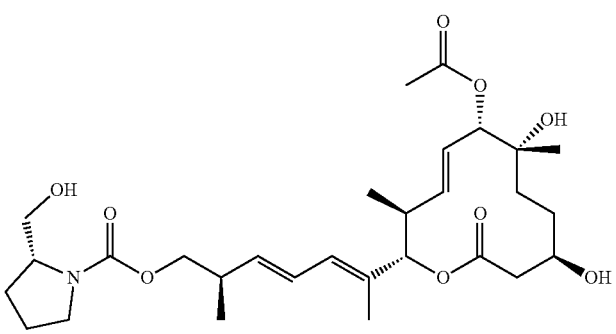 [SMILES: CC(=O)O[C@H]1/C=C/[C@H](C)[C@@H](/C(C)=C/C=C/[C@@H](C)COC(=O)N2CCC[C@@H]2CO)OC(=O)C[C@H](O)CC[C@@]1(C)O]<br>19<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R)-2-(hydroxymethyl)pyrrolidine-1-carboxylate | ¹H NMR (400 MHz, METHANOL-d4) δ: 0.90 (d, J = 6.40 Hz, 3 H) 1.09 (d, J = 6.78 Hz, 3 H) 1.21 (s, 3 H) 1.32-1.47 (m, 2 H) 1.53-1.69 (m, 2 H) 1.77 (s, 3 H) 1.80-1.89 (m, 1 H) 1.90-2.01 (m, 3 H) 2.08 (s, 3 H) 2.55 (br. s., 4 H) 3.35-3.47 (m, 2 H) 3.47-3.67 (m, 2 H) 3.74-3.90 (m, 2 H) 3.90-4.07 (m, 2 H) 5.02-5.16 (m, 2 H) 5.59 (dd, J = 15.18, 9.79 Hz, 1 H) 5.70 (d, J = 9.66 Hz, 2 H) 6.14 (d, J = 10.67 Hz, 1 H) 6.38 (dd, J = 15.06, 11.04 Hz, 1 H) | |

TABLE 1-continued

Structures and analytical data for Compounds 1-60

| Structure, Compound #, and Chemical Name | ¹H NMR data | LCMS data (ES+) |
|---|---|---|
| 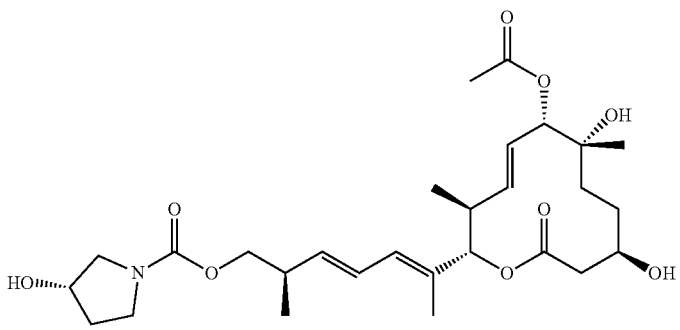 [SMILES: CC(=O)O[C@H]1/C=C/[C@H](C)[C@@H](/C(C)=C/C=C/[C@@H](C)COC(=O)N2CC[C@H](O)C2)OC(=O)C[C@H](O)CC[C@@]1(C)O]<br>20<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (3R)-3-hydroxypyrrolidine-1-carboxylate | ¹H NMR (400 MHz, METHANOL-d4) δ: 0.90 (d, J = 6.78 Hz, 3 H) 1.10 (d, J = 6.78 Hz, 3 H) 1.21 (s, 3 H) 1.33-1.46 (m, 2 H) 1.53-1.70 (m, 2 H) 1.77 (s, 3 H) 1.85-2.06 (m, 3 H) 2.08 (s, 3 H) 2.47-2.70 (m, 4 H) 3.47 (d, J = 4.39 Hz, 3 H) 3.76-3.86 (m, 1 H) 3.92-4.05 (m, 2 H) 4.31-4.46 (m, 1 H) 5.01-5.10 (m, 2 H) 5.57 (dd, J = 15.43 9.79 Hz, 1 H) 5.66-5.82 (m, 2 H) 6.12 (d, J = 10.92 Hz, 1 H) 6.38 (ddd, J = 15.18, 10.85, 0.69 Hz, 1 H) | |
| 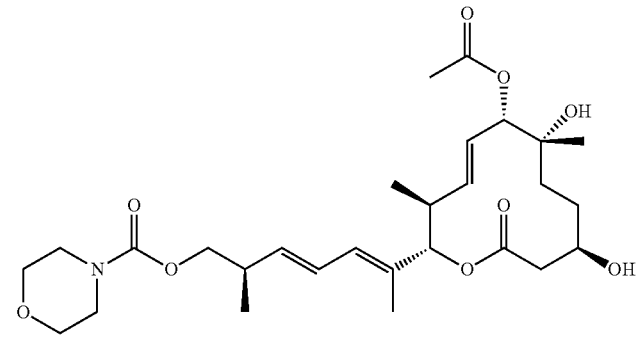 [SMILES: CC(=O)O[C@H]1/C=C/[C@H](C)[C@@H](/C(C)=C/C=C/[C@@H](C)COC(=O)N2CCOCC2)OC(=O)C[C@H](O)CC[C@@]1(C)O]<br>21<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] morpholine-4-carboxylate | ¹H NMR (400 MHz, METHANOL-d4) δ: 0.90 (d, J = 6.65 Hz, 3 H) 1.08 (d, J = 6.78 Hz, 3 H) 1.21 (s, 3 H) 1.30-1.45 (m, 2 H) 1.56-1.69 (m, 2 H) 1.74-1.82 (m, 3 H) 2.08 (s, 3 H) 2.47-2.71 (m, 4 H) 3.39-3.55 (m, 4 H) 3.55-3.71 (m, 4 H) 3.73-3.85 (m, 1 H) 3.95-4.06 (m, 2 H) 4.98-5.16 (m, 2 H) 5.58 (dd, J = 14.93, 9.54 Hz, 1 H) 5.65-5.76 (m, 2 H) 6.13 (d, J = 11.04 Hz, 1 H) 6.38 (ddd, J = 15.18, 10.92, 0.88 Hz, 1 H) | 560.1 |
| 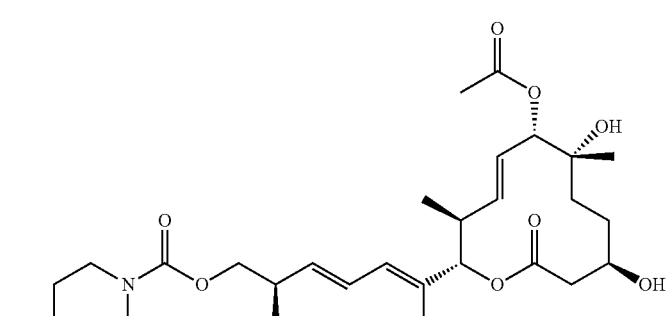<br>22<br>[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] 4-methylpiperazine-1-carboxylate | ¹H NMR (400 MHz, METHANOL-d4) δ: 0.90 (d, J = 6.78 Hz, 3 H) 1.08 (d, J = 6.90 Hz, 3 H) 1.21 (s, 3 H) 1.29-1.45 (m, 3 H) 1.54-1.68 (m, 2 H) 1.77 (d, J = 1.00 Hz, 3 H) 2.08 (s, 3 H) 2.32 (s, 3 H) 2.37-2.47 (m, 4 H) 2.48-2.71 (m, 4 H) 3.44-3.57 (m, 4 H) 3.73-3.88 (m, 1 H) 3.91-4.06 (m, 2 H) 5.02-5.15 (m, 2 H) 5.59 (dd, J = 15.31, 10.04 Hz, 1 H) 5.64-5.77 (m, 2 H) 6.12 (d, J = 10.92 Hz, 1 H) 6.37 (ddd, J = 15.15, 10.89, 0.94 Hz, 1 H) | 551.2 |

TABLE 1-continued

Structures and analytical data for Compounds 1-60

| Structure, Compound #, and Chemical Name | ¹H NMR data | LCMS data (ES+) |
|---|---|---|
| <br>23<br>3-thiazolidinecarboxylic acid [(2R,3E,5E)-6-[(2R,3S,4E,6R,7R,10R)-6-acetyloxy-7,10-dihydroxy-3,7-dimethyl-12-oxo-1-oxacyclododec-4-en-2-yl]-2-methylhepta-3,5-dienyl] ester | ¹H NMR (400 MHz, METHANOL-d4) δ: 0.90 (d, J = 6.78 Hz, 3 H) 1.09 (d, J = 6.78 Hz, 3 H) 1.21 (s, 3 H) 1.31 (s, 4 H) 1.49-1.70 (m, 3 H) 1.73-1.82 (m, 3 H) 2.08 (s, 3 H) 2.55 (s, 4 H) 3.03 (t, J = 6.34 Hz, 2 H) 3.69 (t, J = 6.27 Hz, 2 H) 3.75-3.86 (m, 1 H) 4.02 (d, J = 6.78 Hz, 2 H) 4.45 (s, 2 H) 4.61-4.61 (m, 1 H) 5.08 (s, 2 H) 5.58 (dd, J = 15.18, 9.79 Hz, 1 H) 5.64-5.79 (m, 2 H) 6.12 (d, J = 10.79 Hz, 1 H) 6.37 (ddd, J = 15.15, 10.82, 1.00 Hz, 1 H) | 562.6 |
| <br>24<br>[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.73-0.92 (m, 4 H) 0.94-1.05 (m, 3 H) 1.08-1.34 (m, 8 H) 1.38-1.58 (m, 3 H) 1.61 (br. s., 1 H) 1.66 (s, 3 H) 1.71-1.82 (m, 4 H) 1.87 (d, J = 15.06 Hz, 1 H) 1.97 (s, 1 H) 2.24 (s, 3 H) 2.32 (br. s., 4 H) 2.36-2.58 (m, 4 H) 3.09-3.38 (m, 4 H) 3.39-3.48 (m, 7 H) 3.55-3.73 (m, 2 H) 3.79 (s, 1 H) 3.89 (qd, J = 10.46, 6.78 Hz, 2 H) 4.05 (q, J = 7.03 Hz, 1 H) 4.95 (d, J = 9.29 Hz, 1 H) 5.09 (d, J = 10.54 Hz, 1 H) 5.23 (s, 1 H) 5.49-5.71 (m, 3 H) 6.02 (d, J = 10.54 Hz, 1 H) 6.20 (dd, J = 15.06, 10.79 Hz, 1 H) | |
| <br>25<br>[(2S,3S,4E,6S,7S,10S)-7,10-dihydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, CHLOROFORM-d) δ: 6.20 (dd, J = 15.1, 10.8 Hz, 1H), 6.02 (d, J = 10.8 Hz, 1H), 5.37-5.76 (m, 3H), 5.08 (d, J = 10.5 Hz, 1H), 4.95 (d, J = 9.5 Hz, 1H), 4.40 (br. s., 1H), 3.81-4.00 (m, 2H), 3.64-3.73 (m, 1H), 3.10-3.56 (m, 9H), 2.38-2.62 (m, 4H), 2.24 (s, 3H), 1.81-1.99 (m, 3H), 1.57-1.77 (m, 5H), 1.39-1.52 (m, 1H), 1.17 (s, 3H), 1.09-1.37 (m, 5H), 1.00 (d, J = 6.8 Hz, 3H), 0.83 (d, J = 6.8 Hz, 3H) | 622.7 |

TABLE 1-continued

Structures and analytical data for Compounds 1-60

| Structure, Compound #, and Chemical Name | ¹H NMR data | LCMS data (ES+) |
|---|---|---|
| 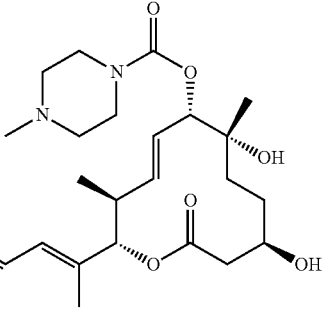<br>26<br>[(2S,3S,4E,6S,7S,10S)-7,10-dihydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclodec-4-en-6-yl] 4-methylpiperazine-1-carboxylate | ¹H NMR (400 MHz, CHLOROFORM-d) δ: 6.21 (dd, J = 15.1, 10.8 Hz, 1H), 6.02 (d, J = 10.8 Hz, 1H), 5.50-5.70 (m, 3H), 5.23 (s, 1H), 5.08 (d, J = 10.5 Hz, 1H), 4.95 (d, J = 9.3 Hz, 1H), 3.80-4.02 (m, 3H), 3.48-3.74 (m, 4H), 3.44 (br. s., 6H), 3.24-3.38 (m, 1H), 2.36-2.59 (m, 5H), 2.32 (br. s., 4H), 2.25 (s, 4H), 1.87-2.08 (m, 2H), 1.58-1.82 (m, 7H), 1.41-1.57 (m, 2H), 1.19-1.36 (m, 3H), 1.17 (s, 3H), 1.08 (br. s., 1H), 1.00 (d, J = 6.8 Hz, 3H), 0.83 (d, J = 6.8 Hz, 3H) | 636.5 |
| 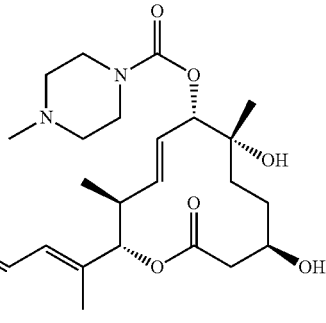<br>27<br>[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclodec-4-en-2-yl]-2-methylhepta-3,5-dienyl] 1,3-dihydroisoindole-2-carboxylate | ¹H NMR (400 MHz, CHLOROFORM-d) δ: 7.15-7.24 (m, 4H), 6.23 (dd, J = 14.7, 10.4 Hz, 1H), 6.03 (d, J = 11.0 Hz, 1H), 5.49-5.69 (m, 2H), 5.08 (d, J = 10.5 Hz, 1H), 4.95 (d, J = 9.3 Hz, 1H), 4.65 (d, J = 16.3 Hz, 3H), 3.89-4.08 (m, 2H), 3.67 (br. s., 1H), 3.35-3.49 (m, 4H), 2.36-2.63 (m, 3H), 2.30 (br. s., 3H), 2.23 (s, 3H), 1.97 (s, 1H), 1.87 (s, 1H), 1.55-1.73 (m, 4H), 1.40-1.55 (m, 2H), 1.09-1.32 (m, 5H), 0.97-1.09 (m, 3H), 0.81 (d, J = 6.5 Hz, 3H) | 654.5 |
| 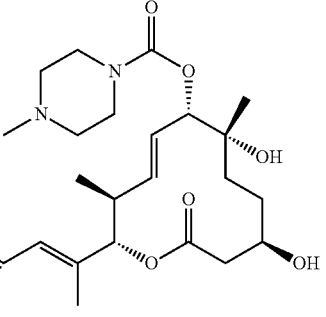<br>28<br>[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclodec-4-en-2-yl]-2-methylhepta-3,5-dienyl] indole-1-carboxylate | ¹H NMR (400 MHz, CHLOROFORM-d) δ: 7.63 (d, J = 8.0 Hz, 1H), 7.25-7.53 (m, 2H), 6.12-6.36 (m, 1H), 6.03 (s, 1H), 6.00 (s, 1H), 5.41-5.67 (m, 2H), 5.04-5.16 (m, 1H), 4.75-5.03 (m, 1H), 4.35-4.54 (m, 1H), 3.89 (d, J = 6.5 Hz, 1H), 3.60-3.77 (m, 1H), 3.54 (d, J = 11.0 Hz, 1H), 3.44 (br. s., 1H), 3.38 (br. s., 1H), 3.05-3.32 (m, 1H), 2.69-2.92 (m, 1H), 2.36-2.62 (m, 2H), 2.22-2.36 (m, 2H), 2.07-2.21 (m, 1H), 1.91-2.06 (m, 1H), 1.87 (d, J = 10.5 Hz, 1H), 1.55-1.76 (m, 3H), 1.13-1.41 (m, 4H), 0.94-1.13 (m, 3H), 0.66-0.93 (m, 3H) | 652.8 |

TABLE 1-continued

Structures and analytical data for Compounds 1-60

| Structure, Compound #, and Chemical Name | ¹H NMR data | LCMS data (ES+) |
|---|---|---|
| 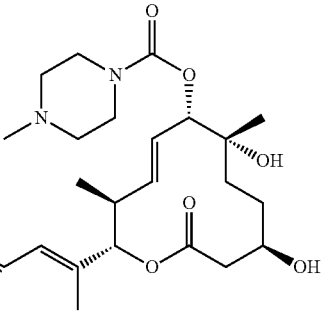<br>29<br>[(2S,3S,4E,6S,7S,10S)-7,10-dihydroxy-2-[(2E,4E,6S)-7-[2-(1-hydroxyethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, CHLOROFORM-d) δ: 0.99-1.12 (m, 3 H) 1.02-1.10 (m, 6 H) 1.16 (d, J = 5.65 Hz, 1 H) 1.24-1.25 (m, 3 H) 1.28-1.42 (m, 2 H) 1.49-1.66 (m, 5 H) 1.74 (d, J = 4.14 Hz, 3 H) 1.92 (m, 1 H) 2.34 (br. s., 3 H) 2.38-2.48 (m, 4 H) 2.49-2.64 (m, 4 H) 3.23-3.38 (m, 1 H) 3.42-3.62 (m, 6 H) 3.62-3.79 (m, 2 H) 3.98 (d, J = 6.40 Hz, 2 H) 5.02 (d, J = 9.41 Hz, 1 H) 5.15 (d, J = 10.67 Hz, 1 H) 5.57-5.73 (m, 3 H) 6.06-6.12 (m, 1 H) 6.28 (dd, J = 16.31, 11.04 Hz, 1 H) | 650.5 |
| 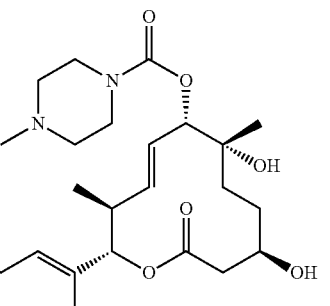<br>30<br>[(2S,3S,4E,6S,7S,10S)-2-[(2E,4E,6R)-7-(2,2-dimethylpyrrolidine-1-carbonyl)oxy-6-methylhepta-2,4-dien-2-yl]-7,10-dihydroxy-3,7-dimethyl-12-oxo-1-oxacyclododec-4-en-6-yl] 4-methylpiperazine-1-carboxylate | ¹H NMR (400 MHz, CHLOROFORM-d) δ: 0.76-1.00 (d, , J = 6.53 Hz 3 H) 1.01-1.12 (d, J = 6.78 Hz, 3 H) 1.23 (s, 3 H) 1.26 (s, 6 H) 1.28-1.43 (m, 4 H) 1.47-1.62 (m, 1 H) 1.72 (s, 3 H) 1.75-1.94 (m, 3 H) 2.51 (s, 3 H) 2.51-2.62 (m, 4 H) 2.74 (br. s., 4 H) 3.41 (m, 1 H) 3.49 (m, 1H) 3.66 (br. s., 4 H) 3.72 (m, 1 H) 3.70-3.82 (m, 2 H) 3.85-4.05 (m, 2 H) 5.02 (d, J = 9.29 Hz, 1 H) 5.15 (d, J = 10.79 Hz, 1 H) 5.58-5.73 (m, 3 H) 6.08 (d, J = 10.16 Hz, 1 H) 6.25 (m, 1 H) | 634.3 |
| 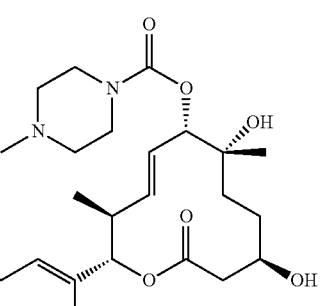<br>31<br>[(2S,3S,4E,6S,7S,10S)-2-[(2E,4E,6R)-7-[(2S,5S)-2,5-dimethylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-methylpiperazine-1-carboxylate | ¹H NMR (400 MHz, METHANOL-d4) δ: 0.90 (d, J = 6.65 Hz, 3 H) 1.09 (d, J = 6.78 Hz, 3 H) 1.13 (d, J = 6.27 Hz, 3 H) 1.16 (d, J = 6.40 Hz, 3 H) 1.24 (s, 3 H) 1.36-1.46 (m, 2 H) 1.50-1.71 (m, 4 H) 1.76 (s, 3 H) 2.07-2.23 (m, 2 H) 2.51-2.70 (m, 7 H) 2.92 (br. s., 4 H) 3.50-3.90 (m, 5 H) 3.91-4.03 (m, 4 H) 4.97 (d, J = 9.66 Hz, 1 H) 5.07 (d, J = 10.67 Hz, 1 H) 5.61 (dd, J = 15.18, 9.66 Hz, 1 H) 5.65-5.79 (m, 2 H) 6.12 (d, J = 10.79 Hz, 1 H) 6.37 (dd, J = 14.93, 10.79 Hz, 1 H) | 634.5 |

TABLE 1-continued

Structures and analytical data for Compounds 1-60

| Structure, Compound #, and Chemical Name | ¹H NMR data | LCMS data (ES+) |
|---|---|---|
| 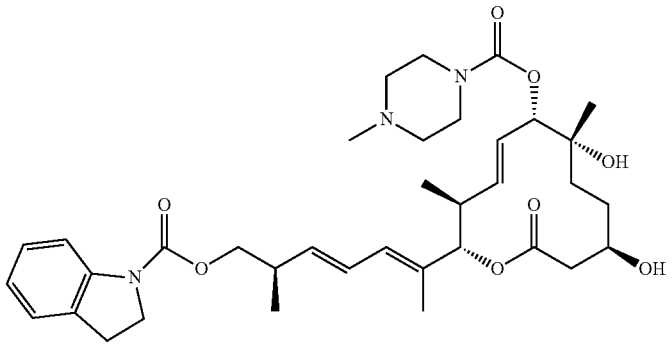 [SMILES: C/C(=C\C=C\[C@@H](C)COC(=O)n1ccc2ccccc21)[C@H]1OC(=O)C[C@H](O)CC[C@@](C)(O)[C@@H](OC(=O)N2CCN(C)CC2)/C=C/[C@@H]1C]<br>32<br>[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclododec-4-en-2-yl]-2-methylhepta-3,5-dienyl] 2,3-dihydroindole-1-carboxylate | ¹H NMR (400 MHz, CHLOROFORM-d) δ: 7.79 (br. s., 1H), 7.45 (s, 1H), 7.19 (s, 3H), 7.08 (d, J = 7.5 Hz, 2H), 6.77-7.00 (m, 1H), 6.13-6.37 (m, 1H), 6.04 (m, 2H), 5.49-5.70 (m, 3H), 5.23 (s, 1H), 5.02-5.16 (m, 1H), 4.95 (d, J = 9.3 Hz, 1H), 4.09-4.37 (m, 1H), 4.05 (d, J = 6.8 Hz, 1H), 3.83-3.99 (m, 2H), 3.65 (d, J = 19.3 Hz, 1H), 3.34-3.50 (m, 4H), 3.05 (t, J = 8.5 Hz, 2H), 2.64 (br. s., 1H), 2.37-2.60 (m, 3H), 2.30 (br. s., 3H), 2.23 (s, 3H), 1.98 (s, 1H), 1.87 (s, 1H), 1.81 (s, 1H), 1.57-1.70 (m, 4H), 1.40-1.57 (m, 3H), 1.11-1.31 (m, 5H), 1.05 (d, J = 6.5 Hz, 3H), 0.70-0.92 (m, 3H) | 654.5 |
| 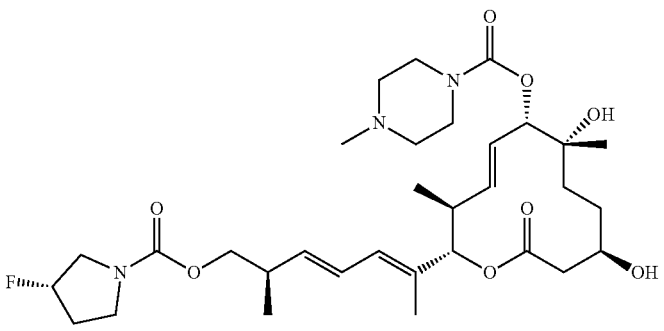 [SMILES: C/C(=C\C=C\[C@@H](C)COC(=O)N1CC[C@H](F)C1)[C@H]1OC(=O)C[C@H](O)CC[C@@](C)(O)[C@@H](OC(=O)N2CCN(C)CC2)/C=C/[C@@H]1C]<br>33<br>[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-methylpiperazine-1-carboxylate | ¹H NMR (400 MHz, METHANOL-d4) δ: 0.90 (d, J = 6.65 Hz, 3 H) 1.05-1.14 (m, 3 H) 1.24 (s, 3 H) 1.34-1.46 (m, 2 H) 1.53-1.71 (m, 2 H) 1.76 (s, 3 H) 1.95-2.30 (m, 2 H) 2.55 (br. s., 5 H) 2.57-2.69 (m, 2 H) 2.74 (br. s., 4 H) 3.40-3.52 (m, 2 H) 3.53-3.86 (m, 7 H) 3.91-4.10 (m, 2 H) 4.97 (d, J = 9.66 Hz, 1 H) 5.07 (d, J = 10.67 Hz, 1 H) 5.25 (dt, J = 52.95, 3.33 Hz, 1 H) 5.60 (dd, J = 15.18, 9.79 Hz, 1 H) 5.65-5.79 (m, 2 H) 6.12 (d, J = 10.79 Hz, 1 H) 6.31-6.43 (m, 1 H) | 625.6 |
| 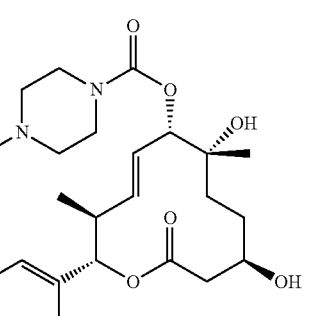<br>34<br>[(2S,3S,4E,6S,7S,10S)-2-[(2E,4E,6R)-7-[(2R)-2-(fluoromethyl)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-methylpiperazine-1-carboxylate | ¹H NMR (400 MHz, METHANOL-d4) δ: 0.91 (d, J = 6.65 Hz, 3 H) 1.09 (d, J = 6.78 Hz, 3 H) 1.24 (s, 3 H) 1.35-1.45 (m, 2 H) 1.54-1.71 (m, 2 H) 1.77 (s, 3 H) 1.81-2.10 (m, 4 H) 2.46 (s, 3 H) 2.54 (d, J = 3.64 Hz, 2 H) 2.62 (br. s., 6 H) 2.72 (br. s., 1 H) 3.35-3.47 (m, 3 H) 3.52-3.74 (m, 4 H) 3.78-3.85 (m, 1 H) 4.00 (d, J = 5.14 Hz, 3 H) 4.27-4.54 (m, 2 H) 4.96 (d, J = 9.66 Hz, 1 H) 5.07 (d, J = 10.67 Hz, 1 H) 5.71 (s, 3 H) 6.12 (d, J = 10.16 Hz, 1 H) 6.37 (dd, J = 15.31, 10.92 Hz, 1 H) | 639.5 |

TABLE 1-continued

Structures and analytical data for Compounds 1-60

| Structure, Compound #, and Chemical Name | ¹H NMR data | LCMS data (ES+) |
|---|---|---|
| 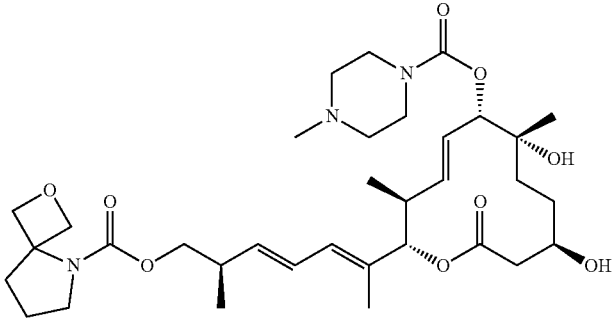<br>35<br>[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclododec-4-en-2-yl]-2-methylhepta-3,5-dienyl] 2-oxa-5-azaspiro[3.4]octane-5-carboxylate | ¹H NMR (400 MHz, CHLOROFORM-d) δ: 0.89 (d, J = 6.65 Hz, 6 H) 1.08 (d, J = 6.65 Hz, 1 H) 1.14 (br. s., 1 H) 1.23 (s, 3 H) 1.27-1.42 (m, 3 H) 1.45-1.64 (m, 1 H) 1.72 (s, 3 H) 1.73-1.93 (m, 2 H) 1.75-1.93 (m, 15 H) 2.26-2.35 (m, 2 H) 2.35 (s, 3 H) 2.45 (br. s., 4 H) 2.48-2.74 (m, 5 H) 3.39 (m, 1 H) 3.45 (m, 1 H) 3.54 (t, J = 4.89 Hz, 4 H) 3.70-3.78 (m, 1 H) 4.01 (m, 1 H) 4.11 (m, 1 H) 4.36 (d, J = 5.52 Hz, 2 H) 5.02 (d, J = 9.41 Hz, 1 H) 5.15 (d, J = 10.67 Hz, 1 H) 5.57-5.75 (m, 3 H) 6.08 (d, J = 10.67 Hz, 1 H) 6.19-6.41 (m, 1 H) | 648.4 |
| 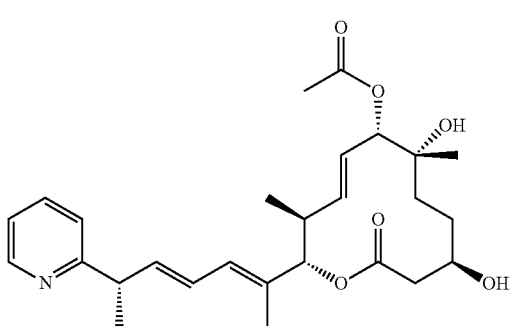 [SMILES: CC(=O)O[C@H]1/C=C/[C@H](C)[C@@H](/C(C)=C/C=C/[C@H](C)c2ccccn2)OC(=O)C[C@H](O)CC[C@@]1(C)O]<br>36<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] acetate | ¹H NMR (400 MHz, CHLOROFORM-d) δ: 0.90 (d, J = 6.78 Hz, 3 H) 1.20 (s, 3 H) 1.25-1.39 (m, 4 H) 1.45 (d, J = 7.03 Hz, 3 H) 1.72 (d, J = 1.00 Hz, 3 H) 2.07 (br. s., 1 H) 2.09 (s, 3 H) 2.45-2.63 (m, 3 H) 3.51 (d, J = 9.41 Hz, 1 H) 3.66-3.81 (m, 2 H) 5.08 (d, J = 9.16 Hz, 1 H) 5.15 (d, J = 10.54 Hz, 1 H) 5.60-5.66 (m, 2 H) 5.99 (dd, J = 15.06, 7.40 Hz, 1 H) 6.11 (d, J = 11.92 Hz, 1 H) 6.27-6.35 (m, 1 H) 7.11 (ddd, J = 7.40, 4.89, 1.13 Hz, 1 H) 7.16 (d, J = 7.91 Hz, 1 H) 7.61 (t, J = 7.36 Hz, 1 H) 8.54 (d, J = 5.02 Hz, 1 H) | 472.2 |
| 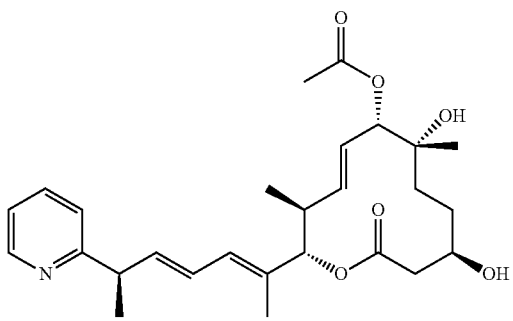 [SMILES: CC(=O)O[C@H]1/C=C/[C@H](C)[C@@H](/C(C)=C/C=C/[C@@H](C)c2ccccn2)OC(=O)C[C@H](O)CC[C@@]1(C)O]<br>37<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] acetate | ¹H NMR (400 MHz, CHLOROFORM-d) δ: 0.86 (d, J = 6.78 Hz, 3 H) 1.20 (s, 3 H) 1.28-1.53 (m, 4 H) 1.44 (d, J = 7.03 Hz, 3 H) 1.73 (d, J = 1.00 Hz, 3 H) 2.04-2.12 (m, 4 H) 2.46-2.61 (m, 3 H) 3.52 (d, J = 10.92 Hz, 1 H) 3.66-3.85 (m, 2 H) 5.07 (d, J = 9.03 Hz, 1 H) 5.15 (d, J = 10.67 Hz, 1 H) 5.55-5.71 (m, 2 H) 6.00 (dd, J = 15.12, 7.47 Hz, 1 H) 6.10 (d, J = 10.79 Hz, 1 H) 6.32 (ddd, J = 15.18, 10.79, 1.13 Hz, 1 H) 7.11 (t, J = 6.13 Hz, 1 H) 7.14-7.18 (m, 1 H) 7.26 (s, 2 H) 7.61 (t, J = 7.63 Hz, 1 H) 8.54 (d, J = 5.00 Hz, 1 H) | 472.2 |

TABLE 1-continued

Structures and analytical data for Compounds 1-60

| Structure, Compound #, and Chemical Name | ¹H NMR data | LCMS data (ES+) |
|---|---|---|
| 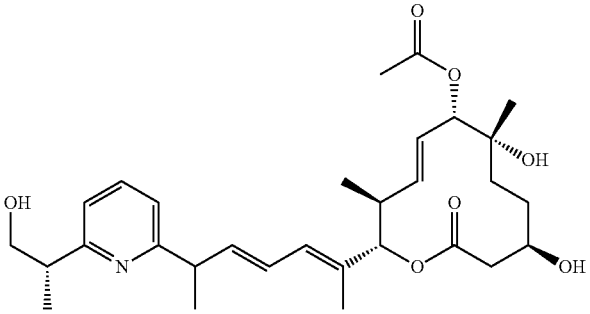 [SMILES: CC(=O)O[C@H]1/C=C/[C@H](C)[C@@H](/C(C)=C/C=C/C(C)c2cccc([C@H](C)CO)n2)OC(=O)C[C@H](O)CC[C@@]1(C)O]<br>38<br>[(2S,3S,4E,6S,7S,10S)-7,10-dihydroxy-2-[(2E,4E)-6-[6-[(2R)-1-hydroxypropan-2-yl]pyridin-2-yl]hepta-2,4-dien-2-yl]-3,7-dimethyl-12-oxo-1-oxacyclododec-4-en-6-yl] acetate | ¹H NMR (400 MHz, CHLOROFORM-d) δ: 0.86-0.92 (m, 3 H) 1.21 (s, 3 H) 1.22-1.39 (m, 4 H) 1.33 (d, J = 7.15 Hz, 3 H) 1.42 (m, 3 H) 1.73 (s, 3 H) 2.07-2.11 (m, 4 H) 2.44-2.69 (m, 4 H) 3.03 (br. s., 1 H) 3.48-3.55 (m, 1 H) 3.64-3.83 (m, 3 H) 3.92-3.99 (m, 1 H) 5.08 (d, J = 8.91 Hz, 1 H) 5.15 (d, J = 10.67 Hz, 1 H) 5.63 (t, J = 8.78 Hz, 2 H) 5.94 (dd, J = 15.18, 7.65 Hz, 1 H) 6.10 (d, J = 10.55 Hz, 1 H) 6.24-6.33 (m, 1 H) 6.99-7.04 (m, 2 H) 7.57 (t, J = 7.66 Hz, 1 H) | 530.3 |
| 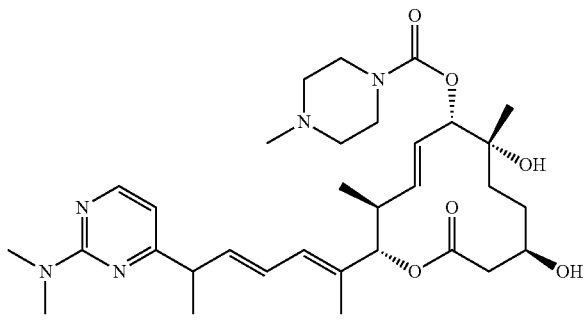 [SMILES: C/C(=C\C=C\C(C)c1ccnc(N(C)C)n1)[C@H]1OC(=O)C[C@H](O)CC[C@@](C)(O)[C@@H](OC(=O)N2CCN(C)CC2)/C=C/[C@@H]1C]<br>39<br>[(2S,3S,4E,6S,7S,10S)-2-[(2E,4E)-6-[2-(dimethylamino)pyrimidin-4-yl]hepta-2,4-dien-2-yl]-7,10-dihydroxy-3,7-dimethyl-12-oxo-1-oxacyclododec-4-en-6-yl] 4-methylpiperazine-1-carboxylate | ¹H NMR (400 MHz, CHLOROFORM-d) δ: 8.10-8.34 (m, 1H), 6.93 (s, 1H), 6.38-6.63 (m, 1H), 6.17-6.32 (m, 1H), 5.52-5.73 (m, 1H), 5.30-5.52 (m, 1H), 5.01-5.16 (m, 1H), 4.95 (d, J = 9.3 Hz, 1H), 3.97-4.09 (m, 1H), 3.93 (br. s., 1H), 3.52 (br. s., 1H), 3.42 (br. s., 1H), 3.35 (br. s., 1H), 2.74 (t, J = 7.3 Hz, 1H), 2.54 (t, J = 7.4 Hz, 1H), 2.46 (br. s., 1H), 1.92-2.19 (m, 3H), 1.82-1.90 (m, 1H), 1.61-1.81 (m, 2H), 1.50 (br. s., 5H), 1.34-1.45 (m, 2H), 1.01-1.10 (m, 2H), 0.94 (dd, J = 6.7, 4.6 Hz, 1H), 0.64-0.90 (m, 3H) | 600.6 |
| 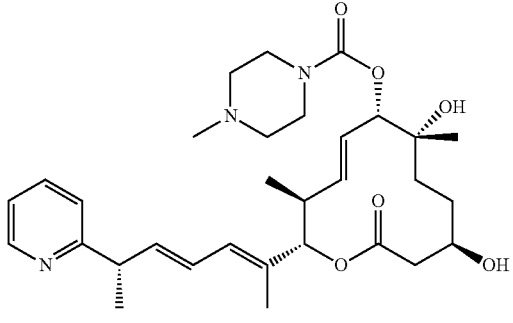<br>40<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate | ¹H NMR (400 MHz, CHLOROFORM-d) δ ppm 0.90 (d, J = 6.78 Hz, 3 H) 1.24 (s, 3 H) 1.28-1.41 (m, 1 H) 1.45 (d, J = 6.90 Hz, 3 H) 1.51-1.71 (m, 3 H) 1.73 (s, 3 H) 1.91 (s, 1 H) 2.42 (s, 3 H) 2.43-2.64 (m, 6 H) 3.47 (m, 4 H) 3.58-3.83 (m, 2 H) 5.01 (d, J = 9.54 Hz, 1 H) 5.14 (d, J = 10.67 Hz, 1 H) 5.51-5.75 (m, 2 H) 5.99 (dd, J = 15.06, 7.53 Hz, 1 H) 6.11 (d, J = 10.79 Hz, 1 H) 6.27-6.34 (m, 1 H) 7.11 (ddd, J = 7.43, 4.86, 1.13 Hz, 1 H) 7.16 (d, J = 7.78 Hz, 1 H) 7.60 (td, J = 7.69, 1.82 Hz, 1 H) 8.54 (d, J = 5.03 Hz, 1 H) | 556.3 |

TABLE 1-continued

Structures and analytical data for Compounds 1-60

| Structure, Compound #, and Chemical Name | ¹H NMR data | LCMS data (ES+) |
|---|---|---|
| 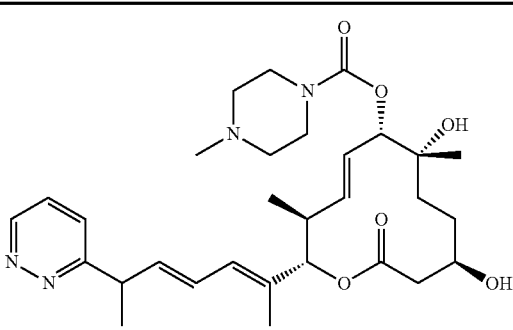<br>41<br>[(2S,3S,4E,6S,7S,10S)-7,10-dihydroxy-3,7-dimethyl-12-oxo-2-[(2E,4E)-6-pyridazin-3-ylhepta-2,4-dien-2-yl]-1-oxacyclododec-4-en-6-yl] 4-methylpiperazine-1-carboxylate | ¹H NMR (CD$_2$Cl$_2$) δ: 8.90-9.14 (m, 1H), 7.68 (d, J = 8.0 Hz, 1H), 7.32-7.54 (m, 1H), 6.29-6.53 (m, 1H), 6.12 (d, J = 10.8 Hz, 1H), 5.85-6.07 (m, 1H), 5.63-5.84 (m, 1H), 5.05-5.23 (m, 1H), 4.98 (d, J = 9.5 Hz, 1H), 3.70 (br. s., 1H), 3.48 (br. s., 2H), 3.30 (br. s., 1H), 2.44-2.65 (m, 2H), 2.35 (d, J = 8.8 Hz, 2H), 2.00-2.20 (m, 1H), 1.82-2.00 (m, 1H), 1.70-1.80 (m, 1H), 1.64 (d, J = 11.0 Hz, 1H), 1.44-1.58 (m, 6H), 1.24-1.43 (m, 2H), 1.20 (s, 1H), 1.12 (d, J = 5.5 Hz, 1H), 0.66-0.91 (m, 3H) | |
| 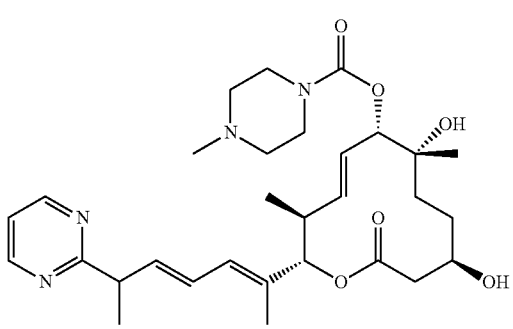 [SMILES: C/C(=C\C=C\C(C)c1ncccn1)[C@H]1OC(=O)C[C@H](O)CC[C@@](C)(O)[C@@H](OC(=O)N2CCN(C)CC2)/C=C/[C@@H]1C]<br>42<br>[(2S,3S,4E,6S,7S,10S)-7,10-dihydroxy-3,7-dimethyl-12-oxo-2-[(2E,4E)-6-pyrimidin-2-ylhepta-2,4-dien-2-yl]-1-oxacyclododec-4-en-6-yl] 4-methylpiperazine-1-carboxylate | ¹H NMR (400 MHz, CHLOROFORM-d) δ: 0.72-0.88 (m, 4 H) 1.09 (d, J = 6.27 Hz, 2 H) 1.13-1.33 (m, 8 H) 1.36-1.46 (m, 4 H) 1.49 (br. s., 6 H) 1.66 (s, 3 H) 1.82 (br. s., 1 H) 2.00 (d, J = 19.32 Hz, 2 H) 2.30 (br. s., 3 H) 2.37-2.64 (m, 3 H) 3.07 (d, J = 7.28 Hz, 2 H) 3.29-3.56 (m, 4 H) 3.67 (br. s., 1 H) 3.73-3.95 (m, 2 H) 4.95 (d, J = 9.29 Hz, 1 H) 5.08 (d, J = 10.79 Hz, 1 H) 5.23 (s, 1 H) 5.47-5.67 (m, 2 H) 5.93-6.16 (m, 2 H) 6.17-6.41 (m, 1 H) 6.93 (s, 1 H) 6.99-7.13 (m, 1 H) 7.45 (s, 1 H) 8.53-8.74 (m, 2 H) | 557.46 |
| 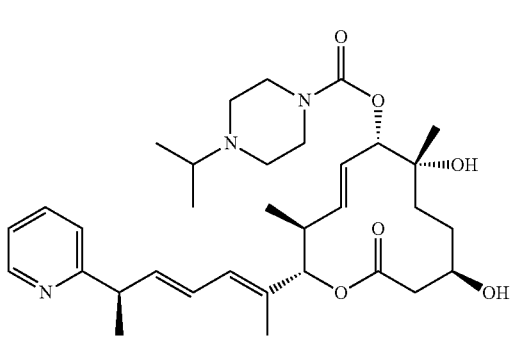 [SMILES: C/C(=C\C=C\[C@@H](C)c1ccccn1)[C@H]1OC(=O)C[C@H](O)CC[C@@](C)(O)[C@@H](OC(=O)N2CCN(C(C)C)CC2)/C=C/[C@@H]1C]<br>43<br>[(2R,3R,4E,6S,7R,10S)-7,10-dihydroxy-3,7-dimethyl-12-oxo-2-[(2E,4E,6R)-6-pyridin-2-ylhepta-2,4-dien-2-yl]-1-oxacyclododec-4-en-6-yl] 4-propan-2-ylpiperazine-1-carboxylate | ¹H NMR (400 MHz, CHLOROFORM-d) δ: 8.57 (d, J = 5.0 Hz, 1H), 7.63 (td, J = 7.7, 1.8 Hz, 1H), 7.18 (d, J = 7.7 Hz, 1H), 7.14 (t, J = 6.1 Hz, 1H), 6.34 (dd, J = 14.6, 10.3 Hz, 1H), 6.14 (d, J = 10.8 Hz, 1H), 6.02 (dd, J = 15.1, 7.5 Hz, 1H), 5.57-5.78 (m, 2H), 5.32 (s, 1H), 5.17 (d, J = 10.8 Hz, 1H), 5.04 (d, J = 9.5 Hz, 1H), 3.60-3.84 (m, 2H), 3.51 (br. s., 4H), 2.76 (br. s., 1H), 2.44-2.67 (m, 6H), 1.98 (s, 1H), 1.66-1.81 (m, 4H), 1.51-1.66 (m, 3H), 1.22-1.49 (m, 8H), 1.08 (d, J = 6.3 Hz, 5H), 0.79-1.00 (m, 3H) | 584.5 |

TABLE 1-continued

Structures and analytical data for Compounds 1-60

| Structure, Compound #, and Chemical Name | ¹H NMR data | LCMS data (ES+) |
|---|---|---|
| 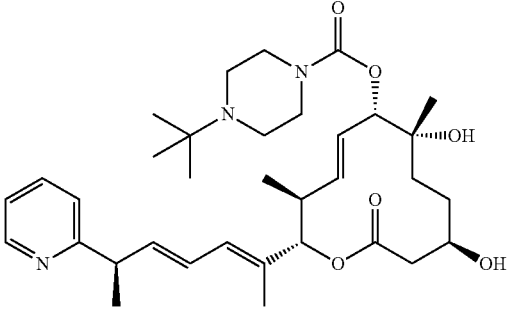 [SMILES: C/C(=C\C=C\[C@@H](C)c1ccccn1)[C@H]1OC(=O)C[C@H](O)CC[C@@](C)(O)[C@@H](OC(=O)N2CCN(C(C)(C)C)CC2)/C=C/[C@@H]1C]<br>44<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-tert-butylpiperazine-1-carboxylate | ¹H NMR (400 MHz, CHLOROFORM-d) δ: 8.48 (d, J = 4.0 Hz, 1H), 7.54 (td, J = 7.7, 1.9 Hz, 1H), 7.09 (d, J = 7.5 Hz, 1H), 7.05 (t, J = 6.2 Hz, 1H), 6.25 (dd, J = 14.6, 11.0 Hz, 1H), 6.04 (d, J = 11.0 Hz, 1H), 5.93 (dd, J = 15.2, 7.4 Hz, 1H), 5.46-5.70 (m, 2H), 5.08 (d, J = 10.5 Hz, 1H), 4.94 (d, J = 9.5 Hz, 1H), 3.54-3.76 (m, 2H), 3.28-3.53 (m, 4H), 2.37-2.59 (m, 5H), 1.89 (br. s., 1H), 1.57-1.71 (m, 4H), 1.42-1.57 (m, 5H), 1.33-1.39 (m, 3H), 1.14-1.30 (m, 5H), 1.01 (br. s., 6H), 0.77-0.93 (m, 3H) | 596.6 |
| 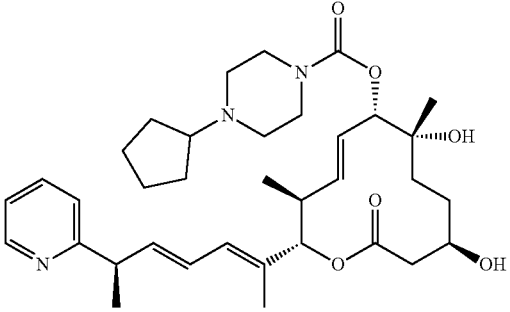 [SMILES: C/C(=C\C=C\[C@@H](C)c1ccccn1)[C@H]1OC(=O)C[C@H](O)CC[C@@](C)(O)[C@@H](OC(=O)N2CCN(C3CCCC3)CC2)/C=C/[C@@H]1C]<br>45<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cyclopentylpiperazine-1-carboxylate | ¹H NMR (400 MHz, CHLOROFORM-d) δ: 8.48 (d, J = 4.9 Hz, 1H), 7.54 (td, J = 7.7, 2.0 Hz, 1H), 7.09 (d, J = 8.1 Hz, 1H), 7.05 (t, J = 6.2 Hz, 1H), 6.25 (ddd, J = 15.1, 10.9, 1.1 Hz, 1H), 6.04 (d, J = 10.8 Hz, 1H), 5.93 (dd, J = 15.1, 7.5 Hz, 1H), 5.48-5.67 (m, 2H), 5.08 (d, J = 10.5 Hz, 1H), 4.94 (d, J = 9.3 Hz, 1H), 3.58-3.73 (m, 2H), 3.36-3.52 (m, 5H), 2.33-2.57 (m, 8H), 1.89 (s, 1H), 1.73-1.83 (m, 2H), 1.57-1.69 (m, 7H), 1.42-1.57 (m, 4H), 1.15-1.40 (m, 10H), 0.74-0.88 (m, 3H) | 610.6 |
| 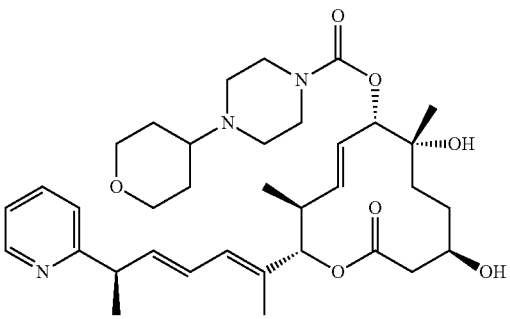 [SMILES: C/C(=C\C=C\[C@@H](C)c1ccccn1)[C@H]1OC(=O)C[C@H](O)CC[C@@](C)(O)[C@@H](OC(=O)N2CCN(C3CCOCC3)CC2)/C=C/[C@@H]1C]<br>46<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(oxan-4-yl)piperazine-1-carboxylate | ¹H NMR (400 MHz, CHLOROFORM-d) δ: 8.48 (ddd, J = 4.9, 1.9, 1.0 Hz, 1H), 7.54 (td, J = 7.7, 1.9 Hz, 1H), 7.09 (d, J = 8.0 Hz, 1H), 7.05 (t, J = 6.1 Hz, 1H), 6.15-6.34 (m, 1H), 6.04 (d, J = 10.8 Hz, 1H), 5.93 (dd, J = 15.1, 7.5 Hz, 1H), 5.48-5.67 (m, 2H), 5.08 (d, J = 10.5 Hz, 1H), 4.94 (d, J = 9.5 Hz, 1H), 3.95 (dd, J = 11.3, 3.8 Hz, 2H), 3.53-3.76 (m, 2H), 3.37-3.49 (m, 5H), 3.22-3.37 (m, 2H), 2.35-2.57 (m, 7H), 1.88 (s, 1H), 1.44-1.70 (m, 11H), 1.14-1.39 (m, 8H), 0.72-0.89 (m, 3H) | 626.6 |

TABLE 1-continued

Structures and analytical data for Compounds 1-60

| Structure, Compound #, and Chemical Name | ¹H NMR data | LCMS data (ES+) |
|---|---|---|
| 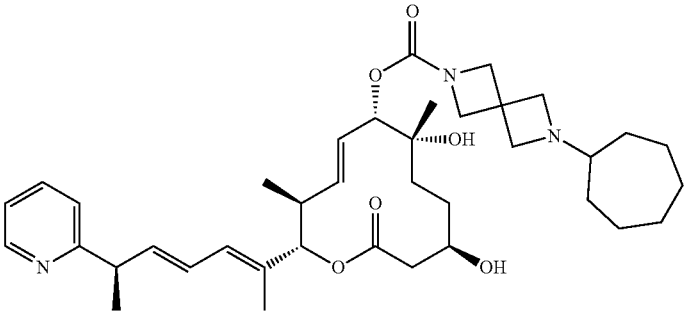 [SMILES: C/C(=C\C=C\[C@@H](C)c1ccccn1)[C@H]1OC(=O)C[C@H](O)CC[C@@](C)(O)[C@@H](OC(=O)N2CC3(C2)CN(C2CCCCCC2)C3)/C=C/[C@@H]1C]<br>47<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 6-cycloheptyl-2,6-diazaspiro[3.3]heptane-2-carboxylate | ¹H NMR (400 MHz, CHLOROFORM-d) δ: 8.48 (d, J = 5.1 Hz, 1H), 7.54 (td, J = 7.7, 1.9 Hz, 1H), 7.09 (d, J = 7.6 Hz, 1H), 7.05 (t, J = 6.0 Hz, 1H), 6.25 (ddd, J = 15.2, 10.8, 1.1 Hz, 1H), 6.04 (d, J = 10.5 Hz, 1H), 5.93 (dd, J = 15.1, 7.5 Hz, 1H), 5.44-5.65 (m, 2H), 5.06 (d, J = 10.5 Hz, 1H), 4.83 (d, J = 9.3 Hz, 1H), 3.91-4.13 (m, 4H), 3.51-3.76 (m, 3H), 3.42 (br. s., 4H), 2.35-2.59 (m, 3H), 2.30 (s, 1H), 2.22 (br. s., 1H), 1.98 (s, 2H), 1.52-1.77 (m, 10H), 1.32-1.51 (m 9H), 1.10-1.32 (m, 9H), 0.72-0.90 (m, 3H) | 650.6 |
| 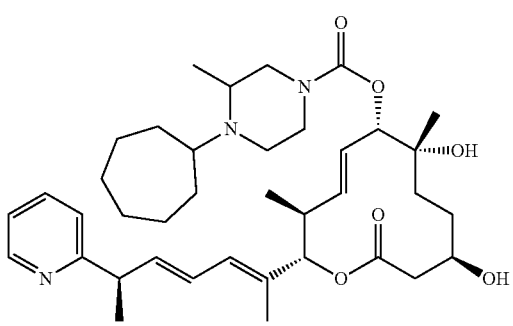<br>48<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptyl-3-methylpiperazine-1-carboxylate | ¹H NMR (400 MHz, CHLOROFORM-d) δ: 8.56 (d, J = 4.9 Hz, 1H), 7.63 (t, J = 7.7 Hz, 1H), 7.18 (d, J = 7.7 Hz, 1H), 7.13 (t, J = 6.1 Hz, 1H), 6.34 (dd, J = 15.3, 10.8 Hz, 1H), 6.13 (d, J = 11.0 Hz, 1H), 6.02 (dd, J = 15.1, 7.5 Hz, 1H), 5.57-5.74 (m, 2H), 5.16 (d, J = 10.8 Hz, 1H), 5.03 (d, J = 9.5 Hz, 1H), 3.92 (br. s., 1H), 3.69-3.83 (m, 3H), 3.53 (d, J = 11.0 Hz, 1H), 2.98 (br. s., 2H), 2.79 (br. s., 2H), 2.48-2.72 (m, 5H), 2.28 (br. s., 1H), 2.01 (br. s., 1H), 1.69-1.79 (m, 7H), 1.66 (br. s., 1H), 1.44-1.63 (m, 10H), 1.23-1.42 (m, 7H), 1.07 (br. s., 3H), 0.85-0.94 (m, 3H) | 652.7 |
| 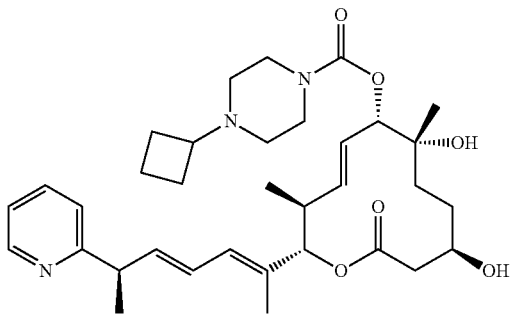<br>49<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cyclobutylpiperazine-1-carboxylate | ¹H NMR (400 MHz, CHLOROFORM-d) δ: 8.56 (d, J = 4.9 Hz, 1H), 7.63 (td, J = 7.7, 1.8 Hz, 1H), 7.18 (d, J = 7.6 Hz, 1H), 7.13 (t, J = 6.1 Hz, 1H), 6.33 (ddd, J = 15.1, 10.9, 1.1 Hz, 1H), 6.13 (d, J = 10.8 Hz, 1H), 6.02 (dd, J = 15.1, 7.5 Hz, 1H), 5.57-5.74 (m, 2H), 5.16 (d, J = 10.5 Hz, 1H), 5.03 (d, J = 9.3 Hz, 1H), 3.68-3.79 (m, 2H), 3.46-3.56 (m, 5H), 2.69-2.77 (m, 1H), 2.49-2.65 (m, 3H), 2.30 (br. s., 4H), 1.97-2.09 (m, 3H), 1.88 (quin, J = 9.1 Hz, 2H), 1.66-1.80 (m, 7H), 1.55 (t, J = 11.9 Hz, 1H), 1.22-1.47 (m, 8H), 0.87-0.93 (m, 3H) | 596.6 |

| Structure, Compound #, and Chemical Name | ¹H NMR data | LCMS data (ES+) |
|---|---|---|
| 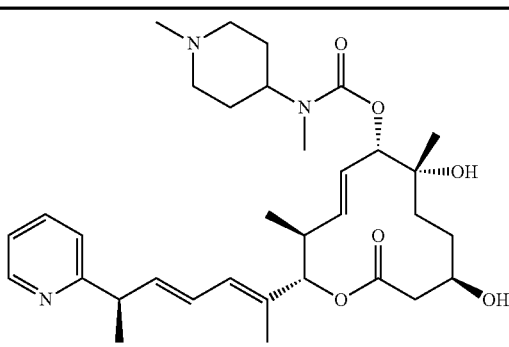<br>50<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] N-methyl-N-(1-methylpiperidin-4-yl)carbamate | ¹H NMR (400 MHz, CHLOROFORM-d) δ: 8.48 (ddd, J = 5.0, 1.8, 1.0 Hz, 1H), 7.54 (t, J = 7.3 Hz, 1H), 7.09 (d, J = 7.6 Hz, 1H), 7.05 (t, J = 6.1 Hz, 1H), 6.14-6.35 (m, 1H), 6.04 (d, J = 9.8 Hz, 1H), 5.93 (dd, J = 15.1, 7.5 Hz, 1H), 5.46-5.68 (m, 2H), 5.08 (d, J = 10.8 Hz, 1H), 4.94 (d, J = 9.5 Hz, 1H), 3.93 (br. s., 1H), 3.51-3.77 (m, 3H), 3.42 (s, 1H), 2.83 (d, J = 11.3 Hz, 2H), 2.73 (s, 3H), 2.37-2.60 (m, 3H), 2.20 (s, 3H), 2.04 (br. s., 1H), 1.89-2.00 (m, 3H), 1.81 (br. s., 1H), 1.46-1.73 (m, 10H), 1.14-1.39 (m, 8H), 0.75-0.86 (m, 3H) | 584.6 |
| 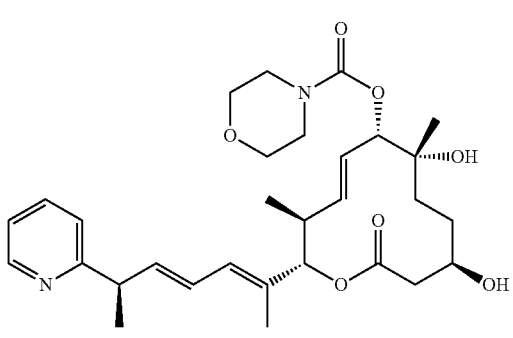 [SMILES: C/C(=C\C=C\[C@@H](C)c1ccccn1)[C@H]1OC(=O)C[C@H](O)CC[C@@](C)(O)[C@@H](OC(=O)N2CCOCC2)/C=C/[C@@H]1C]<br>51<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] morpholine-4-carboxylate | ¹H NMR (400 MHz, CHLOROFORM-d) δ: 8.48 (d, J = 4.9 Hz, 1H), 7.55 (t, J = 7.7 Hz, 1H), 7.10 (d, J = 8.1 Hz, 1H), 7.05 (t, J = 6.2 Hz, 1H), 6.25 (ddd, J = 15.1, 10.8, 1.0 Hz, 1H), 6.05 (d, J = 10.8 Hz, 1H), 5.93 (dd, J = 15.1, 7.5 Hz, 1H), 5.49-5.67 (m, 2H), 5.23 (s, 1H), 5.08 (d, J = 10.5 Hz, 1H), 4.96 (d, J = 9.3 Hz, 1H), 3.54-3.71 (m, 6H), 3.34-3.48 (m, 5H), 2.39-2.58 (m, 3H), 1.97 (s, 1H), 1.85 (s, 1H), 1.59-1.70 (m, 5H), 1.47 (t, J = 11.9 Hz, 1H), 1.15-1.39 (m, 8H), 0.77-0.86 (m, 3H) | 543.5 |
| 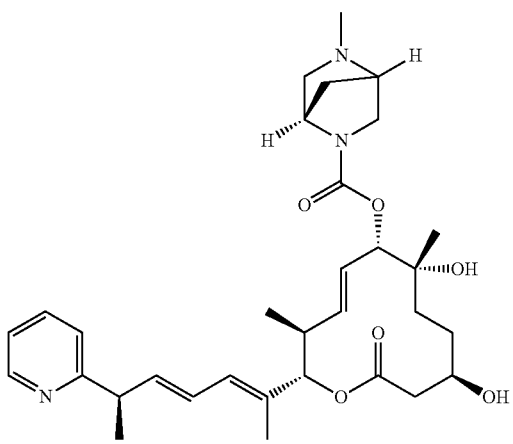 [SMILES: C/C(=C\C=C\[C@@H](C)c1ccccn1)[C@H]1OC(=O)C[C@H](O)CC[C@@](C)(O)[C@@H](OC(=O)N2CC3C[C@@H]2CN3C)/C=C/[C@@H]1C]<br>52<br>[(2R,3R,4E,6S,7R,10S)-7,10-dihydroxy-3,7-dimethyl-12-oxo-2-[(2E,4E,6R)-6-pyridin-2-ylhepta-2,4-dien-2-yl]-1-oxacyclododec-4-en-6-yl] (1S,4R)-5-methyl-2,5-diazabicyclo[2.2.1]heptane-2-carboxylate | ¹H NMR (400 MHz, CHLOROFORM-d) δ: 8.48 (d, J = 4.8 Hz, 1H), 7.54 (td, J = 7.7, 1.8 Hz, 1H), 7.02-7.12 (m, 2H), 6.18-6.31 (m, 1H), 6.06 (s, 1H), 6.03 (s, 1H), 5.93 (dd, J = 15.1, 7.5 Hz, 1H), 5.47-5.67 (m, 2H), 5.08 (d, J = 10.8 Hz, 1H), 4.91 (dd, J = 16.3, 9.5 Hz, 1H), 4.31 (br. s., 1H), 4.22 (br. s., 1H), 3.44-3.70 (m, 4H), 3.42 (br. s., 1H), 3.35 (d, J = 6.0 Hz, 1H), 3.15 (d, J = 9.8 Hz, 1H), 2.91 (d, J = 9.0 Hz, 1H), 2.69-2.80 (m, 1H), 2.61-2.69 (m, 1H), 2.32-2.57 (m, 7H), 2.00 (s, 1H), 1.93 (br. s., 1H), 1.82 (d, J = 9.8 Hz, 1H), 1.57-1.73 (m, 7H), 1.46 (t, J = 13.3 Hz, 1H), 1.14-1.39 (m, 8H), 0.73-0.87 (m, 3H) | 568.5 |

TABLE 1-continued

Structures and analytical data for Compounds 1-60

| Structure, Compound #, and Chemical Name | ¹H NMR data | LCMS data (ES+) |
|---|---|---|
| 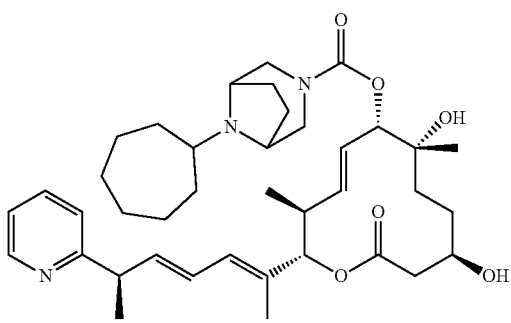 [SMILES: C/C(=C\C=C\[C@@H](C)c1ccccn1)[C@H]1OC(=O)C[C@H](O)CC[C@@](C)(O)[C@@H](OC(=O)N2CC3CCC(C2)N3C2CCCCCC2)/C=C/[C@@H]1C]<br>53<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 8-cycloheptyl-3,8-diazabicyclo[3.2.1]octane-3-carboxylate | ¹H NMR (400 MHz, CHLOROFORM-d) δ: 8.48 (d, J = 5.1 Hz, 1H), 7.69 (d, J = 5.8 Hz, 1H), 7.36-7.61 (m, 1H), 7.00-7.15 (m, 2H), 6.25 (dd, J = 15.1, 10.8 Hz, 1H), 6.04 (d, J = 10.8 Hz, 1H), 5.93 (dd, J = 15.2, 7.4 Hz, 1H), 5.48-5.69 (m, 2H), 5.08 (d, J = 10.5 Hz, 1H), 4.94 (d, J = 9.0 Hz, 1H), 3.53-3.79 (m, 4H), 3.31-3.53 (m, 2H), 2.36-2.61 (m, 3H), 2.28 (br. s., 1H), 1.90 (br. s., 3H), 1.66 (s, 6H), 1.60 (br. s., 2H), 1.54 (br. s., 2H), 1.30-1.51 (m, 10H), 1.25 (d, J = 10.5 Hz, 1H), 1.14-1.22 (m, 3H), 0.80 (d, J = 6.8 Hz, 3H) | 664.9 |
| 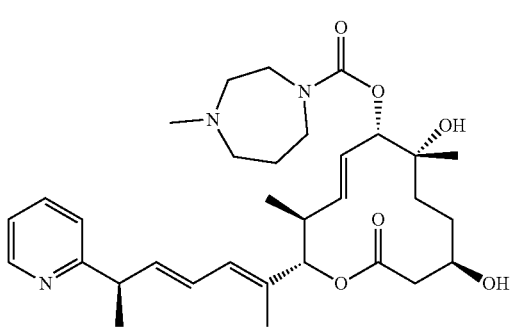 [SMILES: C/C(=C\C=C\[C@@H](C)c1ccccn1)[C@H]1OC(=O)C[C@H](O)CC[C@@](C)(O)[C@@H](OC(=O)N2CCCN(C)CC2)/C=C/[C@@H]1C]<br>54<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methyl-1,4-diazepane-1-carboxylate | ¹H NMR (400 MHz, CHLOROFORM-d) d ppm 0.90 (d, J = 6.78 Hz, 3 H) 1.24-1.49 (m, 9 H) 1.51-1.64 (m, 2 H) 1.64-1.85 (m, 5 H) 2.01 (br. s.,4 H) 2.43-2.58 (m, 5 H) 2.60-2.77 (m, 4 H) 3.48-3.62 (m, 4 H) 3.62-3.82 (m, 3 H) 4.96-5.10 (m, 1 H) 5.17 (d, J = 10.79 Hz, 1 H) 5.58-5.76 (m, 2 H) 6.01 (d, J = 7.53 Hz, 1 H) 6.04 (d, J = 7.53 Hz, 1 H) 6.12 (s, 1 H) 6.15 (s, 1 H) 6.24-6.43 (m, 1 H) 7.10-7.22 (m, 2 H) 7.63 (td, J = 7.72, 1.88 Hz, 1 H) 8.57 (d, J = 4.85 Hz, 1 H) | 570.5 |
| 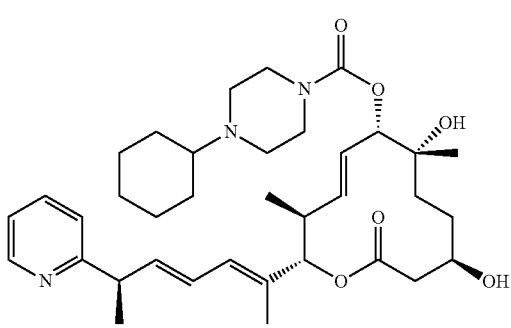 [SMILES: C/C(=C\C=C\[C@@H](C)c1ccccn1)[C@H]1OC(=O)C[C@H](O)CC[C@@](C)(O)[C@@H](OC(=O)N2CCN(C3CCCCC3)CC2)/C=C/[C@@H]1C]<br>55<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cyclohexylpiperazine-1-carboxylate | ¹H NMR (400 MHz, CHLOROFORM-d) d ppm 0.80-1.00 (m, 3 H) 1.13-1.39 (m, 11 H) 1.42-1.48 (m, 3 H) 1.52-1.66 (m, 6 H) 1.66-1.88 (m,7 H) 1.99 (s, 1 H) 2.30 (br. s., 1 H) 2.46-2.66 (m, 7 H) 3.40-3.60 (m, 5 H) 3.64-3.85 (m, 2 H) 5.03 (d, J = 9.29 Hz, 1 H) 5.17 (d, J = 10.79 Hz, 1 H) 5.57-5.75 (m, 2 H) 6.00 (d, J = 7.53 Hz, 1 H) 6.04 (d, J = 7.53 Hz, 1 H) 6.12 (s, 1 H) 6.15 (s, 1 H) 6.27-6.41 (m, 1 H) 7.10-7.22 (m, 2 H) 7.63 (td, J = 7.72, 1.88 Hz, 1 H) 8.57 (d, J = 4.84 Hz, 1 H) | 624.7 |

TABLE 1-continued

Structures and analytical data for Compounds 1-60

| Structure, Compound #, and Chemical Name | $^1$H NMR data | LCMS data (ES+) |
|---|---|---|
| 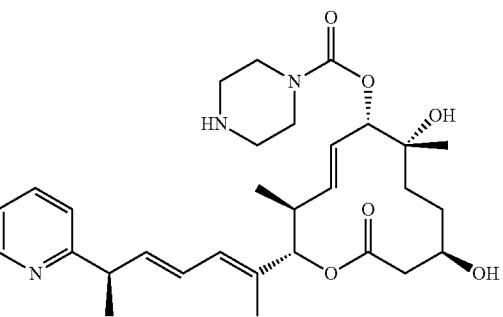<br>56<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] piperazine-1-carboxylate | $^1$H NMR (400 MHz, CHLOROFORM-d) d ppm 0.88 (d, J = 6.78 Hz, 4 H) 1.20-1.46 (m, 7 H) 1.49-1.62 (m, 2 H) 1.66-1.77 (m, 5 H) 1.81 (br. s., 1 H) 1.88 (br. s., 1 H) 2.44-2.66 (m, 3 H) 2.77-2.90 (m, 4 H) 3.02 (s, 1 H) 3.39-3.50 (m, 4 H) 3.61-3.79 (m, 2 H) 5.02 (d, J = 9.54 Hz, 1 H) 5.15 (d, J = 10.54 Hz, 1 H) 5.54-5.74 (m, 2 H) 6.00 (dd, J = 15.06, 7.53 Hz, 1 H) 6.11 (d, J = 10.54 Hz, 1 H) 6.32 (ddd, J = 15.06, 10.79, 1.00 Hz, 1 H) 7.12 (t, J = 6.21 Hz, 1 H) 7.16 (d, J = 8.14 Hz, 1 H) 7.61 (t, J = 7.78 Hz, 1 H) 8.55 (d, J = 4.95 Hz, 1 H) | 542.5 |
| 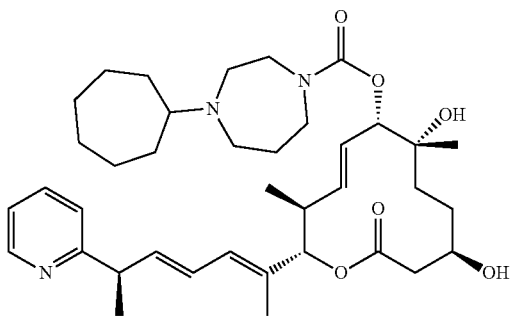<br>57<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptyl-1,4-diazepane-1-carboxylate | $^1$H NMR (400 MHz, CHLOROFORM-d) d ppm 0.82-0.97 (m, 3 H) 1.25-1.37 (m, 4 H) 1.39-1.65 (m, 14 H) 1.75 (s, 7 H) 1.90 (br. s., 1 H) 2.06 (m, 1 H) 2.38 (s, 1 H) 2.49-2.77 (m, 4 H) 2.88 (br. s., 3 H) 3.40-3.62 (m, 3 H) 3.62-3.89 (m, 4 H) 5.03 (t, J = 9.41 Hz, 1 H) 5.17 (d, J = 10.54 Hz, 1H) 5.57-5.76 (m, 2 H) 6.02 (dd, J = 15.31, 7.53 Hz, 1 H) 6.13 (d, J = 10.79 Hz, 1 H) 6.34 (ddd, J = 15.12, 10.73, 1.00 Hz, 1 H) 7.14 (t, J = 6.17 Hz, 1H) 7.18 (d, J = 7.36 Hz, 1 H) 7.28 (s, 2 H) 7.63 (t, J = 7.75 Hz, 1 H) 8.57 (d, J = 4.98 Hz, 1 H) | 652.5 |
| 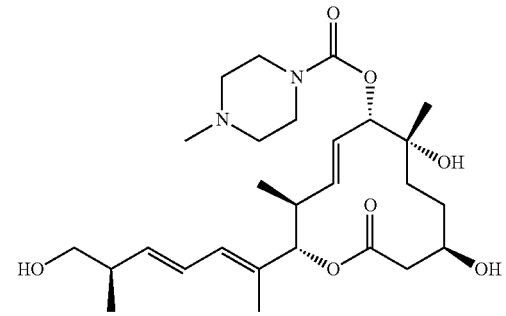 [SMILES: C/C(=C\C=C\[C@@H](C)CO)[C@H]1OC(=O)C[C@H](O)CC[C@@](C)(O)[C@@H](OC(=O)N2CCN(C)CC2)/C=C/[C@@H]1C]<br>58<br>[(2S,3S,4E,6S,7S,10S)-7,10-dihydroxy-2-[(2E,4E,6R)-7-hydroxy-6-methylhepta-2,4-dien-2-yl]-3,7-dimethyl-12-oxo-1-oxacyclododec-4-en-6-yl] 4-methylpiperazine-1-carboxylate | $^1$H NMR (400 MHz, CHLOROFORM-d) δ: ppm 0.81-0.86 (m, 1 H) 0.88-0.93 (m, 3 H) 1.03 (d, J = 6.78 Hz, 3 H) 1.07-1.17 (m, 1 H) 1.21-1.26 (m, 6 H) 1.28-1.34 (m, 2 H) 1.40 (t, J = 7.34 Hz, 4 H) 1.48-1.68 (m, 3 H) 1.74 (s, 3 H) 2.29-2.65 (m, 12 H) 3.10 (d, J = 7.28 Hz, 3 H) 3.42-3.57 (m, 7 H) 3.68-3.78 (m, 1 H) 4.98-5.07 (m, 1 H) 5.12-5.19 (m, 1 H) 5.30 (s, 1 H) 5.54-5.75 (m, 3 H) 6.11 (s, 1 H) 6.28 (s, 1 H) | 509.50 |

TABLE 1-continued

Structures and analytical data for Compounds 1-60

| Structure, Compound #, and Chemical Name | ¹H NMR data | LCMS data (ES+) |
|---|---|---|
| 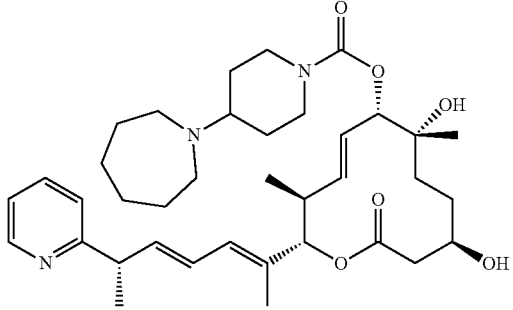<br>59<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(azepan-1-yl)piperidine-1-carboxylate | ¹H NMR (400 MHz, CHLOROFORM-d) δ: ppm 0.86 (s, 1 H) 0.93 (d, J = 6.78 Hz, 2 H) 1.23-1.49 (m, 9 H) 1.54 (d, J = 11.80 Hz, 1 H) 1.61 (br s, 6 H) 1.65-1.77 (m, 4 H) 1.80 (br s, 2 H) 2.00 (br s, 1 H) 2.49-2.66 (m, 4 H) 2.69 (br s, 3 H) 2.80 (br s, 2 H) 3.32 (s, 1 H) 3.52 (d, J = 6.27 Hz, 1 H) 3.62-3.83 (m, 2 H) 4.15 (br s, 2 H) 5.02 (d, J = 9.29 Hz, 1 H) 5.17 (d, J = 10.79 Hz, 1 H) 5.53-5.77 (m, 2 H) 6.01 (dd, J = 15.06, 7.53 Hz, 1 H) 6.13 (d, J = 10.79 Hz, 1 H) 6.33 (ddd, J = 15.12, 10.73, 1.25 Hz, 1 H) 7.14 (t, J = 6.11 Hz, 1 H) 7.18 (d, J = 7.56 Hz, 1 H) 7.28 (s, 3 H) 7.63 (td, J = 7.72, 1.88 Hz, 1 H) 8.57 (d, J = 4.94 Hz, 1 H) | 638.34 |
| 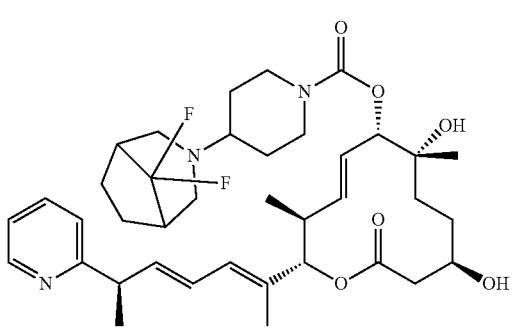 [SMILES: C/C(=C\C=C\[C@@H](C)c1ccccn1)[C@H]1OC(=O)C[C@H](O)CC[C@@](C)(O)[C@@H](OC(=O)N2CCC(N3CC4CCC(C3)C4(F)F)CC2)/C=C/[C@@H]1C]<br>60<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(8,8-difluoro-3-azabicyclo[3.2.1]octan-3-yl)piperidine-1-carboxylate | ¹H NMR (400 MHz, CHLOROFORM-d) δ: ppm 0.90 (d, J = 6.78 Hz, 3 H) 1.25 (s, 3 H) 1.33-1.40 (m, 2 H) 1.41-1.49 (m, 5 H) 1.55-1.62 (m, 4 H) 1.66-1.83 (m, 10 H) 1.99 (s, 1 H) 2.13-2.23 (m, 2 H) 2.43-2.70 (m, 9 H) 2.82-2.95 (m, 2 H) 3.53 (d, J = 10.92 Hz, 1 H) 3.67-3.81 (m, 2 H) 4.02-4.10 (m, 1 H) 4.97-5.07 (m, 1 H) 5.10-5.21 (m, 1 H) 5.57-5.67 (m, 1 H) 5.67-5.76 (m, 1 H) 5.94-6.07 (m, 1 H) 6.08-6.21 (m, 1 H) 6.26-6.40 (m, 1 H) 7.10-7.22 (m, 2 H) 7.57-7.70 (m, 1 H) 8.53-8.61 (m, 1 H) | 686.78 |

Compounds 61-104 (Table 2) were prepared by the method of Scheme 2.

Scheme 2.

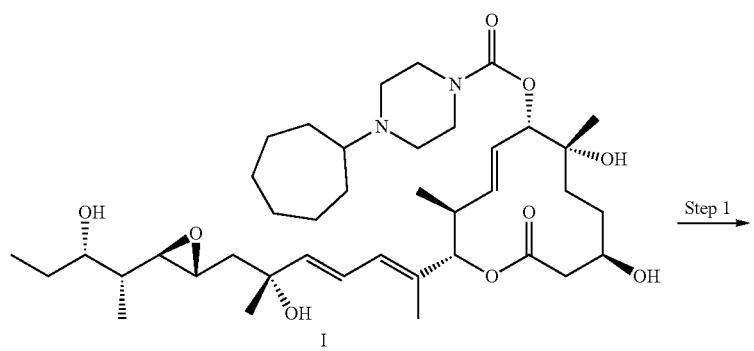

-continued
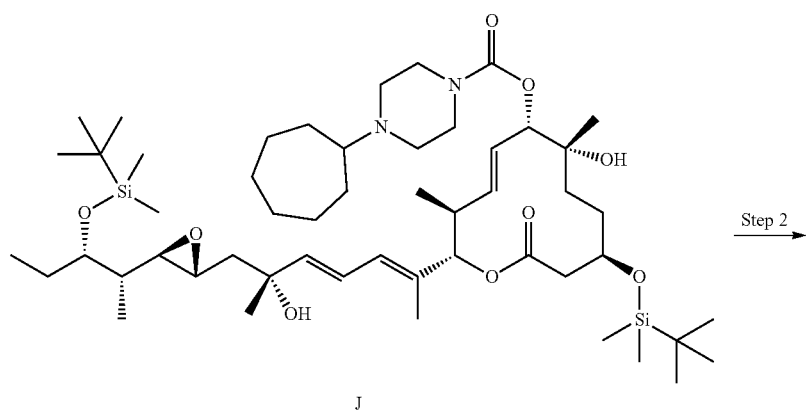
J
Step 2
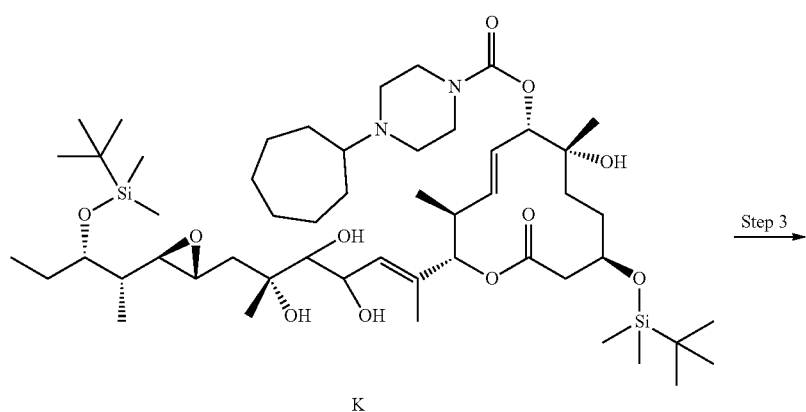
K
Step 3
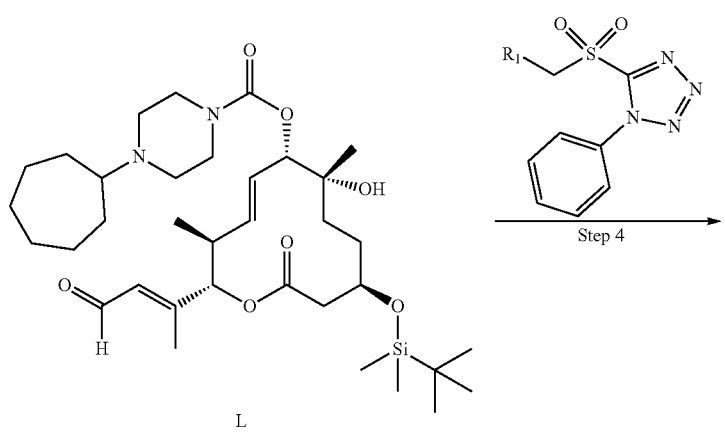
L
Step 4
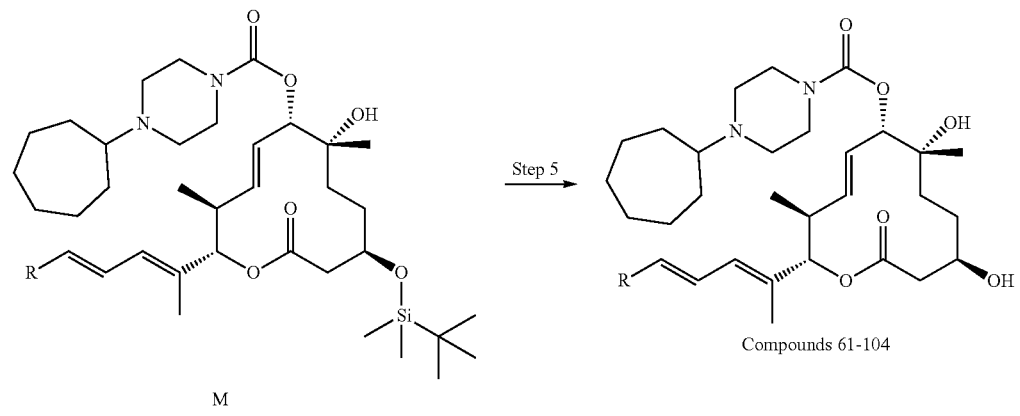
M → Compounds 61-104
Step 5

General Protocol for the Synthesis of Compounds 61-104:

Step 1: A solution of E7107 (I, 3.7 g, 5.1 mmol, 1.0 equiv.) under nitrogen in DMF (100 mL, 0.05M) at 0° C. was treated with imidazole (2.5 g, 36.1 mmol, 7.0 equiv.) and TBSCl (3.9 g, 25.7 mmol, 5.0 equiv.) was added. The reaction was allowed to warm to room temperature and stirred for 20 hours, or until the reaction was determined to be complete by LCMS or TLC. The reaction was diluted with ethyl acetate and the organic layer was washed with brine, dried over sodium sulfate, filtered, and concentrated in vacuo. The resulting oil was purified by silica gel column chromatography (hexanes/ethyl acetate as eluent) to afford the desired product (J, 4.7 g, 5.0 mmol, 96%).

Step 2: To a solution of olefin J (4.7 g, 5.0 mmol, 1.0 equiv.) in THF:$H_2O$ (10:1, 133 mL:13 mL, 0.03M) under nitrogen at 0° C. was added osmium tetroxide (12.4 mL, 1.0 mmol, 0.2 equiv., 2.5% solution) followed by N-methylmorpholine N-oxide (1.16 g, 9.9 mmol, 2.0 equiv.). The reaction was allowed to warm to room temperature and stirred for 13 hours, or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (K, 4.8 g, 4.9 mmol, 99%).

Step 3: To a solution of diol K (4.4 g, 4.5 mmol, 1.0 equiv.) in benzene (100 mL, 0.05M) under nitrogen at room temperature was added lead tetraacetate (4.0 g, 9.0 mmol, 2.0 equiv.). The reaction was stirred for 30 minutes, or until the reaction was determined to be complete by LCMS or TLC. The reaction was quenched with sodium sulfite and diluted with dichloromethane. The organic layer was washed with water, dried over sodium sulfate, filtered, and concentrated in vacuo. The desired product (L, 1.5 g, 2.3 mmol, 52%) was advanced crude.

Step 4: To a solution of the corresponding sulfone (2.5 equiv.) in THF (0.02M) under nitrogen at −78° C. was added KHMDS (2.5 equiv.) dropwise and the reaction was stirred for 10 minutes. Then aldehyde L (1.0 equiv.) in THF (0.5 M) was added dropwise. The reaction was stirred at −78° C. for five hours and then allowed to warm to room temperature overnight. The reaction was quenched with water and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (M).

Step 5: A solution of silyl ether M (1.0 equiv.) in MeOH (0.02M) under nitrogen at room temperature was treated with pTsOH (2.0 equiv.). The reaction was stirred for 2 hours, or until the reaction was determined to be complete by LCMS or TLC. The reaction was then diluted with ethyl acetate and washed with brine, dried over magnesium sulfate, filtered, and concentrated in vacuo. The resulting oil was purified by preparative TLC (dichloromethane/methanol as eluent) to afford the desired product (61-104).

Exemplified Protocol for the Synthesis of Compound 63

Steps 1-3 as above.

Step 4: To a solution of (S)-2-methyl-3-((1-phenyl-1H-tetrazol-5-yl)sulfonyl)propyl pyrrolidine-1-carboxylate (45.0 mg, 0.12 mmol, 2.5 equiv.) in THF (2.0 mL, 0.02M) under nitrogen at −78° C. was added KHMDS (0.23 mL, 0.12 mmol, 2.5 equiv.) dropwise and the reaction was stirred for 10 minutes. Then aldehyde L (30.0 mg, 0.05 mmol, 1.0 equiv.) in THF (0.2 mL) was added dropwise. The reaction was stirred at −78° C. for five hours and then allowed to warm to room temperature overnight. The reaction was quenched with water and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (M, 35 mg, 0.04 mmol, 76%).

Step 5: A solution of silyl ether M (35.0 mg, 0.04 mmol, 1.0 equiv.) in MeOH (2.0 mL, 0.02M) under nitrogen at room temperature was treated with pTsOH (15.0 mg, 0.08 mmol, 2.0 equiv.). The reaction was stirred for 2 hours, or until the reaction was determined to be complete by LCMS or TLC. The reaction was then diluted with ethyl acetate and washed with brine, dried over magnesium sulfate, filtered, and concentrated in vacuo. The resulting oil was purified by preparative TLC (dichloromethane/methanol as eluent) to afford the desired product (compound 63, 22.2 mg, 32 mmol, 80%). $^1$H NMR (400 MHz, METHANOL-d4) δ:0.90 (d, J=6.65 Hz, 3H) 1.09 (d, J=6.78 Hz, 3H) 1.24 (s, 3H) 1.32-1.45 (m, 2H) 1.47-1.85 (m, 15H) 1.85-1.94 (m, 4H) 1.95-2.10 (m, 2H) 2.50-2.68 (m, 4H) 2.96-3.08 (m, 4H) 3.09-3.21 (m, 1H) 3.34-3.39 (m, 4H) 3.52-3.88 (m, 5H) 3.92-4.06 (m, 2H) 4.97 (d, J=9.66 Hz, 1H) 5.07 (d, J=10.67 Hz, 1H) 5.61 (dd, J=15.18, 9.79 Hz, 1H) 5.72 (d, J=9.79 Hz, 2H) 6.12 (dd, J=10.79, 1.00 Hz, 1H) 6.37 (ddd, J=15.12, 10.85, 0.88 Hz, 1H). MS (ES+)=688.5[M+H]$^+$.

TABLE 2

Compounds 61-104

| Structure, Compound #, and Chemical Name | ¹H NMR data | LCMS data (ES+) |
|---|---|---|
| 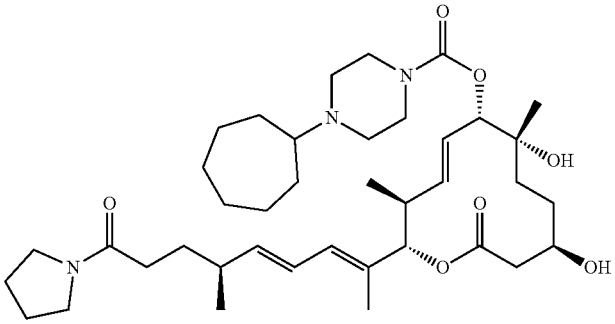 [SMILES: C/C(=C\C=C\[C@@H](C)CCC(=O)N1CCCC1)[C@H]1OC(=O)C[C@H](O)CC[C@@](C)(O)[C@@H](OC(=O)N2CCN(C3CCCCCC3)CC2)/C=C/[C@@H]1C]<br>61<br>[(2S,3S,4E,6S,7S,10S)-7,10-dihydroxy-3,7-dimethyl-2-[(2E,4E,6S)-6-methyl-9-oxo-9-pyrrolidin-1-ylnona-2,4-dien-2-yl]-12-oxo-1-oxacyclododec-4-en-6-yl] 4-cycloheptylpiperazine-1-carboxylate | ¹H NMR (400 MHz, CHLOROFORM-d) δ: 7.19 (s, 2H), 6.05-6.26 (m, 1H), 5.94-6.05 (m, 1H), 5.45-5.69 (m, 3H), 5.08 (d, J = 10.5 Hz, 1H), 4.95 (d, J = 9.5 Hz, 1H), 3.67 (br. s., 2H), 3.28-3.54 (m, 8H), 2.36-2.62 (m, 7H), 2.09-2.32 (m, 3H), 1.86 (dt, J = 13.1, 6.6 Hz, 3H), 1.73-1.81 (m, 3H), 1.55-1.71 (m, 9H), 1.24-1.51 (m, 11H), 1.15-1.22 (m, 4H), 0.97 (d, J = 6.8 Hz, 3H), 0.74-0.91 (m, 3H) | 686.5 |
| 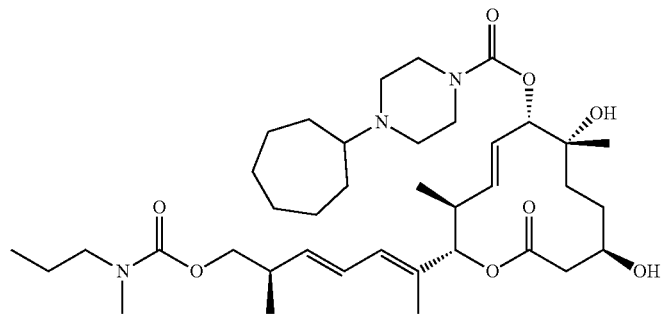 [SMILES: CCCN(C)C(=O)OC[C@H](C)/C=C/C=C(\C)[C@H]1OC(=O)C[C@H](O)CC[C@@](C)(O)[C@@H](OC(=O)N2CCN(C3CCCCCC3)CC2)/C=C/[C@@H]1C]<br>62<br>[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] 4-cycloheptylpiperazine-1-carboxylate | ¹H NMR (400 MHz, METHANOL-d4) δ: 0.69-0.86 (m, 8 H) 0.93-1.01 (m, 2 H) 1.09-1.24 (m, 15 H) 1.29 (d, J = 4.52 Hz, 2 H) 1.37-1.53 (m, 5 H) 1.65 (s, 2 H) 1.74 (d, J = 10.79 Hz, 1 H) 1.91 (s, 1 H) 2.11 (t, J = 7.78 Hz, 1 H) 2.33-2.59 (m, 4 H) 2.61-2.73 (m, 1 H) 2.78 (s, 1 H) 2.91-3.07 (m, 1 H) 3.11 (t, J = 7.28 Hz, 1 H) 3.32-3.41 (m, 1 H) 3.44 (br. s., 1 H) 3.60-3.76 (m, 1H) 3.86 (br. s., 1 H) 3.92-4.12 (m, 1 H) 4.47 (s, 1 H) 4.95 (d, J = 10.79 Hz, 1 H) 5.39 (s, 1 H) 5.40-5.42 (m, 1 H) 5.43-5.70 (m, 2H) 6.00 (d, J = 9.79 Hz, 1 H) 6.18-6.35 (m, 1 H) | |
| 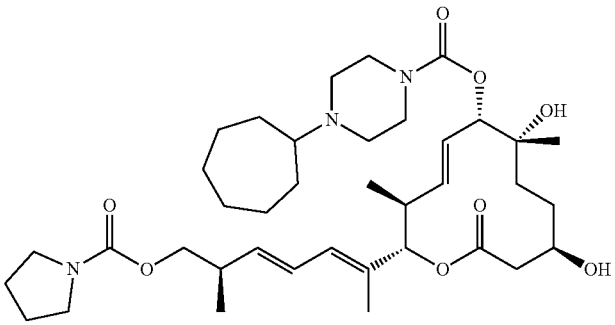 [SMILES: C/C(=C\C=C\[C@@H](C)COC(=O)N1CCCC1)[C@H]1OC(=O)C[C@H](O)CC[C@@](C)(O)[C@@H](OC(=O)N2CCN(C3CCCCCC3)CC2)/C=C/[C@@H]1C]<br>63<br>[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate | ¹H NMR (400 MHz, METHANOL-d4) δ: 0.90 (d, J = 6.65 Hz, 3 H) 1.09 (d, J = 6.78 Hz, 3 H) 1.24 (s, 3 H) 1.32-1.45 (m, 2 H) 1.47-1.85 (m, 15 H) 1.85-1.94 (m, 4 H) 1.95-2.10 (m, 2 H) 2.50-2.68 (m, 4 H) 2.96-3.08 (m, 4 H) 3.09-3.21 (m, 1 H) 3.34-3.39 (m, 4 H) 3.52-3.88 (m, 5 H) 3.92-4.06 (m, 2 H) 4.97 (d, J = 9.66 Hz, 1 H) 5.07 (d, J = 10.67 Hz, 1 H) 5.61 (dd, J = 15.18 9.79 Hz, 1 H) 5.72 (d, J = 9.79 Hz, 2 H) 6.12 (dd, J = 10.79, 1.00 Hz, 1 H) 6.37 (ddd, J = 15.12, 10.85, 0.88 Hz, 1 H) | 688.5 |

TABLE 2-continued

Compounds 61-104

| Structure, Compound #, and Chemical Name | $^1$H NMR data | LCMS data (ES+) |
|---|---|---|
| 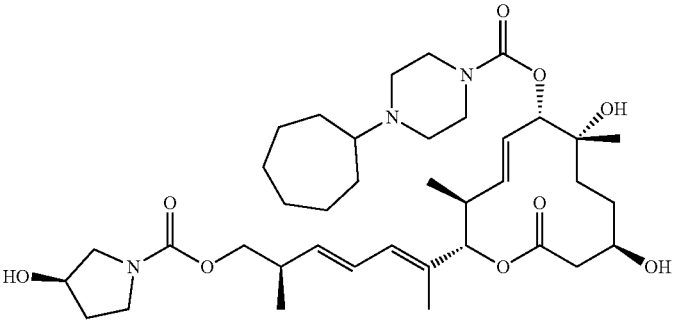 [SMILES: C/C(=C\C=C\[C@@H](C)COC(=O)N1CC[C@@H](O)C1)[C@H]1OC(=O)C[C@H](O)CC[C@@](C)(O)[C@@H](OC(=O)N2CCN(C3CCCCCC3)CC2)/C=C/[C@@H]1C]<br>64<br>[(2S,3S,4E,6S,7S,10S)-7,10-dihydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate | $^1$H NMR (400 MHz, METHANOL-d4) δ: 0.90 (d, J = 6.65 Hz, 3 H) 1.10 (d, J = 6.90 Hz, 3 H) 1.24 (s, 3 H) 1.34-1.47 (m, 2 H) 1.49-2.11 (m, 20 H) 2.12-2.14 (m, 1 H) 2.50-2.68 (m, 4 H) 3.17 (br. s., 4 H) 3.39-3.53 (m, 4 H) 3.61-4.06 (m, 7 H) 4.31-4.45 (m, 1 H) 4.98 (d, J = 9.66 Hz, 1 H) 5.07 (d, J = 10.67 Hz, 1 H) 5.56-5.81 (m, 3 H) 6.12 (d, J = 10.29 Hz, 1 H) 6.37 (dd, J = 15.18, 10.79 Hz, 1 H) | 704.5 |
| 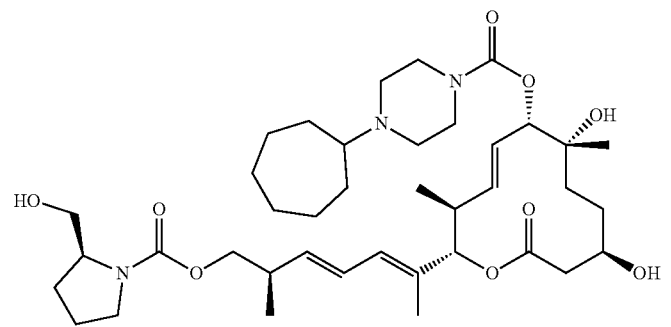 [SMILES: C/C(=C\C=C\[C@@H](C)COC(=O)N1CCC[C@H]1CO)[C@H]1OC(=O)C[C@H](O)CC[C@@](C)(O)[C@@H](OC(=O)N2CCN(C3CCCCCC3)CC2)/C=C/[C@@H]1C]<br>65<br>[(2S,3S,4E,6S,7S,10S)-7,10-dihydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate | $^1$H NMR (400 MHz, METHANOL-d4) δ: 0.91 (d, J = 6.90 Hz, 3 H) 1.10 (d, J = 6.78 Hz, 3 H) 1.20-1.26 (m, 3 H) 1.29-1.43 (m, 4 H) 1.45-1.88 (m, 17 H) 1.91-2.01 (m, 5 H) 2.52-2.65 (m, 4 H) 2.77-2.99 (m, 5 H) 3.36-3.46 (m, 2 H) 3.46-4.06 (m, 10 H) 4.96 (d, J = 9.54 Hz, 1 H) 5.07 (d, J = 10.67 Hz, 1 H) 5.60 (dd, J = 14.93, 9.91 Hz, 1 H) 5.65-5.78 (m, 2 H) 6.12 (d, J = 11.42 Hz, 1 H) 6.37 (dd, J = 14.87, 10.60 Hz, 1 H) | 718.5 |
| 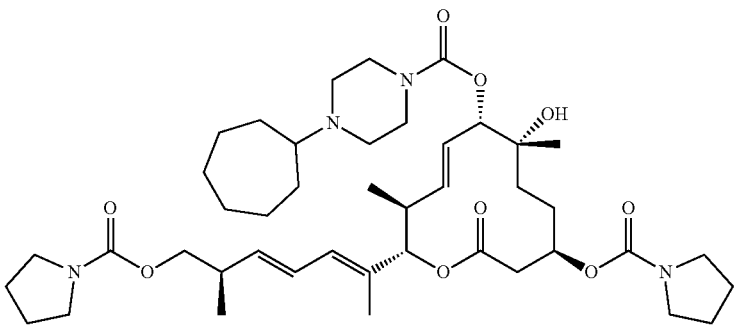 [SMILES: C/C(=C\C=C\[C@@H](C)COC(=O)N1CCCC1)[C@H]1OC(=O)C[C@H](OC(=O)N2CCCC2)CC[C@@](C)(O)[C@@H](OC(=O)N2CCN(C3CCCCCC3)CC2)/C=C/[C@@H]1C]<br>66<br>[(2S,3S,4E,6S,7S,10R)-7-hydroxy-3,7-dimethyl-2-[(2E,4E,6R)-6-methyl-7-(pyrrolidine-1-carbonyloxy)hepta-2,4-dien-2-yl]-12-oxo-10-(pyrrolidine-1-carbonyloxy)-1-oxacyclododec-4-en-6-yl] 4-cycloheptylpiperazine-1-carboxylate | $^1$H NMR (400 MHz, METHANOL-d4) δ: 0.91 (d, J = 6.78 Hz, 3 H) 1.09 (d, J = 6.90 Hz, 3 H) 1.24 (s, 3 H) 1.43-1.95 (m, 28 H) 2.03-2.10 (m, 2 H) 2.56-2.71 (m, 4 H) 3.19 (br. s., 5 H) 3.36-3.40 (m, 4 H) 3.50 (d, J = 1.76 Hz, 1 H) 3.63-3.92 (m, 4 H) 3.93-4.03 (m, 2 H) 4.78 (d, J = 3.39 Hz, 1 H) 4.97 (d, J = 4.77 Hz, 1 H) 4.99 (d, J = 5.77 Hz, 1 H) 5.58-5.82 (m, 3 H) 6.13 (d, J = 10.79 Hz, 1 H) 6.37 (ddd, J = 15.15, 10.89, 0.82 Hz, 1 H) | 785.6 |

TABLE 2-continued

Compounds 61-104

| Structure, Compound #, and Chemical Name | ¹H NMR data | LCMS data (ES+) |
|---|---|---|
| 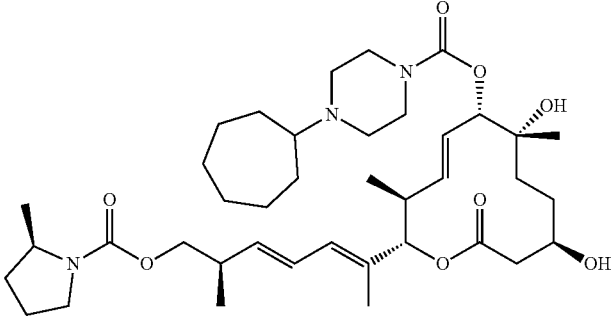 [SMILES: C/C(=C\C=C\[C@@H](C)COC(=O)N1CCC[C@H]1C)[C@H]1OC(=O)C[C@H](O)CC[C@@](C)(O)[C@@H](OC(=O)N2CCN(C3CCCCCC3)CC2)/C=C/[C@@H]1C]<br>67<br>[(2S,3S,4E,6S,7S,10S)-7,10-dihydroxy-3,7-dimethyl-2-[(2E,4E,6R)-6-methyl-7-[(2S)-2-methylpyrrolidine-1-carbonyl]oxyhepta-2,4-dien-2-yl]-12-oxo-1-oxacyclododec-4-en-6-yl] 4-cycloheptylpiperazine-1-carboxylate | ¹H NMR (400 MHz, METHANOL-d4) δ: 0.90 (d, J = 6.78 Hz, 3 H) 1.09 (d, J = 6.78 Hz, 3 H) 1.13-1.21 (m, 3 H) 1.24 (s, 3 H) 1.36-1.73 (m, 13 H) 1.75-1.90 (m, 6 H) 1.92-2.11 (m, 4 H) 2.55 (br. s., 4 H) 3.13 (br. s., 4 H) 3.21-3.29 (m, 1 H) 3.36-3.42 (m, 2 H) 3.59-4.06 (m, 8 H) 4.98 (d, J = 9.66 Hz, 1 H) 5.07 (d, J = 10.54 Hz, 1 H) 5.56-5.80 (m, 3 H) 6.12 (d, J = 11.17 Hz, 1 H) 6.37 (dd, J = 14.74, 10.73 Hz, 1 H) | 702.5 |
| 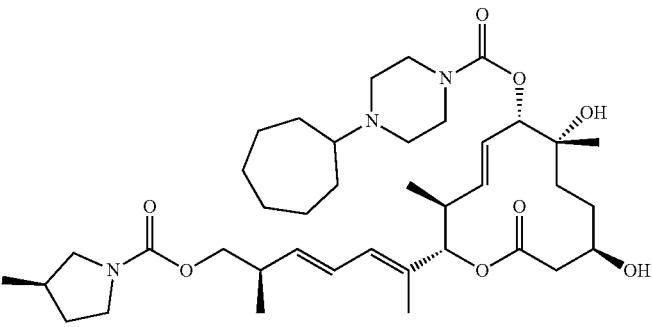 [SMILES: C/C(=C\C=C\[C@@H](C)COC(=O)N1CC[C@@H](C)C1)[C@H]1OC(=O)C[C@H](O)CC[C@@](C)(O)[C@@H](OC(=O)N2CCN(C3CCCCCC3)CC2)/C=C/[C@@H]1C]<br>68<br>[(2S,3S,4E,6S,7S,10S)-7,10-dihydroxy-3,7-dimethyl-2-[(2E,4E,6R)-6-methyl-7-[(3R)-3-methylpyrrolidine-1-carbonyl]oxyhepta-2,4-dien-2-yl]-12-oxo-1-oxacyclododec-4-en-6-yl] 4-cycloheptylpiperazine-1-carboxylate | ¹H NMR (400 MHz, CHLOROFORM-d) δ: 0.92 (d, J = 6.78 Hz, 3 H) 1.02-1.14 (m, 6 H) 1.24-1.27 (m, 3 H) 1.29-1.30 (m, 1 H) 1.33-1.61 (m, 14 H) 1.64-2.09 (m, 21 H) 2.19-2.33 (m, 1 H) 2.45-2.73 (m, 9 H) 2.80-2.99 (m, 1 H) 3.19-3.41 (m, 1 H) 3.54 (br. s., 7 H) 3.80 (s, 1 H) 3.92-4.04 (m, 2 H) 5.04 (d, J = 9.41 Hz, 1 H) 5.18 (d, J = 10.67 Hz, 1 H) 5.69 (s, 3 H) 6.11 (d, J = 10.67 Hz, 1 H) 6.29 (dd, J = 14.93, 10.92 Hz, 1 H) | 702.4 |
| 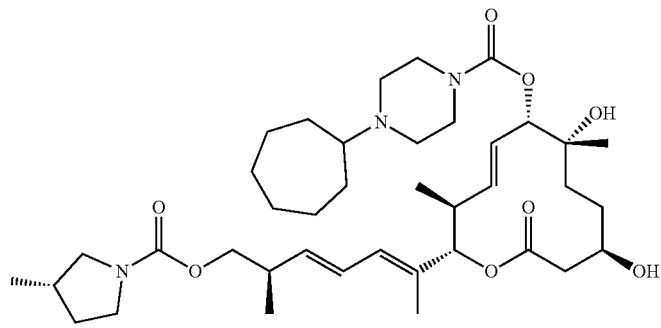 [SMILES: C/C(=C\C=C\[C@@H](C)COC(=O)N1CC[C@H](C)C1)[C@H]1OC(=O)C[C@H](O)CC[C@@](C)(O)[C@@H](OC(=O)N2CCN(C3CCCCCC3)CC2)/C=C/[C@@H]1C]<br>69<br>[(2S,3S,4E,6S,7S,10S)-7,10-dihydroxy-3,7-dimethyl-2-[(2E,4E,6R)-6-methyl-7-[(3R)-3-methylpyrrolidine-1-carbonyl]oxyhepta-2,4-dien-2-yl]-12-oxo-1-oxacyclododec-4-en-6-yl] 4-cycloheptylpiperazine-1-carboxylate | ¹H NMR (400 MHz, CHLOROFORM-d) δ: 0.92 (d, J = 6.65 Hz, 3 H) 1.00-1.14 (m, 6 H) 1.25 (s, 3 H) 1.28-1.65 (m, 13 H) 1.67-1.86 (m, 6 H) 1.91-2.13 (m, 3 H) 2.16-2.32 (m, 1 H) 2.37-2.90 (m, 25 H) 2.94-3.07 (m, 5 H) 3.14-3.41 (m, 3 H) 3.41-3.67 (m, 2 H) 3.80 (br. s., 5 H) 3.89-4.08 (m, 2 H) 5.03 (d, J = 9.16 Hz, 1 H) 5.18 (d, J = 10.67 Hz, 1 H) 5.70 (d, J = 9.29 Hz, 3 H) 6.06-6.15 (m, 1 H) 6.24-6.35 (m, 1 H) | 702.3 |

TABLE 2-continued

Compounds 61-104

| Structure, Compound #, and Chemical Name | $^1$H NMR data | LCMS data (ES+) |
|---|---|---|
| 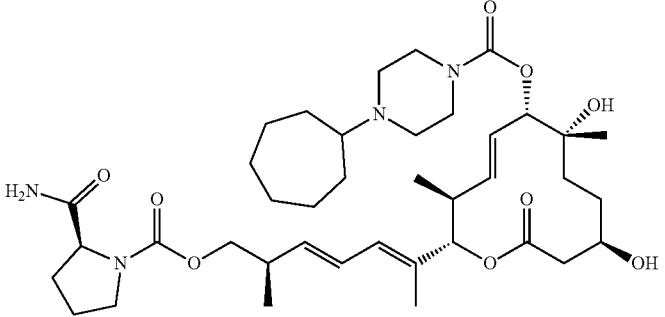 [SMILES: C/C(=C\C=C\[C@@H](C)COC(=O)N1CCC[C@H]1C(N)=O)[C@H]1OC(=O)C[C@H](O)CC[C@@](C)(O)[C@@H](OC(=O)N2CCN(C3CCCCCC3)CC2)/C=C/[C@@H]1C]<br>70<br>[(2S,3S,4E,6S,7S,10S)-2-[(2E,4E,6R)-7-[(2R)-2-carbamoylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, CHLOROFORM-d) δ: 0.92 (d, J = 6.78 Hz, 3 H) 1.09 (d, J = 6.27 Hz, 3 H) 1.25 (s, 3 H) 1.28-1.42 (m, 2 H) 1.44-1.65 (m 9 H) 1.66-1.81 (m, 6 H) 1.84-2.05 (m, 5 H) 2.10-2.71 (m, 19 H) 2.80 (t, J = 4.77 Hz, 4 H) 2.90-3.02 (m, 1 H) 3.51 (s, 2 H) 3.68 (t, J = 4.64 Hz, 4 H) 3.74-3.84 (m, 1 H) 3.74-3.84 (m, 1 H) 3.92-4.13 (m, 2 H) 4.21-4.45 (m, 1 H) 5.03 (d, J = 9.41 Hz, 1 H) 5.16 (d, J = 10.67 Hz, 1 H) 5.42-5.56 (m, 1 H) 5.57-5.82 (m, 3 H) 6.10 (d, J = 11.04 Hz, 1 H) 6.29 (dd, J = 15.06, 11.04 Hz, 1 H) | 731.5 |
| 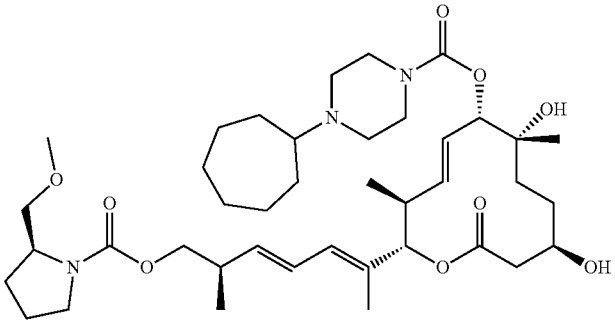 [SMILES: COC[C@@H]1CCCN1C(=O)OC[C@H](C)/C=C/C=C(\C)[C@H]1OC(=O)C[C@H](O)CC[C@@](C)(O)[C@@H](OC(=O)N2CCN(C3CCCCCC3)CC2)/C=C/[C@@H]1C]<br>71<br>[(2S,3S,4E,6S,7S,10S)-7,10-dihydroxy-2-[(2E,4E,6S)-7-[(2R)-2-(methoxymethyl)pyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate | $^1$H NMR (400 MHz, METHANOL-d4) δ: 0.90 (d, J = 6.78 Hz, 3 H) 1.09 (d, J = 6.78 Hz, 3 H) 1.24 (s, 3 H) 1.96 (br. s., 24 H) 2.54 (d, J = 3.64 Hz, 4 H) 3.10 (br. s., 5 H) 3.36-3.42 (m, 2 H) 3.44-3.53 (m, 1 H) 3.57-3.87 (m, 4 H) 3.89-4.09 (m, 3 H) 4.97 (d, J = 9.66 Hz, 1 H) 5.07 (d, J = 10.79 Hz, 1 H) 5.71 (s, 3 H) 6.11 (d, J = 11.04 Hz, 1 H) 6.37 (dd, J = 14.93, 11.42 Hz, 1 H) | 732.4 |
| 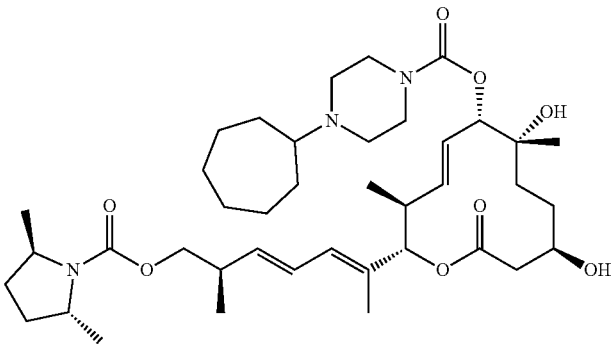 [SMILES: C/C(=C\C=C\[C@@H](C)COC(=O)N1[C@H](C)CC[C@H]1C)[C@H]1OC(=O)C[C@H](O)CC[C@@](C)(O)[C@@H](OC(=O)N2CCN(C3CCCCCC3)CC2)/C=C/[C@@H]1C]<br>72<br>[(2S,3S,4E,6S,7S,10S)-2-[(2E,4E,6R)-7-[(2S,5S)-2,5-dimethylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.90 (d, J = 6.78 Hz, 3 H) 1.09 (d, J = 6.78 Hz, 3 H) 1.15 (dd, J = 11.80, 6.40 Hz, 3 H) 1.23 (s, 6 H) 1.58 (d, J = 10.42 Hz, 15 H) 1.76 (s, 5 H) 1.83-2.21 (m, 4 H) 2.47-2.81 (m, 9 H) 3.98 (d, J = 6.78 Hz, 9 H) 4.96 (d, J = 9.66 Hz, 1 H) 5.07 (d, J = 10.67 Hz, 1 H) 5.58 (dd, J = 15.18, 9.91 Hz, 1 H) 5.64-5.78 (m, 2 H) 6.12 (d, J = 10.67 Hz, 1 H) 6.37 (dd, J = 15.06, 10.79 Hz, 1 H) | 716.4 |

TABLE 2-continued

Compounds 61-104

| Structure, Compound #, and Chemical Name | $^1$H NMR data | LCMS data (ES+) |
|---|---|---|
| 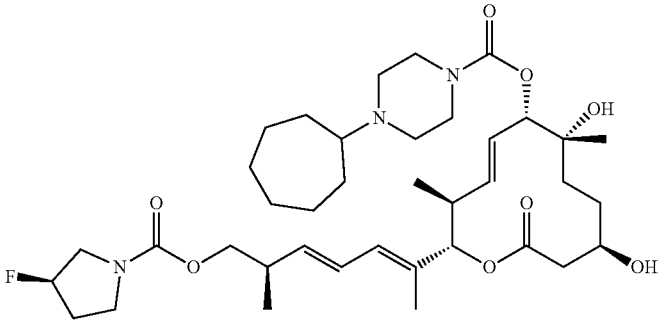 [SMILES: C/C(=C\C=C\[C@@H](C)COC(=O)N1CC[C@@H](F)C1)[C@H]1OC(=O)C[C@H](O)CC[C@@](C)(O)[C@@H](OC(=O)N2CCN(C3CCCCCC3)CC2)/C=C/[C@@H]1C]<br>73<br>[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.90 (d, J = 6.78 Hz, 3 H) 1.09 (d, J = 6.78 Hz, 3 H) 1.24 (s, 3 H) 1.35-1.44 (m, 2 H) 1.76 (s, 16 H) 1.96-2.29 (m, 4 H) 2.51-2.71 (m, 4 H) 3.02-3.14 (m, 4 H) 3.13-3.26 (m, 2 H) 3.40-4.13 (m, 11 H) 4.97 (d, J = 9.66 Hz, 1 H) 5.06 (d, J = 10.79 Hz, 1 H) 5.25 (d, J = 52.70 Hz, 1 H) 5.60 (dd, J = 15.18, 9.66 Hz, 1 H) 5.65-5.81 (m, 2 H) 6.12 (d, J = 10.42 Hz, 1 H) 6.37 (dd, J = 14.87, 10.85 Hz, 1 H) | 706.4 |
| 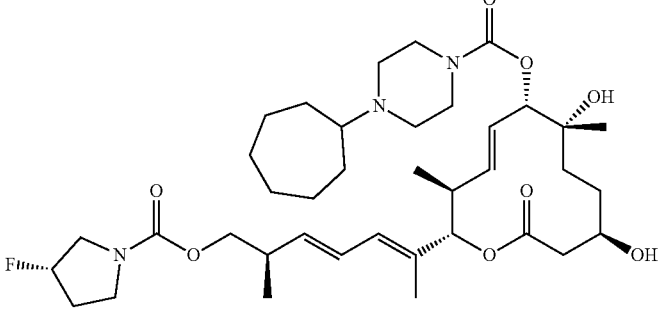<br>74<br>[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.90 (d, J = 6.78 Hz, 3 H) 1.09 (d, J = 6.65 Hz, 3 H) 1.24 (s, 3 H) 1.35-1.46 (m, 2 H) 1.76 (s, 15 H) 1.78-1.88 (m, 2 H) 1.95-2.07 (m, 3 H) 2.51-2.69 (m, 4 H) 3.09 (br. s., 4 H) 3.16-3.25 (m, 2 H) 3.39-4.10 (m, 11 H) 4.98 (d, J = 9.66 Hz, 1 H) 5.07 (d, J = 10.67 Hz, 1 H) 5.25 (dt, J = 53.33, 3.64 Hz, 1 H) 5.61 (dd, J = 15.18, 9.79 Hz, 1 H) 5.72 (m, J = 9.54 Hz, 2 H) 6.12 (d, J = 10.04 Hz, 1 H) 6.31-6.43 (m, 1 H) | 706.4 |
| 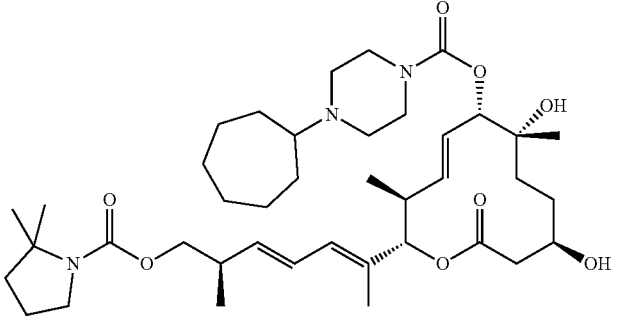 [SMILES: C/C(=C\C=C\[C@@H](C)COC(=O)N1CCCC1(C)C)[C@H]1OC(=O)C[C@H](O)CC[C@@](C)(O)[C@@H](OC(=O)N2CCN(C3CCCCCC3)CC2)/C=C/[C@@H]1C]<br>75<br>[(2S,3S,4E,6S,7S,10S)-2-[(2E,4E,6R)-7-(2,2-dimethylpyrrolidine-1-carbonyl)oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.89-0.92 (m, 3 H) 1.06-1.14 (m, 3 H) 1.24 (s, 3 H) 1.34-1.46 (m, 6 H) 1.76 (s, 24 H) 2.55 (br. s., 4 H) 3.06 (br. s., 5 H) 3.13-3.22 (m, 2 H) 3.38-3.52 (m, 1 H) 3.54-4.12 (m, 8 H) 4.97 (d, J = 9.66 Hz, 1 H) 5.07 (d, J = 10.79 Hz, 1 H) 5.57-5.81 (m, 3 H) 6.12 (d, J = 10.42 Hz, 1 H) 6.31-6.46 (m, 1 H) | 716.5 |

TABLE 2-continued

Compounds 61-104

| Structure, Compound #, and Chemical Name | ¹H NMR data | LCMS data (ES+) |
|---|---|---|
| 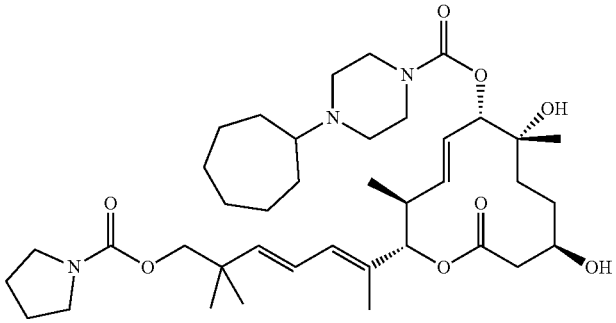 [SMILES: C/C(=C\C=C\C(C)(C)COC(=O)N1CCCC1)[C@H]1OC(=O)C[C@H](O)CC[C@@](C)(O)[C@@H](OC(=O)N2CCN(C3CCCCCC3)CC2)/C=C/[C@@H]1C]<br>76<br>[(2S,3S,4E,6R,7R,10R)-2-[(2E,4E)-6,6-dimethyl-7-(pyrrolidine-1-carbonyloxy)hepta-2,4-dien-2-yl]-7,10-dihydroxy-3,7-dimethyl-12-oxo-1-oxacyclodec-4-en-6-yl] 4-cycloheptylpiperazine-1-carboxylate | ¹H NMR (400 MHz, CHLOROFORM-d) δ: 0.72-0.93 (m, 3 H) 1.01 (d, J = 2.26 Hz, 4 H) 1.12-1.32 (m, 7 H) 1.39-1.56 (m, 8 H) 1.60-1.72 (m, 5 H) 1.73-1.83 (m, 3 H) 1.99 (d, J = 6.27 Hz, 2 H) 2.38-2.58 (m, 3 H) 2.82 (s, 1 H) 2.90 (d, J = 5.77 Hz, 3 H) 3.02-3.19 (m, 1 H) 3.30 (dt, J = 12.86, 6.24 Hz, 4 H) 3.64-3.77 (m, 4 H) 3.77-3.84 (m, 2 H) 4.94 (d, J = 9.29 Hz, 2 H) 5.01-5.18 (m, 2 H) 5.41 (d, J = 12.30 Hz, 1 H) 5.47-5.67 (m, 2 H) 5.71 (d, J = 15.31 Hz, 1 H) 6.02 (d, J = 11.29 Hz, 1 H) 6.07-6.25 (m, 1 H) 6.40-6.50 (m, 1 H) 8.24 (br. s., 1 H) | 702.4 |
| 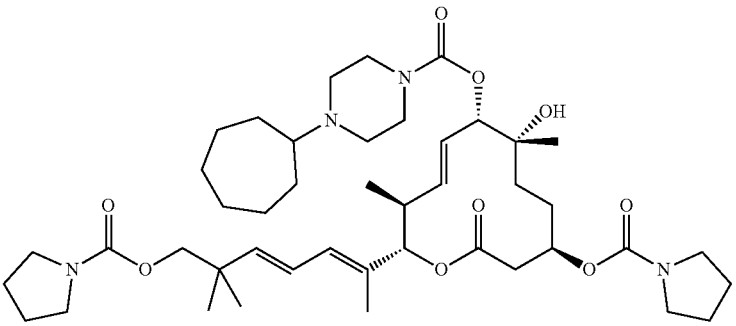<br>77<br>[(2S,3S,4E,6R,7R,10S)-2-[(2E,4E)-6,6-dimethyl-7-(pyrrolidine-1-carbonyloxy)hepta-2,4-dien-2-yl]-7-hydroxy-3,7-dimethyl-12-oxo-10-(pyrrolidine-1-carbonyloxy)-1-oxacyclodec-4-en-6-yl] 4-cycloheptylpiperazine-1-carboxylate | ¹H NMR (400 MHz, CHLOROFORM-d) δ: 0.65-0.92 (m, 4 H) 0.94-1.22 (m, 9 H) 1.23-1.33 (m, 3 H) 1.36-1.57 (m, 8 H) 1.59 (br. s., 1 H) 1.61-1.69 (m, 4 H) 1.79 (br. s., 5 H) 1.87-2.04 (m, 3 H) 2.10 (s, 3 H) 2.25 (br. s., 6 H) 2.33-2.52 (m, 5 H) 2.59 (d, J = 10.54 Hz, 2 H) 2.70-2.86 (m, 3 H) 2.89 (s, 1 H) 2.95 (d, J = 3.51 Hz, 1 H) 2.99-3.07 (m, 1 H) 3.10 (s, 1 H) 3.15 (s, 1 H) 3.22-3.34 (m, 4 H) 3.35-3.52 (m, 1 H) 3.54-3.68 (m, 3 H) 3.70 (br. s., 1 H) 3.74-3.98 (m, 2 H) 4.76 (br. s., 1 H) 4.85-5.02 (m, 2 H) 5.40 (s, 1 H) 5.46-5.75 (m, 3 H) 5.93-6.06 (m, 1 H) 6.07-6.22 (m, 1 H) | 799.48 |
| 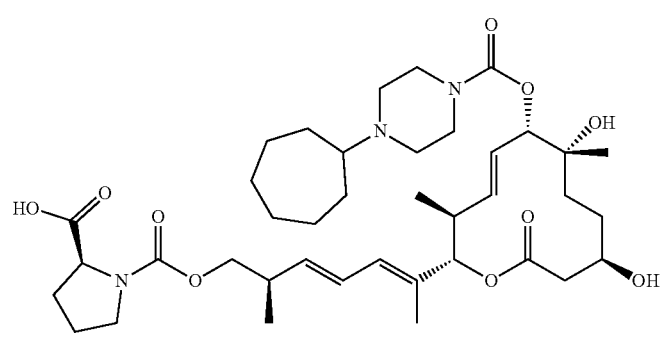 [SMILES: C/C(=C\C=C\[C@@H](C)COC(=O)N1CCC[C@H]1C(=O)O)[C@H]1OC(=O)C[C@H](O)CC[C@@](C)(O)[C@@H](OC(=O)N2CCN(C3CCCCCC3)CC2)/C=C/[C@@H]1C]<br>78<br>(2R)-1-[[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclodec-4-en-2-yl]-2-methylhepta-3,5-dienoxy]carbonyl]pyrrolidine-2-carboxylic acid | ¹H NMR (400 MHz, METHANOL-d4) δ: 0.91 (dd, J = 6.65, 2.76 Hz, 3 H) 1.09 (dd, J = 6.78, 2.26 Hz, 3 H) 1.24 (s, 3 H) 1.36-1.44 (m, 2 H) 1.46-2.10 (m, 22 H) 2.15-2.36 (m, 1 H) 2.51-2.69 (m, 2 H) 3.15 (d, J = 1.51 Hz, 4 H) 3.23-3.30 (m, 1 H) 3.41-3.60 (m, 2 H) 3.63-4.08 (m, 7 H) 4.21-4.30 (m, 1 H) 4.98 (d, J = 9.54 Hz, 1 H) 5.07 (d, J = 10.54 Hz, 1 H) 5.61 (dd, J = 15.06, 9.66 Hz, 1 H) 5.71 (s, 2 H) 6.13 (s, 1 H) 6.30-6.45 (m, 1 H) | 732.5 |

TABLE 2-continued

Compounds 61-104

| Structure, Compound #, and Chemical Name | $^1$H NMR data | LCMS data (ES+) |
|---|---|---|
| 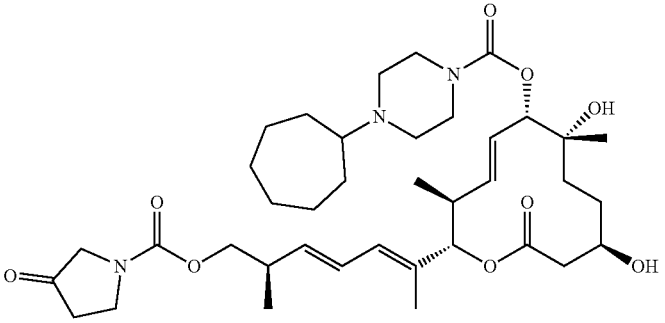 [SMILES: C/C(=C\C=C\[C@@H](C)COC(=O)N1CCC(=O)C1)[C@H]1OC(=O)C[C@H](O)CC[C@@](C)(O)[C@@H](OC(=O)N2CCN(C3CCCCCC3)CC2)/C=C/[C@@H]1C]<br>79<br>[(2S,3S,4E,6S,7S,10S)-7,10-dihydroxy-3,7-dimethyl-2-[(2E,4E,6R)-6-methyl-7-(3-oxopyrrolidine-1-carbonyl)oxyhepta-2,4-dien-2-yl]-12-oxo-1-oxacyclododec-4-en-6-yl] 4-cycloheptylpiperazine-1-carboxylate | $^1$H NMR (400 MHz, METHANOL-d4) δ: 0.89 (d, J = 6.78 Hz, 3 H) 1.05-1.17 (m, 3 H) 1.24 (s, 3 H) 1.33-1.45 (m, 2 H) 1.48-1.89 (m, 16 H) 1.96-2.10 (m, 2 H) 2.51-2.71 (m, 6 H) 3.12 (br. s., 4 H) 3.59-3.88 (m, 9 H) 4.04 (br. s., 2 H) 4.98 (d, J = 9.66 Hz, 1 H) 5.06 (d, J = 10.67 Hz, 1 H) 5.61 (dd, J = 15.18, 9.79 Hz, 1 H) 5.66-5.79 (m, 2 H) 6.12 (d, J = 10.67 Hz, 1 H) 6.39 (dd, J = 15.18, 10.92 Hz, 1 H) | 702.6 |
| 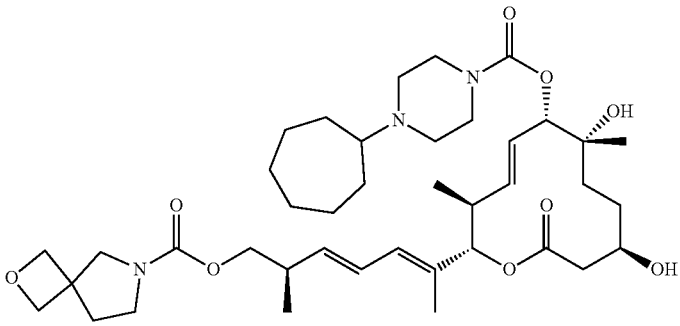 [SMILES: C/C(=C\C=C\[C@@H](C)COC(=O)N1CCC2(COC2)C1)[C@H]1OC(=O)C[C@H](O)CC[C@@](C)(O)[C@@H](OC(=O)N2CCN(C3CCCCCC3)CC2)/C=C/[C@@H]1C]<br>80<br>[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienyl] 2-oxa-7-azaspiro[3.4]octane-7-carboxylate | $^1$H NMR (400 MHz, METHANOL-d4) δ: 0.90 (d, J = 5.90 Hz, 3 H) 1.09 (t, J = 5.65 Hz, 3 H) 1.24 (s, 3H) 1.32-1.45 (m, 2 H) 1.50-1.89 (m, 16 H) 2.01-2.12 (m, 2 H) 2.20 (q, J = 7.19 Hz, 2 H) 2.53-2.70 (m, 4 H) 3.19 (br. s., 4 H) 3.35-3.44 (m, 3 H) 3.81 (d, J = 5.40 Hz, 7 H) 3.99 (d, J = 6.53 Hz, 2 H) 4.55-4.70 (m, 4 H) 4.98 (d, J = 9.54 Hz, 1 H) 5.07 (d, J = 10.67 Hz, 1 H) 5.72 (d, J = 9.66 Hz, 3 H) 6.08-6.18 (m, 1 H) 6.30-6.43 (m, 1 H) | 730.5 |
| 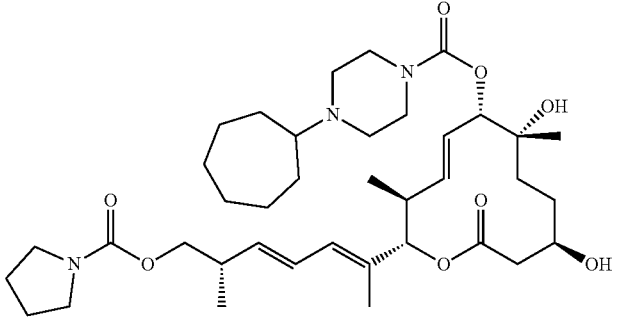 [SMILES: C/C(=C\C=C\[C@H](C)COC(=O)N1CCCC1)[C@H]1OC(=O)C[C@H](O)CC[C@@](C)(O)[C@@H](OC(=O)N2CCN(C3CCCCCC3)CC2)/C=C/[C@@H]1C]<br>81<br>[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate | $^1$H NMR (400 MHz, CHLOROFORM-d) δ: 0.77-0.89 (m, 6 H) 1.00 (d, J = 6.78 Hz, 3 H) 1.12 (d, J = 6.02 Hz, 1 H) 1.15-1.22 (m,4 H) 1.25-1.28 (m, 1 H) 1.29-1.54 (m, 11 H) 1.55-1.81 (m, 14 H) 1.90 (br. s., 1 H) 1.97 (s, 1 H) 2.37-2.58 (m, 8 H) 3.21-3.38 (m, 5 H) 3.38-3.49 (m, 4 H) 3.56-3.75 (m, 1 H) 3.80-3.98 (m, 2 H) 4.05 (d, J = 7.28 Hz, 1 H) 4.95 (d, J = 9.54 Hz, 1 H) 5.08 (d, J = 10.79 Hz, 1 H) 5.23 (s, 1 H) 5.50-5.69 (m, 3 H) 6.01 (d, J = 10.79 Hz, 1 H) 6.10-6.30 (m, 1 H) | 688.65 |

TABLE 2-continued

Compounds 61-104

| Structure, Compound #, and Chemical Name | $^1$H NMR data | LCMS data (ES+) |
|---|---|---|
| 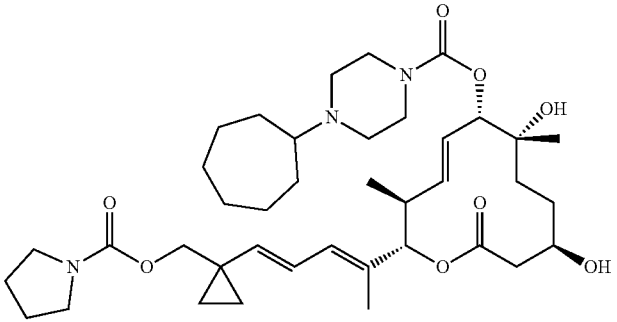<br>82<br>[(2S,3S,4E,6R,7R,10R)-7,10-dihydroxy-3,7-dimethyl-12-oxo-2-[(2E,4E)-5-[1-(pyrrolidine-1-carbonyloxymethyl)cyclopropyl]penta-2,4-dien-2-yl]-1-oxacyclododec-4-en-6-yl] 4-cycloheptylpiperazine-1-carboxylate | $^1$H NMR (400 MHz, CHLOROFORM-d) δ: 0.47-0.61 (m, 2 H) 0.63-0.90 (m, 6 H) 1.02 (s, 1 H) 1.15-1.28 (m, 5 H) 1.30-1.51 (m, 9 H) 1.56 (br. s., 1 H) 1.59-1.68 (m, 5 H) 1.70-1.87 (m, 5 H) 2.35-2.60 (m, 8 H) 2.63-2.75 (m, 2 H) 2.81 (d, J = 0.75 Hz, 1 H) 2.89 (s, 1 H) 3.17-3.39 (m, 4 H) 3.42-3.56 (m, 4 H) 3.57-3.73 (m, 1 H) 3.80 (d, J = 11.04 Hz, 1 H) 3.90-4.13 (m, 2 H) 4.94 (d, J = 9.29 Hz, 1 H) 4.95 (d, J = 9.29 Hz, 1 H) 5.07 (d, J = 10.54 Hz, 1 H) 5.14 (d, J = 10.79 Hz, 1 H) 5.23 (s, 1 H) 5.44-5.66 (m, 3 H) 6.00 (d, J = 11.04 Hz, 1 H) 6.17 (d, J = 10.79 Hz, 1 H) 6.23 (m, J = 10.79 Hz, 1 H) 6.56 (d, J = 11.54 Hz, 1 H) | 700.52 |
| 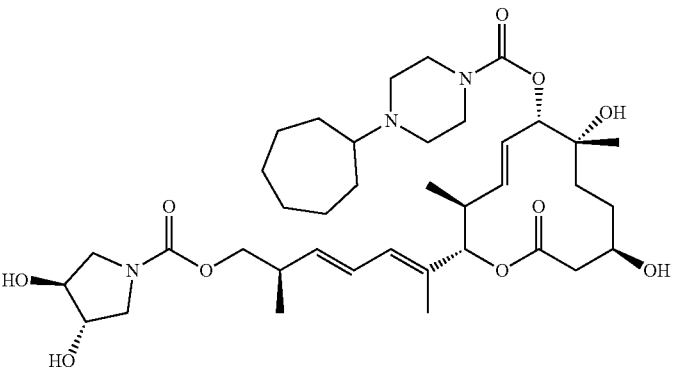 [SMILES: C/C(=C\C=C\[C@@H](C)COC(=O)N1C[C@H](O)[C@@H](O)C1)[C@H]1OC(=O)C[C@H](O)CC[C@@](C)(O)[C@@H](OC(=O)N2CCN(C3CCCCCC3)CC2)/C=C/[C@@H]1C]<br>83<br>[(2S,3S,4E,6S,7S,10S)-2-[(2E,4E,6R)-7-[(3S,4R)-3,4-dihydroxypyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.91 (d, J = 6.78 Hz, 3 H) 1.10 (d, J = 6.78 Hz, 3 H) 1.24 (s, 3 H) 1.34-1.45 (m, 2 H) 1.49-1.90 (m, 16 H) 2.00-2.11 (m, 2 H) 2.51-2.70 (m, 4 H) 3.09-3.21 (m, 4 H) 3.23-3.30 (m, 1 H) 3.37 (s, 1 H) 3.54-3.62 (m, 2 H) 3.63-4.04 (m, 7 H) 4.07 (d, J = 3.26 Hz, 2 H) 4.98 (d, J = 9.66 Hz, 1 H) 5.07 (d, J = 10.79 Hz 1 H) 5.57-5.66 (m, 1 H) 5.67-5.79 (m, 2 H) 6.12 (d, J = 10.79 Hz, 1 H) 6.39 (dd, J = 14.74, 10.35 Hz, 1 H) | 720.5 |
| 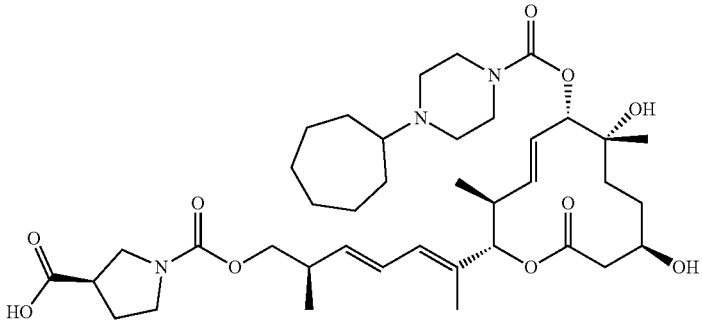 [SMILES: C/C(=C\C=C\[C@@H](C)COC(=O)N1CC[C@@H](C(=O)O)C1)[C@H]1OC(=O)C[C@H](O)CC[C@@](C)(O)[C@@H](OC(=O)N2CCN(C3CCCCCC3)CC2)/C=C/[C@@H]1C]<br>84<br>(3S)-1-[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienoxy]carbonylpyrrolidine-3-carboxylic acid | $^1$H NMR (400 MHz, METHANOL-d4) δ: 0.78 (d, J = 6.78 Hz, 3 H) 0.97 (d, J = 6.65 Hz, 3 H) 1.06-1.17 (m, 3 H) 1.23-1.32 (m, 2 H) 1.33-1.76 (m, 16 H) 1.82-1.93 (m, 2 H) 1.94-2.10 (m, 4 H) 2.35-2.57 (m, 4 H) 2.80-3.07 (m, 6 H) 3.24-3.29 (m, 1 H) 3.31-3.74 (m, 8 H) 3.86 (d, J = 6.53 Hz, 2 H) 4.85 (d, J = 9.66 Hz, 1 H) 4.95 (d, J = 10.79 Hz, 1 H) 5.49 (dd, J = 15.18, 9.79 Hz, 1 H) 5.53-5.70 (m, 2 H) 6.00 (d, J = 10.67 Hz, 1 H) 6.25 (dd, J = 14.87, 11.36 Hz, 1 H) | 732.6 |

TABLE 2-continued

Compounds 61-104

| Structure, Compound #, and Chemical Name | $^1$H NMR data | LCMS data (ES+) |
|---|---|---|
| 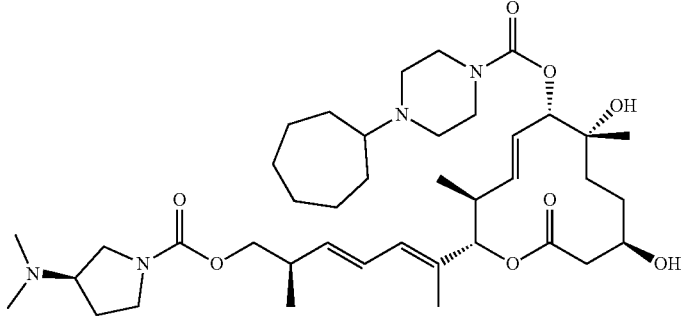 [SMILES: C/C(=C\C=C\[C@@H](C)COC(=O)N1CC[C@@H](N(C)C)C1)[C@H]1OC(=O)C[C@H](O)CC[C@@](C)(O)[C@@H](OC(=O)N2CCN(C3CCCCCC3)CC2)/C=C/[C@@H]1C]<br>85<br>[(2S,3S,4E,6S,7S,10S)-2-[(2E,4E,6R)-7-[(3S)-3-(dimethylamino)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.88 (d, J = 6.78 Hz, 3 H) 1.06 (d, J = 6.90 Hz, 3 H) 1.21 (s, 3 H) 1.31-1.67 (m, 13 H) 1.69-1.98 (m, 8 H) 2.16 (d, J = 8.53 Hz, 1 H) 2.36 (s, 3 H) 2.39 (s, 3 H) 2.47-2.67 (m, 4 H) 2.75-3.02 (m, 6 H) 3.11-3.23 (m, 1 H) 3.49-3.74 (m, 6 H) 3.78 (d, J = 3.39 Hz, 1 H) 3.97 (d, J = 6.27 Hz, 2 H) 4.56 (br. s., 2 H) 4.93 (d, J = 9.66 Hz, 1 H) 5.04 (d, J = 10.67 Hz, 1 H) 5.51-5.62 (m, 1 H) 5.63-5.77 (m, 2 H) 6.09 (d, J = 11.29 Hz, 1 H) 6.34 (dd, J = 14.81, 10.79 Hz, 1 H) | 731.6 |
| 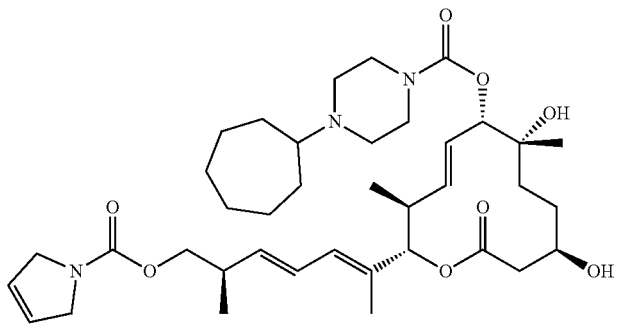<br>86<br>[(2S,3S,4E,6S,7S,10S)-2-[(2E,4E,6R)-7-(2,5-dihydropyrrole-1-carbonyloxy)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.88 (d, J = 6.78 Hz, 3 H) 1.06 (d, J = 6.90 Hz, 3 H) 1.21 (s, 3 H) 1.31-1.67 (m, 13 H) 1.69-1.98 (m, 8 H) 2.16 (d, J = 8.53 Hz, 1 H) 2.36 (s, 3 H) 2.39 (s, 3 H) 2.47-2.67 (m, 4 H) 2.75-3.02 (m, 6 H) 3.11-3.23 (m, 1 H) 3.49-3.74 (m, 6 H) 3.78 (d, J = 3.39 Hz, 1 H) 3.97 (d, J = 6.27 Hz, 2 H) 4.56 (br. s., 2 H) 4.93 (d, J = 9.66 Hz, 1 H) 5.04 (d, J = 10.67 Hz, 1 H) 5.51-5.62 (m, 1 H) 5.63-5.77 (m, 2 H) 6.09 (d, J = 11.29 Hz, 1 H) 6.34 (dd, J = 14.81, 10.79 Hz, 1 H) | 686.6 |
| 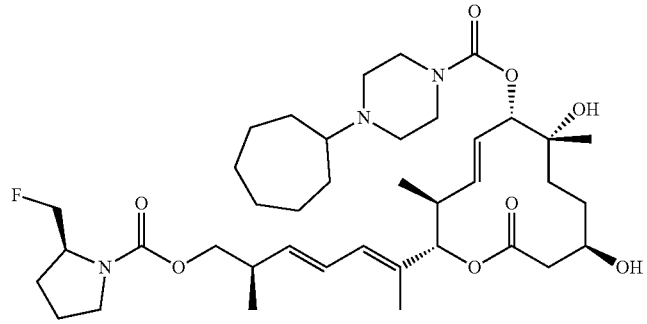 [SMILES: C/C(=C\C=C\[C@@H](C)COC(=O)N1CCC[C@H]1CF)[C@H]1OC(=O)C[C@H](O)CC[C@@](C)(O)[C@@H](OC(=O)N2CCN(C3CCCCCC3)CC2)/C=C/[C@@H]1C]<br>87<br>[(2S,3S,4E,6S,7S,10S)-2-[(2E,4E,6R)-7-[(2R)-2-(fluoromethyl)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, METHANOL-d4) δ: 0.90 (d, J = 6.78 Hz, 3 H) 1.09 (d, J = 6.78 Hz, 3 H) 1.24 (s, 3 H) 1.35-1.46 (m, 2 H) 1.47-1.73 (m, 11 H) 1.74-2.09 (m, 11 H) 2.50-2.69 (m, 4 H) 2.96-3.07 (m, 4 H) 3.07-3.18 (m, 1 H) 3.37 (s, 2 H) 3.53-3.88 (m, 5 H) 3.92-4.06 (m, 3 H) 4.29-4.51 (m, 2 H) 4.95-5.01 (m, 1 H) 5.04-5.10 (m, 1 H) 5.55-5.81 (m, 3 H) 6.12 (d, J = 10.42 Hz, 1 H) 6.37 (dd, J = 15.00, 10.98 Hz, 1 H) | 720.6 |

TABLE 2-continued

Compounds 61-104

| Structure, Compound #, and Chemical Name | ¹H NMR data | LCMS data (ES+) |
|---|---|---|
| 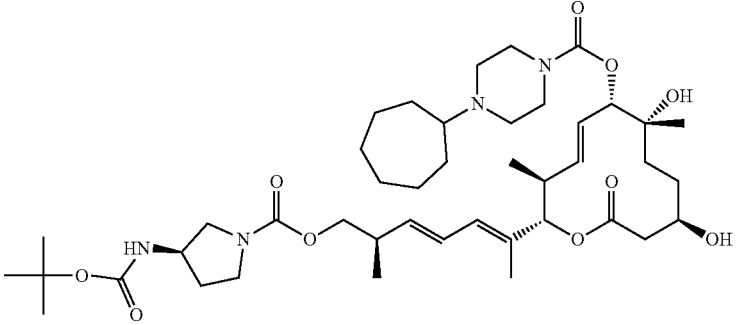 [SMILES: C/C(=C\C=C\[C@@H](C)COC(=O)N1CC[C@@H](NC(=O)OC(C)(C)C)C1)[C@H]1OC(=O)C[C@H](O)CC[C@@](C)(O)[C@@H](OC(=O)N2CCN(C3CCCCCC3)CC2)/C=C/[C@@H]1C]<br>88<br>[(2S,3S,4E,6S,7S,10S)-7,10-dihydroxy-3,7-dimethyl-2-[(2E,4E,6R)-6-methyl-7-[(3S)-3-[(2-methylpropan-2-yl)oxycarbonylamino]pyrrolidine-1-carbonyl]oxyhepta-2,4-dien-2-yl]-12-oxo-1-oxacyclododec-4-en-6-yl] 4-cycloheptylpiperazine-1-carboxylate | ¹H NMR (400 MHz, METHANOL-d4) δ: 0.78 (d, J = 6.65 Hz, 3 H) 0.97 (d, J = 6.78 Hz, 3 H) 1.12 (s, 3 H) 1.24-1.31 (m, 2 H) 1.34 (s, 9 H) 1.38-1.63 (m, 10H) 1.65 (d, J = 0.88 Hz, 3 H) 1.67-1.78 (m, 3 H) 1.89-2.06 (m, 3 H) 2.40-2.56 (m, 4 H) 3.00-3.12 (m, 5 H) 3.24-4.01 (m, 11 H) 4.86 (d, J = 9.66 Hz, 1 H) 4.95 (d, J = 10.67 Hz, 1 H) 5.50 (m, J = 9.66 Hz, 1 H) 5.54-5.67 (m, 2 H) 6.00 (d, J = 10.67 Hz, 1 H) 6.25 (dd, J = 15.06, 10.79 Hz, 1 H) | 803.7 |
| 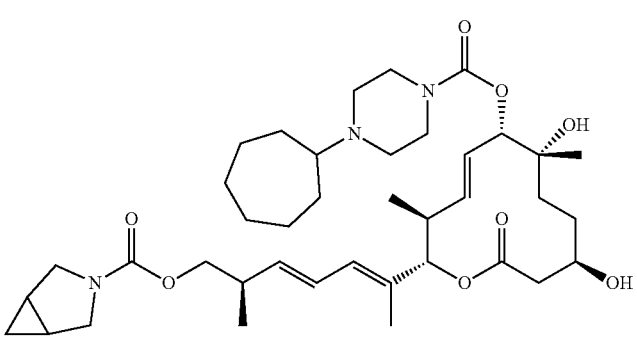 [SMILES: C/C(=C\C=C\[C@@H](C)COC(=O)N1CC2CC2C1)[C@H]1OC(=O)C[C@H](O)CC[C@@](C)(O)[C@@H](OC(=O)N2CCN(C3CCCCCC3)CC2)/C=C/[C@@H]1C]<br>89<br>[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienyl] 3-azabicyclo[3.1.0]hexane-3-carboxylate | ¹H NMR (400 MHz, METHANOL-d4) δ: 0.03-0.02 (m, 1 H) 0.61-0.69 (m, 1 H) 0.83 (d, J = 6.78 Hz, 3 H) 0.99 (d, J = 6.78 Hz, 3 H) 1.16 (s, 3 H) 1.28-1.37 (m, 2 H) 1.39-1.63 (m, 13 H) 1.64-1.78 (m, 5 H) 1.83-1.95 (m, 2 H) 2.44-2.58 (m, 4 H) 2.76-2.86 (m, 6 H) 2.93 (s, 3 H) 3.28-3.34 (m, 2 H) 3.43-3.77 (m, 7 H) 3.80-3.95 (m, 2 H) 4.87-4.91 (m, 2 H) 4.97-5.02 (m, 1 H) 5.48-5.72 (m, 3 H) 6.01-6.08 (m, 1 H) 6.22-6.33 (m, 1 H) | 700.5 |
| 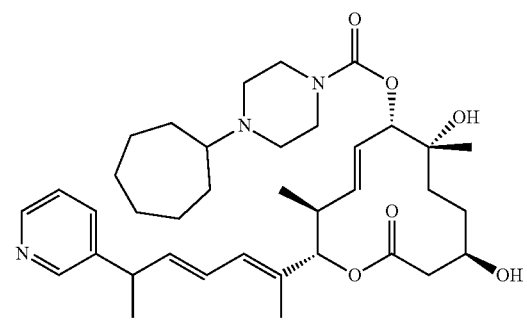 [SMILES: C/C(=C\C=C\C(C)c1cccnc1)[C@H]1OC(=O)C[C@H](O)CC[C@@](C)(O)[C@@H](OC(=O)N2CCN(C3CCCCCC3)CC2)/C=C/[C@@H]1C]<br>90<br>[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.70-0.93 (m, 4 H) 1.00 (d, J = 6.78 Hz, 1 H) 1.12-1.21 (m, 5 H) 1.24-1.50 (m, 14H) 1.55-1.76 (m, 11 H) 1.90 (br. s., 2 H) 2.14 (s, 1 H) 2.36-2.57 (m, 7 H) 3.22-3.43 (m, 5 H) 3.43-3.59 (m, 1 H) 3.68 (br. s., 1 H) 4.94 (d, J = 9.54 Hz, 1 H) 5.08 (d, J = 10.79 Hz, 1 H) 5.44-5.72 (m, 2 H) 5.82 (dd, J = 15.43, 6.90 Hz, 1 H) 6.03 (d, J = 10.54 Hz, 1 H) 6.09-6.25 (m, 1 H) 7.16-7.21 (m, 3 H) 7.44 (d, J = 7.28 Hz, 1 H) 8.41 (br. s., 2 H) | 638.28 |

TABLE 2-continued

Compounds 61-104

| Structure, Compound #, and Chemical Name | ¹H NMR data | LCMS data (ES+) |
|---|---|---|
| 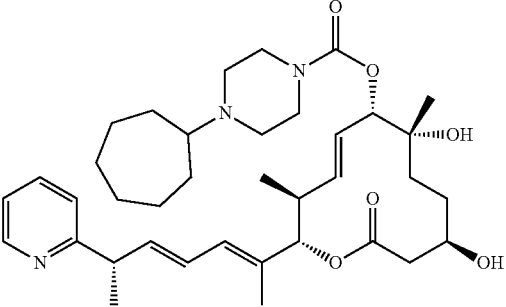 [SMILES: C/C(=C\C=C\[C@H](C)c1ccccn1)[C@H]1OC(=O)C[C@H](O)CC[C@@](C)(O)[C@@H](OC(=O)N2CCN(C3CCCCCC3)CC2)/C=C/[C@@H]1C]<br>91<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.90 (d, J = 6.78 Hz, 3 H) 1.22 (s, 3 H) 1.27-1.56 (m, 10 H) 1.45 (d, J = 6.90 Hz, 3 H) 1.65-1.71 (m, 3 H) 1.72 (s, 3 H) 1.79 (m, 2 H) 1.96 (s, 1 H) 2.43-2.64 (m, 8 H) 3.47 (m, 6 H) 3.58-3.83 (m, 2 H) 5.01 (d, J = 9.54 Hz, 1 H) 5.14 (d, J = 10.67 Hz, 1 H) 5.51-5.75 (m, 2 H) 5.99 (dd, J = 15.06, 7.53 Hz, 1 H) 6.11 (d, J = 10.79 Hz, 1 H) 6.25-6.34 (m, 1 H) 7.11 (ddd, J = 7.43, 4.86, 1.13 Hz, 1 H) 7.16 (d, J = 7.78 Hz, 1 H) 7.60 (td, J = 7.69, 1.82 Hz, 1 H) 8.54 (d, J = 5.03 Hz, 1 H) | 638.5 |
| 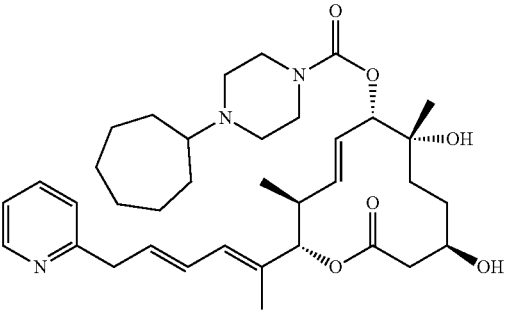 [SMILES: C/C(=C\C=C\Cc1ccccn1)[C@H]1OC(=O)C[C@H](O)CC[C@@](C)(O)[C@@H](OC(=O)N2CCN(C3CCCCCC3)CC2)/C=C/[C@@H]1C]<br>92<br>[(2S,3S,4E,6R,7R,10R)-7,10-dihydroxy-3,7-dimethyl-12-oxo-2-[(2E,4E)-6-pyridin-2-ylhexa-2,4-dien-2-yl]-1-oxacyclododec-4-en-6-yl] 4-cycloheptylpiperazine-1-carboxylate | ¹H NMR (400 MHz, CHLOROFORM-d) δ: 0.89 (d, J = 6.78 Hz, 3 H) 1.23 (s, 3 H) 1.26-1.55 (m, 10 H) 1.63-1.72 (m, 3 H) 1.73 (s, 3 H) 1.79 (m, 2 H) 1.96 (br. s., 1 H) 2.51 (m, 9 H) 3.49 (s, 4 H) 3.65 (d, J = 6.90 Hz, 2 H) 3.74 (m, 2 H) 5.08 (d, J = 10.92 Hz, 1 H) 5.15 (d, J = 10.67 Hz, 1 H) 5.51-5.64 (m, 1 H) 5.65-5.76 (m, 1 H) 5.98 (dt, J = 14.74, 7.18 Hz, 1 H) 6.12 (d, J = 10.67 Hz, 1 H) 6.37 (dd, J = 14.93, 10.79 Hz, 1 H) 7.13 (dd, J = 7.47, 5.08 Hz, 1 H) 7.16 (d, J = 7.78 Hz, 1 H) 7.56-7.66 (m, 1 H) 8.53 (d, J = 4.14 Hz, 1 H) | 624.3 |
| 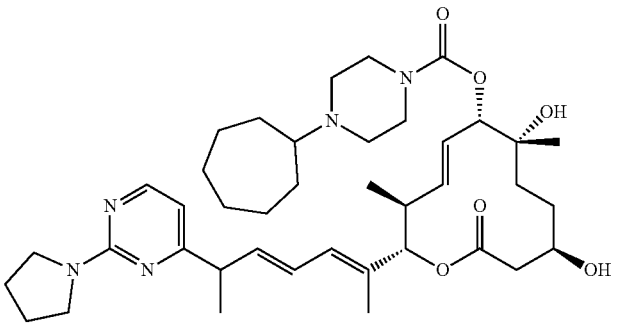 [SMILES: C/C(=C\C=C\C(C)c1ccnc(N2CCCC2)n1)[C@H]1OC(=O)C[C@H](O)CC[C@@](C)(O)[C@@H](OC(=O)N2CCN(C3CCCCCC3)CC2)/C=C/[C@@H]1C]<br>93<br>[(2S,3S,4E,6S,7S,10S)-7,10-dihydroxy-3,7-dimethyl-12-oxo-2-[(2E,4E)-6-(2-pyrrolidin-1-ylpyrimidin-4-yl)hepta-2,4-dien-2-yl]-1-oxacyclododec-4-en-6-yl] 4-cycloheptylpiperazine-1-carboxylate | ¹H NMR (400 MHz, CHLOROFORM-d) δ: 8.01-8.23 (m, 1H), 6.14-6.29 (m, 2H), 6.03 (d, J = 11.5 Hz, 1H), 5.77-5.98 (m, 1H), 5.44-5.68 (m, 2H), 5.23 (s, 1H), 5.08 (d, J = 10.5 Hz, 1H), 4.94 (d, J = 9.3 Hz, 1H), 3.67 (br. s., 2H), 3.31-3.58 (m, 8H), 3.23 (d, J = 3.8 Hz, 1H), 2.37-2.64 (m, 6H), 2.14 (s, 1H), 1.72-1.98 (m, 6H), 1.53-1.71 (m, 8H), 1.37-1.53 (m, 8H), 1.12-1.37 (m, 10H), 0.90-1.07 (m, 1H), 0.70-0.90 (m, 4H) | 708.9 |

TABLE 2-continued

Compounds 61-104

| Structure, Compound #, and Chemical Name | ¹H NMR data | LCMS data (ES+) |
|---|---|---|
| 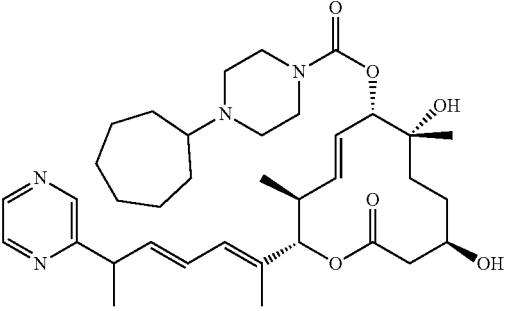 [SMILES: C/C(=C\C=C\C(C)c1cnccn1)[C@H]1OC(=O)C[C@H](O)CC[C@@](C)(O)[C@@H](OC(=O)N2CCN(C3CCCCCC3)CC2)/C=C/[C@@H]1C]<br>94<br>[(2S,3S,4E,6S,7S,10S)-7,10-dihydroxy-3,7-dimethyl-12-oxo-2-[(2E,4E)-6-pyrazin-2-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.64-0.89 (m, 4 H) 1.07-1.32 (m, 7 H) 1.32-1.53 (m, 10 H) 1.59-1.70 (m, 5 H) 1.81 (s, 1 H) 1.89 (br. s., 2 H) 2.33-2.56 (m, 6 H) 2.71 (br. s., 4 H) 2.76-3.03 (m, 2 H) 3.42 (s, 1 H) 3.60 (br. s., 3 H) 3.63-3.90 (m, 2 H) 4.93 (d, J = 9.54 Hz, 1H) 5.08 (d, J = 10.79 Hz, 1 H) 5.23 (s, 1 H) 5.49-5.75 (m, 2 H) 5.90 (dd, J = 15.18, 7.65 Hz, 1 H) 6.04 (d, J = 9.79 Hz, 1 H) 6.14-6.31 (m, 1 H) 8.22 (br. s., 1 H) 8.28-8.38 (m, 1 H) 8.38-8.49 (m, 2 H) | 639.69 |
| 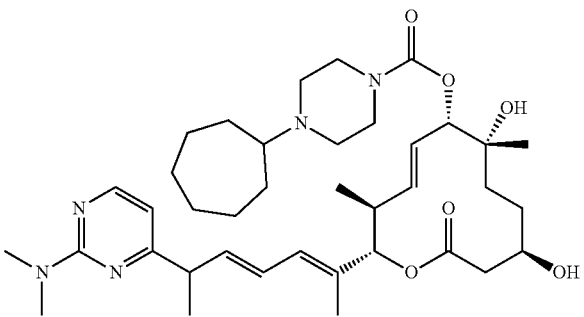 [SMILES: C/C(=C\C=C\C(C)c1ccnc(N(C)C)n1)[C@H]1OC(=O)C[C@H](O)CC[C@@](C)(O)[C@@H](OC(=O)N2CCN(C3CCCCCC3)CC2)/C=C/[C@@H]1C]<br>95<br>[(2S,3S,4E,6S,7S,10S)-2-[(2E,4E)-6-[2-(dimethylamino)pyrimidin-4-yl]hepta-2,4-dien-2-yl]-7,10-dihydroxy-3,7-dimethyl-12-oxo-1-oxacyclododec-4-en-6-yl] 4-cycloheptylpiperazine-1-carboxylate | ¹H NMR (400 MHz, CHLOROFORM-d) δ: 8.03-8.25 (m, 1H), 6.13-6.29 (m, 2H), 6.03 (d, J = 11.5 Hz, 1H), 5.89 (ddd, J = 15.2, 7.9, 4.8 Hz, 1H), 5.48-5.68 (m, 2H), 5.15 (s, 1H), 5.08 (d, J = 10.5 Hz, 1H), 4.77-5.02 (m, 1H), 3.68 (br. s., 1H), 3.27-3.53 (m, 4H), 3.08-3.13 (m, 4H), 2.34-2.58 (m, 6H), 1.89 (br. s., 1H), 1.81 (s, 1H), 1.63-1.75 (m, 4H), 1.60 (br. s., 2H), 1.40-1.54 (m, 11H), 1.37 (br. s., 2H), 1.13-1.34 (m, 8H), 0.70-0.94 (m, 4H) | 682.9 |
| 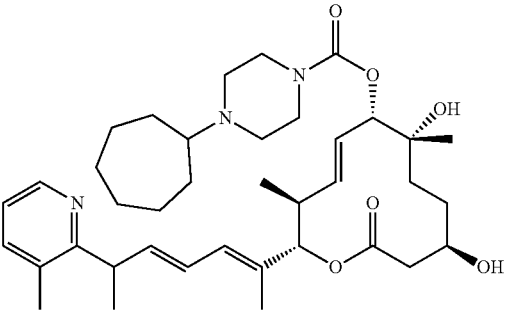<br>96<br>[(2S,3S,4E,6S,7S,10S)-7,10-dihydroxy-3,7-dimethyl-2-[(2E,4E)-6-(3-methylpyridin-2-yl)hepta-2,4-dien-2-yl]-12-oxo-1-oxacyclododec-4-en-6-yl] 4-cycloheptylpiperazine-1-carboxylate | ¹H NMR (400 MHz, CHLOROFORM-d) δ: 0.70-0.92 (m, 4 H) 1.00 (d, J = 6.53 Hz, 1 H) 1.14-1.21 (m, 4 H) 1.24-1.27 (m, 1 H) 1.29-1.55 (m, 14 H) 1.55-1.68 (m, 7 H) 1.72 (br. s., 2 H) 1.89 (br. s., 1 H) 2.14 (s, 1 H) 2.21-2.30 (m, 3 H) 2.34-2.60 (m, 7 H) 3.06 (s, 1 H) 3.16 (s, 1 H) 3.42 (br. s., 5 H) 3.59 (t, J = 7.15 Hz, 1 H) 3.67 (br. s., 1 H) 4.94 (d, J = 9.54 Hz, 1 H) 5.08 (d, J = 10.54 Hz, 1 H) 5.23 (s, 1 H) 5.48-5.74 (m, 2 H) 5.92 (ddd, J = 15.06, 7.53, 4.77 Hz, 1 H) 6.04 (d, J = 10.54 Hz, 1 H) 6.13-6.30 (m, 1 H) 6.78-6.99 (m, 2 H) 8.32 (dd, J = 5.02, 2.26 Hz, 1 H) | |

TABLE 2-continued

Compounds 61-104

| Structure, Compound #, and Chemical Name | $^1$H NMR data | LCMS data (ES+) |
|---|---|---|
| 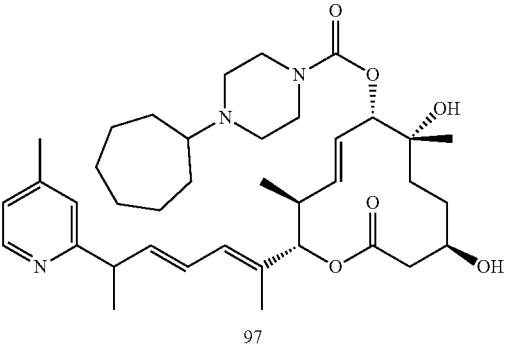<br>97<br>[(2S,3S,4E,6S,7S,10S)-7,10-dihydroxy-3,7-dimethyl-2-[(2E,4E)-6-(4-methylpyridin-2-yl)hepta-2,4-dien-2-yl]-12-oxo-1-oxacyclododec-4-en-6-yl] 4-cycloheptylpiperazine-1-carboxylate | $^1$H NMR (400 MHz, CHLOROFORM-d) δ: 0.73-0.88 (m, 4 H) 1.06 (br. s., 1 H) 1.07 (br. s., 1 H) 1.12 (s, 1 H) 1.15-1.27 (m, 7 H) 1.29 (br. s., 1 H) 1.31-1.49 (m, 11 H) 1.54-1.76 (m, 12H) 1.89 (br. s., 2 H) 2.19-2.31 (m, 3 H) 2.34-2.57 (m, 7 H) 2.69 (s, 1 H) 3.06 (s, 1 H) 3.11-3.27(m, 1 H) 3.27-3.51 (m, 5 H) 3.66 (br. s., 1 H) 3.80 (t, J = 6.90 Hz, 1 H) 4.94 (d, J = 9.54 Hz, 1 H) 5.07 (d, J = 10.79 Hz, 1 H) 5.23 (s, 1 H) 5.48-5.71 (m, 2 H) 5.79-6.05 (m, 2 H) 6.07-6.25 (m, 1 H) 6.88-7.05 (m, 1 H) 7.29-7.41 (m, 1 H) 8.24-8.48 (m, 1 H) | |
| 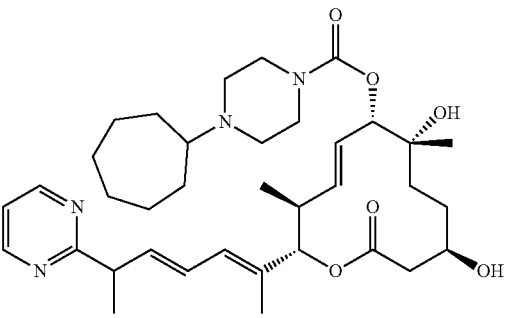<br>98<br>[(2S,3S,4E,6S,7S,10S)-7,10-dihydroxy-3,7-dimethyl-12-oxo-2-[(2E,4E)-6-pyrimidin-2-ylhepta-2,4-dien-2-yl]-1-oxacyclododec-4-en-6-yl] 4-cycloheptylpiperazine-1-carboxylate | $^1$H NMR (400 MHz, CHLOROFORM-d) δ: 0.68-0.92 (m, 4 H) 1.00 (d, J = 6.78 Hz, 1 H) 1.06 (br. s., 1 H) 1.08 (br. s., 1 H) 1.12 (br. s., 1 H) 1.14-1.21 (m, 5 H) 1.24-1.50 (m, 15 H) 1.55-1.69 (m, 7 H) 1.73 (br. s., 2 H) 1.78-1.92 (m, 1 H) 1.98 (s, 1 H) 2.14 (s, 1 H) 2.36-2.58 (m, 7 H) 3.06 (s, 1 H) 3.23 (d, J = 4.02 Hz, 1 H) 3.32-3.50 (m, 5 H) 3.67 (br. s., 1 H) 3.72-3.89 (m, 1 H) 4.05 (q, J = 7.03 Hz, 1 H) 4.94 (d, J = 9.54 Hz, 1 H) 5.08 (d, J = 10.54 Hz, 1 H) 5.44-5.68 (m, 2 H) 5.94-6.16 (m, 2 H) 6.31 (dd, J = 14.43, 10.92 Hz, 1 H) 6.93 (s, 1 H) 7.01-7.12 (m, 1 H) 7.45 (s, 1 H) 8.57-8.67 (m, 2 H) | 639.53 |
| 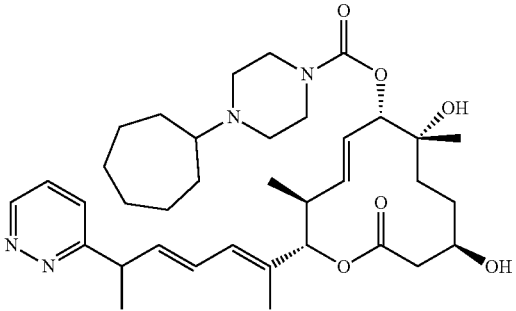<br>99<br>[(2S,3S,4E,6S,7S,10S)-7,10-dihydroxy-3,7-dimethyl-12-oxo-2-[(2E,4E)-6-pyridazin-3-ylhepta-2,4-dien-2-yl]-1-oxacyclododec-4-en-6-yl] 4-cycloheptylpiperazine-1-carboxylate | $^1$H NMR (400 MHz, METHANOL-d4) δ: 0.77 (dd, J = 12.42, 6.65 Hz, 2 H) 1.06-1.17 (m, 2 H) 1.17-1.28 (m, 7 H) 1.39-1.61 (m 9 H) 1.63-1.71 (m, 3 H) 1.80-1.97 (m, 2 H) 2.06 (s, 1 H) 2.27 (s, 1 H) 2.36-2.60 (m, 2 H) 2.96 (br. s., 3 H) 3.11 (q, J = 7.28 Hz, 4 H) 3.50-3.77 (m, 4 H) 3.86 (t, J = 7.15 Hz, 1 H) 4.85 (d, J = 9.79 Hz, 3 H) 4.94 (d, J = 10.54 Hz, 2 H) 5.39 (s, 1 H) 5.48 (ddd, J = 15.31, 9.79, 2.01 Hz, 1 H) 5.61 (ddd, J = 15.25, 9.60, 1.25 Hz, 1 H) 5.90 (dd, J = 15.06, 7.78 Hz, 1 H) 6.03 (d, J = 10.79 Hz, 1 H) 6.20-6.46 (m, 1 H) 7.12-7.21 (m, 1 H) 7.48-7.69 (m, 2 H) 8.97 (br. s., 1 H) | 639.59 |

TABLE 2-continued

Compounds 61-104

| Structure, Compound #, and Chemical Name | ¹H NMR data | LCMS data (ES+) |
|---|---|---|
| 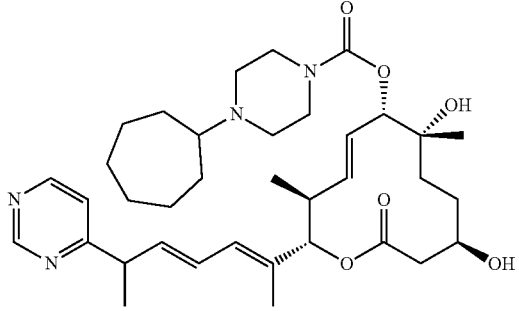<br>100<br>[(2S,3S,4E,6S,7S,10S)-7,10-dihydroxy-3,7-dimethyl-12-oxo-2-[(2E,4E)-6-pyrimidin-4-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.67-0.94 (m, 5 H) 0.94-1.10 (m, 9 H) 1.14-1.27 (m, 10 H) 1.30-1.50 (m, 15 H) 1.53 (br. s., 1 H) 1.58 (br. s., 1 H) 1.61-1.69 (m, 6 H) 1.73 (s, 1 H) 1.79 (d, J = 1.00 Hz, 2 H) 1.86 (d, J = 3.26 Hz, 3 H) 1.97 (s, 1 H) 2.10-2.15 (m, 4H) 2.20-2.32 (m, 2 H) 2.32-2.44 (m, 2 H) 2.51 (br. s., 3 H) 2.71 (br. s., 5 H) 2.87 (br. s., 2 H) 2.98 (q, J = 7.28 Hz, 4 H) 3.05-3.22 (m 2 H) 3.27(d, J = 9.29 Hz, 1 H) 3.36-3.53 (m, 3 H) 3.53-3.72 (m, 6 H) 3.81 (br. s., 2 H) 4.05 (q, J = 7.03 Hz, 2 H) 4.83-5.02 (m, 3 H) 5.23 (s, 1 H) 5.28-5.50 (m, 3 H) 5.50-5.76 (m, 3 H) 6.29 (s, 1 H) 6.33 (s, 1 H) 6.39 (d, J = 11.04 Hz, 1 H) 6.45-6.61 (m, 1 H) 6.63-6.86 (m, 2 H) 6.93 (s, 1 H) 7.32 (dd, J = 5.40, 1.38 Hz, 1 H) 7.45 (s, 2 H) 8.56 (d, J = 5.52 Hz, 1 H) 8.64 (d, J = 5.27 Hz, 2 H) 9.05 (d, J = 1.00 Hz, 2 H) 9.11-9.30 (m, 2 H) | 639.47 |
| 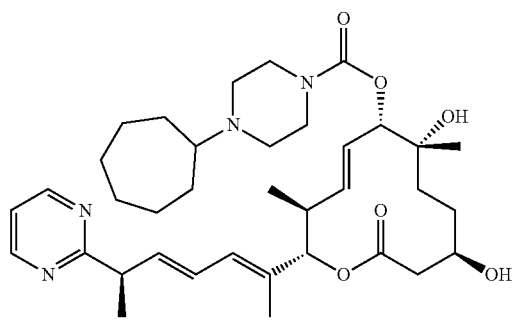 [SMILES: C/C(=C\C=C\[C@@H](C)c1ncccn1)[C@H]1OC(=O)C[C@H](O)CC[C@@](C)(O)[C@@H](OC(=O)N2CCN(C3CCCCCC3)CC2)/C=C/[C@@H]1C]<br>101<br>[(2S,3S,4E,6S,7S,10S)-7,10-dihydroxy-3,7-dimethyl-12-oxo-2-[(2E,4E,6S)-6-pyrimidin-2-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.72-0.87 (m, 3 H) 1.14-1.21 (m, 3 H) 1.25 (br. s., 1 H) 1.27 (s, 1 H) 1.29-1.53 (m, 12 H) 1.56-1.63 (m, 2 H) 1.65-1.74 (m, 4 H) 1.82-2.00 (m, 1 H) 2.10 (s, 1 H) 2.35-2.56 (m, 7 H) 3.32-3.48 (m, 5 H) 3.56-3.73 (m, 1 H) 3.80 (t, J = 7.15 Hz, 1 H) 4.94 (d, J = 9.29 Hz, 1 H) 5.08 (d, J = 10.54 Hz, 1 H) 5.47-5.66 (m, 2 H) 5.94-6.13 (m, 2 H) 6.17-6.35 (m, 1 H) 6.93-7.13 (m, 1 H) 8.59-8.65 (m, 2 H) | 639.53 |
| 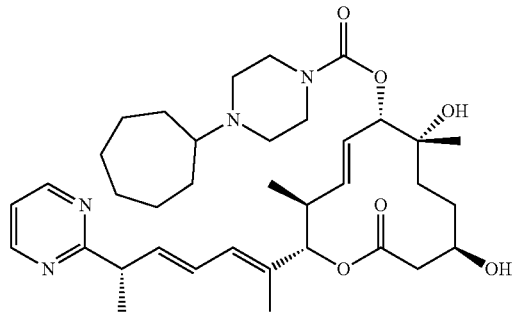 [SMILES: C/C(=C\C=C\[C@H](C)c1ncccn1)[C@H]1OC(=O)C[C@H](O)CC[C@@](C)(O)[C@@H](OC(=O)N2CCN(C3CCCCCC3)CC2)/C=C/[C@@H]1C]<br>102<br>[(2S,3S,4E,6S,7S,10S)-7,10-dihydroxy-3,7-dimethyl-12-oxo-2-[(2E,4E,6S)-6-pyrimidin-2-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.76-0.88 (m, 3 H) 0.91 (br. s., 1 H) 1.14-1.21 (m, 4 H) 1.24-1.50 (m, 12 H) 1.54-1.75 (m, 7H) 1.84-2.00 (m, 2 H) 2.10 (s, 1 H) 2.33-2.56 (m, 7 H) 3.15 (s, 1 H) 3.33-3.48 (m, 7 H) 3.55-3.72 (m, 1 H) 3.79 (t, J = 7.15 Hz, 1 H) 4.04 (s, 1H) 4.94 (d, J = 9.29 Hz, 1 H) 5.08 (d, J = 10.79 Hz, 1H) 5.47-5.67 (m, 2 H) 5.92-6.13 (m, 2 H) 6.21-6.38 (m, 1 H) 7.06 (t, J = 4.89 Hz, 1 H) 7.45 (s, 1 H) 8.61 (d, J = 4.77 Hz, 2 H) | 639.53 |

TABLE 2-continued

Compounds 61-104

| Structure, Compound #, and Chemical Name | ¹H NMR data | LCMS data (ES+) |
|---|---|---|
| 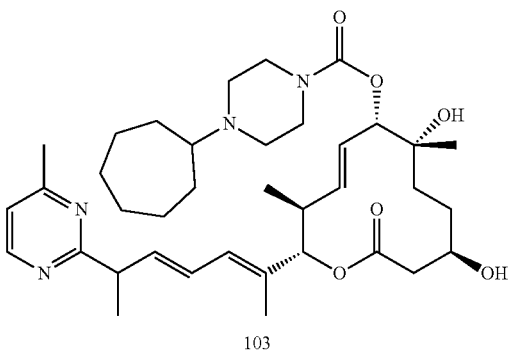<br>103<br>[(2S,3S,4E,6S,7S,10S)-7,10-dihydroxy-3,7-dimethyl-2-[(2E,4E)-6-(4-methylpyrimidin-2-yl)hepta-2,4-dien-2-yl]-12-oxo-1-oxacyclododec-4-en-6-yl] 4-cycloheptylpiperazine-1-carboxylate | ¹H NMR (400 MHz, CHLOROFORM-d) δ: 0.70-0.91 (m, 5 H) 1.00 (d, J = 6.53 Hz, 1 H) 1.15-1.22 (m, 6 H) 1.25 (dd, J = 7.78, 2.51 Hz, 1 H) 1.29-1.49 (m, 14 H) 1.56-1.75 (m, 9 H) 1.81 (s, 1 H) 1.89 (br. s., 1 H) 1.98 (s, 1 H) 2.06-2.28 (m, 1 H) 2.35-2.55 (m, 11 H) 3.23 (d, J = 3.76 Hz, 1 H) 3.39 (br. s., 5 H) 3.54-3.80 (m, 2 H) 4.05 (q, J = 7.03 Hz, 1 H) 4.94 (d, J = 9.29 Hz, 1 H) 5.08 (d, J = 10.79 Hz, 1 H) 5.23 (s, 1 H) 5.45-5.68 (m, 3 H) 5.96-6.15 (m, 2 H) 6.29 (dd, J = 15.18, 10.67 Hz, 1 H) 6.91 (dd, J = 5.14, 2.13 Hz, 1 H) 8.41-8.52 (m, 1 H) | |
| 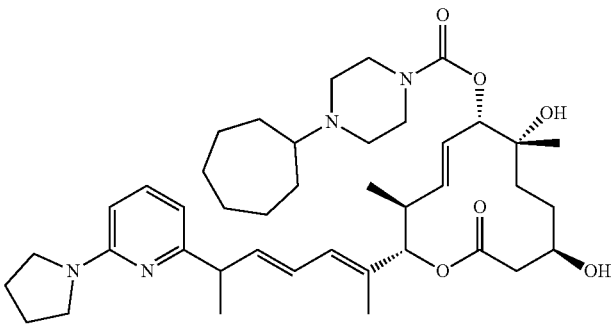 [SMILES: C/C(=C\C=C\C(C)c1cccc(N2CCCC2)n1)[C@H]1OC(=O)C[C@H](O)CC[C@@](C)(O)[C@@H](OC(=O)N2CCN(C3CCCCCC3)CC2)/C=C/[C@@H]1C]<br>104<br>[(2S,3S,4E,6S,7S,10S)-7,10-dihydroxy-3,7-dimethyl-12-oxo-2-[(2E,4E)-6-(6-pyrrolidin-1-ylpyridin-2-yl)hepta-2,4-dien-2-yl]-1-oxacyclododec-4-en-6-yl] 4-cycloheptylpiperazine-1-carboxylate | ¹H NMR (400 MHz, CHLOROFORM-d) δ: 0.68-0.91 (m, 4 H) 1.13-1.22 (m, 4 H) 1.25-1.53 (m, 17 H) 1.53-1.76 (m, 9 H) 1.81-2.00 (m,4 H) 2.35-2.57 (m, 7 H) 3.05-3.30 (m, 1 H) 3.30-3.49 (m, 8 H) 3.67 (br. s., 1 H) 4.94 (d, J = 9.54 Hz, 1 H) 5.08 (d, J = 10.79 Hz, 1 H) 5.23 (s, 1 H)5.45-5.68 (m, 2 H) 5.92-6.13 (m, 3 H) 6.15-6.42 (m, 2 H) 7.22-7.22 (m, 1 H) 7.22-7.32 (m, 1 H) | 707.65 |

Compounds 105-115 were prepared by the method of Scheme 3.

Scheme 3.

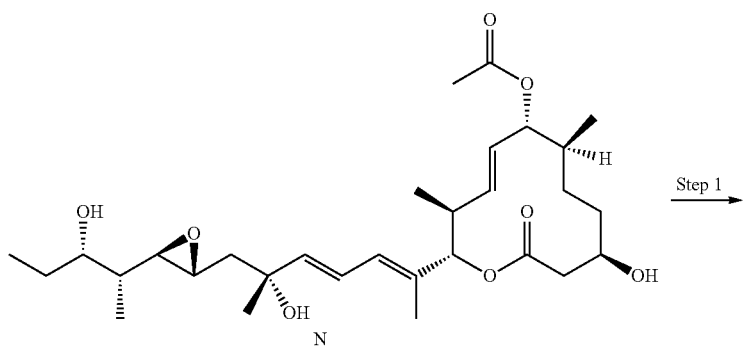

Step 1

-continued
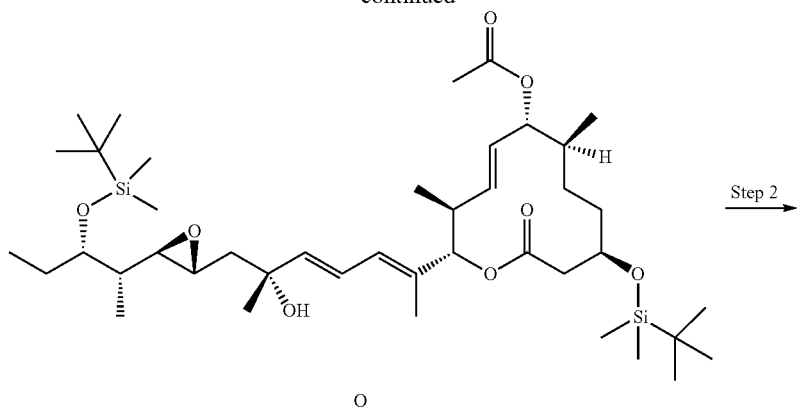
O
Step 2
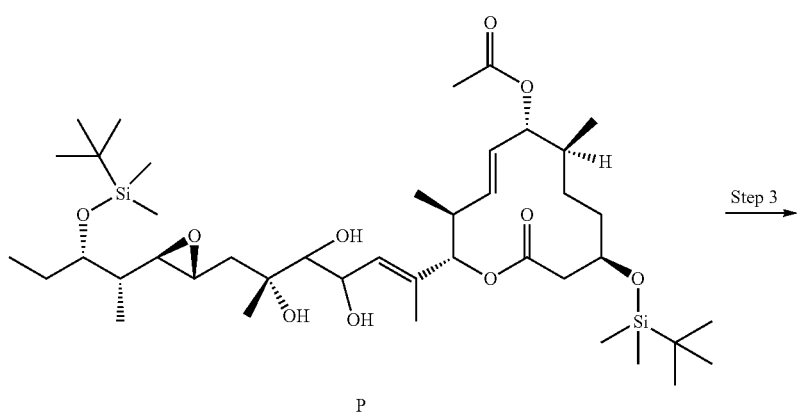
P
Step 3
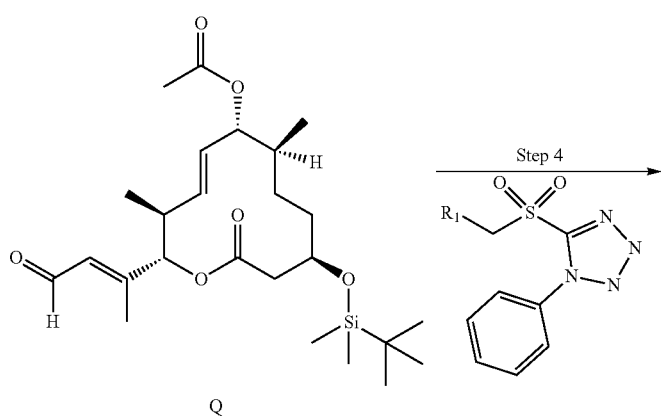
Q
Step 4
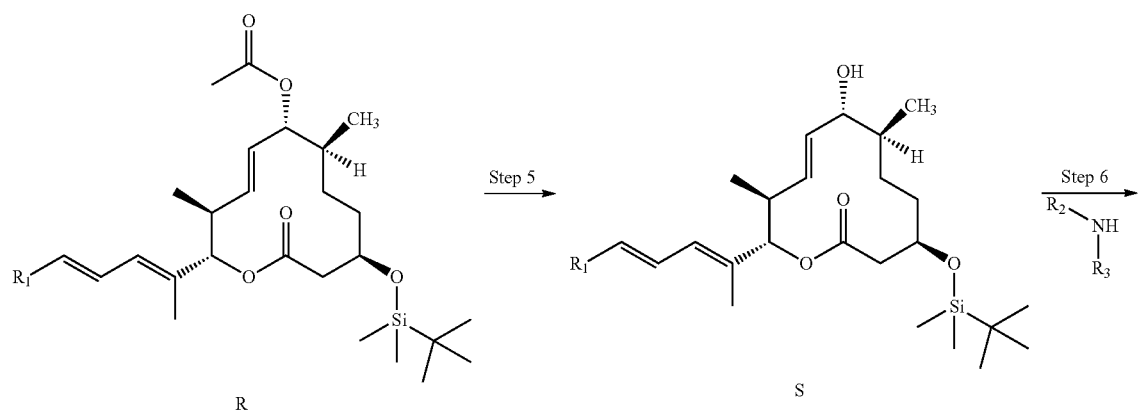
R
Step 5
S
Step 6

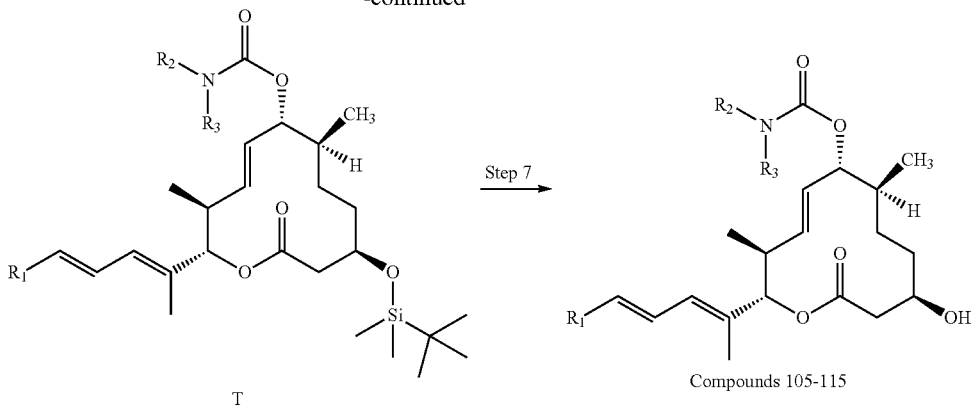

-continued

Compounds 105-115

General Protocol for the Synthesis of Compounds 105-115:

Step 1: A solution of 6-deoxypladienolide D (N, 100.0 mg, 0.2 mmol, 1.0 equiv.) under nitrogen in DMF (8 mL, 0.2M) at 0° C. was treated with imidazole (89.2 mg, 1.3 mmol, 7.0 equiv.) and TBSCl (140.3 mg, 0.9 mmol, 5.0 equiv.). The reaction was allowed to warm to room temperature and stirred for 20 hours, or until the reaction was determined to be complete by LCMS or TLC. The reaction was extracted with ethyl acetate and the organic layer was washed with brine, dried over sodium sulfate, filtered, and concentrated in vacuo. The resulting oil was purified by silica gel column chromatography (hexanes/ethyl acetate as eluent) to afford the desired product (O, 143.0 mg, 0.19 mmol, 100%).

Step 2: To a solution of olefin O (30.0 mg, 0.04 mmol, 1.0 equiv.) in degassed THF:H$_2$O (10:1, 1.0 mL:0.1 mL, 0.01M) under nitrogen at 0° C. was added osmium tetroxide (0.1 mL, 0.008 mmol, 0.2 equiv., 2.5% solution in tert-butanol) followed by N-methylmorpholine N-oxide (9.2 mg, 0.08 mmol, 2.0 equiv.). The reaction was allowed to warm to room temperature and stirred for 30 minutes, or until the reaction was determined to be complete by LCMS or TLC. The reaction was quenched with sodium sulfite, diluted with ethyl acetate, and the organic layer was washed with water, dried over magnesium sulfate, filtered, and concentrated in vacuo. The resulting oil was purified by silica gel column chromatography (dichloromethane/methanol as eluent) to afford the desired product (P, 29.2 mg, 0.04 mmol, 93%).

Step 3: To a solution of triol P (498.2 mg, 0.6 mmol, 1.0 equiv.) in benzene (25 mL, 0.03M) under nitrogen at room temperature was added lead tetraacetate (553.4 mg, 1.2 mmol, 2.0 equiv.). The reaction was stirred for 30 minutes, or until the reaction was determined to be complete by LCMS or TLC. The reaction was concentrated and purified by silica gel column chromatography (hexane/ethyl acetate as eluent) to afford the desired product (Q, 232 mg, 0.5 mmol, 80%).

Step 4: To a solution of the corresponding sulfone (2.5 equiv.) in THF (0.02M) under nitrogen at −78° C. was added KHMDS (2.5 equiv.) dropwise and the reaction was stirred for 20 minutes. Then aldehyde Q (1.0 equiv.) in THF (0.5 M) was added dropwise. The reaction was stirred at −78° C. for 90 minutes and then allowed to warm to −20° C. over 1 hr. The reaction was quenched with aqueous ammonium chloride solution, diluted with ethyl acetate, washed with water, brine, dried over magnesium sulfate, filtered, and concentrated in vacuo. The resulting oil was purified by silica gel column chromatography (hexane/ethyl acetate as eluent) to afford the desired product (R).

Step 5: To a solution of acetate R (1.0 equiv.) in methanol (0.1M) at room temperature was added potassium carbonate (2.5 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting oil (S) was advanced crude into the next step.

Step 6: To a solution of alcohol (S) (1.0 equiv.) in dichloroethane (0.1M) at room temperature was added N,N-dimethylaminopyridine (0.3 equiv.) followed by 4-nitrophenyl chloroformate (4.0 equiv.). The reaction was stirred at room temperature for 24 hours. Next, the corresponding amine (10.0 equiv.) was added at room temperature. After stirring for one hour, the reaction was concentrated and the resulting oil was purified by silica gel column chromatography (hexanes/ethyl acetate as eluent) to afford the desired product (T).

Step 7: To a solution of silyl ether T in methanol (0.1M) at room temperature was added p-methoxytoluenesulfonic acid (2.5 equiv.). The reaction was stirred for 3 hours, or until the reaction was determined to be complete by LCMS or TLC. The reaction was quenched with sodium bicarbonate, diluted with ethyl acetate, washed with water, brine, dried over magnesium sulfate, filtered, and concentrated in vacuo. The resulting oil was purified by silica gel column chromatography (hexane/ethyl acetate as eluent) to afford the desired product (105-115). (Table 3)

Exemplified Protocol for the Synthesis of Compound 114

Steps 1-3 as above.

Step 4: To a solution containing (S)-2-(1-((1-phenyl-1H-tetrazol-5-yl)sulfonyl)propan-2-yl)pyridine (44.0 mg, 0.1 mmol, 2.5 equiv.) and THF (2.0 mL, 0.02M) under nitrogen at −78° C. was added KHMDS (0.27 mL, 0.1 mmol, 2.5 equiv.) dropwise and the reaction was stirred for 20 minutes. Then aldehyde Q (25 mg, 0.05 mmol, 1.0 equiv.) in THF (0.1 mL) was added dropwise. The reaction was stirred at −78° C. for 90 minutes and then allowed to warm to −20° C. over 1 hr. The reaction was quenched with aqueous ammonium chloride solution, diluted with ethyl acetate, washed with water, brine, dried over magnesium sulfate, filtered, and concentrated in vacuo. The resulting oil was purified by silica gel column chromatography (hexane/ethyl acetate as eluent) to afford the desired product (R, 21.0 mg, 0.04 mmol, 69%).

Step 5: To a solution of acetate R (15.2 mg, 0.03 mmol, 1.0 equiv.) in methanol (2 mL, 0.1M) at room temperature was added potassium carbonate (9.1 mg, 0.07 mmol, 2.5 equiv.). The reaction was run for 24 hours, or until the reaction was determined to be complete by LCMS or TLC. The reaction was quenched with water, diluted with ethyl acetate, washed with brine, dried over magnesium sulfate, filtered, and concentrated in vacuo. The resulting oil (S, 14 mg, 0.03 mmol, 100%) was advanced crude into the next step.

Step 6: To a solution of alcohol (S, 4.2 mg, 0.008 mmol, 1.0 equiv.) in dichloromethane (1 mL, 0.1M) at room temperature was added N,N-dimethylaminopyridine (0.3 mg, 0.002 mmol, 0.3 equiv.) followed by 4-nitrophenyl chloroformate (6.4 mg, 0.03 mmol, 4.0 equiv.). The reaction was stirred at room temperature for 24 hours. Next, N-methyl piperazine (0.009 mL, 0.08 mmol, 10.0 equiv.) was added at room temperature. After stirring for one hour, the reaction was concentrated and the resulting oil was purified by silica gel column chromatography (hexanes/ethyl acetate as eluent) to afford the desired product (T, 4.9 mg, 0.007 mmol, 94%).

Step 7: To a solution of silyl ether T (4.9 mg, 0.007 mmol, 1.0 equiv.) in methanol (0.7 mL, 0.1M) at room temperature was added p-methoxytoluenesulfonic acid (3.6 mg, 0.02 mmol, 2.5 equiv.). The reaction was stirred for 3 hours, or until the reaction was determined to be complete by LCMS or TLC. The reaction was quenched with sodium bicarbonate, diluted with ethyl acetate, washed with water, brine, dried over magnesium sulfate, filtered, and concentrated in vacuo. The resulting oil was purified by silica gel column chromatography (hexane/ethyl acetate as eluent) to afford the desired product (compound 114, 3.6 mg, 0.007 mmol, 89%). $^1$H NMR (400 MHz, CHLOROFORM-d) δ: 0.88 (d, J=6.78 Hz, 3H) 0.99 (d, J=6.90 Hz, 3H) 1.13-1.33 (m, 2H) 1.44 (d, J=6.90 Hz, 3H) 1.47-1.51 (m, 1H) 1.73 (d, J=0.75 Hz, 3H) 1.74-1.81 (m, 1H) 1.84-1.97 (m, 1H) 2.30 (s, 3H) 2.36 (br. s., 4H) 2.39-2.61 (m, 3H) 3.41 (m, 1H) 3.49 (br. s., 4H) 3.67-3.74 (m, 2H) 4.86 (t, J=10.04 Hz, 1H) 5.13 (d, J=10.67 Hz, 1H) 5.35 (dd, J=14.93, 9.66 Hz, 1H) 5.54 (dd, J=15.06, 9.91 Hz, 1H) 6.00 (dd, J=15.12, 7.47 Hz, 1H) 6.12 (d, J=10.92 Hz, 1H) 6.32 (ddd, J=15.09, 10.82, 1.07 Hz, 1H) 7.11 (ddd, J=7.53, 4.89, 1.13 Hz, 1H) 7.16 (d, J=7.91 Hz, 1H) 7.61 (td, J=7.65, 1.88 Hz, 1H) 8.55 (d, J=4.96 Hz, 1H), MS (ES+): 540.3 [M+H]$^+$.

Compound 116 was prepared by the method of Scheme 4.

Scheme 4.

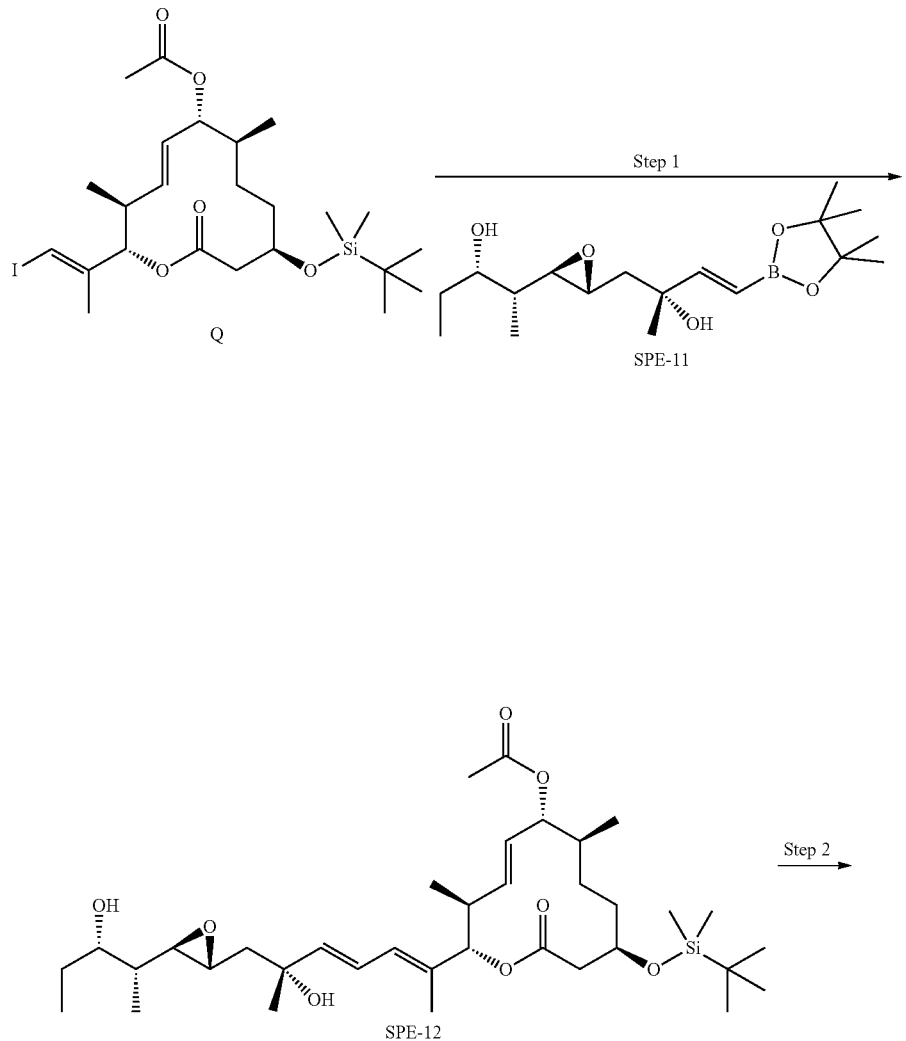

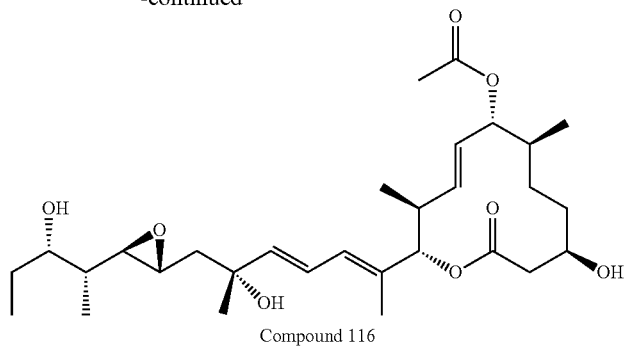

Compound 116

Step 1: To a solution of intermediate Q (35 mg, 0.062 mmol, 1 equiv) and SPE-11 (23.20 mg, 0.068 mmol, 1.1 equiv) in tetrahydrofuran (3 mL) at rt under nitrogen atmosphere, triphenylarsine (18.98 mg, 0.062 mmol, 1 equiv), silver(I) oxide (71.8 mg, 0.31 mmol, 5 equiv), and Tris(dibenzylideneacetone)dipalladium (0) (11.35 mg, 0.012 mmol, 0.2 equiv) were added successively and stirred for 16 hr under dark at the same temperature. The solid was filtered off through Celite and the pad washed with EtOAc. Excess solvent was removed under reduced pressure and the obtained residue was purified with silica gel chromatography (0-50% EtOAc/hexanes) to give the desired product (SPE-12, 17.6 mg, 0.027 mmol, 43.6%.

Step 2: To a solution of SPE-12 (17.6 mg, 0.027 mmol, 1 equiv) in THF (2 mL) was added TBAF (0.216 mL, 0.216 mmol, 8 equiv) at 0° C., then the reaction mixture was gradually warmed up to room temperature and stirred for 2 hr. The reaction mixture was directly applied to silica gel and purified by silica gel chromatography (0-30% EtOAc/hexanes) to give the desired product (Compound 116, 5.2 mg, 9.69 μmol, 35.8%). $^1$H NMR (400 MHz, METHANOL-d4) δ: ppm 0.86-1.02 (m, 15H) 1.37 (d, J=3.51 Hz, 8H) 1.47-1.55 (m, 2H) 1.62-1.71 (m, 3H) 1.79 (s, 3H) 1.85-1.96 (m, 2H) 2.02 (s, 3H) 2.42-2.48 (m, 1H) 2.55-2.63 (m, 2H) 2.65-2.76 (m, 1H) 2.83-2.94 (m, 1H) 3.50-3.62 (m, 1H) 3.80 (s, 2H) 4.89-4.97 (m, 1H) 5.01-5.09 (m, 1H) 5.39-5.56 (m, 2H) 5.82-5.96 (m, 1H) 6.11-6.20 (m, 1H) 6.49-6.62 (m, 1H). MS(ES+): 535.56[M−H]$^-$.

TABLE 3

Compounds 105-116

| Structure, Compound #, and Chemical Name | $^1$H NMR data | LCMS data (ES+) |
|---|---|---|
| 105<br><br>[(2S,3S,4E,6R,7R,10S)-10-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate | $^1$H NMR (400 MHz, CHLOROFORM-d) δ: 0.89 (d, J = 6.78 Hz, 3 H) 0.99 (d, J = 6.78 Hz, 3 H) 1.06 (d, J = 6.78 Hz, 3 H) 1.16-1.32 (m, 2 H) 1.33-1.55 (m, 10 H) 1.61-1.70 (m, 2 H) 1.73 (s, 3 H) 1.76-1.92 (m, 7H) 2.41-2.63 (m, 9H) 3.32 (br. s., 2 H) 3.35-3.53 (m, 7 H) 3.71 (s, 1 H, OH) 3.90-4.01 (m, 2 H) 4.86 (t, J = 10.04 Hz, 1 H) 5.13 (d, J = 10.54 Hz, 1 H) 5.36 (dd, J = 15.00, 9.60 Hz, 1 H) 5.55 (dd, J = 15.00, 9.85 Hz, 1 H) 5.69 (dd, J = 15.12, 7.47 Hz, 1 H) 6.09 (d, J = 10.79 Hz, 1 H) 6.27 (dd, J = 15.12, 10.85 Hz, 1 H) | 672.5 |

TABLE 3-continued

Compounds 105-116

| Structure, Compound #, and Chemical Name | ¹H NMR data | LCMS data (ES+) |
|---|---|---|
| 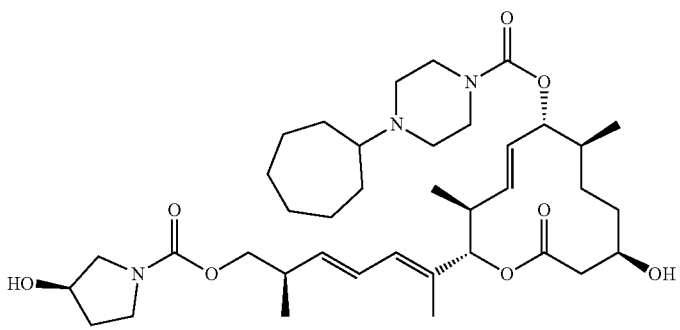<br>106<br><br>[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate | ¹H NMR (400 MHz, CHLOROFORM-d) δ: 0.90 (d, J = 6.65 Hz, 3 H) 0.99 (d, J = 6.78 Hz, 3 H) 1.06 (d. J = 6.78 Hz, 3 H) 1.16-1.33 (m, 2 H) 1.33- 1.56 (m, 10 H) 1.62-1.70 (m, 2 H) 1.73 (s, 3 H) 1.78 (br. s., 2 H) 1.85-2.08 (m, 3 H) 2.37- 2.63 (m, 9 H) 3.31-3.62 (m, 10 H) 3.71 (s, 1 H, OH) 3.90-4.04 (m, 2 H) 4.42- 4.50 (m, 1 H) 4.85 (t, J = 10.04 Hz, 1 H) 5.13 (d, J = 10.67 Hz, 1 H) 5.31- 5.39 (m, 1 H) 5.55 (dd, J = 14.93, 9.91 Hz, 1 H) 5.69 (dd, J = 15.06, 7.53 Hz, 1 H) 6.09 (d, J = 11.29 Hz, 1 H) 6.20-6.31 (m, 1 H | 688.4 |
| 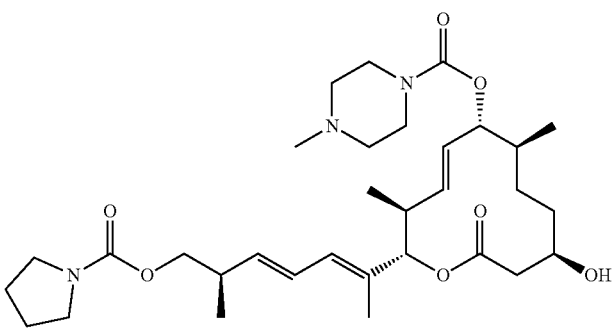<br>107<br><br>[(2S,3S,4E,6R,7R,10S)-10-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.90 (d, J = 6.78 Hz, 3 H) 0.99 (d, J = 6.78 Hz, 3 H) 1.06 (d, J = 6.78 Hz, 3 H) 1.15-1.35 (m, 2 H) 1.36-1.55 (m, 1 H) 1.73 (s, 3 H) 1.77-1.96 (m, 5 H) 2.30 (s, 3 H) 2.36 (br. s., 4 H) 2.41-2.66 (m, 5 H) 3.24-3.44 (m, 4 H) 3.48 (br. s., 4 H) 3.63 (t, J = 6.90 Hz, 1 H) 3.70 (d, J = 7.15 Hz, 1 H) 3.96 (qd, J = 10.37, 6.78 Hz, 2 H) 4.86 (t, J = 9.98 Hz, 1 H) 5.14 (d, J = 10.67 Hz, 1 H) 5.36 (dd, J = 15.06, 9.66 Hz, 1 H) 5.55 (dd, J = 14.93, 9.91 Hz, 1 H) 5.69 (dd, J = 15.12, 7.47 Hz, 1 H) 6.09 (d, J = 10.79 Hz, 1 H) 6.26 (dd, J = 15.25, 10.10 Hz, 1 H) | 590.3 |
| 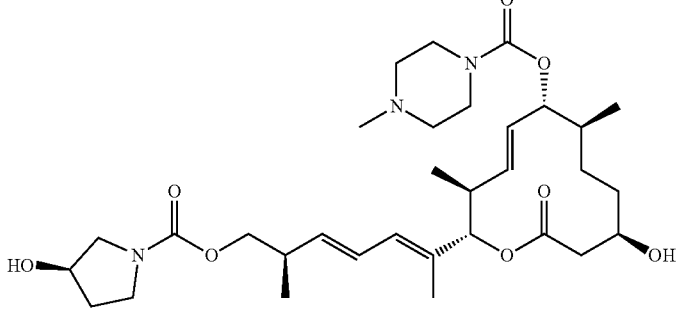<br>108<br><br>[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, CHLOROFORM-d) δ: 0.90 (d, J = 6.65 Hz, 3 H) 0.99 (d, J = 6.78 Hz, 3 H) 1.07 (d, J = 6.90 Hz, 3 H) 1.19-1.25 (m, 1 H) 1.37-1.54 (m, 1 H) 1.73 (s, 3 H) 1.76-1.83 (m, 1 H) 1.87-2.05 (m, 3 H) 2.30 (s, 3 H) 2.35 (br. s., 4 H) 2.44-2.63 (m, 5 H) 3.30-3.60 (m, 9 H) 3.72 (m, 2 H) 3.91-4.03 (m, 2 H) 4.46-4.50 (m, 1 H) 4.86 (t, J = 10.04 Hz, 1 H) 5.13 (d, J = 10.54 Hz, 1 H) 5.32-5.40 (dd, J = 14.93, 10.04 Hz, 1 H) 5.55 (dd, J = 14.93, 9.91 Hz, 1 H) 5.69 (dd, J = 15.31, 7.65 Hz, 1 H) 6.09 (d, J = 10.79 Hz, 1 H) 6.27 (dd, J = 14.81, 11.04 Hz, 1 H) | 606.3 |

TABLE 3-continued

Compounds 105-116

| Structure, Compound #, and Chemical Name | ¹H NMR data | LCMS data (ES+) |
|---|---|---|
| 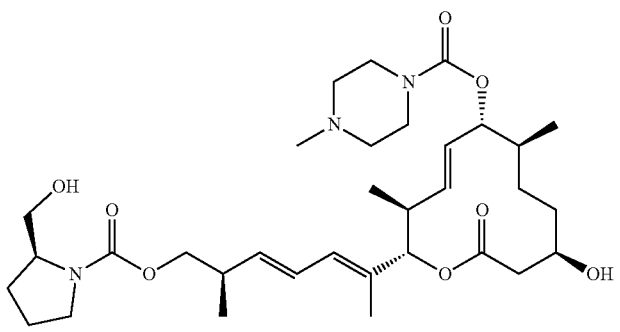<br>109<br>[(2S,3S,4E,6R,7R,10S)-10-hydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, CHLOROFORM-d) δ: 0.90 (d, J = 6.78 Hz, 3 H) 0.99 (d, J = 6.78 Hz, 3 H) 1.07 (d, J = 6.78 Hz, 3 H) 1.15-1.34 (m, 2 H) 1.36-1.53 (m, 1 H) 1.57 (d, J = 6.40 Hz, 1 H) 1.74 (s, 3 H) 1.77-1.93 (m, 3 H) 1.95-2.07 (m, 1 H) 2.42 (s, 3 H) 2.45-2.68 (m, 7 H) 3.17-3.43 (m, 2 H) 3.45-3.73 (m, 9 H) 3.84-4.04 (m, 3 H) 4.86 (t, J = 9.98 Hz, 1 H) 5.14 (d, J = 10.67 Hz, 1 H) 5.36 (dd, J = 15.00, 9.60 Hz, 1 H) 5.56 (dd, J = 15.00, 9.98 Hz, 1 H) 5.68 (dd, J = 15.06, 7.28 Hz, 1 H) 6.09 (d, J = 11.04 Hz, 1 H) 6.27 (dd, J = 15.12, 10.85 Hz, 1 H) | 620.7 |
| 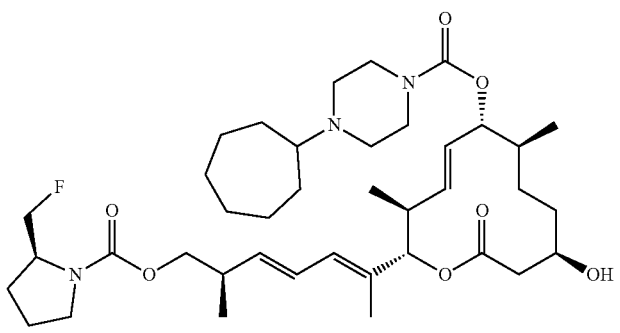<br>110<br>[(2S,3S,4E,6R,7R,10S)-2-[(2E,4E,6R)-7-[(2R)-2-(fluoromethyl)pyrrolidine-1-carbonyl]oxy-6-methylhepta-2,4-dien-2-yl]-10-hydroxy-3,7-dimethyl-12-oxo-1-oxacyclododec-4-en-6-yl] 4-cycloheptylpiperazine-1-carboxylate | ¹H NMR (400 MHz, CHLOROFORM-d) δ: 0.89 (d, J = 6.78 Hz, 3 H) 0.99 (d, J = 6.90 Hz, 3 H) 1.06 (d, J = 6.78 Hz, 3 H) 1.16-1.31 (m, 2 H) 1.38-1.57 (m, 9 H) 1.60-1.70 (m, 3 H) 1.73 (s, 3 H) 1.74-1.95 (m, 5 H) 1.98 (t, J = 5.02 Hz, 2 H) 2.42-2.64 (m, 9 H) 3.32-3.48 (m, 6 H) 3.71 (s, 1 H) 3.99 (br. s., 3 H) 4.17-4.68 (m, 2 H) 4.86 (t, J = 10.04 Hz, 1 H) 5.13 (d, J = 10.67 Hz, 1 H) 5.36 (dd, J = 15.06, 9.66 Hz, 1 H) 5.55 (dd, J = 15.00, 9.85 Hz, 1 H) 5.60-5.73 (m, 1 H) 6.09 (d, J = 10.79 Hz, 1 H) 6.27 (dd, J = 14.81, 10.79 Hz, 1 H) | 704.6 |
| 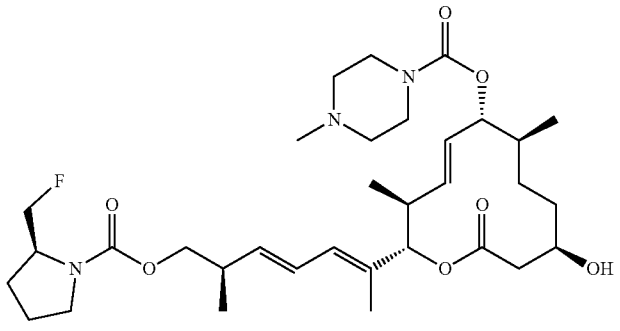<br>111<br>[(2S,3S,4E,6R,7R,10S)-2-[(2E,4E,6R)-7-[(2R)-2-(fluoromethyl)pyrrolidine-1-carbonyl]oxy-6-methylhepta-2,4-dien-2-yl]-10-hydroxy-3,7-dimethyl-12-oxo-1-oxacyclododec-4-en-6-yl] 4-methylpiperazine-1-carboxylate | ¹H NMR (400 MHz, CHLOROFORM-d) δ: 0.89 (d, J = 6.78 Hz, 3 H) 0.99 (d, J = 6.78 Hz, 3 H) 1.06 (d, J = 6.78 Hz, 3 H) 1.15-1.29 (m, 2 H) 1.47 (br. s., 1 H) 1.73 (s, 3 H) 1.78-1.96 (m, 4 H) 1.99 (t, J = 4.89 Hz, 2 H) 2.49 (s, 3 H) 2.49-2.65 (m, 4 H) 2.68 (br. s., 4 H) 3.39 (m, 2 H) 3.63 (br. s., 4 H) 3.66-3.75 (m, 1 H) 3.87-4.08 (m, 3 H) 4.21-4.69 (m, 3 H) 4.86 (t, J = 10.16 Hz, 1 H) 5.14 (d, J = 10.67 Hz, 1 H) 5.35 (dd, J = 15.06, 9.66 Hz, 1 H) 5.56 (dd, J = 14.93, 10.04 Hz, 1 H) 5.67 (m, 1 H) 6.09 (d, J = 10.67 Hz, 1 H) 6.27 (dd, J = 14.81, 10.54 Hz, 1 H) | 622.5 |

TABLE 3-continued

Compounds 105-116

| Structure, Compound #, and Chemical Name | ¹H NMR data | LCMS data (ES+) |
|---|---|---|
| 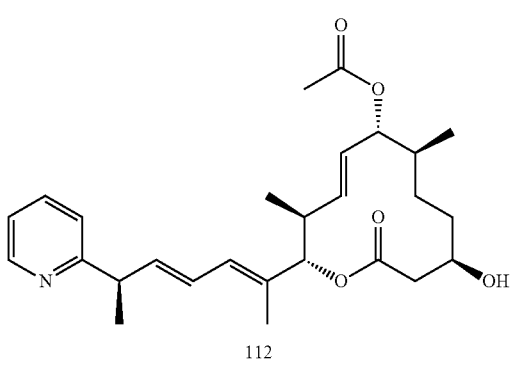 [SMILES: CC(=O)O[C@H]1/C=C/[C@H](C)[C@@H](/C(C)=C/C=C/[C@@H](C)c2ccccn2)OC(=O)C[C@H](O)CC[C@@H]1C]<br>112<br>[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] acetate | ¹H NMR (400 MHz, CHLOROFORM-d) δ: 0.86 (d, J = 6.78 Hz, 3 H) 0.96 (d, J = 6.78 Hz, 3 H) 1.15-1.37 (m, 3 H) 1.45 (d, J = 6.90 Hz, 3 H) 1.74 (s, 3 H) 1.76-1.84 (m, 1H) 1.87-1.96 (m, 1 H) 2.02 (s, 3 H) 2.52 (m, 3 H) 3.41 (d, J = 11.04 Hz, 1 H) 3.69 (m, 2 H) 4.96 (t, J = 10.10 Hz, 1 H) 5.13 (d, J = 10.67 Hz, 1 H) 5.33 (dd, J = 14.93, 9.66 Hz 1 H) 5.54 (dd, J = 14.93, 9.91 Hz , 1 H) 5.99 (dd, J = 14.49, 7.47 Hz, 1 H) 6.11 (d, J = 10.29 Hz, 1 H) 6.34 (m, 1 H) 7.18 (m, 2 H) 7.56-7.66 (m, 1 H) 8.56 (d, J = 4.27 Hz, 1 H) | 455.2 |
| 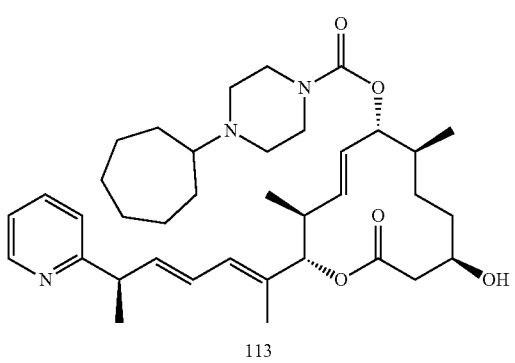 [SMILES: C/C(=C\C=C\[C@@H](C)c1ccccn1)[C@H]1OC(=O)C[C@H](O)CC[C@H](C)[C@@H](OC(=O)N2CCN(C3CCCCCC3)CC2)/C=C/[C@@H]1C]<br>113<br>[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.88 (d, J = 6.78 Hz, 3 H) 0.99 (d, J = 6.78 Hz, 3 H) 1.13-1.33 (m, 3 H) 1.41-1.54 (m, 9 H) 1.44 (d, J = 7.03 Hz, 3 H) 1.68 (m, 2 H) 1.73 (s, 3 H) 1.78 (m, 2 H) 1.83-1.94 (m, 1 H) 2.38-2.61 (m, 8 H) 3.29-3.55 (m, 5 H) 3.64-3.74 (m, 2 H) 4.85 (t, J = 10.04 Hz, 1 H) 5.13 (d, J = 10.67 Hz, 1 H) 5.36 (d, J = 9.66 Hz, 1 H) 5.54 (dd, J = 15.00, 9.98 Hz, 1 H) 6.00 (dd, J = 15.06, 7.53 Hz, 1 H) 6.12 (d, J = 11.04 Hz, 1 H) 6.32 (ddd, J = 15.09, 10.82, 1.07 Hz, 1 H) 7.11 (t, J = 6.17 Hz, 1 H) 7.16 (d, J = 7.78 Hz, 1 H) 7.61 (td, J = 7.69, 1.82 Hz, 1 H) 8.55 (d, J = 4.94 Hz, 1 H) | 622.4 |
| 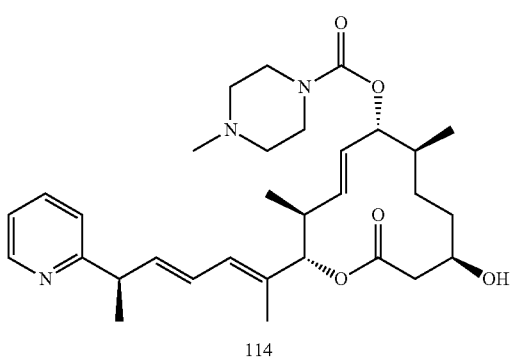 [SMILES: C/C(=C\C=C\[C@@H](C)c1ccccn1)[C@H]1OC(=O)C[C@H](O)CC[C@H](C)[C@@H](OC(=O)N2CCN(C)CC2)/C=C/[C@@H]1C]<br>114<br>[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate | ¹H NMR (400 MHz, CHLOROFORM-d) δ: 0.88 (d, J = 6.78 Hz, 3 H) 0.99 (d, J = 6.90 Hz, 3 H) 1.13-1.33 (m, 2 H) 1.44 (d, J = 6.90 Hz, 3 H) 1.47-1.51 (m, 1 H) 1.73 (d, J = 0.75 Hz, 3 H) 1.74-1.81 (m, 1 H) 1.84-1.97 (m, 1 H) 2.30 (s, 3 H) 2.36 (br. s., 4 H) 2.39-2.61 (m, 3 H) 3.41 (m, 1 H) 3.49 (br. s., 4 H) 3.67-3.74 (m, 2 H) 4.86 (t, J = 10.04 Hz, 1 H) 5.13 (d, J = 10.67 Hz, 1 H) 5.35 (dd, J = 14.93, 9.66 Hz, 1 H) 5.54 (dd, J = 15.06, 9.91 Hz, 1 H) 6.00 (dd, J = 15.12, 7.47 Hz, 1 H) 6.12 (d, J = 10.92 Hz, 1 H) 6.32 (ddd, J = 15.09, 10.82, 1.07 Hz, 1 H) 7.11 (ddd, J = 7.53, 4.89, 1.13 Hz, 1 H) 7.16 (d, J = 7.91 Hz, 1 H) 7.61 (td, J = 7.65, 1.88 Hz, 1 H) 8.55 (d, J = 4.96 Hz, 1 H) | 540.3 |

TABLE 3-continued

Compounds 105-116

| Structure, Compound #, and Chemical Name | $^1$H NMR data | LCMS data (ES+) |
|---|---|---|
| 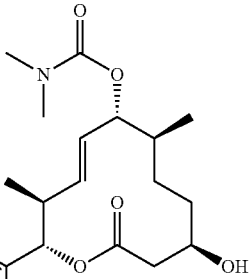<br>115<br>[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] N,N-dimethylcarbamate | $^1$H NMR (400 MHz, CHLOROFORM-d) δ: 0.87 (d, J = 6.78 Hz, 3 H) 0.99 (d, J = 6.90 Hz, 3 H) 1.14-1.35 (m, 2 H) 1.44 (d, J = 7.03 Hz, 3 H) 1.47-1.51 (m, 1 H) 1.73 (d, J = 1.00 Hz, 3 H) 1.76-1.80 (m, 1 H) 1.87-1.96 (m, 1 H) 2.42-2.61 (m, 3 H) 2.88 (s, 6 H) 3.39 (d, J = 10.92 Hz, 1 H) 3.65-3.77 (m, 2 H) 4.83 (t, J = 10.04 Hz, 1 H) 5.13 (d, J = 10.67 Hz, 1 H) 5.35 (dd, J = 15.00, 9.60 Hz, 1 H) 5.54 (dd, J = 14.93, 9.91 Hz, 1 H) 5.99 (dd, J = 15.06, 7.53 Hz, 1 H) 6.11 (d, J = 10.92 Hz, 1 H) 6.33 (dd, J = 14.81, 10.92 Hz, 1 H) 7.09-7.15 (m, 1 H) 7.15-7.21 (m, 1 H) 7.57-7.67 (m, 1 H) 8.55 (d, J = 4.93 Hz, 1 H) | 485.2 |
| 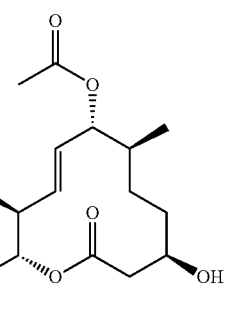<br>116<br>[(2S,3S,4E,6R,7R,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] acetate | $^1$H NMR (400 MHz, METHANOL-d4) δ: ppm 0.86-1.02 (m, 15 H) 1.37 (d, J = 3.51 Hz, 8 H) 1.47-1.55 (m, 2 H) 1.62-1.71 (m, 3 H) 1.79 (s, 3 H) 1.85-1.96 (m, 2 H) 2.02 (s, 3 H) 2.42-2.48 (m, 1 H) 2.55-2.63 (m, 2 H) 2.65-2.76 (m, 1 H) 2.83-2.94 (m, 1 H) 3.50-3.62 (m, 1 H) 3.80 (s, 2 H) 4.89-4.97 (m, 1 H) 5.01-5.09 (m, 1 H) 5.39-5.56 (m, 2 H) 5.82-5.96 (m, 1 H) 6.11-6.20 (m, 1 H) 6.49-6.62 (m, 1 H) | 535.56 |

Compounds 117-134 were prepared by the method of Scheme 5.

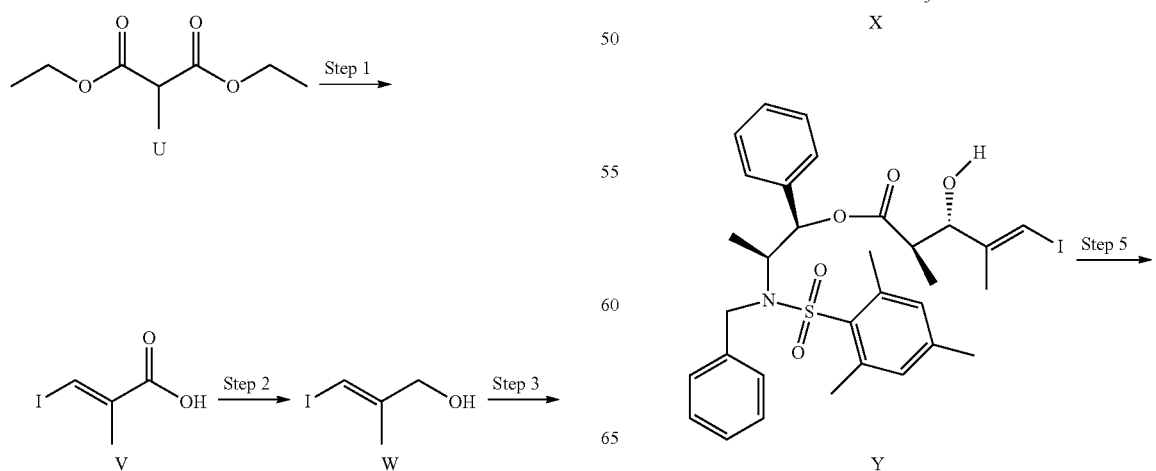

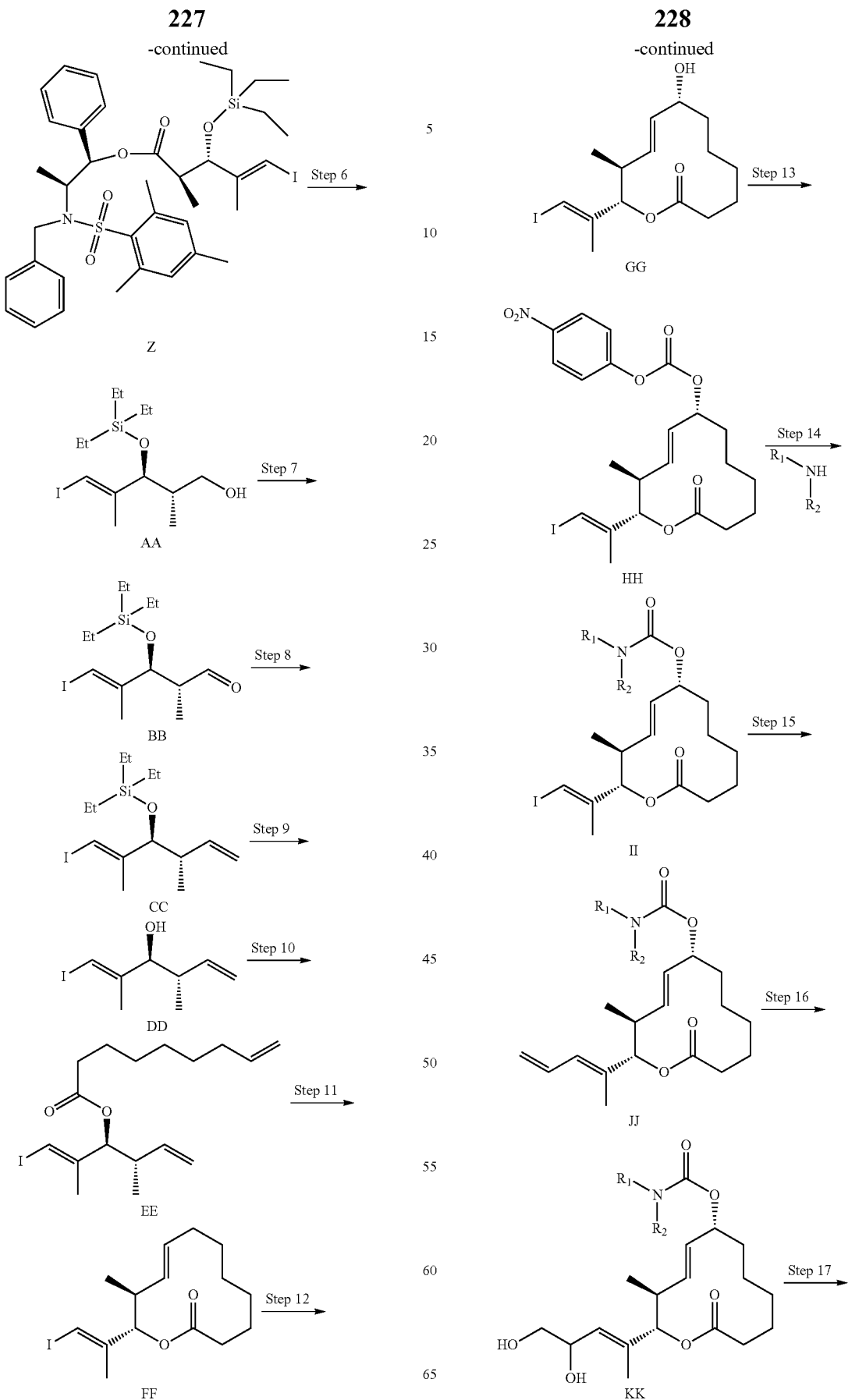

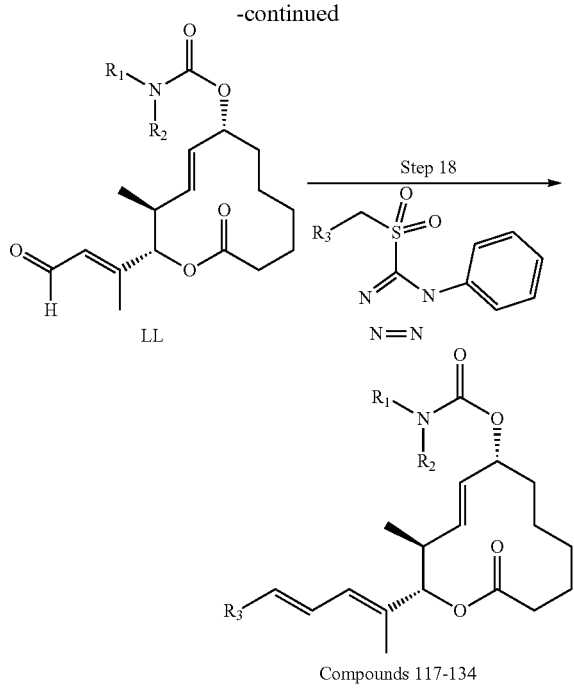

Compounds 117-134

General Protocol for the Synthesis of Compounds 117-134:

Step 1: To a solution of NaH (8.3 g, 207 mmol, 1.2 equiv.) in diethyl ether (400 mL, 0.1M) at 0° C. was added diethyl-2-methylmalonate (U, 30 g, 172 mmol, 1.0 equiv.) dropwise. The reaction was gradually warmed to reflux and stirred at reflux for three hours. The reaction was then cooled to room temperature and iodoform (67.8 g, 172 mmol, 1.0 equiv.) was added dropwise. The reaction was once again heated at reflux for 24 hours, or until the reaction was determined to be complete by LCMS or TLC. The reaction was cooled to 0° C., quenched with 10% aqueous hydrochloric acid, diluted with ether, and washed with water, brine, dried over magnesium sulfate, filtered, and concentrated in vacuo. The resulting oil was then dissolved in ethanol/water/methanol (400 mL, 3:1:1) and KOH (48.3 g, 861 mmol, 5.0 equiv.) was added at room temperature. The solution was then heated to and maintained at 75° C. for 24 hours. The reaction was cooled to room temperature and concentrated in vacuo. The resulting oil was diluted with ethyl acetate and water, extracted into ethyl acetate, dried over magnesium sulfate, filtered, and concentrated in vacuo. The resulting oil was purified by silica gel column chromatography (hexane/ethyl acetate as eluent) to afford the desired product (V, 26 g, 123 mmol, 71%).

Step 2: To a solution of acid V (25.0 g, 118 mmol, 1.0 equiv.) in THF (400 mL, 0.3M) at 0° C. was added lithium aluminum hydride (4.9 g, 130 mmol, 1.1 equiv.). The reaction was gradually warmed to room temperature and stirred for four hours or until the reaction was determined to be complete by LCMS or TLC. The reaction was cooled to 0° C. and quenched with water. The resulting suspension was charged with Rochelle's salt solution (20% by volume) and stirred at room temperature for three hours. The mixture was filtered while washing with ethyl acetate and the volume of the filtrate was reduced in vacuo. Ethyl acetate was added and the organic layer was washed with water, brine, dried over magnesium sulfate, filtered, and concentrated in vacuo. The resulting oil was purified by silica gel column chromatography (hexane/ethyl acetate as eluent) to afford the desired product (W, 15 g, 76 mmol, 64%).

Step 3: To a solution of alcohol W (60 mg, 0.3 mmol, 1.0 equiv.) in diethyl ether (2 mL, 0.1M) at room temperature was added manganese dioxide (395 mg, 4.5 mmol, 15.0 equiv.). The reaction was stirred for two hours or until the reaction was determined to be complete by LCMS or TLC. The reaction was filtered through Celite® and the filtrate was concentrated in vacuo. The crude product (X, 59 mg, 0.30 mmol, 99%) was advanced without purification.

Step 4: To a solution of (1R,2S)-2-(N-benzyl-2,4,6-trimethylphenylsulfonamido)-1-phenylpropyl propionate (1.9 g, 4.4 mmol, 1.0 equiv.), prepared according to literature precedent (Masamune et al. *J. Am. Chem. Soc.* 1997, 119, 2586-2587) in dichloromethane (40 mL, 0.1M) at −78° C. was added triethylamine (1.7 ml, 12.3 mmol, 3.0 equiv.) followed by dropwise addition of dicyclohexyl(((trifluoromethyl)sulfonyl)oxy)borane (2.67 g, 8.0 mmol, 2.0 equiv.). The reaction was stirred at −78° C. for two hours. Next, a solution of (E)-3-iodo-2-methylacrylaldehyde (X, 1.2 g, 6.2 mmol, 1.5 equiv.) in dichloromethane (3 mL) was added dropwise over thirty minutes. The reaction was stirred at −78° C. for two hours and then allowed to warm to 0° C. The reaction was quenched with the addition of aqueous hydrogen peroxide (16 mL, 20.5 mmol) and the reaction was allowed to gradually warm to room temperature. The solvent volume was reduced in vacuo and the solution was diluted with dichloromethane and water. The organic layer was washed with water, brine, dried over magnesium sulfate, filtered, and concentrated in vacuo. The resulting oil was purified by silica gel column chromatography (hexane/ethyl acetate as eluent) to afford the desired product (Y, 1.9 g, 2.8 mmol, 69%).

Step 5: To a solution of alcohol Y (2.8 g, 4.1 mmol, 1.0 equiv.) in dichloromethane (50 mL, 0.1M) at −78° C. was added 2,6-lutidine (1.0 mL, 8.3 mmol, 2.0 equiv.) followed by tert-butyldimethylsilyl trifluoromethanesulfonate (1.1 mL, 4.9 mL, 1.2 equiv.). The reaction was gradually warmed to room temperature and quenched with aqueous ammonium chloride. Ethyl acetate was added and the organic layer was washed with water, brine, dried over magnesium sulfate, filtered, and concentrated in vacuo. The resulting oil was purified by silica gel column chromatography (hexane/ethyl acetate as eluent) to afford the desired product (Z, 2.8 g, 3.5 mmol, 85%).

Step 6: To a solution of ester Z (2.8 g, 3.5 mmol, 1.0 equiv.) in dichloromethane (40 mL, 0.1M) at 0° C. was added DIBAL (8.9 mL, 8.9 mmol, 2.5 equiv.). The reaction was stirred for one hour and then quenched with Rochelle's salt solution (20% by volume) and stirred at room temperature for three hours. The mixture was filtered through Celite® while washing with ethyl acetate and the volume of the filtrate was reduced in vacuo. Ethyl acetate was added and the organic layer was washed with water, brine, dried over magnesium sulfate, filtered, and concentrated in vacuo. The resulting oil was purified by silica gel column chromatography (hexane/ethyl acetate as eluent) to afford the desired product (AA, 1.1 g. 2.8 mmol, 80%).

Step 7: To a solution of alcohol AA (2.97 g, 8.0 mmol, 1.0 equiv.) in dichloromethane (80 mL, 0.1M) at 0° C. was added Dess-Martin periodinane (4.4 g, 10.4 mmol, 1.3 equiv.). The reaction was stirred for two hours or until the reaction was determined to be complete by LCMS or TLC. The reaction was concentrated in vacuo and the resulting oil was purified by silica gel column chromatography (hexane/ethyl acetate as eluent) to afford the desired product (BB, 2.6 g, 7.1 mmol, 88%).

Step 8: To a solution of methyltriphenylphosphonium bromide (11.8 g, 33.0 mmol, 3.0 equiv.) in THF (110 mL, 0.1M) at 0° C. was added n-butyl lithium (13.2 mL, 33.0 mmol, 3.0 equiv.). The reaction was stirred for 30 minutes and then cooled to −78° C. Aldehyde BB (4.1, 11.0 mmol, 1.0 equiv.) in THF (0.5 M) was added dropwise and the reaction was stirred for one hour. The reaction was quenched with ammonium chloride and warmed to room temperature. Ethyl acetate was added and the organic layer was washed with water, brine, dried over magnesium sulfate, filtered, and concentrated in vacuo. The resulting oil was purified by silica gel column chromatography (hexane/ethyl acetate as eluent) to afford the desired product (CC, 3.8 g, 10.4 mmol, 94%).

Step 9: To a solution of olefin CC (0.1 g, 0.4 mmol, 1.0 equiv.) in THF (4 mL, 0.1M) at 0° C. was added TBAF (0.45 mL, 0.4 mmol, 1.1 equiv.). The reaction was stirred for 30 minutes or until the reaction was determined to be complete by LCMS or TLC. Diethyl ether was added and the organic layer was washed with water, brine, dried over magnesium sulfate, filtered, and concentrated in vacuo. The crude product (DD, 0.1 g, 0.4 mmol, 99%) was advanced without purification.

Step 10: To a solution of alcohol DD (0.15 g, 0.4 mmol, 1.0 equiv.) in dichloromethane (4 mL, 0.1M) at 0° C. was added EDC (0.10 g, 0.5 mmol, 1.3 equiv.) followed by nonenoic acid (0.08 g, 0.4 mmol, 1.1 equiv.) and DMAP (catalytic). The reaction was gradually warmed to room temperature and stirred overnight. Ethyl acetate was added and the organic layer was washed with water, brine, dried over magnesium sulfate, filtered, and concentrated in vacuo. The resulting oil was purified by silica gel column chromatography (hexane/ethyl acetate as eluent) to afford the desired product (EE, 0.13 g, 0.33 mmol, 81%).

Step 11: To a solution of ester EE (0.5 g, 1.3 mmol, 1.0 equiv.) in degassed toluene (65 mL, 0.05M) at room temperature was added benzoquinone (0.007 g, 0.06 mmol, 0.05 equiv.) followed by Hoyveda-Grubbs catalyst (0.08 g, 0.13, 0.1 equiv.). The reaction was gradually warmed to 60° C. and stirred overnight. Once determined to be complete by TLC or LCMS, the reaction was concentrated. The crude material (FF) was used in the following step without further purification Step 12: To a solution of macrocycle FF (1.0 equiv.) in dioxane (65 mL, 0.05M) was added selenium dioxide (0.4 g, 3.8 mmol, 3.0 equiv.) at room temperature. The reaction was heated to 80° C. for 3 hours. Ethyl acetate was added, and the organic layer was washed with water and saturated sodium bicarbonate, dried over magnesium sulfate, filtered, and concentrated in vacuo. The resulting oil was purified by silica gel column chromatography (hexane/ethyl acetate as eluent) to afford the desired product (GG, 0.3 g, 0.8 mmol, 64%).

Step 13: To a solution of alcohol GG (1.0 equiv.) in MTBE (0.1M) at room temperature was added triethylamine (5.0 equiv.), para-nitrophenylchloroformate (3.0 equiv.), DMAP (catalytic) and the reaction was stirred overnight. Once determined to be complete by TLC or LCMS, the reaction was quenched with water. Ethyl acetate was added and the organic layer was washed with water, saturated sodium bicarbonate, dried over magnesium sulfate, filtered, and concentrated in vacuo. The crude product (HH) was advanced without purification.

Step 14: To a solution of carbonate HH (1.0 equiv.) in MTBE (0.1M) at room temperature was added the corresponding amine (2.0 equiv.). Once determined to be complete by TLC or LCMS, the reaction was concentrated and the resulting oil was purified by silica gel column chromatography (hexane/ethyl acetate as eluent) to afford the desired product (II).

Step 15: To a solution of vinyl iodide II (1.0 equiv.) in THF (0.1M) at room temperature was added vinyl pinacol boronate (2.5 equiv.), silver oxide (5.0 equiv.), triphenylarsine (1.2 equiv.), and $Pd_2(dba)_3$ (0.15 equiv.). The reaction was stirred at room temperature overnight. Once determined to be complete by TLC or LCMS, the reaction was filtered through Celite®. Dichloromethane was added and the organic layer was washed with water and saturated sodium bicarbonate, dried over magnesium sulfate, filtered, and concentrated in vacuo. The resulting oil was purified by silica gel column chromatography (dichloromethane/methanol as eluent) to afford the desired product (JJ).

Step 16: To a solution of diene JJ (1.0 equiv.) in $THF:H_2O$ (0.1M) at 0° C. was added N-methylmorpholine N-oxide (1.2 equiv.) and osmium tetroxide in t-BuOH (0.1 equiv.). The reaction was stirred at room temperature overnight. Once determined to be complete by TLC or LCMS, the reaction was quenched by addition of aqueous sodium bicarbonate. Ethyl acetate was added and the organic layer was washed with water, saturated sodium bicarbonate, dried over magnesium sulfate, filtered, and concentrated in vacuo. The crude material (KK) was advanced without further purification.

Step 17: To a solution of diol KK (1.0 equiv.) in benzene (0.1M) at room temperature was added lead tetraacetate (1.2 equiv.). The reaction was stirred at room temperature for 40 minutes or until determined to be complete by TLC or LCMS. The reaction was quenched by addition of $Na_2S_2O_3$ and then sodium bicarbonate. Dichloromethane was added, and the organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (LL).

Step 18: To a solution of the corresponding sulfone (2.5 equiv.) in THF (0.1M) at −78° C. was added KHMDS (2.5 equiv.) and the reaction was stirred at −78° C. for one hour. Next, a solution of aldehyde LL in THF (1.0 equiv.) was added dropwise at −78° C. The reaction was allowed to warm gradually to −20° C. and stirred at −20° C. for two hours. The reaction was quenched with aqueous sodium bicarbonate and ethyl acetate was added. The organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (117-134).

Exemplified Protocol for the Synthesis of Compound 128

Steps 1-12 as above.

Step 13: To a solution of alcohol GG (0.30 g, 0.8 mmol, 1.0 equiv.) in MTBE (3.0 mL, 0.1M) at room temperature was added triethylamine (0.55 mL, 4.0 mmol, 5.0 equiv.), para-nitrophenyl chloroformate (0.24 g, 1.2 mmol, 2.0 equiv.), and DMAP (0.12 g, 0.9 mmol, 1.2 equiv.) and the reaction was stirred overnight. Once determined to be complete by TLC or LCMS, the reaction was quenched with water. Ethyl acetate was added and the organic layer was washed with water, saturated sodium bicarbonate, dried over magnesium sulfate, filtered, and concentrated in vacuo. The crude product (HH) was advanced without purification.

Step 14: To a solution of carbonate HH (1.0 equiv.) in MTBE (0.1M) at room temperature was added N-methylpiperazine (0.13 mL, 1.2 mmol, 1.5 equiv.). Once determined to be complete by TLC or LCMS, the reaction was concentrated and the resulting oil was purified by silica gel column chromatography (hexane/ethyl acetate as eluent) to afford the desired product (II, 0.30 g, 0.5 mmol, 67.5%).

Step 15: To a solution of vinyl iodide II (0.15 g, 0.30 mmol, 1.0 equiv.) in THF (3.0 mL, 0.1M) at room temperature was added vinyl pinacol boronate (0.13 mL, 0.30 mmol, 2.5 equiv.), silver oxide (0.35 g, 1.50 mmol, 5.0 equiv.), triphenylarsine (0.11 g, 0.36 mmol, 1.2 equiv.), and $Pd_2(dba)_3$ (0.04 g, 0.04 mmol, 0.15 equiv.). The reaction was stirred at room temperature overnight. Once determined to be complete by TLC or LCMS, the reaction was filtered through Celite®. Dichloromethane was added and the organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (JJ, 0.12 g, 0.3 mmol, 96%).

Step 16: To a solution of diene JJ (0.12 g, 0.3 mmol, 1.0 equiv.) in $THF:H_2O$ (4 mL:0.4 mL, 0.1M) at 0° C. was added N-methylmorpholine N-oxide (0.04 g, 0.35 mmol, 1.2 equiv.) and osmium tetroxide in t-BuOH (0.37 mL, 0.03 mmol, 0.1 equiv.). The reaction was stirred at room temperature overnight. Once determined to be complete by TLC or LCMS, the reaction was quenched by addition of aqueous sodium bicarbonate. Ethyl acetate was added and the organic layer was washed with water, saturated sodium bicarbonate, dried over magnesium sulfate, filtered, and concentrated in vacuo. The crude material (JJ, 0.13 g, 0.3 mmol, 100%) was advanced without further purification.

Step 17: To a solution of diol KK (0.10 g, 0.23 mmol, 1.0 equiv.) in acetone (3.0 mL, 0.1M) at room temperature was added diacetoxyiodobenzene (0.12 g, 0.27 mmol, 1.2 equiv.). The reaction was stirred at room temperature for 40 minutes or until determined to be complete by TLC or LCMS. The reaction was quenched by addition of $Na_2S_2O_3$ and then sodium bicarbonate. Dichloromethane was added, and the organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (LL, 0.05 g, 0.11 mmol, 49%).

Step 18: To a solution of (S)-2-(1-((1-phenyl-1H-tetrazol-5-yl)sulfonyl)propan-2-yl)pyridine (0.08 g, 0.25 mmol, 2.5 equiv.) in THF (0.6 mL, 0.1M) at −78° C. was added KHMDS (0.50 mL, 0.25 mmol, 2.5 equiv.) and the reaction was stirred at −78° C. for one hour. Next, a solution of aldehyde LL (0.04 g, 0.1 mmol, 1.0 equiv.) in THF (0.1 mL.) was added dropwise at −78° C. The reaction was allowed to warm gradually to −20° C. and stirred at −20° C. for two hours. The reaction was quenched with aqueous sodium bicarbonate and ethyl acetate was added. The organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (compound 128, 0.03 g, 0.06 mmol, 60%). $^1$H NMR (400 MHz, CHLOROFORM-d) δ: 0.87 (d, J=6.76 Hz, 3H) 1.25 (br. s, 4H) 1.43 (d, J=6.8 Hz, 3H) 1.60 (br. s., 4H) 1.76-1.85 (m, 3H) 2.22 (m, 1H) 2.31 (br. s, 4H), 2.37 (br. s, 4H) 2.45-2.53 (m, 1H) 3.48 (br. s., 4H) 3.70 (m, 1H) 4.99-5.12 (m, 2H) 5.36 (m, 1H) 5.43-5.51 (m, 1H) 5.98 (dd, J=15.06, 7.53 Hz, 1H) 6.13 (d, J=11.17 Hz, 1H) 6.32 (ddd, J=15.06, 10.92, 1.13 Hz, 1H) 7.11 (t, J=6.14 Hz, 1H) 7.16 (d, J=8.08 Hz, 1H) 7.61 (td, J=7.69, 1.82 Hz, 1H) 8.54 (d, J=4.96 Hz, 1H). MS (ES+)=510.1 $[M+H]^+$.

TABLE 4

Compounds 117-134

| Structure, Compound #, and Chemical Name | $^1$H NMR data | LCMS data (ES+) |
|---|---|---|
| 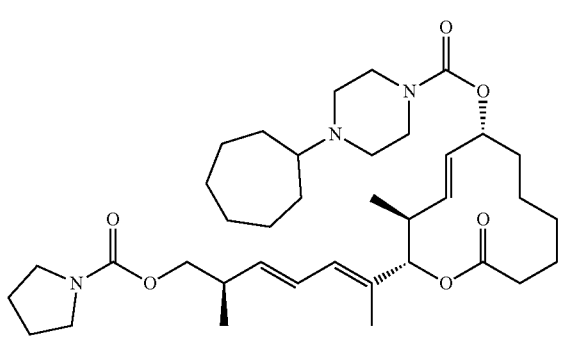<br>117<br>[(2S,3S,4E,6R)-3-methyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate | $^1$H NMR (400 MHz, CHLOROFORM-d) δ: 0.84 (d, J = 6.78 Hz, 3 H) 1.00 (d, J = 6.78 Hz, 3 H) 1.20 (d, J = 2.76 Hz, 3 H) 1.37-1.60 (m, 12 H) 1.62-1.72 (m, 6 H) 1.72-1.84 (m, 7 H) 1.89-2.33 (m, 19 H) 2.38-2.61 (m, 3 H) 2.74 (br. s., 4 H) 2.90-3.02 (m, 1 H) 3.30 (m, J = 6.02, 6.02 Hz, 4 H) 3.56-3.67 (m, 3 H) 3.90 (qd, J = 10.35, 6.71 Hz, 2 H) 4.91-5.08 (m, 2 H) 5.25-5.36 (m, 1 H) 5.38-5.47 (m, 1 H) 5.62 (dd, J = 15.12, 7.47 Hz, 1 H) 6.04 (dd, J = 10.79, 1.00 Hz, 1 H) 6.21 (ddd, J = 15.31, 10.79, 1.00 Hz, 1 H) | 642.4 |

TABLE 4-continued

Compounds 117-134

| Structure, Compound #, and Chemical Name | ¹H NMR data | LCMS data (ES+) |
|---|---|---|
| 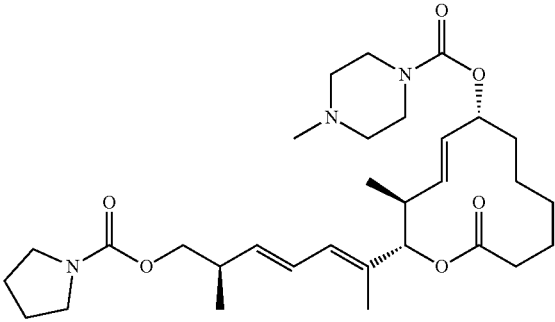

118

[(2S,3S,4E,6R)-3-methyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.89 (d, J = 6.8 Hz, 3 H) 1.06 (d, J = 6.8 Hz, 3 H) 1.06 (d, J = 6.8 Hz, 3 H) 1.18-1.36 (m, 4 H) 1.41-1.67 (m, 4 H) 1.73 (m, 3 H) 1.84 (m, 6 H) 2.12-2.27 (m, 1 H) 2.32 (br. s, 4 H) 2.38 (br. s, 4H) 2.43-2.63 (m, 2 H) 3.26-3.44 (m, 4 H) 3.49 (br. s., 4 H) 3.91-4.01 (m, 2 H) 4.12 (d, J = 7.15 Hz, 1 H) 5.02 (d, J = 10.6 Hz, 1H) 5.06-5.13 (m, 1 H) 5.37 (dd, J = 14.93, 9.41 Hz, 1 H) 5.48 (dd, J = 15.06, 9.66 Hz, 1 H) 5.67 (dd, J = 15.12, 7.47 Hz, 1 H) 6.10 (d, J = 10.79 Hz, 1 H) 6.23-6.31 (m, 1 H) | 560.4 |
| 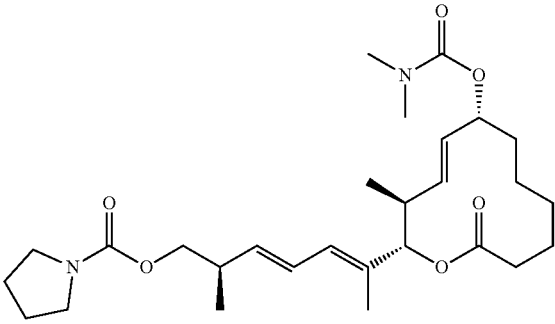

119

[(2R,3E,5E)-6-[(2S,3S,4E,6R)-6-(dimethylcarbamoyloxy)-3-methyl-12-oxo-1-oxacyclododec-4-en-2-yl]-2-methylhepta-3,5-dienyl] pyrrolidine-1-carboxylate | ¹H NMR (400 MHz, CHLOROFORM-d) δ: 0.88 (d, J = 6.76 Hz, 3 H) 1.06 (d, J = 6.8 Hz, 3 H) 1.25 (m, 4 H) 1.45-1.63 (m, 4 H) 1.73 (s, 3 H) 1.79-1.89 (m, 6 H) 2.18-2.25 (m, 1 H) 2.29-2.37 (m, 1 H) 2.45-2.63 (m, 2 H) 2.87 (s, 6 H) 3.36 (br. s., 4 H) 3.91-4.00 (m, 2 H) 5.00 -5.11 (m, 2 H) 5.34-5.51 (m, 2 H) 5.67 (dd, J = 15.12, 7.34 Hz, 1 H) 6.10 (d, J = 10.92 Hz, 1 H) 6.23-6.31 (m, 1 H) | 505.5, 527.4 |
| 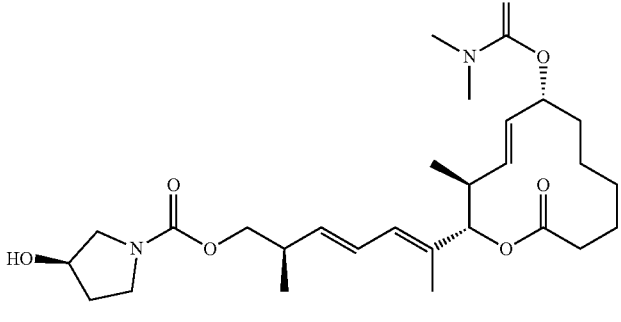

120

[(2R,3E,5E)-6-[(2S,3S,4E,6R)-6-(dimethylcarbamoyloxy)-3-methyl-12-oxo-1-oxacyclododec-4-en-2-yl]-2-methylhepta-3,5-dienyl] (3R)-3-hydroxypyrrolidine-1-carboxylate | ¹H NMR (400 MHz, CHLOROFORM-d) δ: 0.89 (d, J = 6.78 Hz, 3 H) 1.08 (d, J = 6.8 Hz, 3 H) 1.14 (s, 1 H) 1.20-1.33 (m, 4 H) 1.46-1.63 (m, 4 H) 1.73 (s, 3 H) 1.77-1.90 (m, 2 H) 1.90-2.04 (m, 2 H) 2.24-2.26 (m, 1 H) 2.29-2.38 (m, 1 H) 2.46-2.64 (m, 2 H) 2.87 (s, 6 H) 3.52 (br. s., 4 H) 3.92-4.02 (m, 2 H) 4.43-4.50 (m, 1 H) 4.98-5.11 (m, 2 H) 5.35-5.51 (m, 2 H) 5.67 (dd, J = 15.18, 7.65 Hz, 1 H) 6.10 (d, J = 11.04 Hz, 1 H) 6.23-6.31 (m, 1 H) | 543.3 |

TABLE 4-continued

Compounds 117-134

| Structure, Compound #, and Chemical Name | ¹H NMR data | LCMS data (ES+) |
|---|---|---|
| 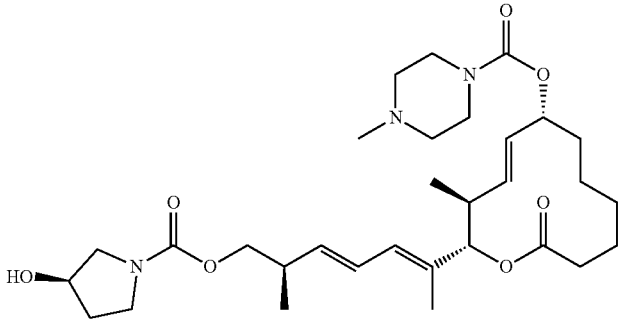<br>121<br>[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-oxacyclododec-4-en-6-yl] 4-methylpiperazine-1-carboxylate | ¹H NMR (400 MHz, CHLOROFORM-d) δ: 0.89 (d, J = 6.76 Hz, 2 H) 1.06 (d, J = 6.8 Hz, 2 H) 1.19-1.33 (m, 4 H) 1.41 (br. s., 1 H) 1.47-1.56 (m, 4 H) 1.61 (br. s., 2 H) 1.73 (s, 3 H) 1.79-1.87 (m, 2 H) 1.87-2.04 (m, 2 H) 2.22-2.24 (m, 1 H) 2.33 (br. s, 4H), 2.39 (br. s, 4 H) 2.47-2.53 (m, 1 H) 2.56-2.63 (m, 1 H) 3.41-3.57 (m, 8 H) 3.91-4.02 (m, 2 H) 4.45-4.49 (m, 1 H) 4.98-5.13 (m, 2 H) 5.37 (dd, J = 15.06, 9.41 Hz, 1 H) 5.48 (dd, J = 15.00, 9.60 Hz, 1 H) 5.67 (dd, J = 15.12, 7.22 Hz, 1 H) 6.10 (d, J = 11.29 Hz, 1 H) 6.23-6.31 (m, 1 H) | 576.4 |
| 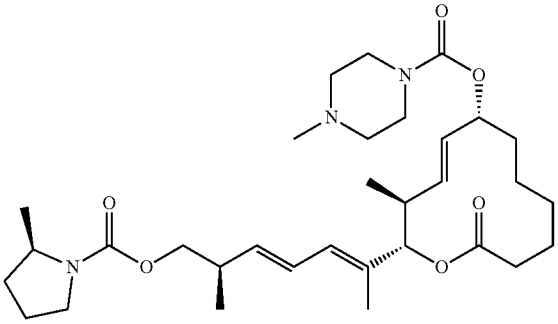<br>122<br>[(2S,3S,4E,6R)-3-methyl-2-[(2E,4E,6R)-6-methyl-7-[(2S)-2-methylpyrrolidine-1-carbonyl]oxyhepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.88 (d, J = 6.72 Hz, 2 H) 1.06 (d, J = 6.76 Hz, 2 H) 1.14 (br. s., 2 H) 1.19 (br. s, 2 H) 1.26 (br. s., 4 H) 1.47 (br. s, 1 H) 1.54 (s, 3 H) 1.57 (br. s, 4 H) 1.72 (s, 3 H) 1.76-1.91 (m, 4 H) 1.93-2.03 (m, 1 H) 2.2-2.4 (m, 1 H) 2.31 (br. s, 4 H) 2.38 (br. s., 4 H) 2.41-2.63 (m, 2 H) 3.40 (br. s., 2 H) 3.49 (br. s., 4 H) 3.86-4.04 (m, 3 H) 5.02 (d, J = 10.68 Hz, 1H) 5.06-5.13 (m, 1 H) 5.34-5.42 (m, 1 H) 5.44-5.52 (m, 1 H) 5.66 (dd, J = 15.00, 7.97 Hz, 1 H) 6.10 (d, J = 11.04 Hz, 1 H) 6.27 (dd, J = 14.81, 11.04 Hz, 1 H) | 574.6 |
| 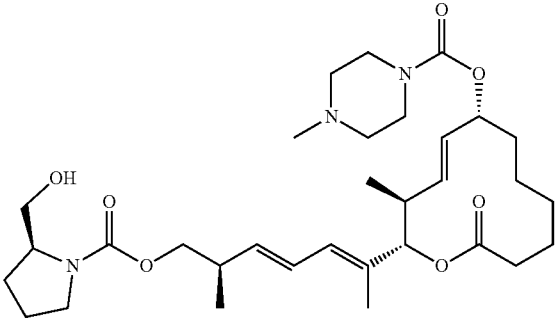<br>123<br>[(2S,3S,4E,6R)-2-[(2E,4E,6R)-7-[(2R)-2-(hydroxymethyl)pyrrolidine-1-carbonyl]oxy-6-methylhepta-2,4-dien-2-yl]-3-methyl-12-oxo-1-oxacyclododec-4-en-6-yl] 4-methylpiperazine-1-carboxylate | ¹H NMR (400 MHz, CHLOROFORM-d) δ: 0.88 (d, J = 6.76 Hz, 3 H) 1.06 (d, J = 6.8 Hz, 3 H) 1.25 (m, 4 H) 1.43-1.67 (m, 4 H) 1.73 (s, 3 H) 1.77-1.89 (m, 3 H) 1.96-2.03 (m, 1 H) 2.22-2.25 (m, 1 H) 2.31 (br. s, 4H) 2.37 (br. s, 4 H) 2.47-2.53 (m, 1H) 2.58-2.64 (m, 1H) 3.32-3.42 (m, 1 H) 3.44-3.69 (m, 5 H) 2.58-3.66 (m, 2H) 3.92-4.03 (m, 3 H) 5.02 (d, J = 10.68 Hz, 1H), 5.06-5.13 (m, 1 H) 5.30-5.51 (m, 2 H) 5.66 (dd, J = 15.18, 7.53 Hz, 1 H) 6.10 (d, J = 10.92 Hz, 1 H) 6.27 (dd, J = 15.12, 10.85 Hz, 1 H) | 590.5 |

TABLE 4-continued

Compounds 117-134

| Structure, Compound #, and Chemical Name | ¹H NMR data | LCMS data (ES+) |
|---|---|---|
| 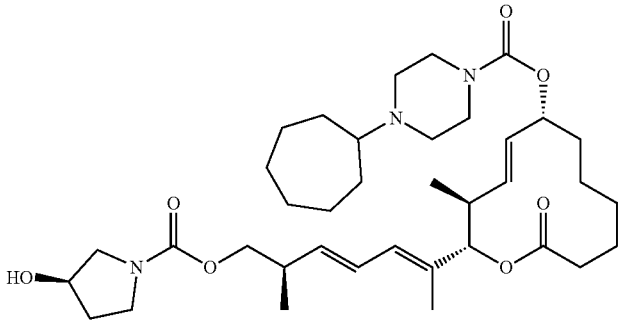<br>124<br>[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-oxacyclododec-4-en-6-yl] 4-cycloheptylpiperazine-1-carboxylate | ¹H NMR (400 MHz, CHLOROFORM-d) δ: 0.89 (d, J = 6.76 Hz, 3 H) 1.06 (d, J = 6.8 Hz, 3 H) 1.26 (br. s, 4 H) 1.38-1.63 (m, 13 H) 1.64-1.77 (m, 6 H) 1.80 (m, 2 H) 1.88-2.05 (m, 2 H) 2.17-2.26 (m, 1 H) 2.28-2.40 (m, 1 H) 2.42-2.63 (m, 6 H) 3.33-3.56 (m, 8 H) 3.84-4.03 (m, 2 H) 4.48 (br. s, 1 H) 4.97-5.12 (m, 3 H) 5.31-5.51 (m, 2 H) 5.67 (dd, J = 15.06, 7.03 Hz, 1 H) 6.09 (d, J = 10.79 Hz, 1 H) 6.17-6.38 (m, 1 H) | 658.5 |
| 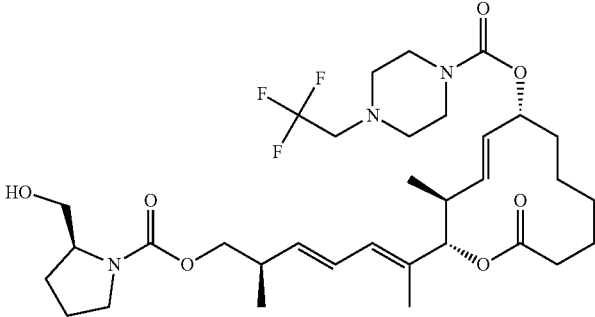<br>125<br>[(2S,3S,4E,6R)-2-[(2E,4E,6R)-7-[(2R)-2-(hydroxymethyl)pyrrolidine-1-carbonyl]oxy-6-methylhepta-2,4-dien-2-yl]-3-methyl-12-oxo-1-oxacyclododec-4-en-6-yl] 4-(2,2,2-trifluoroethyl)piperazine-1-carboxylate | ¹H NMR (400 MHz, CHLOROFORM-d) δ: 6.12-6.31 (m, 1H), 6.04 (m, 1H), 5.59 (dd, J = 15.1, 7.5 Hz, 1H), 5.36-5.46 (m, 1H), 5.23-5.36 (m, 1H), 4.90-5.08 (m, 2H), 4.31 (d, J = 5.3 Hz, 1H), 3.84-3.99 (m, 3H), 3.81 (br. s., 1H), 3.69-3.78 (m, 1H), 3.50-3.66 (m, 2H), 3.36-3.47 (m, 4H), 3.17-3.35 (m, 1H), 2.91 (q, J = 9.5 Hz, 2H), 2.40-2.60 (m, 5H), 2.08-2.35 (m, 2H), 1.86-2.02 (m, 1H), 1.64-1.82 (m, 6H), 1.38-1.64 (m, 6H), 0.94-1.08 (m, 3H), 0.82 (d, J = 6.8 Hz, 3H) | 658.8 |
| 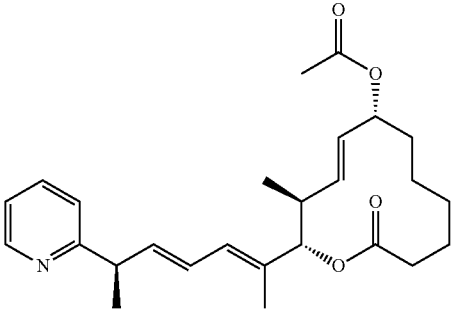<br>126<br>[(2S,3S,4E,6R)-3-methyl-12-oxo-2-[(2E,4E,6S)-6-pyridin-2-ylhepta-2,4-dien-2-yl]-1-oxacyclododec-4-en-6-yl] acetate | ¹H NMR (400 MHz, CHLOROFORM-d) δ: 0.86 (d, J = 6.78 Hz, 3 H) 1.21-1.31 (m, 4 H) 1.44 (d, J = 7.03 Hz, 3 H) 1.47-1.60 (m, 2 H) 1.73 (d, J = 1.00 Hz, 3 H) 1.76-1.91 (m, 2 H) 2.00 (s, 3 H) 2.22 (dt, J = 13.87, 4.80 Hz, 1 H) 2.33 (ddd, J = 13.77, 11.95, 4.14 Hz, 1 H) 2.43-2.54 (m, 1 H) 3.70 (quin, J = 6.93 Hz, 1 H) 5.02 (d, J = 10.67 Hz, 1 H) 5.17 (td, J = 10.07, 4.96 Hz, 1 H) 5.35 (dd, J = 14.93, 9.54 Hz, 1 H) 5.48 (dd, J = 14.93, 9.66 Hz, 1 H) 5.98 (dd, J = 15.12, 7.59 Hz, 1 H) 6.12 (d, J = 10.92 Hz, 1 H) 6.32 (ddd, J = 15.09, 10.82, 1.07 Hz, 1 H) 7.11 (ddd, J = 7.53, 4.89, 1.13 Hz, 1 H) 7.16 (d, J = 7.91 Hz, 1 H) 7.61 (td, J = 7.69, 1.82 Hz, 1 H) 8.55 (d, J = 4.88 Hz, 1 H) | 426.1 |

TABLE 4-continued

Compounds 117-134

| Structure, Compound #, and Chemical Name | ¹H NMR data | LCMS data (ES+) |
|---|---|---|
| 127<br><br>[(2S,3S,4E,6R)-3-methyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.87 (d, J = 6.90 Hz, 4 H) 1.20-1.33 (m, 10 H) 1.44 (d, J = 7.03 Hz, 3 H) 1.46-1.69 (m, 10 H) 1.73 (s, 3 H) 1.79 (m, 4 H) 2.17-2.25 (m, 1 H) 2.27-2.39 (m, 1 H) 2.47 (m, 5 H) 3.07-3.27 (m, 1 H) 3.43 (br. s., 4 H) 3.70 (quin, J = 7.03 Hz, 1 H) 4.99-5.03 (m, 1 H) 5.08 (td, J = 9.82, 4.45 Hz, 1 H) 5.32-5.40 (m, 1 H) 5.42-5.51 (m, 1 H) 5.97 (dd, J = 15.06, 7.40 Hz, 1 H) 6.12 (d, J = 11.42 Hz, 1 H) 6.28-6.36 (m, 1 H) 7.11 (ddd, J = 7.53, 4.89, 1.13 Hz, 1 H) 7.16 (d, J = 7.91 Hz, 1 H) 7.61 (t, J = 7.65 Hz, 1 H) 8.54 (d, J = 4.88 Hz, 1 H) | 592.3 |
| 128<br><br>[(2S,3S,4E,6R)-3-methyl-12-oxo-2-[(2E,4E,6S)-6-pyridin-2-ylhepta-2,4-dien-2-yl]-1-oxacyclododec-4-en-6-yl] 4-methylpiperazine-1-carboxylate | ¹H NMR (400 MHz, CHLOROFORM-d) δ: 0.87 (d, J = 6.76 Hz, 3 H) 1.25 (br. s, 4H) 1.43 (d, J = 6.8 Hz, 3 H) 1.60 (br. s., 4 H) 1.76-1.85 (m, 3 H) 2.22 (m, 1 H) 2.31 (br. s, 4H) 2.37 (br. s, 4H) 2.45-2.53 (m, 1H) 3.48 (br. s., 4 H) 3.70 (m, 1 H) 4.99-5.12 (m, 2 H) 5.36 (m, 1 H) 5.43-5.51 (m, 1 H) 5.98 (dd, J = 15.06, 7.53 Hz, 1 H) 6.13 (d, J = 11.17 Hz, 1 H) 6.32 (ddd, J = 15.06, 10.92, 1.13 Hz, 1 H) 7.11 (t, J = 6.14 Hz, 1 H) 7.16 (d, J = 8.08 Hz, 1 H) 7.61 (td, J = 7.69, 1.82 Hz, 1 H) 8.54 (d, J = 4.96 Hz, 1 H) | 510.1 |
| 129<br><br>[(2S,3S,4E,6R)-3-methyl-12-oxo-2-[(2E,4E,6S)-6-pyridin-2-ylhepta-2,4-dien-2-yl]-1-oxacyclododec-4-en-6-yl] N,N-dimethylcarbamate | ¹H NMR (400 MHz, CHLOROFORM-d) δ: 0.87 (d, J = 6.76 Hz, 3 H) 1.25 (br. s, 4H) 1.43 (d, J = 6.8 Hz, 3H) 1.46-1.64 (m, 2 H) 1.73 (s, 3H) 1.76-1.86 (m, 2 H) 2.21 (m, 1 H) 2.27-2.37 (m, 1 H) 2.43-2.54 (m, 1 H) 2.87 (s, 6 H) 3.71 (t, J = 7.03 Hz, 1 H) 4.99-5.10 (m, 2 H) 5.34-5.50 (m, 2 H) 5.97 (dd, J = 15.06, 7.53 Hz, 1 H) 6.12 (d, J = 10.92 Hz, 1 H) 6.32 (dd, J = 15.18, 10.79 Hz, 1 H) 7.11 (t, J = 6.13 Hz, 1 H) 7.17 (d, J = 7.52 Hz, 1 H) 7.61 (t, J = 7.25 Hz, 1 H) 8.54 (d, J = 4.96 Hz, 1 H) | 455.2 |

TABLE 4-continued

Compounds 117-134

| Structure, Compound #, and Chemical Name | ¹H NMR data | LCMS data (ES+) |
|---|---|---|
| 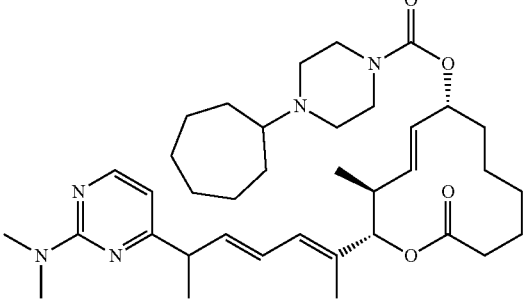<br>130<br>[(2S,3S,4E,6R)-2-[(2E,4E)-6-[2-(dimethylamino)pyrimidin-4-yl]hepta-2,4-dien-2-yl]-3-methyl-12-oxo-1-oxacyclododec-4-en-6-yl] 4-cycloheptylpiperazine-1-carboxylate | | 636.9 |
| 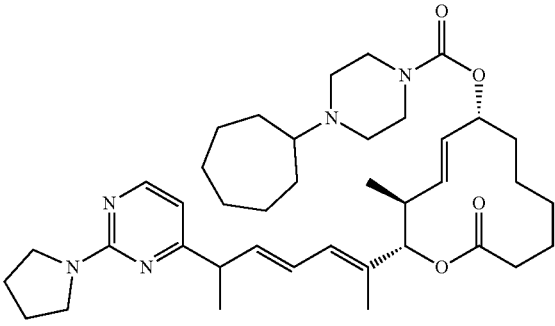<br>131<br>[(2S,3S,4E,6R)-3-methyl-12-oxo-2-[(2E,4E)-6-(2-pyrrolidin-1-ylpyrimidin-4-yl)hepta-2,4-dien-2-yl]-1-oxacyclododec-4-en-6-yl] 4-cycloheptylpiperazine-1-carboxylate | ¹H NMR (400 MHz, CHLOROFORM-d) δ: 8.15-8.34 (m, 1H), 7.39 (s, 1H), 6.23-6.42 (m, 2H), 6.14 (d, J = 11.3 Hz, 1H), 5.97 (ddd, J = 15.1, 7.8, 3.9 Hz, 1H), 5.30-5.58 (m, 2H), 4.94-5.18 (m, 2H), 3.60 (t, J = 6.3 Hz, 3H), 3.29-3.56 (m, 4H), 2.51 (d, J = 6.8 Hz, 4H), 2.30-2.44 (m, 1H), 2.16-2.29 (m, 1H), 1.91-2.11 (m, 4H), 1.70-1.89 (m, 6H), 1.64 (br. s., 5H), 1.45-1.62 (m, 8H), 1.34-1.44 (m, 4H), 1.18-1.33 (m, 4H), 1.10 (br. s., 1H), 0.78-1.02 (m, 3H) | 662.9 |
| 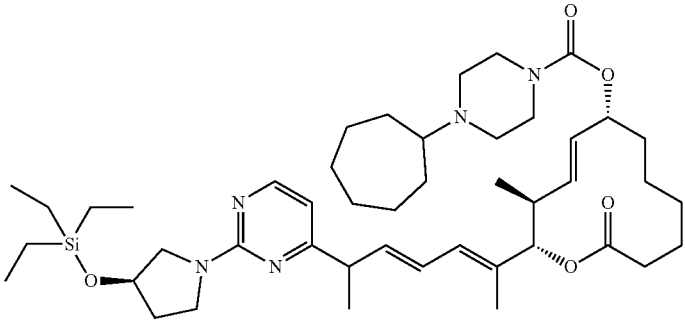<br>132<br>[(2S,3S,4E,6R)-3-methyl-12-oxo-2-[(2E,4E)-6-[2-[(3S)-3-triethylsilyloxypyrrolidin-1-yl]pyrimidin-4-yl]hepta-2,4-dien-2-yl]-1-oxacyclododec-4-en-6-yl] 4-cycloheptylpiperazine-1-carboxylate | ¹H NMR (400 MHz, CHLOROFORM-d) δ: 8.03 (dd, J = 5.3, 1.8 Hz, 1H), 7.20 (s, 1H), 6.05-6.23 (m, 2H), 5.96 (d, J = 10.8 Hz, 1H), 5.74-5.87 (m, 1H), 5.13-5.38 (m, 2H), 4.82-5.01 (m, 2H), 4.35 (d, J = 4.3 Hz, 1H), 3.43-3.60 (m, 3H), 3.34 (d, J = 3.3 Hz, 1H), 3.20-3.31 (m, 4H), 2.42 (br. s., 1H), 2.33 (br. s., 4H), 2.01-2.27 (m, 3H), 1.72-1.96 (m, 3H), 1.65 (br. s., 6H), 1.58 (s, 4H), 1.51 (d, J = 7.0 Hz, 2H), 1.18-1.44 (m, 14H), 0.96-1.14 (m, 4H), 0.71-0.85 (m, 11H), 0.46 (q, J = 7.9 Hz, 5H) | 793.3 |

TABLE 4-continued

Compounds 117-134

| Structure, Compound #, and Chemical Name | ¹H NMR data | LCMS data (ES+) |
|---|---|---|
| 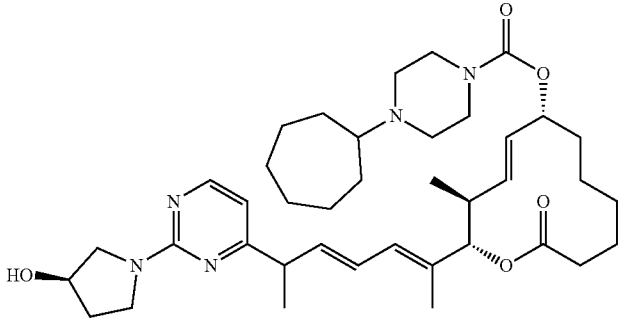<br>133<br>[(2S,3S,4E,6R)-2-[(2E,4E)-6-[2-[(3R)-3-hydroxypyrrolidin-1-yl]pyrimidin-4-yl]hepta-2,4-dien-2-yl]-3-methyl-12-oxo-1-oxacyclododec-4-en-6-yl] 4-cycloheptylpiperazine-1-carboxylate | ¹H NMR (400 MHz, CHLOROFORM-d) δ: 8.13 (dd, J = 5.0, 2.3 Hz, 1H), 7.64 (dd, J = 5.8, 3.3 Hz, 1H), 7.34-7.55 (m, 1H), 6.20-6.38 (m, 1H), 6.05 (d, J = 11.3 Hz, 1H), 5.78-5.93 (m, 1H), 5.36-5.65 (m, 2H), 4.87-5.13 (m, 2H), 4.53 (br. s., 1H), 3.91-4.19 (m, 3H), 3.53-3.81 (m, 5H), 3.31-3.48 (m, 3H), 3.18 (d, J = 11.5 Hz, 2H), 2.64-2.85 (m, 1H), 2.47-2.63 (m, 1H), 2.42 (br. s., 1H), 2.34 (br. s., 1H), 2.20-2.31 (m, 1H), 2.17 (d, J = 6.0 Hz, 1H), 1.84-2.12 (m, 3H), 1.57-1.81 (m, 8H), 1.55 (s, 2H), 1.51 (s, 4H), 1.39-1.46 (m, 2H), 1.10 (br. s., 1H), 0.94 (dd, J = 6.8, 4.8 Hz, 1H), 0.69-0.90 (m, 7H) | 678.9 |
| 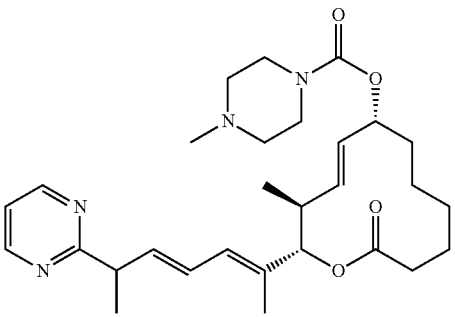<br>134<br>[(2S,3S,4E,6R)-3-methyl-12-oxo-2-[(2E,4E)-6-pyrimidin-2-ylhepta-2,4-dien-2-yl]-1-oxacyclododec-4-en-6-yl] 4-methylpiperazine-1-carboxylate | ¹H NMR (400 MHz, CHLOROFORM-d) δ: 0.79-1.00 (m, 3 H) 1.28 (t, J = 7.15 Hz, 4 H) 1.42-1.67 (m, 6 H) 1.76 (s, 3 H) 1.78 -1.94 (m, 2 H) 2.07 (s, 1 H) 2.20-2.41 (m, 8 H) 2.52 (ddd, J = 10.04, 6.78, 3.26 Hz, 1 H) 3.40-3.57 (m, 4 H) 3.88 (t, J = 7.28 Hz, 1 H) 4.14 (q, J = 7.28 Hz, 1 H) 4.97-5.19 (m, 2 H) 5.38 (dd, J = 14.93, 9.41 Hz, 1 H) 5.44-5.57 (m, 1 H) 6.02-6.21 (m, 2 H) 6.27-6.46 (m, 1 H) 7.08-7.21 (m, 1 H) 8.69-8.76 (m, 2 H) | 511.32 |

Compounds 135-138 were prepared according to the method of Scheme 6.

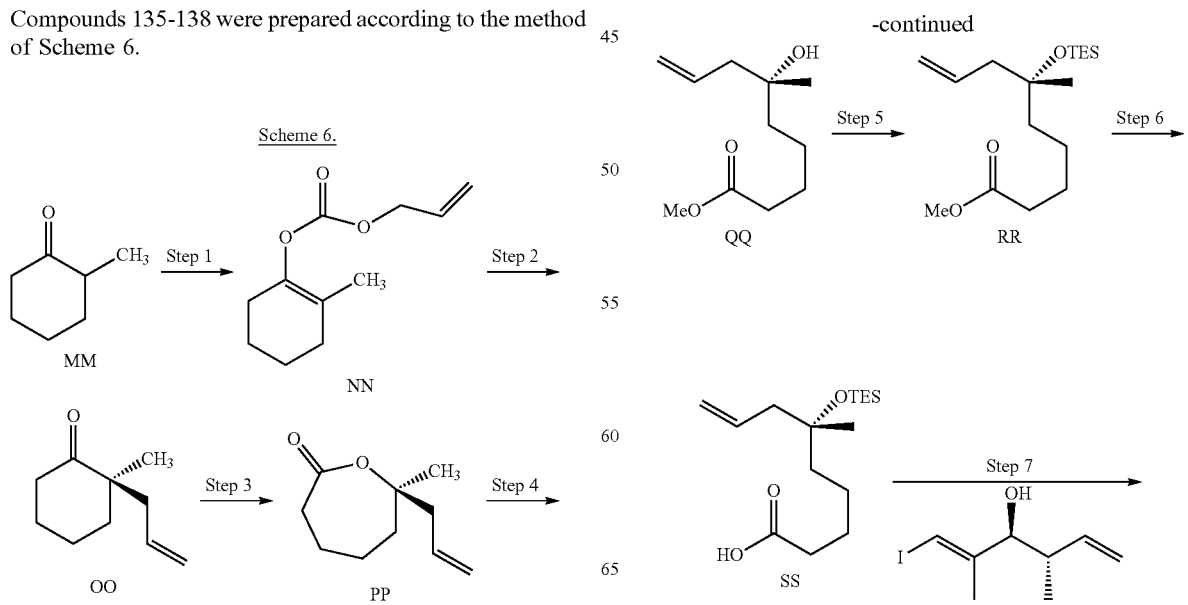

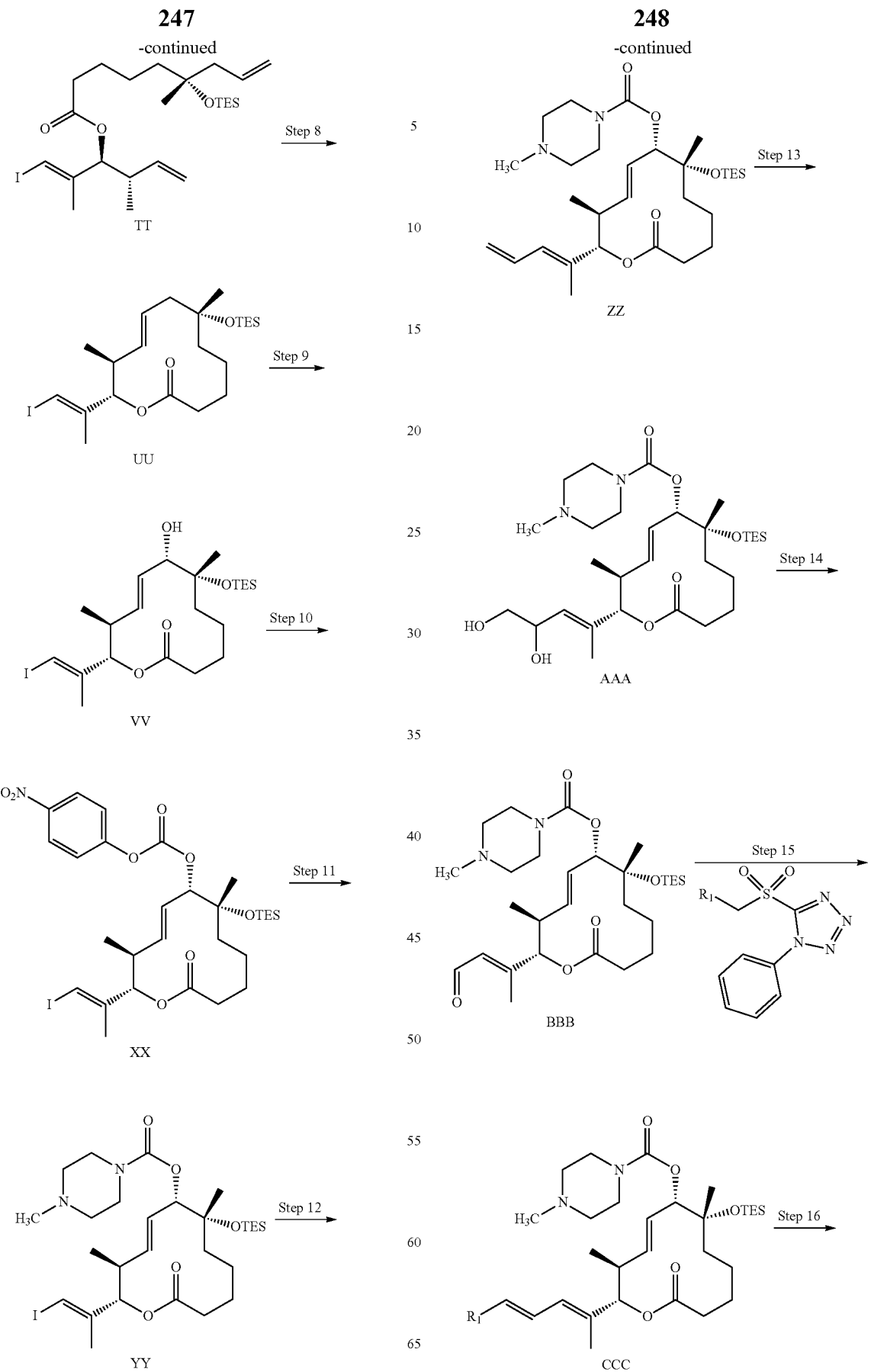

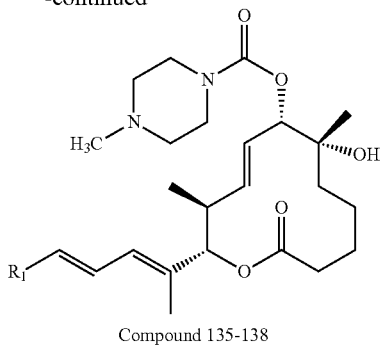

Compound 135-138

General Protocol for the Synthesis of Compounds 135-138:

Step 1: To a solution of potassium tert-butoxide (1.05 g, 8.9 mmol, 1.05 equiv.) under nitrogen in DMF (20 mL, 0.4M) at room temperature was added 2-methylcyclohexanone MM (1.1 mL, 8.9 mmol, 1.0 equiv.) and the reaction was stirred for 15 hours. The reaction was cooled to 0° C. and allyl chloroformate (1.1 mL, 10.7 mmol, 1.2 equiv) was added dropwise over 5 min. and stirred for 30 min. The reaction was allowed to warm to room temperature and quenched into water. The reaction was extracted with 2:1 dichloromethane/hexanes, dried over magnesium sulfate, filtered, and concentrated in vacuo. The crude material was purified by silica gel column chromatography (hexanes/diethyl ether as eluent) to afford the desired product (allyl (2-methylcyclohex-1-en-1-yl) carbonate, NN, 0.7 g, 3.6 mmol, 40%).

Step 2: To a mixture of (R)-2-[2-(diphenylphosphino)phenyl]-4-isopropyl-4,5-dihydrooxazole NN (0.01 g, 0.03 mmol, 0.1 equiv.) and of tris(dibenzylideneacetone)dipalladium(0) (0.01 g, 0.01 mmol, 0.05 equiv.) was added degassed THF (2.5 mL, 0.01M) under argon. The reaction was allowed to stir at room temperature for 30 min. Allyl (2-methylcyclohex-1-en-1-yl) carbonate (0.1 g, 0.25 mmol, 1.0 equiv.) was added and stirred for 8 hr. Then the reaction was allowed to stand at −20° C. for 16 hr. The reaction was concentrated in vacuo and the resulting crude material was purified by silica gel column chromatography (pentane/diethyl ether as eluent) to afford the desired product ((R)-2-allyl-2-methylcyclohexanone, OO, (0.02 g, 0.12 mmol, 46%).

Step 3: To a solution of OO (33 mg, 0.22 mmol, 1.0 equiv.) in dichloromethane (4.0 mL, 0.05M) at 0° C. was added sodium bicarbonate (0.13 g, 1.2 mmol, 5.6 equiv.) followed by the addition of peracetic acid (0.17 mL, 0.76 mmol, 30% wt in acetic acid, 3.5 equiv.). The reaction was allowed to warm to room temperature over 4 hours and then stirred at room temperature for an additional 10 hours. The reaction was quenched with sodium bicarbonate and extracted with dichloromethane. The organic layer was dried over sodium sulfate and concentrated in vacuo to afford the desired product (R)-7-allyl-7-methyloxepan-2-one (PP, 0.04 g, 0.22 mmol, 100%) which was advanced crude into the next step.

Step 4: To a solution of PP (0.04 g, 0.22 mmol, 1.0 equiv.) in anhydrous methanol (6.0 mL, 0.04M) under nitrogen at room temperature was added triethylamine (0.15 mL, 5 equiv.). The reaction was stirred for 8 hours at 90° C. The reaction was cooled to room temperature and potassium carbonate (6.0 mg, 0.04 mmol, 0.2 equiv.) was added. The reaction was stirred for an additional 14 hours at room temperature after which time the reaction was determined to be complete by LCMS or TLC. The reaction was filtered and concentrated to afford the desired product (QQ, 0.04 g, 0.22 mmol, 100%) which was advanced crude into the next step.

Step 5: To a cooled solution of QQ (0.7 g, 3.6 mmol, 1.0 equiv.) and 2,6-lutidine (0.8 mL, 7.2 mmol, 2 equiv.) in dichloromethane (7 mL, 0.05M) at −78° C. was added dropwise triethylsilyl trifluoromethansulfonate (0.98 mL, 4.3 mmol, 1.2 equiv.). The reaction was stirred at −78° C. for 1 hour after which time the reaction was determined to be complete by LCMS or TLC. The reaction was allowed to warm to room temperature, quenched with sodium bicarbonate, and extracted with dichloromethane. The combined organic fractions were washed with water, brine, dried over sodium sulfate, filtered, and concentrated in vacuo. The resulting residue was purified by silica gel column chromatography (hexane/ethyl acetate as eluent) to afford the desired product (RR, 0.7 g, 2.3 mmol, 63%).

Step 6: To a cooled solution of RR (0.04 g, 0.13 mmol, 1 equiv.) in THF (2.5 mL, 0.06M) at 0° C. was added hydrogen peroxide (0.06 mL, 30%, 5 equiv.), followed by a solution of lithium hydroxide (0.07 g, 0.64 mmol, 5 equiv.) in water (0.5 mL). The reaction was warmed to room temperature, methanol (8 mL) was added, and the reaction was stirred for 48 hours at room temperature. The reaction was quenched with sodium sulfite followed by saturated citric acid. The mixture was diluted with ethyl acetate, washed with brine, dried over magnesium sulfate, filtered, and concentrated in vacuo. The residue was purified by silica gel column chromatography (hexane/ethyl acetate as eluent) to afford the desired product (SS, 0.02 g, 0.06 mmol, 47%).

Step 7: To a solution of acid SS (0.02 g, 0.06 mmol, 1.0 equiv.) in dichloromethane (1.0 mL, 0.06M) at room temperature was added 1-ethyl-3-(3-dimethylaminopropyl)carbodiimide (0.02 g, 0.09 mmol, 1.5 equiv) and a solution of (3S,4S,E)-1-iodo-2,4-dimethylhexa-1,5-dien-3-ol (0.023 g, 0.09 mmol, 1.5 equiv.). The reaction was run for 16 hours and determined to be complete by TLC. The reaction was quenched with water, diluted with ethyl acetate, washed with brine, dried over sodium sulfate, filtered, and concentrated in vacuo. The residue was purified by silica gel column chromatography (hexane/ethyl acetate as eluent) to afford the desired product (TT, 0.02 g, 0.04 mmol, 63%).

Step 8: To a degassed solution of olefin TT (0.02 g, 0.04 mmol, 1.0 equiv.) and benzoquinone (0.4 mg, 0.004 mmol, 0.1 equiv) in toluene (10.0 mL, 0.04M) under nitrogen at 20° C. was added the Hoveyda-Grubbs catalyst (0.006 g, 0.01 mmol, 0.2 equiv.). The reaction was stirred at 50° C. for 2 hours or until the reaction was determined to be complete by LCMS or TLC. The reaction was diluted with ethyl acetate, and the organic layer was washed with sodium bicarbonate, water, brine, dried over magnesium sulfate, filtered, and concentrated in vacuo. The residue was purified by silica gel column chromatography (ethyl acetate/hexanes as eluent) to afford the desired product (UU, 0.01 g, 0.02 mmol, 53%).

Step 9: To a solution of macrocycle UU (0.01 g, 0.02 mmol, 1.0 equiv.) in dioxane (2 mL, 0.1M) under nitrogen was added selenium dioxide (0.007 g, 0.06 mmol, 3.0 equiv.) under nitrogen at room temperature. The reaction was stirred at 85° C. for 20 hours. The reaction was diluted with ethyl acetate, and the organic layer was washed with sodium bicarbonate, water, brine, dried over magnesium sulfate, filtered, and concentrated in vacuo. The residue was purified by silica gel column chromatography (ethyl acetate/hexanes as eluent) to afford the desired product (VV, 0.007 g, 0.013 mmol, 68%).

Step 10: To a solution of alcohol VV (1.0 equiv.) in MTBE (0.1M) at room temperature was added triethylamine (5.0 equiv.), para-nitrophenylchloroformate (3.0 equiv.), and DMAP (catalytic) and the reaction was stirred overnight. Once determined to be complete by TLC or LCMS, the reaction was quenched with water. Ethyl acetate was added and the organic layer was washed with water, saturated sodium bicarbonate, dried over magnesium sulfate, filtered, and concentrated in vacuo. The crude product (XX) was advanced without purification.

Step 11: To a solution of carbonate XX (1.0 equiv.) in MTBE (0.1M) at room temperature was added the corresponding amine (2.0 equiv.). Once determined to be complete by TLC or LCMS, the reaction was concentrated and the resulting oil was purified by silica gel column chromatography (hexane/ethyl acetate as eluent) to afford the desired product (YY).

Step 12: To a solution of vinyl iodide YY (1.0 equiv.) in THF (0.1M) at room temperature was added vinyl pinacol boronate (4.0 equiv.), silver oxide (5.0 equiv.), triphenylarsine (1.2 equiv.), and $Pd_2(dba)_3$ (0.15 equiv.). The reaction was stirred at room temperature overnight. Once determined to be complete by TLC or LCMS, the reaction was filtered through Celite®. Dichloromethane was added and the organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (ZZ).

Step 13: To a solution of diene ZZ (1.0 equiv.) in THF:$H_2O$ (0.1M) at 0° C. was added N-methylmorpholine N-oxide (1.2 equiv.) and osmium tetroxide in t-BuOH (0.1 equiv.). The reaction was stirred at room temperature overnight. Once determined to be complete by TLC or LCMS, the reaction was quenched by addition of aqueous sodium bicarbonate. Ethyl acetate was added and the organic layer was washed with water, saturated sodium bicarbonate, dried over magnesium sulfate, filtered, and concentrated in vacuo. The crude material (AAA) was advanced without further purification.

Step 14: To a solution of diol AAA (1.0 equiv.) in acetone: $H_2O$ (0.1M) at room temperature was added diacetoxyiodobenzene (1.2 equiv.). The reaction was stirred at room temperature for 40 minutes or until determined to be complete by TLC or LCMS. The reaction was quenched by addition of sodium thiosulfite and then sodium bicarbonate. Dichloromethane was added, and the organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (BBB).

Step 15: To a solution of the corresponding sulfone (1.0 equiv.) in THF (0.1M) at −78° C. was added KHMDS (3.0 equiv.) and the reaction was stirred at −78° C. for one hour. Next, a solution of aldehyde BBB in THF (1.0 equiv.) was added dropwise at −78° C. The reaction was allowed to warm gradually to −20° C. and stirred at −20° C. for two hours. The reaction was quenched with aqueous sodium bicarbonate and ethyl acetate was added. The organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (CCC).

Step 16: To a solution of silyl ether CCC in methanol (0.1M) at room temperature was added p-methoxytoluenesulfonic acid (2.5 equiv.). The reaction was stirred for 3 hours, or until the reaction was determined to be complete by LCMS or TLC. The reaction was quenched with sodium bicarbonate, diluted with ethyl acetate, washed with water and brine, dried over magnesium sulfate, filtered, and concentrated in vacuo. The resulting oil was purified by silica gel column chromatography (hexane/ethyl acetate as eluent) to afford the desired product (135-138), (Table 5).

Exemplified Protocol for the Synthesis of Compound 135

Steps 1-9 as above.

Step 10: To a solution of alcohol VV (0.007 g, 0.013 mmol, 1.0 equiv.) in MTBE (1.0 mL, 0.1M) at room temperature was added triethylamine (0.02 mL, 0.09 mmol, 7.0 equiv.), para-nitrophenyl chloroformate (0.009 g, 0.05 mmol, 3.5 equiv.), and DMAP (2.0 mg, 0.016 mmol, 1.2 equiv.). The reaction was stirred overnight. Once determined to be complete by TLC or LCMS, the reaction was quenched with water. Ethyl acetate was added and the organic layer was washed with water, saturated sodium bicarbonate, dried over magnesium sulfate, filtered, and concentrated in vacuo. The crude product (XX) was advanced without purification.

Step 11: To a solution of carbonate XX (1.0 equiv.) in MTBE (1.0 mL, 0.1M) at room temperature was added N-methylpiperazine (0.007 mL, 0.07 mmol, 5.0 equiv.). Once determined to be complete by TLC or LCMS, the reaction was concentrated and the resulting oil was purified by silica gel column chromatography (hexane/ethyl acetate as eluent) to afford the desired product (YY, 0.008 g, 0.012 mmol, 92%).

Step 12: To a solution of vinyl iodide YY (0.01 g, 0.015 mmol, 1.0 equiv.) in THF (1.0 mL, 0.01M) at room temperature was added vinyl pinacol boronate (0.013 mL, 0.08 mmol, 5.0 equiv.), silver oxide (18.0 mg, 0.08 mmol, 5.0 equiv.), triphenylarsine (5.7 mg, 0.02 mmol, 1.2 equiv.), and $Pd_2(dba)_3$ (3.0 mg, 0.003 mmol, 0.15 equiv.). The reaction was stirred at room temperature overnight. Once determined to be complete by TLC or LCMS, the reaction was filtered through Celite®. Dichloromethane was added and the organic layer was washed with water and saturated sodium bicarbonate, dried over magnesium sulfate, filtered, and concentrated in vacuo. The resulting oil was purified by silica gel column chromatography (dichloromethane/methanol as eluent) to afford the desired product (ZZ, 0.009 g, 0.016 mmol, >95%).

Step 13: To a solution of diene ZZ (0.009 g, 0.016 mmol, 1.0 equiv.) in THF:$H_2O$ (2.0 mL:0.2 mL, 0.1M) at 0° C. was added N-methylmorpholine N-oxide (3.2 mg, 0.03 mmol, 1.5 equiv.) and osmium oxide in t-BuOH (0.05 mL, 0.004 mmol, 0.2 equiv.). The reaction was stirred at room temperature overnight. Once determined to be complete by TLC or LCMS, the reaction was quenched by addition of aqueous sodium bicarbonate. Ethyl acetate was added and the organic layer was washed with water, saturated sodium bicarbonate, dried over magnesium sulfate, filtered, and concentrated in vacuo. The crude material (AAA, 0.008 g, 0.014 mmol, 75%) was advanced without further purification.

Step 14: To a solution of diol AAA (0.07 g, 0.12 mmol, 1.0 equiv.) in acetone:$H_2O$ (5 mL:0.5 mL, 0.02M) at room temperature was added diacetoxyiodobenzene (0.048 g, 0.15 mmol, 1.2 equiv.). The reaction was stirred at room temperature for 40 minutes or until determined to be complete by TLC or LCMS. The reaction was quenched by addition of sodium thiosulfilte and then sodium bicarbonate. Dichloromethane was added, and the organic layer was washed with water, saturated sodium bicarbonate, dried over magnesium sulfate, filtered, and concentrated in vacuo. The resulting oil was purified by silica gel column chromatography (dichloromethane/methanol as eluent) to afford the desired product (BBB, 60 mg, 0.11 mmol, 87%).

Step 15: To a solution of (S)-2-methyl-3-((1-phenyl-1H-tetrazol-5-yl)sulfonyl)propyl pyrrolidine-1-carboxylate (0.026 g, 0.07 mmol, 2.5 equiv.) in THF (2.0 mL, 0.01M) at −78° C. was added KHMDS (0.14 mL, 0.07 mmol, 2.5 equiv.) and the reaction was stirred at −78° C. for one hour. Next, a solution of aldehyde BBB (0.015 g, 0.03 mmol, 1.0 equiv.) was added dropwise at −78° C. The reaction was allowed to warm gradually to −20° C. and stirred at −20° C. for two hours. The reaction was quenched with aqueous sodium bicarbonate and ethyl acetate was added. The organic layer was washed with water and saturated sodium bicarbonate, dried over magnesium sulfate, filtered, and concentrated in vacuo. The resulting oil was purified by silica gel column chromatography (dichloromethane/methanol as eluent) to afford the desired product (CCC, 0.016 mg, 0.023 mmol, 76%).

Step 16: To a solution of silyl ether CCC (0.016 g, 0.023 mmol, 1 equiv.) in methanol (0.2 mL, 0.1M) at room temperature was added p-methoxytoluenesulfonic acid (8.0 mg, 0.04 mmol, 1.5 equiv.). The reaction was stirred for 3 hours, or until the reaction was determined to be complete by LCMS or TLC. The reaction was quenched with sodium bicarbonate, diluted with ethyl acetate, washed with water, brine, dried over magnesium sulfate, filtered, and concentrated in vacuo. The resulting oil was purified by silica gel column chromatography (hexane/ethyl acetate as eluent) to afford the desired product (compound 135, 7 mg, 0.012 mmol, 44%). $^1$H NMR (400 MHz, METHANOL-d4) δ: 0.89 (d, J=6.78 Hz, 3H) 1.09 (d, J=6.90 Hz, 3H) 1.13-1.31 (m, 5H) 1.35-1.53 (m, 2H) 1.75-1.80 (m, 3H) 1.82-1.94 (m, 5H) 1.94-2.08 (m, 1H) 2.39 (s, 2H) 2.53-2.66 (m, 2H) 2.69 (s, 3H) 2.94 (br. s., 4H) 3.34-3.40 (m, 4H) 3.70 (br. s., 4H) 3.91-4.03 (m, 2H) 4.93-4.99 (m, 1H) 5.07-5.13 (m, 1H) 5.55 (dd, J=15.12, 9.85 Hz, 1H) 5.71 (m, J=9.79 Hz, 2H) 6.13 (d, J=10.67 Hz, 1H) 6.37 (ddd, J=15.12, 10.85, 1.00 Hz, 1H). MS (ES+)=590.5 [M+H]$^+$.

TABLE 5

Compounds 135-138

| Structure, Compound #, and Chemical Name | $^1$H NMR data | LCMS data (ES+) |
|---|---|---|
| 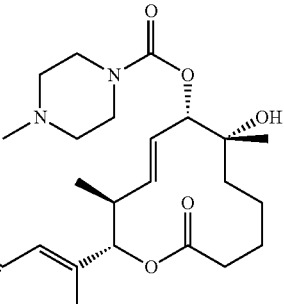 135<br><br>[(2S,3S,4E,6S,7S)-7-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | $^1$H NMR (400 MHz, METHANOL-d4) δ: 0.89 (d, J = 6.78 Hz, 3 H) 1.09 (d, J = 6.90 Hz, 3 H) 1.13-1.31 (m, 5 H) 1.35-1.53 (m, 2 H) 1.75-1.80 (m, 3 H) 1.82-1.94 (m, 5 H) 1.94-2.08 (m, 1 H) 2.39 (s, 2 H) 2.53-2.66 (m, 2 H) 2.69 (s, 3 H) 2.94 (br. s., 4 H) 3.34-3.40 (m, 4 H) 3.70 (br. s., 4 H) 3.91-4.03 (m, 2 H) 4.93-4.99 (m, 1 H) 5.07-5.13 (m, 1 H) 5.55 (dd, J = 15.12, 9.85 Hz, 1 H) 5.71 (m, J = 9.79 Hz, 2 H) 6.13 (d, J = 10.67 Hz, 1 H) 6.37 (ddd, J = 15.12, 10.85, 1.00 Hz, 1 H) | 590.5 |
| 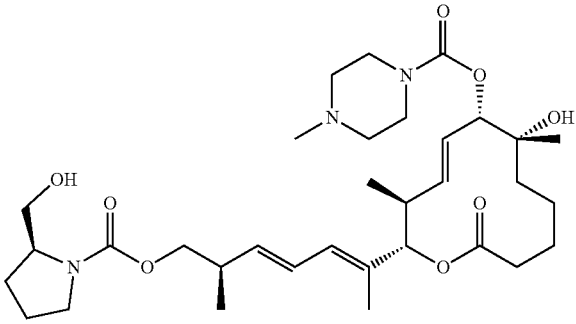 136<br><br>[(2S,3S,4E,6S,7S)-7-hydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | $^1$H NMR (400 MHz, METHANOL-d4) δ: 0.89 (d, J = 6.65 Hz, 3 H) 1.10 (d, J = 6.78 Hz, 3 H) 1.13-1.31 (m, 5 H) 1.35-1.53 (m, 2 H) 1.78 (s, 3 H) 1.81-2.08 (m, 6 H) 2.25-2.46 (m, 2 H) 2.52-2.62 (m, 1 H) 2.64 (s, 3 H) 2.88 (d, J = 2.01 Hz, 4 H) 3.36-3.45 (m, 2 H) 4.00 (d, J = 7.15 Hz, 10 H) 4.95 (d, J = 9.79 Hz, 1 H) 5.10 (d, J = 10.67 Hz, 1 H) 5.55 (dd, J = 15.18, 9.91 Hz, 1 H) 5.70 (m, J = 3.14 Hz, 2 H) 6.11 (d, J = 10.29 Hz, 1 H) 6.38 (dd, J = 15.00, 10.73 Hz, 1 H) | 620.5 |

TABLE 5-continued

Compounds 135-138

| Structure, Compound #, and Chemical Name | $^1$H NMR data | LCMS data (ES+) |
|---|---|---|
| 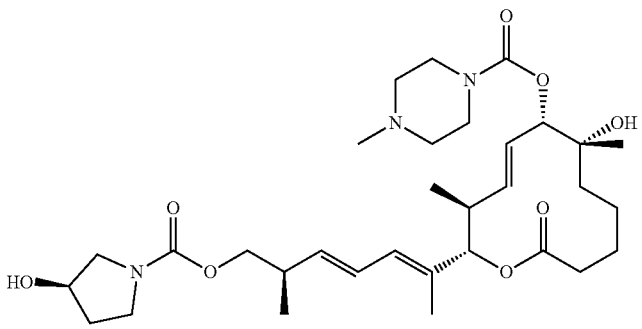<br>137<br>[(2S,3S,4E,6S,7S)-7-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | $^1$H NMR (400 MHz, METHANOL-d4) δ: 0.89 (d, J = 6.65 Hz, 3 H) 1.09 (d, J = 6.90 Hz, 3 H) 1.21 (s, 5 H) 1.31 (s, 8 H) 1.78 (d, J = 0.88 Hz, 3 H) 1.80-2.09 (m, 5 H) 2.32 (s, 3 H) 2.42 (t, J = 5.08 Hz, 6 H) 2.51-2.71 (m, 2 H) 3.41-3.75 (m, 8 H) 3.99 (m, J = 6.71, 4.08 Hz, 2 H) 4.38 (br. s., 1 H) 4.94 (d, J = 9.79 Hz, 1 H) 5.10 (d, J = 10.67 Hz, 1 H) 5.54 (dd, J = 15.18, 9.91 Hz, 1 H) 5.70 (d, J = 9.79 Hz, 2 H) 6.11 (d, J = 10.16 Hz, 1 H) 6.38 (dd, J = 15.06, 10.54 Hz, 1 H) | 606.5 |
| 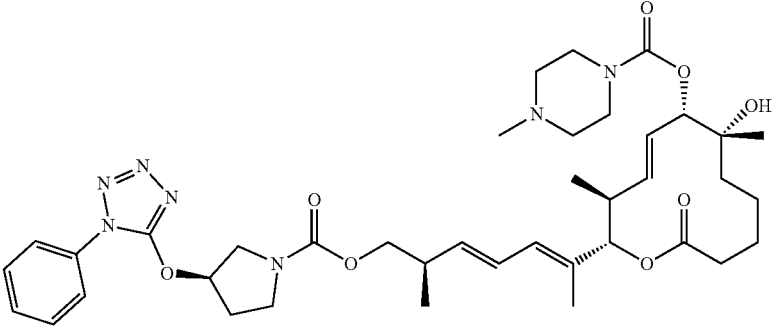<br>138<br>[(2S,3S,4E,6S,7S)-7-hydroxy-3,7-dimethyl-2-[(2E,4E,6R)-6-methyl-7-[(3S)-3-(1-phenyltetrazol-5-yl)oxypyrrolidine-1-carbonyl]oxyhepta-2,4-dien-2-yl]-12-oxo-1-oxacyclododec-4-en-6-yl] 4-methylpiperazine-1-carboxylate | $^1$H NMR (400 MHz, METHANOL-d4) δ: 0.77-0.92 (m, 3 H) 1.07 (t, J = 7.65 Hz, 3 H) 1.13-1.31 (m, 5 H) 1.33-1.52 (m, 2 H) 1.72 (s, 3 H) 1.80-1.91 (m, 1 H) 1.92-2.07 (m, 1 H) 2.22-2.46 (m, 4 H) 2.51 (s, 3 H) 2.55-2.65 (m, 1 H) 2.69 (br. s., 4 H) 3.42-3.91 (m, 9 H) 3.99 (d, J = 6.02 Hz, 2 H) 4.94 (d, J = 9.79 Hz, 1 H) 5.01-5.11 (m, 1 H) 5.45-5.59 (m, 1 H) 5.60-5.79 (m, 3 H) 5.97-6.14 (m, 1 H) 6.35 (dd, J = 14.81, 10.79 Hz, 1 H) 7.50-7.66 (m, 3 H) 7.71 (d, J = 7.53 Hz, 2 H) | 750.5 |

Compounds 139-142 were prepared by the method of Scheme 7.

Scheme 7.

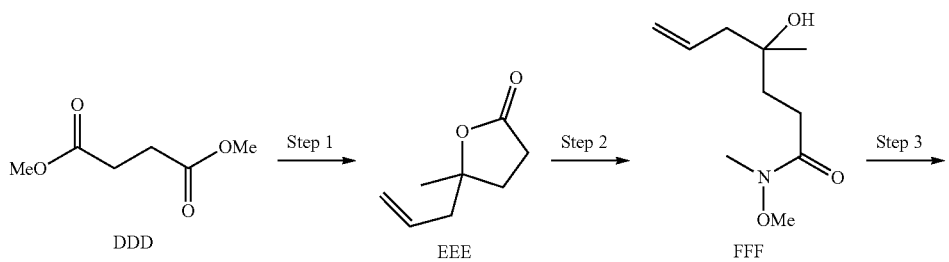

-continued
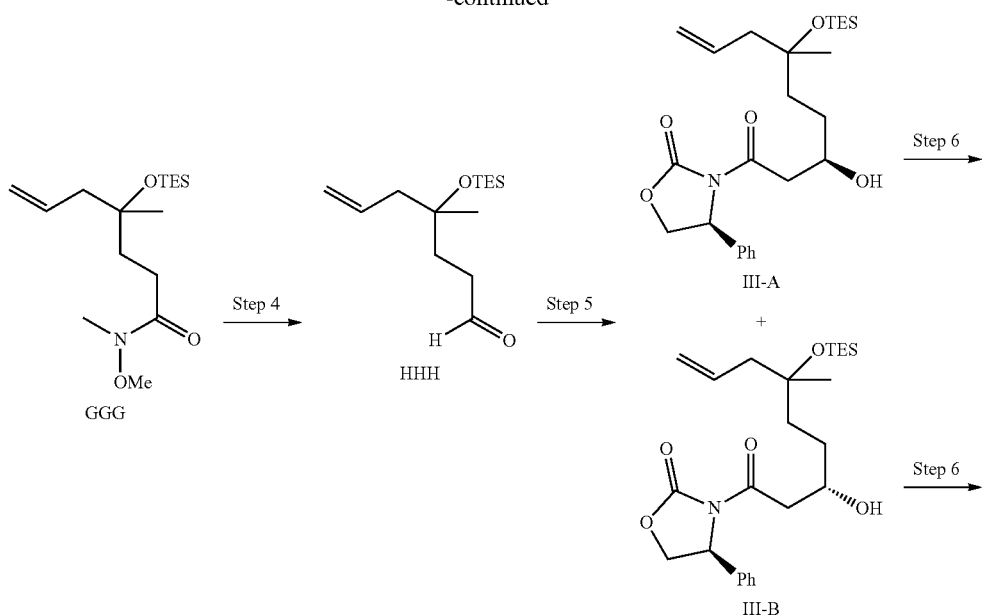
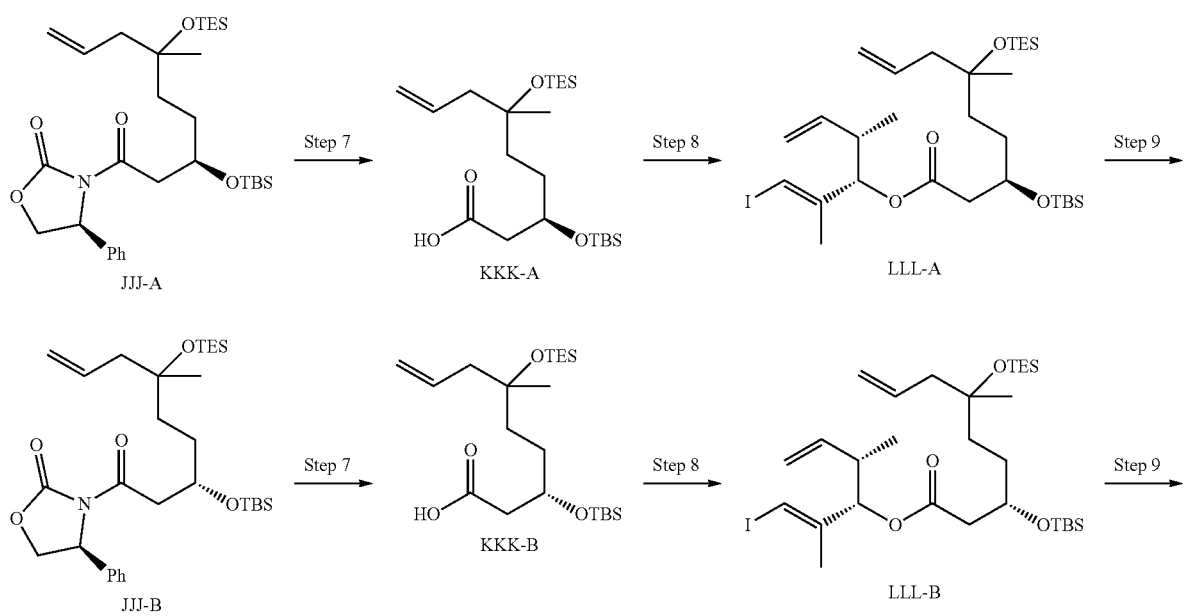

259
-continued
260
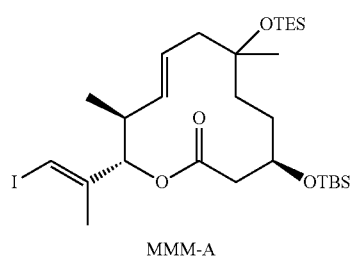
MMM-A
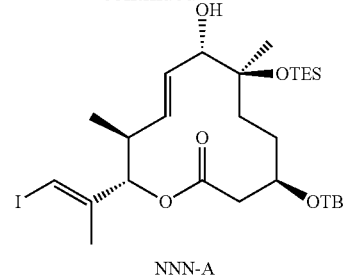
NNN-A
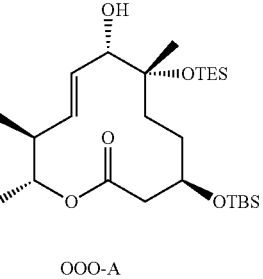
OOO-A
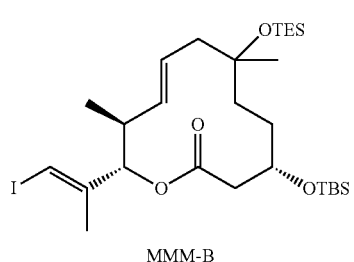
MMM-B
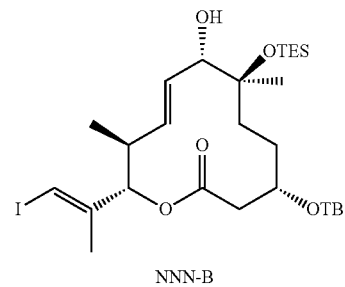
NNN-B
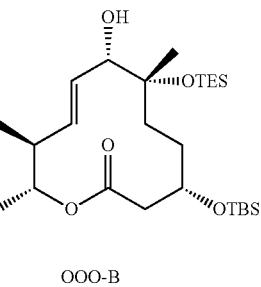
OOO-B
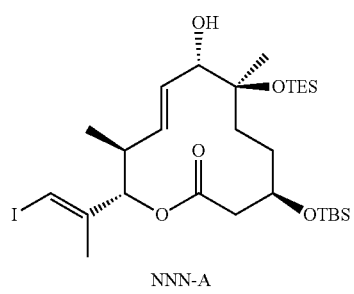
NNN-A
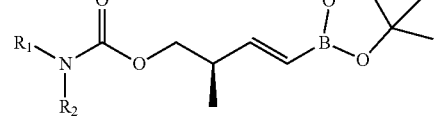
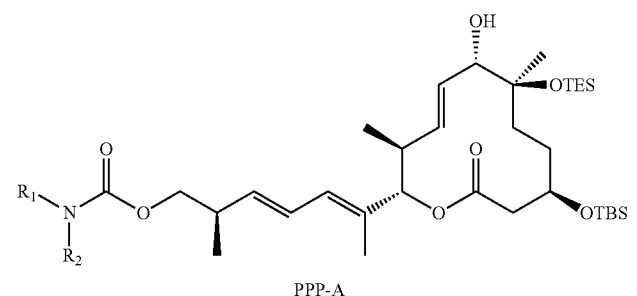
PPP-A
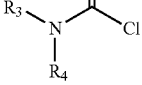
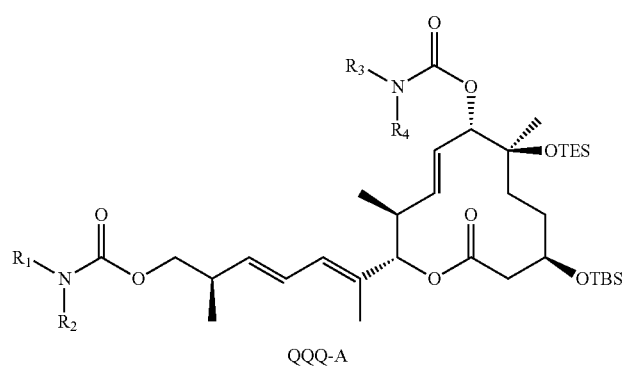
QQQ-A

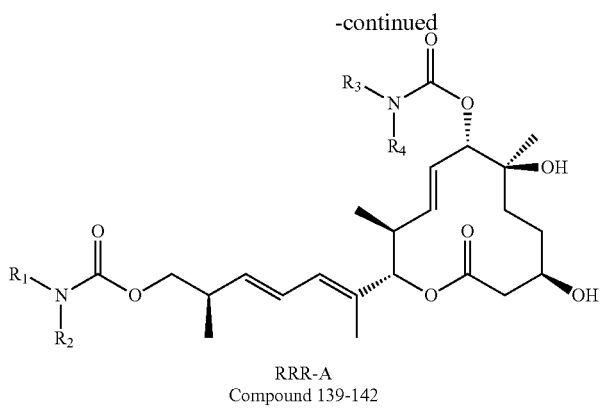

RRR-A
Compound 139-142

General Protocol for the Synthesis of Compounds 139-142

Step 1: To a solution of methyl 4-oxopentanoate DDD (10.0 g, 76.8 mmol, 1.0 equiv.) and allyltrimethylsilane (13.4 mL, 84.5 mmol, 1.1 equiv.) under nitrogen in THF (13.4 mL, 6M) at room temperature was added TBAF (1.0 g, 3.8 mmol, 0.05 equiv.) and 4 Å molecular sieves (0.2 equiv. wt). The reaction was stirred at reflux for 36 hours. The reaction was filtered and concentrated in vacuo. The crude material was purified by silica gel column chromatography (hexanes/ethyl acetate as eluent) to afford the desired product (5-allyl-5-methyldihydrofuran-2(3H)-one) (EEE, 5.8 g, 21.7 mmol, 28%).

Step 2: To a cooled solution of N,O-dimethylhydroxylamine hydrochloride (1.7 g, 17.8 mmol, 5.0 equiv.) in THF (20.0 mL, 0.9M) under nitrogen at 0° C. was added trimethylaluminum (7.1 mL, 14.3 mmol, 4.0 equiv.). The reaction was stirred at room temperature for 30 min. A solution of 5-allyl-5-methyldihydrofuran-2(3H)-one, EEE, (0.5 g, 3.6 mmol, 1.0 equiv.) in THF (5.0 mL) was added at 0° C. and the reaction was stirred for 2 hours. The reaction was poured onto a cooled mixture of ethyl acetate and saturated potassium tartrate and stirred for 15 mins. The organic layer was separated and the aqueous layer was extracted with diethyl ether. The combined organic fractions were dried over sodium sulfate, filtered, and concentrated in vacuo to afford the desired product (4-hydroxy-N-methoxy-N,4-dimethylhept-6-enamide, FFF) which was advanced crude into the next step.

Step 3: To a solution of 4-hydroxy-N-methoxy-N,4-dimethylhept-6-enamide FFF (1.0 equiv) in DMF (20.0 mL, 0.9M) at room temperature was added 1H-imidazole (1.2 g, 17.8 mmol, 5.0 equiv.) and chlorotriethylsilane (2.4 mL, 14.3 mmol, 4.0 equiv.). The reaction was stirred at room temperature for 12 hours. The reaction was diluted with brine and extracted with diethyl ether. The combined organic fractions were dried over sodium sulfate, filtered, and concentrated in vacuo. The resulting residue was purified by silica gel column chromatography (hexanes/ethyl acetate as eluent) to afford the desired product (N-methoxy-N,4-dimethyl-4-((triethylsilyl)oxy)hept-6-enamide (GGG, 0.56 g, 1.8 mmol, 50%).

Step 4: To a solution of amide GGG (0.25 g, 0.79 mmol, 1.0 equiv.) in THF (6.0 mL, 0.13M) under nitrogen at −78° C. was added DIBAL-H (1.3 mL, 1.3 mmol, 1.6 equiv.) and stirred for one hour. The reaction was quenched with aqueous hydrochloric acid (1M) and stirred for an additional 15 min. The reaction was extracted with ethyl acetate and the combined organic fractions were concentrated in vacuo. The residue was purified by silica gel column chromatography (hexanes/ethyl acetate as eluent) to afford the desired product (4-methyl-4-((triethylsilyl)oxy)hept-6-enal, HHH, 0.19 g, 0.74 mmol, 93%).

Step 5: To a solution of (S)-3-acetyl-4-benzyloxazolidin-2-one HHH (0.15 g, 0.68 mmol, 1 equiv.) in dichloromethane (3.0 mL, 0.2M) under nitrogen at −78° C. was added dibutyl(((trifluoromethyl)sulfonyl)oxy)borane (0.75 mL, 0.75 mmol, 1M toluene, 1.1 equiv.), followed by diisopropylethylamine (0.15 mL, 0.89 mmol, 1.3 equiv.). The reaction was sucessively stirred at −78° C. for 15 min., at 0° C. for 1 hour, and then at −78° C. for 30 min. To the cooled reaction mixture was added dropwise 4-methyl-4-((triethylsilyl)oxy)hept-6-enal (0.17 g, 0.68 mmol, 1.0 equiv.) followed by stirring at room temperature for 2 hours. The reaction was quenched with ammonia chloride and extracted with dichloromethane. The combined organic fractions were dried over sodium sulfate and concentrated in vacuo. The residue was purified by silica gel column chromatography (hexanes/ethyl acetate as eluent) to afford the desired diastereomeric products as a separable mixture (III-A and III-B). The stereochemistry of each diastereoisomer was assigned according to their NOE data and cross peak between H4 and H8.

III-A

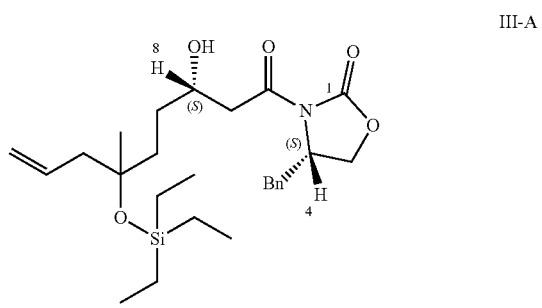

$^1$H NMR (CHLOROFORM-d) δ: 7.09-7.28 (m, 2H), 5.74 (dd, J=17.7, 9.2 Hz, 1H), 4.96 (d, J=11.8 Hz, 1H), 4.54-4.65 (m, 1H), 3.99-4.14 (m, 1H), 3.15-3.27 (m, 1H), 3.05-3.14 (m, 1H), 3.00-3.04 (m, 1H), 2.88-2.98 (m, 1H), 2.63-2.71 (m, 1H), 2.15 (d, J=6.3 Hz, 1H), 1.52-1.59 (m, 1H), 1.20-1.49 (m, 4H), 1.10-1.16 (m, 1H), 0.68-0.91 (m, 7H), 0.47-0.56 (m, 2H).

$^{13}$C NMR (CHLOROFORM-d) δ: 171.2, 153.5, 153.4, 135.4, 135.3, 135.2, 135.1, 135.0, 135.0, 129.4, 129.0, 129.0, 128.9, 127.4, 127.4, 127.3, 117.2, 117.2, 117.1, 117.1, 77.3, 76.4, 75.0, 74.9, 68.5, 66.3, 66.2, 66.2, 66.1, 55.2, 55.2, 55.1, 55.1, 47.3, 46.9, 38.0, 37.9, 37.8, 33.8, 31.2, 31.1, 31.0, 29.8, 27.8, 27.7, 27.6, 27.6, 26.6, 26.5, 26.5, 25.8, 25.5, 25.5, 25.3, 19.2, 19.1, 19.0, 18.9, 14.1, 14.0, 14.0, 13.9, 13.8, 13.8, 7.2, 6.9.

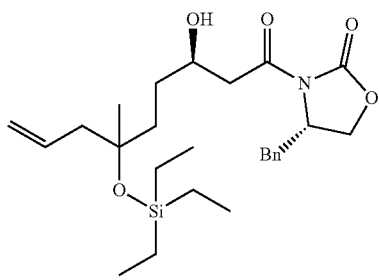

III-B $^1$H NMR (CHLOROFORM-d) δ: 7.27-7.37 (m, 6H), 7.22 (d, J=6.8 Hz, 4H), 5.78-5.87 (m, 1H), 5.03-5.09 (m, 3H), 4.66-4.74 (m, 2H), 4.06-4.25 (m, 6H), 3.28-3.34 (m, 2H), 3.05-3.12 (m, 3H), 2.79-2.83 (m, 1H), 2.57 (s, 2H), 2.20-2.29 (m, 3H), 1.59-1.70 (m, 4H), 1.45-1.54 (m, 2H), 1.31-1.41 (m, 1H), 1.20-1.29 (m, 6H), 0.93-1.00 (m, 15H), 0.57-0.64 (m, 9H).

$^{13}$C NMR (CHLOROFORM-d) δ: 172.8, 172.8, 171.1, 170.3, 153.7, 153.5, 135.3, 135.1, 135.0, 135.0, 129.4, 129.0, 129.0, 128.9, 127.4, 127.4, 117.2, 117.2, 76.8, 75.0, 75.0, 68.6, 68.5, 66.3, 66.1, 60.4, 55.1, 55.1, 55.0, 53.5, 47.3, 47.0, 42.9, 42.8, 38.0, 38.0, 37.8, 37.8, 31.1, 31.1, 30.7, 27.8, 27.6, 26.6, 25.5, 23.8, 21.0, 19.1, 14.2, 14.0, 13.9, 13.7, 7.2, 6.9, 6.8, 6.6.

Similar protocols were used for III-A and III-B

Step 6: To a solution of alcohol III-A (1.0 equiv) in DMF (0.09M) at room temperature was added 1H-imidazole (5.0 equiv.) and tert-butylchlorodimethylsilane (2.5 equiv.). The reaction was stirred under nitrogen at room temperature for 3 hours. The reaction was diluted with brine and extracted with ethyl acetate. The combined organic fractions were dried over sodium sulfate, filtered, and concentrated in vacuo. The resulting residue was purified by silica gel column chromatography (hexanes/ethyl acetate as eluent) to afford the desired product (JJJ-A).

Step 7: To a cooled solution JJJ-A (1.0 equiv.) in THF (0.9M) at 0° C. was added hydrogen peroxide (7.6 equiv.), followed by a solution of lithium hydroxide (8.0 equiv.) in water (0.8M). The reaction was stirred at 0° C. for 1 hour and then at room temperature for 3 hours. The reaction was quenched with sodium thiosulfate. The mixture was extracted with ethyl acetate, acidified to pH 3, and extracted with ethyl acetate. The organic layer was dried over sodium sulfate, filtered, and concentrated in vacuo. The residue was purified by silica gel column chromatography (hexanes/ethyl acetate as eluent) to afford the desired acid (KKK-A).

Step 8: To a solution of acid KKK-A (1.0 equiv.) and freshly prepared (3S,4S,E)-1-iodo-2,4-dimethylhexa-1,5-dien-3-ol (1.4 equiv.) (For protocols related to the synthesis of (3S, 4S,E)-1-iodo-2,4-dimethylhexa-1,5-dien-3-ol, see: Kumar, V. P.; Chandrasekhar, S. Org. Lett. 2013, 15, 3610-3613) in dichloromethane (0.08M) at room temperature was added 1-ethyl-3-(3-dimethylaminopropyl)carbodiimide (1.3 equiv) and DMAP (catalytic). The reaction was stirred at room temperature for 16 hours and determined to be complete by TLC. The reaction was concentrated in vacuo and the residue was purified by silica gel column chromatography (hexane/ethyl acetate) to afford the desired ester (LLL-A).

Step 9: To a degassed solution of olefin LLL-A (1.0 equiv.) and benzoquinone (0.05 equiv) in toluene (0.01M) under nitrogen at 20° C. was added the Hoveyda-Grubbs catalyst 0.1 equiv.). The reaction was stirred at 50° C. for 2 hours or until the reaction was determined to be complete by LCMS or TLC. The reaction was diluted with ethyl acetate, and the organic layer was washed with sodium bicarbonate, water, brine, dried over magnesium sulfate, filtered, and concentrated in vacuo. The residue was purified by silica gel column chromatography (ethyl acetate/hexanes as eluent) to afford the desired product (MMM-A).

Step 10: To solution of solution of macrocycle MMM-A (1.0 equiv.) in dioxane (0.1M) under nitrogen was added selenium dioxide (4.0 equiv.) under nitrogen at room temperature. The reaction was stirred at 85° C. for 20 hours. The reaction was diluted with ethyl acetate, and the organic layer was washed with sodium bicarbonate, water, brine, dried over magnesium sulfate, filtered, and concentrated in vacuo. The residue was purified by silica gel column chromatography (ethyl acetate/hexanes as eluent) to afford the desired diastereoisomer products: a separable mixture (NNN-A) and (OOO-A). The stereochemistry of each diastereoisomer was assigned according to their COSY, HMBC, HMQC and NOESY data.

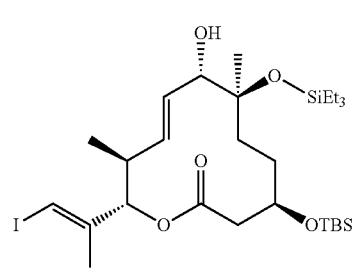

NNN-A $^1$H NMR (400 MHz, CHLOROFORM-d) δ ppm −0.03-0.03 (m, 4H) 0.49-0.63 (m, 5H) 0.80-0.94 (m, 15H) 1.16-1.23 (m, 3H) 1.25-1.45 (m, 3H) 1.39-1.50 (m, 6H) 1.63-1.86 (m, 3H) 2.06 (s, 1H) 2.22-2.48 (m, 2H) 3.73 (dd, J=8.16, 3.89 Hz, 1H) 3.92 (d, J=10.29 Hz, 1H) 3.88-3.96 (m, 1H) 5.06 (d, J=10.79 Hz, 1H) 5.33 (dd, J=15.06, 9.79 Hz, 1H) 5.49 (dd, J=15.06, 9.79 Hz, 1H) 6.40 (d, J=1.00 Hz, 1H) 6.37-6.44 (m, 1H) 7.20 (s, 3H).

$^{13}$C NMR (100 MHz, CHLOROFORM-d) δ ppm −4.9, −4.8, 6.8, 7.1, 16.5, 18.1, 19.3, 22.9, 25.8, 29.0, 36.9, 40.4, 40.6, 70.2, 76.7, 78.2, 79.3, 80.8, 83.8, 128.9, 138.4, 143.8, 168.7.

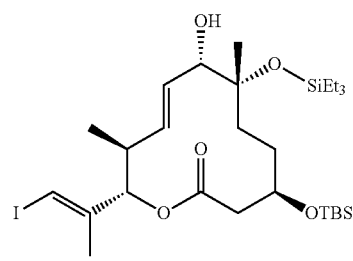

OOO-A $^1$H NMR (400 MHz, CHLOROFORM-d) δ ppm −0.03-0.02 (m, 6H) 0.47-0.68 (m, 6H) 0.78-0.95 (m, 21H) 1.15-1.35 (m, 6H) 1.37-1.58 (m, 7H) 1.66-1.80 (m, 3H) 2.24-2.48

(m, 3H) 2.56 (d, J=10.79 Hz, 1H) 3.49 (t, J=10.16 Hz, 1H) 3.64-3.80 (m, 1H) 5.05 (d, J=10.54 Hz, 1H) 5.29 (dd, J=15.31, 9.79 Hz, 1H) 5.53 (dd, J=15.31, 9.54 Hz, 1H) 6.38 (d, J=1.00 Hz, 1H) 7.19 (s, 3H).

$^{13}$C NMR (101 MHz, CHLOROFORM-d) δ ppm −4.8, −4.7, 6.8, 7.1, 16.6, 18.1, 19.2, 24.6, 25.7, 25.8, 30.7, 37.8, 40.6, 41.0, 70.8, 77.2, 77.8, 77.9, 80.5, 83.6, 130.9, 135.6, 143.9, 168.6. NNN-B and OOO-B were isolated using similar procedures starting from III-B

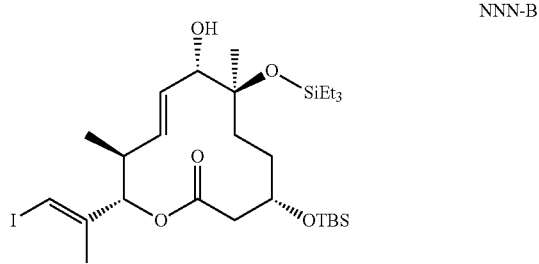

NNN-B $^1$H NMR (400 MHz, CHLOROFORM-d) δ ppm −0.06-0.04 (m, 6H) −0.02-0.02 (m, 6H) 0.48-0.66 (m, 6H) 0.77-0.94 (m, 20H) 1.16-1.25 (m, 4H) 1.26-1.44 (m, 2H) 1.50 (s, 2H) 1.56-1.72 (m, 2H) 1.74-1.80 (m, 3H) 2.04 (s, 1H) 2.29-2.49 (m, 3H) 2.40-2.50 (m, 1H) 3.80-4.02 (m, 1H) 4.24 (td, J=6.34, 2.64 Hz, 1H) 5.16 (d, J=10.54 Hz, 1H) 5.31-5.41 (m, 2H) 6.39 (d, J=1.00 Hz, 1H) 7.20 (s, 1H).

$^{13}$C NMR (100 MHz, CHLOROFORM-d) δ ppm −5.2, −4.8, 6.7, 7.2, 16.5, 18.0, 19.2, 23.1, 25.8, 26.5, 32.1, 40.6, 40.9, 68.5, 77.2, 78.0, 79.0, 80.0, 83.7, 129.5, 137.9, 143.8, 170.1.

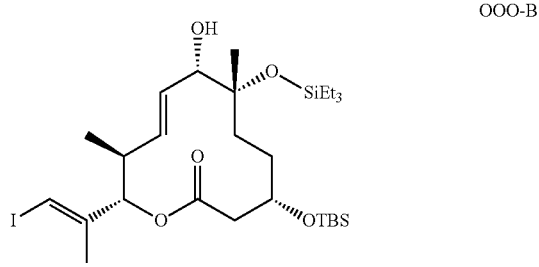

OOO-B $^1$H NMR (400 MHz, CHLOROFORM-d) δ ppm −0.03-0.04 (m, 6H) 0.49-0.70 (m, 6H) 0.78-0.98 (m, 21H) 1.13-1.35 (m, 7H) 1.51 (s, 3H), 1.55-1.67 (m, 1H) 1.69-1.88 (m, 4H) 2.31-2.52 (m, 3H) 2.60 (d, J=11.04 Hz, 1H) 3.45 (t, J=10.29 Hz, 1H) 4.16-4.32 (m, 1H) 5.05-5.25, (m, 2H) 5.57 (dd, J=15.31, 9.79 Hz, 1H) 6.40 (d, J=1.00 Hz, 1H) 7.22 (s, 1H).

$^{13}$C NMR (100 MHz, CHLOROFORM-d) δ ppm −4.90, 6.8, 6.9, 6.9, 7.1, 7.2, 16.4, 17.8, 19.1, 24.3, 25.6, 25.8, 28.1, 29.7, 31.6, 40.4, 41.2, 67.8, 77.2, 77.7, 78.0, 79.9, 83.6, 131.6, 134.6, 143.9, 170.0.

Step 11: To a solution of NNN-A (1.0 equiv.) in THF (0.1M) at room temperature was added the corresponding 4,4,5,5-tetramethyl-2-vinyl-1,3,2-dioxaborolane (2.0 equiv.), monosilver(I) monosilver(III) monooxide (5.0 equiv.), triphenylarsine (1.2 equiv.), and tetrakis(triphenylphosphine) palladium (0.15 equiv.). The reaction mixture was heated at 60° C. for 30 minutes, or until the reaction was determined to be complete by LCMS or TLC. Upon completion, the reaction was cooled down to room temperature, the mixture was then filtered through Celite®, washed with dichloromethane and concentrated in vacuo. The crude material was purified by silica gel chromatography (dichloromethane/methanol as eluent) to afford the desired product (PPP-A)

Step 12: To a solution of alcohol PPP-A (1.0 equiv.) in dichloromethane (0.1M) at room temperature was added DMAP (0.5 equiv.) followed by 4-nitrophenyl chloroformate (2.0 equiv.). The reaction was stirred at room temperature for three hours. Next, the corresponding amine (3.0 equiv.) was added at room temperature. After stirring for one hour, the reaction was quenched with water and diluted with dichloromethane. The organic layer was washed with 1N sodium hydroxide solution, and the organic layer was concentrated. The resulting oil was purified by silica gel column chromatography (hexanes/ethyl acetate as eluent) to afford the desired product (QQQ-A).

Step 13: To a solution of silyl ether QQQ-A (1 equiv.) in methanol (0.1M) at room temperature was added p-methoxytoluenesulfonic acid (1.5 equiv.). The reaction was stirred for 3 hours, or until the reaction was determined to be complete by LCMS or TLC. The reaction was quenched with sodium bicarbonate, diluted with ethyl acetate, washed with water, brine, dried over magnesium sulfate, filtered, and concentrated in vacuo. The resulting oil was purified by silica gel column chromatography (dichloromethane/methanol as eluent) to afford the desired product (RRR-A).

Other diastereoisomers (OOO-A, NNN-B and OOO-B) were subjected to the procedures to afford compounds 139-142.

Exemplified Protocol for the Synthesis of Compound 140

Steps 1-5 as above.

Step 6: To a solution of alcohol III-A (0.14 g, 0.3 mmol, 1.0 equiv) in DMF (3.2 mL, 0.09M) at room temperature was added 1H-imidazole (0.10 g, 1.5 mmol, 5.0 equiv.) and tert-butylchlorodimethylsilane (0.11 g, 0.75 mmol, 2.5 equiv.). The reaction was stirred under nitrogen at room temperature for 3 hours. The reaction was diluted with brine and extracted with ethyl acetate. The combined organic fractions were dried over sodium sulfate, filtered, and concentrated in vacuo. The resulting residue was purified by silica gel column chromatography (hexanes/ethyl acetate as eluent) to afford the desired product (JJJ-A, 0.16 g, 0.27 mmol, 92%).

Step 7: To a cooled solution of JJJ-A (0.16 g, 0.27 mmol, 1.0 equiv.) in THF (0.9M) at 0° C. was added hydrogen peroxide (0.25 mL, 2.3 mmol, 30%, 7.6 equiv.), followed by a solution of lithium hydroxide (0.06 g, 2.4 mmol, 8.0 equiv.) in water (3.0 mL, 0.8M). The reaction was stirred at 0° C. for 1 hour and then at room temperature for 3 hours. The reaction was quenched with sodium thiosulfate. The mixture was extracted with ethyl acetate, acidified to pH 3, and extracted with ethyl acetate. The organic layer was dried over sodium sulfate, filtered, and concentrated in vacuo. The residue was purified by silica gel column chromatography (hexanes/ethyl acetate as eluent) to afford the desired acid (KKK-A, 0.10 g, 0.24 mmol, 80%).

Step 8: To a solution of acid KKK-A (0.10 g, 0.24 mmol, 1.0 equiv.) and (3S,4S,E)-1-iodo-2,4-dimethylhexa-1,5-dien-3-ol (0.16 g, 0.45 mmol, 1.9 equiv.) in dichloromethane (3.0 mL, 0.08M) at room temperature was added 1-ethyl-3-(3-dimethylaminopropyl)carbodiimide (0.06 g, 0.31 mmol, 1.3 equiv) and one crystal of DMAP. The reaction was stirred at room temperature for 16 hours and determined to be complete by TLC. The reaction was concentrated in vacuo and the residue was purified by silica gel column chromatography (hexane/ethyl acetate) to afford the desired ester (LLL-A, 0.17 g, 0.25 mmol, >95%).

Step 9: To a degassed solution of olefin LLL-A (41.0 mg, 0.06 mmol, 1.0 equiv.) and benzoquinone (0.4 mg, 0.003 mmol, 0.05 equiv) in toluene (6.0 mL, 0.01M) under nitrogen at 20° C. was added the Hoveyda-Grubbs catalyst (4.0 mg, 0.006 mmol, 0.1 equiv.). The reaction was stirred at 50° C. for 2 hours or until the reaction was determined to be complete by LCMS or TLC. The reaction was diluted with ethyl acetate, and the organic layer was washed with sodium bicarbonate, water, brine, dried over magnesium sulfate, filtered, and concentrated in vacuo. The crude macrocycle (MMM-A) was carried on to the next step without further purification.

Step 10: To a solution of macrocycle MMM-A (1.0 equiv.) in dioxane (2 mL, 0.1M) under nitrogen was added selenium dioxide (30.0 mg, 0.25 mmol, 4.0 equiv.) under nitrogen at room temperature. The reaction was stirred at 85° C. for 20 hours. The reaction was diluted with ethyl acetate, and the organic layer was washed with sodium bicarbonate, water, brine, dried over magnesium sulfate, filtered, and concentrated in vacuo. The residue was purified by silica gel column chromatography (ethyl acetate/hexanes as eluent) to afford the desired separable diastereoisomer products as (NNN-A, 5.5 mg, 0.008 mmol, 13%) and (OOO-A, 6.4 mg, 0.010 mmol, 16%).

Step 11: To a solution of NNN-A (10.0 mg, 0.015 mmol, 1.0 equiv.) in THF (1.0 mL, 0.01M) at room temperature was added (R,E)-2-methyl-4-(4,4,5,5-tetramethyl-1,3,2-dioxaborolan-2-yl)but-3-en-1-yl pyrrolidine-1-carboxylate (18.0 mg, 0.06 mmol, 3.8 equiv.), monosilver(I) monosilver(III) monooxide (14.2 mg, 0.06 mmol, 4.0 equiv.), triphenylarsine (5.6 mg, 0.02 mmol, 1.2 equiv.), and tetrakis(triphenylphosphine) palladium (2.1 mg, 0.002 mmol, 0.15 equiv.). The reaction mixture was heated to 60° C. for 30 minutes, or until the reaction was determined to be complete by LCMS or TLC. Upon completion, the reaction was cooled down to room temperature, the mixture was then filtered through Celite®, washed with dichloromethane and concentrated in vacuo. The crude material was purified by silica gel chromatography (dichloromethane/methanol as eluent) to afford the desired product (PPP-A, 5.3 mg, 0.006 mmol, 80%).

Step 12: To a solution of alcohol PPP-A (5.0 mg, 0.007 mmol, 1.0 equiv.) in dichloromethane (0.5 mL, 0.01M) at room temperature was added N,N-dimethylaminopyridine (0.4 mg, 0.003 mmol, 0.5 equiv.) followed by 4-nitrophenyl chloroformate (5.0 mg, 0.02 mmol, 3.5 equiv.). The reaction was stirred at room temperature for three hours. Next, N-methyl piperazine (0.004 mL, 0.03 mmol, 4.5 equiv.) was added at room temperature. After stirring for one hour, the reaction was quenched with water and diluted with dichloromethane. The organic layer was washed with 1N sodium hydroxide solution, and the organic layer was concentrated. The resulting crude carbamate (QQQ-A) was used in the nest step without further purification.

Step 13: To a solution of carbamate QQQ-A (1.0 equiv.) in methanol (0.1M) at room temperature was added p-methoxytoluenesulfonic acid (2.7 mg, 0.014 mmol, 2.0 equiv.). The reaction was stirred for 3 hours, or until the reaction was determined to be complete by LCMS or TLC. The reaction was quenched with sodium bicarbonate, diluted with ethyl acetate, washed with water, brine, dried over magnesium sulfate, filtered, and concentrated in vacuo. The resulting oil was purified by silica gel column chromatography (dichloromethane/methanol as eluent) to afford the desired product (compound 140, 2.7 mg, 0.005 mmol, 63%).
$^1$H NMR (400 MHz, CHLOROFORM-d) δ: 0.00 (s, 1H) 0.06 (s, 1H) 0.65 (s, 1H) 0.74-0.96 (m, 3H) 0.98-1.18 (m, 3H) 1.18-1.45 (m, 5H) 1.61 (d, J=7.28 Hz, 1H) 1.68-1.81 (m, 2H) 1.84 (br. s., 3H) 2.05 (d, J=11.80 Hz, 2H) 2.37 (s, 4H) 2.44 (d, J=14.56 Hz, 2H) 2.50-2.77 (m, 5H) 3.13 (d, J=18.32 Hz, 1H) 3.24 (d, J=6.27 Hz, 1H) 3.26-3.42 (m, 3H) 3.31 (br. s., 1H) 3.37 (br. s., 2H) 3.56 (br. s., 2H) 3.48-3.64 (m, 3H) 3.64 (br. s., 1H) 3.70 (d, J=2.26 Hz, 1H) 3.82-4.03 (m, 2H) 5.16 (dd, J=10.04, 8.03 Hz, 2H) 5.29 (s, 1H) 5.39 (dd, J=14.93, 10.16 Hz, 1H), 5.52-5.75 (m, 2H) 6.09 (d, J=11.29 Hz, 1H) 6.17-6.40 (m, 1H) 6.98 (s, 1H) 7.25 (s, 5H) 7.51 (s, 1H).

TABLE 6

Compounds 139-142

| Structure, Compound#, and Chemical Name | $^1$H NMR data | LCMS data (ES+) |
|---|---|---|
| 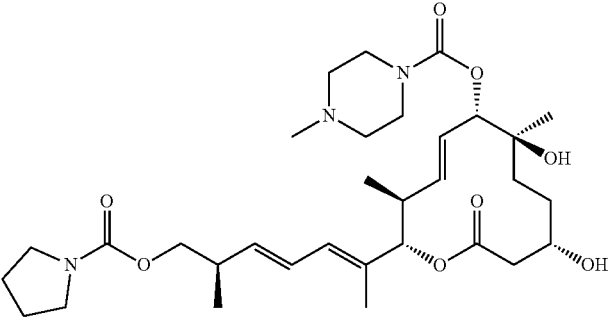<br>139<br>[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | $^1$H NMR (400 MHz, CHLOROFORM-d) δ: 0.00 (s, 1 H) 0.72-0.91 (m, 4 H) 0.92-1.09 (m, 4 H) 1.10-1.30 (m, 4 H) 1.34-1.56 (m, 3 H) 1.56-1.69 (m, 4 H) 1.72-1.81 (m, 4 H) 1.84 (br. s., 1 H) 2.22-2.40 (m, 5 H) 2.40-2.57 (m, 7 H) 3.05 (s, 2 H) 3.09 (s, 1 H) 3.19 (br. s., 1 H) 3.22-3.28 (m, 2 H) 3.31 (br. s., 2 H) 3.49 (br. s., 4 H) 3.64 (s, 1 H) 3.78-4.01 (m, 2 H) 4.31 (br. s., 1 H) 4.89-5.11 (m, 2 H) 5.35 (dd, J = 15.31,10.04 Hz, 1 H) 5.51 (dd, J = 14.81, 9.79 Hz, 1 H) 5.62 (dd, J = 15.06, 7.53 Hz, 1 H) 6.03 (d, J = 10.79 Hz, 1 H) 6.20 (dd, J = 14.93, 10.92 Hz, 1 H) 7.19 (s, 2H) | |

TABLE 6-continued

Compounds 139-142

| Structure, Compound#, and Chemical Name | ¹H NMR data | LCMS data (ES+) |
|---|---|---|
| 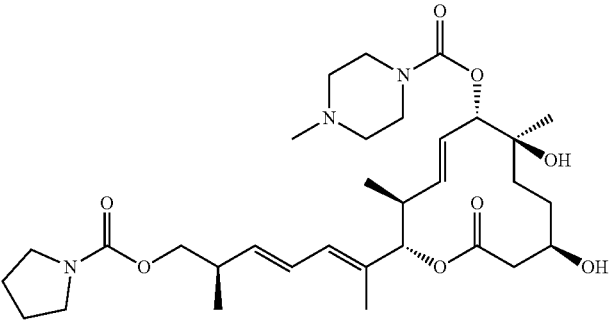<br>140<br><br>[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.00 (s, 1 H) 0.06 (s, 1 H) 0.65 (s, 1 H) 0.74-0.96 (m, 3 H) 0.98-1.18 (m, 3 H) 1.18-1.45 (m, 5H) 1.61 (d, J = 7.28 Hz, 1 H) 1.68-1.81 (m, 2 H) 1.84 (br. s., 3 H) 2.05 (d, J = 11.80 Hz, 2 H) 2.37 (s, 4 H) 2.44 (d, J = 14.56 Hz, 2 H) 2.50-2.77 (m, 5 H) 3.13 (d, J = 18.32 Hz, 1 H) 3.24 (d, J = 6.27 Hz, 1 H) 3.26-3.42 (m, 3 H) 3.31 (br. s., 1 H) 3.37 (br. s., 2 H) 3.56 (br. s., 2 H) 3.48-3.64 (m, 3H) 3.64 (br. s., 1 H) 3.70 (d, J = 2.26 Hz, 1 H) 3.82-4.03 (m, 2 H) 5.16 (dd, J = 10.04, 8.03 Hz, 2 H) 5.29 (s, 1 H) 5.39 (dd, J = 14.93, 10.16 Hz, 1 H), 5.52-5.75 (m, 2 H) 6.09 (d, J = 11.29 Hz, 1 H) 6.17-6.40 (m, 1 H) 6.98 (s, 1 H) 7.25 (s, 5 H) 7.51 (s, 1 H) | |
| 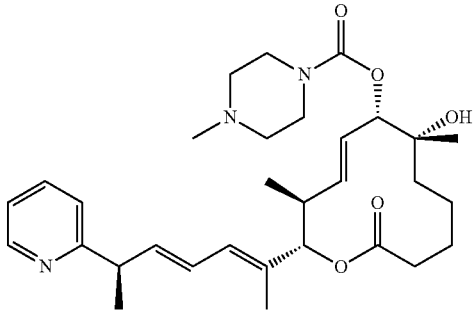<br>141<br><br>[(2S,3S,4E,6S,7S)-7-hydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate | ¹H NMR (400 MHz, METHANOL-d4) δ: 0.87 (d, J = 6.78 Hz, 3 H) 1.16-1.25 (m, 5 H) 1.45 (d, J = 7.03 Hz, 5 H) 1.77 (s, 3 H) 1.81-1.91 (m, 1 H) 1.92-2.10 (m, 1 H) 2.26-2.38 (m, 2 H) 2.45 (s, 3 H) 2.55-2.65 (m, 5 H) 3.43-3.85 (m, 5 H) 4.94 (d, J = 9.79 Hz, 1 H) 5.09 (d, J = 10.67 Hz, 1 H) 5.53 (dd, J = 15.06, 9.91 Hz, 1 H) 5.73 (m, J = 9.66 Hz, 1 H) 6.00 (dd, J = 15.18, 7.53 Hz, 1 H) 6.13 (d, J = 10.67 Hz, 1 H) 6.39 (dd, J = 15.06, 10.79 Hz, 1 H) 7.26-7.30 (m, 1 H) 7.35 (d, J = 7.91 Hz, 1 H) 7.79 (td, J = 7.72, 1.76 Hz, 1 H) 8.46 (d, J = 4.52 Hz, 1 H) | 562.3 |
| 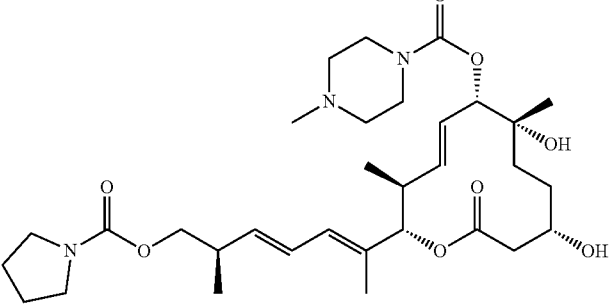<br>142<br><br>[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.00 (s, 1 H) 0.65-0.90 (m, 3 H) 0.91-1.07 (m, 3 H) 1.09-1.24 (m, 3 H) 1.28-1.45 (m, 2 H) 1.46-1.74 (m, 6 H) 1.78 (br. s., 4 H) 2.03 (br. s., 5 H) 2.35 (s, 4 H) 2.40-2.55 (m, 6 H) 2.82 (s, 1 H) 2.89 (s, 1 H) 3.25 (d, J = 5.27 Hz, 2 H) 3.31 (br. s., 2 H) 3.54 (br. s., 3 H) 3.89 (qd, J = 10.71, 6.78 Hz, 2 H) 4.30 (br. s., 1 H) 4.94 (dd, J = 18.07, 10.04 Hz, 2 H) 5.48 (dd, J = 15.31, 10.04 Hz, 1 H) 5.55-5.83 (m, 2 H) 5.55-5.72 (m, 1 H) 6.02 (d, J = 11.29 Hz, 1 H) 6.20 (dd, J = 14.31, 11.04 Hz, 1 H) 6.93 (s, 1 H) 7.19 (s, 6 H) 7.45 (s, 1 H) | |

Synthesis of Sulfone Intermediates for Preparation of Urea Compounds

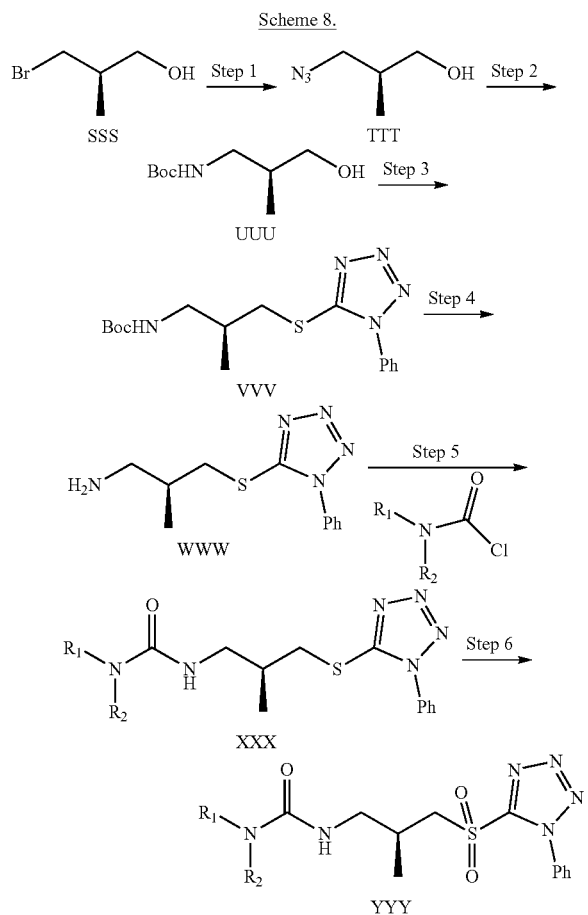

General Protocol for the Synthesis of Sulfone Urea Side Chain

Step 1: To a solution of R(−)-3-bromo-2-methyl-1-propanol SSS (4.0 g, 26.1 mmol, 1.0 equiv.) in DMF (20.0 mL, 1.3M), was added sodium azide (5.1 g, 78.4 mmol, 3.0 equiv.). The mixture was warmed up to 100° C. and stirred at 100° C. for 4 hours, or until the reaction was determined to be complete by LCMS or TLC. After cooling down to room temperature, the mixture was filtered to remove solid, and washed with diethyl ether. The filtrate was washed with water and brine. After drying over sodium sulfate, filtration and evaporation of the solvent, the crude azido derivative (TTT, 2.4 g, 20.8 mmol, 78%) was used in the next step.

Step 2: To the mixture of (S)-3-azido-2-methylpropan-1-ol TTT (2.4 g, 20.8 mmol, 1.0 equiv.) and BOC-anhydride (6.8 g, 31.3 mmol, 1.5 equiv.) in THF (100 mL, 0.2M) under nitrogen was added Pd—C (2.2 g, 2.1 mmol, 0.1 equiv.). The reaction was purged and then placed under hydrogen atmosphere, and stirred for 16 hours, or until the reaction was determined to be complete by LCMS or TLC. The reaction atmosphere was substituted with nitrogen and the precipitate was removed via filtration through Celite®. The Celite® was washed with MeOH and the solvent was removed under reduced pressure. The crude material was purified by silica gel column chromatography (hexane/ethyl acetate) to give the desired product (UUU, 2.6 g, 13.8 mmol, 66%).

Step 3: To the solution of Boc-protected amine UUU (2.6 g, 13.8 mmol, 1.0 equiv.), 1-phenyl-1H-tetrazole-5-thiol (2.6 g, 14.5 mmol, 1.05 equiv.) and triphenylphosphine (3.8 g, 14.5 mmol, 1.05 equiv.) in THF (100 mL, 0.1M) at 0° C., DIAD (3.2 ml, 16.5 mmol, 1.2 equiv.) was added dropwise. The reaction mixture maintained at 0° C. and stirred for 2 hours, or until the reaction was determined to be complete by LCMS or TLC. The reaction mixture was then diluted with ethyl acetate, and washed with water and brine. After drying over sodium sulfate, filtration and evaporation of solvent, the crude material was purified via silica gel (hexane/ethyl acetate) to give the desired product (VVV, 4.3 g, 12.2 mmol, 89%).

Step 4: To the solution of the tetrazole VVV (0.4 g, 1.1 mmol, 1.0 equiv.) in dichloromethane (7.0 mL, 0.14M) at 0° C., trifluoroacetic acid (3.5 mL, 45.4 mmol, 40.0 equiv.) was added. The reaction mixture was allowed to warm up to 23° C. and stirred for 1 hour, or until the reaction was determined to be complete by LCMS or TLC. The solvent was removed under reduced pressure, and the reaction was diluted with ethyl acetate. The organic layer was washed with sodium bicarbonate and brine. After drying over sodium sulfate, filtration and evaporation of the solvent, the crude amine (WWW, 0.3 g, 1.0 mmol, 90%) was used in the next step.

Step 5: To the solution of the amine WWW (1.0 equiv.) in dichloromethane (0.1M) at 0° C., diisopropylethylamine (4.0 equiv.) and the corresponding carbamic chloride (2.0 equiv.) were added and stirred for 2 hours at the same temperature. Once completion of reaction was confirmed by LCMS or TLC, the solution was diluted with dichloromethane. The organic layer was washed with ammonium chloride, sodium bicarbonate, and brine. After drying with sodium sulfate, filtration and evaporation of the solvent, the crude was purified with silica gel (dichloromethane/methanol) to give the desired urea (XXX).

Step 6: To a solution of urea XXX (1.0 equiv.) in ethanol (0.1M) at 0° C. was added dropwise a premixed yellow solution of ammonium molybdate tetrahydrate (0.3 equiv.) in 33% hydrogen peroxide (10 equiv.). The reaction mixture was allowed to warm up to room temperature and stirred for 4 hours, or until the reaction was determined to be complete by LCMS or TLC. The reaction mixture was diluted in ethyl acetate then sodium thiosulfate was added at 0° C. and stirred for 20 minutes. The organic layer was then washed with water, brine, and dried over sodium sulfate. After evaporation of the solvent, the residue was purified by silica gel column chromatography (dichloromethane/methanol) to give the desired sulfone (YYY).

Exemplified Protocol for the Synthesis of (S)—N-(2-methyl-3-((1-phenyl-1H-tetrazol-5-yl)sulfonyl)propyl)pyrrolidine-1-carboxamide.

Steps 1-4 as above.

Step 5: To the solution of the amine WWW (0.1 g, 0.4 mmol, 1 equiv.) in dichloromethane (4.4 mL, 0.1M) at 0° C., diisopropylethylamine (0.3 mL, 1.7 mmol, 4 equiv.) and pyrrolidine-1-carbonyl chloride (0.1 mL, 0.8 mmol, 2.0 equiv.) were added and stirred for an additional 2 hours at the same temperature. Once completion of reaction was confirmed by LCMS or TLC, the solution was diluted with dichloromethane. The organic layer was washed with ammonium chloride, sodium bicarbonate, and brine. After drying with sodium sulfate, filtration and evaporation of the solvent, the crude was purified by silica gel column chromatography (dichloromethane/methanol) to give the desired urea (XXX, 0.13 g, 0.4 mmol, 91%).

Step 6: To a solution of product urea XXX (0.1 g, 0.4 mmol, 1.0 equiv.) in ethanol (3.0 mL, 0.1M) at 0° C. was added dropwise a premixed yellow solution of ammonium molybdate tetrahydrate (0.1 g, 0.12 mmol, 0.3 equiv.) in 33% hydrogen peroxide (0.4 mL, 4.0 mmol, 10 equiv.). The reaction mixture was allowed to warm up to room temperature and stirred for 4 hours, or until the reaction was determined to be complete by LCMS or TLC. The reaction mixture was diluted in ethyl acetate and sodium thiosulfate was added at 0° C. Stirring was continued for an additional 20 minutes. The organic layer was then washed with water, brine, and dried over sodium sulfate. After evaporation of the solvent, the residue was purified by silica gel column chromatography (dichloromethane/methanol) to give the desired sulfone, (S)—N-(2-methyl-3-((1-phenyl-1H-tetrazol-5-yl)sulfonyl)propyl)pyrrolidine-1-carboxamide (0.1 g, 0.28 mmol, 68%).

Compounds 143 and 144 were prepared using sulfone YYY according to Scheme 9.

General Protocol for the Synthesis of Urea Compounds 143-144

Step 1: To a solution of sulfone YYY (2.5 equiv.) in THF (0.02M) under nitrogen at −78° C. was added KHMDS (2.5 equiv.) dropwise and the reaction was stirred for 20 minutes. Then aldehyde L (1.0 equiv.) in THF (0.5 M) was added dropwise. The reaction was stirred at −78° C. for 90 minutes and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (ZZZ).

Step 2: To a solution of product ZZZ (1.0 equiv.) in methanol (0.1M) was added p-toluenesulfonic acid (3.0 equiv.) at room temperature. The reaction was stirred for 2 hours, or until the reaction was determined to be complete

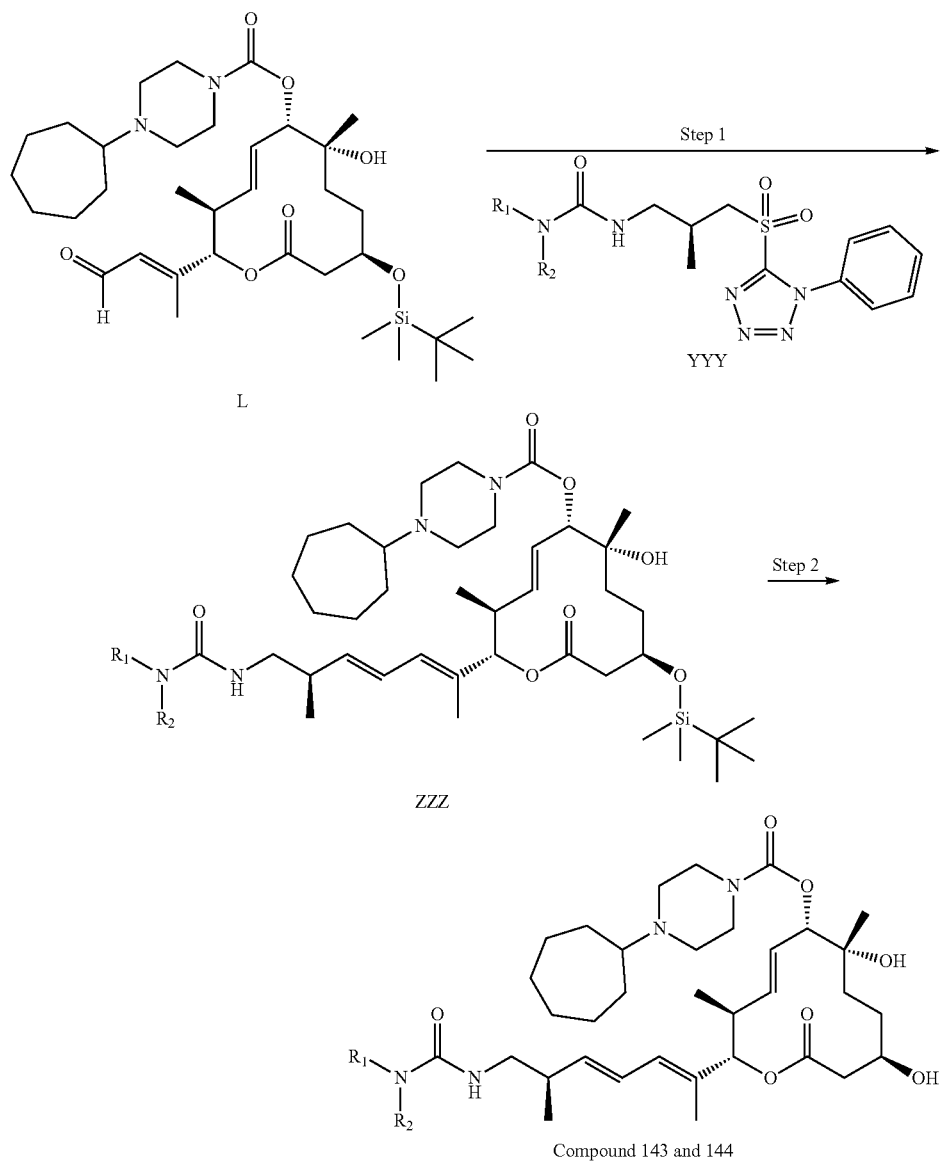

Scheme 9.

Compound 143 and 144 by LCMS or TLC. The reaction was quenched with sodium bicarbonate. The mixture was diluted with EtOAc. The aqueous layer was extracted with EtOAc. The combined organic layers were washed with brine, dried over sodium sulfate and concentrated in vacuo. The crude residue was purified by silica gel column chromatography (dichloromethane/methanol as eluent) to afford the desired product (compounds 143-144).

Exemplified Protocol for the Synthesis of Urea Compound 143

Step 1: To a solution of (S)—N-(2-methyl-3-((1-phenyl-1H-tetrazol-5-yl)sulfonyl)propyl)pyrrolidine-1-carboxamide YYY (43.7 mg, 0.12 mmol, 2.5 equiv.) in THF (3.0 mL, 0.02M) under nitrogen at −78° C. was added dropwise KHMDS (0.23 mL, 0.12 mmol, 2.5 equiv.) and the reaction was stirred for 20 minutes. Then aldehyde L (30.0 mg, 0.05 mmol, 1.0 equiv.) in THF was added dropwise. The reaction was stirred at −78° C. for 90 minutes and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (ZZZ, 23.3 mg, 0.03 mmol, 63%).

Step 2: To a solution of product ZZZ (23.3 mg, 0.03 mmol, 1.0 equiv.) in methanol (3.0 mL, 0.1M) was added p-toluenesulfonic acid (16.6 mg, 0.09 mmol, 3.0 equiv.) at room temperature. The reaction was stirred for 2 hours, or until the reaction was determined to be complete by LCMS or TLC. The reaction was quenched with sodium bicarbonate. The mixture was diluted with EtOAc. The aqueous layer was extracted with EtOAc. The combined organic layers were washed with brine, dried over sodium sulfate and concentrated in vacuo. The crude residue was purified by silica gel column chromatography (dichloromethane/methanol as eluent) to afford the desired product (compound 143, 15.6 mg, 0.02 mmol, 78%). $^1$H NMR (400 MHz, CHLOROFORM-d) δ: 0.91 (d, J=6.78 Hz, 3H) 0.99-1.08 (d, J=6.65 Hz, 3H) 1.27 (d, J=5.27 Hz, 3H) 1.30-1.61 (m, 17H) 1.90 (s, 3H) 1.60-2.06 (m, 3H) 2.45-2.67 (m, 4H) 2.70-2.84 (m, 5H) 2.84-2.97 (m, 1H) 2.95-3.13 (m, 1H) 3.22-3.36 (m, 4H) 3.61-3.71 (m, 4H) 3.73-3.81 (m, 1H) 5.02 (d, J=9.41 Hz, 1H) 5.16 (d, J=10.67 Hz, 1H) 5.56-5.75 (m, 3H) 6.06-6.12 (d, J=10.92 Hz, 1H) 6.27 (dd, J=15.12, 11.11 Hz, 1H). MS (ES+)=687.6 [M+H]$^+$.

Compound 145 was prepared by the method of Scheme 10.

Scheme 9

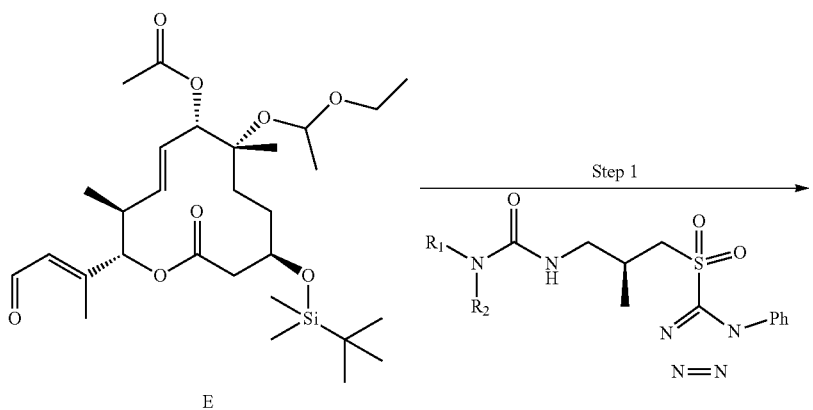

E

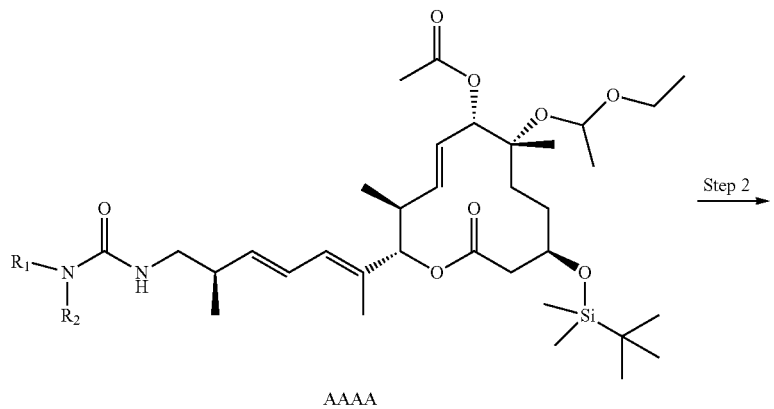

AAAA

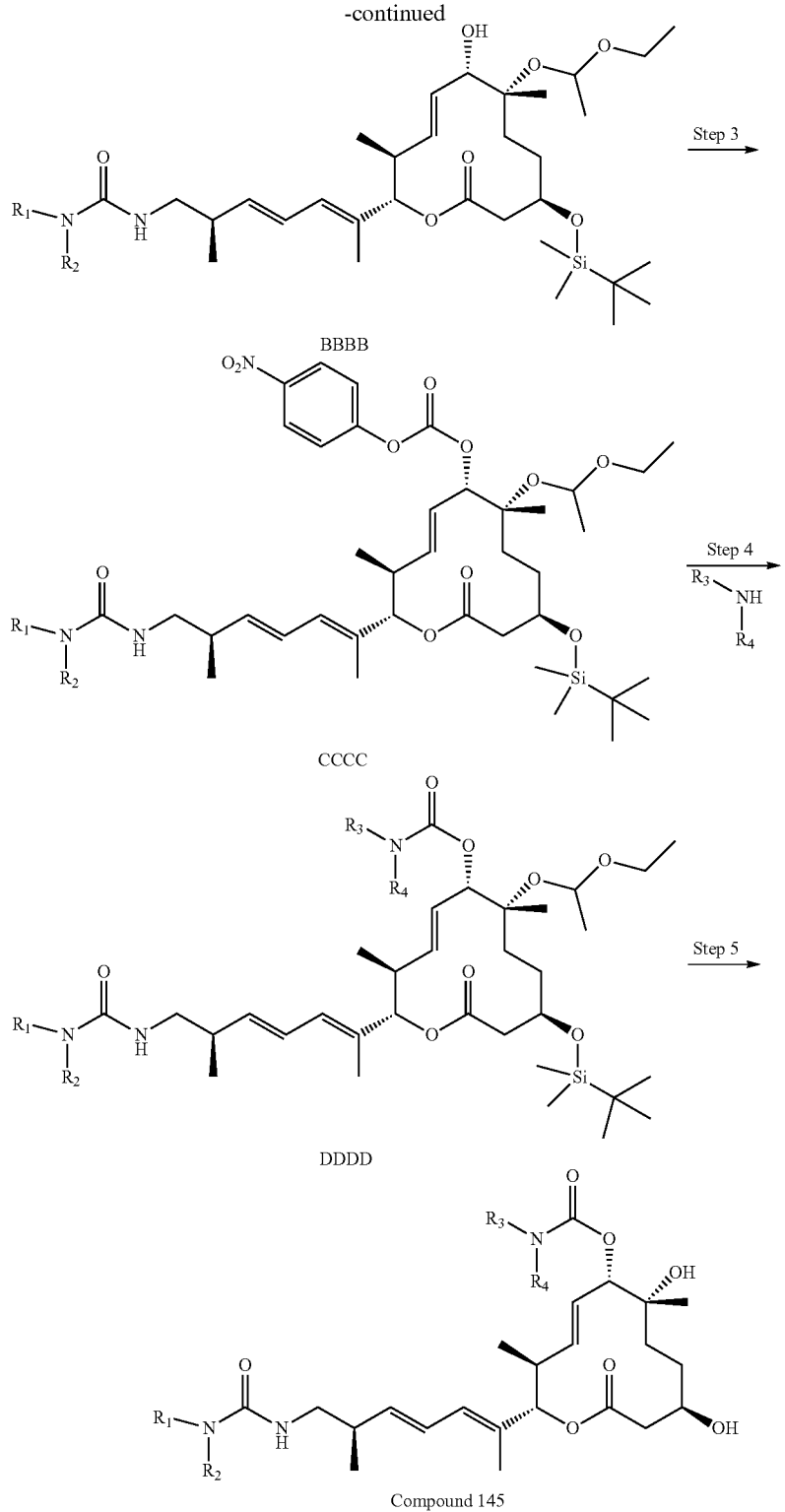

Compound 145

Exemplified Protocol for the Synthesis of Urea Compound 145

Step 1: To a solution of (S)—N-(2-methyl-3-((1-phenyl-1H-tetrazol-5-yl)sulfonyl)propyl)pyrrolidine-1-carboxamide (34.1 mg, 0.09 mmol, 2.5 equiv.) in THF (2.0 mL, 0.02M) under nitrogen at −78° C. was added KHMDS (0.18 mL, 0.09 mmol, 2.5 equiv.) dropwise and the reaction was stirred for 20 minutes. Then aldehyde E (20.0 mg, 0.04 mmol, 1.0 equiv.) in THF (0.5 M) was added dropwise. The reaction was stirred at −78° C. for 90 minutes and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (AAAA, 15.8 mg, 0.02 mmol, 62%).

Step 2: To a solution of urea AAAA (25.2 mg, 0.04 mmol, 1.0 equiv.) in methanol (3.0 mL, 0.01M) was added potassium carbonate (14.8 mg, 0.11 mmol, 3.0 equiv.) and stirred at room temperature. After 3 hours, or until the reaction was determined to be complete by LCMS or TLC, the reaction was quenched with ammonium chloride at 0° C. The mixture was then diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired secondary alcohol (BBBB, 26.0 mg, 0.04 mmol, >95%).

Step 3: To a solution of alcohol BBBB (26.0 mg, 0.04 mmol, 1.0 equiv.) in dichloromethane (2.0 mL, 0.1M) was added diisopropylethylamine (0.05 mL, 0.27 mmol, 7.0 equiv.) and DMAP (1.4 mg, 0.01 mmol, 0.3 equiv.) at 0° C. Then a solution of 4-nitrophenyl carbonochloridate (31.5 mg, 0.16 mmol, 4.0 equiv.) in dichloromethane (0.1M) was added slowly. The reaction was warmed up to room temperature and stirred for 3 hours, or until the reaction was determined to be complete by LCMS or TLC. The reaction was quenched with sodium bicarbonate and diluted with dichloromethane. The aqueous layer was extracted with dichloromethane. The combined organic layers were washed with brine, dried over sodium sulfate and concentrated in vacuo. The crude protected carbonate (CCCC) was used in the next step without further purification.

Step 4: To a solution of carbonate CCCC (1.0 equiv.) in THF (0.1M) at room temperature was added N-methylpiperazine (0.04 mL, 0.4 mmol, 10.0 equiv.) at room temperature. After stirring for one hour, or until the reaction was determined to be complete by LCMS or TLC, the reaction was quenched with water and diluted with ethyl acetate, washed with 1N sodium hydroxide solution, and the organic layer was concentrated. The resulting oil was purified by silica gel column chromatography (dichloromethane/methanol as eluent) to afford the desired product (DDDD, 15.1 mg, 0.02 mmol, 49%).

Step 5: To a solution of carbamate DDDD (15.2 mg, 0.02 mmol, 1.0 equiv.) in methanol (2.0 mL, 0.01M) at room temperature was added p-methoxytoluenesulfonic acid (11.0 mg, 0.06 mmol, 3.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 145, 4.5 mg, 0.008 mmol, 39%). $^1$H NMR (400 MHz, CHLOROFORM-d) δ: 0.73-0.89 (m, 3H) 0.90-1.04 (m, 3H) 1.08-1.33 (m, 6H) 1.40-1.58 (m, 2H) 1.59-1.71 (m, 4H) 1.75-1.90 (m, 4H) 2.24 (s, 3H) 2.31 (br. s., 3H) 2.34-2.57 (m, 3H) 2.90-3.16 (m, 1H) 3.16-3.30 (m, 4H) 3.37-3.50 (m, 4H) 3.53-3.77 (m, 1H) 4.13 (t, J=5.77 Hz, 1H) 4.95 (d, J=9.54 Hz, 1H) 5.08 (d, J=10.79 Hz, 1H) 5.49-5.67 (m, 2H) 6.02 (d, J=11.04 Hz, 1H) 6.10-6.34 (m, 1H). MS (ES+)=605.5 [M+H]$^+$.

Compound 146 was prepared by the method of Scheme 11

Scheme 11.

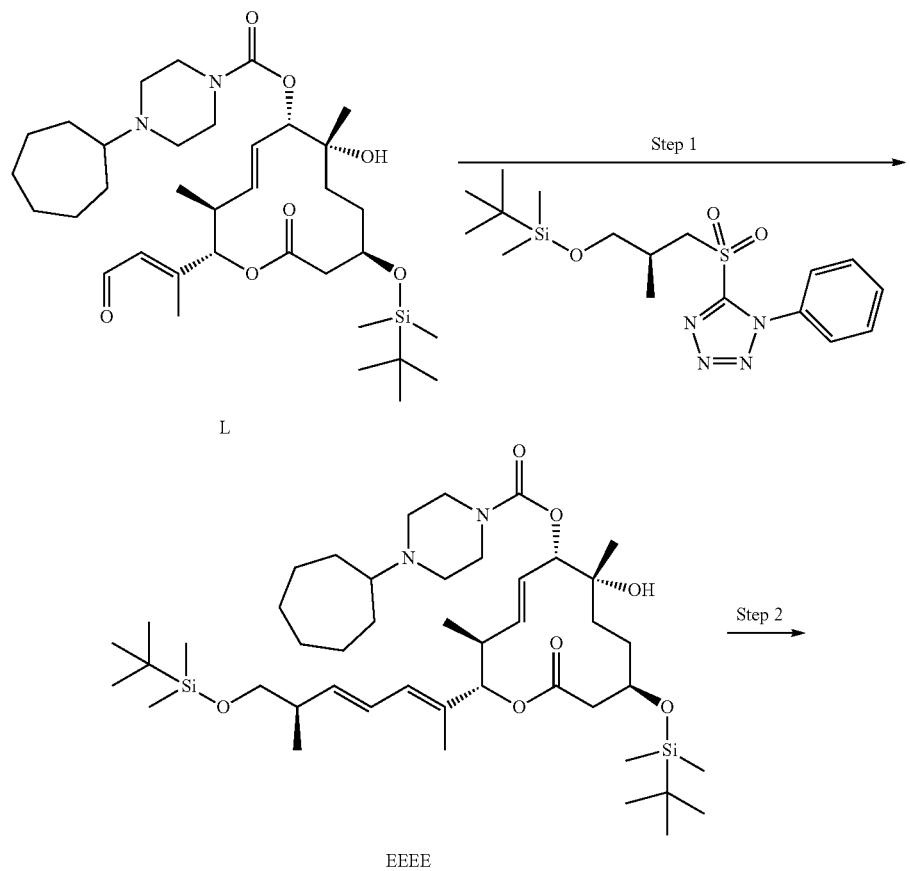

-continued
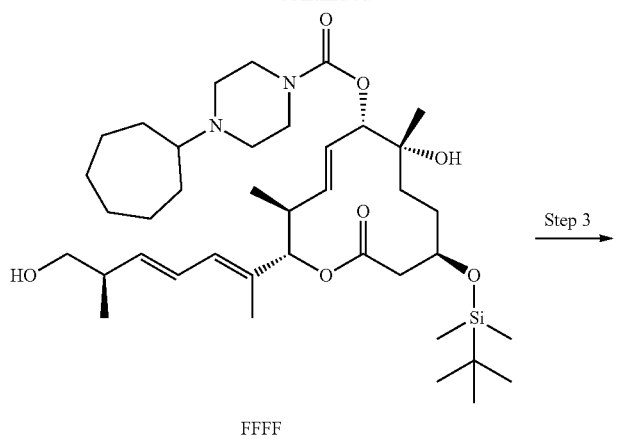
FFFF
Step 3
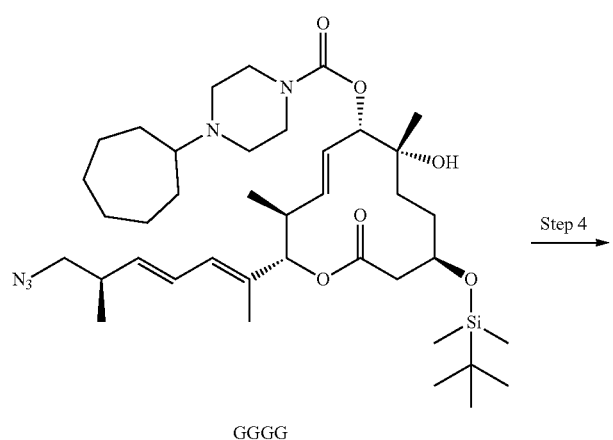
GGGG
Step 4
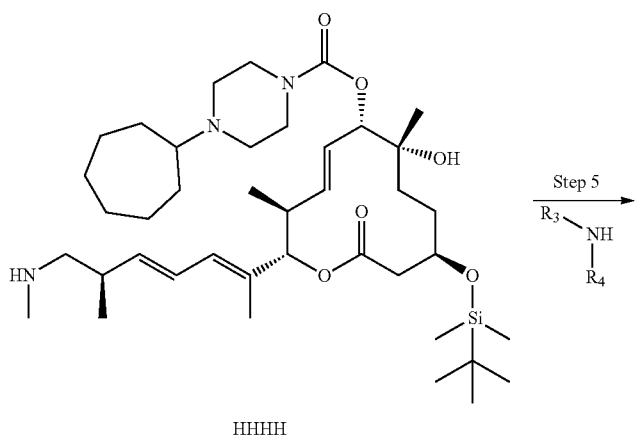
HHHH
Step 5
R₃—NH—R₄

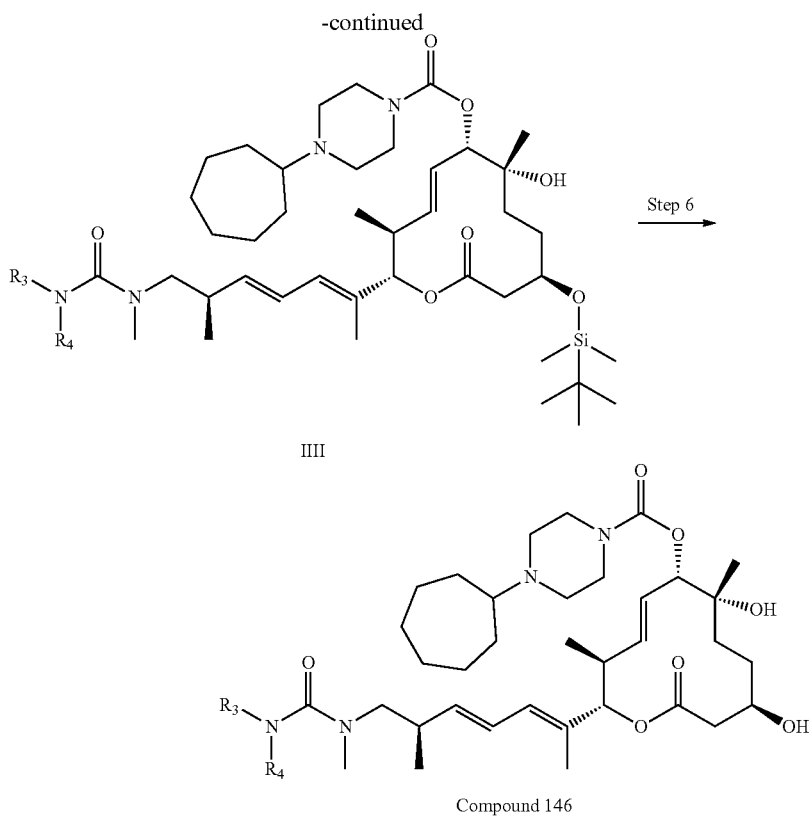

Compound 146

Exemplified Protocol for the Synthesis of Urea Compound 146

Step 1: To a solution of (S)-5-((3-((tert-butyldimethylsily) oxy)-2-methylpropyl)sulfonyl)-1-phenyl-1H-tetrazole (29.3 mg, 0.07 mmol, 2.0 equiv.) in THF (2.0 mL, 0.02M) under nitrogen at −78° C. was added KHMDS (0.15 mL, 0.07 mmol, 2.0 equiv.) dropwise and the reaction was stirred for 20 minutes. Then aldehyde L (24.0 mg, 0.04 mmol, 1.0 equiv.) in THF (0.5 M) was added dropwise. The reaction was stirred at −78° C. for 90 minutes and then allowed to warm to −20° C. over 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired diene (EEEE, 15.6 mg, 0.02 mmol, 51.5%).

Step 2: To a solution of diene EEEE (15.6 mg, 0.02 mmol, 1.0 equiv.) in methanol (2.0 mL, 0.02M) was added p-toluenesulfonic acid (2.3 mg, 0.01 mmol, 0.6 equiv.) at room temperature. The reaction was stirred for 2 hours, or until the reaction was determined to be complete by LCMS or TLC. The reaction was quenched with sodium bicarbonate. The mixture was diluted with ethyl acetate. The aqueous layer was extracted with ethyl acetate. The combined organic layers were washed with brine, dried over sodium sulfate and concentrated in vacuo. The crude residue was purified by silica gel column chromatography (hexanes/ethyl acetate as eluent) to afford the desired alcohol (FFFF, 9.0 mg, 0.01 mmol, 60%).

Step 3: To a solution of alcohol FFFF (7.5 mg, 0.01 mmol, 1.0 equiv.) in dichloromethane (1.0 mL, 0.01M) was added DMAP (1.6 mg, 0.01 mmol, 1.3 equiv.) and tosyl chloride (2.0 mg, 0.01 mmol, 1.0 equiv.) at 0° C. The reaction was warmed up to room temperature and the reaction was stirred for 24 hours, or until the reaction was determined to be complete by LCMS or TLC. The reaction was then quenched with water and washed with brine. After drying over sodium sulfate, filtration and evaporation of solvent, the crude tosylate (1 equiv.) was then dissolved in DMF (1.0 mL, 0.01M) and sodium azide (2.7 mg, 0.04 mmol, 4.0 equiv.) was added. The reaction was warmed to 70° C. and stirred for 4 hours, or until the reaction was determined to be complete by LCMS or TLC. Upon completion, the excess of solvent was removed and the crude material was purified by silica gel column chromatography (dichloromethane/methanol as eluent) to afford the desired azide (GGGG, 6.0 mg, 0.01 mmol, 96%).

Step 4: To a solution of dichloromethane (1.0 mL, 0.01M) containing azide GGGG (7.5 mg, 0.01 mmol, 1.0 equiv.) was added a trimethylphosphine (0.02 mL, 0.02 mmol, 2.0 equiv.) toluene solution (1M) at room temperature. The reaction was stirred for 3 hours, or until the reaction was determined to be complete by LCMS or TLC. Paraformaldehyde (1.5 mg, 0.05 mmol, 5.0 equiv.) was added at room temperature and the mixture was stirred for 5 hours, or until the reaction was determined to be complete by LCMS or TLC. Methanol was added (1 mL/1.0 equiv. of GGGG) and the reaction was cooled to 0° C. Sodium borohydride (2.0 mg, 0.05 mmol, 5.0 equiv.) was added and the reaction was stirred at 0° C. for 1 hour or until the reaction was determined to be complete by LCMS or TLC. The reaction was then quenched with sodium bicarbonate, extracted with dichloromethane, and dried over sodium sulfate. After filtration and evaporation, the crude amine (HHHH, 7.4 mg, 0.01 mmol, >95%) was used in the next step without further purification.

Step 5: To a solution of amine HHHH (7.0 mg, 0.01 mmol, 1 equiv.) in dichloromethane (1.0 mL, 0.01M) was added triethylamine (0.005 mL, 0.04 mmol, 4.0 equiv.) at room temperature. The reaction mixture was then cooled down to 0° C. and then pyrrolidine-1-carbonyl chloride (2.6 mg, 0.02 mmol, 2.0 equiv.) was added slowly. After warming up to room temperature, the reaction was stirred for 3 hours, or until the reaction was determined to be complete by LCMS or TLC. Upon completion of the reaction, excess of solvent was removed and crude material was then purified using silica gel chromatography (dichloromethane/methanol as eluent) to afford the desired urea (IIII, 2.5 mg, 0.003 mmol, 32%).

Step 6: A solution of urea IIII (2.5 mg, 0.003 mmol, 1.0 equiv.) in methanol (2.0 mL, 0.01M) at room temperature was added p-methoxytoluenesulfonic acid (1.2 mg, 0.006 mmol, 2.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 146, 1.8 mg, 0.003 mmol, 84%). $^1$H NMR (400 MHz, CHLOROFORM-d) δ: 0.84-1.08 (m, 10H) 1.25-1.41 (m, 9H) 1.44-1.68 (m, 8H) 1.70-1.85 (m, 5H) 1.88-2.05 (m, 3H) 2.42-2.65 (m, 6H) 2.80-2.95 (m, 6H) 3.08-3.18 (m, 2H) 3.54-3.73 (m, 5H) 3.78 (br. s., 1H) 4.94 (d, J=9.66 Hz, 1H) 5.04 (d, J=10.67 Hz, 1H) 5.54-5.63 (m, 2H) 5.66-5.77 (m, 1H) 6.08 (d, J=11.04 Hz, 1H) 6.31 (dd, J=14.87, 10.98 Hz, 1H), MS (ES+)=701.4 [M+H]$^+$.

TABLE 7

Compounds 143-146

| Structure, Compound #, and Chemical Name | $^1$H NMR data | LCMS data (ES+) |
|---|---|---|
| 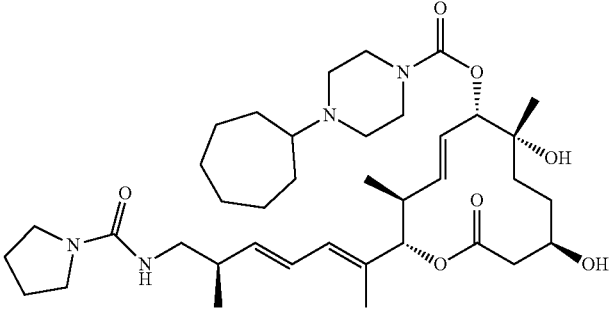<br>143<br>[(2S,3S,4E,6S,7S,10S)-7,10-dihydroxy-3,7-dimethyl-2-[(2E,4E,6R)-6-methyl-7-(pyrrolidine-1-carbonylamino)hepta-2,4-dien-2-yl]-12-oxo-1-oxacyclododec-4-en-6-yl] 4-cycloheptylpiperazine-1-carboxylate | $^1$H NMR (400 MHz, CHLOROFORM-d) δ: 0.91 (d, J = 6.78 Hz, 3 H) 0.99-1.08 (d, J = 6.65 Hz, 3 H) 1.27 (d, J = 5.27 Hz, 3 H) 1.30-1.61 (m, 17 H) 1.90 (s, 3 H) 1.60-2.06 (m, 3 H) 2.45-2.67 (m, 4 H) 2.70-2.84 (m, 5 H) 2.84-2.97 (m, 1 H) 2.95-3.13 (m, 1 H) 3.22-3.36 (m, 4 H) 3.61-3.71 (m, 4 H) 3.73-3.81 (m, 1 H) 5.02 (d, J = 9.41 Hz, 1 H) 5.16 (d, J = 10.67 Hz, 1 H) 5.56-5.75 (m, 3 H) 6.06-6.12 (d, J = 10.92 Hz, 1 H) 6.27 (dd, J = 15.12, 11.11 Hz, 1 H) | 687.6 |
| 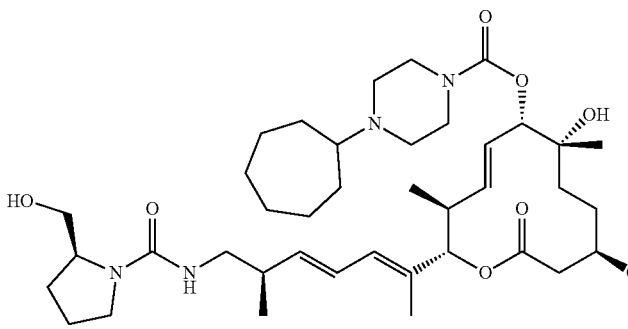<br>144<br>[(2S,3S,4E,6S,7S,10S)-7,10-dihydroxy-2-[(2E,4E,6R)-7-[[(2R)-2-(hydroxymethyl)pyrrolidine-1-carbonyl]amino]-6-methylhepta-2,4-dien-2-yl]-3,7-dimethyl-12-oxo-1-oxacyclododec-4-en-6-yl] 4-cycloheptylpiperazine-1-carboxylate | $^1$H NMR (400 MHz, CHLOROFORM-d) δ: 0.71-0.92 (m, 4 H) 0.93-1.13 (m, 4 H) 1.15-1.25 (m, 5 H) 1.27 (br. s., 1 H) 1.30-1.54 (m, 12 H) 1.56-1.67 (m, 7 H) 1.69-1.76 (m, 2 H) 1.80-1.95 (m, 3 H) 2.36-2.57 (m, 8 H) 2.98 (ddd, J = 13.18, 8.03, 4.89 Hz, 1 H) 3.09 (s, 1 H) 3.14-3.33 (m, 3 H) 3.33-3.49 (m, 6 H) 3.57 (d, J = 10.29 Hz, 1 H) 3.61-3.82 (m, 1 H) 3.86-4.13 (m, 1 H) 4.49 (br. s., 1 H) 4.94 (d, J = 9.54 Hz, 2 H) 5.08 (d, J = 10.54 Hz, 1 H) 5.46-5.68 (m, 3 H) 6.02 (d, J = 11.04 Hz, 1 H) 6.20 (dd, J = 15.18, 10.67 Hz, 1 H) | 717.7 |

TABLE 7-continued

Compounds 143-146

| Structure, Compound #, and Chemical Name | ¹H NMR data | LCMS data (ES+) |
|---|---|---|
| 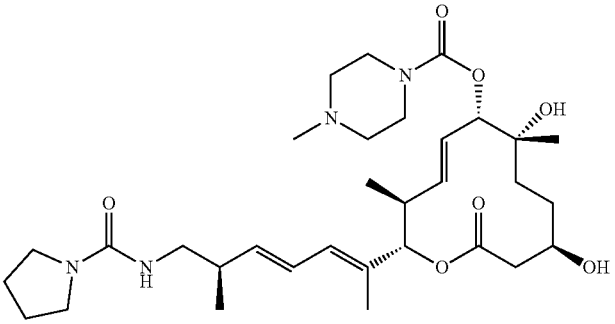<br>145<br>[(2S,3S,4E,6S,7S,10S)-7,10-dihydroxy-3,7-dimethyl-2-[(2E,4E,6R)-6-methyl-7-(pyrrolidine-1-carbonylamino)hepta-2,4-dien-2-yl]-12-oxo-1-oxacyclododec-4-en-6-yl] 4-methylpiperazine-1-carboxylate | ¹H NMR (400 MHz, CHLOROFORM-d) δ: 0.73-0.89 (m, 3 H) 0.90-1.04 (m, 3 H) 1.08-1.33 (m, 6 H) 1.40-1.58 (m, 2 H) 1.59-1.71 (m, 4 H) 1.75-1.90 (m, 4 H) 2.24 (s, 3 H) 2.31 (br. s., 3 H) 2.34-2.57 (m, 3 H) 2.90-3.16 (m, 1 H) 3.16-3.30 (m, 4 H) 3.37-3.50 (m, 4 H) 3.53-3.77 (m, 1 H) 4.13 (t, J = 5.77 Hz, 1 H) 4.95 (d, J = 9.54 Hz, 1 H) 5.08 (d, J = 10.79 Hz, 1 H) 5.49-5.67 (m, 2 H) 6.02 (d, J = 11.04 Hz, 1 H) 6.10-6.34 (m, 1 H) | 605.5 |
| 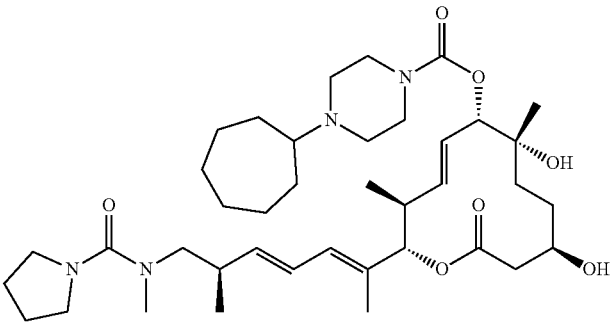<br>146<br>[(2S,3S,4E,6S,7S,10S)-7,10-dihydroxy-3,7-dimethyl-2-[(2E,4E,6R)-6-methyl-7-[methyl(pyrrolidine-1-carbonyl)amino]hepta-2,4-dien-2-yl]-12-oxo-1-oxacyclododec-4-en-6-yl] 4-cycloheptylpiperazine-1-carboxylate | ¹H NMR (400 MHz, CHLOROFORM-d) δ: 0.84-1.08 (m, 10 H) 1.25-1.41 (m, 9 H) 1.44-1.68 (m, 8 H) 1.70-1.85 (m, 5 H) 1.88-2.05 (m, 3 H) 2.42-2.65 (m, 6 H) 2.80-2.95 (m, 6 H) 3.08-3.18 (m, 2 H) 3.54-3.73 (m, 5 H) 3.78 (br. s., 1 H) 4.94 (d, J = 9.66 Hz, 1 H) 5.04 (d, J = 10.67 Hz, 1 H) 5.54-5.63 (m, 2 H) 5.66-5.77 (m, 1 H) 6.08 (d, J = 11.04 Hz, 1 H) 6.31 (dd, J = 14.87, 10.98 Hz, 1 H) | 701.4 |

Compound 147 was prepared as shown in Scheme 12.

Scheme 12.

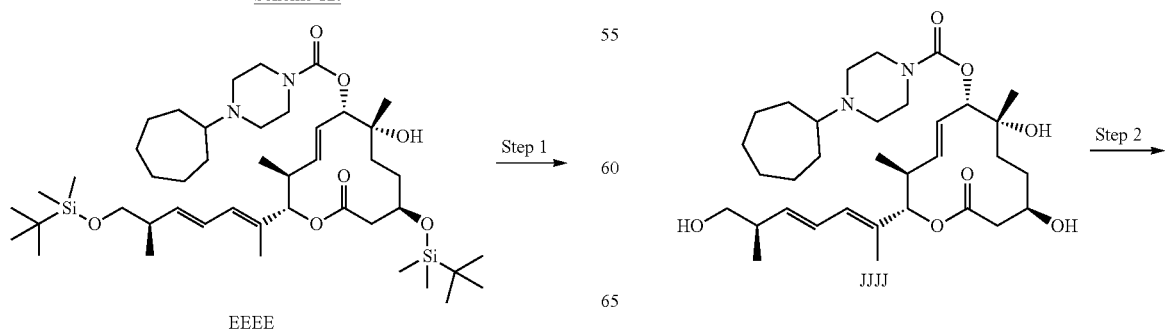

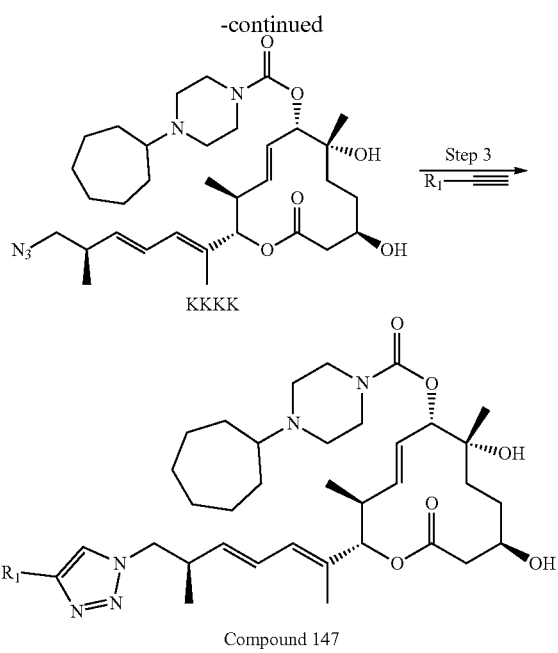

Protocol for the Synthesis of Compound 147

Step 1: To a solution of compound diene EEEE (22.0 mg, 0.03 mmol, 1.0 equiv.) in methanol (2.0 mL, 0.01M) was added p-toluenesulfonic acid (15.5 mg, 0.08 mmol, 3.0 equiv.) at room temperature. The reaction was stirred for 2 hours, or until the reaction was determined to be complete by LCMS or TLC. The reaction was quenched with sodium bicarbonate. The mixture was diluted with EtOAc. The aqueous layer was extracted with EtOAc. The combined organic layers were washed with brine, dried over sodium sulfate and concentrated in vacuo. The crude residue was purified by silica gel chromatography (hexanes/ethyl acetate as eluent) to afford the desired diol (JJJJ, 5.0 mg, 0.008 mmol, 32%).

Step 2: To a solution of diene JJJJ (6.0 mg, 0.01 mmol, 1 equiv.) in dichloromethane (1.0 mL, 0.01M) was added DMAP (1.6 mg, 1.3 equiv.) and tosyl chloride (2.0 mg, 0.01 mmol, 1.0 equiv.) at 0° C. The reaction was warmed up to room temperature and the reaction was stirred for 24 hours, or until the reaction was determined to be complete by LCMS or TLC. The reaction was then quenched with water, and washed with brine. After drying over sodium sulfate, filtration and evaporation of solvent, the crude tosylate (1 equiv.) was then dissolved in DMF (1.0 mL, 0.01M) and sodium azide (2.6 mg, 0.04 mmol, 4.0 equiv.) was added. The reaction was warmed to 70° C. and stirred for 4 hours, or until the reaction was determined to be complete by LCMS or TLC. Upon completion, the excess of solvent was removed and the crude material was purified by silica gel chromatography (dichloromethane/methanol as eluent) to afford the desired azide (KKKK, 6.0 mg, 0.01 mmol, 96%).

Step 3: To a solution of product KKKK (5.0 mg, 0.008 mmol, 1.0 equiv.) in water/tert-butanol/dichloromethane (0.1M, 1/2/1, 0.25/0.5/0.25 mL) was added ethynylcyclopropane (2.2 mg, 0.03 mmol, 4.0 equiv.), copper (II) sulfate (2.0 mg, 0.01 mmol, 1.5 equiv.), and sodium (R)-5-((S)-1, 2-dihydroxyethyl)-4-hydroxy-2-oxo-2,5-dihydrofuran-3-olate (3.2 mg, 0.02 mmol, 2.0 equiv.). The reaction was stirred at room temperature for 7 hours, or until the reaction was determined to be complete by LCMS or TLC. Upon completion, the excess of solvent was removed and the crude material was purified by silica gel chromatography (dichloromethane/methanol as eluent) to afford the desired triazole (Compound 147, 2.5 mg, 0.004 mmol, 45%). $^1$H NMR (400 MHz, METHANOL-d4) 0.78-0.98 (m, 6H) 0.99-1.06 (m, 3H) 1.19-1.28 (m, 4H) 1.28-1.43 (m, 2H) 1.50-1.62 (m, 14H) 1.63-1.75 (m, 6H) 1.85-1.99 (m, 2H) 2.41-2.68 (m, 7H) 2.73-2.89 (m, 1H) 3.39-3.62 (m, 4H) 3.75 (br. s., 2H) 4.07-4.26 (m, 2H) 5.01 (d, J=9.54 Hz, 1H) 5.13 (d, J=10.67 Hz, 1H) 5.55-5.74 (m, 3H) 6.01-6.07 (m, 1H) 6.10-6.20 (m, 1H), MS (ES+)=683.5 [M+H]$^+$.

Compound 148 was prepared by the method of Scheme 13.

Scheme 13.

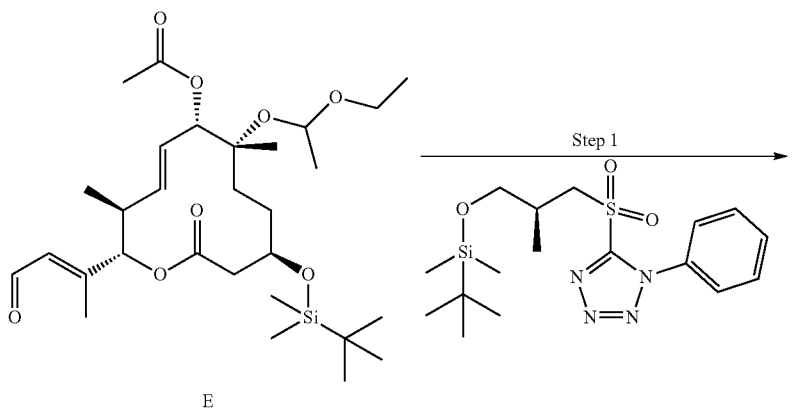

E

291
-continued
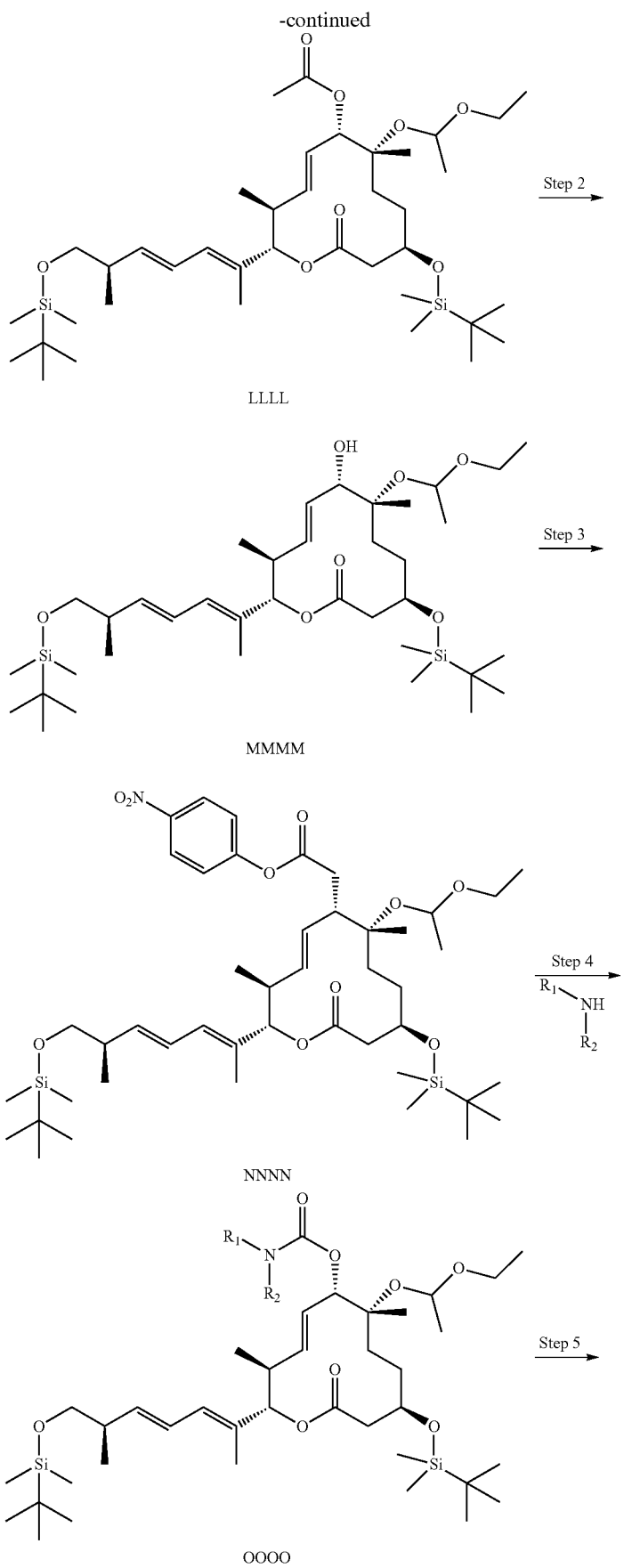
LLLL
MMMM
NNNN
OOOO
292

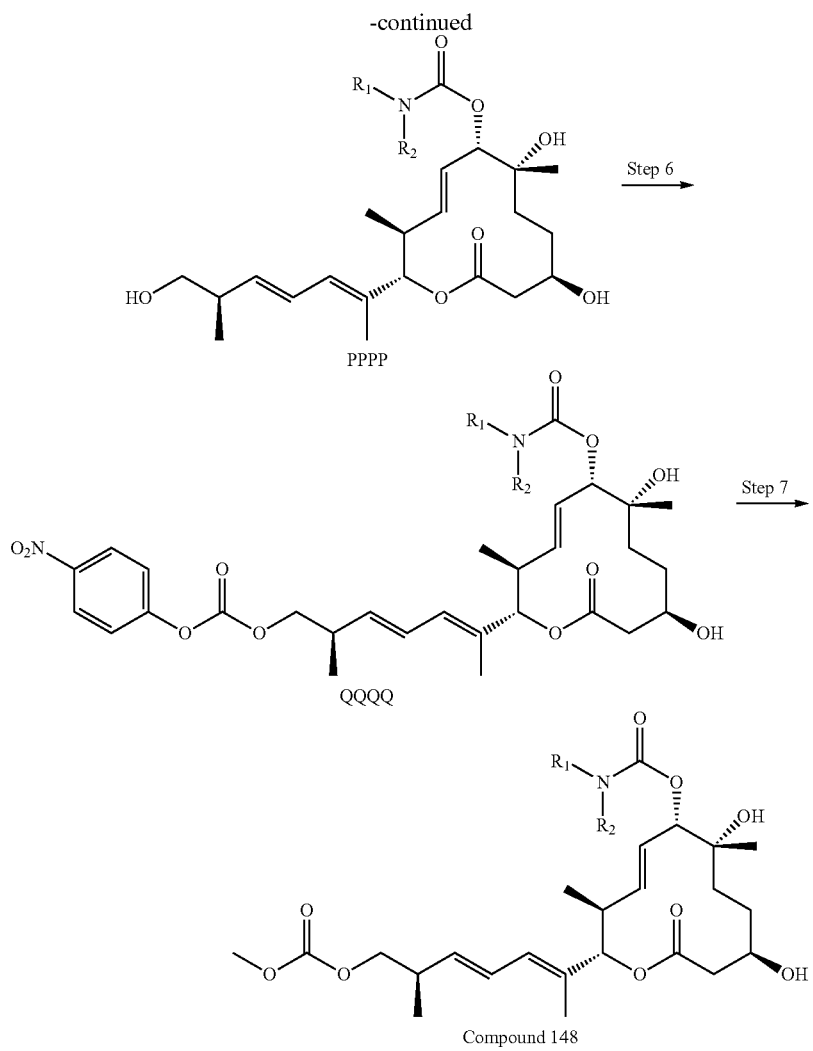

Protocol for the Synthesis of Compound 148

Step 1: To a solution of (S)-5-((3-((tert-butyldimethylsilyl)oxy)-2-methylpropyl)sulfonyl)-1-phenyl-1H-tetrazole (104.0 mg, 0.26 mmol, 2.5 equiv.) in THF (10.0 mL, 0.01M) under nitrogen at −78° C. was added KHMDS (0.52 mL, 0.26 mmol, 2.5 equiv.) dropwise and the reaction was stirred for 20 minutes. Then aldehyde E (58.0 mg, 0.1 mmol, 1.0 equiv.) in THF (0.5 M) was added dropwise. The reaction was stirred at −78° C. for 90 minutes and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired diene (LLLL, 45.0 mg, 0.06 mmol, 59%).

Step 2: To a solution of diene LLLL (40.0 mg, 0.05 mmol, 1.0 equiv.) in methanol (4.0 mL, 0.01M) was added potassium carbonate (19.1 mg, 0.14 mmol, 2.5 equiv.) and the reaction was stirred at room temperature. After 3 hours, or until the reaction was determined to be complete by LCMS or TLC, the reaction was quenched with ammonium chloride at 0° C. The mixture was then diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired secondary alcohol (MMMM, 40.0 mg, 0.06 mmol, >95%).

Step 3: To a solution of alcohol MMMM (40.0 mg, 0.06 mmol, 1.0 equiv.) in dichloromethane (6.0 mL, 0.01M) was added triethylamine (0.06 mL, 0.4 mmol, 7.0 equiv.), and DMAP (2.1 mg, 0.02 mmol, 0.3 equiv.) at 0° C. Then a solution of 4-nitrophenyl carbonochloridate (47.2 mg, 0.23 mmol, 4.0 equiv.) in dichloromethane (0.1M) was added slowly. The reaction was warmed up to room temperature and stirred for 3 hours, or until the reaction was determined to be complete by LCMS or TLC. The reaction was quenched with sodium bicarbonate and diluted with dichloromethane. The aqueous layer was extracted with dichloromethane. The combined organic layers were washed with brine, dried over sodium sulfate and concentrated in vacuo. The crude protected carbonate (NNNN) was used in the next step without further purification.

Step 4: To a solution of carbamate NNNN (1.0 equiv.) in THF (6.0 mL, 0.01M) at room temperature was added N-methyl piperazine (0.07 mL, 0.58 mmol, 10.0 equiv.). After stirring for one hour, or until the reaction was determined to be complete by LCMS or TLC, the reaction was quenched with water and diluted with EtOAc. The organic layer was washed with 1N sodium hydroxide solution and the organic layer was concentrated. The resulting oil was purified by silica gel column chromatography (dichloromethane/methanol as eluant) to afford the desired carbamate (OOOO, 37.0 mg, 0.04 mmol, 78%).

Step 5: To a solution of carbamate OOOO (37.0 mg, 0.05 mmol, 1.0 equiv.) in methanol (4.0 mL, 0.01M) at room temperature was added p-methoxytoluenesulfonic acid (19.1 mg, 0.1 mmol, 2.2 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired alcohol (PPPP, 18.5 mg, 0.04 mmol, 80%).

Step 6: To a solution of alcohol PPPP (45.0 mg, 0.09 mmol, 1.0 equiv.) in dichloromethane (1.0 mL, 0.08M) was added triethylamine (0.15 mL, 0.9 mmol, 10.0 equiv.), and DMAP (2.2 mg, 0.02 mmol, 0.2 equiv.) at 0° C. Then a solution of 4-nitrophenyl carbonochloridate (26.7 mg, 0.13 mmol, 1.5 equiv.) in dichloromethane (0.1M) was added slowly. The reaction was warmed up to room temperature and stirred for 3 hours, or until the reaction was determined to be complete by LCMS or TLC. The reaction was quenched with sodium bicarbonate and diluted with dichloromethane. The aqueous layer was extracted with dichloromethane. The combined organic layers were washed with brine, dried over sodium sulfate and concentrated in vacuo. The crude carbonate (QQQQ) was used in the next step without further purification.

Step 7: To a solution of carbonate QQQQ (1.0 equiv.) in dichloromethane (1.0 mL, 0.03M) at room temperature was added the require amine (5.0 equiv.) at room temperature. After stirring for one hour, or until the reaction was determined to be complete by LCMS or TLC, the mixture was concentrated. The resulting oil was purified by silica gel column chromatography (dichloromethane/methanol as eluant) to afford the corresponding carbamate and desired carbonate as a minor by product (compound 148, 1.0 mg, 0.002 mmol, 4.7%). $^1$H NMR (400 MHz, METHANOL-d4) δ: 0.91 (d, J=6.65 Hz, 3H) 1.09 (d, J=6.78 Hz, 3H) 1.11-1.19 (m, 1H) 1.23 (s, 3H) 1.30-1.46 (m, 3H) 1.50-1.69 (m, 2H) 1.77 (s, 3H) 2.40 (s, 3H) 2.46-2.71 (m, 7H) 3.41-3.70 (m, 4H) 3.75 (s, 3H) 3.78-3.84 (m, 1H) 3.92-4.09 (m, 2H) 4.96 (d, J=9.54 Hz, 1H) 5.07 (d, J=10.67 Hz, 1H) 5.53-5.81 (m, 3H) 6.11 (d, J=10.54 Hz, 1H) 6.38 (dd, J=15.00, 10.85 Hz, 1H), MS (ES+)=566.5 [M+H]$^+$.

Compound 149 was prepared according to Scheme 14.

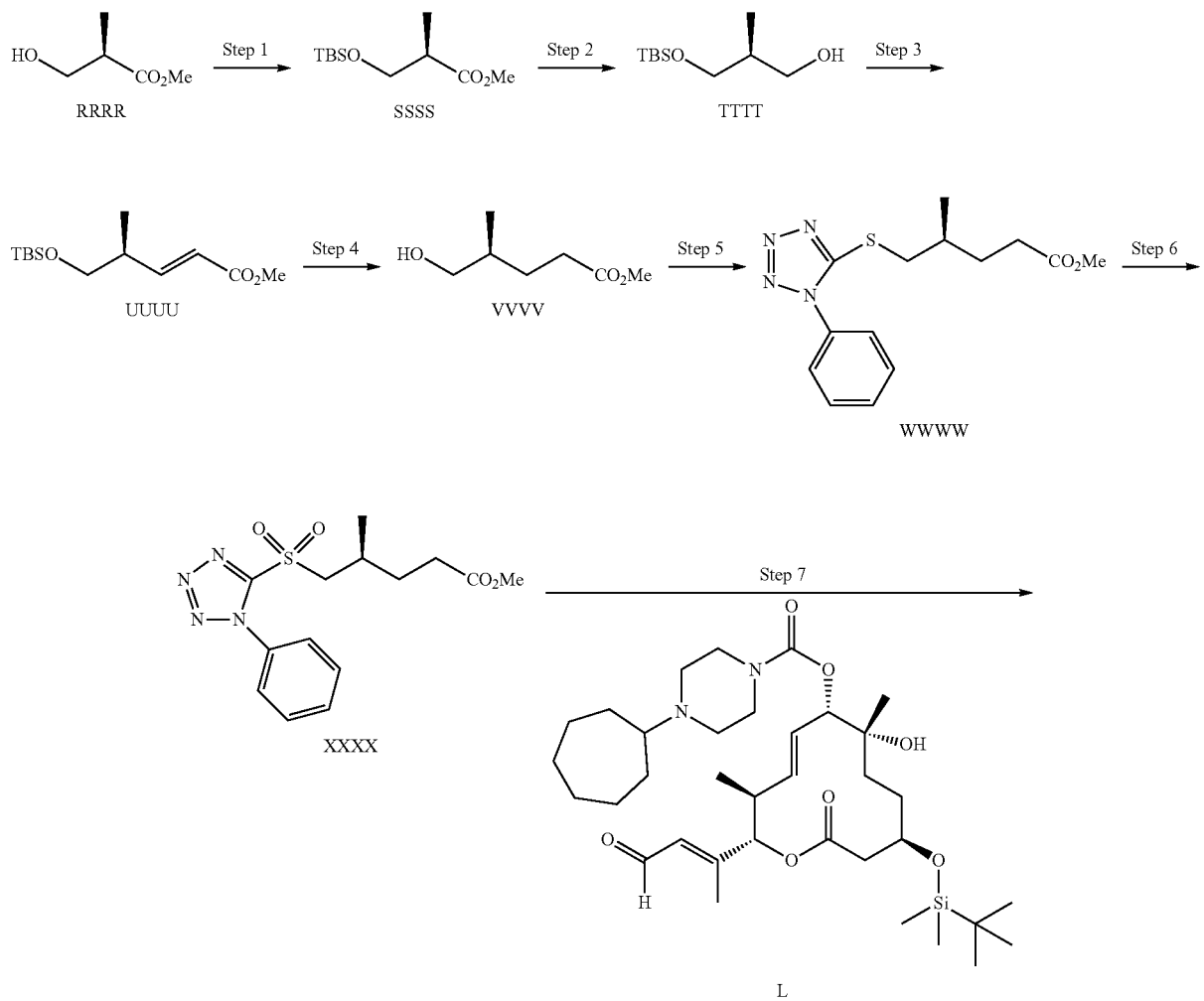

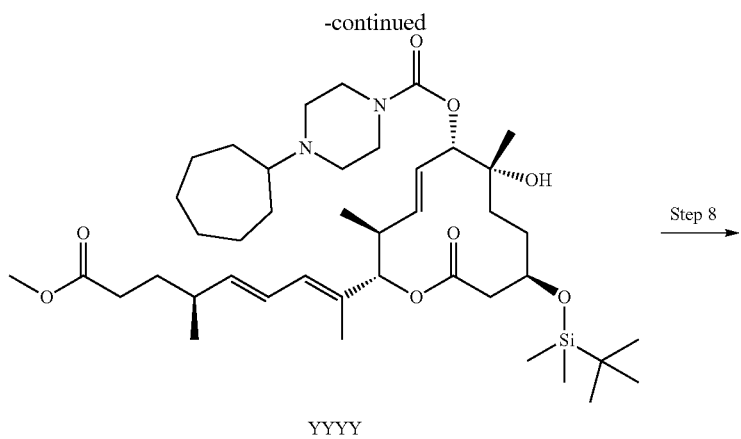

YYYY

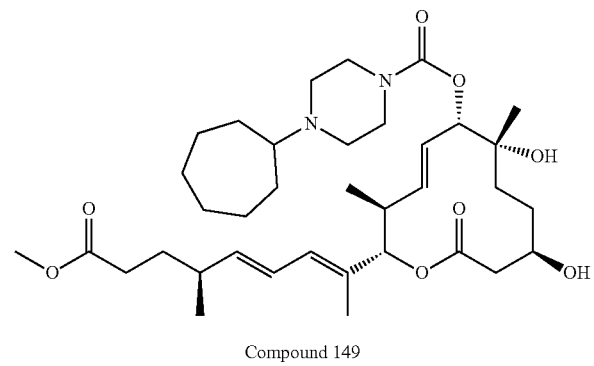

Compound 149

Protocol for the Synthesis of Compound 149

Step 1: To a solution of (R)-methyl 3-hydroxy-2-methylpropanoate RRRR (5.0 g, 42.3 mmol, 1.0 equiv.) in dichloromethane (125 mL, 0.3 M) was added imidazole (4.3 g, 63.5 mmol, 1.5 equiv.) followed by TBS-Cl (6.2 g, 63.5 mmol, 1.2 equiv.) and the reaction was stirred at room temperature for 6 hours, or until the reaction was determined to be complete by LCMS or TLC. The reaction was then quenched with water. The organic layer was then washed with brine and dried over sodium sulfate. After filtration, the solvent was removed in vacuo and the residue was purified by silica gel column chromatography (hexane/ethyl acetate as eluant) to afford the desired product to give the desired protected ester (SSSS, 7.0 g, 30.1 mmol, 71%).

Step 2: To a stirred solution of TBS protected ester SSSS (7.0 g, 30.1 mmol, 1.0 equiv.) in dry dichloromethane (80 mL, 0.2M) at −10° C. was added DIBAL-H (1.0 M solution in toluene, 75.3 mL, 75.3 mmol 2.5 equiv.) under nitrogen. The reaction mixture was stirred at 0° C. for 30 minutes and allowed to warm to room temperature and further stirred for an additional 2 hours, or until the reaction was determined to be complete by LCMS or TLC. After the excess DIBAL-H was decomposed with an excess of methanol, the mixture was poured into a sodium potassium tartrate solution (10 g in 100 mL water) with vigorous stirring until the layers were separated. The aqueous layer was extracted with diethyl ether and the combined organic extracts were washed with brine, dried over sodium sulfate and concentrated. The crude product was purified by silica gel column chromatography (hexane/ethyl acetate as eluant) to afford the desired product (TTTT, 4.8 g, 23.5 mmol, 78%).

Step 3: To a solution of TBS protected alcohol TTTT (1.0 g, 4.9 mmol, 1.0 equiv.) in dichloromethane (20 mL, 0.1M) was added sodium bicarbonate (0.8 g, 9.8 mmol, 2.0 equiv.) at room temperature. Then a solution of DMP (3.1 g, 7.3 mmol, 1.5 equiv.) in dichloromethane (5 mL) was added dropwise. The reaction was stirred for 2 hours, or until the reaction was determined to be complete by LCMS or TLC. The solvent was removed and the crude aldehyde was then quickly purified on a silica plug (hexane/ethyl acetate as eluant). The aldehyde was then dissolved in benzene (25 mL, 0.1M) and methyl (triphenylphosphoranylidene)acetate (1.6 g, 4.9 mmol, 1.0 equiv.) was added to the reaction at room temperature and the reaction was stirred for 10 hours, or until the reaction was determined to be complete by LCMS or TLC. After concentration, the residue was purified by silica gel column chromatography (hexane/ethyl acetate as eluant) to afford the desired ester (UUUU, 400 mg, 1.6 mmol, 32%).

Step 4: To a solution of the ester UUUU (200 mg, 0.77 mmol, 1.0 equiv.) in methanol (7 mL, 0.1M) was added palladium/carbon (10%, 82 mg, 0.77 mmol Pd, 0.1 equiv.) under a nitrogen atmosphere. The reaction was then placed under a hydrogen atmosphere and stirred at room temperature for 2 hours, or until the reaction was determined to be complete by LCMS or TLC. Upon completion, the hydrogen atmosphere was replaced by a nitrogen atmosphere and then the palladium/carbon was filtered off on a Celite® pad and the excess solvent was removed to give the desired product (VVVV, 101 mg, 0.691 mmol, 89%).

Step 5: To a solution of ester VVVV (100 mg, 0.68 mmol, 1.0 equiv.) in THF (4 mL, 0.1M) was added triphenylphosphine (206 mg, 0.79 mmol, 1.15 equiv.) followed by 1-phenyl-1H-tetrazole-5-thiol (134 mg, 0.75 mmol, 1.1 equiv.). The reaction was degassed with nitrogen and a solution of DIAD (180 mg, 0.89 mmol, 1.3 equiv.) in THF (2 mL) was added slowly. The reaction was then stirred at room temperature for 1 hour, or until the reaction was determined to be complete by LCMS or TLC. The solvent was removed. The crude residue was then purified by silica gel column chromatography (hexane/ethyl acetate as eluant) to afford the desired product (WWWW, 110 mg, 0.36 mmol, 53%).

Step 6: To a solution of sulfide WWWW (25 mg, 0.082 mmol, 1.0 equiv.) in ethanol (1 mL, 0.1M) at 0° C. was added dropwise a premixed yellow solution of ammonium molybdate tetrahydrate (20 mg, 0.016 mmol, 0.2 equiv.) in hydrogen peroxide (33% in water, 0.084 mL, 0.82 mmol, 10.0 equiv.). The reaction mixture was allowed to warm up to room temperature and stirred for 4 hours, or until the reaction was determined to be complete by LCMS or TLC. The reaction mixture was diluted in ethyl acetate then sodium thiosulfate was added at 0° C. and the reaction was stirred for 20 minutes. The organic layer was then washed with water, brine, and dried over sodium sulfate. After evaporation of the solvent, the residue was purified by silica gel column chromatography (hexane/ethyl acetate) to give the desired sulfone (XXXX, 17 mg, 0.050 mmol, 62%).

Step 7: To a solution of the sulfone XXXX (23 mg, 0.069 mmol, 1.5 equiv.) in THF (1 mL, 0.02M) under nitrogen at −78° C. was added KHMDS (0.5 M in toluene, 0.19 mL, 0.092 mmol, 2.0 equiv.) dropwise and the reaction was stirred for 20 minutes. Then aldehyde L (30 mg, 0.046 mmol, 1.0 equiv.) (see Scheme 2) in THF (1 mL) was added dropwise. The reaction was stirred at −78° C. for 90 minutes and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (YYYY, 12 mg, 0.016 mmol, 34%).

Step 8: To a solution of ester YYYY (11 mg, 0.014 mmol, 1.0 equiv.) in methanol (1.5 mL, 0.01M) at room temperature was added p-methoxytoluenesulfonic acid (8.3 mg, 0.043 mmol, 3.0 equiv.). The reaction was stirred for 2 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 149, 6 mg, 0.0093 mmol, 64%). $^1$H NMR (400 MHz, CHLOROFORM-d) δ: 7.19 (s, 4H), 6.04-6.30 (m, 1H), 5.83-6.04 (m, 1H), 5.45-5.71 (m, 3H), 5.08 (d, J=10.8 Hz, 1H), 4.95 (d, J=9.5 Hz, 1H), 3.68 (br. s., 1H), 3.59 (s, 2H), 3.36-3.51 (m, 3H), 3.08-3.36 (m, 2H), 2.37-2.62 (m, 6H), 2.09-2.37 (m, 3H), 1.92-2.04 (m, 1H), 1.87 (br. s., 1H), 1.38-1.67 (m, 15H), 1.10-1.37 (m, 8H), 0.88-1.00 (m, 3H), 0.84 (d, J=6.8 Hz, 3H). MS (ES+)=647.5.

Compound 150 was prepared as shown in Scheme 15.

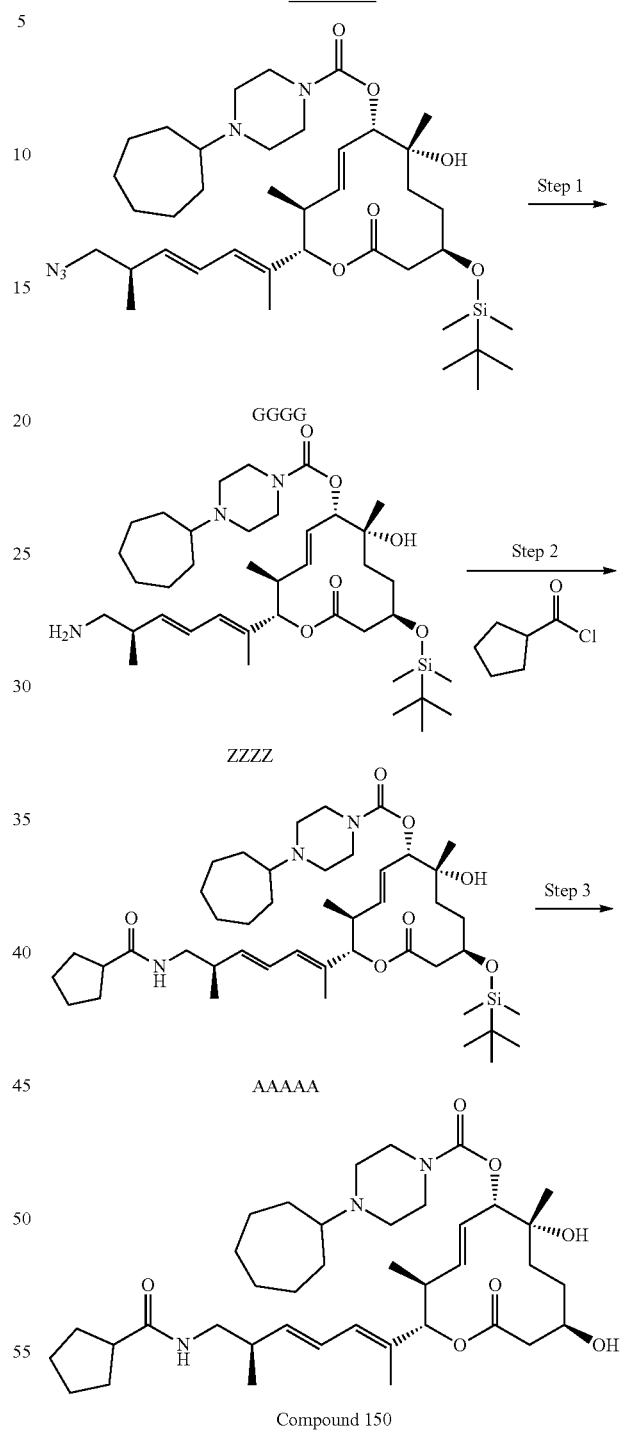

Compound 150

Protocol for the Synthesis of Compound 150

Step 1: To a solution of a azide GGGG (8 mg, 0.013 mmol, 1.0 equiv.) in dichloromethane (1 mL, 0.02M) was added trimethyl phosphine (1.0 molar solution, 0.026 mL, 0.026 mmol, 2.0 equiv) and the reaction was heated at 50° C. for 1 hour, or until the reaction was determined to be complete by LCMS or TLC. Water (1.0 mL, 4.0 equiv.) was added and the reaction mixture was heated at 50° C. for 3 hours, or until the reaction was determined to be complete by LCMS or TLC. The solvent was removed to give the crude amine ZZZZ (7.5 mg, 0.013 mmol, 98%).

Step 2: To a solution of amine ZZZZ (4.0 mg, 0.0068 mmol, 1.0 equiv.) in dichloromethane (0.5 mL, 0.01M) was added triethylamine (0.005 mL, 0.029 mmol, 4.0 equiv.) at room temperature. The reaction mixture was then cooled down to 0° C. and then cyclopentanecarbonyl chloride (0.0015 mL, 0.014 mmol, 2.0 equiv.) was added slowly. After warming up to room temperature, the reaction was stirred for 3 hours, or until the reaction was determined to be complete by LCMS or TLC. Upon completion of the reaction, excess of solvent was removed and crude material was then purified using silica gel chromatography (dichloromethane/methanol as eluent) to afford the desired amide (AAAAA 2.42 mg, 0.0035 mmol, 52%).

Step 3: To a solution of amide AAAAA (21 mg, 0.026 mmol, 1.0 equiv.) in methanol (1 mL, 0.25M) at room temperature was added p-methoxytoluenesulfonic acid (12.5 mg, 0.066 mmol, 2.5 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 150, 12.9 mg, 0.019 mmol, 72%). $^1$H NMR (400 MHz, CHLOROFORM-d) δ: 0.91 (d, J=6.65 Hz, 3H) 1.04 (d, J=6.65 Hz, 3H) 1.27 (s, 3H)) 1.20-1.62 (m, 18H) 1.65-1.78 (m, 5H) 1.79-1.87 (m, 2H) 190-2.01 (m, 2H) 2.37-2.67 (m, 5H) 2.72-2.84 (br.s., 4H) 2.87-2.98 (m, 1H) 3.04-3.14 (m, 1H) 3.25-3.36 (m, 1H) 3.66 (br. s., 4H) 3.71-3.80 (m, 1H) 5.02 (d, J=9.41 Hz, 1H) 5.16 (d, J=10.67 Hz, 1H) 5.43 (t, J=5.34 Hz, 1H) 5.55-5.66 (m, 2H) 5.67 (dd, J=15.06, 9.29 Hz, 1H) 6.09 (d, J=11.17 Hz, 1H) 6.25 (dd, J=15.00, 10.85 Hz, 1H). MS (ES+)=686.6 [M+H]$^+$.

Compound 151 was prepared according to the method of Scheme 16.

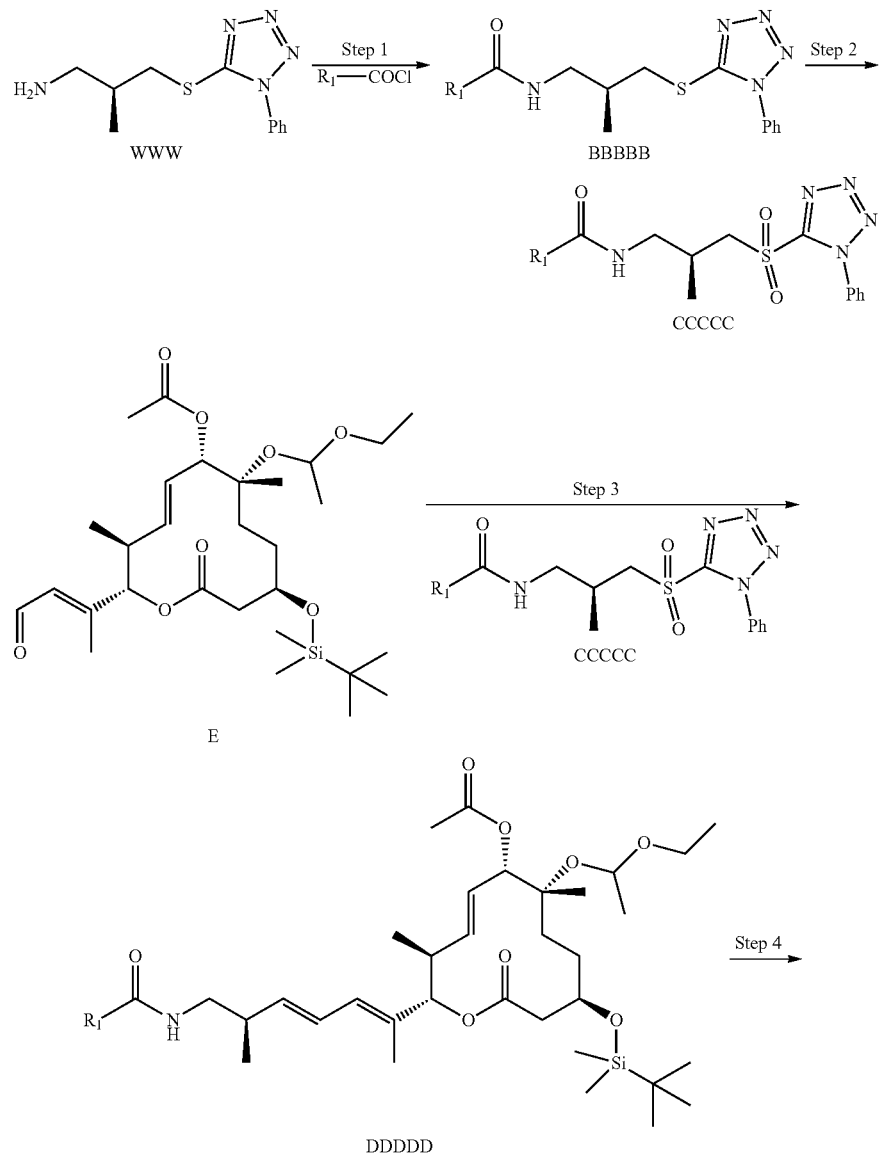

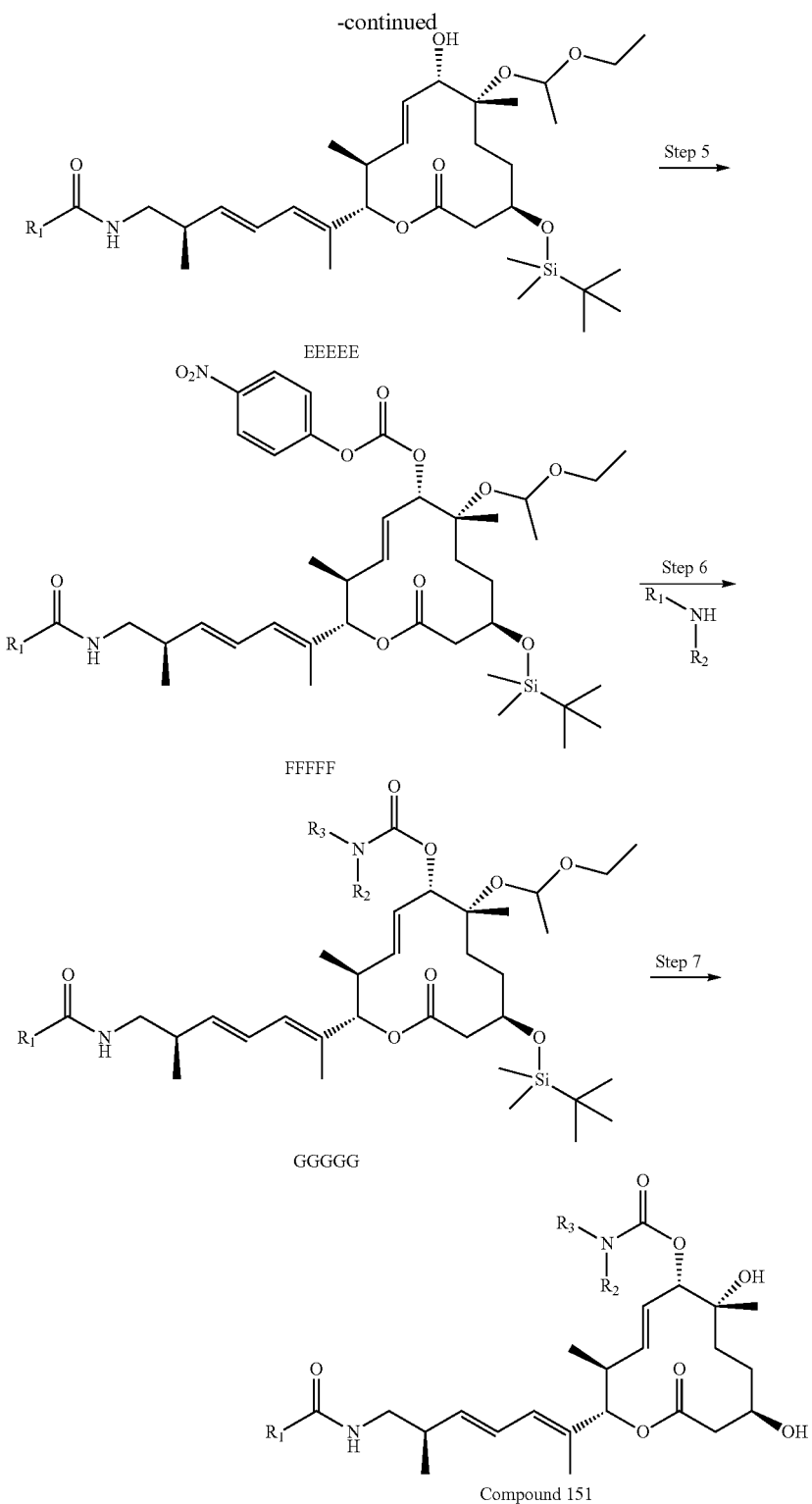

Protocol for the Synthesis of Compound 151

Step 1: To a solution of amine WWW (95 mg, 0.38 mmol, 1.0 equiv.) in dichloromethane (4 mL, 0.1M) at 0° C. was added triethylamine (0.21 mL, 1.52 mmol, 4 equiv.) followed by cyclopentanecarbonyl chloride (101 mg, 0.76 mmol, 2 equiv.). The reaction was warmed to room temperature and was stirred for 10 hours, or until the reaction was determined to be complete by LCMS or TLC. The reaction mixture was concentrated and the crude material was then purified by silica gel column chromatography (hexane/ethyl acetate) to give the desired amide (BBBBB, 49 mg, 0.14 mmol, 37%).

Step 2: To a solution of product BBBBB (49 mg, 0.14 mmol, 1.0 equiv.) in ethanol (4 mL, 0.03M) at 0° C. was added dropwise a premixed yellow solution of ammonium molybdate tetrahydrate (33 mg, 0.028 mmol, 0.3 equiv.) in hydrogen peroxide (0.15 mL, 1.4 mmol, 10 equiv. 33%). The reaction mixture was allowed to warm up to room temperature and stirred for 4 hours, or until the reaction was determined to be complete by LCMS or TLC. The reaction mixture was diluted in ethyl acetate then sodium thiosulfate was added at 0° C. and the reaction was stirred for 20 minutes. The organic layer was then washed with water, brine, and dried over sodium sulfate. After evaporation of the solvent, the residue was purified by silica gel column chromatography (hexane/ethyl acetate) to give the desired sulfone CCCCC (49 mg, 0.13 mmol, 92%).

Step 3: To a solution of sulfone CCCCC (13.6 mg, 0.36 mmol, 2.0 equiv.) in THF (15 mL, 0.01M) under nitrogen at −78° C. was added KHMDS (0.5 M in toluene, 0.14 mL, 0.072 mmol, 4.0 equiv.) dropwise and the reaction was stirred for 20 minutes. Then aldehyde E (10 mg, 0.018 mmol, 1.0 equiv.) in THF (0.5 M) was added dropwise. The reaction was stirred at −78° C. for 90 minutes and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (DDDDD, 4 mg, 0.0057 mmol, 31%).

Step 4: To a solution of product DDDDD (4 mg, 0.0057 mmol, 1.0 equiv.) in methanol (0.5 mL, 0.01M) was added potassium carbonate (1.6 mg, 0.011 mmol, 2.0 equiv.) and the reaction was stirred at room temperature. After 3 hours, or until the reaction was determined to be complete by LCMS or TLC, the reaction was quenched with ammonium chloride at 0° C. The mixture was then diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired secondary alcohol (EEEEE, 4 mg, 0.0048 mmol, 85%).

Step 5: To a solution of alcohol EEEEE (4 mg, 0.006 mmol, 1.0 equiv.) in dichloromethane (0.7 mL, 0.006M) was added triethylamine (0.0086 uL, 0.06 mmol, 10.0 equiv.), and DMAP (1.4 mg, 0.012 mmol, 2.0 equiv.) at 0° C. Then a solution of 4-nitrophenyl carbonochloridate (4.86 mg, 0.024 mmol, 4.0 equiv.) in dichloromethane (0.3 mL) was added slowly. The reaction was warmed up to room temperature and stirred for 3 hours, or until the reaction was determined to be complete by LCMS or TLC. The reaction was quenched with sodium bicarbonate and diluted with dichloromethane. The aqueous layer was extracted with dichloromethane. The combined organic layers were washed with brine, dried over sodium sulfate and concentrated in vacuo. The crude protected carbonate (FFFFF) was used in the next step without further purification.

Step 6: To a solution of carbonate FFFFF (1.0 equiv.) in THF (1.0 mL, 0.06M) at room temperature was added N-methyl piperazine (0.0067 uL, 10.0 equiv.). After stirring for one hour, or until the reaction was determined to be complete by LCMS or TLC, the reaction was quenched with water and diluted with ethyl acetate. The organic layer was washed with 1N sodium hydroxide solution, and concentrated. The resulting oil was purified by silica gel column chromatography (dichloromethane/methanol as eluant) to afford the desired product (GGGGG, 3 mg, 0.0038 mmol, 63%).

Step 7: To a solution of carbamate GGGGG (3.0 mg, 0.0038 mmol, 1.0 equiv.) in methanol (1 mL, 0.004M) at room temperature was added p-methoxytoluenesulfonic acid (1.4 mg, 0.0076 mmol, 2.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 151, 1.5 mg, 0.0022 mmol, 58%). $^1$H NMR (400 MHz, METHANOL-d4) δ: 0.88 (d, J=6.78 Hz, 3H) 1.02 (d, J=6.78 Hz, 3H) 1.21 (m, 3H) 1.27-1.44 (m, 6H) 1.53-1.72 (m, 6H) 1.74 (s, 3H) 1.76-1.84 (m, 2H) 2.35 (s, 3H) 2.41-2.63 (m, 10H) 3.05-3.17 (m, 2H) 3.54 (br.s., 1H) 3.79 (br. s., 1H) 4.94 (d, J=9.66 Hz, 1H) 5.04 (d, J=10.54 Hz, 1H) 5.54-5.64 (m, 2H) 5.65-5.77 (m, 1H) 6.02-6.13 (m, 1H) 6.22-6.34 (m, 1H) 7.78-7.86 (m, 1H), MS (ES+)=604.4 [M+H]$^+$.

Compound 152 was prepared according to the method of Scheme 17.

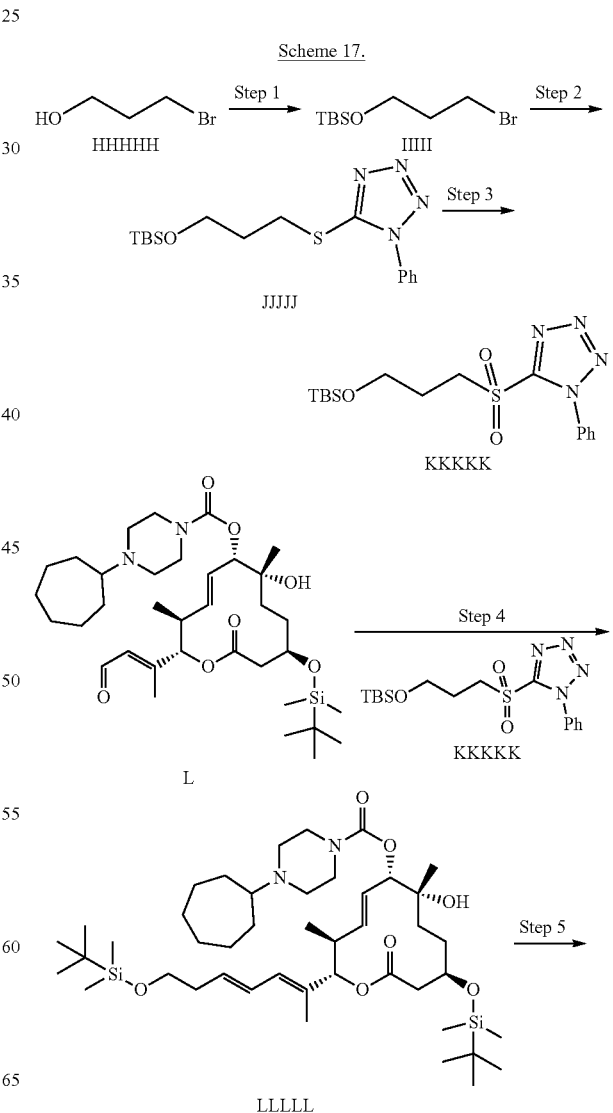

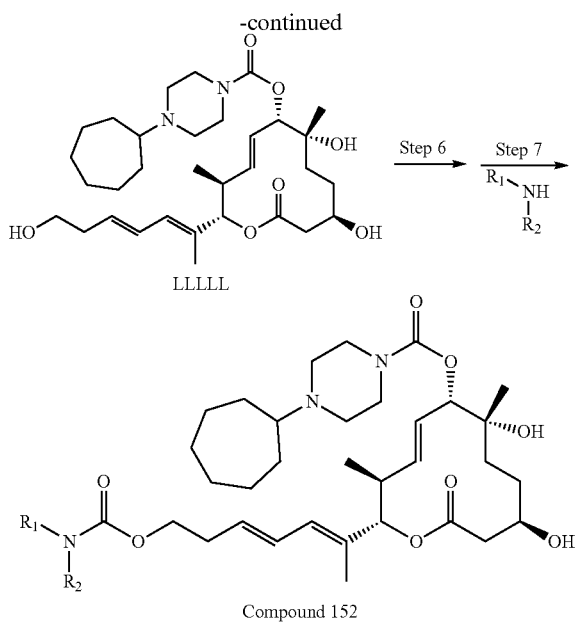

Compound 152

Protocol for the Synthesis of Compound 152

Step 1: To a solution of 3-bromo-propan-1-ol HHHHH (2.0 g, 14.4 mmol, 1.0 equiv.) in dimethylformamide (40 mL, 0.3M) was added imidazole (1.47 g, 21.6 mmol, 1.5 equiv.) followed by TBS-Cl (3.3 g, 21.6 mmol, 1.5 equiv.). The reaction was stirred at room temperature for 6 hours, or until the reaction was determined to be complete by LCMS or TLC. The reaction was then quenched with water. The aqueous layer was then extracted with diethyl ether. The combined organic layers were washed with brine and dried over sodium sulfate. After filtration, the solvent was removed in vacuo and the residue was purified by silica gel column chromatography (hexane/ethyl acetate as eluant) to afford the desired protected alcohol (IIIII, 2.91 g, 10.9 mmol, 76%).

Step 2: To a suspension of sodium hydride (55% suspension in mineral oil, 0.32 g, 7.9 mmol, 1.0 equiv.) in DMF (15 mL, 0.5M) was added 1-phenyl-1H-tetrazole-5-thiol (1.4 g, 7.9 mmol, 1.0 equiv.) at 0° C. The mixture was stirred for 1 hour. Then a solution of (3-bromopropoxy)(tertbutyl)dimethylsilane IIIII (2.0 g, 7.9 mmol, 1.0 equiv.) was added to the reaction. The reaction was heated to and maintained at 50° C. for 10 hours, or until the reaction was determined to be complete by LCMS or TLC. The reaction was then quenched with water. The excess of DMF was removed in vacuo. Then the residue was diluted in brine and extracted with diethyl ether. The combined organic layers were washed with brine, dried over MgSO4, filtered and the solvent removed in vacuo. The residue was purified by silica gel column chromatography (hexane/ethyl acetate) to afford the desired terazole JJJJJ (2.5 g, 7.2 mmol, 91%).

Step 3: To a solution of the tetrazole JJJJJ (2.5 g, 7.2 mmol, 1.0 equiv.) in ethanol (45 mL, 0.1M) at 0° C. was added dropwise a premixed yellow solution of ammonium molybdate tetrahydrate (0.89 g, 0.72 mmol, 0.1 equiv.) in hydrogen peroxide (7.3 mL, 72 mmol, 10 equiv. 33%). The reaction mixture was allowed to warm up to room temperature and stirred for 4 hours, or until the reaction was determined to be complete by LCMS or TLC. The reaction mixture was diluted in ethyl acetate, sodium thiosulfate was added at 0° C. and the reaction was stirred for 20 minutes. The organic layer was then washed with water, brine, and dried over sodium sulfate. After evaporation of the solvent, the residue was purified by silica gel column chromatography (hexane/ethyl acetate) to give the desired sulfone (KKKKK, 1.7 g, 4.4 mmol, 62%).

Step 4: To a solution of the sulfone KKKKK (74 mg, 0.19 mmol, 2.5 equiv.) in THF (4 mL, 0.02M) under nitrogen at −78° C. was added KHMDS (0.5 M in toluene, 0.39 mL, 0.19 mmol, 2.5 equiv.) dropwise and the reaction was stirred for 20 minutes. Then aldehyde L (50 mg, 0.077 mmol, 1.0 equiv.) in THF (1 mL) was added dropwise. The reaction was stirred at −78° C. for 2 hours and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (LLLLL, 30.6 mg, 0.038 mmol, 49%).

Step 5: To a solution of product LLLLL (30.6 mg, 0.038 mol, 1.0 equiv.) in methanol (3 mL, 0.01M) at room temperature was added p-methoxytoluenesulfonic acid (7.2 mg, 0.038 mmol, 1.0 equiv.). The reaction was stirred for 5 hours, or until the reaction was determined to be complete by LCMS or TLC. The reaction was quenched with sodium bicarbonate, diluted with ethyl acetate and washed with water and brine, dried over magnesium sulfate, filtered, and concentrated in vacuo. The resulting oil was purified by silica gel column chromatography (dichloromethane/methanol as eluent) to afford the desired product (MMMMM, 10.7 mg, 0.019 mmol, 49%).

Step 6 and 7: To a stirred solution of product MMMMM (6.2 mg, 0.011 mmol, 1.0 equiv.) in 1,2-dichloromethane (1 mL, 0.01M) at 23° C. was added DMAP (0.66 mg, 0.054 mmol, 0.5 equiv.) and DIPEA (0.019 mL, 0.107 mmol, 10.0 equiv.). Then, 4-nitrophenyl chloroformate (6.5 mg, 0.032 mmol, 3.0 equiv.) was added to the mixture. After 16 hours, or until the reaction was determined to be complete by LCMS or TLC, pyrrolidine (7.7 mg, 0.11 mmol, 10.0 equiv.) was added and the reaction was stirred for another 4 hours. Dichloromethane was added to the reaction mixture. The organic layer was then washed with water and brine. After drying over sodium sulfate, filtration and evaporation, the crude material was purified by silica gel column chromatography (ethyl acetate/methanol) to give the desired product (compound 152, 2.67 mg, 0.0040 mmol, 37%). $^1$H NMR (400 MHz, CHLOROFORM-d) δ: 0.71-0.88 (m, 6H) 0.98-1.06 (m, 1H) 1.13-1.27 (m, 13H) 1.29-1.52 (m, 10H) 1.56 (br. s., 9H) 1.61-1.70 (m, 4H) 1.73 (br. s., 2H) 1.89 (br. s., 2H) 2.34-2.59 (m, 7H) 3.41 (d, J=5.27 Hz, 4H) 3.65-3.78 (m, 2H) 4.11 (t, J=6.78 Hz, 2H) 4.88-5.02 (m, 1H) 5.08 (d, J=10.54 Hz, 1H) 5.43-5.68 (m, 3H) 6.01 (d, J=10.29 Hz, 1H) 6.25 (dd, J=15.06, 11.04 Hz, 1H), MS (ES+)=674.3 [M+14]$^+$.

Compound 153 was prepared according to the method of Scheme 18
Scheme 18.
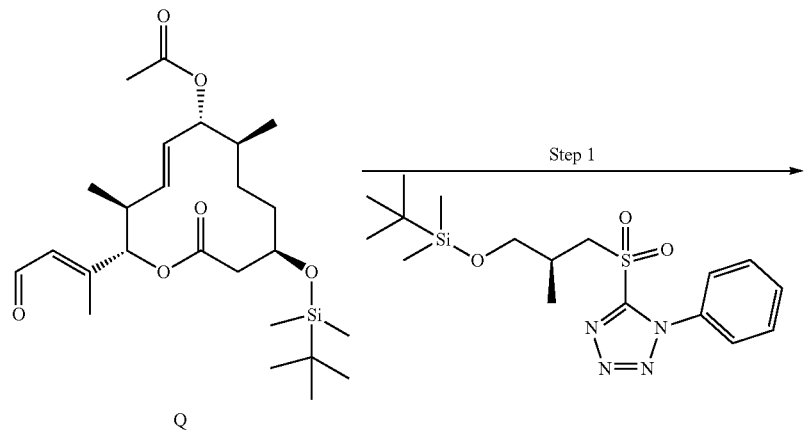
Q
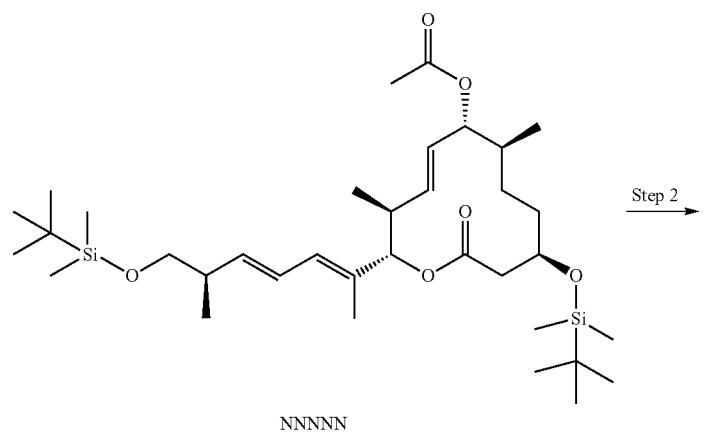
NNNNN
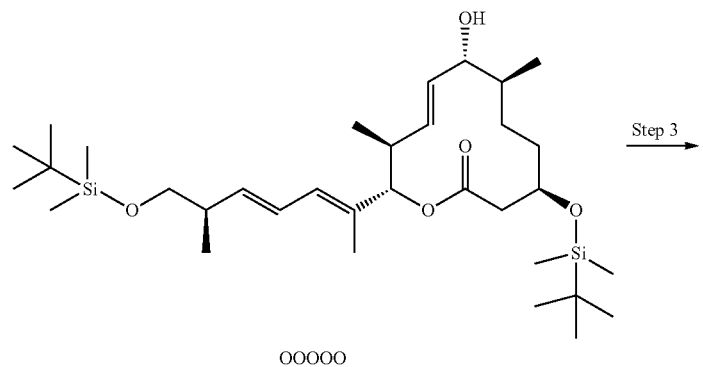
OOOOO -continued

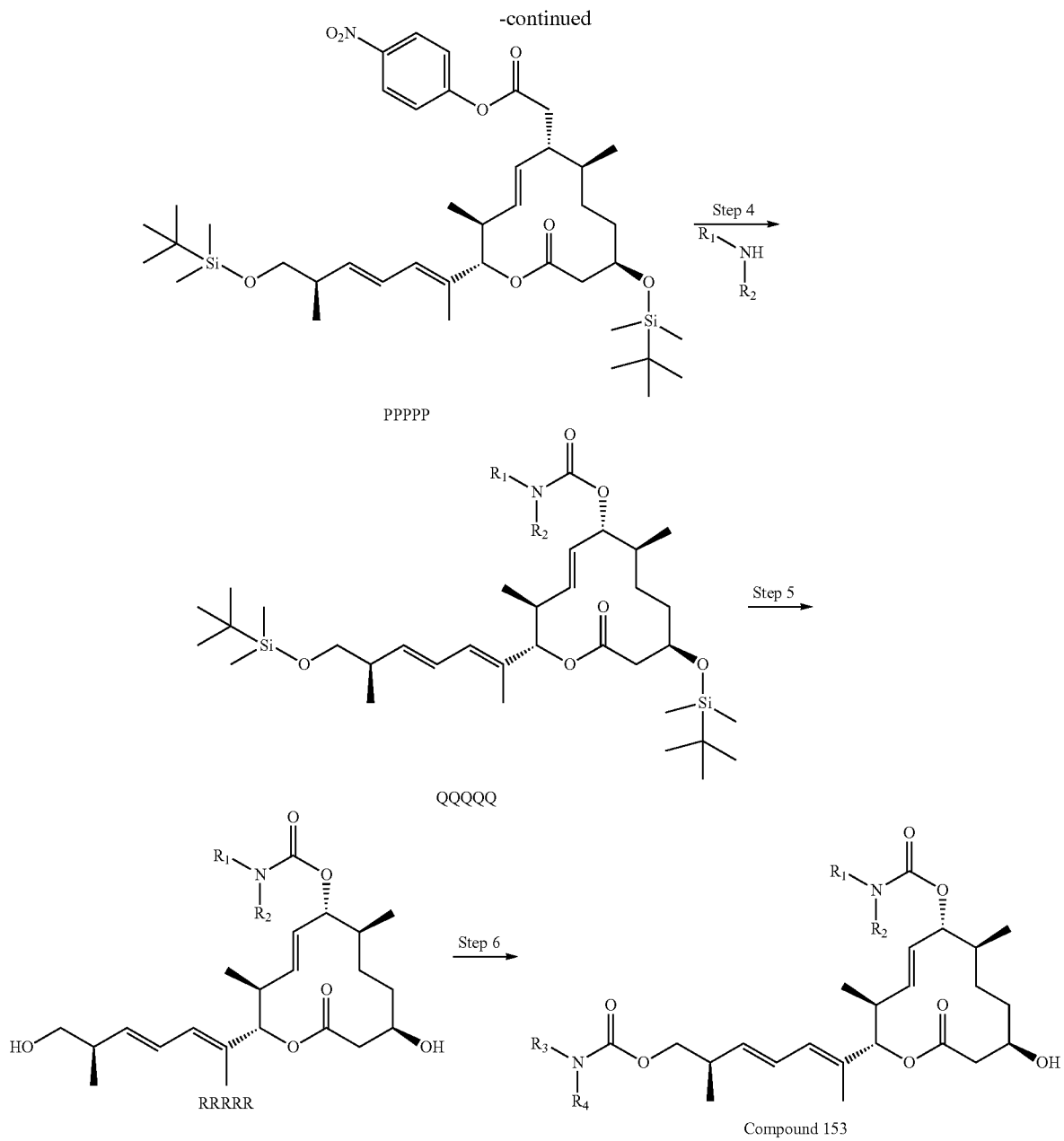

PPPPP

QQQQQ

RRRRR

Compound 153

Protocol for the Synthesis of Compound 153

Step 1: To a solution of (S)-5-((3-((tert-butyldimethylsilyl)oxy)-2-methylpropyl)sulfonyl)-1-phenyl-1H-tetrazole (212 mg, 0.54 mmol, 2.5 equiv.) in THF (3 mL, 0.04M) under nitrogen at −78° C. was added KHMDS (0.5 M in toluene, 1.1 mL, 0.54 mmol, 2.5 equiv.) dropwise and the reaction was stirred for 20 minutes. Then aldehyde Q (100 mg, 0.21 mmol, 1.0 equiv.) in THF (1 mL) was added dropwise. The reaction was stirred at −78° C. for 2 hours and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (NNNNN, 105 mg, 0.17 mmol, 77%).

Step 2: To a solution of product NNNNN (101 mg, 0.16 mmol, 1.0 equiv.) in methanol (4 mL, 0.04M) was added potassium carbonate (55 mg, 0.40 mmol, 2.5 equiv.) and the reaction was stirred at room temperature. After 3 hours, or until the reaction was determined to be complete by LCMS or TLC, the reaction was quenched with ammonium chloride at 0° C. The mixture was then diluted with ethyl acetate, washed with water, brine, dried over magnesium sulfate, filtered, and concentrated in vacuo. The resulting oil was purified by silica gel column chromatography (hexane/ethyl acetate as eluent) to afford the desired secondary alcohol (OOOOO, 52 mg, 0.087 mmol, 55%).

Step 3: To a solution of alcohol OOOOO (20 mg, 0.034 mmol, 1.0 equiv.) in dichloromethane (4 mL, 0.01M) was added triethylamine (0.033 mL, 0.24 mmol, 7.0 equiv.) and DMAP (1.2 mg, 0.01 mmol, 0.3 equiv.) at 0° C. Then a solution of 4-nitrophenyl carbonochloridate (27.1 mg, 0.13 mmol, 4.0 equiv.) in dichloromethane (1 mL) was added slowly. The reaction was warmed up to room temperature and stirred for 3 hours or until the reaction was determined to be complete by LCMS or TLC. The reaction was quenched with sodium bicarbonate and diluted with dichloromethane. The aqueous layer was extracted with dichloromethane. The combined organic layers were washed with brine, dried over sodium sulfate and concentrated in vacuo. The crude protected carbonate (PPPPP) was used in the next step without further purification.

Step 4: To a solution of carbonate PPPPP (1.0 equiv.) in THF (4 mL, 0.01M) at room temperature was added N-methyl piperazine (34 mg, 0.34 mmol, 10.0 equiv.). After stirring for one hour, or until the reaction was determined to be complete by LCMS or TLC, the reaction was quenched with water and diluted with ethyl acetate. The organic layer was washed with 1N sodium hydroxide solution concentrated. The resulting oil was purified by silica gel column chromatography (dichloromethane/methanol as eluant) to afford the desired product (QQQQQ, 24 mg, 0.033 mmol, 99%).

Step 5: To a solution of product QQQQQ (24 mg, 0.033 mmol, 1.0 equiv.) in methanol (2 mL, 0.02M) at room temperature was added p-methoxytoluenesulfonic acid (9.5 mg, 0.05 mmol, 1.5 equiv.). The reaction was stirred for 5 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (RRRRR, 14.0 mg, 0.028 mmol, 85%).

Step 6: To a stirred solution of product RRRRR (4.0 mg, 0.008 mmol, 1.0 equiv.) in 1,2-dichloromethane (1.0 mL, 0.01M) at 23° C. was added DMAP (0.2 mg, 0.0016 mmol, 0.2 equiv.) and DIPEA (0.01 mL, 0.057 mmol, 7.0 equiv.). Then, 4-nitrophenyl chloroformate (2.5 mg, 0.012 mmol, 1.5 equiv.) was added to the mixture. After 12 hours, or until the reaction was determined to be complete by LCMS or TLC, (R)-pyrrolidin-3-ol x (4.0 mg, 0.032 mmol, 4.0 equiv.) was added and stirred for another 4 hours. Dichloromethane was added to the reaction mixture. The organic layer was then washed with water and brine. After drying over sodium sulfate, filtration and evaporation, the crude material was purified by silica gel column chromatography (dichloromethane/methanol as eluent) to give the desired product (compound 153, 3.2 mg, 0.0081 mmol, 65%). $^1$H NMR (400 MHz, CHLOROFORM-d) δ: 0.91 (d, J=6.78 Hz, 3H) 0.97-1.03 (m, 6H) 1.44-1.55 (m, 2H) 1.67-1.85 (m, 5H) 1.86-2.01 (m, 2H) 2.37-2.62 (m, 11H) 3.02 (br. s., 1H) 3.20-3.32 (m, 1H) 3.38-3.63 (m, 9H) 3.68-3.75 (m, 2H) 3.79-4.10 (m, 2H) 4.40-4.48 (m, 1H) 4.86 (t, J=10.10 Hz, 1H) 5.14 (dd, J=10.48, 5.58 Hz, 1H) 5.28-5.41 (m, 2H) 5.55 (dd, J=14.93, 9.91 Hz, 1H) 6.20 (t, J=11.23 Hz, 1H) 6.36 (br. d, J=11.17 Hz, 1H). MS (ES+)=606.5 [M+H]$^+$.

Compound 154 was prepared according to the method of Scheme 19.

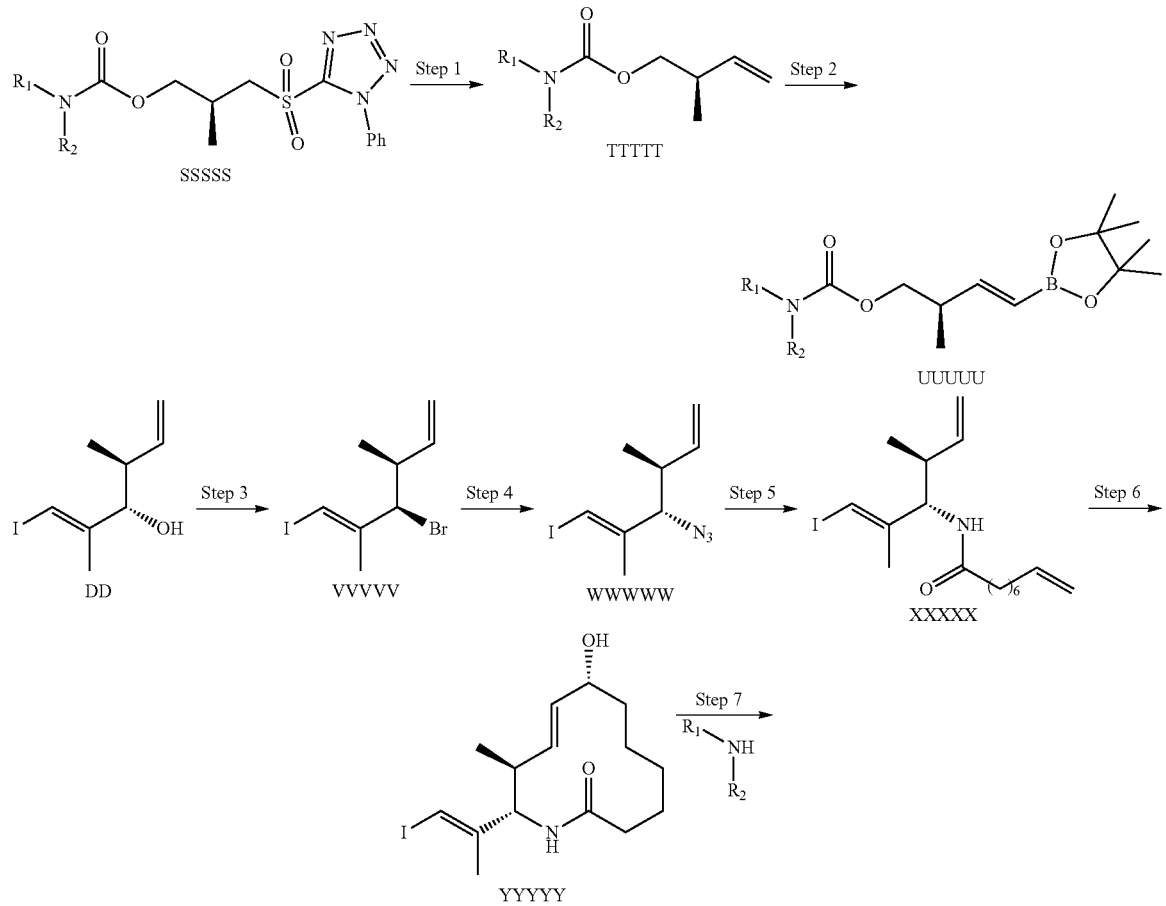

Scheme 19.

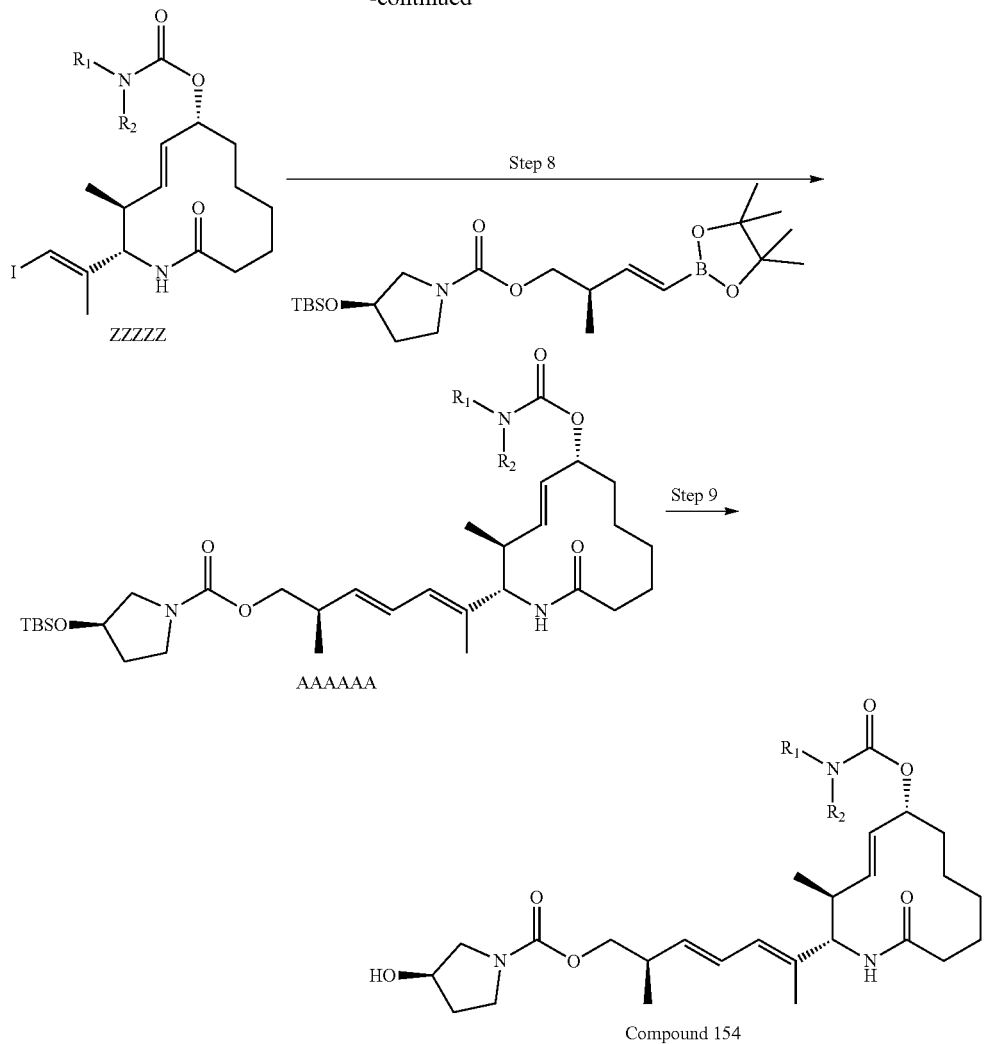

Compound 154

Protocol for the Synthesis of Compound 154

Step 1: To a solution of (R)—(S)-2-methyl-3-((1-phenyl-1H-tetrazol-5-yl)sulfonyl)propyl 3-((tert-butyldimethylsilyl)oxy)pyrrolidine-1-carboxylate SSSSS (100.0 mg, 0.20 mmol, 1.0 equiv.) in THF (4 mL, 0.04M) was added slowly potassium bis(trimethylsilyl)amide (0.5 M in toluene, 1.2 mL, 0.59 mmol, 3 equiv.) at −78° C. The reaction was stirred for 15 minutes and (1H-benzo[d][1,2,3]triazol-1-yl)methanol (58.5 mg, 0.39 mmol, 2.0 equiv.) was added at −78° C. The reaction was stirred for 2 hours at −78° C. and warmed to room temperature over 1 hour. The reaction was quenched with ammonium chloride, and extracted with ethyl acetate. The combined organic layers were washed with brine, dried over sodium sulfate and concentrated in vacuo. The crude material was then purified by silica gel column chromatography (hexane/ethyl acetate as eluent) to afford the desired terminal alkene (TTTTT, 40 mg, 0.13 mmol, 65%).

Step 2: To a solution of alkene TTTTT (40 mg, 0.13 mmol, 1.0 equiv.) in 1,2-dichloroethane (2.0 mL, 0.1M) was added 4,4,5,5-tetramethyl-2-vinyl-1,3,2-dioxaborolane (39.3 mg, 0.26 mmol, 2.0 equiv.). The reaction was purged with nitrogen and Hoveyda-Grubbs II catalyst (8.0 mg, 0.013 mmol, 0.1 equiv.) was added and the reaction was stirred at 50° C. for 16 hours. The mixture was filtered through Celite®, the Celite® was washed with dichloromethane and the filtrate was concentrated in vacuo. The crude material was then purified by silica gel column chromatography (hexane/ethyl acetate as eluent) to afford the desired product (UUUUU, 31 mg, 0.063 mmol, 50%).

Step 3: To a solution of (3S,4S,E)-1-iodo-2,4-dimethylhexa-1,5-dien-3-ol DD (240 mg, 0.95 mmol, 1.0 equiv.) in dichloromethane (7 mL, 0.2 M) was added triphenylphosphine (400 mg, 1.5 mmol, 1.6 equiv.) and a solution of NBS (288 mg, 1.6 mmol, 1.7 equiv.) in dichloromethane (1 mL, 0.1M) using a syringe pump at 0° C. The reaction was stirred at 0° C. for 2 hours, or until the reaction was determined to be complete by LCMS or TLC, before being quenched with a sodium sulfite solution. The mixture was extracted with ethyl acetate, washed with sodium bicarbonate, brine, and dried over sodium sulfate. After evaporation of the solvent in vacuo, the crude material was purified by silica gel column chromatography (hexane/ethyl acetate as eluent) to afford the desired bromo derivative (VVVVV, 270 mg, 0.86 mmol, 90%).

Step 4: To a solution of bromo derivative VVVVV (270 mg, 0.86 mmol, 1.0 equiv.) in DMF (5 mL, 0.2 M) was added sodium azide (23 mg, 3.4 mmol, 4.0 equiv.). The reaction was heated to and maintained at 50° C. for 1 hour, or until the reaction was determined to be complete by LCMS or TLC. Upon completion, the reaction was cooled down to room temperature; the mixture was then filtered through a silica gel plug (ethyl acetate). After concentration, the azido derivative (WWWWW, 200 mg, 0.722 mmol, 84%) was used directly in the next step.

Step 5: To a solution of azide derivative WWWWW (22 mg, 0.079 mmol, 1.0 equiv.) in THF (2 mL, 0.04M) was added trimethylphosphine (1.0 M, 0.16 mL, 0.6 mmol, 2.0 equiv.) at −10° C. The reaction was then warmed to room temperature and stirred at room temperature for 30 minutes or until the reaction was determined to be complete by LCMS or TLC. Then water (4.3 mL, 0.24 mmol, 3.0 equiv.) was added and the reaction was stirred at room temperature for 5 hours, or until the reaction was determined to be complete by LCMS or TLC. Upon completion, non-8-enoic acid (25 mg, 0.16 mmol, 2.0 equiv.), HOBt (13 mg, 0.087 mmol, 1.1 equiv.), Hunig's base (0.047 mL, 0.32 mmol, 4.0 equiv.) and EDCI (16.7 mg, 0.087 mmol, 1.1 equiv.) were added and the mixture was stirred for 3 hours or until the reaction was determined to be complete by LCMS or TLC. The solvent was then evaporated in vacuo, ethyl acetate was added and the organic layer was extracted with sodium bicarbonate and brine. After drying over sodium sulfate, filtration and evaporation of solvent in vacuo, the crude material was purified by silica gel chromatography (hexanes/ethyl acetate as eluent) to afford the desired amide (XXXXX, 11 mg, 0.028 mmol, 36%).

Step 6: To a degassed solution of amide XXXXX (18 mg, 0.046 mmol, 1.0 equiv.) and benzoquinone (0.25 mg, 0.002 mmol, 0.05 equiv.) in toluene (4.6 mL, 0.01M) was added Hoveyda-Grubbs II catalyst (2.9 mg, 0.0046 mmol, 0.1 equiv.). The mixture was stirred in an oil bath at 65° C. under a nitrogen atmosphere for 12 hours, or until the reaction was determined to be complete by LCMS or TLC. The reaction mixture was cooled down to room temperature and filtered through a Celite® and silica gel pad. The solvent was then removed and the crude material was dissolved in dioxane (1 mL, 0.05M), and selenium dioxide (15.4 mg, 0.14 mmol, 3.0 equiv.) was added. The mixture was heated to and maintained at 80° C. for 5 hours or until the reaction was determined to be complete by LCMS or TLC. The mixture was cooled down to room temperature and was diluted with ethyl acetate. The organic layer was washed with sodium bicarbonate, brine and dried over sodium sulfate. The solvent was removed in vacuo and the crude macrocycle was used in the next step without further purification (YYYYY, 18 mg, 0.048 mmol).

Step 7: To a solution of macrocycle YYYYY (17 mg, 0.046 mmol, 1.0 equiv.) in 1,2-dichloroethane (2 mL, 0.02 M) was added nitrophenyl chloroformate (23.2 mg, 0.12 mmol, 2.5 equiv.), triethylamine (0.045 mL, 0.322 mmol, 7.0 equiv.), and DMAP (5.6 mg, 0.046 mmol, 1.0 equiv.). The reaction was stirred at room temperature for 12 hours or until the reaction was determined to be complete by LCMS or TLC. N-methyl piperazine (14 mg, 0.14 mmol, 3.0 equiv.) was then added and the reaction was stirred at room temperature for 2 hours, or until the reaction was determined to be complete by LCMS or TLC. The mixture was then directly subjected to purification by silica gel chromatography (dichloromethane/methanol as eluent) to afford the desired carbamate (ZZZZZ, 15 mg, 0.029 mmol, 63%).

Step 8: To a solution of carbamate ZZZZZ (7 mg, 0.014 mmol, 1.0 equiv.) in THF (1 mL, 0.1M) at room temperature was added (R)—(R,E)-2-methyl-4-(4,4,5,5-tetramethyl-1,3,2-dioxaborolan-2-yl)but-3-en-1-yl 3-((tert-butyldimethylsilyl)oxy)pyrrolidine-1-carboxylate UUUUU (8 mg, 0.018 mmol, 1.3 equiv.), monosilver(I) monosilver(III) monooxide (16 mg, 0.07 mmol, 5.0 equiv.), and tetrakis(triphenylphosphine) palladium (0.8 mg, 0.007 mmol, 0.05 equiv.). The reaction mixture was heated to and maintained at 60° C. for 30 minutes or until the reaction was determined to be complete by LCMS or TLC. Upon completion, the reaction was cooled down to room temperature, filtered through Celite®, washed with dichloromethane and concentrated in vacuo. The crude material was purified by silica gel chromatography (dichloromethane/methanol as eluent) to afford the desired product (AAAAAA, 3.0 mg, 0.0044 mmol, 31%).

Step 8-2: To a solution of carbamate AAAAAA (3.0 mg, 0.0044 mmol, 1.0 equiv.) in methanol (1 mL, 0.004M) at room temperature was added p-methoxytoluenesulfonic acid (4.1 mg, 0.022 mmol, 5.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 154, 2.4 mg, 0.0042 mmol, 96%). $^1$H NMR (400 MHz, CHLOROFORM-d) δ: 0.97 (d, J=6.53 Hz, 3H) 1.07 (d, J=6.78 Hz, 3H) 1.31-1.70 (m, 7H) 1.71 (s, 3H) 1.80-2.06 (m, 3H) 2.21-2.32 (m, 2H) 2.32 (s, 3H) 2.39 (br. s., 4H) 2.56-2.64 (m, 1H) 3.42-3.59 (m, 6H) 3.91-4.02 (m, 2H) 4.15-4.26 (m, 1H) 4.45-4.50 (m, 1H) 5.14 (td, J=10.04, 5.14 Hz, 1H) 5.26-5.40 (m, 2H) 5.58 (dd, J=15.06, 10.04 Hz, 1H) 5.65 (dd, J=15.12, 7.47 Hz, 1H) 6.06 (d, J=10.41 Hz, 1H) 6.27 (dd, J=14.62, 11.23 Hz, 1H). MS (ES+)=575.4 [M+H]$^+$.

Compound 155 was prepared according to the method of Scheme 20.

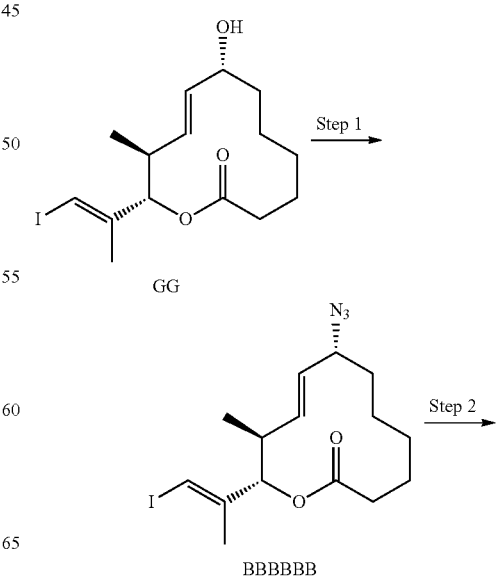

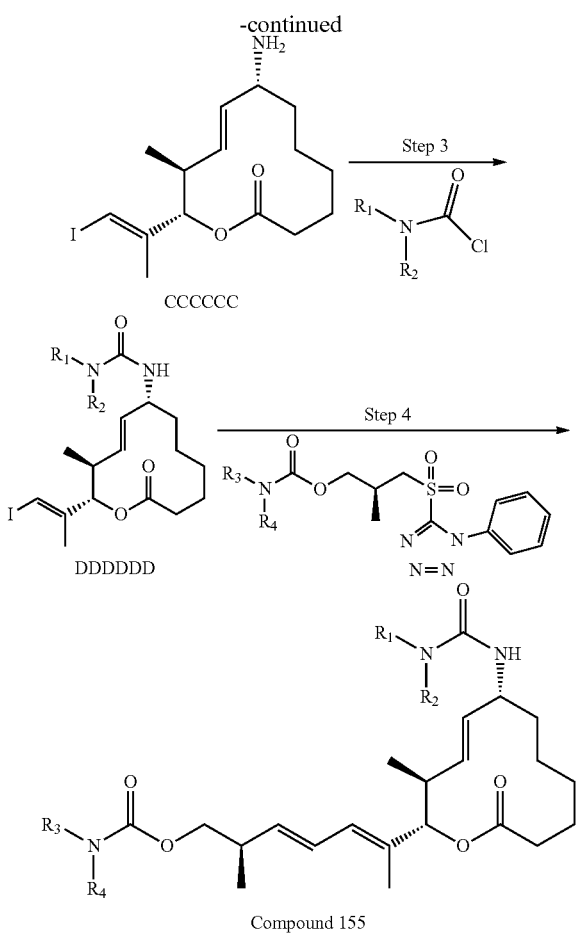

Protocol for the Synthesis of Compound 155

Step 1: To a solution of macrocycle (8R,11S,12S,E)-8-hydroxy-12-((E)-1-iodoprop-1-en-2-yl)-11-methyloxacyclododec-9-en-2-one GG (0.20 g, 0.53 mmol, 1.0 equiv.) in dichloromethane (5.3 mL, 0.1M) was added PPh$_3$ (0.28 g, 1.0 mmol, 2.0 equiv.) and CBr$_4$ (0.35 g, 1.0 mmol, 2.0 equiv.) at 0° C. The reaction was stirred at room temperature for 3 hours, or until the reaction was determined to be complete by LCMS or TLC. The reaction mixture was then quenched with water and aqueous layer extracted with dichloromethane. The combined organic layers were then washed with brine, dried over MgSO4 and filtered. The solvent was removed in vacuo and the residue was then diluted in DMF (5.3 mL, 0.1M). Sodium azide (0.14 g, 2.1 mmol, 4.0 equiv.) was added and the reaction was warmed to 70° C. for 12 hours, or until the reaction was determined to be complete by LCMS or TLC. Upon completion, the solvent was removed and the crude material was purified by silica gel column chromatography (hexanes/ethyl acetate as eluent) to afford the desired azide (BBBBBB, 0.17 g, 0.20 mmol, 39%).

Step 2: To a solution of azide BBBBBB (0.16 g, 0.20 mmol, 1.0 equiv.) in THF (0.1M) was added trimethyl phosphine (0.035 mL, 0.40 mmol, 2.0 equiv.) and the reaction was stirred at 50° C. for 1 hours, or until the reaction was determined to be complete by LCMS or TLC. Water (0.014 mL, 0.8 mmol, 4.0 equiv.) was added and the reaction mixture was heated at 50° C. for 3 hours, or until the reaction was determined to be complete by LCMS or TLC. The solvent was removed and the crude material was purified by silica gel column chromatography (dichloromethane/methanol as eluent) to afford the desired amine (CCCCCC, 0.06 g, 0.16 mmol, 79%).

Step 3: To a solution of amine CCCCCC (0.08 g, 0.21 mmol, 1.0 equiv.) in dichloromethane (2.0 mL, 0.1M) at 0° C. was added triethylamine (0.12 mL, 0.85 mmol, 4.0 equiv.), DMAP (26.1 mg, 0.21 mmol, 1.0 equiv.) followed by 4-methylpiperazine-1-carbonyl chloride (0.07 g, 0.43 mmol, 2.0 equiv.). The reaction was warmed to room temperature and was stirred for 7 hours, or until the reaction was determined to be complete by LCMS or TLC. The reaction was quenched with sodium bicarbonate. The organic layer was washed with water and brine. After drying over sodium sulfate and filtration, the solvent was removed in vacuo. The residue was purified by silica gel column chromatography (dichloromethane/methanol as eluent) to afford the desired urea (DDDDDD, 0.069 g, 0.14 mmol, 65%).

Step 4: To a solution of DDDDDD (3.0 mg, 0.006 mmol, 1.0 equiv.) in THF (0.5 mL, 0.1M) at room temperature was added (R,E)-2-methyl-4-(4,4,5,5-tetramethyl-1,3,2-dioxaborolan-2-yl)but-3-en-1-yl pyrrolidine-1-carboxylate SSSSS (3.7 mg, 0.012 mmol, 2.0 equiv.), monosilver(I) monosilver(III) monooxide (6.9 mg, 0.03 mmol, 5.0 equiv.), triphenylarsine (2.2 mg, 0.007 mmol, 1.2 equiv.), and tetrakis(triphenylphosphine) palladium (0.82 mg, 0.009, 0.15 equiv.). The reaction mixture was heated at 60° C. for 30 minutes, or until the reaction was determined to be complete by LCMS or TLC. Upon completion, the reaction was cooled down to room temperature, the mixture was then filtered through Celite®, the Celite® was washed with dichloromethane and concentrated in vacuo. The crude material was purified by silica gel chromatography (dichloromethane/methanol as eluent) to afford the desired product (Compound 155, 2.7 mg, 0.0048 mmol, 81%). $^1$H NMR (400 MHz, CHLOROFORM-d) δ: 0.78-0.97 (m, 6 H) 1.06 (d, J=6.78 Hz, 3H) 1.16-1.39 (m, 4H) 1.43-1.61 (m, 2H) 1.76-1.87 (m, 2H) 2.22-2.47 (m, 7H) 2.55-2.64 (m, 1H) 3.30-3.41 (m, 8H) 3.90-4.00 (m, 2H) 4.15-4.28 (m, 4H) 5.02 (d, J=10.67 Hz, 1H) 5.14-5.30 (m, 3H) 5.35-5.45 (m, 2H) 5.67 (dd, J=15.06, 7.53 Hz, 1H) 6.10 (d, J=11.42 Hz, 1H) 6.23-6.30 (m, 1H) 6.45 (d, J=0.88 Hz, 1H), MS (ES+)=559.5 [M+H]$^+$.

Compound 156 was prepared according to the method of Scheme 21.
Scheme 21.
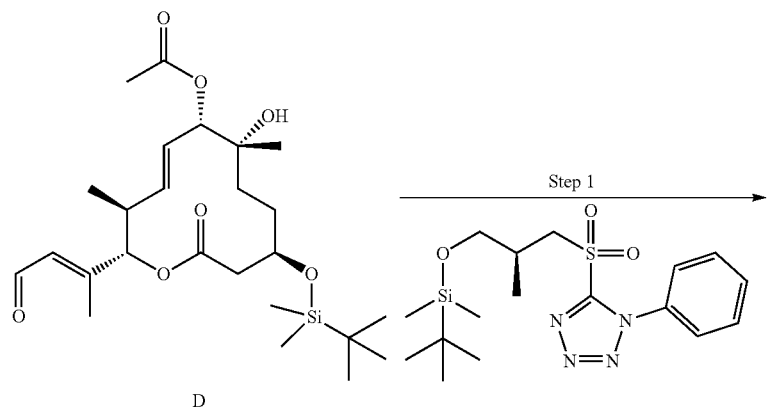
D
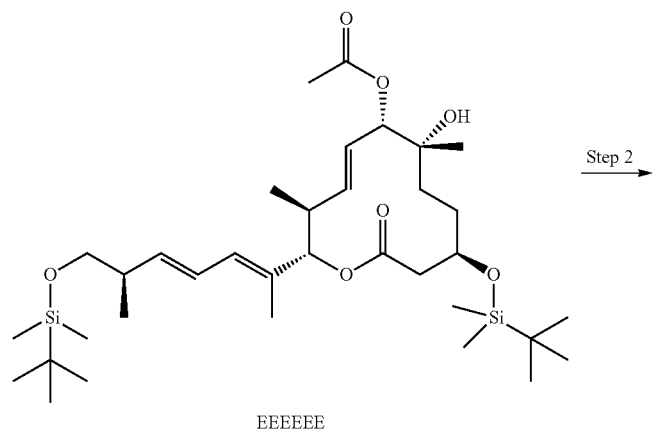
EEEEEE
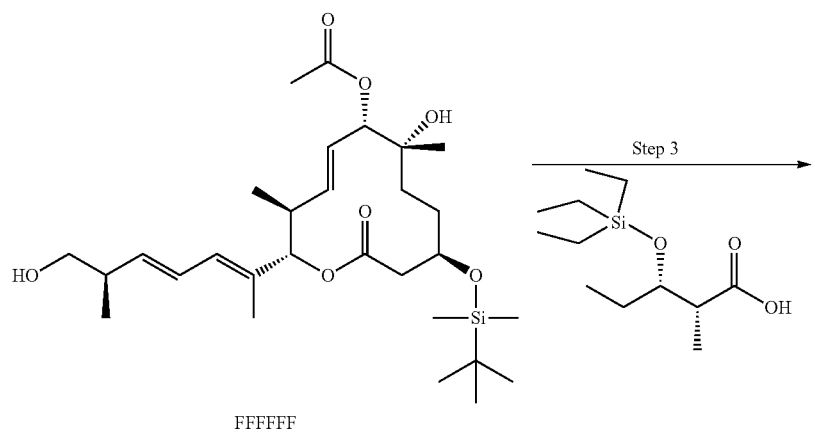
FFFFFF

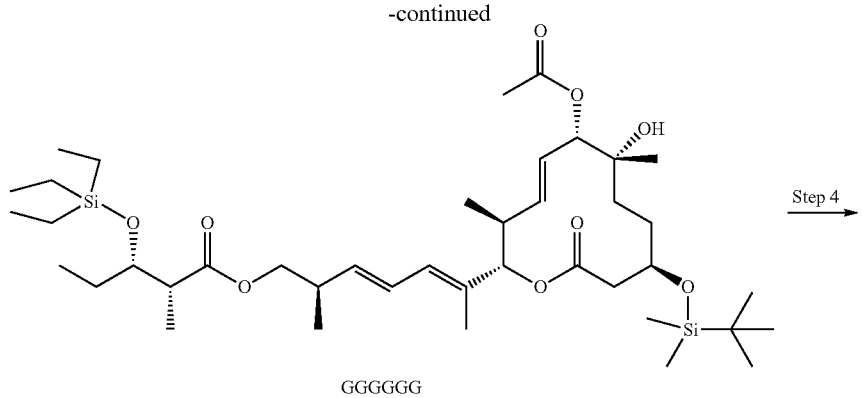

GGGGGG

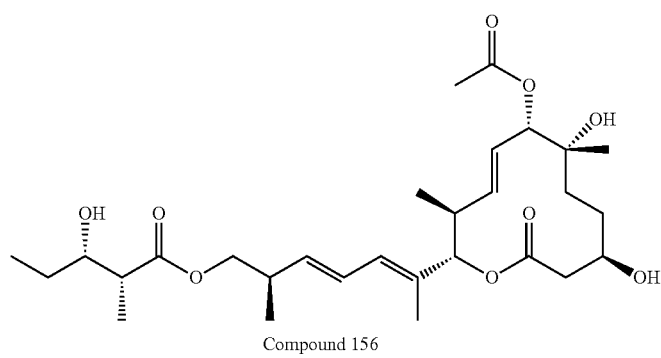 [SMILES: CC[C@H](O)[C@@H](C)C(=O)OC[C@H](C)/C=C/C=C(\C)[C@H]1OC(=O)C[C@H](O)CC[C@@](C)(O)[C@@H](OC(C)=O)/C=C/[C@@H]1C]

Compound 156

Protocol for the Synthesis of Compound 156

Step 1: To a solution of (S)-5-((3-((tert-butyldimethylsilyl)oxy)-2-methylpropyl)sulfonyl)-1-phenyl-1H-tetrazole (0.066 g, 0.17 mmol, 2.0 equiv.) in THF (2.0 mL, 0.04M) under nitrogen at −78° C. was added KHMDS (0.33 mL, 0.17 mmol, 2.0 equiv.) dropwise and the reaction was stirred for 20 minutes. Then aldehyde D (0.040 g, 0.08 mmol, 1.0 equiv.) in THF (0.2 mL) was added dropwise. The reaction was stirred at −78° C. for 2 hours and then allowed to warm to −20° C. over 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (EEEEEE, 0.036 g, 0.06 mmol, 68%).

Step 2: To a solution of EEEEEE (0.037 g, 0.06 mmol, 1.0 equiv.) in methanol (2.0 mL, 0.03M) at room temperature was added pyridinium p-toluenesulfonate (0.015 g, 0.06 mmol, 1.0 equiv.). The reaction was stirred for 6 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired primary alcohol (FFFFFF, 0.02 g, 0.04 mmol, 68%).

Step 3: To a solution of primary alcohol FFFFFF (5.0 mg, 0.009 mmol, 1.0 equiv.) and acid (2R,3S)-2-methyl-3-((triethylsilyl)oxy)pentanoic acid (3.5 mg, 0.014 mmol, 1.5 equiv.) in dichloromethane (0.3 mL, 0.03M) was added diisopropylethyamine (0.003 mL, 0.02 mmol, 2.0 equiv.), DMAP (1.1 mg, 0.009 mmol, 1.0 equiv.) and COMU (6.0 mg, 0.014 mmol, 1.5 equiv.) at 0° C. The reaction mixture was warmed up to room temperature and stirred for 16 hours or until the reaction was determined to be complete by LCMS or TLC. Upon completion, the reaction was diluted with dichloromethane, washed with water, brine and dried over sodium sulfate. After filtration, and evaporation, the crude material was purified by silica gel column chromatography (hexanes/ethyl acetate as eluent) to afford the desired ester GGGGGG (5.0 mg, 0.006 mmol, 70%).

Step 4: To a solution of ester GGGGGG (4.0 mg, 0.005 mmol, 1.0 equiv.) in methanol (0.1 mL, 0.005M) at room temperature was added p-methoxytoluenesulfonic acid (1.0 mg, 0.005 mmol, 1.0 equiv.). The reaction was stirred for 3 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (dichloromethane/methanol as eluent) to afford the desired product (compound 156, 1.2 mg, 0.002 mmol, 40%). $^1$H NMR (400 MHz, METHANOL, d4) δ: 6.60 (dd, J=15.1, 11.0 Hz, 1H), 6.17 (d, J=11.0 Hz, 1H), 5.86 (dt, J=15.2, 6.3 Hz, 1H), 5.66-5.78 (m, 1H), 4.96-5.19 (m, 2H), 4.67 (d, J=6.5 Hz, 1H), 3.78-4.00 (m, 1H), 3.73 (ddd, J=8.3, 5.8, 4.5 Hz, 1H), 3.15 (s, 1H), 2.44-2.67 (m, 3H), 2.07-2.10 (m, 2H), 1.75-1.86 (m, 2H), 1.57-1.67 (m, 1H), 1.37-1.55 (m, 3H), 1.15-1.24 (m, 4H), 0.82-1.07 (m, 5H), MS (ES+)=561.3 [M+Na]$^+$.

Compound 157 was prepared by the method of Scheme 22.

Scheme 22.

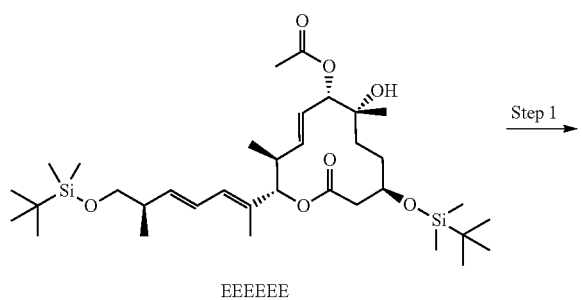

EEEEEE

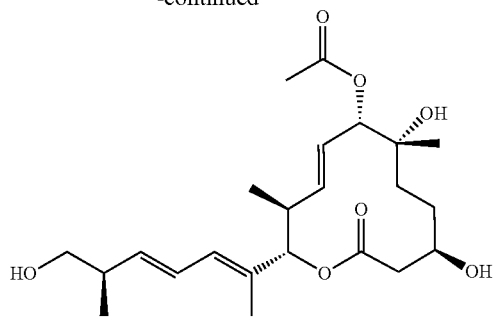

Compound 157

Step 1: Intermediate EEEEEE (40.6 mg, 0.062 mmol, 1.0 equiv) was dissolved in EtOH (2 mL) and PPTS (1.562 mg, 6.217 μmol, 0.1 equiv) was added. The reaction mixture was stirred for 1 hr at rt. Then, the solvent was removed. The residue was purified by silica gel chromatography (25-80% EtOAc/hexanes) to give desired product (Compound 157, 2.7 mg, 6.36 μmol, 10%). $^1$H NMR (400 MHz, CHLOROFORM-d) δ: ppm 0.72-0.89 (m, 3H) 0.97 (d, J=6.78 Hz, 3H) 1.11-1.35 (m, 7H) 1.42-1.56 (m, 2H) 1.56-1.71 (m, 4H) 2.02 (s, 3H) 2.34-2.58 (m, 3H) 3.32-3.54 (m, 3H) 3.56-3.83 (m, 1H) 5.01 (d, J=9.03 Hz, 1H) 5.09 (d, J=10.54 Hz, 1H) 5.50-5.65 (m, 3H) 6.03 (d, J=10.79 Hz, 1H) 6.25 (ddd, J=15.06, 10.79, 1.00 Hz, 1H). MS(ES+): 425.30 [M+H]$^+$.

Compounds 158-160 were prepared by the method of Scheme 23.

Scheme 23

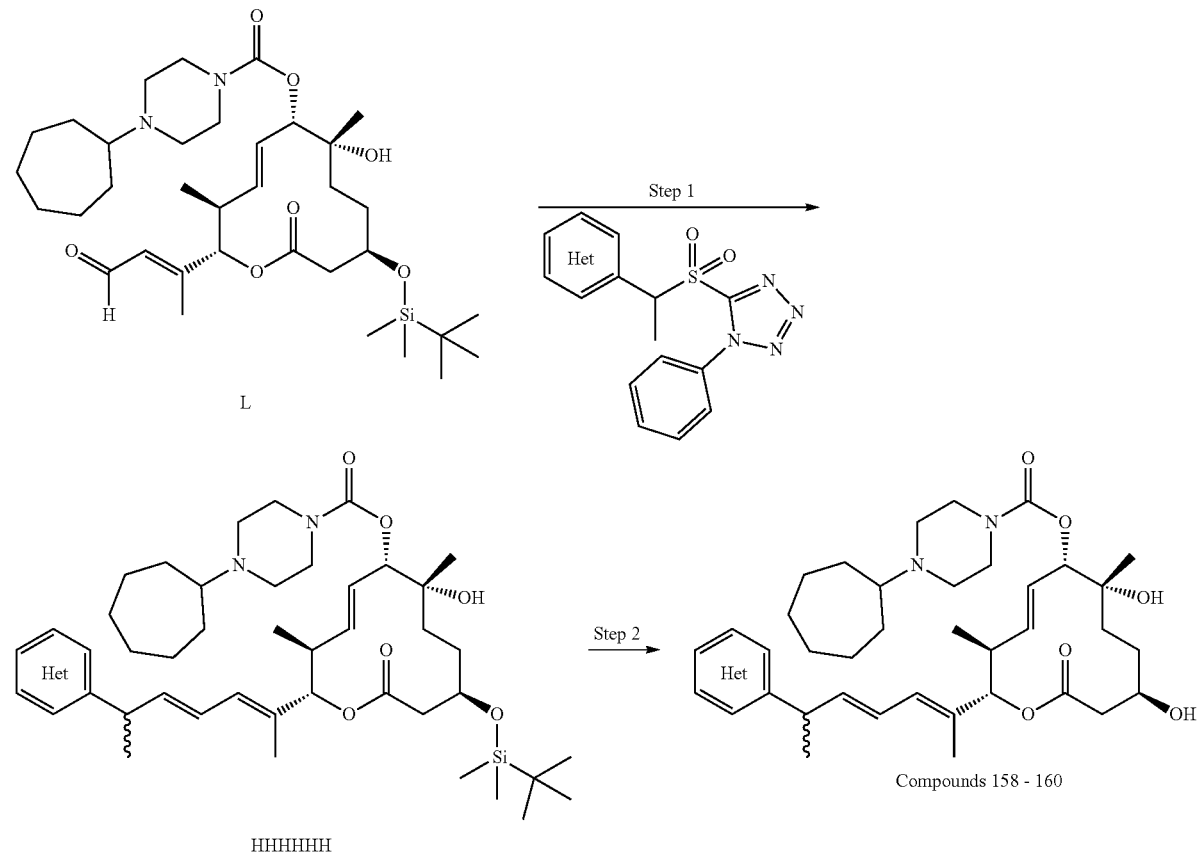

Compounds 158 - 160

General Protocol for the Synthesis of Compounds 158-160

Step 1: To a solution of the corresponding sulfone (2.5 equiv.) in THF (0.02M) under nitrogen at −78° C. was added KHMDS (2.5 equiv.) dropwise and stirred for 20 minutes. Then aldehyde L (1.0 equiv.) in THF (0.5 M) was added dropwise. The reaction was stirred at −78° C. for 2 hours and then allowed to warm to −20° C. over 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (HHHHHH)

Step 2: To a solution of carbamate HHHHHH (1.0 equiv.) in methanol (0.1M) at room temperature was added pyridinium p-toluenesulfonate (5.0 equiv.). The reaction was stirred for 6 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexanes/ethyl acetate as eluent) to afford the desired carbamate (compounds 158-160). The two diastereoisomers could be isolated after preparative HPLC. Column: Waters Xbridge C18 5 μm OBD 19×150 mm. Mobile phase A: 0.1% NH$_4$OH in water (pH 10), Mobile phase B: 0.1% NH$_4$OH in 100% acetonitrile. Mobile phase conditions: isocratic 45% B in 10 min 30 mL/min.

Exemplified Protocol for the Synthesis of Compound 90 and separation of the two epimers, Compound 159 and Compound 160

Step 1: To a solution 3-(1-((1-phenyl-1H-tetrazol-5-yl)sulfonyl)propan-2-yl)pyridine (0.15 g, 0.45 mmol, 2.1 equiv.) in THF (4.8 mL, 0.04M) under nitrogen at −78° C. was added KHMDS (0.46 mL, 0.46 mmol, 2.2 equiv.) dropwise and the reaction was stirred for 20 minutes. Then aldehyde L (0.13 g, 0.21 mmol, 1.0 equiv.) in THF (0.2 mL) was added dropwise. The reaction was stirred at −78° C. for 2 hours and then allowed to warm to −20° C. for 1 hour. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (HHHHHH, 0.08 g, 0.11 mmol, 53%).

Step 2: To a solution of carbamate HHHHHH (0.08 g, 0.11 mmol, 1.0 equiv.) in methanol (1.0 mL, 0.1M) at room temperature was added pyridinium p-toluenesulfonate (0.1 g, 0.55 mmol, 5.0 equiv.). The reaction was stirred for 6 hours, or until the reaction was determined to be complete by LCMS or TLC. The reaction was quenched with sodium bicarbonate and diluted with ethyl acetate. The organic layer was washed with water, brine, dried over magnesium sulfate, filtered, and concentrated in vacuo. The resulting oil was purified by silica gel column chromatography (hexanes/ethyl acetate as eluent) to afford the desired carbamate (compound 90, 0.015 g, 0.02 mmol, 22%) as a mixture of epimers at C16. $^1$H NMR (400 MHz, CHLOROFORM-d) δ: 0.70-0.93 (m, 4H) 1.00 (d, J=6.78 Hz, 1H) 1.12-1.21 (m, 5H) 1.24-1.50 (m, 14H) 1.55-1.76 (m, 11H) 1.90 (br. s., 2H) 2.14 (s, 1H) 2.36-2.57 (m, 7H) 3.22-3.43 (m, 5H) 3.43-3.59 (m, 1H) 3.68 (br. s., 1H) 4.94 (d, J=9.54 Hz, 1H) 5.08 (d, J=10.79 Hz, 1H) 5.44-5.72 (m, 2H) 5.82 (dd, J=15.43, 6.90 Hz, 1H) 6.03 (d, J=10.54 Hz, 1H) 6.09-6.25 (m, 1H) 7.16-7.21 (m, 3H) 7.44 (d, J=7.28 Hz, 1H) 8.41 (br. s., 2H), MS (ES+)=638.8 [M+H]$^+$.

The mixture was then subjected to preparative HPLC separation using the following parameters: Column: Waters Xbridge C18 5 μm OBD 19×150 mm. Mobile phase A: 0.1% NH$_4$OH in water (pH 10), Mobile phase B: 0.1% NH$_4$OH in 100% acetonitrile. Mobile phase conditions: isocratic 45% B in 10 min 30 mL/min. fraction 1, rt=5.9 min, fraction 2, rt=6.9 min.

Compound 159 (fraction 1, WiDr GI$_{50}$=13.3 nM, Panc05.04 GI$_{50}$=15.0 nM) $^1$H NMR (400 MHz, CHLOROFORM-d) δ: 0.82-1.00 (m, 3H) 1.24-1.31 (m, 4H) 1.34-1.60 (m, 12H) 1.65-1.88 (m, 8H) 1.96-2.12 (m, 1H) 2.45-2.67 (m, 7H) 3.50 (br. s., 4H) 3.59 (t, J=7.03 Hz, 1H) 3.68-3.88 (m, 1H) 4.95-5.10 (m, 1H) 5.17 (d, J=10.54 Hz, 1H) 5.54-5.79 (m, 2H) 5.90 (dd, J=15.06, 7.03 Hz, 1H) 6.12 (d, =10.79 Hz, 1H) 6.27 (ddd, J=15.06, 10.79, 1.25 Hz, 1H) 7.26 (d, J=4.77 Hz, 1H) 7.54 (dt, J=4.51 Hz, 1H) 8.41-8.58 (m, 2H).

Compound 160 (fraction 2, WiDr GI$_{50}$=29.5 nM, Panc05.04 GI$_{50}$=15.8 nM) $^1$H NMR (400 MHz, CHLOROFORM-d) δ: 0.87-0.97 (m, 3H) 1.23-1.30 (m, 4H) 1.32-1.60 (m, 12H) 1.64-1.78 (m, 7H) 1.78-1.93 (m, 2H) 1.99 (br. s., 1H) 2.42-2.68 (m, 6H) 3.37-3.64 (m, 5H) 3.76 (d, J=6.53 Hz, 1H) 5.03 (d, J=9.54 Hz, 1H) 5.17 (d, J=10.54 Hz, 1H) 5.54-5.78 (m, 2H) 5.91 (dd, J=14.93, 6.90 Hz, 1H) 6.12 (d, J=11.54 Hz, 1H) 6.18-6.40 (m, 1H) 7.27 (s, 1H) 7.41-7.66 (m, 1H) 8.40-8.60 (m, 2H).

Carbamate (Scheme 24) and Heterocycle (Scheme 25) Side-chain Julia Fragments Synthesis

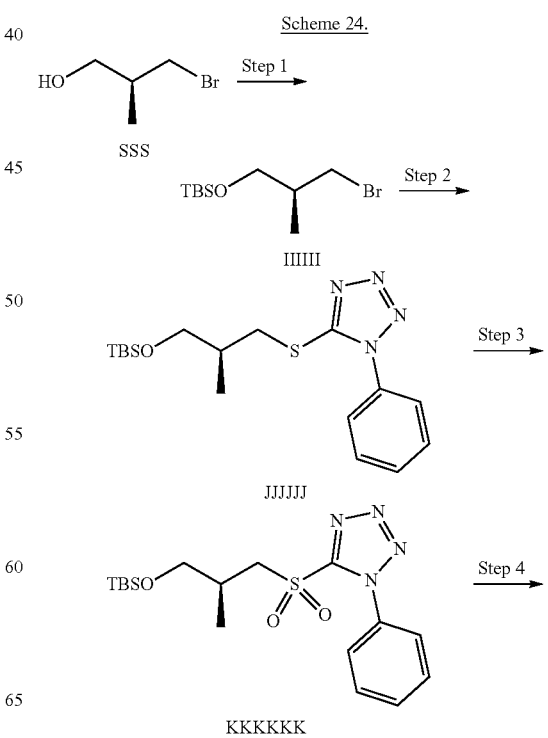

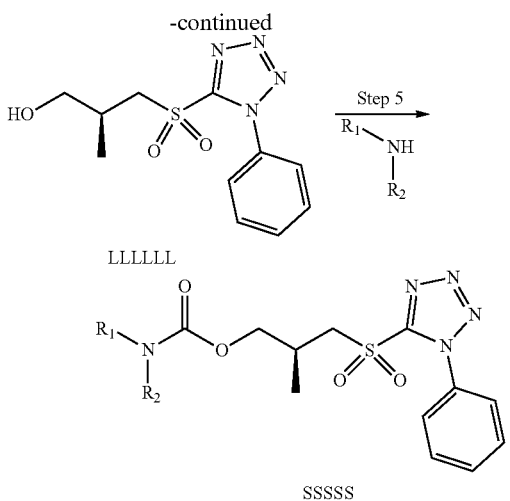

General Protocol for the Synthesis of Carbamate Julia Fragment

Step 1: To a solution of (S)-3-bromo-2-methylpropanol SSS (10.0 g, 65.3 mmol, 1.0 equiv.) in dichloromethane (300 mL, 0.1M) at 0° C. was added imidazole (6.7 g, 98.0 mmol, 1.5 equiv.) followed by TBSCl (11.8 g, 78.4 mmol, 1.2 equiv.). The reaction was allowed to warm to room temperature and stirred at room temperature overnight. Once determined to be complete by TLC or LCMS, the reaction was filtered. The filtrate was washed with water, saturated sodium bicarbonate, dried over magnesium sulfate, filtered, and concentrated in vacuo. The crude material was purified by silica gel column chromatography (hexane/ethyl acetate) to give the desired protected alcohol (IIIII, 13.5 g, 50.5 mmol, 77%).

Step 2: To a solution of NaH (2.4 g, 60.6 mmol, 1.2 equiv.) in DMF (200 mL, 0.2M) at 0° C. was added 1-phenyl-1H-tetrazole-5-thiol (9.9 g, 55.6 mmol, 1.1 equiv.) and the reaction was stirred for 1 hour. Next, a solution of bromide HIM (13.5 g, 50.5 mmol, 1.0 equiv.) was added at 0° C. and the reaction was gradually heated to 80° C. for ten hours. Once determined to be complete by TLC or LCMS, the reaction was cooled to 0° C. and quenched with water. The reaction was concentrated and the resulting oil was purified by silica gel column chromatography (hexane/ethyl acetate as eluent) to afford the desired product (JJJJJJ, 15.6 g, 42.8 mmol, 85%).

Step 3: To a solution of tetrazole JJJJJJ (2.4 g, 6.5 mmol, 1.0 equiv.) in ethanol (60 mL, 0.1M) at 0° C. was added ammonium molybdate tetrahydrate (0.8 g, 0.65 mmol, 0.1 equiv.) and hydrogen peroxide (6.6 mL, 64.7 mmol, 10.0 equiv., 30% solution in water). The reaction was allowed to warm to room temperature and stirred at room temperature for four hours or until the reaction was determined to be complete by LCMS or TLC. The reaction was quenched with water and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired sulfone (KKKKKK, 2.2 g, 5.4 mmol, 84%).

Step 4: To a solution of sulfone KKKKKK (1.0 g, 2.5 mmol, 1.0 equiv.) in methanol (25.0 mL, 0.1M) at room temperature was added p-toluenesulfonic acid (0.1 g, 0.5 mmol, 0.2 equiv.). The reaction was stirred for 1 hour, or until the reaction was determined to be complete by LCMS or TLC. The reaction was quenched with aqueous sodium bicarbonate solution, and diluted with ethyl acetate. The organic layer was washed with water, brine, dried over magnesium sulfate, filtered, and concentrated in vacuo. The crude product (LLLLLL, 0.7 g, 2.5 mmol, 100%) was advanced without further purification.

Step 5: To a solution of alcohol LLLLLL (1.0 equiv.) in dichloromethane (0.1M) at −10° C. was added DMAP (1.1 equiv.), DIEA (1.1 equiv.) and 4-nitrophenylchloroformate (1.1 equiv.). The reaction was allowed to warm to room temperature and stirred at room temperature overnight or until the reaction was determined to be complete by LCMS or TLC. Next, the reaction was cooled to 0° C. and the corresponding amine was added. The reaction was allowed to warm to room temperature and stirred at room temperature for five hours. The reaction was diluted with ethyl acetate and washed with water, brine, dried over magnesium sulfate, filtered, and concentrated in vacuo. The resulting oil was purified by silica gel column chromatography (hexane/ethyl acetate as eluent) to afford the desired sulfone (SSSSS).

Exemplified Protocol for the Synthesis of (S)-2-methyl-3-((1-phenyl-1H-tetrazol-5-yl)sulfonyl)propyl pyrrolidine-1-carboxylate Steps 1-4 as above.

Step 5: To a solution of alcohol LLLLLL (0.25 g, 0.89 mmol, 1.0 equiv.) in dichloromethane (1.5 mL, 0.5M) at −10° C. was added DMAP (0.16 g, 1.3 mmol, 1.5 equiv.), DIEA (1.2 mL, 7.09 mmol, 8.0 equiv.) and 4-nitrophenyl chloroformate (0.7 g, 3.5 mmol, 4.0 equiv.). The reaction was allowed to warm to room temperature and stirred at room temperature overnight or until the reaction was determined to be complete by LCMS or TLC. Next, the reaction was cooled to 0° C. and pyrrolidine (0.37 mL, 4.4 mmol, 5 equiv.) was added. The reaction was allowed to warm to room temperature and stirred at room temperature for five hours. The reaction was diluted with ethyl acetate and washed with water, brine, dried over magnesium sulfate, filtered, and concentrated in vacuo. The resulting oil was purified by silica gel column chromatography (hexane/ethyl acetate as eluent) to afford the desired product (S)-2-methyl-3-((1-phenyl-1H-tetrazol-5-yl)sulfonyl)propyl pyrrolidine-1-carboxylate (0.32 g, 0.84 mmol, 95%). $^1$H NMR (400 MHz, CHLOROFORM-d) δ: 7.67-7.77 (m, 2H), 7.59-7.67 (m, 3H), 4.18-4.29 (m, 1H), 4.12 (dd, J=14.7, 4.3 Hz, 1H), 3.98 (dd, J=11.0, 7.0 Hz, 1H), 3.58 (dd, J=14.7, 8.2 Hz, 1H), 3.34-3.46 (m, 4H), 2.61-2.74 (m, 1H), 1.83-1.98 (m, 4H), 1.23 (d, J=6.9 Hz, 3H).

Protocol for the Synthesis of 2-(3-methyl-1-((1-phenyl-1H-tetrazol-5-yl)sulfonyl)butan-2-yl)pyridine Scheme 25.

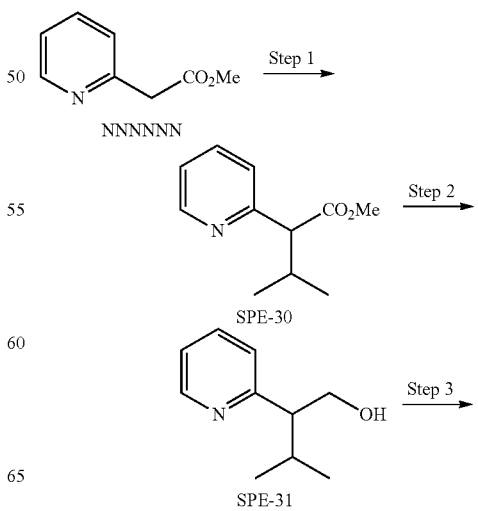

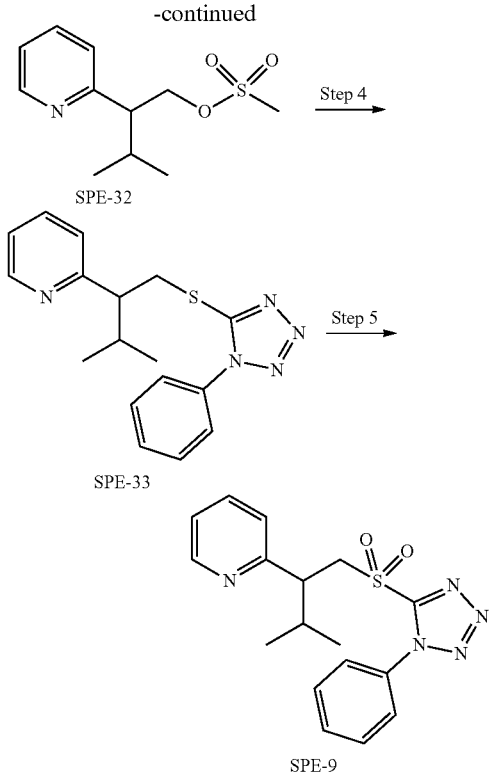

SPE-32

SPE-33

SPE-9

Step 1: NNNNNN (704 mg, 4.657 mmol, 1 equiv) was dissolved in THF (22.100 mL) at 0° C. and sodium tert-butoxide (470 mg, 4.89 mmol, 1.05 equiv) was added. This reaction solution turned bright yellow and was stirred for 30 min at this temperature. Then, 2-iodopropane (0.931 mL, 9.314 mmol, 2 equiv) was added and the reaction solution was stirred at rt for 3 hrs. The reaction mixture was quenched with sat. aq. ammonium chloride and the THF was evaporated by rotavap. The remaining aqueous was extracted with EtOAc twice and the combined organics were washed with brine, dried over sodium sulfate, filtered, and concentrated to give the desired crude product (SPE-30, 477.5 mg, 2.471 mmol, 53.1%).

Step 2: SPE-30 (477.5 mg, 2.471 mmol, 1 equiv) was dissolved in THF (25.300 mL) at 0° C. and lithium aluminium hydride (2.97 mL, 2.965 mmol, 1.2 equiv) was added dropwise. The reaction mixture was warmed to rt over 30 min then stirred at rt. The reaction mixture was carefully quenched with water, sodium hydroxide, and water, then stirred for 30 min. The ppt was filtered off and the solvent evaporated. The residue was extracted with ether and the combined organics were washed with water and brine then dried over sodium sulfate, filtered, and concentrated to give the crude desired product (SPE-31, 238 mg, 1.441 mmol, 58%).

Step 3: SPE-31 (238 mg, 1.44 mmol, 1 equiv) was dissolved in DCM (8805 μL) at 0° C. and triethylamine (221 μl, 1.584 mmol, 1.1 equiv) was added. Mesyl chloride (118 μL, 1.512 mmol, 1.05 equiv) was added dropwise and the reaction mixture stirred at this temperature for 30 min. The reaction was quenched with sat. aq. sodium bicarbonate and the aqueous re-extracted with DCM. The combined organics were washed with brine, dried over sodium sulfate, filtered, and concentrated to give crude desired product (SPE-32, 202 mg, 0.830 mmol, 57.6%).

Step 4: SPE-32 (202 mg, 0.83 mmol, 1 equiv) was dissolved in DMF (8035 μL) at rt and cesium carbonate (379 mg, 1.162 mmol, 1.4 equiv) was added followed by 1-phenyl-1H-tetrazole-5-thiol (178 mg, 0.996 mmol, 1.2 equiv). The mixture was stirred at 50° C. for 72 hrs. Brine was added and the aqueous layer was extracted 3× with ether. The combined organics were washed with water and brine then dried over sodium sulfate, filtered, and concentrated. Purification by column chromatography (0-100% EtOAc/hexanes) was completed to give the desired product (SPE-33, 130.3 mg, 0.400 mmol, 48.2%).

Step 5: SPE-33 (130.3 mg, 0.40 mmol, 1 equiv) was suspended in EtOH (2922 μL) at −10° C. and ammonium molybdate tetrahydrate (24.74 mg, 0.02 mmol, 0.05 equiv) was added followed by hydrogen peroxide (204 μL, 2.002 mmol, 5 equiv). The reaction mixture was stirred at this temperature for 3 hrs. Then, 3 mL THF was added and the reaction mixture was stirred at rt for 36 hrs. The mixture was quenched with water and aq. sodium metabisulfite. The reaction was diluted with EtOAc, the layers separated, then the organics washed with aq. sodium thiosulfate and water. The organics were dried over sodium sulfate, filtered, and concentrated. Purification by column chromatography (0-100% EtOAc/hexanes) was completed to give the desired product (SPE-9, 92 mg, 0.257 mmol, 64.3% yield). $^1$H NMR (400 MHz, CHLOROFORM-d) δ: ppm 0.78-0.88 (m, 3H) 0.93-1.02 (m, 3H) 2.02-2.17 (m, 1H) 3.29-3.44 (m, 1H) 3.94-4.06 (m, 1H) 4.59-4.72 (m, 1H) 7.10-7.19 (m, 2H) 7.60 (s, 6H) 8.38-8.47 (m, 1H). MS(ES+): 358.30 [M+H]$^+$.

Protocol for the Synthesis of Compound 161

Scheme 26.

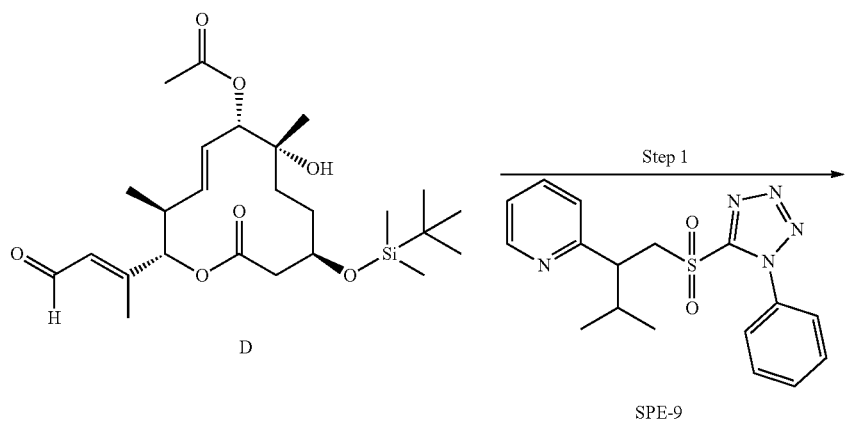

D

SPE-9

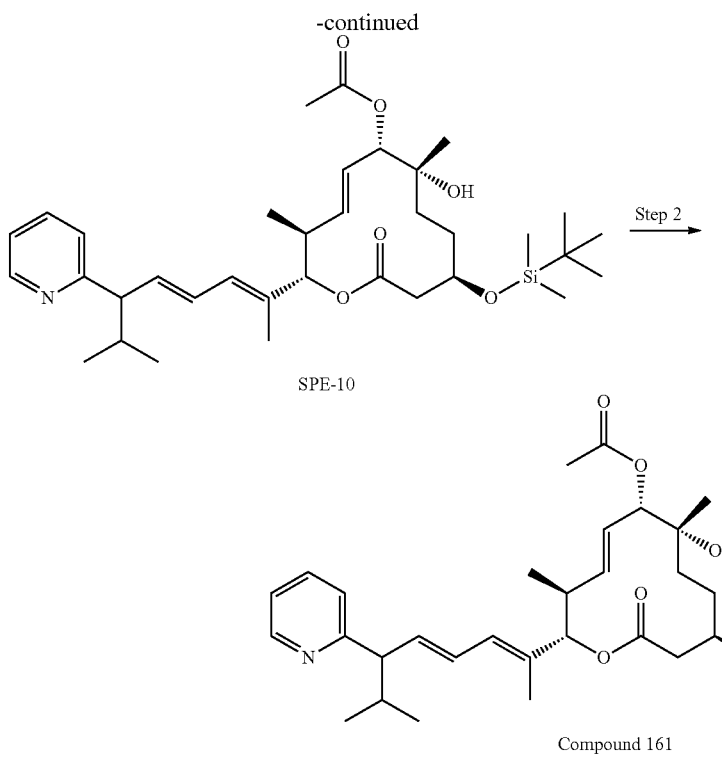

SPE-10

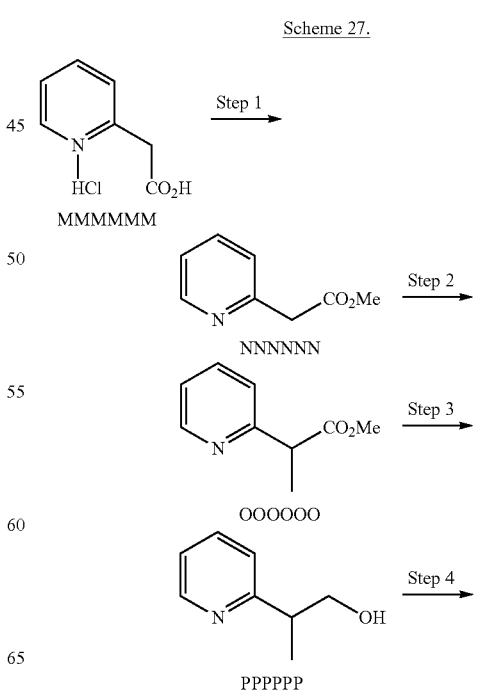

Compound 161

Step 1: To a solution of SPE-9 (93 mg, 0.261 mmol, 1.8 equiv) in 1:4 DMF (247 μL)/THF (998 μL) at −78° C. was added slowly 0.6 M NaHMDS (375 μl, 0.225 mmol, 1.55M) so as to maintain the reaction temperature below −70° C. This was stirred for 30 min at this temperature. To this cooled yellow solution was added dropwise slowly a solution of aldehyde D (70 mg, 0.145 mmol, 1 equiv) in THF (198 μL). The reaction temperature was maintained below −65° C. The aldehyde vessel was rinsed with THF and added dropwise to the cooled reaction mixture. This was then stirred between −70 to −60° C. for 1 hr (set cryocoil to −65° C.). Then, the cryocoil was set to −50° C. and the reaction mixture was let stir at that temperature o/n. The reaction mixture was warmed to −40° C. and solid ammonium chloride (33.9 mg, 0.634 mmol, 4.37 equiv) was added. The reaction was further warmed to 0° C. and water was added followed by toluene. The aqueous layer was separated and the organic layer was then washed with brine. The organics were dried over sodium sulfate, filtered, and concentrated. Purification by column chromatography (0-40% MTBE/hexanes with long hold at 40% MTBE/hexanes to elute product) was completed to give desired product (SPE-10, 29 mg, 0.047 mmol, 32.6%).

Step 2: SPE-10 (29 mg, 0.047 mmol, 1 equiv) was dissolved in THF (240 μL) and TBAF (94 μL, 0.094 mmol, 2 equiv) was added. The solution was stirred at rt o/n. The solution was diluted with water and extracted with EtOAc. The organics were then washed with brine and the organics were dried over sodium sulfate, filtered, and concentrated. Purification by column chromatography (0-100% EtOAc/hexanes) was completed to give desired product (Compound 161, 14.4 mg, 0.028 mmol, 61%). $^1$H NMR (400 MHz, METHANOL-d4) δ: ppm 0.76 (dd, J=6.59, 1.32 Hz, 3H) 0.78-0.87 (m, 1H) 0.91 (d, J=6.65 Hz, 2H) 0.99 (d, J=6.78 Hz, 3H) 1.20 (s, 3H) 1.33-1.43 (m, 2H) 1.55-1.65 (m, 2H) 1.70-1.79 (m, 3H) 2.00-2.04 (m, 1H) 2.05-2.19 (m, 4H) 2.53 (br dd, J=15.75, 3.33 Hz, 3H) 3.11-3.22 (m, 1H) 3.73-3.85 (m, 1H) 5.03-5.09 (m, 2H) 5.51-5.63 (m, 1H) 5.66-5.76 (m, 1H) 5.99 (dd, J=15.00, 9.60 Hz, 1H) 6.13 (br d, J=10.79 Hz, 1H) 6.32-6.43 (m, 1H) 7.23-7.38 (m, 2H) 7.72-7.83 (m, 1H) 8.41-8.52 (m, 1H). MS(ES+): 500.58 [M+H]$^+$.

General Protocol for the Synthesis of (S)-2-(1-((1-phenyl-1H-tetrazol-5-yl)sulfonyl)propan-2-yl)pyridine Scheme 27.

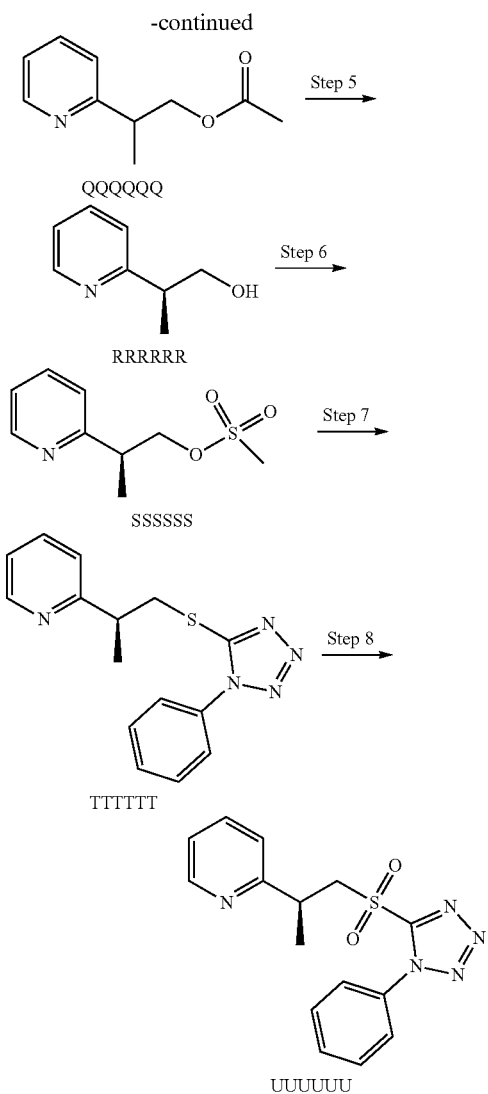

were washed with brine, and dried over magnesium sulfate. After filtration and evaporation of the solvent, the mixture was concentrated in vacuo. The resulting methyl ester (OOOOOO, 41.3 g, 250 mmol, 91%) was advanced without purification.

Step 3: To a solution of methyl ester OOOOOO (43.0 g, 260.3 mmol, 1.0 equiv.) in THF (1500 mL, 0.1M) at 0° C. was added lithium aluminum hydride (312 mL, 312.4 mmol, 1.2 equiv., solution in THF) dropwise. The reaction was allowed to warm gradually to 0° C. for 30 minutes and then to room temperature for 1 hour or until the reaction was determined to be complete by LCMS or TLC. The reaction was carefully quenched with water, sodium hydroxyde and water. After stirring the mixture for 30 minutes, the white precipitate was filtered off and the solvent was removed in vacuo. The reaction was then extracted with diethyl ether and the combined organic fractions were washed with water, brine, dried over magnesium sulfate, filtered, and concentrated in vacuo. The resulting alcohol (PPPPPP, 30.0 g, 219.0 mmol, 84%) was advanced without purification.

Step 4: To a solution of alcohol PPPPPP (30.0 g, 219.0 mmol, 1.0 equiv.) in dichloromethane (700 mL, 0.3M) at 0° C. was added triethylamine (61.5 mL, 437.4 mmol, 2.0 equiv), and DMAP (2.7 g, 21.9 mmol, 0.1 equiv.). Acetic anhydride (24.8 mL, 262.4 mmol, 1.2 equiv.) was added and the reaction mixture was stirred for 30 minutes or until the reaction was determined to be complete by LCMS or TLC. The reaction was quenched with ammonium chloride, and organic layer washed with brine, dried over magnesium sulfate and filtered. The resulting solution was then evaporated and the crude acetate (QQQQQQ, 37.0 g, 206.0 mmol, 94%) was used in the following step without further purification.

Step 5: A solution of acetate QQQQQQ (39.4 g, 219.8 mmol, 1.0 equiv.) was dissolved in diethyl ether (100 mL) and then 118 g of silica gel was added. The excess of ether was removed in vacuo and the crude solid was then diluted in pH 7 aqueous buffer (1970 mL, 0.1M). (sodium hydroxyde/sodium phosphate monobasic/water) Then porcine pancreatic lipase type II (3.3 g, (15 mg/mmol)) was added and the reaction was stirred at 37° C. for four hours or until determined to be complete by TLC or LCMS. (After four hours, conversion reached 40% according to ELSD and the enantiomeric excess was determined by chiral SFC, and showed an enantiomeric ratio of 13:1 S:R). The silica gel was filtered off and the aqueous layer was extracted with ethyl acetate three times. The combined organic layers were washed with brine, dried over magnesium sulfate and concentrated. The product was purified by silica gel column chromatography (hexanes:ethyl acetate as eluant) to afford the desired alcohol (RRRRRR, 12.5 g, 91 mmol, 41%).

Step 6: To a solution of alcohol RRRRRR (12.5 g, 91.0 mmol, 1.00 equiv.) in dichloromethane (570 mL, 0.16M) at room temperature was added triethylamine (13.9 mL, 100.1 mmol, 1.1 equiv). The reaction was cooled down to 0° C. and then methanesulfonyl chloride (7.44 mL, 95.5 mmol, 1.05 equiv) was added. The reaction was stirred at 0° C. for 30 minutes or until determined to be complete by TLC or LCMS. The reaction was quenched with sodium bicarbonate and the layers were separated. The aqueous layer was then extracted with dichloromethane. The combined organic layers were washed with brine, dried over magnesium sulfate, and concentrated in vacuo. The resulting sulfonate SSSSSS (19.2 g, 89 mmol, 98%) was advanced without additional purification.

Step 7: To a solution of sulfonate SSSSSS (19.2 g, 89 mmol, 1.0 equiv.) in DMF (120 mL, 0.1M) at room tem- Step 1: To a solution of 2-(pyridin-2-yl)acetic acid hydrochloride salt MMMMMM (50.0 g, 288.0 mmol, 1.0 equiv.) in methanol (500 mL, 0.5M) at 0° C. was added thionyl chloride (31.5 mL, 432.0 mmol, 1.5 equiv.) dropwise. The reaction was stirred at 0° C. for 60 minutes or until the reaction was determined to be complete by LCMS or TLC. The reaction was carefully quenched with sodium carbonate and the aqueous layer extracted with ethyl acetate. The combined organic layers were washed with water, brine, dried over magnesium sulfate, filtered, and concentrated in vacuo. The resulting product (NNNNNN, 41.5 g, 275.0 mmol, 95%) was used in the next step without further purification.

Step 2: To a solution of ester NNNNNN (41.5 g, 275.0 mmol, 1.0 equiv.) in THF (1500 mL, 0.2M) at 0° C. was added sodium 2-methylpropan-2-olate (28.6 g, 288.3 mmol, 1.05 equiv.) and the reaction mixture was stirred for 30 minutes at 0° C. before addition of iodomethane (34.3 mL, 549.1 mmol, 2.0 equiv.). The reaction was stirred at room temperature for 1 hour or until the reaction was determined to be complete by LCMS or TLC. The reaction was quenched with ammonium chloride and the excess of solvent was removed in vacuo. The crude material was then extracted with ethyl acetate. The combined organic layers perature was added cesium carbonate (40.7 g, 125.0 mmol, 1.4 equiv.) and 1-phenyl-1H-tetrazole-5-thiol (19.1 g, 107.1 mmol, 1.2 equiv.). The resulting mixture was stirred at 50° C. for 48 hours, or until determined to be complete by TLC or LCMS. After cooling the mixture to room temperature, brine was added and the aqueous layer was extracted three times with diethyl ether. The combined organic layers were washed with water, brine, and dried over magnesium sulfate. After filtration, the solvent was removed in vacuo and the residue was purified using silica gel column chromatography (hexanes/ethyl acetate) to give the desired product (TTTTTT, 28.9 g, 88 mmol, 99%).

Step 8: To a solution of sulfide TTTTTT (31.5 g, 105.9 mmol, 1.0 equiv.) in EtOH (700 mL, 0.1M) at −10° C. was added ammonium molybdate tetrahydrate (6.5 g, 5.3 mmol, 0.05 equiv.) and hydrogen peroxide (108 mL, 1060 mmol, 5.0 equiv., 33% aqueous solution). The reaction was stirred at −10° C. for four hours or until determined to be complete by TLC or LCMS. The reaction was quenched with water and sodium metabisulfite solution. The crude product was collected by filtration and was purified by silica gel column chromatography (hexanes:ethyl acetate as eluant) to afford the desired product (UUUUUU, 23.2 g, 70.4 mmol, 66%). $^1$H NMR (400 MHz, CHLOROFORM-d) δ: 1.50 (d, J=7.03 Hz, 3H) 1.66 (br. s., 1H) 3.75 (quind, 1H) 3.94 (dd, J=14.81, 5.02 Hz, 1H) 4.55 (dd, J=14.68, 7.91 Hz, 1H) 7.14-7.22 (m, 2H) 7.29 (s, 1H) 7.57-7.70 (m, 6H) 8.44-8.49 (m, 1H).

Racemic 2-(1-((1-phenyl-1H-tetrazol-5-yl)sulfonyl)propan-2-yl)pyridine could be prepared using a similar synthetic strategy as described in scheme 23 by skipping steps 5 and 6 (Lipase resolution).

Other heterocyclic Julia fragments, including (3-(1-((1-phenyl-1H-tetrazol-5-yl)sulfonyl)propan-2-yl)pyridine, 4-(1-phenyl-1H-tetrazol-5-yl)sulfonyl)propan-2-yl)pyridine, 4-(2-methyl-3-((1-phenyl-1H-tetrazol-5-yl)sulfonyl)propan-2-yl)pyrimidine, and 3-(1(1-((1-phenyl-1H-tetrazol-5-yl)sulfonyl)propan-2-yl)pyridazine, were prepared in a similar manner (steps 5 and 6 (lipase resolution) were skipped to produce a racemic mixture at C16) starting with the corresponding heterocycle.

Preparation of racemic Compounds 36 and 37

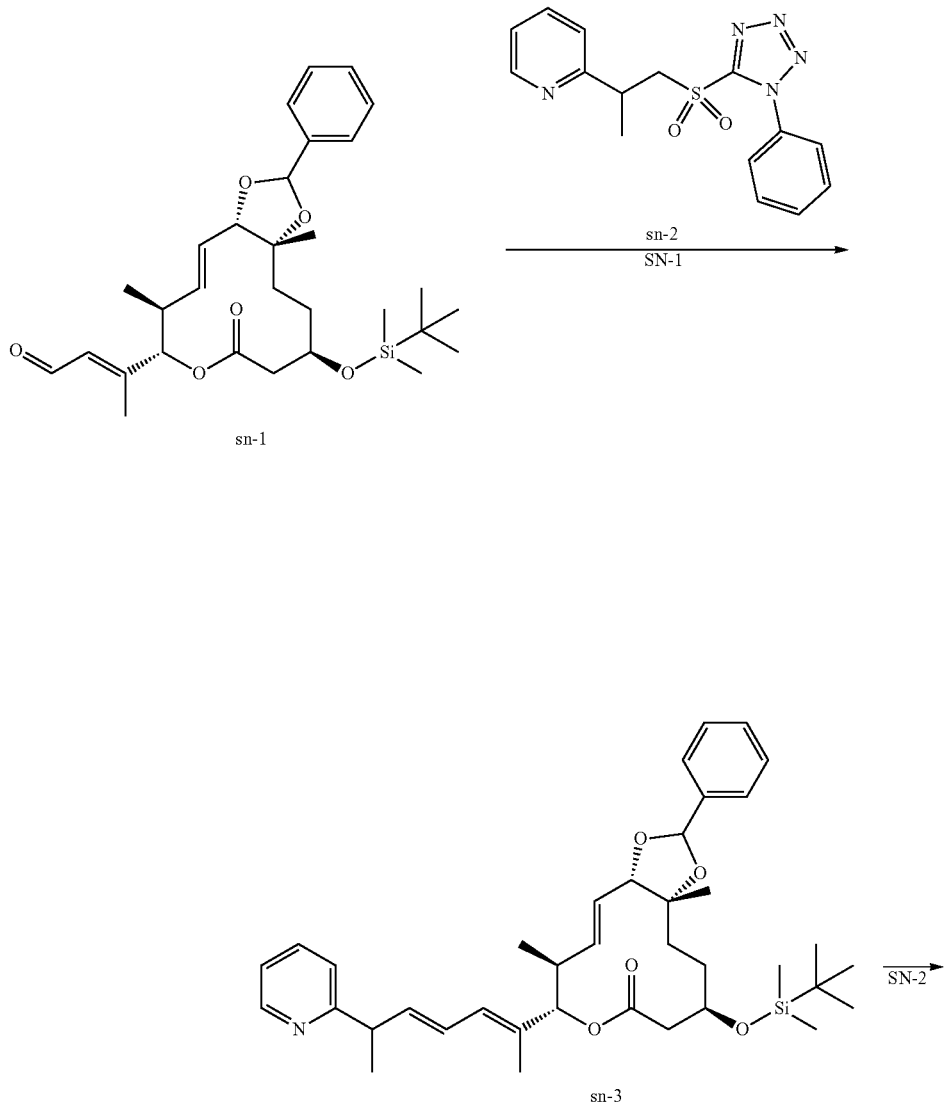

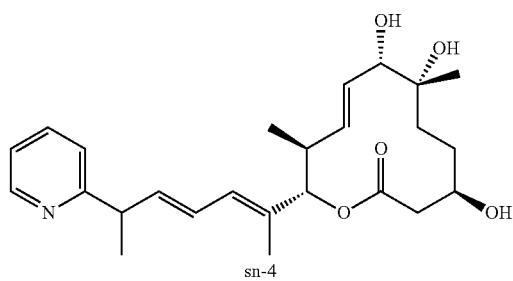

sn-4

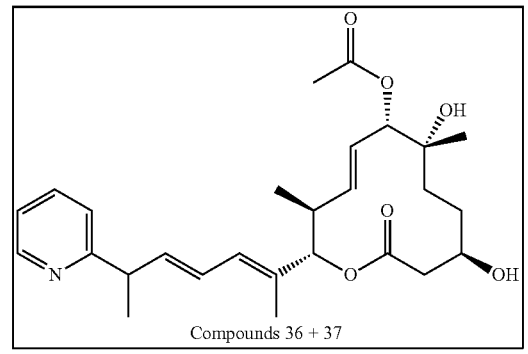

Compounds 36 + 37

Step SN-1: To a stirred solution of sn-2 (2.55 equiv.) in THF (30 mL) at −78° C. under $N_2$ was added KHMDS (2.55 equiv., 0.5M solution in toluene) slowly. The reaction was stirred at −78° C. for 30 minutes. Next, aldehyde sn-1 (1 g, 1.89 mmol, 1.0 equiv.) in THF (10 mL, final conc. 0.047M) was added slowly at −78° C. and the reaction was stirred for 3.5 hours at the same temperature, or until the reaction was determined to be complete by LCMS or TLC. The reaction was allowed to warm to room temperature. The reaction mixture was diluted with water and ethyl acetate. The aqueous layer was extracted with additional ethyl acetate and the combined organic layers were washed with brine, dried over magnesium sulfate, filtered, and concentrated in vacuo. The residue was purified by silica gel column chromatography (heptane/ethyl acetate as eluent) to afford the desired product sn-3 (1.08 g, 90%). LCMS data (ES+) M+Na 654.4.

Step SN-2: A stirred solution of the protected macrolide sn-3 (530 mg, 0.837 mmol, 1.0 equiv.) in acetic acid/water (4:1) (0.042M) was heated at 80° C. for 8 hours under $N_2$. The reaction mixture was evaporated and the resulting residue was dissolved with water and ethyl acetate. The aqueous solution was adjusted to pH=9 by the addition of saturated aqueous $NaHCO_3$ solution. The resulting aqueous layer was extracted with additional ethyl acetate. The combined organic layers were washed with brine, dried over magnesium sulfate, filtered, and concentrated in vacuo. The residue was purified by silica gel column chromatography (heptane/ethyl acetate as eluent) to afford the desired product sn-4 (127 mg, 35%). LCMS data (ES+) M+430.2.

Step SN-3: To a stirred solution of the triol sn-4 (127 mg, 0.296 mmol, 1.0 equiv.) in dichloromethane (0.05M) at 0° C. under $N_2$, triethylamine (2 equiv.), acetic anhydride (1 equiv.) and 4-dimethylaminopyridine (0.2 equiv.) were added. The resulting mixture was stirred at 0° C. for 1 hour or until the reaction was determined to be complete by LCMS or TLC. The reaction was quenched with saturated aqueous $NaHCO_3$ solution and ethyl acetate was added. The aqueous layer was extracted with ethyl acetate. The combined organic layers were washed with water and brine, dried over magnesium sulfate, filtered, and concentrated in vacuo. The residue was purified by silica gel column chromatography (heptane/ethyl acetate as eluent) to afford the mixture of Compounds 36 and 37 (112 mg, 80%).

$^1$H NMR (400 MHz, CHLOROFORM-d) δ: 0.83-0.96 (m, 3H) 1.17-1.82 (m, 13H) 2.08 (s, 3H) 2.43-2.70 (m, 3H) 3.40-3.83 (m, 3H) 5.07 (d, J=8.8 Hz, 1H) 5.14 (d, J=10.8 Hz, 1H) 5.53-5.73 (m, 2H) 5.92-6.05 (m, 1H) 6.07-6.18 (m, 1H) 6.25-6.38 (m, 1H) 7.06-7.21 (m, 2H) 7.56-7.69 (m, 1H) 8.48-8.60 (m, 1H).

LCMS data (ES+) M+Na 494.1.

The intermediate of macrolide aldehyde sn-1 was prepared as previously reported (R. M. Kanada and D. Ito et. al., Angew. Chem. Int. Ed. 2007, 46, 4350-4355), and sn-2 was prepared in an analogous manner as described in Scheme 23.

Protocol for Synthesis of Compound 162

Scheme 29.

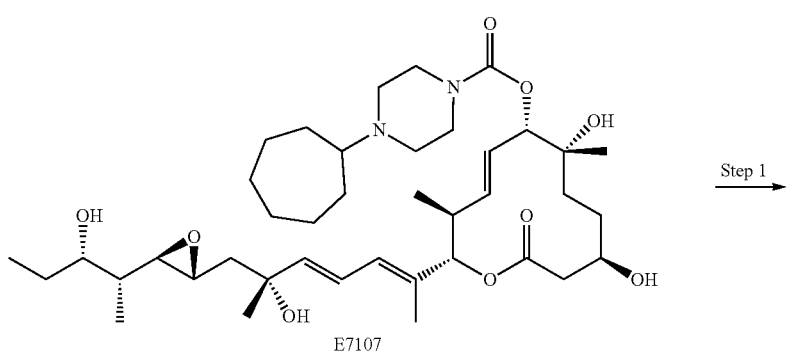

E7107

Step 1

-continued

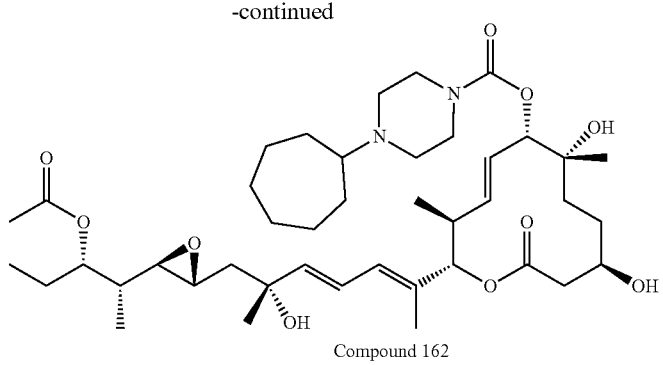

Compound 162

Step 1: To a solution of E7107 (30 mg, 0.042 mmol, 1.0 equiv) in DCE (1 mL) was added DMAP (1.020 mg, 8.34 μm, 0.2 equiv), Hunig's base (0.037 mL, 0.209 mmol, 5.0 equiv) and acetic anhydride (4.72 μL, 0.05 mmol, 1.2 equiv). After 2 hrs, the reaction mixture was evaporated. Purification by silica gel chromatography (0-10% MeOH/DCM) was completed to give desired product (Compound 162, 24 mg, 0.032 mmol, 76%). ¹H NMR (400 MHz, CHLOROFORM-d) δ: ppm 0.01 (d, J=4.52 Hz, 6H) 0.76-0.88 (m, 14H) 0.99 (d, J=6.78 Hz, 3H) 1.14 (s, 3H) 1.18-1.25 (m, 3H) 1.31-1.59 (m, 8H) 1.63 (d, J=0.75 Hz, 4H) 2.03 (s, 4H) 2.27-2.58 (m, 4H) 2.71-2.86 (m, 3H) 3.10-3.24 (m, 2H) 3.71-3.82 (m, 1H) 3.89 (d, J=6.78 Hz, 2H) 4.89 (d, J=10.67 Hz, 1H) 5.01 (d, J=9.29 Hz, 1H) 5.50-5.65 (m, 3H) 6.05 (s, 1H) 6.12-6.28 (m, 1H). MS(ES+): 761.73 [M+H]⁺.

TABLE 8

Compounds 147-162

| Structure, Compound #, and Chemical Name | ¹H NMR data | LCMS data (ES+) |
|---|---|---|
| 147<br>[(2S,3S,4E,6S,7S,10S)-2-[(2E,4E,6R)-7-(4-cyclopropyltriazol-1-yl)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | ¹H NMR (400 MHz, METHANOL-d4) 0.78-0.98 (m, 6 H) 0.99-1.06 (m, 3 H) 1.19-1.28 (m, 4 H) 1.28-1.43 (m, 2 H) 1.50-1.62 (m, 14 H) 1.63-1.75 (m, 6 H) 1.85-1.99 (m, 2 H) 2.41-2.68 (m, 7 H) 2.73-2.89 (m, 1 H) 3.39-3.62 (m, 4 H) 3.75 (br. s., 2 H) 4.07-4.26 (m, 2 H) 5.01 (d, J = 9.54 Hz, 1 H) 5.13 (d, J = 10.67 Hz, 1 H) 5.55-5.74 (m, 3 H) 6.01-6.07 (m, 1 H) 6.10-6.20 (m, 1 H) | 683.5 |
| 148<br>[(2S,3S,4E,6S,7S,10S)-7,10-dihydroxy-2-[(2E,4E,6S)-7-methoxycarbonyloxy-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, METHANOL-d4) δ: 0.91 (d, J = 6.65 Hz, 3 H) 1.09 (d, J = 6.78 Hz, 3 H) 1.11-1.19 (m, 1 H) 1.23 (s, 3 H) 1.30-1.46 (m, 3 H) 1.50-1.69 (m, 2 H) 1.77 (s, 3 H) 2.40 (s, 3 H) 2.46-2.71 (m, 7 H) 3.41-3.70 (m, 4 H) 3.75 (s, 3 H) 3.78-3.84 (m, 1 H) 3.92-4.09 (m, 2 H) 4.96 (d, J = 9.54 Hz, 1 H) 5.07 (d, J = 10.67 Hz, 1 H) 5.53-5.81 (m, 3 H) 6.11 (d, J = 10.54 Hz, 1 H) 6.38 (dd, J = 15.00, 10.85 Hz, 1 H) | 566.5 |

TABLE 8-continued

Compounds 147-162

| Structure, Compound #, and Chemical Name | ¹H NMR data | LCMS data (ES+) |
|---|---|---|
| 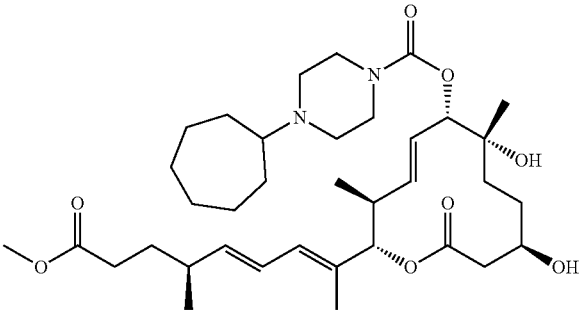<br>149<br>[(2S,3S,4E,6S,7S,10S)-7,10-dihydroxy-2-[(2E,4E,6R)-9-methoxy-6-methyl-9-oxonona-2,4-dien-2-yl]-3,7-dimethyl-12-oxo-1-oxacyclododec-4-en-6-yl] 4-cycloheptylpiperazine-1-carboxylate | ¹H NMR (400 MHz, CHLOROFORM-d) δ: 7.19 (s, 4H), 6.04-6.30 (m, 1H), 5.83-6.04 (m, 1H), 5.45-5.71 (m, 3H), 5.08 (d, J = 10.8 Hz, 1H), 4.95 (d, J = 9.5 Hz, 1H), 3.68 (br. s., 1H), 3.59 (s, 2H), 3.36-3.51 (m, 3H), 3.08-3.36 (m, 2H), 2.37-2.62 (m, 6H), 2.09-2.37 (m, 3H), 1.92-2.04 (m, 1H), 1.87 (br. s., 1H), 1.38-1.67 (m, 15H), 1.10-1.37 (m, 8H), 0.88-1.00 (m, 3H), 0.84 (d, J = 6.8 Hz, 3H) | 647.5 |
| 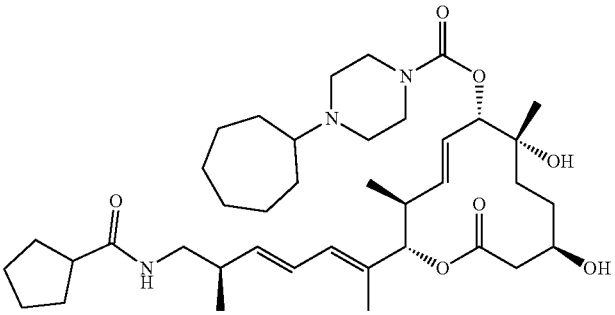<br>150<br>[(2S,3S,4E,6S,7S,10S)-2-[(2E,4E,6R)-7-(cyclopentanecarbonylamino)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | ¹H NMR (400 MHz, CHLOROFORM-d) δ: 0.91 (d, J = 6.65 Hz, 3 H) 1.04 (d, J = 6.65 Hz, 3 H) 1.27 (s, 3 H)) 1.20-1.62 (m, 18 H) 1.65-1.78 (m, 5 H) 1.79-1.87 (m, 2 H) 190-2.01 (m, 2 H) 2.37-2.67 (m, 5 H) 2.72-2.84 (br. s., 4 H) 2.87-2.98 (m, 1 H) 3.04-3.14 (m, 1 H) 3.25-3.36 (m, 1 H) 3.66 (br. s., 4 H) 3.71-3.80 (m, 1 H) 5.02 (d, J = 9.41 Hz, 1 H) 5.16 (d, J = 10.67 Hz, 1 H) 5.43 (t, J = 5.34 Hz, 1 H) 5.55-5.66 (m, 2 H) 5.67 (dd, J = 15.06, 9.29 Hz, 1 H) 6.09 (d, J = 11.17 Hz, 1 H) 6.25 (dd, J = 15.00, 10.85 Hz, 1 H) | 686.6 |
| 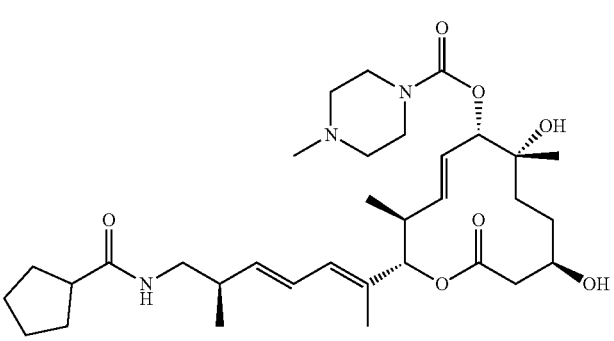<br>151<br>[(2S,3S,4E,6S,7S,10S)-2-[(2E,4E,6R)-7-(cyclopentanecarbonylamino)-6-methylhepta-2,4-dien-2-yl]-7,10-dihydroxy-3,7-dimethyl-12-oxo-1-oxacyclododec-4-en-6-yl] 4-methylpiperazine-1-carboxylate | ¹H NMR (400 MHz, METHANOL-d4) 0.88 (d, J = 6.78 Hz, 3 H) 1.02 (d, J = 6.78 Hz, 3 H) 1.21 (m, 3 H) 1.27-1.44 (m, 6 H) 1.53-1.72 (m, 6 H) 1.74 (s, 3 H) 1.76-1.84 (m, 2 H) 2.35 (s, 3 H) 2.41-2.63 (m, 10 H) 3.05-3.17 (m, 2 H) 3.54 (br. s., 1 H) 3.79 (br. s., 1 H) 4.94 (d, J = 9.66 Hz, 1 H) 5.04 (d, J = 10.54 Hz, 1 H) 5.54-5.64 (m, 2 H) 5.65-5.77 (m, 1 H) 6.02-6.13 (m, 1 H) 6.22-6.34 (m, 1 H) 7.78-7.86 (m, 1 H) | 604.4 |

TABLE 8-continued

Compounds 147-162

| Structure, Compound #, and Chemical Name | ¹H NMR data | LCMS data (ES+) |
|---|---|---|
| 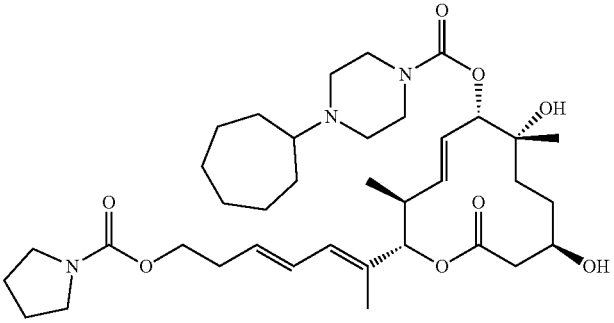<br>152<br>4-cycloheptyl-1-piperazinecarboxylic acid [(2R,3S,4E,6R,7R,10R)-7,10-dihydroxy-3,7-dimethyl-12-oxo-2-[(2E,4E)-7-[oxo(1-pyrrolidinyl)methoxy]hepta-2,4-dien-2-yl]-1-oxacyclododec-4-en-6-yl] ester | ¹H NMR (400 MHz, CHLOROFORM-d) δ: 0.71-0.88 (m, 6 H) 0.98-1.06 (m, 1 H) 1.13-1.27 (m, 13 H) 1.29-1.52 (m, 10 H) 1.56 (br. s., 9 H) 1.61-1.70 (m, 4 H) 1.73 (br. s., 2 H) 1.89 (br. s., 2 H) 2.34-2.59 (m, 7 H) 3.41 (d, J = 5.27 Hz, 4 H) 3.65-3.78 (m, 2 H) 4.11 (t, J = 6.78 Hz, 2 H) 4.88-5.02 (m, 1 H) 5.08 (d, J = 10.54 Hz, 1 H) 5.43-5.68 (m, 3 H) 6.01 (d, J = 10.29 Hz, 1 H) 6.25 (dd, J = 15.06, 11.04 Hz, 1 H) | 674.3 |
| 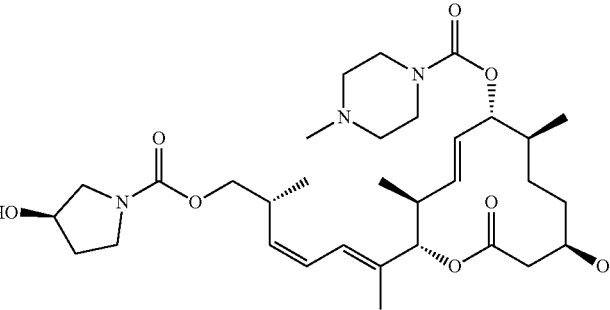<br>153<br>[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, CHLOROFORM-d) δ: 0.91 (d, J = 6.78 Hz, 3 H) 0.97-1.03 (m, 6 H) 1.44-1.55 (m, 2 H) 1.67-1.85 (m, 5 H) 1.86-2.01 (m, 2 H) 2.37-2.62 (m, 11 H) 3.02 (br. s., 1 H) 3.20-3.32 (m, 1 H) 3.38-3.63 (m, 9 H) 3.68-3.75 (m, 2 H) 3.79-4.10 (m, 2 H) 4.40-4.48 (m, 1 H) 4.86 (t, J = 10.10 Hz, 1 H) 5.14 (dd, J = 10.48, 5.58 Hz, 1 H) 5.28-5.41 (m, 2 H) 5.55 (dd, J = 14.93, 9.91 Hz, 1 H) 6.20 (t, J = 11.23 Hz, 1 H) 6.36 (br. d, J = 11.17 Hz, 1 H) | 606.5 |
| 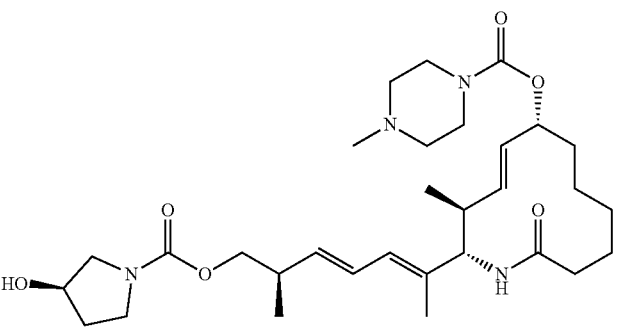<br>154<br>[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-azacyclododec-4-en-6-yl] 4-methylpiperazine-1-carboxylate | ¹H NMR (400 MHz, CHLOROFORM-d) δ: 0.97 (d, J = 6.53 Hz, 3 H) 1.07 (d, J = 6.78 Hz, 3 H) 1.31-1.70 (m, 7 H) 1.71 (s, 3 H) 1.80-2.06 (m, 3 H) 2.21-2.32 (m, 2 H) 2.32 (s, 3 H) 2.39 (br. s., 4 H) 2.56-2.64 (m, 1 H) 3.42-3.59 (m, 6 H) 3.91-4.02 (m, 2 H) 4.15-4.26 (m, 1 H) 4.45-4.50 (m, 1 H) 5.14 (td, J = 10.04, 5.14 Hz, 1 H) 5.26-5.40 (m, 2 H) 5.58 (dd, J = 15.06, 10.04 Hz, 1 H) 5.65 (dd, J = 15.12, 7.47 Hz, 1 H) 6.06 (d, J = 10.41 Hz, 1 H) 6.27 (dd, J = 14.62, 11.23 Hz, 1 H) | 575.4 |

TABLE 8-continued

Compounds 147-162

| Structure, Compound #, and Chemical Name | ¹H NMR data | LCMS data (ES+) |
|---|---|---|
| 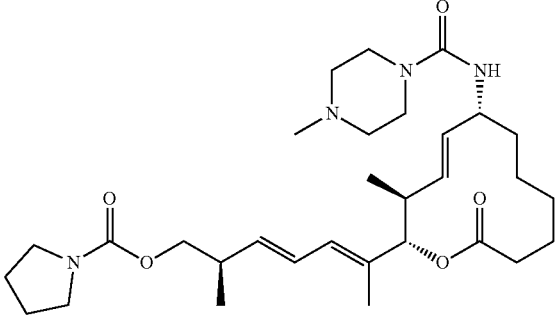<br>155<br>[(2R,3E,5E)-2-methyl-6-[(2S,3S,4E,6R)-3-methyl-6-[(4-methylpiperazine-1-carbonyl)amino]-12-oxo-1-oxacyclododec-4-en-2-yl]hepta-3,5-dienyl] pyrrolidine-1-carboxylate | ¹H NMR (400 MHz, CHLOROFORM-d) δ: 0.78-0.97 (m, 6 H) 1.06 (d, J = 6.78 Hz, 3 H) 1.16-1.39 (m, 4 H) 1.43-1.61 (m, 2 H) 1.76-1.87 (m, 2 H) 2.22-2.47 (m, 7 H) 2.55-2.64 (m, 1 H) 3.30-3.41 (m, 8 H) 3.90-4.00 (m, 2 H) 4.15-4.28 (m, 4 H) 5.02 (d, J = 10.67 Hz, 1 H) 5.14-5.30 (m, 3 H) 5.35-5.45 (m, 2 H) 5.67 (dd, J = 15.06, 7.53 Hz, 1 H) 6.10 (d, J = 11.42 Hz, 1 H) 6.23-6.30 (m, 1 H) 6.45 (d, J = 0.88 Hz, 1 H) | 559.5 |
| 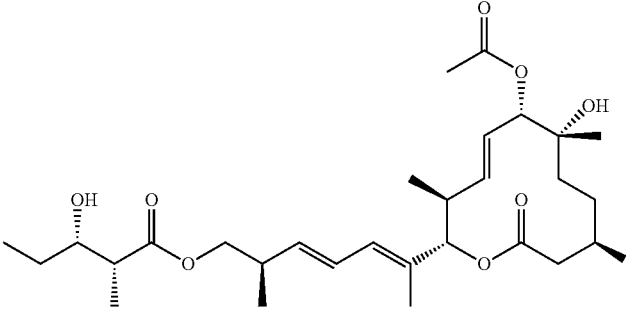<br>156<br>[(2S,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R,3R)-3-hydroxy-2-methylpentanoate | ¹H NMR (400 MHz, METHANOL-d4) δ: 0.79 (d, J = 6.8 Hz, 2 H) 0.84 (t, J = 7.5 HZ, 1H) 0.97 (d, J = 6.78 Hz, 1 H) 1.05-1.09 (m, 2 H) 1.14-1.32 (m, 5 H) 1.36 (dt, J = 7.84, 3.98 Hz, 1 H) 1.44-1.59 (m, 1 H) 1.65 (d, J = 1.00 Hz, 2 H) 1.96 (s, 2 H) 2.16-2.39 (m, 3 H) 3.03 (dt, J = 3.51, 2.01 Hz, 2 H) 3.38 (dt, J = 3.26, 1.63 Hz, 1 H) 3.46-3.63 (m, 1 H) 3.69 (br. s., 1 H) 3.78-4.04 (m, 1 H) 4.46 (br. s., 1 H) 4.67 (s, 1 H) 4.95 (d, J = 10.04 Hz, 2 H) 5.46-5.65 (m, 2 H) 5.99 (d, J = 12.05 Hz, 1 H) 6.25 (dd, J = 15.94, 10.92 Hz, 1 H) | (M + Na) 561.3 |
| 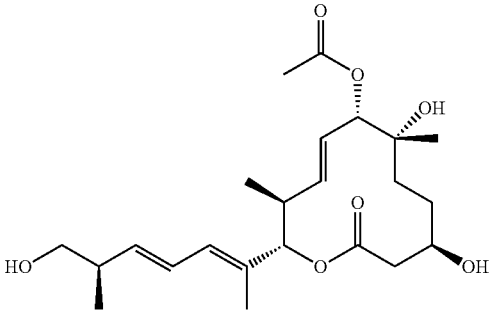<br>157<br>[(2S,3S,4E,6S,7S,10S)-7,10-dihydroxy-2-[(2E,4E,6R)-7-hydroxy-6-methylhepta-2,4-dien-2-yl]-3,7-dimethyl-12-oxo-1-oxacyclododec-4-en-6-yl] acetate | ¹H NMR (400 MHz, CHLOROFORM-d) δ: ppm 0.72-0.89 (m, 3 H) 0.97 (d, J = 6.78 Hz, 3 H) 1.11-1.35 (m, 7 H) 1.42-1.56 (m, 2 H) 1.56-1.71 (m, 4 H) 2.02 (s, 3 H) 2.34-2.58 (m, 3 H) 3.32-3.54 (m, 3 H) 3.56-3.83 (m, 1 H) 5.01 (d, J = 9.03 Hz, 1 H) 5.09 (d, J = 10.54 Hz, 1 H) 5.50-5.65 (m, 3 H) 6.03 (d, J = 10.79 Hz, 1 H) 6.25 (ddd, J = 15.06, 10.79, 1.00 Hz, 1 H) | 425.30 |

TABLE 8-continued

Compounds 147-162

| Structure, Compound #, and Chemical Name | ¹H NMR data | LCMS data (ES+) |
|---|---|---|
| 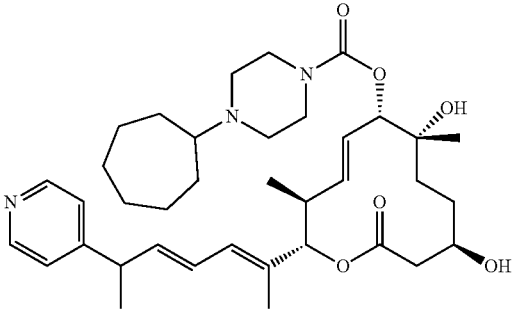<br>158<br>[(2S,3S,4E,6S,7S,10S)-7,10-dihydroxy-3,7-dimethyl-12-oxo-2-[(2E,4E)-6-pyridin-4-ylhepta-2,4-dien-2-yl]-1-oxacyclododec-4-en-6-yl] 4-cycloheptylpiperazine-1-carboxylate | ¹H NMR (400 MHz, DICHLOROMETHANE-d2) δ: 8.48 (d, J = 3.6 Hz, 2H), 7.14 (d, J = 4.6 Hz, 2H), 6.31 (dddd, J = 15.2, 10.8, 4.5, 1.3 Hz, 1H), 6.10 (dd, J = 10.8, 1.0 Hz, 1H), 5.87 (dd, J = 15.0, 7.5 Hz, 1H), 5.63-5.74 (m, J = 9.7 Hz, 1H), 5.55 (ddd, J = 15.4, 10.2, 1.8 Hz, 1H), 5.13 (d, J = 10.7 Hz, 1H), 4.97 (d, J = 9.7 Hz, 1H), 3.64-3.78 (m, 1H), 3.53 (quin, J = 7.0 Hz, 1H), 3.41 (br. s., 4H), 3.31 (br. d, J = 7.2 Hz, 1H), 2.55 (d, J = 3.5 Hz, 3H), 2.46 (br. s., 4H), 1.74 (d, J = 1.3 Hz, 4H), 1.70-1.81 (m, 4H), 1.59-1.70 (m, 3H), 1.39 (d, J = 13.3 Hz, 1H), 1.34-1.58 (m, 11H), 1.25-1.34 (m, 3H), 1.20 (s, 3H), 0.88 (dd, J = 8.2, 6.9 Hz, 3H) | 638.5 |
| 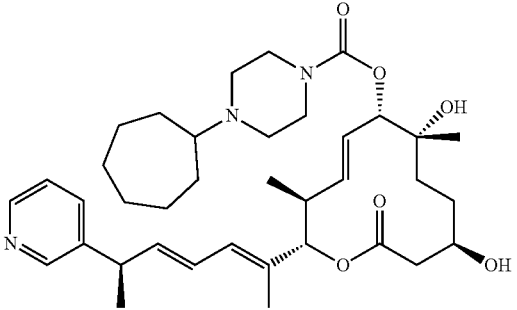<br>159<br>[(2S,3S,4E,6S,7S,10S)-7,10-dihydroxy-3,7-dimethyl-12-oxo-2-[(2E,4E,6S)-6-pyridin-3-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.82-1.00 (m, 3 H) 1.24-1.31 (m, 4 H) 1.34-1.60 (m, 12 H) 1.65-1.88 (m, 8 H) 1.96-2.12 (m, 1 H) 2.45-2.67 (m, 7 H) 3.50 (br. s., 4 H) 3.59 (t, J = 7.03 Hz, 1 H) 3.68-3.88 (m, 1 H) 4.95-5.10 (m, 1 H) 5.17 (d, J = 10.54 Hz, 1 H), 5.54-5.79 (m, 2 H) 5.90 (dd, J = 15.06, 7.03 Hz, 1 H) 6.12 (d, = 10.79 Hz, 1 H) 6.27 (ddd, J = 15.06, 10.79, 1.25 Hz, 1 H) 7.26 (d, J = 4.77 Hz, 1 H) 7.54 (dt, J = 4.51 Hz, 1 H) 8.41-8.58 (m, 2 H) | 638.5 |
| 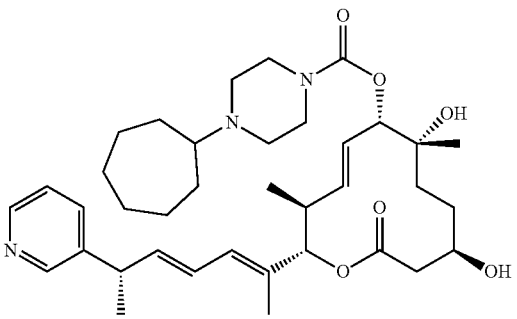<br>160<br>[(2S,3S,4E,6S,7S,10S)-7,10-dihydroxy-3,7-dimethyl-12-oxo-2-[(2E,4E,6S)-6-pyridin-3-ylhepta-2,4-dien-2-yl]-1-oxacyclododec-4-en-6-yl] 4-cycloheptylpiperazine-1-carboxylate | ¹H NMR (400 MHz, CHLOROFORM-d) δ: 0.87-0.97 (m, 3 H) 1.23-1.30 (m, 4 H) 1.32-1.60 (m, 12 H) 1.64-1.78 (m, 7 H) 1.78-1.93 (m, 2 H) 1.99 (br. s., 1 H) 2.42-2.68 (m, 6 H) 3.37-3.64 (m, 5 H) 3.76 (d, J = 6.53 Hz, 1 H) 5.03 (d, J = 9.54 Hz, 1 H) 5.17 (d, J = 10.54 Hz, 1 H) 5.54-5.78 (m, 2 H) 5.91 (dd, J = 14.93, 6.90 Hz, 1 H) 6.12 (d, J = 11.54 Hz, 1 H) 6.18-6.40 (m, 1 H) 7.27 (s, 1 H) 7.41-7.66 (m, 1 H) 8.40-8.60 (m, 2 H) | 638.4 |

TABLE 8-continued

Compounds 147-162

| Structure, Compound #, and Chemical Name | $^1$H NMR data | LCMS data (ES+) |
|---|---|---|
| <br>161<br>[(2S,3S,4E,6S,7S,10S)-7,10-dihydroxy-3,7-dimethyl-2-[(2E,4E)-7-methyl-6-pyridin-2-ylocta-2,4-dien-2-yl]-12-oxo-1-oxacyclododec-4-en-6-yl] acetate | $^1$H NMR (400 MHz, METHANOL-d4) δ: ppm 0.76 (dd, J = 6.59, 1.32 Hz, 3 H) 0.78-0.87 (m, 1 H) 0.91 (d, J = 6.65 Hz, 2 H) 0.99 (d, J = 6.78 Hz, 3 H) 1.20 (s, 3 H) 1.33-1.43 (m, 2 H) 1.55-1.65 (m, 2 H) 1.70-1.79 (m, 3 H) 2.00-2.04 (m, 1 H) 2.05-2.19 (m, 4 H) 2.53 (br dd, J = 15.75, 3.33 Hz, 3 H) 3.11-3.22 (m, 1 H) 3.73-3.85 (m, 1 H) 5.03-5.09 (m, 2 H) 5.51-5.63 (m, 1 H) 5.66-5.76 (m, 1 H) 5.99 (dd, J = 15.00, 9.60 Hz, 1 H) 6.13 (br d, J = 10.79 Hz, 1 H) 6.32-6.43 (m, 1 H) 7.23-7.38 (m, 2 H) 7.72-7.83 (m, 1 H) 8.41-8.52 (m, 1 H) | 500.58 |
| <br>162<br>[(2S,3S,4E,6S,7S,10S)-2-[(2E,4E,6S)-7-[(2R,3R)-3-[(2R,3R)-3-acetyloxypentan-2-yl]oxiran-2-yl]-6-hydroxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate | $^1$H NMR (400 MHz, CHLOROFORM-d) δ: ppm 0.01 (d, J = 4.52 Hz, 6 H) 0.76-0.88 (m, 14 H) 0.99 (d, J = 6.78 Hz, 3 H) 1.14 (s, 3 H) 1.18-1.25 (m, 3 H) 1.31-1.59 (m, 8 H) 1.63 (d, J = 0.75 Hz, 4 H) 2.03 (s, 4 H) 2.27-2.58 (m, 4 H) 2.71-2.86 (m, 3 H) 3.10-3.24 (m, 2 H) 3.71-3.82 (m, 1 H) 3.89 (d, J = 6.78 Hz, 2 H) 4.89 (d, J = 10.67 Hz, 1 H) 5.01 (d, J = 9.29 Hz, 1 H) 5.50-5.65 (m, 3 H) 6.05 (s, 1 H) 6.12-6.28 (m, 1 H) | 761.73 |

Synthesis of Compounds 163-174

Synthesis of Compound 163

Scheme 30.

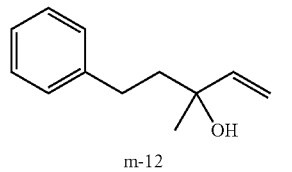

m-12

-continued

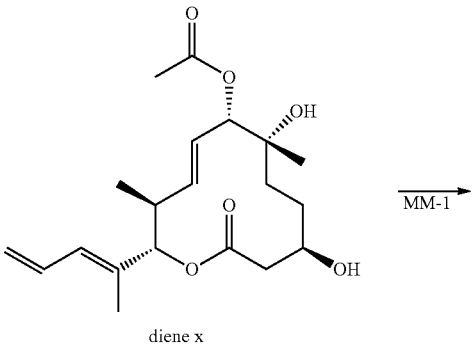

diene x

MM-1 →

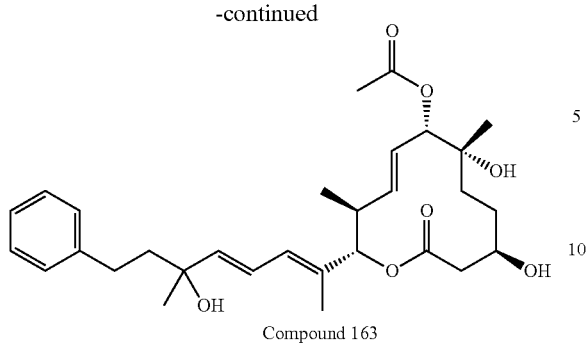

Compound 163

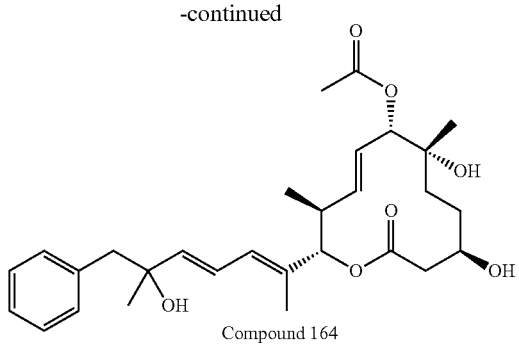

Compound 164

Step MM-1: To a mixture of macrolide diene x (15 mg, 0.041 mmol, 1.0 equiv.) and commercially available allylic alcohol m-12 (3.0 equiv.) in dichloromethane (0.014M) was added Hoveyda-Grubbs II catalyst (0.1 equiv.). The reaction mixture was stirred at reflux under a nitrogen atmosphere for 1 hour, or until the reaction was determined to be completed by TLC. The reaction mixture was cooled to room temperature and concentrated in vacuo. The crude product was purified by silica gel column chromatography (heptane:ethyl acetate as eluant) to afford the title Compound 163 (12.6 mg, 59%). $^1$H NMR (400 MHz, CHLOROFORM-d) δ: 0.90 (d, J=6.4 Hz, 3H) 1.21 (s, 3H) 1.23-1.47 (m, 5H) 1.48-1.74 (m, 4H) 1.77 (s, 3H) 1.79-1.94 (m, 2H) 2.10 (s, 3H) 2.47-2.74 (m, 5H) 3.54 (d, J=10.4 Hz, 1H) 3.75 (br. s., 1H) 5.09 (d, J=8.8 Hz, 1H) 5.18 (d, J=10.8 Hz, 1H) 5.58-5.72 (m, 2H) 5.86 (d, J=15.2 Hz, 1H) 6.13 (d, J=10.8 Hz, 1H) 6.48 (dd, J=15.2, 10.8 Hz, 1H) 7.10-7.22 (m, 3H) 7.23-7.31 (m, 2H). LCMS data (ES+) M+Na 537.3.

The intermediate diene x was prepared as previously reported (R. M. Kanada and D. Ito et. al., *Angew. Chem. Int. Ed.* 2007, 46, 4350-4355).

Synthesis of Compound 164

Scheme 31.

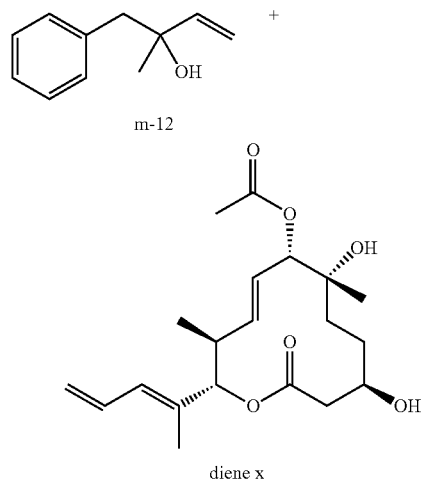

The title Compound 164 (6.8 mg, 61%) was prepared from commercially available allylic alcohol m-12 (6.0 equiv.) and macrolide diene x (8.4 mg, 0.23 mmol, 1.0 equiv.) in an analogous manner as described for step MM-1. $^1$H NMR (400 MHz, CHLOROFORM-d) δ: 0.80-0.95 (m, 3H) 1.15-1.46 (m, 5H) 1.60-1.78 (m, 9H) 1.90 (s, 1H) 2.10 (s, 3H) 2.45-2.67 (m, 3H) 3.51 (d, J=10.8 Hz, 1H) 3.76 (br. s., 1H) 5.09 (d, J=8.8 Hz, 1H) 5.17 (d, J=10.4 Hz, 1H) 5.57-5.71 (m, 2H) 6.06 (d, J=14.8 Hz, 1H) 6.14 (d, J=10.0 Hz, 1H) 6.50 (ddd, J=15.2, 10.8, 8.4 Hz, 1H) 7.21-7.30 (m, 1H) 7.31-7.39 (m, 2H) 7.40-7.49 (m, 2H). LCMS data (ES+) M+Na 509.3.

Synthesis of Compound 165

Scheme 32.

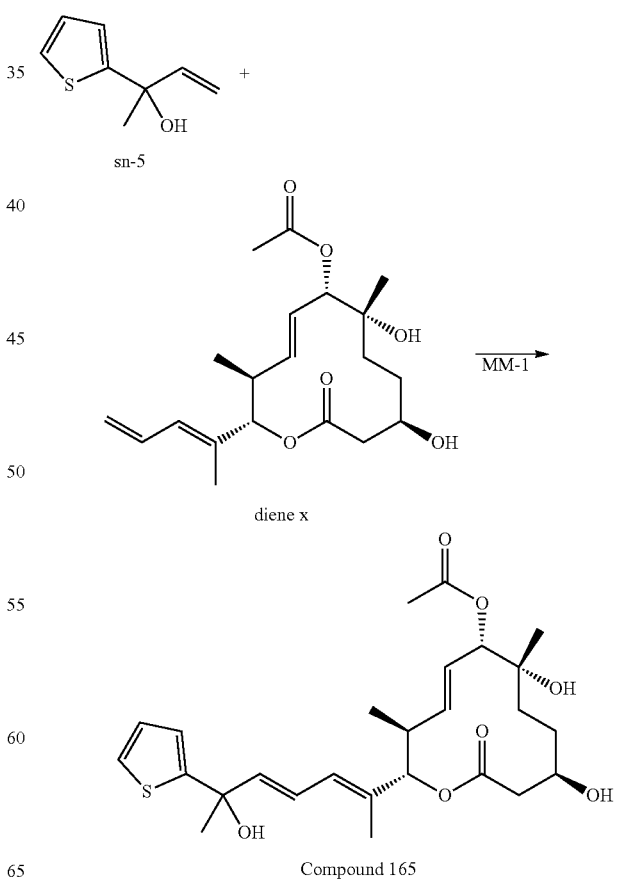

Compound 165

The title Compound 165 (5.3 mg, 46%) was prepared from commercially available thiophene sn-5 (29.9 mg, 0.194 mmol, 8.3 equiv.) and macrolide diene x (8.6 mg, 0.0235 mmol, 1.0 equiv.) in an analogous manner as described for MM-1. $^1$H NMR (400 MHz, CHLOROFORM-d) δ: 0.82-0.98 (m, 3H) 1.15-1.44 (m, 8H) 1.47-1.88 (m, 5H) 1.99-2.26 (m, 5H) 2.44-2.74 (m, 3H) 3.44-3.61 (m, 1H) 3.75 (br. s., 1H) 5.02-5.26 (m, 2H) 5.53-5.75 (m, 2H) 6.00-6.22 (m, 2H) 6.47-6.63 (m, 1H) 6.89-7.03 (m, 2H) 7.17-7.35 (m, 1H). LCMS data (ES+) M+Na 515.1.

Synthesis of Compound 166

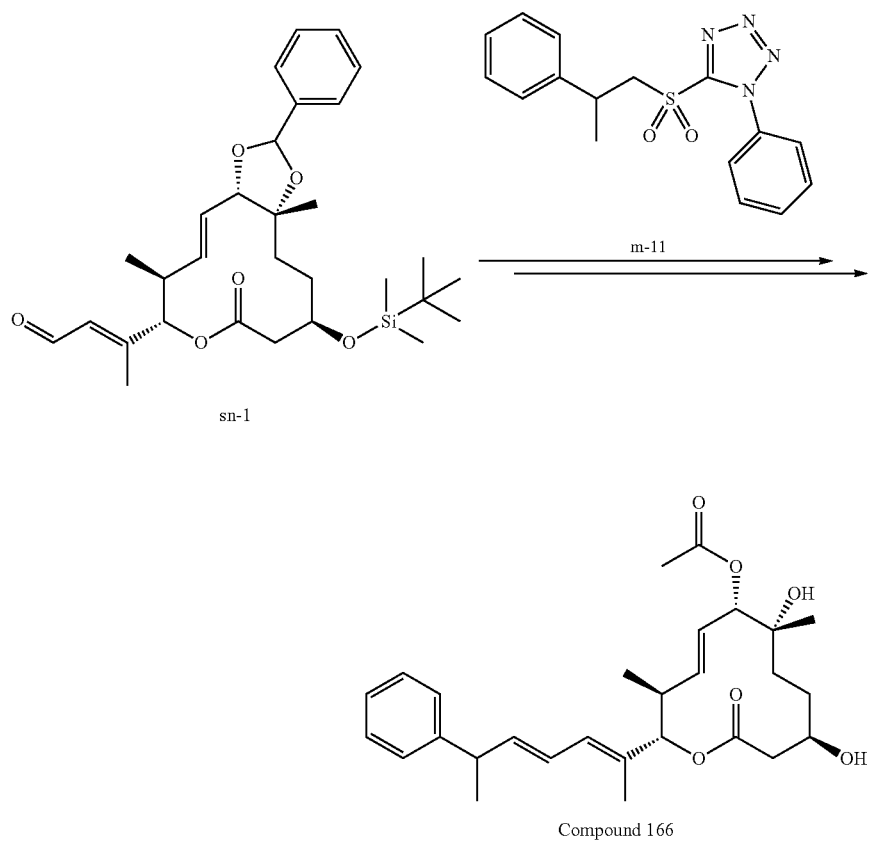

Compound 166

The title Compound 166 was prepared in an analogous manner to previously described reaction of Julia fragments with aldehydes. The intermediate of macrolide aldehyde sn-1 was prepared as previously reported (R. M. Kanada and D. Ito et. al., *Angew. Chem. Int. Ed.* 2007, 46, 4350-4355). The sulfone intermediate m-11 was prepared in the following manner.

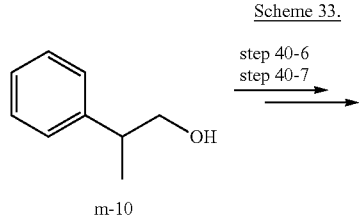

-continued

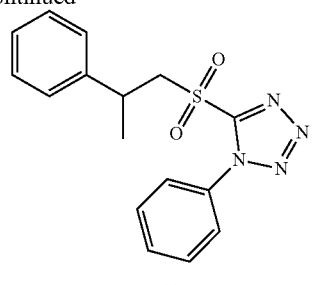

The sulfone intermediate m-11 (48 mg, 22% in 2 steps) was prepared from commercially available alcohol m-10 in an analogous manner as described in Scheme 23. LCMS data (ES+) M+Na 319.06.

Synthesis of Compound 167
Scheme 34.
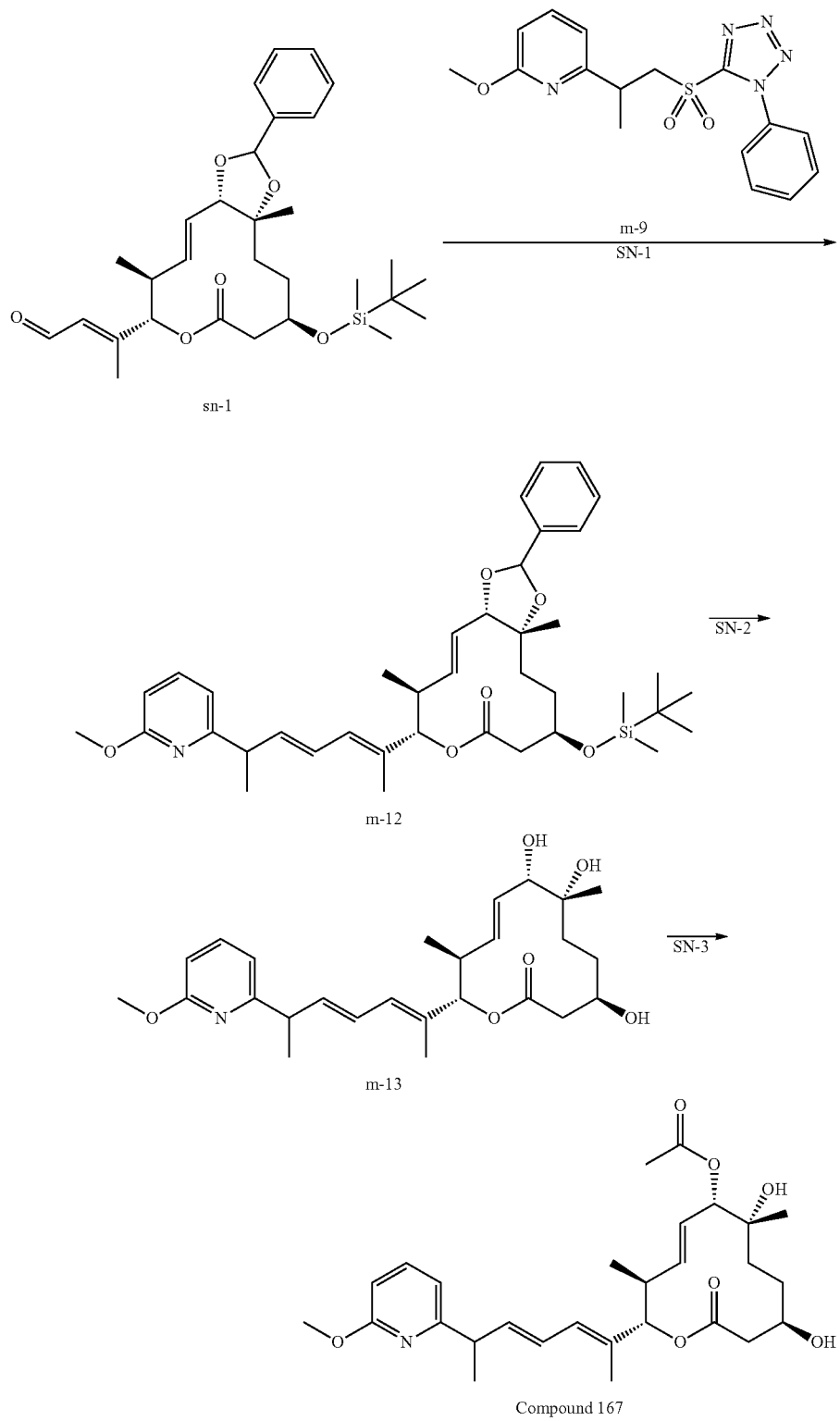
Coupling product m-12 (62 mg, 99%) was prepared from aldehyde sn-1 (50 mg, 0.095 mmol, 1.0 equiv.) and sulfone m-9 (2.5 equiv.) in an analogous manner as described for step SN-1. LCMS data (ES+) M+Na 684.31. Triol m-13 (21 mg, 49%) was prepared in an analogous manner as described for step SN-2.

The title Compound 167 (2.8 mg, 12%) was prepared from triol m-13 in an analogous manner as described for step SN-3. ¹H NMR (400 MHz, CHLOROFORM-d) δ: 0.80-0.95 (m, 3H) 1.21 (s, 3H) 1.24-1.73 (m, 8H) 1.74 (s, 3H) 2.09 (s, 3H) 2.42-2.67 (m, 3H) 3.48-3.62 (m, 2H) 3.74 (br. s., 1H) 3.93 (s, 3H) 5.08 (d, J=8.40 Hz, 1H) 5.16 (d, J=10.40 Hz, 1H) 5.57-5.70 (m, 2H) 5.99-6.07 (m, 1H) 6.11 (d, J=10.80 Hz, 1H) 6.25-6.34 (m, 1H) 6.54 (d, J=7.20 Hz, 1H) 6.70 (d, J=7.20 Hz, 1H) 7.48 (t, J=8.00 Hz, 1H). LCMS data (ES+) M+Na 524.2.

The sulfone intermediate m-9 was prepared in the following manner.

Scheme 35.

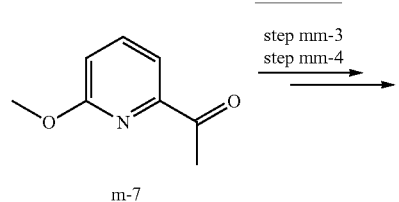

step mm-3
step mm-4
⟶

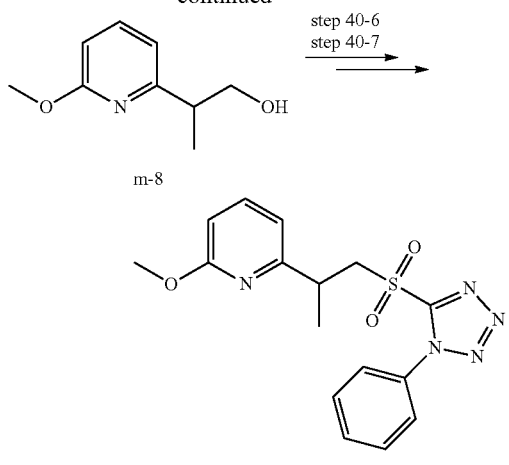

Compound m-8 (426 mg, 63% in 2 steps) was prepared in an analogous manner as described for step mm-3 and step mm-4. LCMS data (ES+) M+Na 189.95.

Compound m-9 (490 mg, 65% in 2 steps) was prepared in an analogous manner as described in Scheme 23. LCMS data (ES+) M+Na 381.98.

Synthesis of Compound 168

Scheme 36.

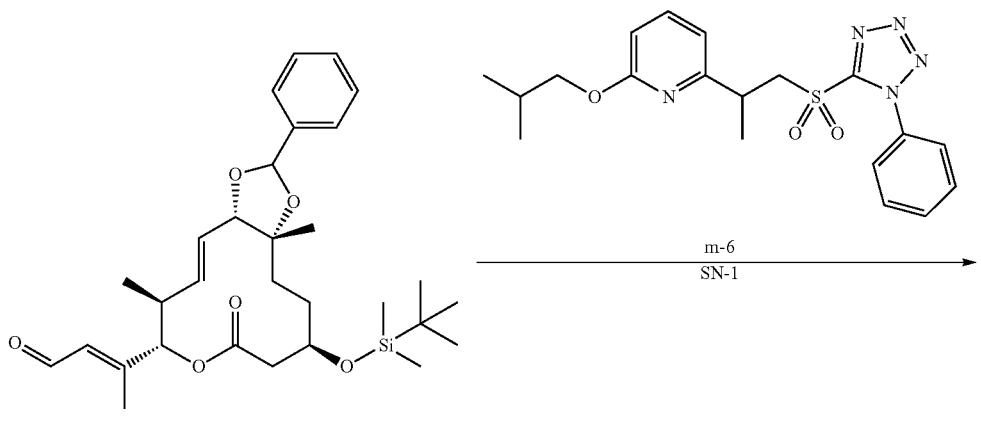

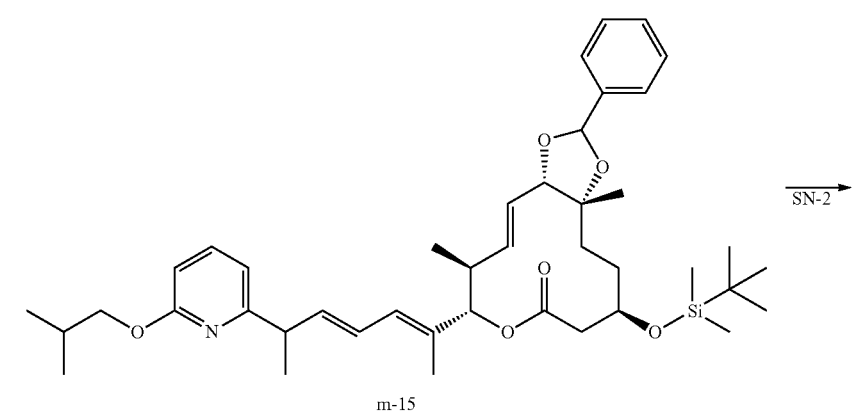

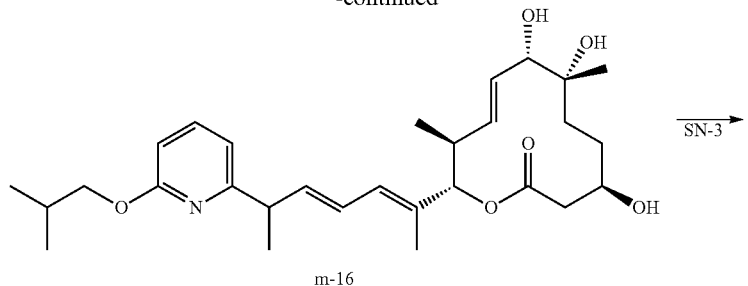

m-16

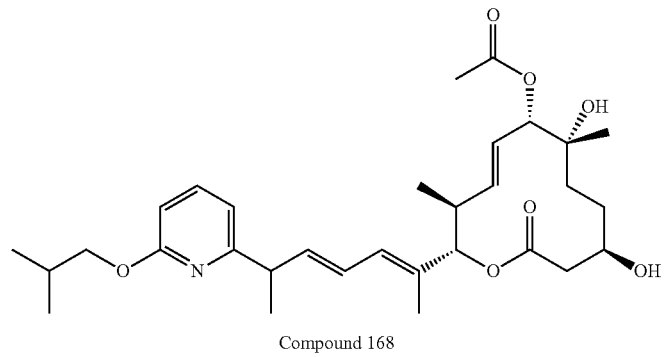

Compound 168

Coupling product m-15 (35 mg, 52%) was prepared from aldehyde sn-1 (50 mg, 0.095 mmol, 1.0 equiv.) and sulfone m-6 (2.0 equiv.) in an analogous manner as described for step SN-1. LCMS data (ES+) M+Na 726.40. Triol m-16 (11 mg, 45%) was prepared in an analogous manner as described for step SN-2.

The title Compound 168 (9.4 mg, 75%) was prepared from m-16 in an analogous manner as described for step SN-3. $^1$H NMR (400 MHz, CHLOROFORM-d) δ: 0.84-0.94 (m, 3H) 1.00 (s, 3H) 1.02 (s, 3H) 1.21 (s, 3H) 1.22-1.44 (m, 5H) 1.49-1.59 (m, 1H) 1.64-1.76 (m, 4H) 2.04-2.12 (m, 5H) 2.46-2.66 (m, 3H) 3.49-3.58 (m, 2H) 3.68-3.80 (m, 1H) 4.04-4.09 (m, 2H) 5.08 (d, J=8.8 Hz, 1H) 5.16 (d, J=11.2 Hz, 1H) 5.57-5.70 (m, 2H) 5.98-6.06 (m, 1H) 6.11 (d, J=10.8 Hz, 1H) 6.25-6.34 (m, 1H) 6.53 (dd, J=8.4, 4.0 Hz, 1H) 6.67 (dd, J=7.2, 4.0 Hz, 1H) 7.46 (t, J=7.6 Hz, 1H).

The sulfone intermediate m-6 was prepared as described below.

Scheme 37.

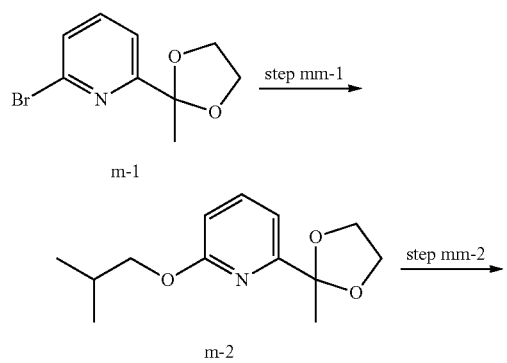

m-1 m-2

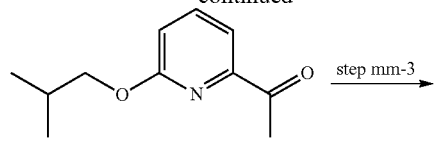

m-3

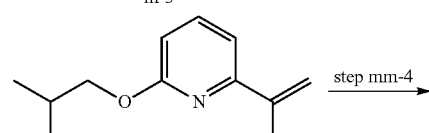

m-4

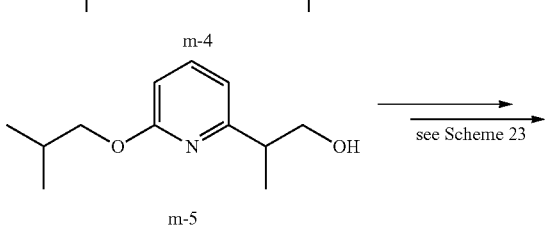

m-5

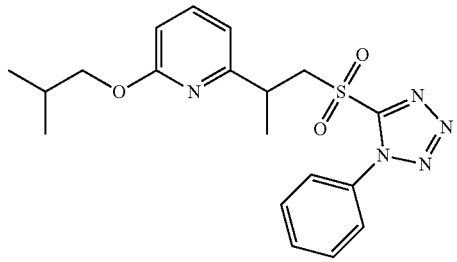

m-6

Step mm-1: A solution of isobutanol (1.2 equiv.) in DME (2 ml) was added to a suspension of potassium tert-butoxide (1.3 equiv.) in DME (3 ml, final conc. 0.41M) at room temperature. After being stirred at 50° C. for 30 minutes, bromopyridine m-1 (0.5 g, 2.05 mmol, 1.0 equiv.) was added to the mixture. After being stirred at reflux for 2 hours, the reaction mixture was cooled to room temperature, quenched with water and ethyl acetate was added. The organic layer was washed with water, brine, dried over magnesium sulfate, filtered, and concentrated in vacuo. The crude product m-2 (0.49 g) was used in the next step without further purification.

Step mm-2: To a solution of dioxolan m-2 (0.49 g, 2.05 mmol, 1.0 equiv.) in THF (0.27M) was added 5N hydrochloric acid (6.1 equiv.). After being stirred at room temperature for 3 hours, the reaction mixture was quenched with 5N sodium hydroxide solution. The aqueous layer was extracted with ethyl acetate and the organic layer was washed with water, brine, dried over magnesium sulfate, filtered, and concentrated in vacuo. The crude product m-3 (0.39 g) was used in the next step without further purification.

Step mm-3: To a suspension of methyltriphenylphosphonium iodide (1.3 equiv.) in THF (0.2M) at 0° C. was added n-butyl lithium (1.3 equiv., solution in n-hexane) dropwise. The reaction was stirred at 0° C. for 20 minutes. Next, a solution of pyridine methyl ketone m-3 (0.39 g, 2 mmol, 1.0 equiv) in THF was added dropwise. The reaction was stirred at 0° C. for 30 minutes. The reaction was quenched with water and ethyl acetate was added. The organic layer was washed with water and brine, dried over magnesium sulfate, filtered, and concentrated in vacuo. The crude product was purified by silica gel column chromatography (heptane:ethyl acetate as eluant) to afford the desired product m-4 (0.35 g, 91%). $^1$H NMR (400 MHz, CHLOROFORM-d) δ: 1.01 (d, J=6.8 Hz, 6H) 2.06-2.17 (m, 1H) 2.17 (s, 3H) 4.11 (d, J=6.4 Hz, 2H) 5.23 (s, 1H) 5.97 (s, 1H) 6.62 (d, J=8.0 Hz, 1H) 6.99 (d, J=7.6 Hz, 1H) 7.52 (dd, J=8.0, 7.6 Hz, 1H).

Step mm-4: To a solution of olefin m-4 (0.35 g, 1.82 mmol, 1.0 equiv.) in dichloromethane (0.18M) at 0° C. was added 9-BBN (2.5 equiv., solution in hexane). The reaction was stirred at 50° C. for 4.5 hours. After cooling to 0° C., the reaction was quenched with water, 5N sodium hydroxide solution (4.0 equiv.) and 30% aqueous hydrogen peroxide solution (4.0 equiv.). After being stirred at room temperature for 1 hour, the mixture was extracted with ethyl acetate. The organic layer was washed with aqueous sodium thiosulfate solution, water, brine, dried over magnesium sulfate, filtered, and concentrated in vacuo. The crude product was purified by silica gel column chromatography (heptane: ethyl acetate as eluant) to afford the desired product m-5 (0.26 g, 68%). LCMS data (ES+) M+Na 232.02.

The desired intermediate m-6 (315 mg, 63% in 2 steps) was prepared in an analogous manner as described for Scheme 23. LCMS data (ES+) M+Na 402.08.

Synthesis of Compound 169

Scheme 38.

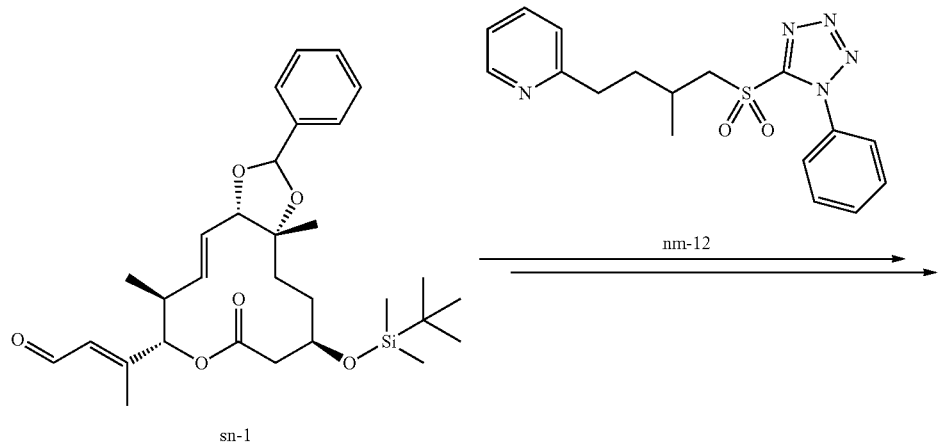

sn-1

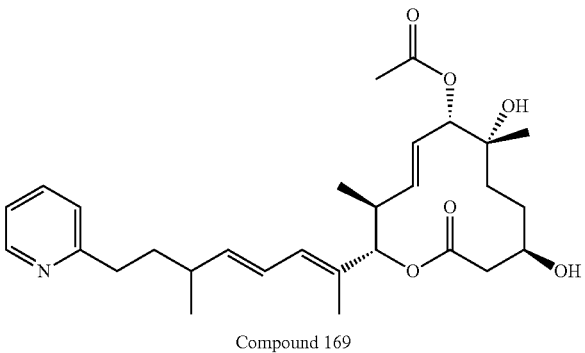

Compound 169

The title compound 169 (0.30 mg, 0.8% in 3 steps) was prepared from aldehyde sn-1 (40.0 mg, 0.076 mmol, 1.00 equiv.) and nm-12 (1.81 equiv.) in an analogous manner as described for step SN-1, SN-2 and SN-3. MS(ES+): 522.16 (M+Na+).

The sulfone intermediate nm-12 was prepared in the following manner.

Scheme 39.

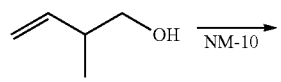

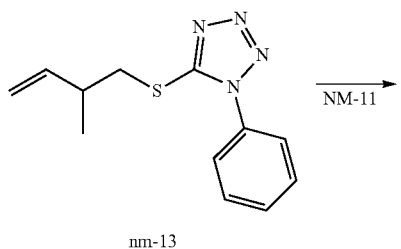

nm-13

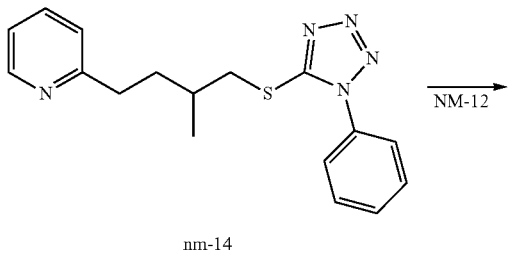

nm-14

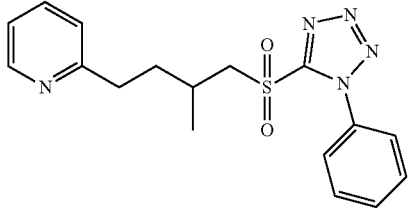

nm-12

Step NM-10: nm-13 (600 mg) was prepared from 2-methyl-3-buten-1-ol (200 mg, 2.32 mmol, 1.00 equiv.) in an analogous manner as described in Scheme 23. $^1$H NMR (400 MHz, CHLOROFORM-d) δ: 1.16-1.81 (m, 3H) 2.65-2.72 (m, 1H) 3.40-3.43 (m, 2H) 5.03-5.11 (m, 2H) 5.71-5.80 (m, 1H) 7.27-7.35 (m, 1H) 7.51-7.59 (m, 4H). Step NM-11: 9-BBN (3.00 equiv., 0.4 M solution in THF) was added dropwise to a solution of nm-13 (300 mg, 1.22 mmol, 1.00 equiv.) in THF (2.5 mL) at 0° C. under N$_2$. The reaction mixture was stirred at room temperature for 3 h. This mixture was added to a solution of 2-bromopyridine (1.20 equiv.), tetrakis(triphenylphosphine)palladium (0.20 equiv.) and potassium carbonate (4.00 equiv.) in dimethylformamide (4.00 mL) and distilled water (1.50 mL). The reaction mixture was stirred at 90° C. for 4 hours under N$_2$. The reaction mixture was cooled to room temperature, filtered, extracted with ethyl acetate, washed with water and brine, dried over magnesium sulfate, filtered, and concentrated in vacuo. The residue was purified by silica gel column chromatography (heptane/ethyl acetate as eluent) to afford the desired product nm-14 along with a by-product (254 mg). The crude product nm-14 (254 mg) was used in the next step without further purification.

Step NM-12: nm-12 (49.0 mg, 11% in 2 steps) was prepared from nm-14 (254 mg, 0.78 mmol, 1.00 equiv.) in an analogous manner as described for Scheme 23. MS(ES+): 379.90 (M+Na+).

Synthesis of Compound 170

Scheme 40.

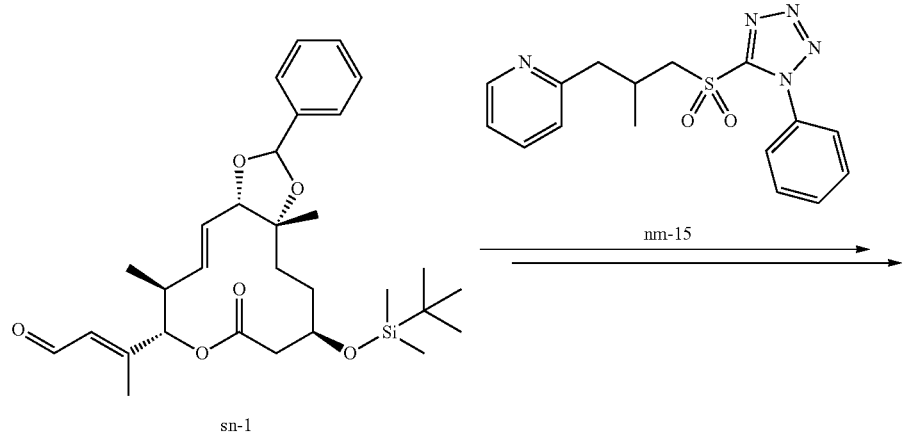

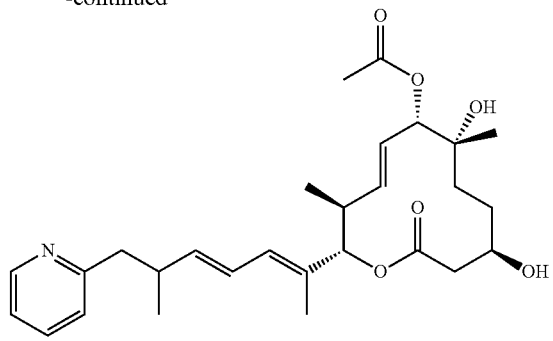

Compound 170

The title compound 170 (5.44 mg, 13% in 3 steps) was prepared from aldehyde sn-1 (40.0 mg, 0.085 mmol, 1.00 equiv.) and nm-15 (1.72 equiv.) in an analogous manner as described for step SN-1, SN-2 and SN-3. $^1$H NMR (400 MHz, CHLOROFORM-d) δ: 0.86-0.89 (m, 3H) 1.03 (d, J=6.40 Hz, 3H) 1.21 (s, 3H) 1.24-1.41 (m, 2H) 1.51-1.61 (m, 2H) 1.68 (s, 3H) 2.09 (s, 3H) 2.47-2.54 (m, 2H) 2.60-2.63 (m, 1H) 2.69-2.88 (m, 3H) 3.55 (d, J=10.8 Hz, 1H) 3.71-3.82 (m, 1H) 5.09 (d, J=9.2 Hz, 1H) 5.14 (d, J=10.8 Hz, 1H) 5.58-5.67 (m, 2H) 5.69-5.77 (m, 1H) 6.03-6.06 (m, 1H) 6.12-6.20 (m, 1H) 7.08-7.12 (m, 2H) 7.55-7.60 (m, 1H) 8.54-8.5 (m, 1H). MS(ES+): 508.07 (M+Na$^+$).

The sulfone intermediate nm-15 was prepared in the following manner.

Scheme 41.

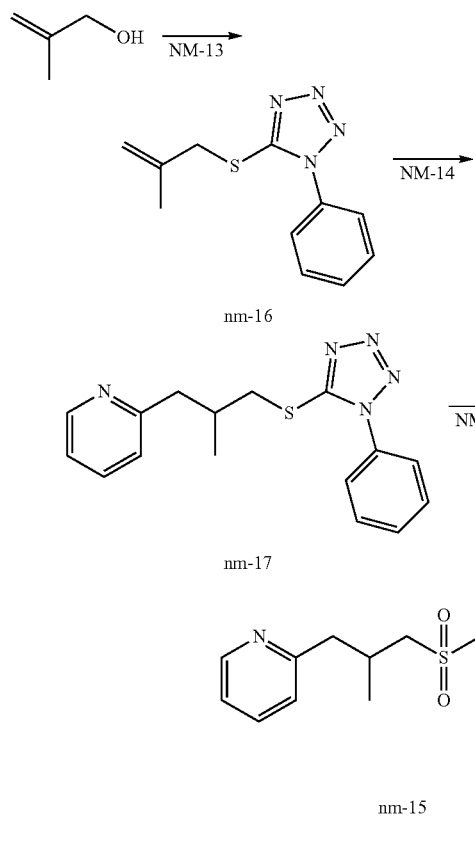

Step NM-13: nm-16 (2.84 g, 88%) was prepared from methallyl alcohol (1.00 g, 13.9 mmol, 1.00 equiv.) in an analogous manner as described for step #40-6. $^1$H NMR (400 MHz, CHLOROFORM-d) δ: 1.84 (s, 3H) 4.05 (s, 2H) 4.94-4.96 (m, 1H) 5.09-5.10 (m, 1H) 7.54-7.59 (m, 5H).

Step NM-14: nm-17 (150 mg, 56%) was prepared from nm-16 (200 mg, 0.861 mmol, 1.00 equiv.) in an analogous manner as described for step NM-11. $^1$H NMR (400 MHz, CHLOROFORM-d) δ: 1.01 (d, J=6.80 Hz, 3H) 2.52-2.57 (m, 1H) 2.72-2.78 (m, 1H) 2.97-3.02 (m, 1H) 3.37-3.42 (m, 1H) 3.49-3.54 (m, 1H) 7.11-7.16 (m, 2H) 7.52-7.66 (m, 6H) 8.52-8.54 (m, 1H).

Step NM-15: nm-15 (50.0 mg, 30%) was prepared from nm-17 (150 mg, 0.482 mmol, 1.00 equiv.) in an analogous manner as described for Scheme 23. MS(ES+): 365.92 (M+Na$^+$).

Synthesis of Compound 171

Scheme 42.

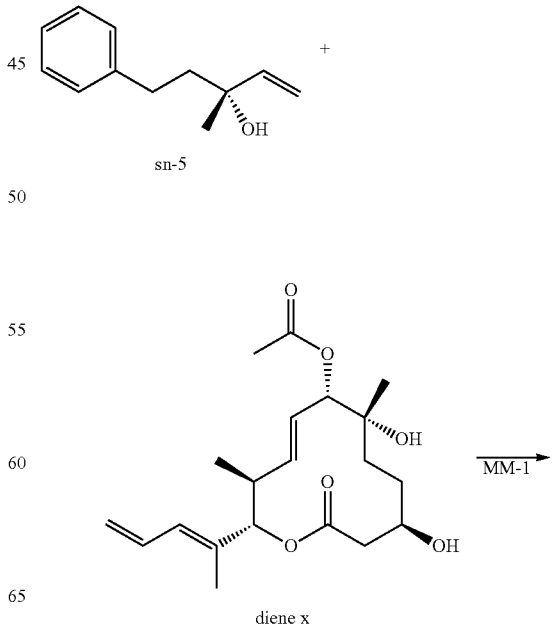

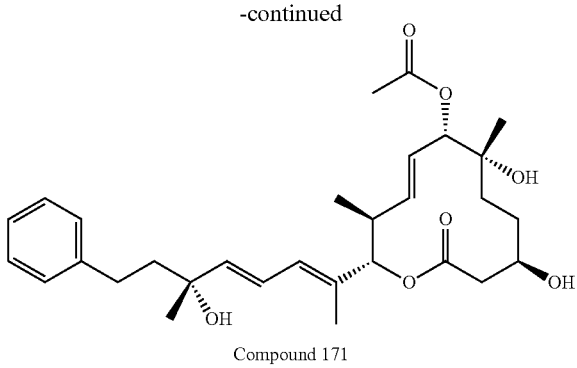

Compound 171

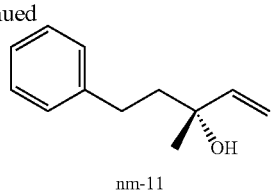

nm-11

The title Compound 171 (2.37 mg, 11.3%) was prepared from diene x (15 mg, 0.041 mmol, 1.0 equiv.) and sn-5 (3.00 equiv.) in an analogous manner as described for step MM-1. $^1$H NMR (400 MHz, CHLOROFORM-d) δ: 0.91 (d, J=6.80 Hz, 3H) 1.22 (s, 3H) 1.37 (s, 3H) 1.22-1.58 (m, 4H) 1.68-1.74 (m, 1H) 1.78 (s, 3H) 1.81-1.90 (m, 1H) 2.08 (br. s., 1H), 2.10 (s, 3H) 2.50-2.57 (m, 2H), 2.59-2.69 (m, 3H) 3.52 (d, J=10.8 Hz, 1H), 3.73-3.76 (m, 1H) 5.09 (d, J=9.20 Hz, 1H) 5.18 (d, J=10.8 Hz, 1H) 5.59-5.71 (m, 1H) 5.86 (d, J=15.2 Hz, 1H) 6.13 (d, J=10.8 Hz, 1H) 6.47 (d, J=15.2 Hz, 1H) 6.49 (d, J=15.2 Hz, 1H) 7.18-7.19 (m, 2H) 7.25-7.29 (m, 3H). MS(ES+): 537.2 (M+Na$^+$).

The intermediate allelic alcohol nm-11 was prepared as described in following manner.

Scheme 43.

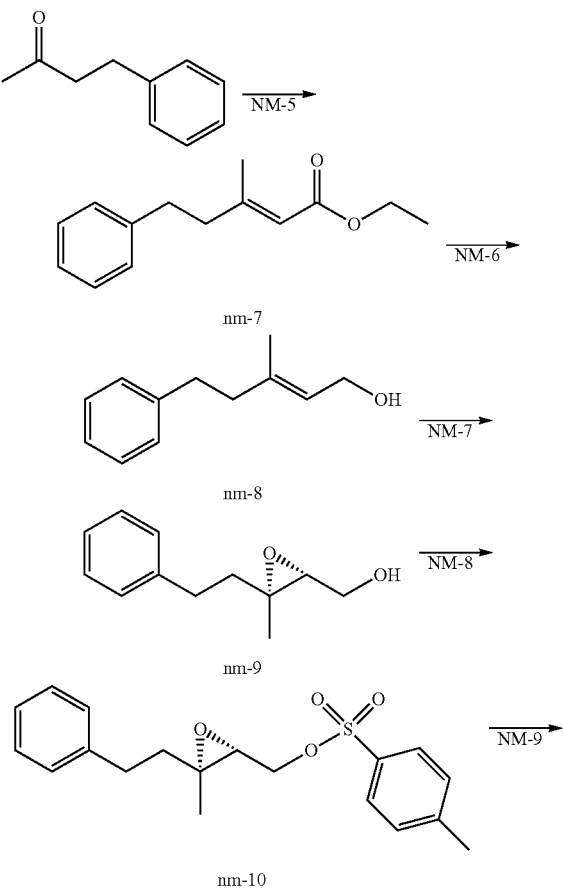

Step NM-5: To a stirred solution of the triethyl phosphonoacetate (1.30 equiv.) in THF (0.673 M) was added sodium hydride (1.50 equiv., >60% purity) at 0° C. under N$_2$. The reaction mixture was stirred at room temperature for 60 min. Benzylacetone (3.00 g, 20.2 mmol, 1.00 equiv.) was added to the reaction mixture at room temperature, then the reaction mixture was stirred at room temperature overnight. The reaction mixture was diluted with water and ethyl acetate, the organic layer was washed with brine, dried over magnesium sulfate, filtered, and concentrated in vacuo. The residue was purified by silica gel column chromatography (heptane/ethyl acetate as eluent) to afford the desired product nm-7 (4.30 g, 98%). $^1$H NMR (400 MHz, CHLOROFORM-d) δ: 1.26-1.29 (m, 3H) 2.21 (s, 3H) 2.42-2.46 (m, 2H) 2.76-2.81 (m, 4H) 4.12-4.17 (m, 2H) 5.69 (s, 3H) 7.16-7.31 (m, 5H).

Step NM-6: To a stirred solution of nm-7 (4.30 g, 19.7 mmol, 1.00 equiv.) in toluene (0.281 M) was added dropwise diisobutylaluminum hydride (2.20 equiv., 1.02 M solution in toluene) at −78° C. under N2. The reaction mixture was stirred at −78° C. for 2.5 hours. The reaction mixture was diluted with water, sat. potassium sodium tartrate, ethyl acetate, and stirred at room temperature for 1 hour. The organic layer was washed with brine, dried over magnesium sulfate, filtered, and concentrated in vacuo. The residue was purified by silica gel column chromatography (heptane/ethyl acetate as eluent) to afford the desired product nm-8 (1.75 g, 50%). $^1$H NMR (400 MHz, CHLOROFORM-d) δ: 1.72 (s, 3H) 2.30-2.34 (m, 2H) 2.71-2.76 (m, 2H) 4.12-4.13 (m, 2H) 5.38-5.43 (m, 1H) 5.69 (s, 3H) 7.16-7.30 (m, 5H).

Step NM-7: To a solution of titanium isopropoxide (1.20 equiv.) and 4 Å molecular sieves (1.00 g) in dichloromethane (10 mL) was added (−)-diethyl-D-tartrate (1.50 equiv.) in dichloromethane (2.0 mL) at −20° C. under N$_2$. The reaction mixture was stirred at −20° C. for 10 min. nm-8 (1.75 g, 9.93 mmol, 1.00 equiv.) in dichloromethane (2.0 mL) was added to the reaction mixture at −20° C. The reaction mixture was cooled to −30° C., and tert-butyl hydroperoxide (2.00 equiv., 6.0 M solution in nonane) in dichloromethane (1.0 mL, final conc. 0.66 M) was added to the reaction mixture. The reaction mixture was stirred at −30° C. for 60 min. A solution of water (20 mL), iron sulfate heptahydrate (1.43 equiv.) and D-(−)-tartaric acid (12.0 equiv.) was added to the reaction mixture, then stirred at 0° C. for 20 min. The reaction mixture was diluted with ethyl acetate and further extracted with ethyl acetate. A 1N NaOH aqueous solution (10 mL) was added to the organic layer and the mixture was stirred at room temperature for 30 min. Then, water was added to the mixture. The organic layer was washed with water, brine, dried over magnesium sulfate, filtered, and concentrated in vacuo. The residue was purified by silica gel column chromatography (heptane/ethyl acetate as eluent) to afford the mixture of desired product nm-9 and (−)-diethyl-D-tartrate. The crude product nm-9 (1.90 g) was used in the next step without further purification.

Step NM-8: A mixture of crude product nm-9 (1.90 g, 9.88 mmol, 1.00 equiv.), p-toluenesulfonyl chloride (2.00 equiv.) and triethylamine (5.00 equiv.) in dichloromethane (15 mL, 0.659 M) was stirred at room temperature for 60 min under $N_2$. The reaction mixture was diluted with water and ethyl acetate. The organic layer was washed with brine, dried over magnesium sulfate, filtered, and concentrated in vacuo. The residue was purified by silica gel column chromatography (heptane/ethyl acetate as eluent) to afford the desired product nm-10 with by-product (3.80 g). The crude product nm-10 (3.80 g) was used in the next step without further purification.

Step NM-9: Sodium iodide (4.00 equiv.) was added to a mixture of crude product nm-10 (1.00 g, 2.89 mmol, 1.00 equiv.) in THF (20 mL, 0.145 M) at room temperature. The reaction mixture was stirred at 70° C. for 60 min. After nm-10 was no longer detected by TLC, zinc copper couple (5.00 equiv.) was added to the reaction mixture. The reaction mixture was stirred at reflux for 3 hours. The reaction mixture was diluted with ethyl acetate, filtered through Celite®, washed with brine, dried over magnesium sulfate, filtered, and concentrated in vacuo. The residue was purified by silica gel column chromatography (heptane/ethyl acetate as eluent) to afford the desired product nm-11 (249 mg). $^1$H NMR (400 MHz, CHLOROFORM-d) δ: 1.35 (s, 3H) 1.82-1.89 (m, 2H) 2.62-2.69 (m, 2H) 5.10-5.13 (m, 1H) 5.25-5.29 (m, 1H) 5.94-6.01 (m, 1H) 7.16-7.30 (m, 5H).

Synthesis of Compound 172

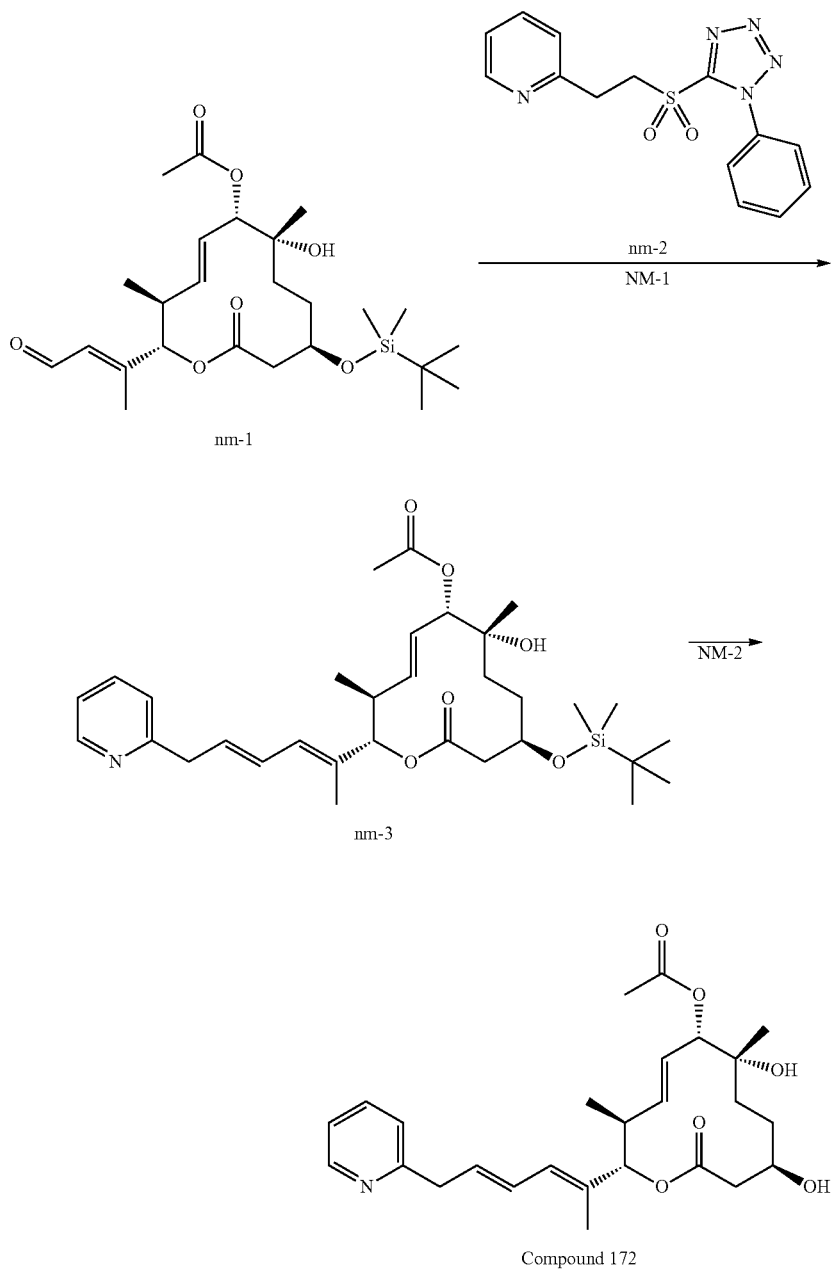

Step NM-1: To a stirred solution of nm-2 (50.0 mg, 0.159 mmol, 1.52 equiv.) in THF (2.00 mL) at −78° C. under N₂ was slowly added KHMDS (1.60 equiv., 0.50 M solution in toluene). The reaction mixture was stirred at −78° C. for 60 minutes. Aldehyde nm-1 (50.0 mg, 0.104 mmol, 1.0 equiv.) in THF (1.00 mL, final conc. 0.035 M) was added slowly at −78° C. At the same temperature, the reaction mixture was stirred for 60 min. The reaction mixture was allowed to warm to room temperature. The reaction mixture was diluted with water and ethyl acetate. The aqueous layer was extracted with ethyl acetate. The combined organic layers were washed with brine, dried over magnesium sulfate, filtered, and concentrated in vacuo. The residue was purified by silica gel column chromatography (heptane/ethyl acetate as eluent) to afford the desired product nm-3 (32.0 mg, 54%).

Step NM-2: To a stirred solution of the nm-3 (18.0 mg, 0.032 mmol, 1.0 equiv.) in THF (0.032 M) was slowly added tetrabutylammonium fluoride (2.00 equiv., 1.00 M solution in THF) at room temperature under N₂. The reaction mixture was stirred at room temperature for 60 min. Tetrabutylammonium fluoride (2.00 equiv., 1.00 M solution in THF) was added to the reaction mixture, and then the reaction was stirred at room temperature for 30 min. The reaction mixture was diluted with water and ethyl acetate. The aqueous layer was extracted with ethyl acetate. The combined organic layers were washed with brine, dried over magnesium sulfate, filtered, and concentrated in vacuo. The residue was purified by preparative silica gel column chromatography (ethyl acetate only) to afford the title Compound 172 (3.57 mg, 25%). ¹H NMR (400 MHz, CHLOROFORM-d) δ: 0.89 (d, J=6.80 Hz, 3H) 1.21 (s, 3H) 1.22-1.70 (m, 4H) 1.74 (s, 3H) 2.10 (s, 3H) 2.48-2.64 (m, 3H) 3.48-3.62 (m, 1H) 3.65 (d, J=6.80 Hz, 2H) 3.72-3.78 (m, 1H) 5.08 (d, J=8.80 Hz, 1H) 5.16 (d, J=10.40 Hz, 1H) 5.57-5.70 (m, 2H) 5.94-6.02 (m, 1H) 6.13 (d, J=11.2 Hz, 1H) 6.34-6.41 (m, 1H) 7.11-7.18 (m, 2H) 7.59-7.63 (m, 1H) 8.53-8.55 (m, 1H). MS(ES+): 480.18 [M+Na⁺].

The aldehyde intermediate nm-1 was prepared as previously described (R. M. Kanada and D. Ito et. al., *PCT Int. Appl*, 2007, WO2007043621) and sulfone intermediate nm-2 was prepared in the following manner.

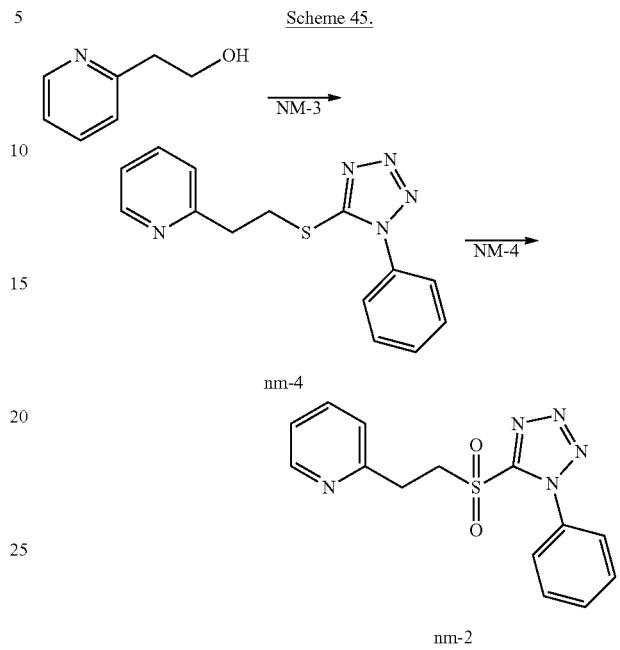

Scheme 45.

Step NM-3: Sulfide nm-4 (2.03 g, 88%) was prepared from 2-(2-hydroxyethyl)-pyridine (1.00 g, 8.12 mmol, 1.00 equiv.) in an analogous manner as described in Scheme 23. ¹H NMR (400 MHz, CHLOROFORM-d) δ: 3.37-3.41 (m, 2H) 3.81-3.86 (m, 2H) 7.16-7.25 (m, 2H) 7.52-7.66 (m, 6H) 8.55-8.57 (m, 1H), MS(ES+): 305.98 [M+Na⁺].

Step NM-4: Sulfone nm-2 (132 mg, 40%) was prepared from nm-4 (300 mg, 1.06 mmol, 1.00 equiv.) in an analogous manner as described in Scheme 23. 1H NMR (400 MHz, CHLOROFORM-d) δ: 3.46-3.50 (m, 2H) 4.25-4.29 (m, 2H) 7.16-7.24 (m, 2H) 7.58-7.72 (m, 6H) 8.49-8.50 (m, 1H), MS(ES+): 337.90 [M+Na⁺].

Synthesis of Compound 173

Scheme 46.

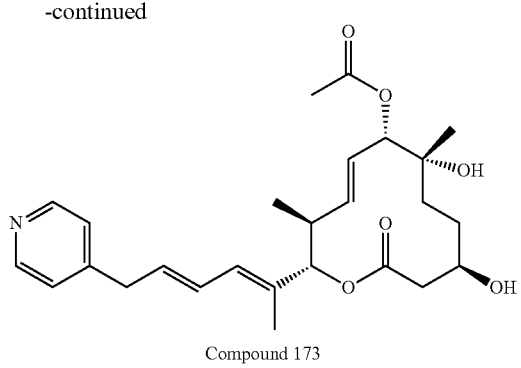

Compound 173

The title compound 173 (0.40 mg, 1.4% in 2 steps) was prepared from nm-1 (30 mg, 0.062 mmol, 1.00 equiv.) and nm-5 (2.55 equiv.) in an analogous manner as described for steps NM-1 and 2. ¹H NMR (400 MHz, CHLOROFORM-d) δ: 0.89 (d, J=6.80 Hz, 3H) 1.21 (s, 3H) 1.22-1.81 (m, 4H) 1.73 (s, 3H) 2.10 (s, 3H) 2.48-2.65 (m, 3H) 3.44-3.52 (m, 3H) 3.73-3.78 (m, 1H) 5.08 (d, J=9.20 Hz, 1H) 5.16 (d, J=10.8 Hz, 1H) 5.58-5.71 (m, 2H) 5.82-5.89 (m, 1H) 6.10-6.13 (m, 1H) 6.28-6.34 (m, 1H) 7.11-7.13 (m, 2H) 8.50-8.52 (m, 2H). MS(ES+): 480.18 (M+Na⁺).

The sulfone intermediate nm-5 (357 mg, crude) was prepared from 4-(2-hydroxyl-ethyl)pyridine (1.00 g, 8.12 mmol, 1.00 equiv.) in an analogous manner as described for step NM-3 and NM-4. ¹H NMR (400 MHz, CHLOROFORM-d) δ: 3.29-3.33 (m, 2H) 4.02-4.07 (m, 2H) 7.22-7.23 (m, 2H) 7.44-7.72 (m, 6H) 8.59-8.60 (m, 1H).

Synthesis of Compound 174

Scheme 47.

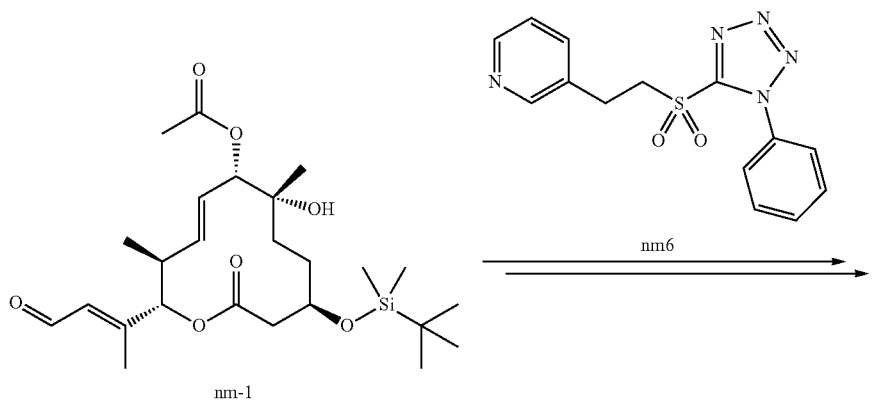

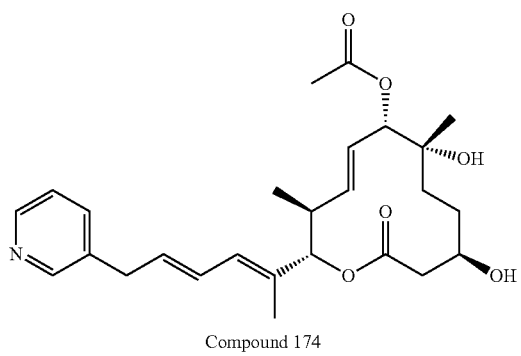

Compound 174

The title Compound 174 (3.71 mg, 13.0% in 2 steps) was prepared from nm-1 (30 mg, 0.062 mmol, 1.00 equiv.) and nm-6 (2.55 equiv.) in an analogous manner as described for steps NM-1 and NM-2. ¹H NMR (400 MHz, CHLOROFORM-d) δ: 0.89 (d, J=6.80 Hz, 3H) 1.21 (s, 3H) 1.22-1.73 (m, 4H) 1.73 (s, 3H) 2.10 (s, 3H) 2.48-2.65 (m, 3H) 3.46 (d, J=6.80 Hz, 2H) 3.51 (d, J=11.2 Hz, 1H) 3.72-3.76 (m, 1H) 5.08 (d, J=8.80 Hz, 1H) 5.15 (d, J=10.8 Hz, 1H) 5.57-5.72 (m, 2H) 5.83-5.90 (m, 1H) 6.09-6.12 (m, 1H) 6.26-6.32 (m, 1H) 7.21-7.26 (m, 1H) 7.48-7.52 (m, 1H) 8.45-8.48 (m, 2H). MS(ES+): 480.18 (M+Na⁺).

The sulfone intermediate nm-6 (2.30 g, crude) was prepared from 3-(2-hydroxyethyl)-pyridine (1.00 g, 8.12 mmol, 1.00 equiv.) in an analogous manner as described for step NM-3 and NM-4. ¹H NMR (400 MHz, CHLOROFORM-d) δ: 3.28-3.34 (m, 2H) 4.01-4.05 (m, 2H) 7.25-7.31 (m, 2H) 7.44-7.73 (m, 6H) 8.55-8.56 (m, 1H).

TABLE 9

Compounds 163-174

| Structure, Compound #, and Chemical Name | ¹H NMR data | LCMS data (ES+) |
|---|---|---|
| 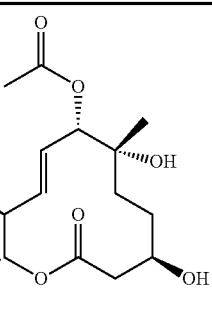<br>163<br>[(2S,3S,4E,6R,7R,10R)-7,10-dihydroxy-2-[(2E,4E)-6-hydroxy-6-methyl-8-phenylocta-2,4-dien-2-yl]-3,7-dimethyl-12-oxo-1-oxacyclododec-4-en-6-yl] acetate | 1H NMR (400 MHz, CHLOROFORM-d) δ: 0.90 (d, J = 6.4 Hz, 3 H) 1.21 (s, 3 H) 1.23-1.47 (m, 5 H) 1.48-1.74 (m, 4 H) 1.77 (s, 3 H) 1.79-1.94 (m, 2 H) 2.10 (s, 3 H) 2.47-2.74 (m, 5 H) 3.54 (d, J = 10.4 Hz, 1 H) 3.75 (br. s., 1 H) 5.09 (d, J = 8.8 Hz, 1 H) 5.18 (d, J = 10.8 Hz, 1 H) 5.58-5.72 (m, 2 H) 5.86 (d, J = 15.2 Hz, 1 H) 6.13 (d, J = 10.8 Hz, 1 H) 6.48 (dd, J = 15.2, 10.8 Hz, 1 H) 7.10-7.22 (m, 3 H) 7.23-7.31 (m, 2 H) | 537.3 (M + Na⁺) |
| 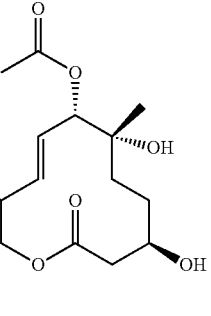<br>164<br>[(2S,3S,4E,6R,7R,10R)-7,10-dihydroxy-2-[(2E,4E)-6-hydroxy-6-phenylhepta-2,4-dien-2-yl]-3,7-dimethyl-12-oxo-1-oxacyclodec-4-en-6-yl] acetate | 1H NMR (400 MHz, CHLOROFORM-d) δ: 0.80-0.95 (m, 3 H) 1.15-1.46 (m, 5 H) 1.60-1.78 (m, 9 H) 1.90 (s, 1 H) 2.1 (s, 3 H) 2.45-2.67 (m, 3 H) 3.51 (d, J = 10.8 Hz, 1 H) 3.76 (br. s., 1 H) 5.09 (d, J = 8.8 Hz, 1 H) 5.17 (d, J = 10.4 Hz, 1 H) 5.57-5.71 (m, 2 H) 6.06 (d, J = 14.8 Hz, 1 H) 6.14 (d, J = 10.0 Hz, 1 H) 6.50 (ddd, J = 15.2, 10.8, 8.4 Hz, 1 H) 7.21-7.30 (m, 1 H) 7.31-7.39 (m, 2 H) 7.40-7.49 (m, 2 H) | 509.3 (M + Na⁺) |
| 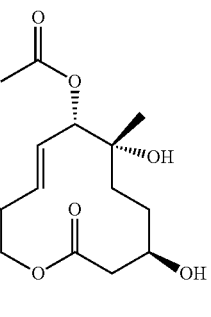<br>165<br>[(2S,3S,4E,6R,7R,10R)-7,10-dihydroxy-2-[(2E,4E)-6-hydroxy-6-thiophen-2-ylhepta-2,4-dien-2-yl]-3,7-dimethyl-12-oxo-1-oxacyclododec-4-en-6-yl] acetate | 1H NMR (400 MHz, CHLOROFORM-d) δ: 0.82-0.98 (m, 3 H) 1.15-1.44 (m, 8 H) 1.47-1.88 (m, 5 H) 1.99-2.26 (m, 5 H) 2.44-2.74 (m, 3 H) 3.44-3.61 (m, 1 H) 3.75 (br. s., 1 H) 5.02-5.26 (m, 2 H) 5.53-5.75 (m, 2 H) 6.00-6.22 (m, 2 H) 6.47-6.63 (m, 1 H) 6.89-7.03 (m, 2 H) 7.17-7.35 (m, 1 H) | 515.1 (M + Na⁺) |

TABLE 9-continued

Compounds 163-174

| Structure, Compound #, and Chemical Name | $^1$H NMR data | LCMS data (ES+) |
|---|---|---|
| 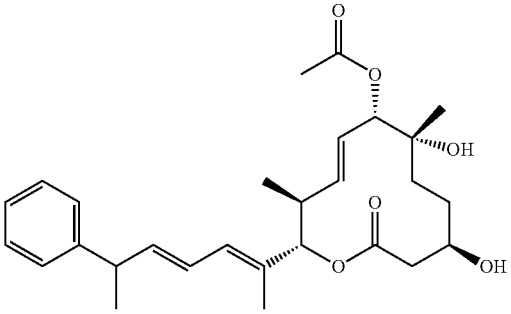<br>166<br>[(2S,3S,4E,6S,7S,10S)-7,10-dihydroxy-3,7-dimethyl-12-oxo-2-[(2E,4E)-6-phenylhepta-2,4-dien-2-yl]-1-oxacyclododec-4-en-6-yl] acetate | 1H NMR (400 MHz, CHLOROFORM-d) δ: 0.82-0.95 (m, 3H), 1.21 (s, 3 H) 1.21-1.45 (m, 5H) 1.48-1.49 (m, 2H) 1.63-1.78 (m, 5 H) 2.09 (s, 3 H) 2.45-2.68 (m, 3 H), 3.54 (q, J = 7.2 Hz, 1 H), 3.75 (br. s., 1 H) 5.08 (d, J = 9.2 Hz, 1 H) 5.15 (d, J = 10.4 Hz, 1 H) 5.57-5.72 (m, 2 H) 5.93 (ddd, J = 15.2, 7.2, 2.4 Hz, 1 H) 6.10 (d, J = 10.4 Hz, 1 H) 6.17-6.28 (m, 1H), 7.16-7.32 (m, 5 H) | 493.2 (M + Na$^+$) |
| 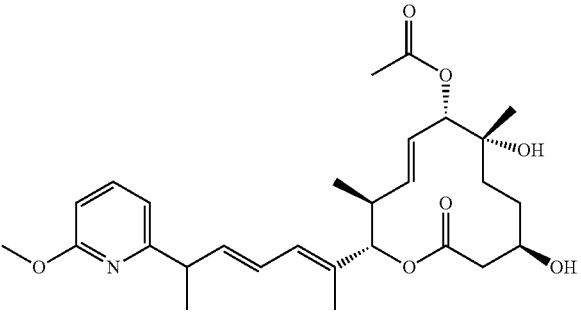<br>167<br>[(2S,3S,4E,6S,7S,10S)-7,10-dihydroxy-2-[(2E,4E)-6-(6-methoxypyridin-2-yl)hepta-2,4-dien-2-yl]-3,7-dimethyl-12-oxo-1-oxacyclododec-4-en-6-yl] acetate | 1H NMR (400 MHz, CHLOROFORM-d) δ: 0.80-0.95 (m, 3 H) 1.21 (s, 3 H) 1.24-1.73 (m, 8 H) 1.74 (s, 3 H) 2.09 (s, 3 H) 2.42-2.67 (m, 3 H) 3.48-3.62 (m, 2 H) 3.74 (br. s., 1 H) 3.93 (s, 3 H) 5.08 (d, J = 8.40 Hz, 1 H) 5.16 (d, J = 10.40 Hz, 1 H) 5.57-5.70 (m, 2 H) 5.99-6.07 (m, 1 H) 6.11 (d, J = 10.80 Hz, 1 H) 6.25-6.34 (m, 1 H) 6.54 (d, J = 7.20 Hz, 1 H) 6.70 (d, J = 7.20 Hz, 1 H) 7.48 (t, J = 8.00 Hz, 1 H) | 524.2 (M + Na$^+$) |
| 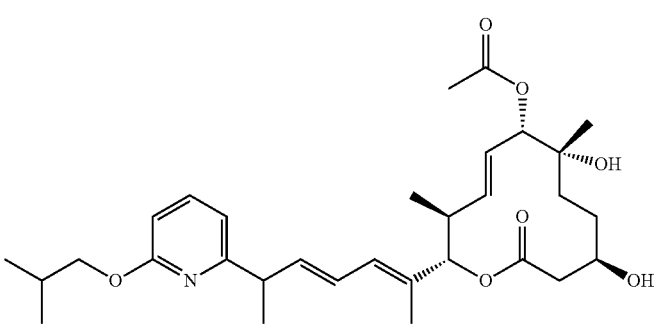<br>168<br>[(2S,3S,4E,6S,7S,10S)-7,10-dihydroxy-3,7-dimethyl-2-[(2E,4E)-6-[6-(2-methylpropoxy)pyridin-2-yl]hepta-2,4-dien-2-yl]-12-oxo-1-oxacyclododec-4-en-6-yl] acetate | 1H NMR (400 MHz, CHLOROFORM-d) δ: 0.84-0.94 (m, 3 H) 1.00 (s, 3 H) 1.02 (s, 3 H) 1.21 (s, 3 H) 1.22-1.44 (m, 5 H) 1.49-1.59 (m, 1 H) 1.64-1.76 (m, 4 H) 2.04-2.12 (m, 5 H) 2.46-2.66 (m, 3 H) 3.49-3.58 (m, 2 H) 3.68-3.80 (m, 1 H) 4.04-4.09 (m, 2 H) 5.08 (d, J = 8.8 Hz, 1 H) 5.16 (d, J = 11.2 Hz, 1 H) 5.57-5.70 (m, 2 H) 5.98-6.06 (m, 1 H) 6.11 (d, J = 10.8 Hz, 1 H) 6.25-6.34 (m, 1 H) 6.53 (dd, J = 8.4, 4.0 Hz, 1 H) 6.67 (dd, J = 7.2, 4.0 Hz, 1 H) 7.46 (t, J = 7.6 Hz, 1 H) | |

TABLE 9-continued

Compounds 163-174

| Structure, Compound #, and Chemical Name | ¹H NMR data | LCMS data (ES+) |
|---|---|---|
| 169 [(2S,3S,4E,6S,7S,10S)-7,10-dihydroxy-3,7-dimethyl-2-[(2E,4E)-6-methyl-8-pyridin-2-ylocta-2,4-dien-2-yl]-12-oxo-1-oxacyclododec-4-en-6-yl] acetate | | 522.16 (M + Na⁺) |
| 170 [(2S,3S,4E,6S,7S,10S)-7,10-dihydroxy-3,7-dimethyl-2-[(2E,4E)-6-methyl-7-pyridin-2-ylhepta-2,4-dien-2-yl]-12-oxo-1-oxacyclododec-4-en-6-yl] acetate | 1H NMR (400 MHz, CHLOROFORM-d) δ: 0.86-0.89 (m, 3 H) 1.03 (d, J = 6.40 Hz, 3 H) 1.21 (s, 3 H) 1.24-1.41 (m, 2 H) 1.51-1.61 (m, 2 H) 1.68 (s, 3 H) 2.09 (s, 3 H) 2.47-2.54 (m, 2 H) 2.60-2.63 (m, 1 H) 2.69-2.88 (m, 3 H) 3.55 (d, J = 10.8 Hz, 1 H) 3.71-3.82 (m, 1 H) 5.09 (d, J = 9.2 Hz, 1 H) 5.14 (d, J = 10.8 Hz, 1 H) 5.58-5.67 (m, 2 H) 5.69-5.77 (m, 1 H) 6.03-6.06 (m, 1 H) 6.12-6.20 (m, 1 H) 7.08-7.12 (m, 2 H) 7.55-7.60 (m, 1 H) 8.54-8.55 (m, 1 H) | 508.07 (M + Na⁺) |
| 171 [(2S,3S,4E,6R,7R,10R)-7,10-dihydroxy-2-[(2E,4E,6R)-6-hydroxy-6-methyl-8-phenylocta-2,4-dien-2-yl]-3,7-dimethyl-12-oxo-1-oxacyclododec-4-en-6-yl] acetate | 1H NMR (400 MHz, CHLOROFORM-d) δ: 0.91 (d, J = 6.80 Hz, 3 H) 1.22 (s, 3 H) 1.37 (s, 3 H) 1.22-1.58 (m, 4 H) 1.68-1.74 (m, 1 H) 1.78 (s, 3 H) 1.81-1.90 (m, 1 H) 2.08 (br. s., 1 H), 2.10 (s, 3 H) 2.50-2.57 (m, 2 H), 2.59-2.69 (m, 3 H) 3.52 (d, J = 10.8 Hz, 1 H), 3.73-3.76 (m, 1 H) 5.09 (d, J = 9.20 Hz, 1 H) 5.18 (d, J = 10.8 Hz, 1 H) 5.59-5.71 (m, 1 H) 5.86 (d, J = 15.2 Hz, 1 H) 6.13 (d, J = 10.8 Hz, 1 H) 6.47 (d, J = 15.2 Hz, 1 H) 6.49 (d, J = 15.2 Hz, 1 H) 7.18-7.19 (m, 2 H) 7.25-7.29 (m, 3 H) | 537.2 (M + Na⁺) |

TABLE 9-continued

Compounds 163-174

| Structure, Compound #, and Chemical Name | ¹H NMR data | LCMS data (ES+) |
|---|---|---|
| 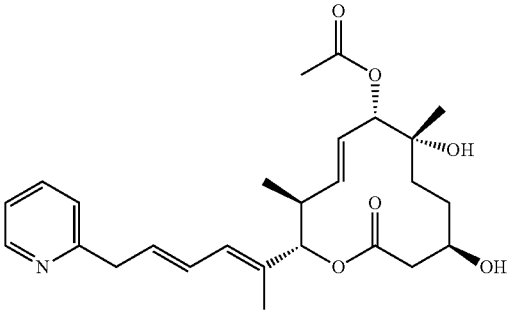<br>172<br>[(2S,3S,4E,6R,7R,10R)-7,10-dihydroxy-3,7-dimethyl-12-oxo-2-[(2E,4E)-6-pyridin-2-ylhexa-2,4-dien-2-yl]-1-oxacyclododec-4-en-6-yl] acetate | 1H NMR (400 MHz, CHLOROFORM-d) δ: 0.89 (d, J = 6.80 Hz, 3 H) 1.21 (s, 3 H) 1.22-1.70 (m, 4 H) 1.74 (s, 3 H) 2.10 (s, 3 H) 2.48-2.64 (m, 3 H) 3.48-3.62 (m, 1 H) 3.65 (d, J = 6.80 Hz, 2 H) 3.72-3.78 (m, 1H) 5.08 (d, J = 8.80 Hz, 1 H) 5.16 (d, J = 10.40 Hz, 1 H) 5.57-5.70 (m, 2 H) 5.94-6.02 (m, 1 H) 6.13 (d, J = 11.2 Hz, 1 H) 6.34-6.41 (m, 1 H) 7.11-7.18 (m, 2H) 7.59-7.63 (m, 1 H) 8.53-8.55 (m, 1 H) | 480.18 (M + Na⁺) |
| 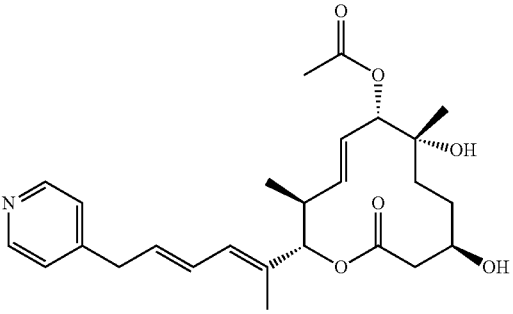<br>173<br>[(2S,3S,4E,6R,7R,10R)-7,10-dihydroxy-3,7-dimethyl-12-oxo-2-[(2E,4E)-6-pyridin-3-ylhexa-2,4-dien-2-yl]-1-oxacyclododec-4-en-6-yl] acetate | 1H NMR (400 MHz, CHLOROFORM-d) δ: 0.89 (d, J = 6.80 Hz, 3 H) 1.21 (s, 3 H) 1.22-1.81 (m, 4 H) 1.73 (s, 3 H) 2.10 (s, 3 H) 2.48-2.65 (m, 3H) 3.44-3.52 (m, 3 H) 3.73-3.78 (m, 1H) 5.08 (d, J = 9.20 Hz, 1 H) 5.16 (d, J = 10.8 Hz, 1 H) 5.58-5.71 (m, 2 H) 5.82-5.89 (m, 1 H) 6.10-6.13 (m, 1 H) 6.28-6.34 (m, 1 H) 7.11-7.13 (m, 2H) 8.50-8.52 (m, 2 H) | 480.18 (M + Na⁺) |
| 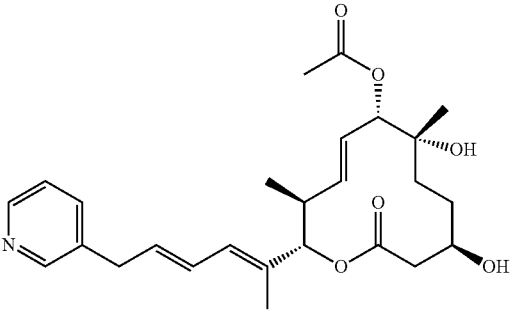<br>174<br>[(2S,3S,4E,6R,7R,10R)-7,10-dihydroxy-3,7-dimethyl-12-oxo-2-[(2E,4E)-6-pyridin-4-ylhexa-2,4-dien-2-yl]-1-oxacyclododec-4-en-6-yl] acetate | 1H NMR (400 MHz, CHLOROFORM-d) δ: 0.89 (d, J = 6.80 Hz, 3 H) 1.21 (s, 3 H) 1.22-1.73 (m, 4 H) 1.73 (s, 3 H) 2.10 (s, 3 H) 2.48-2.65 (m, 3 H) 3.46 (d, J = 6.80 Hz, 2 H) 3.51 (d, J = 11.2 Hz, 1 H) 3.72-3.76 (m, 1H) 5.08 (d, J = 8.80 Hz, 1 H) 5.15 (d, J = 10.8 Hz, 1 H) 5.57-5.72 (m, 2 H) 5.83-5.90 (m, 1 H) 6.09-6.12 (m, 1 H) 6.26-6.32 (m, 1 H) 7.21-7.26 (m, 1H) 7.48-7.52 (m, 1 H) 8.45-8.48 (m, 2 H) | 480.18 (M + Na⁺) |

Protocol for Synthesis of Compound 175
Scheme 48.
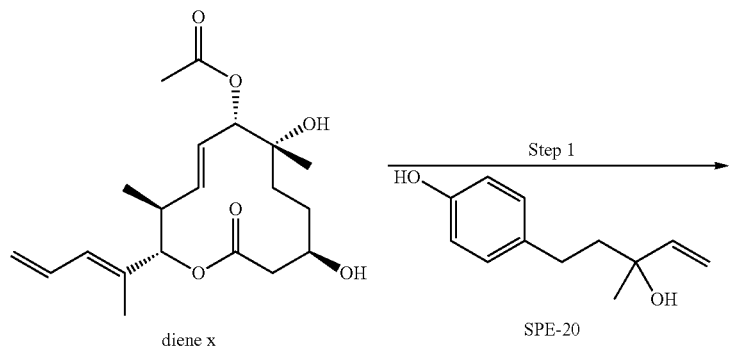
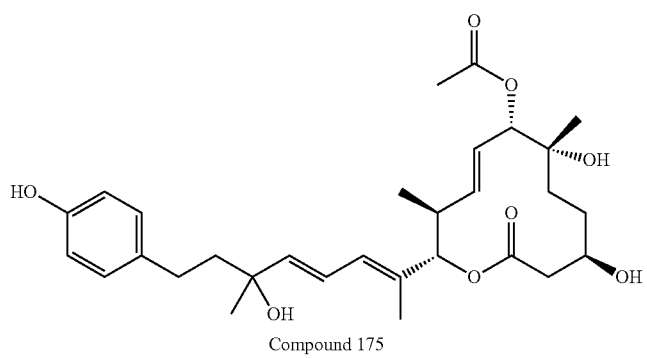
Compound 175
Compound 175 was synthesized in an analogous manner as Compound 163. MS(ES+): 553.35 [M+Na]⁺.
Protocol for Synthesis of Compound 176
Scheme 49.
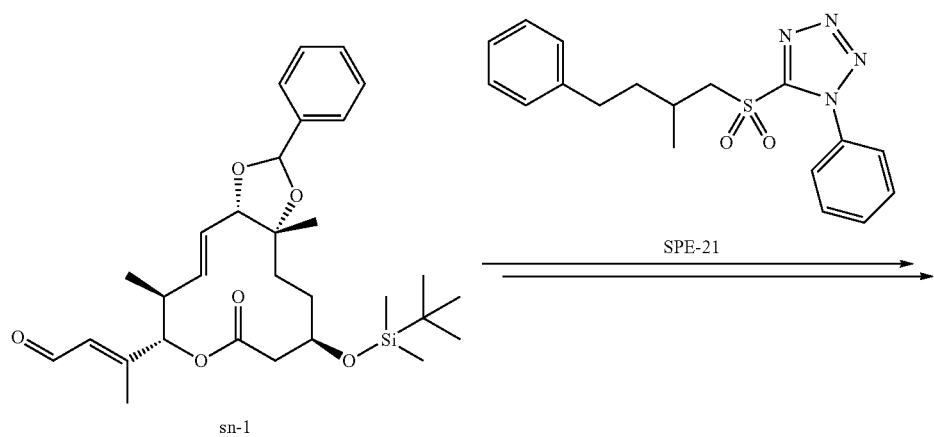

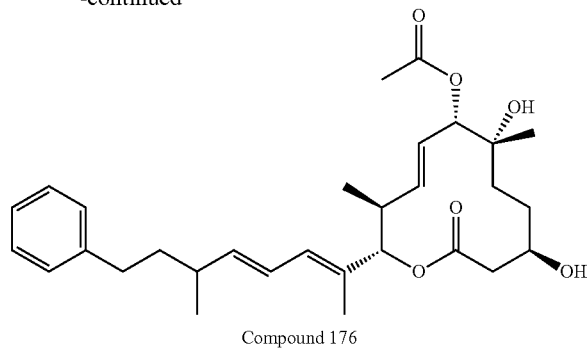
Compound 176
Compound 176 was prepared from aldehyde sn-1 (1 equiv) and SPE-21 (1.81 equiv.) in an analogous manner as described for step SN-1, SN-2 and SN-3. MS(ES+): 521.42 (M+Na$^+$).
Protocol for Synthesis of Compound 177
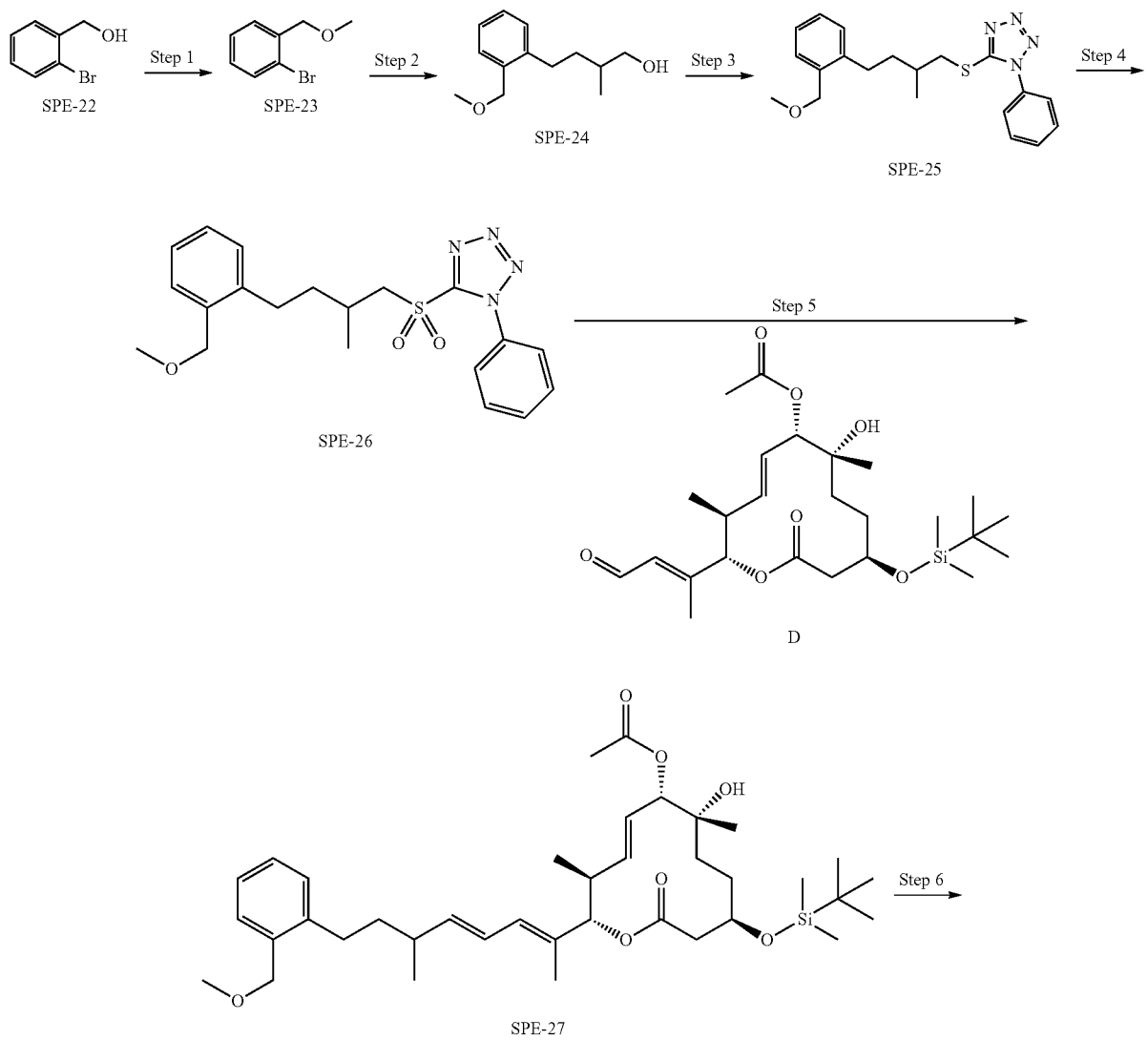
Scheme 50.

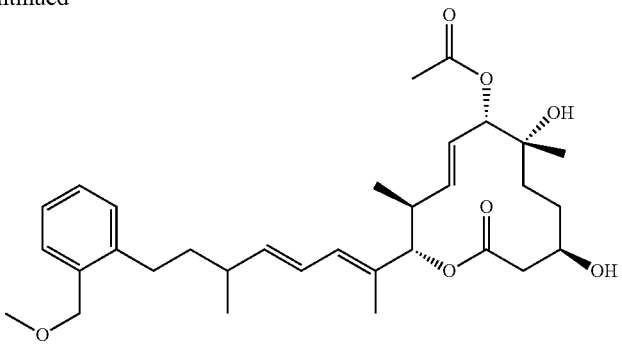

Compoound 177

Step 1: To a suspension of sodium hydride (55% oil dispersion in mineral oil, 10.7 mmol, 1 equiv) in DMF (10 mL) at 0° C. was added a solution of SPE-22 (2.0 g, 10.7 mmol, 1 equiv) dropwise at and was stirred for 30 minutes. Then iodomethane (2 ml, 32.1 mmol, 3 equiv) was added dropwise and then allowed to warm up to room temperature over 4 hrs. The reaction was quenched with saturated ammonium chloride solution and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (SPE-23, 997 mg, 4.96 mmol, 46%).

Step 2: To a solution of 2-methylbut-3-en-1-ol (651 mg, 3.24 mmol, 1 equiv) in THF (1.25 mL) was added 9-BBN (0.5 M THF solution, 11.6 mL, 5.8 mmol, 1.8 equiv) at 0° C. dropwise. The mixture was then warmed up to room temperature and was stirred for 2.5 hours. To the reaction mixture, was added pre-mixed solution of SPE-23 (651 mg, 3.24 mmol), tetrakis(triphenylphosphine)palladium(0) (189 mg, 0.232 mmol, 0.07) and potassium carbonate (962 mg, 6.96 mmol, 2.14 equiv) in DMF (24 mL) and H$_2$O (0.75 mL). The resulting mixture was warmed up to 90° C. and was stirred for 4 hours. The reaction mixture was diluted with ethyl acetate and water. Phase separated and organic layer was washed with H$_2$O and brine, then was dried over MgSO$_4$. Solid was filtered out and solvent was removed in vacuo. The obtained residue was purified by silica gel chromatography (Heptane/EtOAc=75/25) to give a product (SPE-24, 368 mg, 1.77 mmol, 76% yield).

Step 3: To a solution of SPE-24 (368 mg, 1.77 mmol, 1 equiv) in THF (4 mL) at 0° C. was added 1-phenyl-1H-tetrazole-5-thiol (378 mg, 2.12 mmol, 1.2 equiv), triphenyl phosphine (557 mg, 2.12 mmol, 1.2 equiv) and diisopropyl azodicarboxylate (452 mg, 2.12 mmol, 1.2 equiv) and was stirred for 3 hours. The reaction was diluted with ethyl acetate and H$_2$O. The organic layer was washed with water, brine, dried over magnesium sulfate, filtered, and concentrated in vacuo. The resulting oil was purified by silica gel column chromatography (hexane/ethyl acetate as eluent) to afford the desired product (SPE-25, 310 mg, 0.841 mmol, 48%).

Step 4: To a solution of SPE-26 (310 mg, 0.84 mmol, 1 equiv) in ethanol (3 mL) was added a solution of ammonium molybdate tetrahydrate (104 mg, 0.084 mmol, 0.1 equiv) in hydrogen peroxide (35% aqueous solution, 1 ml, 12.6 mmol, 15 equiv) at room temperature The reaction mixture was stirred for 16 hours. The reaction mixture was diluted with ethyl acetate and water. Phase separated and organic layer was washed with H$_2$O, saturated aq. NaS$_2$O$_3$, and brine, then was dried over magnesium sulfate. Solid was filtered out and solvent was removed in vacuo. The obtained residue was purified by silica gel chromatography (Heptane/AcOEt=2/1) to afford the desired product (SPE-27, 236 mg, 0.589 mmol, 70% yield).

Step 5: To a solution of SPE-27 (0.035 g, 0.087 mmol, 1.4 equiv) in THF (3.0 mL) under nitrogen at −78° C. was added KHMDS (0.5 M in THF solution, 0.20 mL, 0.10 mmol, 1.6 equiv) dropwise and the reaction was stirred for 1 hour. Then aldehyde D (0.030 g, 0.062 mmol, 1.0 equiv) in THF (0.2 mL) was added dropwise. The reaction was stirred at −78° C. for 3 hours. The reaction was quenched with ammonium chloride and diluted with ethyl acetate. The organic layer was washed with water, brine, dried over magnesium sulfate, filtered, and concentrated in vacuo. The resulting oil was purified by silica gel column chromatography (hexane/ethyl acetate as eluent) to afford the desired product (SPE-27, 0.024 g, 0.037 mmol, 59%).

Step 6: To a solution of SPE-27 (24.0 mg, 0.037 mmol, 1.0 equiv.) in THF (2.0 mL, 0.02 M) at room temperature was added tributylammonium fluoride (1.0 M THF solution, 1.1 ml, 1.1 mmol, 30 equiv.) The reaction was stirred for 1 hour. The reaction was diluted with ethyl acetate and H$_2$O. The organic layer was washed with water, brine, dried over magnesium sulfate, filtered, and concentrated in vacuo. The resulting oil was purified by silica gel column chromatography (hepatnes/ethyl acetate as eluent) to afford the desired product (Compound 177, 6.8 mg, 0.012 mmol, 34%). $^1$H NMR (400 MHz, CHLOROFORM, d) δ: 0.90 (d, J=6.8 Hz, 3H) 1.07 (d, J=6.8 Hz, 3H) 1.21 (s, 3H) 1.24-1.38 (m, 3H) 1.51-1.70 (m, 4H) 1.74 (s, 3H) 2.05 (s, 3H) 2.27 (quin, J=6.8 Hz, 1H) 2.49-2.66 (m, 5H) 3.38 (s, 3H) 3.55 (d, J=10.8 Hz, 2H) 3.73-3.78 (m, 1H) 4.44 (s, 2H) 5.08-5.19 (m, 2H) 5.61-5.73 (m, 3H) 6.09-6.26 (m, 2H) 7.16-7.32 (m, 5H). MS(ES+): 565.36 [M+Na]$^+$.

Protocol for Synthesis of Compound 178
Scheme 51.
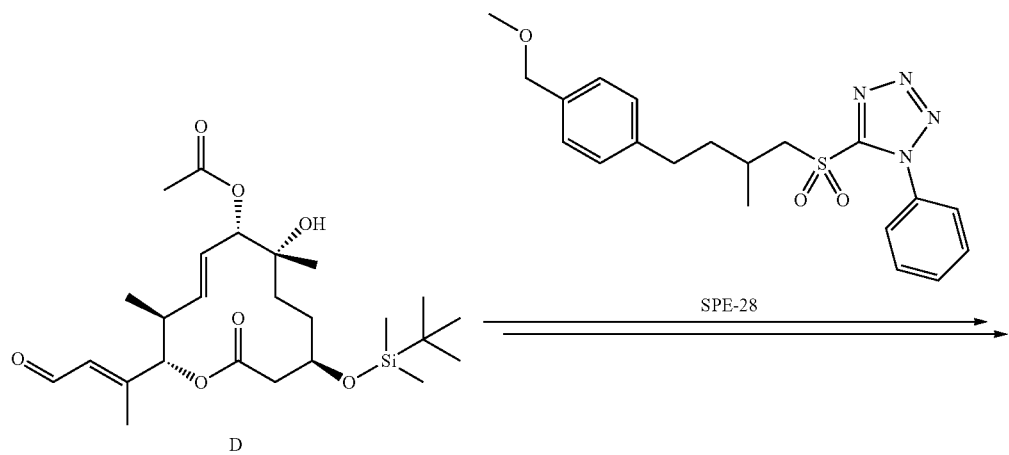
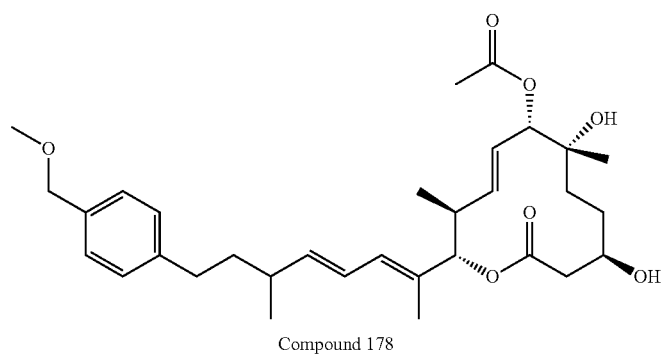
Compound 178
Compound 178 (12.3 mg, 36.4% in 2 steps) was prepared from aldehyde D (30.0 mg, 0.062 mmol, 1.00 equiv.) and sulfone SPE-28 (1.34 equiv.) in an analogous manner as described in Compound 182. $^1$H NMR (400 MHz, CHLOROFORM, d) δ: 0.90 (d, J=6.8 Hz, 3H) 1.07 (d, J=6.8 Hz, 3H) 1.21 (s, 3H) 1.24-1.41 (m, 3H) 1.51-1.70 (m, 4H) 1.73 (s, 3H) 2.05 (s, 3H) 2.20-2.24 (m, 1H) 2.49-2.66 (m, 5H) 3.38 (s, 3H) 3.56 (d, J=10.8 Hz, 2H) 3.73-3.78 (m, 1H) 4.42 (s, 2H) 5.08-5.18 (m, 2H) 5.63-5.70 (m, 3H) 6.07-6.22 (m, 2H) 7.15 (d, J=8.0 Hz, 2H) 7.24 (d, J=8.0 Hz, 2H). MS(ES+): 565.37 [M+Na]$^+$.
Protocol for Synthesis of Compound 179
Scheme 52.
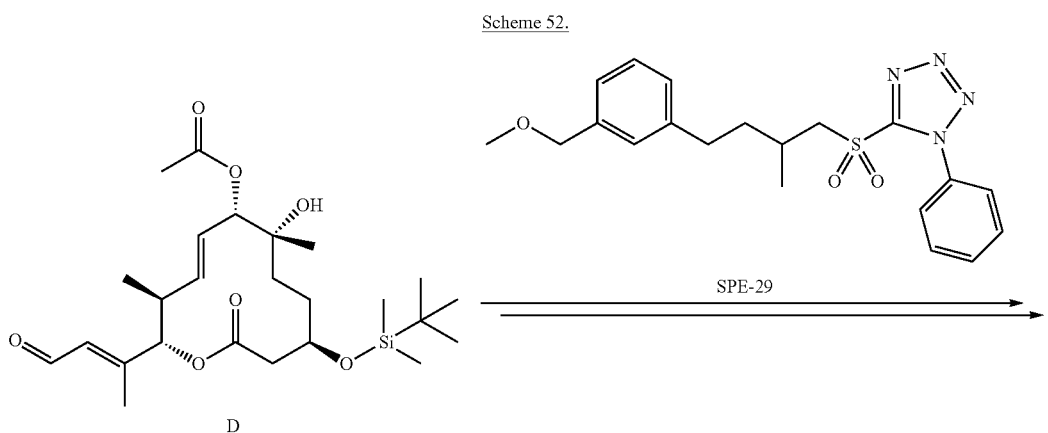

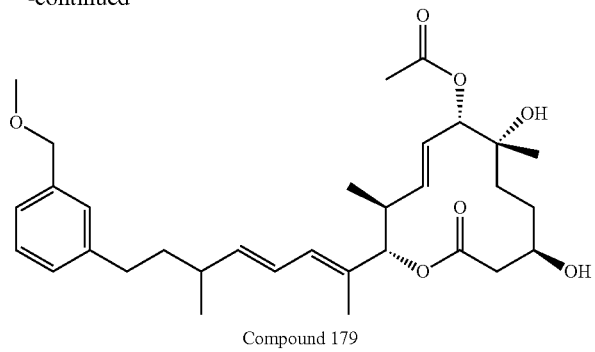

Compound 179

Compound 179 (11.5 mg, 34.1% in 2 steps) was prepared from aldehyde D (30.0 mg, 0.062 mmol, 1.00 equiv.) and sulfone SPE-29 (1.34 equiv.) in an analogous manner as described in Compound 177. $^1$H NMR (400 MHz, CHLOROFORM, d) δ: 0.90 (d, J=6.8 Hz, 3H) 1.05 (d, J=6.8 Hz, 3H) 1.21 (s, 3H) 1.24-1.42 (m, 3H) 1.52-1.72 (m, 4H) 1.74 (s, 3H) 2.10 (s, 3H) 2.20-2.26 (m, 1H) 2.50-2.66 (m, 5H) 3.38 (s, 3H) 3.56 (dd, J=10.8, 3.2 Hz, 2H) 3.72-3.78 (m, 1H) 4.43 (s, 2H) 5.08-5.18 (m, 2H) 5.59-5.71 (m, 3H) 6.08-6.23 (m, 2H) 7.09-7.27 (m, 5H). MS(ES+): 565.41 [M+Na]$^+$.

Protocol for Synthesis of Compound 180

Scheme 53.

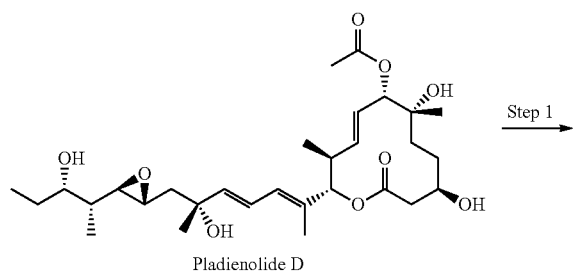

Pladienolide D

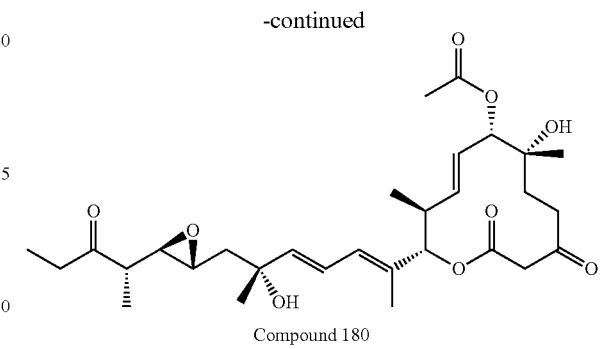

Compound 180

To a solution of Pladienolide D (136 mg, 0.246 mmol, 1 equiv) in dichloromethane (4 mL) at room temperature was added Dess-Martin periodinane (209 mg, 0.492 mmol, 2.0 equiv.). The resulting solution was stirred for 10 minutes, and then was diluted with ethyl acetate. The organic layer was washed with water and brine, then was dried over sodium sulfate, solid was filtered off, and solvent was removed in vacuo. The obtained residue was purified by NH-silica gel chromatography (heptane/ethyl acetate as eluent) to afford desired product (Compound 180, 66.1 mg, 0.12 mmol, 49% yield). MS(ES+): 571.36 [M+Na]$^+$.

Protocol for Synthesis of Compound 181

Scheme 54.

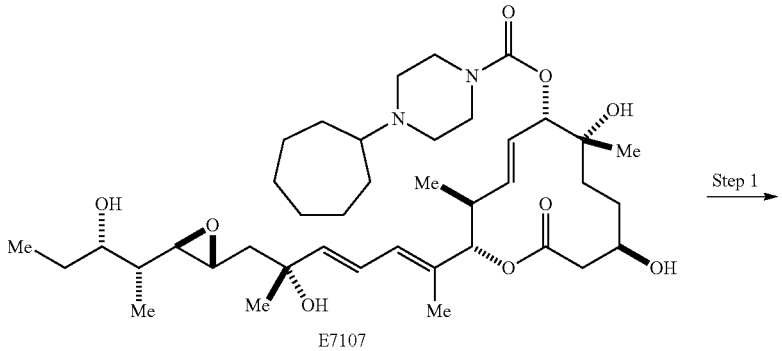

E7107

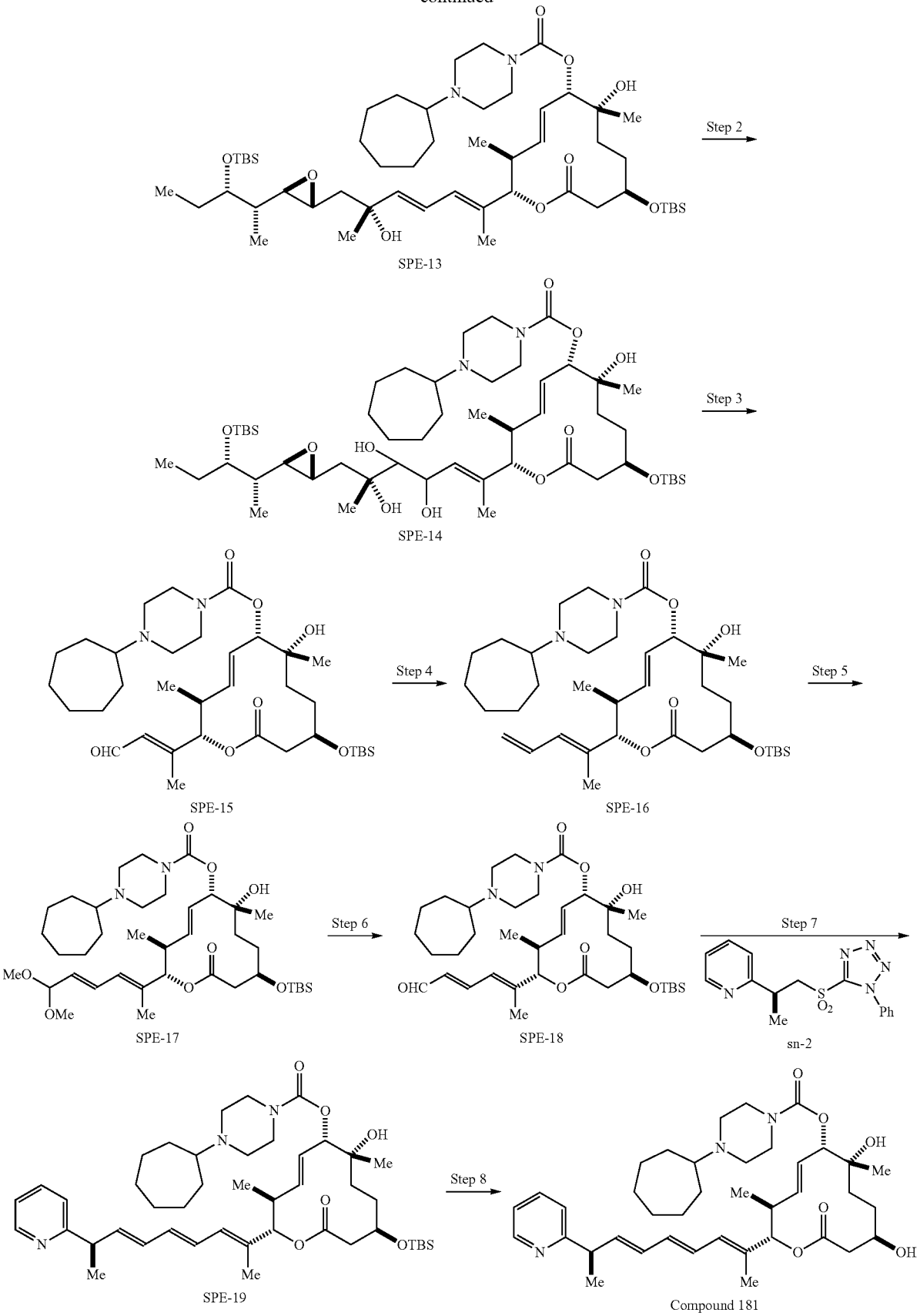

Step 1: E7107 (48.00 g, 66.8 mmol, 1 equiv) was dissolved in DMF (96 mL) and then imidazole (31.8 g, 467 mmol, 7 equiv) was added. Upon complete dissolution of imidazole, the mixture was cooled to 3° C. TBSC1 (30.2 g, 200 mmol, 3 equiv) was added and stirring was continued at 3-5° C. for 2 hours. The mixture was allowed to warm up to room temperature (18-19° C.) and stirring continued for 22 hours. The mixture was diluted with MTBE (192 mL) and cooled to 3° C. Water (192 mL) was added while maintaining T-internal below 15° C. and resultant mixture was transferred to a separation funnel. Water (96 mL) and MTBE (96 mL) were used to rinse the reactor. Rinsate was also transferred to the separation funnel and mixed well. The org layer was separated and set aside. Aqueous layer was extracted with MTBE twice (288 mL×2). All the organic layers were combined, sequentially washed with: (1) water (96 mL), (2) 30 wt % aqueous NaCl (96 mL, 492.79 mmol) and partially concentrated to give 631 g yellow solution (silylation crude mixture), 1.58 g aliquot of which, corresponding to 1/400 of crude mixture, was subjected to purification by silica gel chromatography (25-50% MTBE/heptane) to give the desired product (SPE-13, 172 mg).

Step 2: Another 1.58 g aliquot of the crude SPE-13 was concentrated, dissolved in acetone (1.6 mL) and diluted with water (0.4 mL). NMO (0.078 g, 0.68 mmol) was added followed by 2.5 wt % $OsO_4$ solution in water (0.34 ml, 0.033 mmol). After overnight stirring (16 hr), the mixture was diluted with toluene (0.8 mL), cooled to 0° C. and quenched with 20 wt % aqueous sodium sulfite (0.8 g). The mixture was partially concentrated and extracted with EtOAc twice (4 mL×2). All the organic layers were combined, washed with 36 wt % aqueous NaCl (0.4 mL) and concentrated. Crude product thus obtained was purified by Biotage 25M (EtOAc 100% and EtPAc-MeOh 19:1 v/v) to give the desired product (SPE-14, 117 mg).

Step 3: SPE-14 (80 mg, 0.082 mmol, 1 equiv) was dissolved in acetonitrile (1.6 mL) and treated with lead tetraacetate (Pb(AcO)$_4$; 74 mg, 0.17 mmol, 2 equiv) at room temperature. After 30 min, mixture was diluted with ethyl acetate (3.2 mL), filtered and washed with a mixture of 20 wt % aqueous sodium sulfite ($Na_2SO_3$, 0.3 g, 0.5 mmol, 7.3 equiv) and 9 wt % aqueous sodium bicarbonate (0.3 g, 0.3 mmol, 3.6 equiv). The organic layer was separated and set aside. The aqueous layer was extracted with ethyl acetate (3.2 mL). All the organic layers were combined, washed with 36 wt % aqueous sodium chloride (0.60 mL), and concentrated. Brownish crude oil thus obtained was purified by short $SiO_2$ plug column (EtOAc 100% & EtOAc 100% & EtOAc-MeOH 9:1 v/v) to give the desired product (SPE-15, 30 mg).

Step 4: (Methyl)triphenylphosphonium bromide (1.28 g, 3.59 mmol, 2.2 equiv) was suspended in THF (10.5 mL) and cooled to −10° C. 1 M potassium tert-butoxide solution in THF (3.2 mL, 3.2 mmol, 2 equiv) was added (T-internal reached −6.1° C.) and the resultant yellow mixture was stirred at −10° C. After 30 min, the mixture was cooled to below −70° C. A solution of SPE-15 (1.049 g, 1.62 mmol, 1 equiv) in THF (2.1 mL) was added (T≤−65° C.). Additional THF (2.1 mL) was used for rinse. Dry ice/acetone bath was replaced with dry ice/acetonitrile bath to have the mixture warmed up to approx. −45° C. After 30 min, 28 wt % aqueous ammonium chloride (1 g) was added and the mixture was allowed to warm up to −10° C., diluted with toluene (31.5 mL) and water (2 mL). The organic layer was separated, washed with 36 wt % aqueous sodium chloride (3 mL), concentrated and purified by Biotage Snap Ultra 100 g (0-100% EtOAc/acetone) to give the desired product (SPE-16, 310 mg).

Step 5-6: SPE-16 (0.110 g, 0.17 mmol, 1 equiv) was dissolved in 1,2-dichloroethane (2.3 mL). Acrolein dimethyl acetal (0.20 ml, 1.7 mmol, 10 equiv), benzoquinone (0.5 mg) and Hoveyda-Grubbs $2^{nd}$ generation catalyst (14 mg, 0.017 mmol, 0.1 equiv) were added. The resultant mixture was heated at 50° C. Additional reagents were charged at the following time points: 1 hr—acrolein dimethyl acetal (0.20 ml, 1.7 mmol, 10 equiv), 2 hr—Acrolein dimethyl acetal (0.20 ml, 1.7 mmol, 10 equiv), 3 hr—Hoveyda-Grubbs 2nd generation catalyst (14 mg, 0.017 mmol, 0.1 equiv) and acrolein dimethyl acetal (0.20 ml, 1.7 mmol, 10 equiv). Heating was continued for extra 5 hr and the mixture was let cool down to ambient temp. The mixture was directly loaded on silica gel column for purification (heptane-MTBE 1:1, heptane-EtOAc 9:1) to give crude SPE-17. This was dissolved in dichloromethane (1 mL) and treated with formic acid (0.1 mL) at room temperature for 10 minutes. 9 wt % aqueous sodium bicarbonate (3 g) was carefully added and the mixture was extracted with ethyl acetate twice (4 mL×2). All the organic layers were combined, concentrated and purified by silica gel chromatography (EtOAc 100% & EtOAc-acetone 3:1) to give the desired product (SPE-18, 10 mg)

Step 7-8: sn-2 (10.8 mg, 0.033 mmol, 2 equiv) was dissolved in THF (0.1 mL). DMF (0.025 mL) was added and the mixture was cooled to −70° C. 0.5 M solution of 1 M NaHMDS solution in THF (0.037 ml, 0.037 mmol, 2.5 equiv) was added (→65° C.). A solution of SPE-18 (0.010 g, 0.015 mmol, 1 equiv) in THF (0.1 mL) was added. (→60° C.). THF (0.2 mL) was used for rinse. After 30 min, dry ice/acetone bath was replaced with dry ice/MeCN bath. The mixture was allowed to warm up to −45° C. to −50° C. After 1 hr, the reaction was quenched with 28 wt % aqueous ammonium chloride (0.1 g). The mixture was warmed up to 0° C., and then diluted with ethyl acetate (6 mL) and water (0.2 mL). The organic layer was separated, washed with 36 wt % aqueous sodium chloride (0.3 mL), concentrated and purified by silica gel chromatography (50-100% EtOAc/heptane) to give the desired product (SPE-19, 10 mg). SPE-19 was dissolved in THF (0.3 mL) and treated with 1 M TBAF solution in THF (0.030 mL, 0.03 mmol) at room temperature. After overnight stirring, the mixture was concentrated and purified by Sift plug (MTBE 100% to MTBE-acetone 2:1) to give the desired product (Compound 181, 3 mg). $^1$H NMR (400 MHz, CDCl$_3$) □□ 8.54 (1H, m), 7.60 (1H, m), 7.09-7.17 (2H, m), 6.22-6.36 (2H, m), 6.14 (1H, m), 5.99 (1H, dd, J=7 Hz and 15 Hz), 5.68 (1H, dd, J=10 Hz and 15 Hz), 5.59 (1H, dd, J=10 Hz and 15 Hz), 5.16 (1H, d, J=10 Hz), 5.01 (1H, d, J=10 Hz), 3.6-3.8 (2H, m), 3.4-3.5 (5H, m), 2.4-2.6 (8H, m), 1.96 (1H, s), 1.2-1.8 (16H, m), 1.73 (3H, s), 1.44 (3H, d, J=7 Hz), 1.22 (3H, s), 0.87 (3H, d, J=7 Hz).

Protocol for Synthesis of Compound 182

Scheme 55.

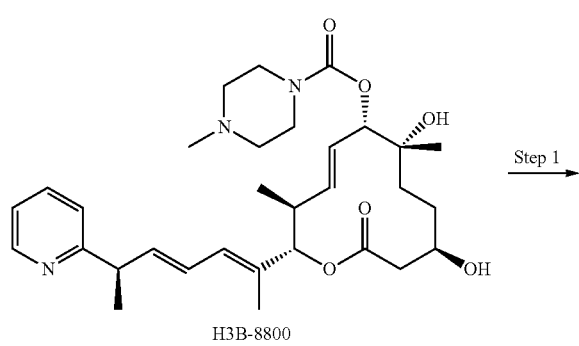

H3B-8800

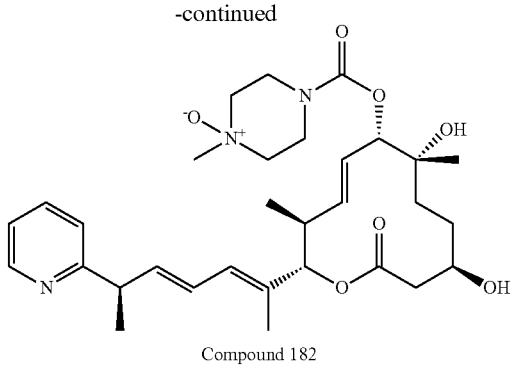

Compound 182

Step 1: To H3B-8800 (55 mg, 0.099 mmol, 1 equiv) in DCE (5 mL), mCPBA (17.08 mg, 0.099 mmol, 1.0 equiv) was added and stirred for 1 hr. The reaction mixture was evaporated and purified by preparative HPLC to give the desired product (Compound 182, 21 mg, 0.037 mmol, 37%). $^1$H NMR (400 MHz, CDCl3) δ: 0.80-1.00 (m, 3H) 1.23-1.48 (m, 6H) 1.50-1.63 (m, 1H) 1.65-1.83 (m, 4H) 2.41-2.68 (m, 5H) 3.19-3.36 (m, 7H) 3.67-3.85 (m, 2H) 3.91 (br s, 2H) 4.02 (br s, 2H), 5.03 (br d, J=9.54 Hz, 1H) 5.17 (d, J=10.54 Hz, 1H) 5.57-5.77 (m, 2H) 6.02 (dd, J=15.18, 7.40 Hz, 1H) 6.13 (br d, J=11.04 Hz, 1H) 6.34 (dd, J=15.06, 10.79 Hz, 1H) 7.14 (t, J=6.18 Hz, 1H) 7.18 (d, J=7.14 Hz, 1H) 7.28 (s, 2H) 7.63 (td, J=7.65, 1.76 Hz, 1H) 8.56 (d, J=5.11 Hz, 1H). MS(ES+): 572.69 [M+H]$^+$.

Compounds 183 and 184 were synthesized according to Scheme 56.

Scheme 56.

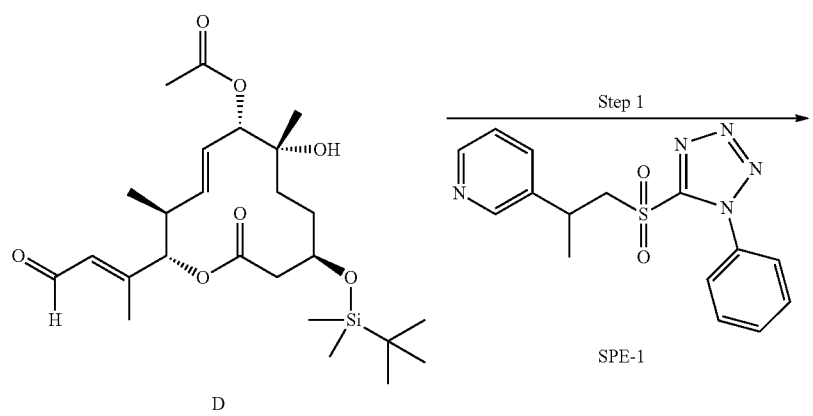

D

SPE-1

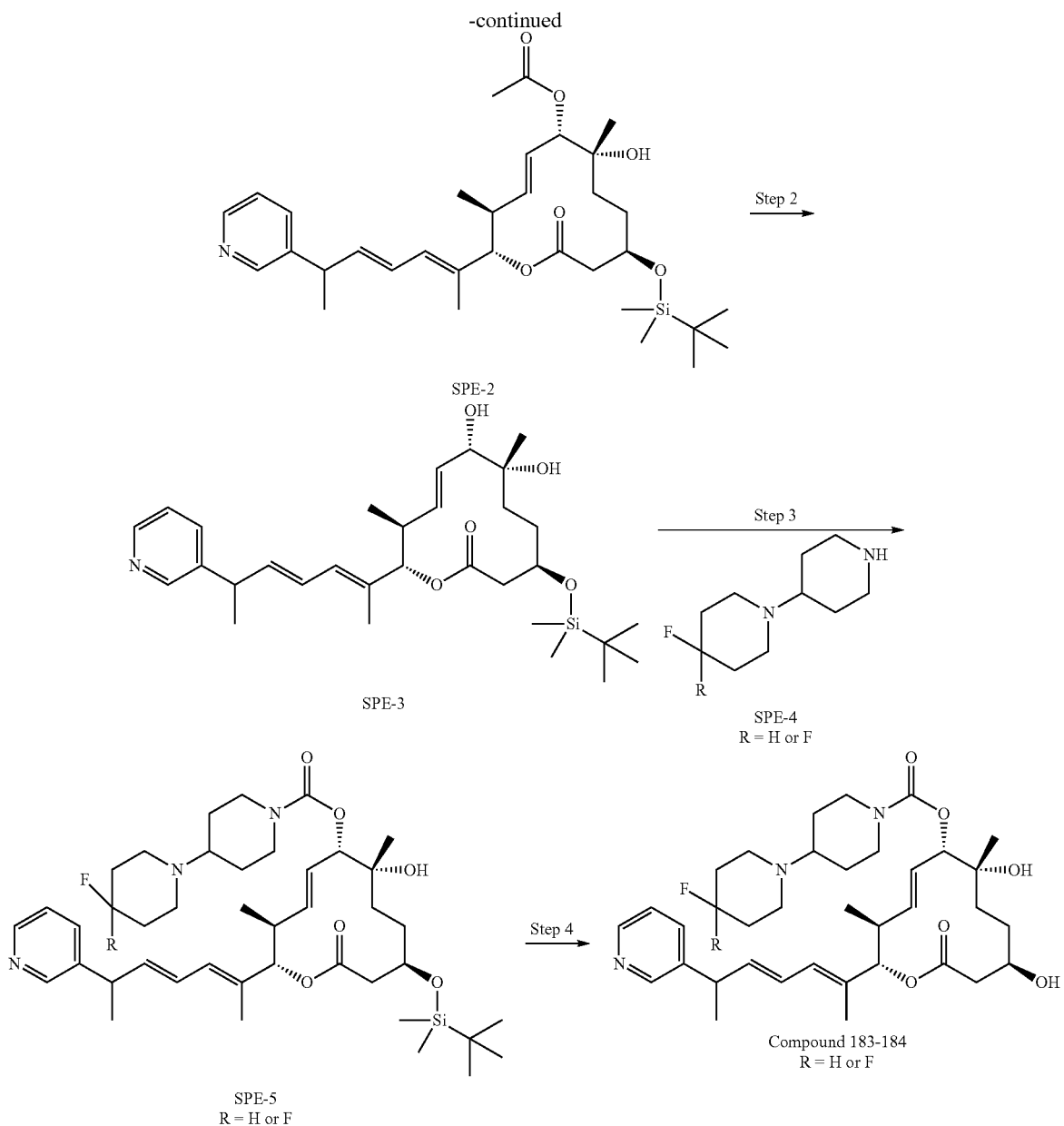

SPE-5
R = H or F

Compound 183-184
R = H or F

Exemplified Protocol for Synthesis of Compound 183

Step 1: To a solution of SPE-1 (246 mg, 0.746 mmol, 1.8 equiv) in a 1:2 ratio DMF (0.5 mL)/THF (1 mL) at −78° C. was added dropwise NaHMDS (0.829 mL, 0.829 mmol, 2.0 equiv) by slow addition to ensure internal does not exceed −60° C. The yellow solution was stirred at −78° C. for 30 mins. Then a solution of D (200 mg, 0.414 mmol, 1 equiv) in THF (1 mL) was added dropwise at such a rate to ensure the reaction temperature remained below −60° C. The flask was rinsed with additional THF (1 mL) and the reaction mixture stirred for 1 hr at −78. The bath temp was increased to −50° C. over 20 mins and then allowed to stir between −50° C. to −45° C. for 2 hrs. Solid ammonium chloride (22.16 mg, 0.414 mmol, 1 equiv) was added in one portion. The bath was slowly allowed to warm to 0° C. The mixture was extracted with EtOAc, washed with brine, dried over sodium sulfate, filtered, and concentrated. Purification of the resulting residue by column chromatography (0-100% EtOAc/hexanes) was completed to give the desired product (SPE-2, 320 mg, 0.382 mmol, 92%).

Step 2: To a solution of SPE-2 (320 mg, 0.382 mmol, 1 equiv) in MeOH (3 mL) at rt was added solid potassium carbonate (74.0 mg, 0.535 mmol, 1.4 equiv) in one portion. The reaction mixture was stirred at rt for 2.5 hrs. Then, it was cooled to 0° C. and solid ammonium chloride (28.6 mg, 0.535 mmol, 1 equiv) was added along with water (2 mL). This mixture was extracted with EtOAc, washed brine, dried over sodium sulfate, filtered, and concentrated. The resulting residue was purified by silica gel chromatography (0-100% EtOAc/hexanes) to give the desired product (SPE-3, 148 mg, 0.272 mmol, 71%).

Step 3: To a 0° C. solution of SPE-4 (17.87 mg, 0.069 mmol, 1.5) in DCM (1 mL) and Hunig'sBase (0.048 mL, 0.276 mmol, 6.0 equiv) was added phosgene (0.065 ml, 0.092 mmol, 2 equiv) (in Toluene). The reaction mixture was stirred for 30 min at 0° C., then warmed to rt. The reaction mixture was concentrated by rotavap and high vacuum. The residue was dissolved in THF (1 mL) and SPE-3 (25 mg, 0.046 mmol, 1 equiv) and DMAP (22.47 mg, 0.184 mmol, 4 equiv) were added. The reaction mixture was stirred at rt for 1 hr. The reaction mixture was then cooled to 0° C. and a 1M toluene solution of NaHMDS (0.184 ml, 0.184 mmol, 4 equiv) was added. This was stirred for 2 hrs at this temperature. The reaction mixture was quenched with ammonium chloride solution and extracted with EtOAc, dried over sodium sulfate, filtered, and concentrated. Purification by silica gel chromatography (10% MeOH/EtOAc) was completed to give the desired product (SPE-5, 21 mg, 0.028 mmol, 60%).

Step 4: To SPE-5 (21 mg, 0.028 mmol, 1 equiv) in methanol (0.5 mL), P-TOLUENESULFONIC ACID MONOHYDRATE (10.6 mg, 0.056 mmol, 2 equiv) was added at rt. After 3 hr, the reaction was quenched with sat. NaHCO3 solution. The aqueous was extracted with EtOAc, followed by washing with brine, drying over sodium sulfate, filtering, and concentration to give the crude product. Purification by silica gel chromatography (0-20% MeOH/EtOAc) was completed to give the desired product (Compound 183, 15.7 mg, 0.024 mmol, 88%). $^1$H NMR (400 MHz, METHANOL-d4) δ: ppm 0.86-0.92 (m, 3H) 1.14-1.18 (m, 1H) 1.21-1.24 (m, 3H) 1.27 (s, 2H) 1.36-1.48 (m, 7H) 1.57-1.69 (m, 2H) 1.76 (s, 3H) 1.81-1.98 (m, 6H) 2.50-2.62 (m, 6H) 2.72-2.87 (m, 4H) 3.62-3.70 (m, 1H) 3.75-3.84 (m, 1H) 4.91-4.97 (m, 1H) 5.02-5.10 (m, 1H) 5.52-5.64 (m, 1H) 5.67-5.79 (m, 1H) 5.89-6.00 (m, 1H) 6.10-6.19 (m, 1H) 6.32-6.42 (m, 1H) 7.35-7.45 (m, 1H) 7.70-7.81 (m, 1H) 8.37-8.41 (m, 1H) 8.42-8.45 (m, 1H). MS(ES+): 642.64 [M+H]$^+$.

Protocol for the Synthesis of Compound 185

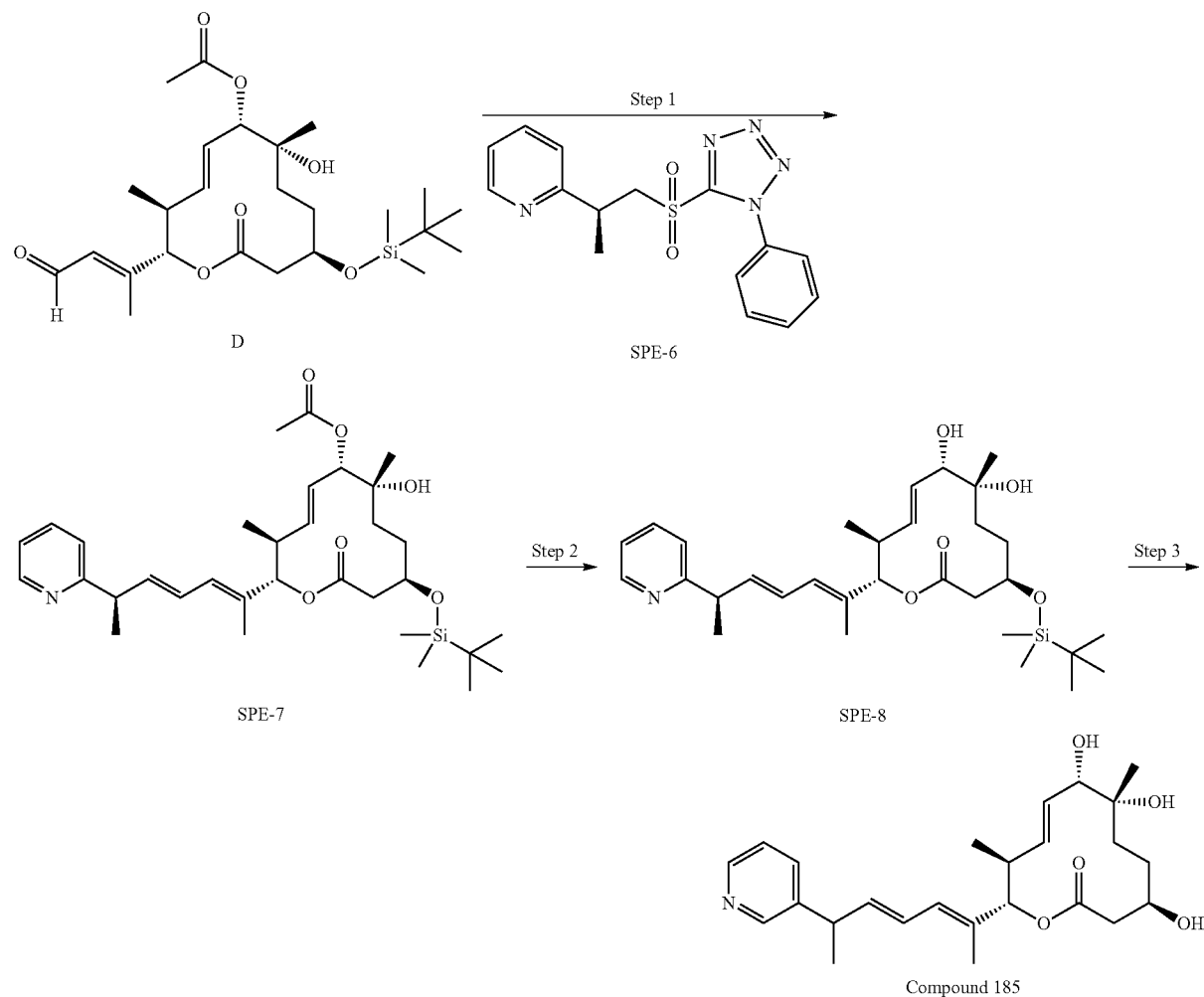

Scheme 57.

Step 1: To a solution of SPE-6 (184 mg, 0.559 mmol, 1.8 equiv) in 1:4 DMF (529 μL)/THF (2139 μL) at −78° C. was added dropwise 1M NaHMDS (482 μL, 0.482 mmol, 1.55 equiv) via slow addition to ensure internal does not exceed −60° C. The yellow solution was stirred at −78° C. for 30 mins. Then a solution of intermediate D (150 mg, 0.311 mmol, 1 equiv) in THF (425 μL) was added dropwise at such a rate as to ensure the temperature remained below −60° C. The aldehyde container was rinsed with additional THF and added to main flask. The reaction mixture was stirred for 1 hr, maintaining bath temp between −70° C. to −60° C. The bath temperature was increased to −50° C. over 20 mins. This was then allowed to stir between −50° C. to −45° C. for 2 hrs in an acetonitrile-dry ice bath. After 2 hrs, solid AMMONIUM CHLORIDE (72.6 mg, 1.358 mmol, 4.37 equiv) was added in one portion and bath was allowed to slowly warm to 0° C. Added toluene and water at 0° C. and the combined organics were washed with brine. The organics were dried over sodium sulfate, filtered, and concentrated. Purification by column chromatography (0-40% MTBE/hexanes with long hold at 40% gave desired product as a mixture with some aldehyde D (SPE-7, 57.8 mg, 0.099 mmol, 31.7%).

Step 2: To a solution of SPE-7 (29.2 mg, 0.05 mmol, 1 equiv) in MeOH (252 µL) at rt was added solid potassium carbonate (9.64 mg, 0.07 mmol, 1.4 equiv) in one portion. At 2 hours, the reaction mixture was cooled to 0° C. and sat aq ammonium chloride was added. The aqueous was extracted with EtOAc and washed with brine. The organics were dried over sodium sulfate, filtered, and concentrated. The crude product (SPE-8, 12.6 mg, 0.023 mmol, 46.5%) was taken into the next step without further purification.

Step 3: SPE-8 (24.2 mg, 0.045 mmol, 1 equiv) was dissolved in methanol (225 µL) and tosic acid (16.93 mg, 0.089 mmol, 2 equiv) was added. The reaction mixture was stirred at rt for 1 hr. The reaction was quenched with sat. aq. sodium bicarbonate and extracted with 10% MeOH/DCM. The combined organics were dried over sodium sulfate, filtered, and concentrated. Purification by column chromatography (0-20% MeOH/DCM) was completed to give the desired product (Compound 185, 9.2 mg, 0.021 mmol, 48.1% yield) as a crusty oil/white solid. 1H NMR (400 MHz, METHANOL-d4) δ: ppm 0.90 (d, J=6.78 Hz, 3H) 1.28 (s, 4H) 1.35-1.39 (m, 2H) 1.45 (d, J=7.03 Hz, 3H) 1.53-1.62 (m, 2H) 1.76 (d, J=0.88 Hz, 3H) 2.53 (s, 3H) 3.69-3.80 (m, 4H) 5.03-5.08 (m, 1H) 5.34-5.44 (m, 1H) 5.48-5.53 (m, 1H) 5.67-5.78 (m, 1H) 5.92-6.03 (m, 1H) 6.09-6.18 (m, 1H) 6.33-6.44 (m, 1H) 7.23-7.32 (m, 1H) 7.32-7.39 (m, 1H) 7.72-7.84 (m, 1H) 8.40-8.50 (m, 1H). MS(ES+): 430.43 [M+H]⁺.

TABLE 10

Compounds 175-185

| Structure, Compound #, and Chemical Name | ¹H NMR data | LCMS data (ES+) |
|---|---|---|
| 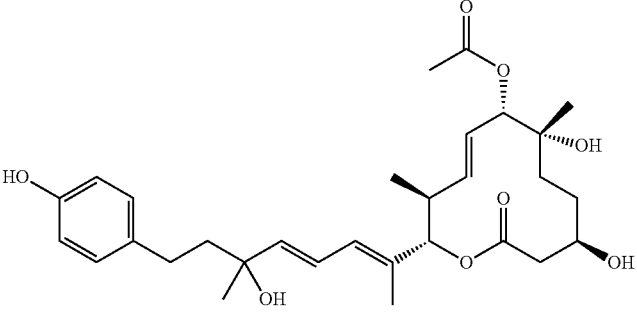<br>175<br>[(2S,3S,4E,6R,7R,10R)-7,10-dihydroxy-2-[(2E,4E)-6-hydroxy-8-(4-hydroxyphenyl)-6-methylocta-2,4-dien-2-yl]-3,7-dimethyl-12-oxo-1-oxacyclododec-4-en-6-yl] acetate | | 553.35 |
| 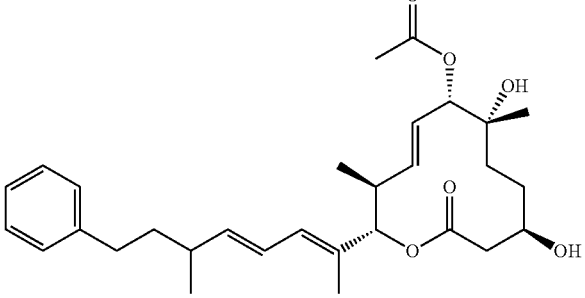<br>176<br>[(2S,3S,4E,6S,7S,10S)-7,10-dihydroxy-3,7-dimethyl-2-[(2E,4E)-6-methyl-8-phenylocta-2,4-dien-2-yl]-12-oxo-1-oxacyclododec-4-en-6-yl] acetate | | 521.42 |

TABLE 10-continued

Compounds 175-185

| Structure, Compound #, and Chemical Name | $^1$H NMR data | LCMS data (ES+) |
|---|---|---|
| 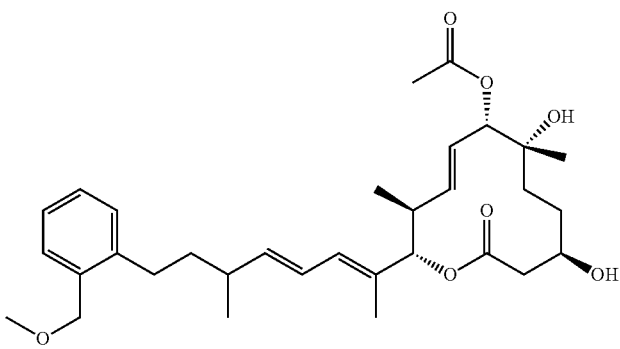<br>177<br>[(2S,3S,4E,6S,7S,10S)-7,10-dihydroxy-2-[(2E,4E)-8-[2-(methoxymethyl)phenyl]-6-methylocta-2,4-dien-2-yl]-3,7-dimethyl-12-oxo-1-oxacyclododec-4-en-6-yl] acetate | $^1$H NMR (400 MHz, CHLOROFORM, d) δ: 0.90 (d, J = 6.8 Hz, 3 H) 1.07 (d, J = 6.8 Hz, 3 H) 1.21 (s, 3 H) 1.24-1.38 (m, 3 H) 1.51-1.70 (m, 4 H) 1.74 (s, 3 H) 2.05 (s, 3 H) 2.27 (quin, J = 6.8 Hz, 1 H) 2.49-2.66 (m, 5 H) 3.38 (s, 3H) 3.55 (d, J = 10.8 Hz, 2 H) 3.73-3.78 (m, 1 H) 4.44 (s, 2 H) 5.08-5.19 (m, 2 H) 5.61-5.73 (m, 3 H) 6.09-6.26 (m, 2 H) 7.16-7.32 (m, 5 H) | 565.36 |
| 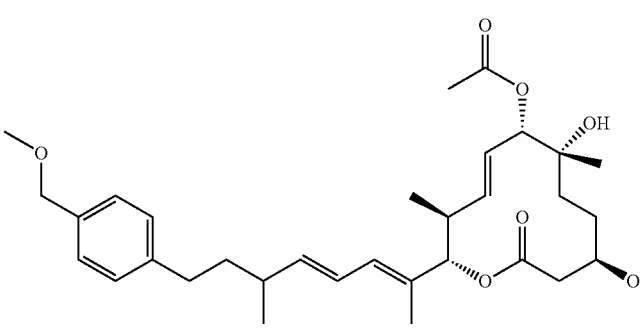<br>178<br>[(2S,3S,4E,6S,7S,10S)-7,10-dihydroxy-2-[(2E,4E)-8-[4-(methoxymethyl)phenyl]-6-methylocta-2,4-dien-2-yl]-3,7-dimethyl-12-oxo-1-oxacyclododec-4-en-6-yl] acetate | $^1$H NMR (400 MHz, CHLOROFORM, d) δ: 0.90 (d, J = 6.8 Hz, 3 H) 1.07 (d, J = 6.8 Hz, 3 H) 1.21 (s, 3 H) 1.24-1.41 (m, 3 H) 1.51-1.70 (m, 4 H) 1.73 (s, 3 H) 2.05 (s, 3 H) 2.20-2.24 (m, 1 H) 2.49-2.66 (m, 5 H) 3.38 (s, 3 H) 3.56 (d, J = 10.8 Hz, 2 H) 3.73-3.78 (m, 1 H) 4.42 (s, 2 H) 5.08-5.18 (m, 2 H) 5.63-5.70 (m, 3 H) 6.07-6.22 (m, 2 H) 7.15 (d, J = 8.0 Hz, 2 H) 7.24 (d, J = 8.0 Hz, 2 H) | 565.37 |
| 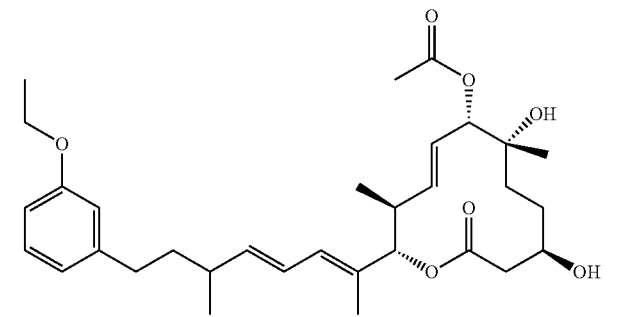<br>179<br>[(2S,3S,4E,6S,7S,10S)-7,10-dihydroxy-2-[(2E,4E)-8-[3-(methoxymethyl)phenyl]-6-methylocta-2,4-dien-2-yl]-3,7-dimethyl-12-oxo-1-oxacyclododec-4-en-6-yl] acetate | $^1$H NMR (400 MHz, CHLOROFORM, d) δ: 0.90 (d, J = 6.8 Hz, 3 H) 1.05 (d, J = 6.8 Hz, 3 H) 1.21 (s, 3 H) 1.24-1.42 (m, 3 H) 1.52-1.72 (m, 4 H) 1.74 (s, 3 H) 2.10 (s, 3 H) 2.20-2.26 (m, 1 H) 2.50-2.66 (m, 5 H) 3.38 (s, 3H) 3.56 (dd, J = 10.8, 3.2 Hz, 2 H) 3.72-3.78 (m, 1 H) 4.43 (s, 2 H) 5.08-5.18 (m, 2 H) 5.59-5.71 (m, 3 H) 6.08-6.23 (m, 2 H) 7.09-7.27 (m, 5 H) | 565.41 |

TABLE 10-continued

Compounds 175-185

| Structure, Compound #, and Chemical Name | ¹H NMR data | LCMS data (ES+) |
|---|---|---|
| 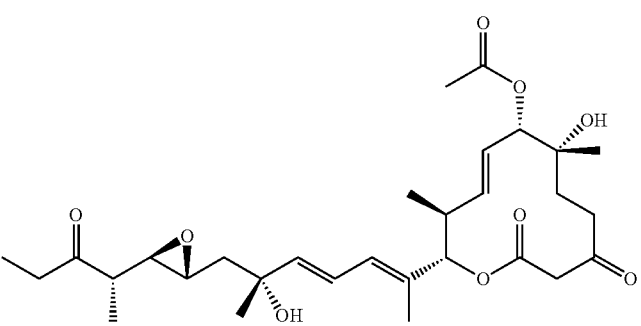<br>180<br>[(2S,3S,4E,6S,7S)-7-hydroxy-2-[(2E,4E,6S)-6-hydroxy-6-methyl-7-[(2R,3R)-3-[(2S)-3-oxopentan-2-yl]oxiran-2-yl]hepta-2,4-dien-2-yl]-3,7-dimethyl-10,12-dioxo-1-oxacyclododec-4-en-6-yl] acetate | | 571.36 |
| 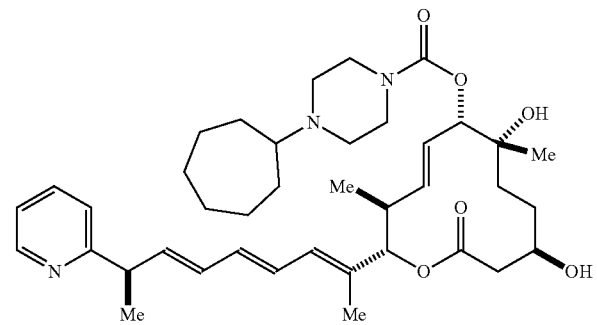<br>181<br>[(2S,3S,4E,6S,7S,10S)-7,10-dihydroxy-3,7-dimethyl-12-oxo-2-[(2E,4E,6E,8S)-8-pyridin-2-ylnona-2,4,6-trien-2-yl]-1-oxacyclododec-4-en-6-yl] 4-cycloheptylpiperazine-1-carboxylate | ¹H NMR (400 MHz, CDCl₃) δ: 8.54 (1H, m), 7.60 (1H, m), 7.09-7.17 (2H, m), 6.22-6.36 (2H, m), 6.14 (1H, m), 5.99 (1H, dd, J = 7 Hz and 15 Hz), 5.68 (1H, dd, J = 10 Hz and 15 Hz), 5.59 (1H, dd, J = 10 Hz and 15 Hz), 5.16 (1H, d, J = 10 Hz), 5.01 (1H, d, J = 10 Hz), 3.6-3.8 (2H, m), 3.4-3.5 (5H, m), 2.4-2.6 (8H, m), 1.96 (1H, s), 1.2-1.8 (16H, m), 1.73 (3H, s), 1.44 (3H, d, J = 7 Hz), 1.22 (3H, s), 0.87 (3H, d, J = 7 Hz) | |
| 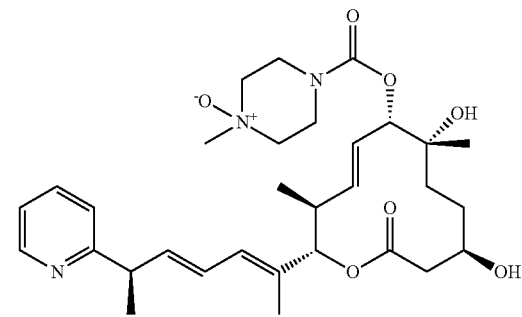<br>182<br>[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methyl-4-oxidopiperazin-4-ium-1-carboxylate | ¹H NMR (400 MHz, CDCl3) δ: 0.80-1.00 (m, 3 H) 1.23-1.48 (m, 6 H) 1.50-1.63 (m, 1 H) 1.65-1.83 (m, 4 H) 2.41-2.68 (m, 5 H) 3.19-3.36 (m, 7 H) 3.67-3.85 (m, 2 H) 3.91 (br s, 2 H) 4.02 (br s, 2 H), 5.03 (br d, J = 9.54 Hz, 1 H) 5.17 (d, J = 10.54 Hz, 1 H) 5.57-5.77 (m, 2 H) 6.02 (dd, J = 15.18, 7.40 Hz, 1 H) 6.13 (br d, J = 11.04 Hz, 1 H) 6.34 (dd, J = 15.06, 10.79 Hz, 1 H) 7.14 (t, J = 6.18 Hz, 1 H) 7.18 (d, J = 7.14 Hz, 1 H) 7.28 (s, 2 H) 7.63 (td, J = 7.65, 1.76 Hz, 1 H) 8.56 (d, J = 5.11 Hz, 1 H) | 572.69 |

TABLE 10-continued

Compounds 175-185

| Structure, Compound #, and Chemical Name | ¹H NMR data | LCMS data (ES+) |
|---|---|---|
| 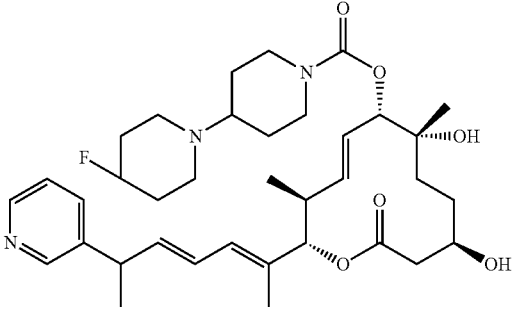<br>183<br>[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-(4-fluoropiperidin-1-yl)piperidine-1-carboxylate | ¹H NMR (400 MHz, METHANOL-d4) δ: ppm 0.86-0.92 (m, 3 H) 1.14-1.18 (m, 1 H) 1.21-1.24 (m, 3 H) 1.27 (s, 2 H) 1.36-1.48 (m, 7 H) 1.57-1.69 (m, 2 H) 1.76 (s, 3 H) 1.81-1.98 (m, 6 H) 2.50-2.62 (m, 6 H) 2.72-2.87 (m, 4 H) 3.62-3.70 (m, 1 H) 3.75-3.84 (m, 1 H) 4.91-4.97 (m, 1 H) 5.02-5.10 (m, 1 H) 5.52-5.64 (m, 1 H) 5.67-5.79 (m, 1 H) 5.89-6.00 (m, 1 H) 6.10-6.19 (m, 1 H) 6.32-6.42 (m, 1 H) 7.35-7.45 (m, 1 H) 7.70-7.81 (m, 1 H) 8.37-8.41 (m, 1 H) 8.42-8.45 (m, 1 H) | 642.64 |
| 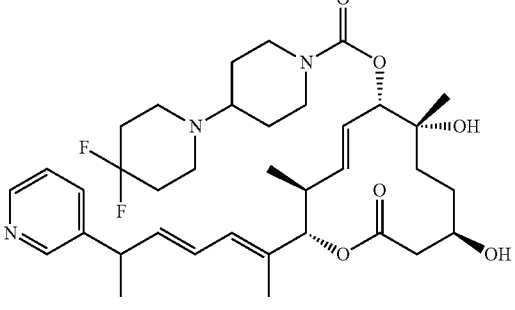<br>184<br>[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-(4,4-difluoropiperidin-1-yl)piperidine-1-carboxylate | ¹H NMR (400 MHz, CHLOROFORM-d) δ: ppm 0.89-0.93 (m, 3 H) 1.25 (s, 3 H) 1.26-1.30 (m, 3 H) 1.32-1.51 (m, 1 H) 1.32-1.41 (m, 1 H) 1.43 (dd, J = 7.03, 2.26 Hz, 4 H) 1.49-1.58 (m, 1 H) 1.62-1.85 (m, 9 H) 1.93-2.06 (m, 5 H) 2.17-2.22 (m, 2 H) 2.49-2.68 (m, 9 H) 2.73-2.88 (m, 2 H) 3.45-3.54 (m, 1 H) 3.55-3.63 (m, 1 H) 3.70-3.81 (m, 1 H) 4.17-4.27 (m, 1 H) 4.98-5.04 (m, 1 H) 5.17 (d, J = 10.67 Hz, 1 H) 5.55-5.66 (m, 1 H) 5.67-5.78 (m, 1 H) 5.86-5.97 (m, 1 H) 6.12 (d, J = 10.79 Hz, 1 H) 6.19-6.32 (m, 1 H) 7.22-7.27 (m, 1 H) 7.47-7.58 (m, 1 H) 8.44-8.54 (m, 1 H) | 660.53 |
| 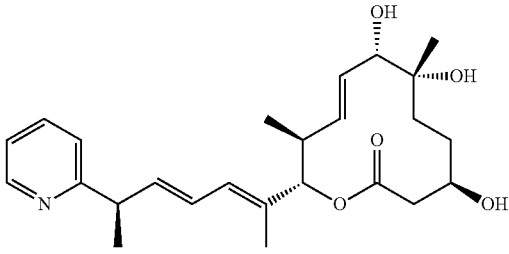<br>185<br>(4S,7S,8S,9E,11S,12S)-4,7,8-trihydroxy-7,11-dimethyl-12-[(2E,4E,6S)-6-pyridin-2-ylhepta-2,4-dien-2-yl]-1-oxacyclododec-9-en-2-one | ¹H NMR (400 MHz, METHANOL-d4) δ: ppm 0.90 (d, J = 6.78 Hz, 3 H) 1.28 (s, 4 H) 1.35-1.39 (m, 2 H) 1.45 (d, J = 7.03 Hz, 3 H) 1.53-1.62 (m, 2 H) 1.76 (d, J = 0.88 Hz, 3 H) 2.53 (s, 3 H) 3.69-3.80 (m, 4 H) 5.03-5.08 (m, 1 H) 5.34-5.44 (m, 1 H) 5.48-5.53 (m, 1 H) 5.67-5.78 (m, 1 H) 5.92-6.03 (m, 1 H) 6.09-6.18 (m, 1 H) 6.33-6.44 (m, 1 H) 7.23-7.32 (m, 1 H) 7.32-7.39 (m, 1 H) 7.72-7.84 (m, 1 H) 8.40-8.50 (m, 1 H) | 430.43 |

Compounds 186-196 were synthesized according to Scheme 58.

Protocol for the synthesis of Compound 186

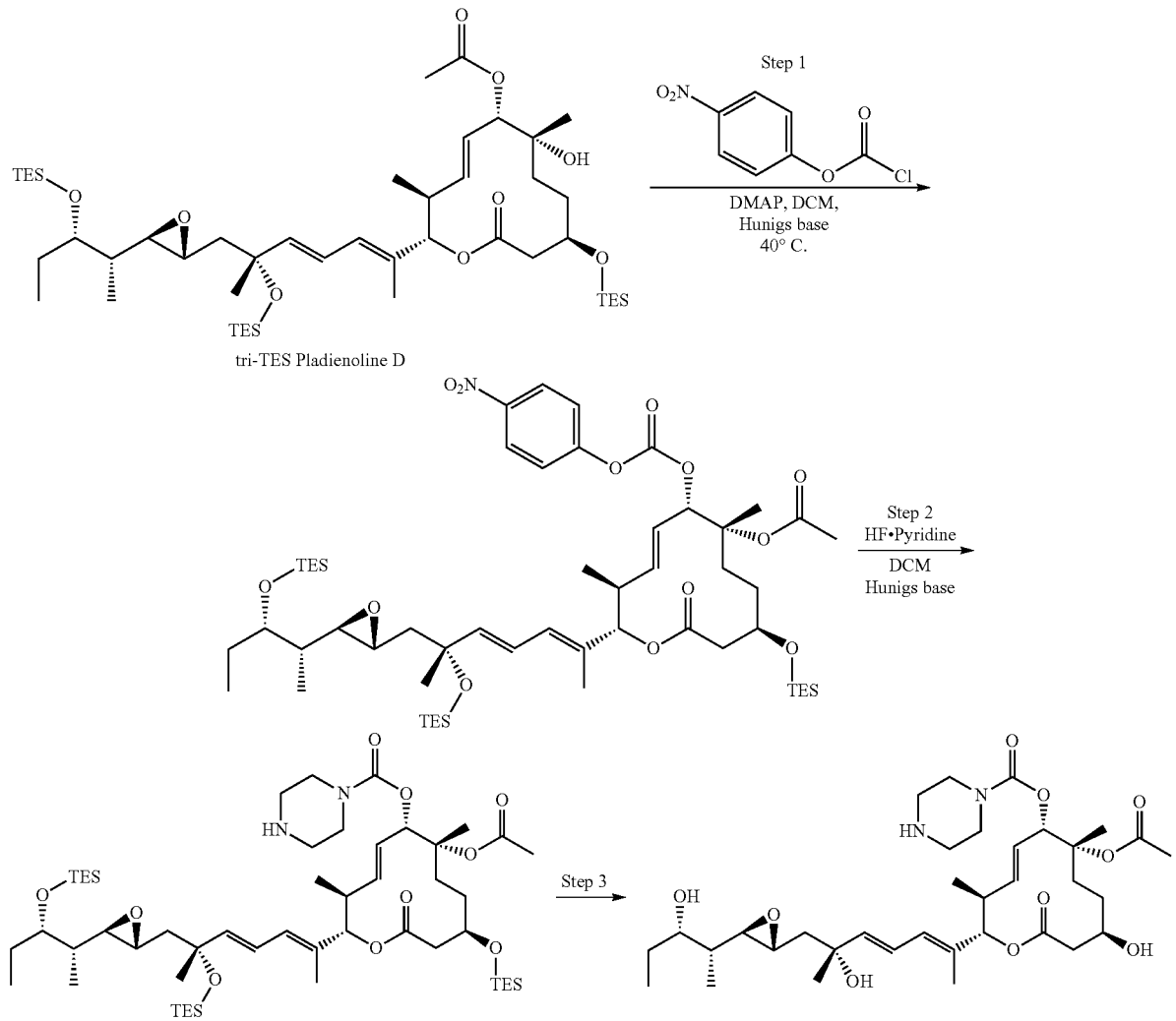

Scheme 58.

tri-TES Pladienoline D

Step 1: To a solution of tri-TES Pladienolide D (160 mg, 0.179 mmol) in 1,2-dichloroethane (5 mL) at 20° C. was added DMAP (32.7 mg, 0.268 mmol), triethyl amine (0.75 mL, 5.36 mmol) and 4-nitrophenyl chloroformate (360 mg, 1.787 mmol). The reaction mixture was stirred at 40° C. for 4 days, and at 60° C. for 2 hours. The reaction mixture was diluted with EtOAc and washed with water, then the layers were separated. The aqueous layer was extracted with EtOAc (2×). The combined organic extracts were successively washed with water and brine, dried over $MgSO_4$, filtered, and concentrated in vacuo. Flash chromatography afforded (2S,3S,6S,7R,10R,E)-7-acetoxy-3,7-dimethyl-2-4R,2E,4E)-6-methyl-6-((triethylsilyl)oxy)-7-((2R,3R)-3-((2S,3S)-3-((triethylsilyl)oxy)pentan-2-yl)oxiran-2-yl) hepta-2,4-dien-2-yl)-12-oxo-10-((triethylsilypoxy) oxacyclododec-4-en-6-yl piperazine-1-carboxylate (150 mg, 79% yield).

$^1$H-NMR (400 MHz, CHCl$_3$-d): δ ppm 0.48-0.71 (m, 24H) 0.78-0.85 (m, 7H) 0.86-0.93 (m, 5H) 0.94-1.03 (m, 34H) 1.18-1.22 (m, 2H) 1.22-1.26 (m, 2H) 1.35-1.43 (m, 4H) 1.43-1.52 (m, 4H) 1.54 (s, 4H) 1.56-1.65 (m, 3H) 1.68-1.72 (m, 3H) 1.75 (br d, J=0.75 Hz, 2H) 1.84-1.95 (m, 1H) 2.01-2.06 (m, 2H) 2.09 (s, 2H) 2.11 (s, 2H) 2.33-2.52 (m, 4H) 2.57 (dd, J=8.09, 2.07 Hz, 2H) 2.80-2.90 (m, 1H) 3.66-3.80 (m, 1H) 3.82-3.93 (m, 2H) 4.92-5.13 (m, 2H) 5.63-5.68 (m, 1H) 5.69-5.74 (m, 1H) 5.75-5.83 (m, 2H) 6.12 (br d, J=10.67 Hz, 1H) 6.41 (ddd, J=15.15, 11.01, 5.08 Hz, 1H) 7.50 (d, J=9.41 Hz, 2H) 8.35 (d, J=9.29 Hz, 2H).

Step 2: To a solution of (2S,3S,6S,7R,10R,E)-3,7-dimethyl-2-4R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-6-(((4-nitrophenoxy)carbonyl)oxy)-12-oxo-10-((triethylsilyl)oxy)oxacyclododec-4-en-7-yl acetate in DCM (1 mL) was added piperazine (0.447 g, 5.195 mmol) and Hunig's base (0.9 mL, 5.195 mmol). The resulting yellowish suspension was stirred for 6 hours. Reaction mixture was concentrated and chromatographed over silica gel to afford (2S,3S,6S,7R,10R,E)-7-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy) oxacyclododec-4-en-6-yl piperazine-1-carboxylate (1.0 g, 0.844 mmol, 81% yield). LC/MS (ESI, m/z), 1008.1 [M+H]$^+$.

Step 3: 2S, 3S,6S,7R,10R,E)-7-acetoxy-3,7-dimethyl-2-((R,2E,4E)-6-methyl-6-((triethylsilyl)oxy)-7-((2S,3S)-3-

((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (1.09 g, 0.92 mmol), DCM (20.71 mL, 321.826 mmol), and DIPEA (19.91 mL, 114.018 mmol) were combined and cooled to −78° C. Hydrogen fluoride-pyridine (0.518 g, 5.232 mmol) was added and the reaction allowed to warm to RT and stirred overnight. LC/MS suggested de-silylation. the reaction mixture was cooled in an icebath. Saturated NaHCO₃ was added and stirred and extracted with DCM. The organic layers were combined, dried over an. NA₂SO₄ and concentrated and chromatographed to afford (2S,3S,6S,7R,10R,E)-7-acetoxy-10-hydroxy-2-((R,2E,4E)-6-hydroxy-7-((2S,3S)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (225 mg, 36.8%). LC/MS (ESI, m/z), 665.6 [M+H]⁺.

¹H-NMR (400 MHz, CHCl₃-d): δ ppm 0.87-0.92 (m, 6H) 0.94 (t, J=7.40 Hz, 3H) 1.16-1.31 (m, 1H) 1.35 (s, 3H) 1.40-1.56 (m, 4H) 1.59 (s, 3H) 1.66 (br dd, J=14.68, 7.03 Hz, 3H) 1.76-1.80 (m, 3H) 1.87 (dd, J=14.12, 5.46 Hz, 1H) 2.05 (s, 3H) 2.30-2.41 (m, 1H) 2.50 (d, J=3.76 Hz, 2H) 2.56-2.72 (m, 2H) 2.90 (br d, J=2.01 Hz, 1H) 3.19 (br t, J=5.14 Hz, 4H) 3.50-3.59 (m, 1H) 3.71 (br s, 4H) 3.77-3.89 (m, 1H) 5.01-5.13 (m, 2H) 5.58-5.71 (m, 1H) 5.71-5.81 (m, 1H) 5.88 (d, J=15.31 Hz, 1H) 6.15 (br d, J=10.79 Hz, 1H) 6.53 (dd, J=15.18, 10.92 Hz, 1H).

Protocol for synthesizing Compound 187

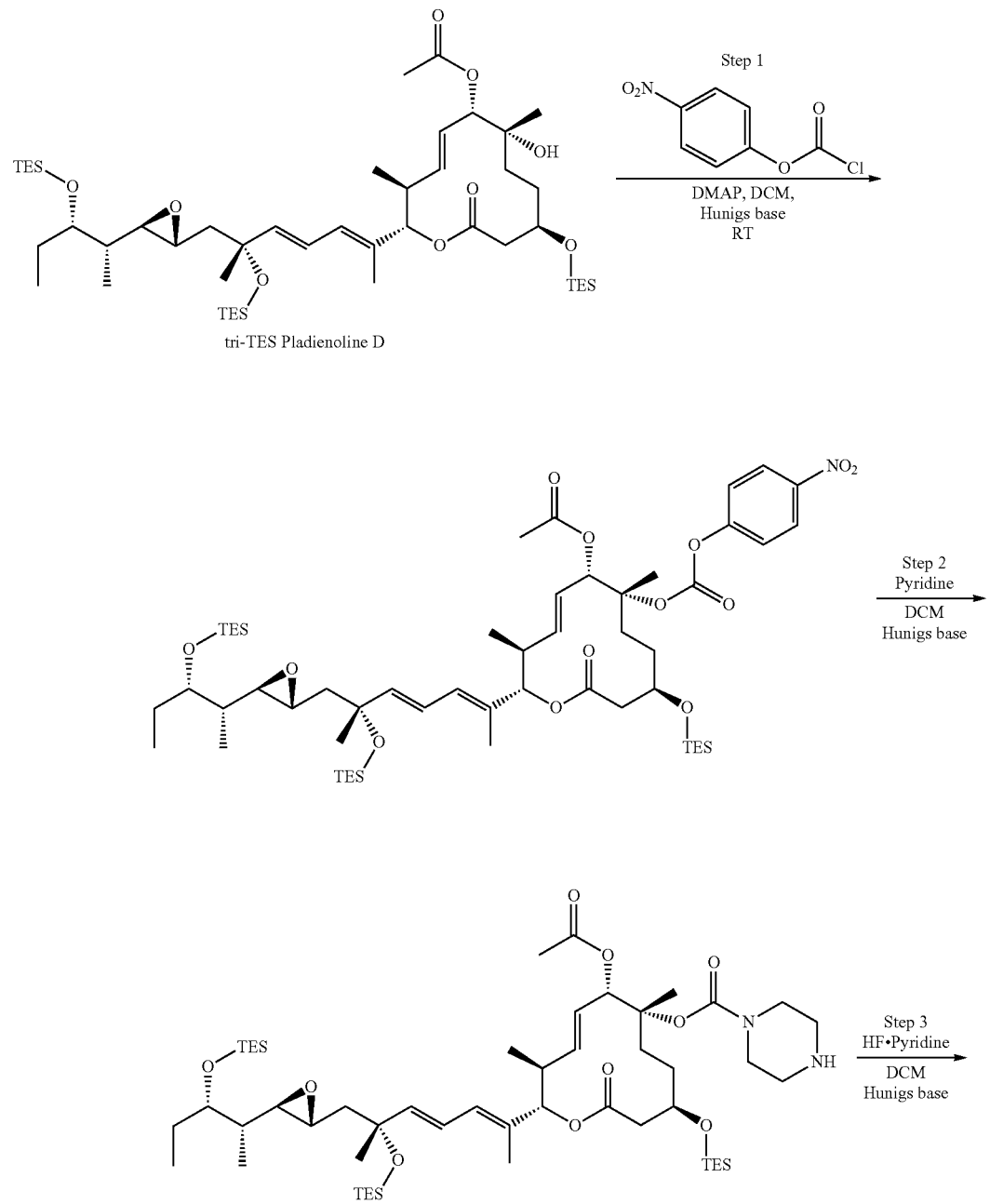

Scheme 59.

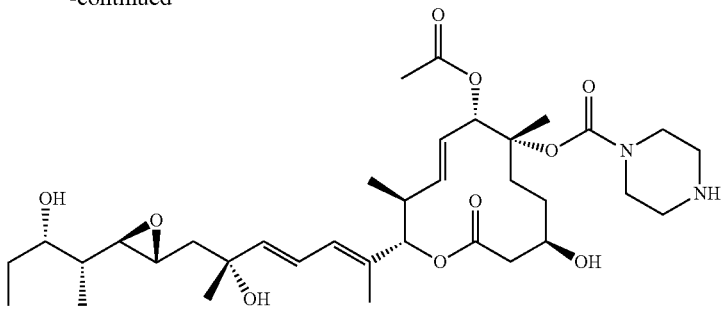

Step 1: To a solution of tri-TES-Pladienolide D (200 mg, 0.223 mmol) in dichloromethane (2 mL) at 0° C. was added DMAP (409 mg, 3.35 mmol) and 4-nitrophenyl chloroformate (338 mg, 1.675 mmol). The reaction mixture was stirred at RT for 7 days, diluted with EtOAc and water, then the layers were separated. The aqueous layer was extracted with EtOAc (2×), and the combined organic extracts were washed with brine. The combined organic layers were dried over $Na_2SO_4$, filtered and concentrated in vacuo. Flash chromatography afforded (2S,3S,6S,7R,10R,E)-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-7-(((4-nitrophenoxy)carbonyl)oxy)-12-oxo-10-((triethylsilyl)oxy)oxacyclododec-4-en-6-yl acetate. (170 mg, 72% yield).

$^1$H-NMR (400 MHz, $CHCl_3$-d): δ ppm 0.54-0.67 (m, 18H) 0.78-1.03 (m, 36H) 1.19-1.32 (m, 1H) 1.39 (s, 3H) 1.43-1.52 (m, 3H) 1.55-1.63 (m, 3H) 1.64 (s, 3H) 1.74 (s, 3H) 1.88 (dd, J=13.80, 5.02 Hz, 1H) 2.13 (s, 3H) 2.23-2.37 (m, 1H) 2.39-2.48 (m, 2H) 2.51-2.63 (m, 2H) 2.84 (s, 1H) 3.69-3.77 (m, 1H) 3.82-4.00 (m, 1H) 5.04 (d, J=10.79 Hz, 1H) 5.24 (d, J=9.03 Hz, 1H) 5.67-5.84 (m, 3H) 6.12 (d, J=10.16 Hz, 1H) 6.42 (dd, J=15.06, 11.04 Hz, 1H) 7.42 (d, J=9.29 Hz, 2H) 8.29 (d, J=9.16 Hz, 2H).

Step 2: To a solution of (2S,3S,6S,7R,10R,E)-3,7-dimethyl-2-4R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-7-((4-nitrophenoxy)carbonyl)oxy)-12-oxo-10-((triethylsilyl)oxy)oxacyclododec-4-en-6-yl acetate (100 mg, 0.094 mmol) in DCM was added piperazine and DMAP. The resulting yellowish suspension was stirred for 6 hours. The reaction mixture was concentrated to give the crude product. Flash chromatography afforded (2S,3S,6S,7R,10R,E)-6-acetoxy-3,7-dimethyl-2-4R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl piperazine-1-carboxylate (95 mg, 100%). LC/MS (ESI, m/z), 1008.8 [M+H]$^+$.

$^1$H-NMR (400 MHz, $CHCl_3$-d): δ ppm 0.42-0.70 (m, 22H) 0.79-0.84 (m, 7H) 0.86-0.91 (m, 4H) 0.92-1.03 (m, 30H) 1.15-1.30 (m, 2H) 1.37-1.42 (m, 3H) 1.44-1.52 (m, 3H) 1.56-1.62 (m, 2H) 1.62-1.68 (m, 1H) 1.71-1.76 (m, 3H) 1.83-1.93 (m, 1H) 2.03-2.11 (m, 4H) 2.36-2.45 (m, 2H) 2.45-2.53 (m, 2H) 2.54-2.64 (m, 1H) 2.78-2.86 (m, 1H) 2.86-3.07 (m, 4H) 3.32-3.45 (m, 1H) 3.45-3.64 (m, 3H) 3.69-3.78 (m, 1H) 3.79-3.94 (m, 1H) 5.00 (d, J=10.54 Hz, 1H) 5.18 (s, 1H) 5.54-5.79 (m, 3H) 5.98-6.21 (m, 1H) 6.33-6.57 (m, 1H) 6.84-6.96 (m, 3H) 8.02-8.35 (m, 2H) 8.06-8.08 (m, 1H).

Step 3: To a solution of (2S,3S,6S,7R,10R,E)-6-acetoxy-3,7-dimethyl-2-((R,2E,4E)-6-methyl-6-((triethylsilyl)oxy)-7-((2R,3R)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-7-yl piperazine-1-carboxylate in (95 mg, 0.094 mmol) in THF (3 mL) was added TBAF (0.424 mL, 1 M, 0.424 mmol) and stirred at RT for 10 hours. The mixture as concentrated and diluted with EtOAc, washed with water and brine. The organic layer was separated and dried with $Na_2SO_4$, filtered and concentrated in vacuo. HPLC purification afforded (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methyl-hepta-2,4-dien-2-yl)-3,7-dimethyl-12-oxooxacyclododec-4-en-7-yl piperazine-1-carboxylate (16 mg, 26%). LC/MS (ESI, m/z), 665.6 [M+H]$^+$.

$^1$H-NMR (400 MHz, $CHCl_3$-d): δ ppm 0.90 (dd, J=6.84, 2.20 Hz, 6H) 0.94 (t, J=7.40 Hz, 3H) 1.20-1.30 (m, 1H) 1.34 (s, 3H) 1.39-1.54 (m, 3H) 1.55 (s, 3H) 1.59-1.73 (m, 3H) 1.78 (d, J=0.88 Hz, 3H) 1.86 (dd, J=13.99, 5.46 Hz, 1H) 2.05 (s, 3H) 2.39-2.53 (m, 3H) 2.55-2.65 (m, 1H) 2.67 (dd, J=8.03, 2.26 Hz, 1H) 2.89 (s, 1H) 3.22 (br s, 4H) 3.50-3.57 (m, 1H) 3.58-3.90 (m, 5H) 5.08 (d, J=10.67 Hz, 1H) 5.18 (d, J=9.03 Hz, 1H) 5.58-5.78 (m, 2H) 5.88 (d, J=15.31 Hz, 1H) 6.10-6.23 (m, 1H) 6.53 (dd, J=15.25, 10.98 Hz, 1H).

TABLE 11

Compounds 175-185

| Structure, Compound #, and Chemical Name | ¹H NMR data | LCMS data (ES+) |
|---|---|---|
| 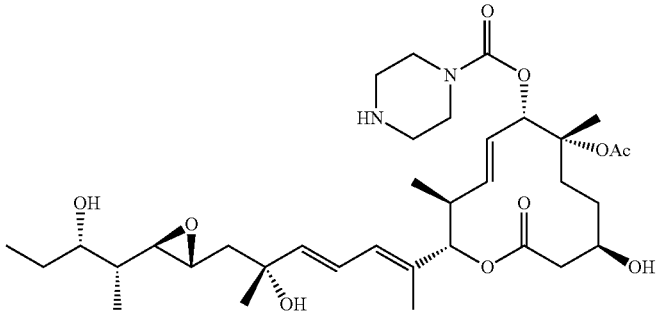<br>186<br>[(2S,3S,4E,6S,7S,10S)-7-acetyloxy-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] piperazine-1-carboxylate | ¹H-NMR (400 MHz, CHCl₃-d): δ ppm 0.87-0.92 (m, 6 H) 0.94 (t, J = 7.40 Hz, 3 H) 1.16-1.31 (m, 1 H) 1.35 (s, 3 H) 1.40-1.56 (m, 4 H) 1.59 (s, 3 H) 1.66 (br dd, J = 14.68, 7.03 Hz, 3 H) 1.76-1.80 (m, 3 H) 1.87 (dd, J = 14.12, 5.46 Hz, 1 H) 2.05 (s, 3 H) 2.30-2.41 (m, 1 H) 2.50 (d, J = 3.76 Hz, 2 H) 2.56-2.72 (m, 2 H) 2.90 (br d, J = 2.01 Hz, 1 H) 3.19 (br t, J = 5.14 Hz, 4 H) 3.50-3.59 (m, 1 H) 3.71 (br s, 4 H) 3.77-3.89 (m, 1 H) 5.01-5.13 (m, 2 H) 5.58-5.71 (m, 1 H) 5.71-5.81 (m, 1 H) 5.88 (d, J = 15.31 Hz, 1 H) 6.15 (br d, J = 10.79 Hz, 1 H) 6.53 (dd, J = 15.18, 10.92 Hz, 1 H) | LC/MS (ESI, m/z), 665.6 [M + H]⁺ |
| 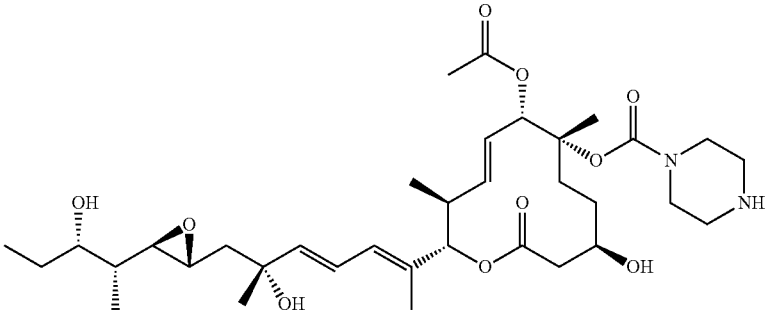<br>187<br>[(2S,3S,4E,6S,7S,10S)-6-acetoxy-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-7-yl] piperazine-1-carboxylate | ¹H-NMR (400 MHz, CHCl₃-d): δ ppm 0.90 (dd, J = 6.84, 2.20 Hz, 6 H) 0.94 (t, J = 7.40 Hz, 3 H) 1.20-1.30 (m, 1 H) 1.34 (s, 3 H) 1.39-1.54 (m, 3 H) 1.55 (s, 3 H) 1.59-1.73 (m, 3 H) 1.78 (d, J = 0.88 Hz, 3 H) 1.86 (dd, J = 13.99, 5.46 Hz, 1 H) 2.05 (s, 3 H) 2.39-2.53 (m, 3 H) 2.55-2.65 (m, 1 H) 2.67 (dd, J = 8.03, 2.26 Hz, 1 H) 2.89 (s, 1 H) 3.22 (br s, 4 H) 3.50-3.57 (m, 1 H) 3.58-3.90 (m, 5 H) 5.08 (d, J = 10.67 Hz, 1 H) 5.18 (d, J = 9.03 Hz, 1 H) 5.58-5.78 (m, 2 H) 5.88 (d, J = 15.31 Hz, 1 H) 6.10-6.23 (m, 1 H) 6.53 (dd, J = 15.25, 10.98 Hz, 1 H) | LC/MS (ESI, m/z), 665.6 [M + H]⁺ |
| 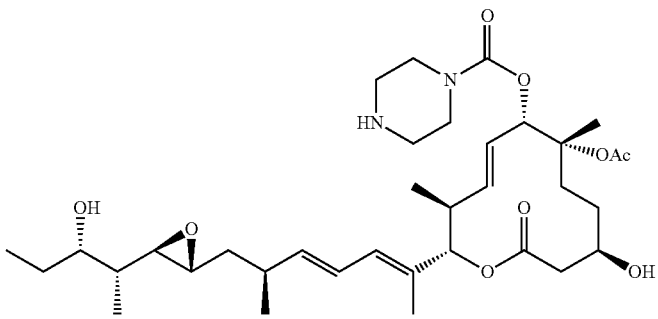<br>188<br>[(2S,3S,4E,6S,7S,10S)-7-acetyloxy-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] piperazine-1-carboxylate | ¹H-NMR (400 MHz, CHCl₃-d): δ ppm 0.87-1.01 (m, 10 H) 1.08 (d, J = 6.78 Hz, 3 H) 1.27-1.63 (m, 12 H) 1.66-1.74 (m, 1 H) 1.76 (s, 3 H) 1.97-2.10 (m, 3 H) 2.35-2.57 (m, 5 H) 2.58-2.65 (m, 1 H) 2.65-2.71 (m, 1 H) 2.77 (td, J = 5.93, 2.32 Hz, 1 H) 2.89-3.05 (m, 4 H) 3.07-3.34 (m, 8 H) 3.50-3.68 (m, 5 H) 3.72-3.88 (m, 1 H) 4.88-5.09 (m, 1 H) 5.18 (d, J = 10.67 Hz, 1 H) 5.50-5.84 (m, 3 H) 6.01-6.13 (m, 1 H) 6.19-6.36 (m, 1 H). | LC/MS (ESI, m/z), 649.7 [M + H]⁺ |

TABLE 11-continued

Compounds 175-185

| Structure, Compound #, and Chemical Name | ¹H NMR data | LCMS data (ES+) |
|---|---|---|
| 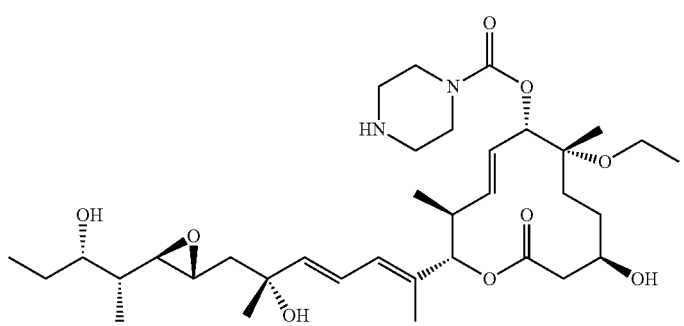<br>189<br>[(2S,3S,4E,6S,7R,10R)-7-ethoxy-10-hydroxy-2-[(2E,4E,6R)-6-hydroxy-7-[(2R,3R)-3-[(2S,3S)-3-hydroxypentan-2-yl]oxiran-2-yl]-6-methylhepta-2,4-dien-2-yl]-3,7-dimethyl-12-oxo-1-oxacyclododec-4-en-6-yl] 4-methylpiperazine-1-carboxylate | ¹H NMR (400 MHz, METHANOL-d4) δ ppm 0.76-0.87 (m, 9H), 1.03-1.09 (m, 3H), 1.10-1.13 (m, 3H), 1.13-1.19 (m, 1H), 1.20-1.27 (m, 3H), 1.29-1.48 (m, 6H), 1.51-1.59 (m, 1H), 1.65-1.71 (m, 3H), 1.73-1.81 (m, 1H), 2.20 (s, 3H), 2.27-2.34 (m, 4H), 2.34-2.44 (m, 2H), 2.44-2.53 (m, 1H), 2.53-2.59 (m, 1H), 2.76-2.83 (m, 1H), 3.23-3.26 (m, 1H), 3.34-3.52 (m, 7H), 3.67-3.75 (m, 1H), 4.86-4.92 (m, 1H), 4.92-4.99 (m, 1H), 5.41-5.51 (m, 1H), 5.60-5.71 (m, 1H), 5.72-5.82 (m, 1H), 6.00-6.07 (m, 1H), 6.37-6.48 (m, 1H). | LC/MS (ESI, m/z): 665.73 [M + H]⁺ |
| 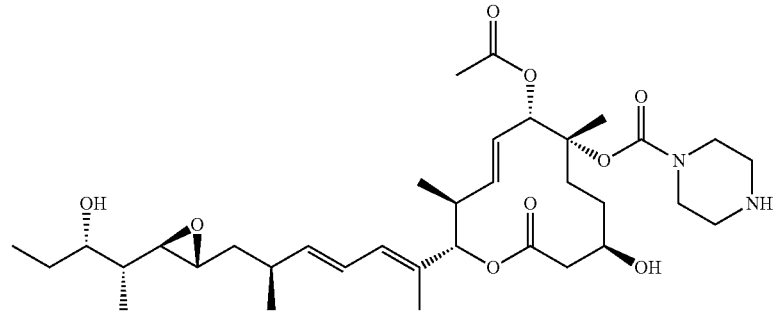<br>190<br>[(2S,3S,4E,6S,7S,10S)-6-acetyloxy-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-7-yl] piperazine-1-carboxylate | ¹H NMR (400 MHz, CHCl₃-d) δ ppm 0.84-1.01 (m, 11 H) 1.08 (d, J = 6.78 Hz, 3 H) 1.29-1.64 (m, 10 H) 1.63-1.73 (m, 1 H) 1.76 (s, 3 H) 1.94-2.12 (m, 4 H) 2.37-2.58 (m, 4 H) 2.59-2.65 (m, 1 H) 2.68 (dd, J = 7.40, 2.26 Hz, 1 H) 2.77 (td, J = 5.93, 2.32 Hz, 1 H) 3.01-3.30 (m, 4 H) 3.49 (s, 1 H) 3.54-3.67 (m, 2 H) 3.69-3.92 (m, 5 H) 4.13-4.78 (m, 11 H) 5.13-5.24 (m, 2 H) 5.48-5.61 (m, 1 H) 5.62-5.74 (m, 2 H) 6.04-6.13 (m, 1 H) 6.18-6.32 (m, 1 H) | LC/MS (ESI, m/z), 649.6 [M + H]⁺ |
| 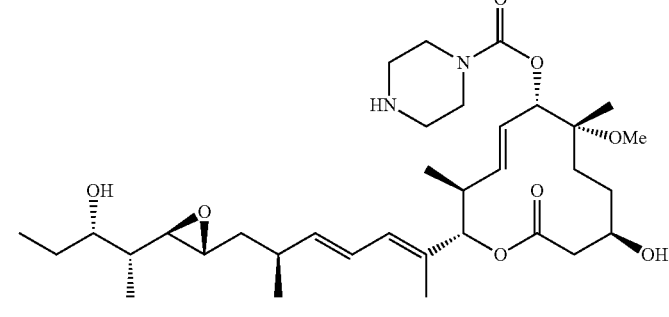<br>191<br>[(2S,3S,4E,6S,7S,10S)-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-7-methoxy-3,7-dimethoxy-12-oxo-1-oxacyclododec-4-en-6-yl] piperazine-1-carboxylate | ¹H-NMR (400 MHz, MeOH-d4): δ ppm 0.88-0.99 (m, 9 H) 1.10 (d, J = 6.78 Hz, 3 H) 1.24 (s, 4 H) 1.42-1.69 (m, 8 H) 1.77 (d, J = 0.88 Hz, 3 H) 2.43-2.63 (m, 4 H) 2.64-2.70 (m, 1 H) 2.71-2.82 (m, 5 H) 3.34 (br s, 3 H) 3.37 (s, 2 H) 3.42-3.57 (m, 5 H) 3.79-3.89 (m, 1 H) 5.06 (s, 2 H) 5.54-5.63 (m, 1 H) 5.64-5.80 (m, 2 H) 6.07-6.16 (m, 1 H) 6.29-6.40 (m, 1 H) | LC/MS (ESI, m/z), 621.6 [M + H]⁺ |

TABLE 11-continued

Compounds 175-185

| Structure, Compound #, and Chemical Name | $^1$H NMR data | LCMS data (ES+) |
|---|---|---|
| 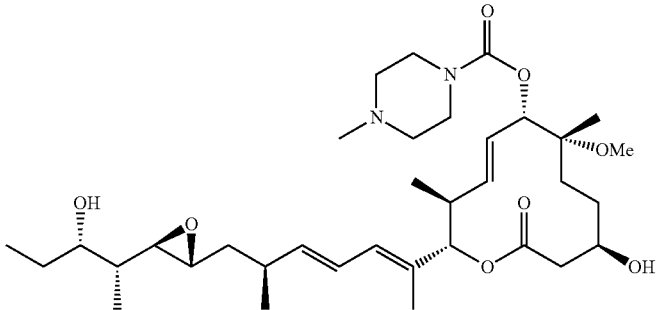<br>192<br>[(2S,3S,4E,6S,7S,10S)-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] 4-methylpiperazine-1-carboxylate | $^1$H-NMR (400 MHz, MeOH-d4): δ ppm 0.88-1.00 (m, 9 H) 1.10 (d, J = 6.65 Hz, 3 H) 1.16-1.27 (m, 4 H) 1.40-1.70 (m, 8 H) 1.77 (d, J = 0.88 Hz, 3 H) 2.28-2.36 (m, 3 H) 2.42 (br t, J = 5.08 Hz, 3 H) 2.47-2.61 (m, 4 H) 2.68 (dd, J = 8.22, 2.20 Hz, 1 H) 2.74 (td, J = 5.99, 2.20 Hz, 1 H) 3.13-3.17 (m, 1 H) 3.34-3.38 (m, 3 H) 3.47-3.58 (m, 5 H) 3.81-3.87 (m, 1 H) 5.01-5.10 (m, 2 H) 5.54-5.81 (m, 3 H) 6.06-6.15 (m, 1 H) 6.34 (dd, J = 15.00, 10.98 Hz, 1 H) | LC/MS (ESI, m/z), 635.8 [M + H] |
| 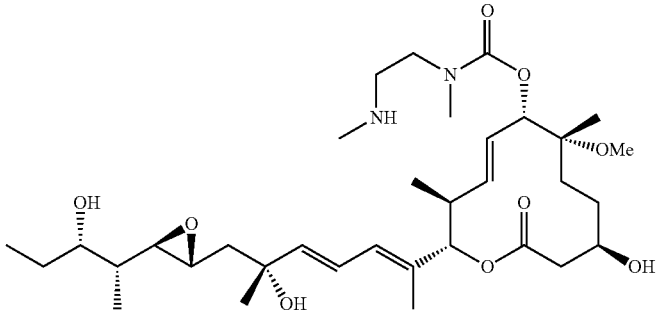<br>193<br>[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] N-methyl-N-[2-(methylamino)ethyl]carbamate | $^1$H-NMR (400 MHz, MeOH-d4): δ ppm 0.92 (br d, J = 6.53 Hz, 9 H), 1.25 (br s, 4 H), 1.36 (s, 3 H), 1.41-1.74 (m, 6 H), 1.45-1.59 (m, 1 H), 1.64-1.72 (m, 1 H), 1.80 (s, 3 H), 1.85-1.94 (m, 1 H), 2.42 (s, 3 H), 2.50-2.63 (m, 3 H), 2.65-2.73 (m, 1 H), 2.73-2.80 (m, 2 H), 2.88-3.01 (m, 4 H), 3.35-3.38 (m, 3 H), 3.35-3.40 (m, 3 H), 3.41-3.48 (m, 2 H), 3.52-3.57 (m, 1 H), 3.78-3.89 (m, 1 H), 5.00-5.13 (m, 2 H), 5.53-5.64 (m, 1 H), 5.71-5.82 (m, 1 H), 5.84-5.94 (m, 1 H), 6.12-6.19 (m, 1 H), 6.49-6.61 (m, 1 H) | LC/MS (ESI, m/z), 639.7 [M + H]$^+$ |
| 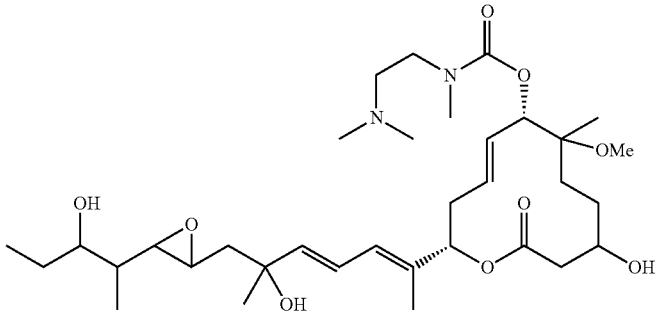<br>194<br>[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl] N-methyl-N-[2-(dimethylamino)ethyl]carbamate | | LC/MS (ESI, m/z), 653.79 [M + H]$^+$ |

TABLE 11-continued

Compounds 175-185

| Structure, Compound #, and Chemical Name | $^1$H NMR data | LCMS data (ES+) |
|---|---|---|
| 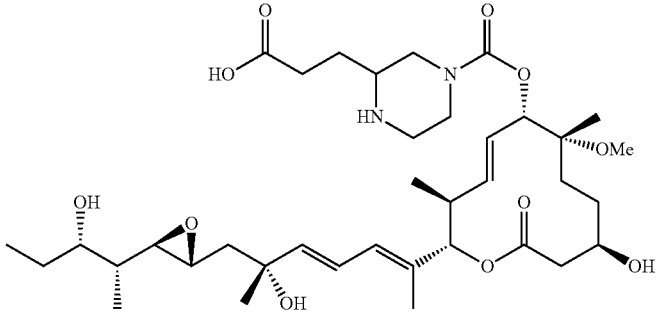<br>195<br>3-[4-[[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl]oxycarbonyl]piperazin-2-yl]propanoic acid | $^1$H-NMR (400 MHz, DMSO-d6): δ ppm 0.71-0.77 (m, 9 H), 1.03 (s, 5 H), 1.14-1.20 (m, 6 H), 1.23-1.33 (m, 5 H), 1.36-1.48 (m, 5 H), 1.63 (s, 3 H), 1.67-1.75 (m, 1 H), 2.13-2.24 (m, 4 H), 2.58-2.64 (m, 1 H), 2.68-2.81 (m, 2 H), 3.20-3.20 (m, 3 H), 3.61-3.77 (m, 4 H), 4.28-4.39 (m, 1 H), 4.44-4.53 (m, 1 H), 4.79-4.88 (m, 2 H), 5.28-5.43 (m, 1 H), 5.52-5.66 (m, 1 H), 5.73-5.85 (m, 1 H), 5.94-6.04 (m, 1 H), 6.27-6.41 (m, 1 H), 6.43-6.53 (m, 2 H), 8.19-8.29 (m, 1 H) | LC/MS (ESI, m/z), 709.5 [M + H]$^+$ |
| 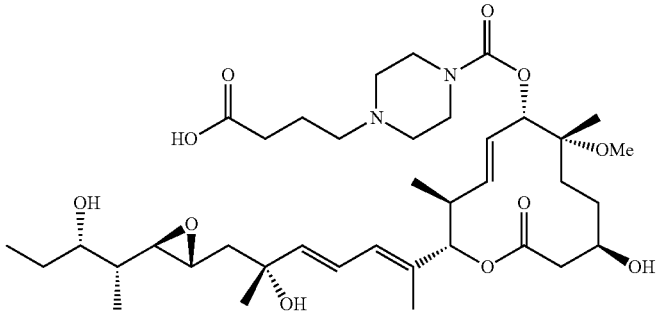<br>196<br>4-[4-[[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl]oxycarbonyl]piperazin-1-yl]butanoic acid | $^1$H NMR (400 MHz, DMSO-d6) δ ppm 0.75 (s, 9H), 1.03 (s, 3H), 1.16 (s, 3H), 1.16-1.17 (m, 1H), 1.23-1.33 (m, 4H), 1.36-1.47 (m, 2H), 1.53-1.60 (m, 2H), 1.63 (s, 3H), 1.67-1.75 (m, 1H), 2.10-2.35 (m, 10H), 2.47-2.53 (m, 2H), 2.65-2.73 (m, 1H), 3.15 (s, 3H), 3.27-3.32 (m, 4H), 3.58-3.68 (m, 1H), 4.25-4.39 (m, 1H), 4.45-4.52 (m, 1H), 4.69-4.78 (m, 1H), 4.80-4.88 (m, 2H), 5.29-5.42 (m, 1H), 5.53-5.66 (m, 1H), 5.72-5.84 (m, 1H), 5.93-6.05 (m, 1H), 6.27-6.41 (m, 1H), 8.38-8.46 (m, 1H) | LC/MS (ESI, m/z), 723.43 [M + H]$^+$ |

Compounds 197-200 were synthesized according to Scheme 60.

Scheme 60.

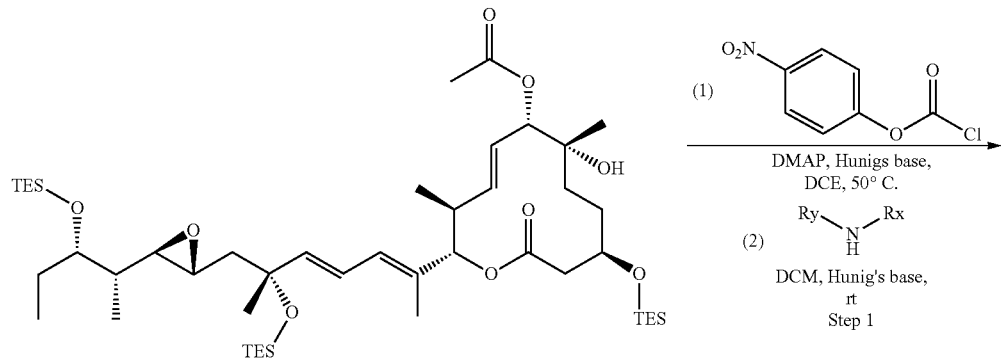

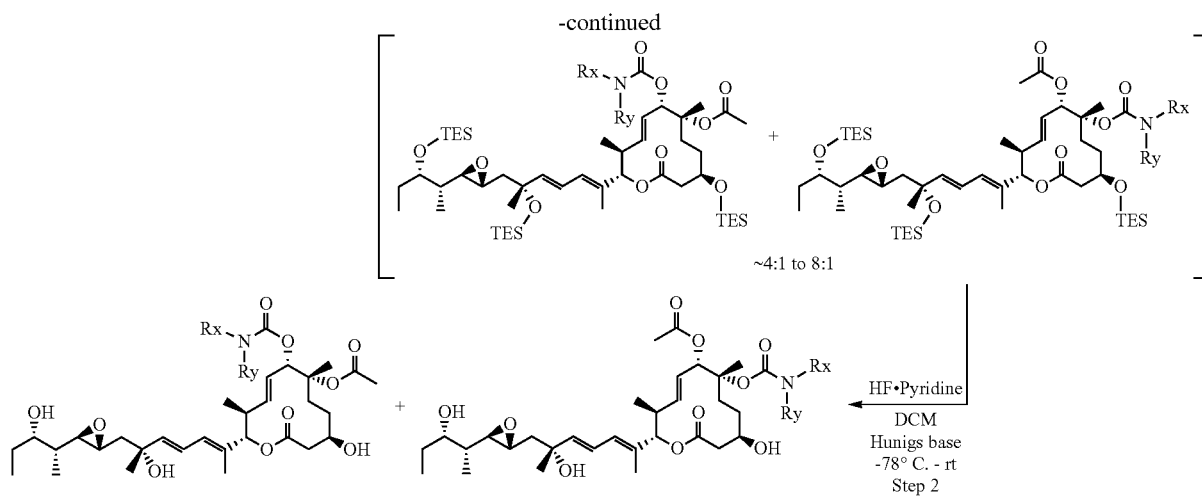

Step 1

To a solution of tri-TES Pladienolide D (1.0 equiv.) in 1,2-dichloroethane (0.2 M) at 20° C. was added DMAP (1.5 equiv.), triethylamine (30 equiv.) and 4-nitrophenyl chloroformate (10 equiv.). The reaction mixture was stirred at 40° C. for 4 days, and then for 2 h at 60° C. The reaction mixture was diluted with EtOAc and washed with water, then the layers were separated. The aqueous layer was extracted with EtOAc (2×). The combined organic extracts were successively washed with water and brine, dried over MgSO$_4$, filtered and concentrated in vacuo. Flash column chromatography (EtOAc in Hexane; silica gel) afford the intermediate carbonate. To a mixture of the intermediate carbonate (1.0 equiv.) in DCM (0.2 M) were added triethylamine (3.0 equiv.) and amine (2.0 equiv.) and the resulting mixture was stirred at RT for 1 hour. The reaction mixture was then concentrated and chromatographed (DCM/MeOH; silica gel) to afford the carbamate intermediate as a mixture of regio-isomers.

Step 2

The regio-isomeric mixture of carbamate intermediate (1.0 equiv.) was dissolved in DCM (0.04 M). Hünig's base (124 equiv.) was added and the reaction mixture was cooled to −78° C. and hydrogen fluoride pyridine (30 equiv.) was added dropwise before warming the mixture to rt and stirring overnight at rt. The reaction mixture was then cooled to −78° C. and saturated sodium bicarbonate was added dropwise. After addition of sodium bicarbonate, the mixture was warmed to rt. The organic layer was isolated and the aqueous layer was extracted with DCM (3×). The combined organic layers were dried over anhydrous sodium sulfate, filtered, and concentrated in vacuo. The resulting residue was purified by reverse-phase HPLC purification to afford the each of desired regio-isomeric products.

TABLE 12

Compounds 197-200

| Structure, Compound #, and Chemical Name | $^1$H NMR data | LCMS data (ES+) |
|---|---|---|
| 197<br>(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl (1S,4S)-2,5-diazabicyclo[2.2.1]heptane-2-carboxylate | $^1$H-NMR (400 MHz, MeOH-d$_4$): δ ppm 0.85-0.98 (m, 9 H) 1.25 (td, J = 7.40, 4.14 Hz, 1 H) 1.34 (s, 3 H) 1.42-1.69 (m, 9 H) 1.79 (s, 4 H) 1.82-1.96 (m, 2 H) 2.04 (d, J = 9.29 Hz, 3 H) 2.33 (br d, J = 10.04 Hz, 1 H) 2.47-2.54 (m, 2 H) 2.57-2.72 (m, 2 H) 2.87-2.92 (m, 1 H) 3.03 (br s, 2 H) 3.33-3.43 (m, 2 H) 3.43-3.57 (m, 2 H) 3.77-3.84 (m, 1 H) 3.86-3.94 (m, 1 H) 4.50 (br s, 1 H) 4.97-5.11 (m, 2 H) 5.60-5.68 (m, 1 H) 5.73-5.82 (m, 1 H) 5.88 (d, J = 15.31 Hz, 1 H) 6.15 (br d, J = 11.04 Hz, 1 H) 6.53 (dd, J = 15.25, 10.98 Hz, 1 H) 8.54 (s, 1 H) | LC/MS (ESI, m/z), 677.6 [M + H]$^+$ |

TABLE 12-continued

Compounds 197-200

| Structure, Compound #, and Chemical Name | $^1$H NMR data | LCMS data (ES+) |
|---|---|---|
| 198<br>(2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl 2,5-diazabicyclo[2.2.1]heptane-2-carboxylate | $^1$H-NMR (400 MHz, CHCl$_3$-d): δ ppm | LC/MS (ESI, m/z), 677 [M + H]$^+$ |
| 199<br>(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-propylpiperazine-1-carboxylate | $^1$H-NMR (400 MHz, MeOH-d$_4$): δ ppm 0.88-0.98 (m, 9 H) 1.26 (td, J = 7.40, 4.27 Hz, 1 H) 1.32-1.39 (m, 3 H) 1.44-1.70 (m, 9 H) 1.80 (s, 3 H) 1.83-1.92 (m, 1 H) 2.05 (s, 3 H) 2.32-2.46 (m, 1 H) 2.47-2.70 (m, 11 H) 2.91 (td, J = 5.77, 2.26 Hz, 1 H) 3.43-3.61 (m, 5 H) 3.69 (t, J = 5.83 Hz, 2 H) 3.81 (br dd, J = 9.79, 3.39 Hz, 1 H) 5.00-5.11 (m, 2 H) 5.64 (dd, J = 15.18, 9.66 Hz, 1 H) 5.73-5.81 (m, 1 H) 5.86-5.94 (m, 1 H) 6.15 (br d, J = 10.29 Hz, 1 H) 6.54 (dd, J = 15.25, 10.98 Hz, 1 H) | LC/MS (ESI, m/z), 709.7 [M + H]$^+$ |
| 200<br>(2R,3S,6S,7R,10R,E)-6-acetoxy-10-hydroxy-2-((2S,6R,E)-6-hydroxy-7-((2R,3R)-3-((2R,3S)-3-hydroxypentan-2-yl)oxiran-2-yl)-6-methylhept-4-en-2-yl)-3,7-dimethyl-12-oxooxacyclododec-4-en-7-yl (4-(2-hydroxyethyl)piperazine-1-carboxylate | $^1$H-NMR (400 MHz, CHCl$_3$-d): δ ppm | LC/MS (ESI, m/z), 709.8 [M + H]$^+$ |

Example 201

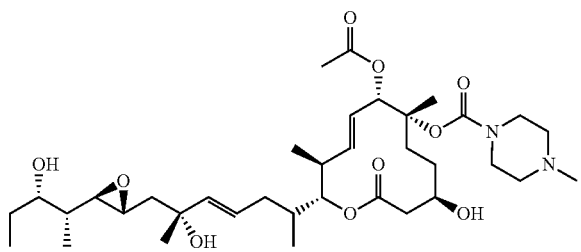 [SMILES: CC[C@H](O)[C@@H](C)[C@H]1O[C@@H]1C[C@@](C)(O)/C=C/CC(C)[C@H]1OC(=O)C[C@H](O)CC[C@@](C)(OC(=O)N2CCN(C)CC2)[C@@H](OC(C)=O)/C=C/[C@@H]1C]

To a mixture of (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl piperazine-1-carboxylate (230 mg, 0.346 mmol; Example 187) in DCM (8 mL) was added sodium triacetoxyborohydride (4 equiv.) and then formaldehyde (104 mg, 3.459 mmol) as an aqueous solution. The mixture was stirred for 20 minutes at rt. After stirring, the mixture was diluted with methanol and then concentrated in vacuo onto silica and purified by silica gel chromatography (0-15% MeOH/DCM) and concentrated in vacuo to afford (2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl 4-methylpiperazine-1-carboxylate (160 mg, 0.236 mmol, 68.1% yield) as a colorless oil.

LCMS (ESI, m/z), [M+H]$^+$ 679.2.

Example 202

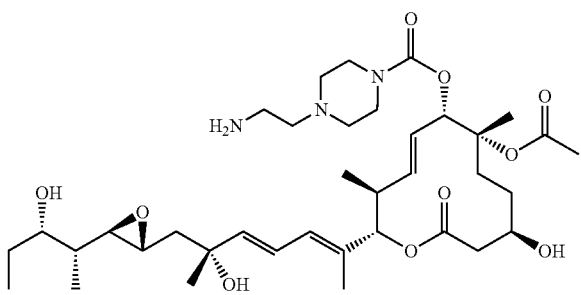 [SMILES: CC[C@H](O)[C@@H](C)[C@H]1O[C@@H]1C[C@@](C)(O)/C=C/C=C(\C)[C@H]1OC(=O)C[C@H](O)CC[C@@](C)(OC(C)=O)[C@@H](OC(=O)N2CCN(CCN)CC2)/C=C/[C@@H]1C]

To a mixture of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (55 mg, 0.083 mmol; Example 186) in DCM (3 mL) was added (9H-fluoren-9-yl)methyl (2-oxoethyl)carbamate (46.5 mg, 0.165 mmol) and sodium triacetoxyborohydride (52.6 mg, 0.248 mmol). The mixture was stirred at rt for 20 minutes and then concentrated in vacuo. The resulting residue was purified by silica gel column chromatography (0-10% MeOH/DCM) and concentrated in vacuo. The isolated material was diluted with DMF (3 mL) and to that mixture was added diethylamine (121 mg, 1.655 mmol). The mixture was stirred until it the starting material was consumed at rt before concentrating in vacuo. The resulting residue was purified via reverse phase HPLC to afford (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl-4-(2-aminoethyl) piperazine-1-carboxylate (6 mg, 8.48 μmol, 10.25% yield) as a white solid. $^1$H NMR (400 MHz, DMSO-d6): δ ppm 0.74-0.86 (m, 9H) 1.04-1.15 (m, 1H) 1.23 (s, 3H) 1.26-1.40 (m, 3H) 1.45 (s, 4H) 1.47-1.51 (m, 1H), 1.52-1.63 (m, 1H) 1.69 (s, 3H) 1.73-1.82 (m, 1H) 1.99 (s, 3H) 2.13-2.42 (m, 9H) 2.53-2.65 (m, 4H) 2.72-2.80 (m, 1H), 3.35-3.41 (m, 3H) 3.65-3.76 (m, 1H) 4.36-4.46 (m, 1H) 4.57-4.66 (m, 1H) 4.79-4.85 (m, 1H) 4.87-4.95 (m, 2H) 5.43-5.56 (m, 1H) 5.64-5.77 (m, 1H) 5.80-5.91 (m, 1H) 6.01-6.12 (m, 1H) 6.33-6.49 (m, 1H). LCMS (ESI, m/z), 708.2 [M+H]$^+$

Example 203

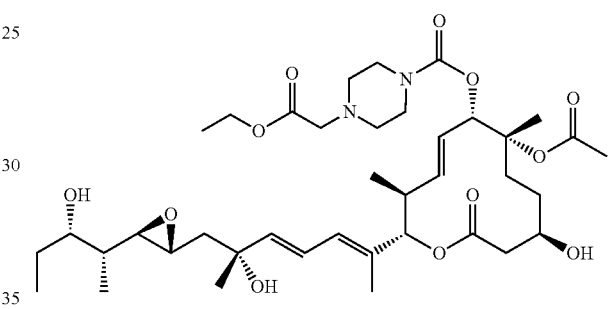

To a solution of (2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (25 mg, 0.038 mmol; Example 186) in acetone (2 mL) was added ethyl 2-bromoacetate (7.54 mg, 0.045 mmol) and potassium carbonate (3 equiv.). The resulting mixture was stirred for 25 minutes before adding additional bromo acetate (2 equiv.) and stirring at rt for 1 hour. Subsequently, the mixture was diluted with ethyl acetate and washed with brine. The organic layer was isolated, dried over sodium sulfate, filtered, and concentrated in vacuo. The resulting residue was purified by flash column chromatography (0-15% MeOH/DCM) to provide (2S,3S,6S,7R,10R,E)-7-acetoxy-10-hydroxy-2-((R,2E,4E)-6-hydroxy-7-((2R,3R)-3-((2R,3 S)-3-hydroxypentan-2-yl)oxiran-2-yl)-6-methylhepta-2,4-dien-2-yl)-3,7-dimethyl-12-oxooxacyclododec-4-en-6-yl 4-(2-ethoxy-2-oxoethyl) piperazine-1-carboxylate (12 mg, 0.016 mmol, 42.5% yield) as a colorless oil. LCMS (ESI, m/z), [M+H]$^+$751.3

Examples 204 and 205

Examples 204 and 205 were prepared via the sequence outlined in Scheme 61.

Scheme 61.
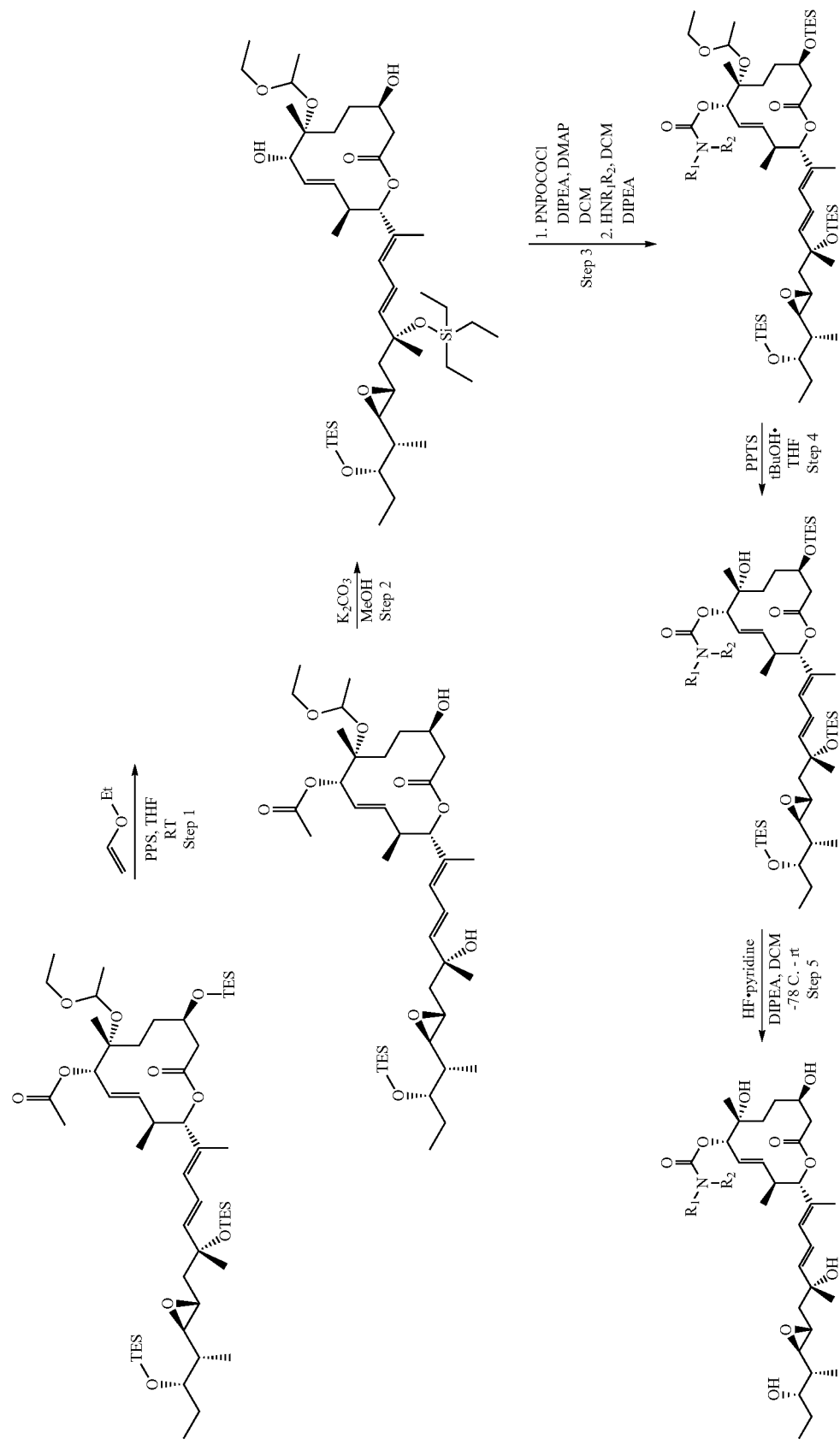

Step 1:

A mixture of (2S,3S,6S,7R,10R,E)-7-hydroxy-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy) oxacyclododec-4-en-6-yl acetate (0.626 g, 0.699 mmol), THF (4.58 mL, 55.925 mmol), ethyl vinyl ether (2.69 ml, 27.963 mmol), PPTS (0.044 g, 0.175 mmol) was stirred overnight. Triethylamine (0.8 eq) was added to the reaction mixture and stirred for several minutes before extracting with saturated aqueous sodium bicarbonate. The aqueous layer was isolated and extracted with EtOAc. The combined organic layers were dried over anhydrous sodium sulfate, filtered, and contrated in vacuo to afford (2S,3S,6S,7R,10R,E)-7-(1-ethoxyethoxy)-3,7-dimethyl-2-4R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl acetate as a mixture of diastereomers (636 mg, 0.657 mmol, 94% yield).

$^1$H NMR (400 MHz, CDCl$_3$) δ ppm 0.60 (q, J=7.65 Hz, 19H) 0.78-0.92 (m, 10H) 0.96 (t, J=7.91 Hz, 28H) 1.16-1.30 (m, 8H) 1.32-1.35 (m, 1H) 1.38 (br s, 5H) 1.43-1.62 (m, 7H) 1.71 (d, J=6.65 Hz, 4H) 2.02-2.08 (m, 3H) 2.33-2.53 (m, 3H) 2.53-2.59 (m, 1H) 2.79-2.87 (m, 1H) 3.42-3.67 (m, 2H) 3.68-3.76 (m, 1H) 3.78-3.86 (m, 1H) 4.94-5.13 (m, 2H) 5.14-5.20 (m, 1H) 5.57-5.78 (m, 3H) 6.03-6.13 (m, 1H) 6.35-6.47 (m, 1H).

Step 2:

A mixture of (2S,3S,6S,7R,10R,E)-7-(1-ethoxyethoxy)-3,7-dimethyl-2-4R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy) oxacyclododec-4-en-6-yl acetate (1.4 g, 1.447 mmol), potassium carbonate (0.300 g, 2.17 mmol), and methanol (14.47 mL, 1.447 mmol) was stirred for 1 hr. EtOAc and saturated aqueous ammonium chloride were added to the mixture and the organic layer was isolated. The aqueous layer was then extracted three times with EtOAc, and the organic layers were combined, dried over anhydrous sodium sulfate, filtered, and concentrated to dryness to afford (4R,7R,8S,11S,12S,E)-7-(1-ethoxyethoxy)-8-hydroxy-7,11-dimethyl-12-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-4-((triethylsilyl)oxy)oxacyclododec-9-en-2-one (1 g, 1.080 mmol, 74.7% yield).

Step 3:

(4R,7R,8S,11S,12S,E)-7-(1-ethoxyethoxy)-8-hydroxy-7,11-dimethyl-12-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-4-((triethylsilyl)oxy)oxacyclododec-9-en-2-one (1 g, 1.08 mmol), DCM (0.1 M), Hünig's Base (5.0 equiv.), DMAP (1.0 equiv.), and 4-nitrophenyl chloroformate (1.8 equiv.) were combined and stirred overnight. Aqueous sodium hydroxide (1N) was added to the resulting mixture and the organic layer was isolated. The aqueous layer was then extracted three times with DCM. The organic layers were combined, dried over anhydrous sodium sulfate, filtered, and concentrated in vacuo. The resulting residue was diluted with DCM (0.1 M), and to that mixture was added Hünig's Base (5.0 equiv.) and amine (3.0 equiv.), followed by stirring for 2 hours. The resulting mixture was then purified by silica gel chromatography (1-10% MeOH in DCM) to afford carbamate intermediate.

Carbamate Intermediate #1:

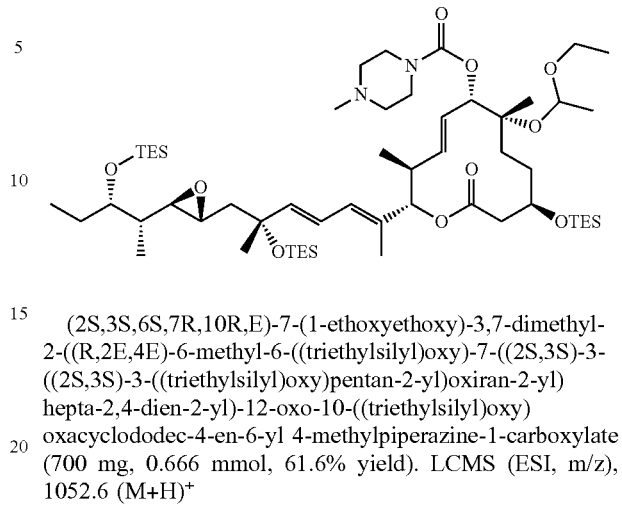

(2S,3S,6S,7R,10R,E)-7-(1-ethoxyethoxy)-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl) hepta-2,4-dien-2-yl)-12-oxo-10-((triethylsilyl)oxy) oxacyclododec-4-en-6-yl 4-methylpiperazine-1-carboxylate (700 mg, 0.666 mmol, 61.6% yield). LCMS (ESI, m/z), 1052.6 (M+H)$^+$ $^1$H NMR (400 MHz, MeOH-d4) δ ppm 0.60-0.70 (m, 18H) 0.82-1.03 (m, 38H) 1.12-1.26 (m, 5H) 1.26-1.36 (m, 6H) 1.43 (s, 3H) 1.45-1.64 (m, 7H) 1.77 (s, 4H) 1.88-1.99 (m, 1H) 2.30 (s, 3H) 2.36-2.46 (m, 5H) 2.46-2.65 (m, 3H) 2.82-2.93 (m, 1H) 3.55 (s, 6H) 3.71-3.81 (m, 1H) 3.84-3.98 (m, 1H) 4.88-5.00 (m, 2H) 5.09-5.18 (m, 1H) 5.52-5.63 (m, 1H) 5.72-5.88 (m, 2H) 6.09-6.19 (m, 1H) 6.45-6.57 (m, 1H).

Carbamate Intermediate #2

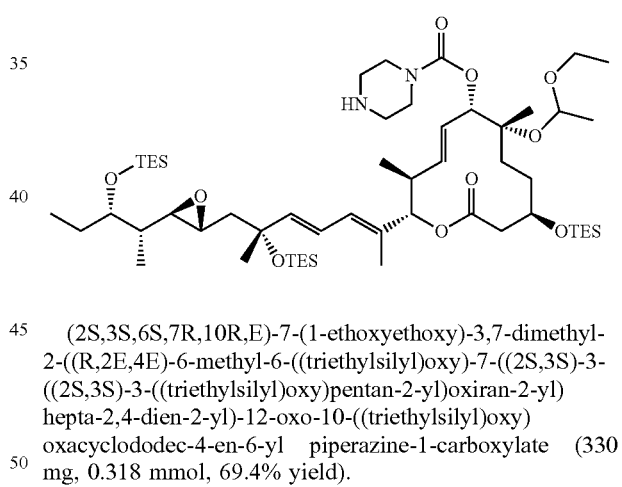

(2S,3S,6S,7R,10R,E)-7-(1-ethoxyethoxy)-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl) hepta-2,4-dien-2-yl)-12-oxo-10-((triethylsilyl)oxy) oxacyclododec-4-en-6-yl piperazine-1-carboxylate (330 mg, 0.318 mmol, 69.4% yield).

Step 4:

Tert-butanol (0.16 M), THF (0.08 M), and PPTS (3.0 equiv.) were combined and stirred at RT. (2S,3S,6S,7R,10R,E)-7-(1-ethoxyethoxy)-3,7-dimethyl-2-((R,2E,4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl 4-methylpiperazine-1-carboxylate (1.0 equiv.) was added to the mixture and it was stirred overnight. Subsequently, saturated brine was added and the mixture was stirred for 30 minutes. The organic layer was isolated and the aqueous layer was extracted three times with DCM. The organic layers were combined, dried over anhydrous sodium sulfate, filtered, concentrated in vacuo, and the resulting residue was purified by silica gel chromatography (0-100% EtOAc in Hexane) to afford tri-TES protected intermediate.

437

Tri-TES Protected Intermediate #1:

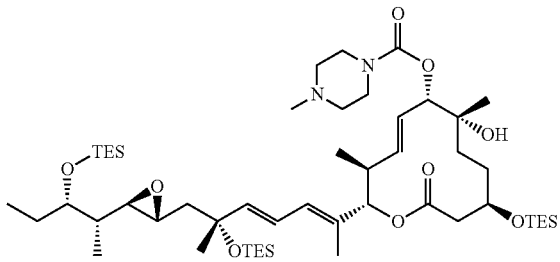

(2S,3S,6S,7R,10R,E)-7-hydroxy-3,7-dimethyl-2-((R,2E, 4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl 4-methylpiperazine-1-carboxylate (172 mg, 0.176 mmol, 41.1% yield) LCMS (ESI, m/z), 980.144 (M+H)$^+$ Tri-TES Protected Intermediate #2:

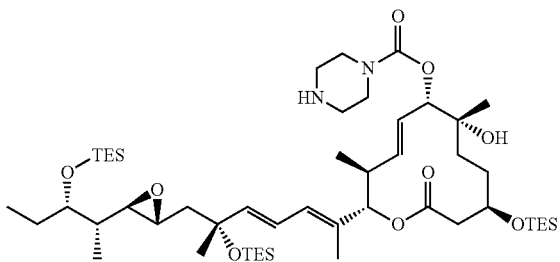

(2S,3S,6S,7R,10R,E)-7-hydroxy-3,7-dimethyl-2-((R,2E, 4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl piperazine-1-carboxylate (0.49 g, 96%) LCMS (ESI, m/z), 966.1 (M+H)$^+$.

Step 5:

(2S,3S,6S,7R,10R,E)-7-hydroxy-3,7-dimethyl-2-((R,2E, 4E)-6-methyl-6-((triethylsilyl)oxy)-7-((2S,3S)-3-((2S,3S)-3-((triethylsilyl)oxy)pentan-2-yl)oxiran-2-yl)hepta-2,4-dien-2-yl)-12-oxo-10-((triethylsilyl)oxy)oxacyclododec-4-en-6-yl 4-methylpiperazine-1-carboxylate (100 mg, 0.102 mmol), DCM (371 equiv.), and DIPEA (191 equiv.) were combined and cooled to −78° C. Hydrogen fluoride-pyridine (30 equiv) was added and the mixture was warmed to RT and stirred overnight. The mixture was then cooled in an icebath, and then saturated aqueous sodium bicarbonate was added. The resulting mixture was extracted with DCM and the organic layers were combined, dried over anhydrous sodium sulfate, filtered, concentrated in vacuo, and chromatographed on silica gel (MeOH/DCM) to afford the desired compound.

438

Example 204

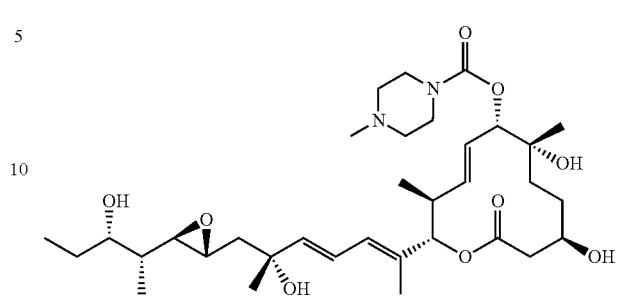

(2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-methylpiperazine-1-carboxylate (31.6 mg, 0.050 mmol, 48.6% yield)

MS (ESI, m/z), 637.6 (M+H)$^+$ $^1$H NMR (400 MHz, MeOH-d4) δ ppm 0.86-0.98 (m, 9H) 1.20-1.23 (m, 3H) 1.23-1.32 (m, 2H), 1.34 (s, 3H) 1.35-1.70 (m, 7H) 1.78 (d, J=0.75 Hz, 3H) 1.83-1.93 (m, 1H) 2.30 (s, 3H) 2.41 (br t, J=4.77, Hz, 4H) 2.52 (dd, J=3.39, 1.63 Hz, 3H) 2.65-2.72 (m, 1H) 2.86-2.95 (m, 1H) 3.38-3.73 (m, 5H) 3.76-3.88 (m, 1H) 4.95 (s, 1H) 5.03-5.13 (m, 1H) 5.51-5.63 (m, 1H) 5.66-5.78 (m, 1H) 5.82-5.93 (m, 1H), 6.08-6.20 (m, 1H) 6.48-6.61 (m, 1H).

Example 205

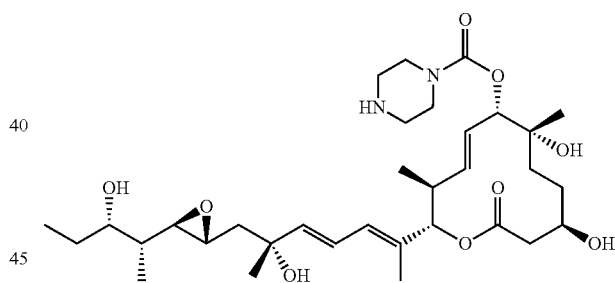

(2S,3S,6S,7R,10R,E)-7,10-dihydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate (50 mg, 78% yield)

MS (ESI, m/z), 623.7 (M+H)$^+$ $^1$H NMR (400 MHz, MeOH-d4) δ ppm 0.88-0.99 (m, 9H) 0.98-1.05 (m, 2H) 1.25 (s, 4H) 1.21-1.27 (m, 1H) 1.34-1.37 (m, 4H) 1.48-1.73 (m, 5H) 1.76-1.83 (m, 3H) 1.85-1.93 (m, 1H) 2.46-2.74 (m, 4H) 2.88-2.95 (m, 1H) 3.21 (s, 4H) 3.51-3.60 (m, 1H) 3.78 (s, 5H) 4.94-5.01 (m, 1H) 5.05-5.11 (m, 1H) 5.56-5.66 (m, 1H) 5.70-5.79 (m, 1H) 5.86-5.93 (m, 1H) 6.08-6.24 (m, 1H) 6.45-6.63 (m, 1H)

Biological Assays

Cell Viability Assay Protocol

Cells (WiDr and Panc05.04 obtained from ATCC) were seeded in 96-well plates, with 2000 cells/100 µL/well, and incubated overnight. Spent media was removed, and fresh media containing 9 different concentrations of compound (100 µL/well) were added, with DMSO concentration from compound stock solution adjusted to be 0.1%. Each compound treatment was done in duplicate or triplicate at each concentration.

Another plate with cells seeded was dedicated as a time zero (Tz) plate, to which was added 0.1% DMSO in media (100 µL/well) followed by CellTiter-Glo® reagent (Promega Corporation, Madison, Wisconsin) (50 µL/well) for ATP measurement as a surrogate of cell viability. Average value from measurement of multiple wells of this plate is used as Tz. Compound-treated plates were incubated for 72 hr at 37° C. Then, CellTiter-Glo® reagent (50 µL/well) was added and ATP was measured. Average value from measurement of the duplicate or triplicate compound-treated wells is used as Ti, and seeded plates with medium having 0.1% DMSO without compound is used as control growth (C).

Percentage growth inhibition/Percentage viability was calculated as:

[(Ti−Tz)/(C−Tz)]×100 for concentrations for which Ti>/=Tz

[(Ti−Tz)/Tz]×100 for concentrations for which Ti<Tz.
*time zero (Tz), control growth (C), and test growth in the presence of compound (Ti) Percentage growth inhibition/Percentage viability are plotted versus compound concentration to determine $E_{max}$.

Growth inhibition of 50% ($GI_{50}$) was calculated from [(Ti−Tz)/(C−Tz)]×100=50, which is the drug concentration resulting in a 50% reduction in the net increase of ATP in control growth (C) during the compound treatment.

In Vitro Splicing (biochemical) Assay Protocol

Biotin-labeled pre-mRNA of an adenovirus type 2 construct with a deletion of intervening sequence (Ad2) (Berg, M. G., et al. 2012 Mol. Cell Bio., 32(7):1271-83) was prepared by in vitro transcription. The Ad2 construct containing Exon 1 (41 nucleotides), Intron (231 nucleotides), and Exon 2 (72 nucleotides) was generated by gene synthesis and cloned into the EcoRI and XbaI sites of pGEM®-3Z vector (Promega) by Genewiz® (South Plainfield, New Jersey). The plasmid was then linearized by XbaI digestion and purified. In vitro transcription and purification of transcribed pre-mRNA were performed using the MEGAscript® T7 transcription kit (Invitrogen™, Life Technologies™, Grand Island, New York) and MEGAclear™ transcription clean-up kit (Invitrogen™, Life Technologies™, Grand Island, New York), respectively, following the manufacturer's instructions. The ratio of biotin-16-UTP (Roche Diagnostics Corporation, Indianapolis, Indiana) to cold UTP was 1:13 to incorporate approximately two biotin molecules per spliced Ad2 mRNA.

In vitro splicing assay was performed at 30° C. in 25 µL reaction mixtures containing 95 µg HeLa nuclear extract (Promega Corporation, Madison, Wisconsin), 47 nM Ad2 pre-mRNA, 25U RNasin RNase inhibitor (Promega Corporation, Madison, Wisconsin), 1× SP buffer (0.5 mM ATP, 20 mM creatine phosphate, 1.6 mM $MgCl_2$), and compounds in DMSO (with 1% final concentration of DMSO). After 90 min of incubation, the reaction was stopped by addition of 18 µL of 5M NaCl, and the mixtures were incubated with 10 µL of M-280 streptavidin-coated magnetic beads (Invitrogen™, Life Technologies, Grand Island, New York) for 30 min at room temperature to capture Ad2 pre- and spliced mRNA. The beads were washed twice with 100 uL buffer containing 10 mM Tris pH=7.5, 1 mM EDTA and 2M NaCl, and then incubated in RNA gel loading buffer containing 95% formamide at 70° C. for 10 min to elute the RNAs. Ad2 RNAs were resolved by 6% TBE-UREA gel, transferred to a nylon membrane, UV cross-linked, and probed with an IRDye® labeled streptavidin (LI-COR, Lincoln, Nebraska). The amount of spliced RNA was quantified by measuring the band fluorescent intensity using LI-COR Image Studio software.

Results

Data are reported in Table 13 below. $E_{max}$ refers to the maximum achievable response to a compound in a tested dose range, with a negative value indicating cellular lethality. A larger negative $E_{max}$ value indicates greater cellular lethality for a particular compound. For example, in Panc 05.04 cells, a mutant SF3B1 cell line, the larger negative $E_{max}$ value indicates that Compound 1 had greater cellular lethality than Compound 7.

WiDr-R cells are colon cancer cells which have a chemically-induced R1074H mutation and have been shown to be resistant to pladienolide B in terms of growth inhibition (Yokoi, A., et al., 2011 FEBS Journal, 278:4870-4880). The counter-screening of compounds in this viability assay with a "resistant" WiDr-R cell line may indicate whether these compounds have off-target effect(s). Compounds that lack growth inhibitory ($GI_{50}$) activity in the resistant WiDr-R cell line but maintain activity in the parental WiDr cell line suggests that on-mechanism splicing modulation is responsible for the growth inhibition which is observed in the parental WiDr cell line.

Scintillation Proximity Assay (SPA) with [$^3$H]-labelled Pladienolide Probe

Batch immobilization of anti-SF3B1 antibody (MBL) to anti-mouse PVT SPA scintillation beads (PerkinElmer) was prepared as follows: for every 2.5 mg of nuclear extracts, 5 µg anti-SF3B1 antibody and 1.5 mg of beads were mixed in 150 µl PBS. The antibody-bead mixture was incubated for 30 min at RT and centrifuged at 18,000 g for 5 min. 150 µl PBS was used to resuspend every 1.5 mg antibody-bead mixture. The beads were suspended and added to the prepared nuclear extracts. The slurry was incubated for 2 h at 4° C. with gentle mixing. The beads were then collected by centrifuging at 18,000 g for 5 min, and washed twice with PBS+0.1% Triton X-100. After a final centrifugation step, every 1.5 mg of beads was suspended with 150 µl of PBS. The SF3b complexes were tested for [$^3$H]-labelled pladienolide probe binding ([$^3$H]-PB), synthesized as previously described (Kotake et al., 2007). 100 µL binding reactions were prepared with 50 µl bead slurry and by adding varying concentrations of PB or PB—OH, and after 30 min pre-incubation, 2.5 nM [$^3$H]—PB was added. The mixture was incubated for 30 min, and luminescence signals were read using a MicroBeta2 Plate Counter (PerkinElmer). Prism 6 (Graphpad) was used for non-linear regression curve fitting of the data.

Key for Table 13:
WiDr cells=Colon cancer cells; wildtype SF3B1
WiDr-R cells=Colon cancer cells; chemically-induced SF3B1 mutant which is resistant to E7107 (R1074H mutation) Panc 05.04 cells=Pancreatic cancer cells; Q699H and K700E mutations in SF3B1
SPA=Scintillation proximity assay

TABLE 13

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
| --- | --- | --- | --- | --- | --- |
| 1 | −87.275 | 27.349 | 26.401 | >1000 | 4.355 |
| 2 | −92.825 | 326.677 | 554.751 | >10000 | 53.368 |
| 3 | 40.550 | 4589.385 | 1941.512 | >10000 | 472.770 |

TABLE 13-continued
Biological Activity of Example Compounds
| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 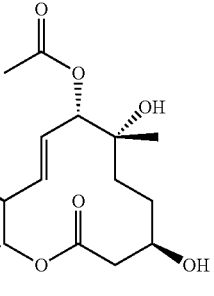 4 | −91.760 | 42.549 | 39.130 | >1000 | 6.215 |
| 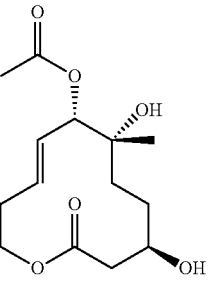 5 | −94.128 | 20.087 | 4.826 | >1000 | 2.746 |
| 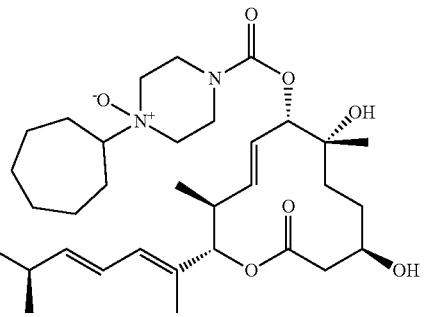 6 | −94.410 | 250.128 | 172.085 | >10000 | |
| 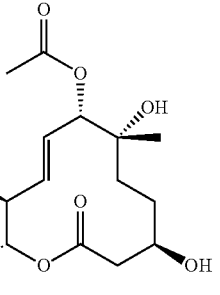 7 | −91.152 | 74.414 | 46.727 | >10000 | 17.965 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 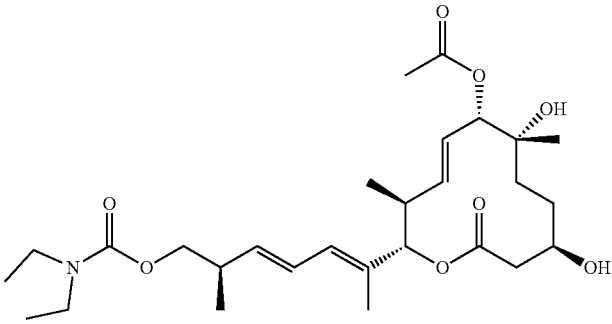 8 | −92.151 | 25.017 | 21.224 | >10000 | 2.397 |
| 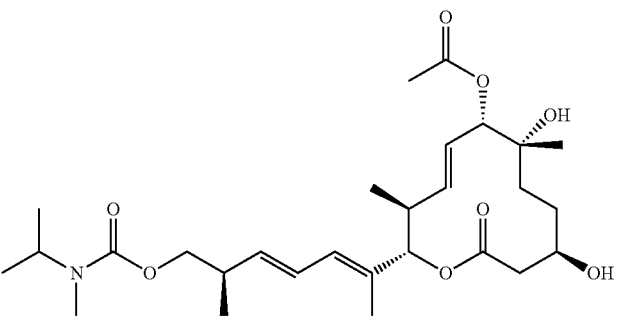 9 | −87.370 | 54.563 | 32.637 | >10000 | 4.853 |
| 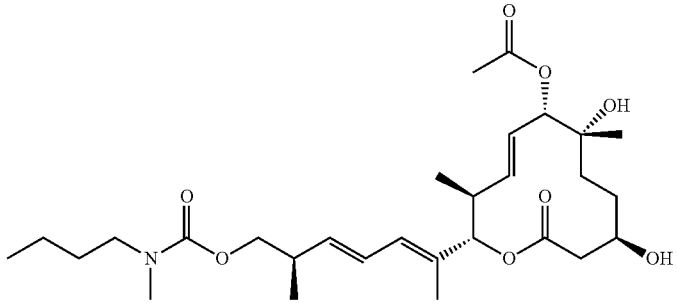 10 | | 198.03 | 86.457 | >10000 | |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| Compound 11 | | 587.41 | 307.763 | >10000 | |
| Compound 12 | 40.097 | 2090.471 | 8131.147 | >10000 | |
| Compound 13 | −90.898 | 76.514 | 71.613 | >1000 | 60.673 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 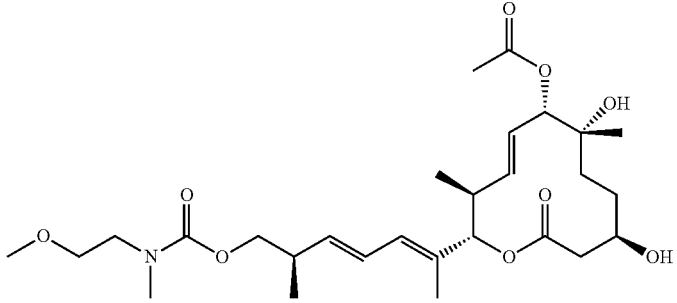 14 | −96.801 | 64.282 | 246.764 | >1000 | |
| 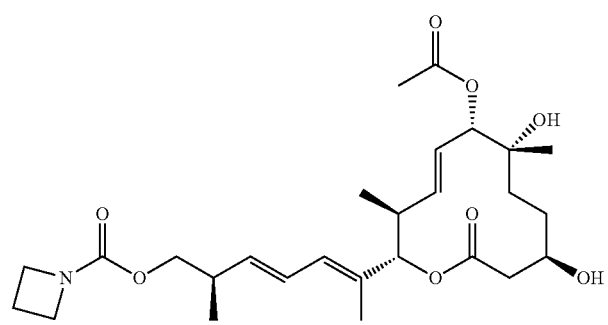 15 | −91.832 | 44.669 | 137.681 | >10000 | 10.740 |
| 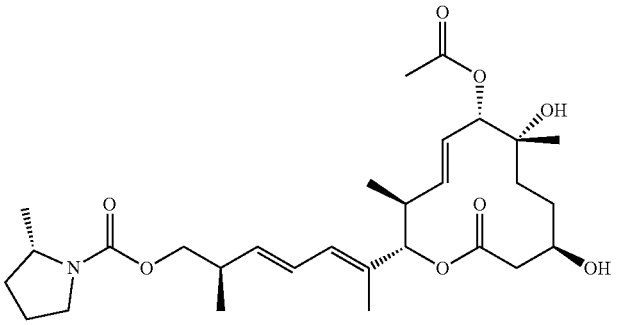 16 | −89.983 | 52.598 | 38.111 | >10000 | 27.299 |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 17 | −79.344 | 2.110 | 0.983 | >1000 | 2.721 |
| 18 | −74.649 | 82.242 | 49.693 | >10000 | 15.049 |
| 19 | −83.432 | 35.134 | 24.651 | >10000 | 80.359 |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| Compound 20 | −89.552 | 45.075 | 51.472 | >10000 | 96.546 |
| Compound 21 | | 15.45 | 91.252 | >10000 | |
| Compound 22 | −88.833 | 203.085 | 105.995 | >1000 | 235.639 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 23 | | 67.97 | 62.92 | >1000 | |
| 24 | −90.269 | 3.051 | 3.832 | >1000 | 2.103 |
| 25 | −94.750 | 88.064 | 89.925 | >1000 | |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 26 | −77.223 | 20.340 | 29.407 | >1000 | 14.018 |
| 27 | −56.00 | 35.40 | 33.788 | >1000 | |
| 28 | −92.84 | 30.49 | 36.628 | >1000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 29 | −85.416 | 10.054 | 14.697 | >1000 | |
| 30 | −93.737 | 7.817 | 9.605 | >1000 | 3.729 |
| 31 | −68.065 | 1.123 | 1.035 | >1000 | 2.772 |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 32 | −97.033 | 16.654 | 19.777 | >1000 | |
| 33 | −90.19 | 4.86 | 2.844 | >1000 | |
| 34 | −82.07 | 2.25 | 1.697 | >1000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 35 | 90.700 | 31.462 | 47.213 | >1000 | 9.557 |
| 36 | 1.960 | 545.544 | 204.979 | >10000 | 234.867 |
| 37 | −16.082 | 537.655 | 230.686 | >10000 | 45.128 |
| 38 | −28.235 | 408.252 | 343.407 | >10000 | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 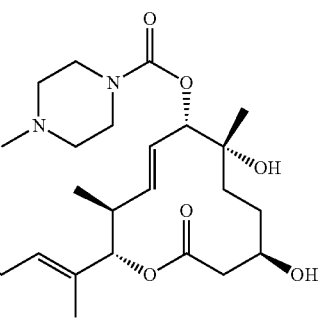 39 | 6.969 | 1288.909 | 252.246 | >1000 | |
| 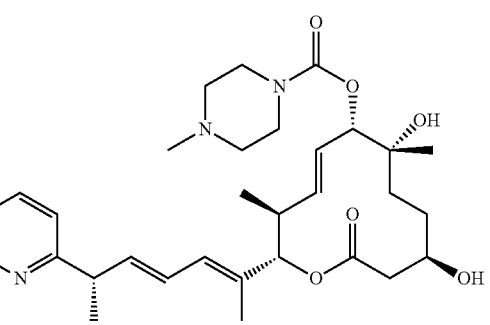 40 | −49.209 | 53.638 | 34.307 | >1000 | 5.693 |
| 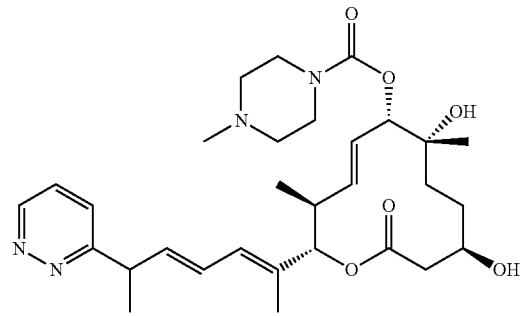 41 | −90.908 | 59.215 | 18.672 | >1000 | 9.201 |
| 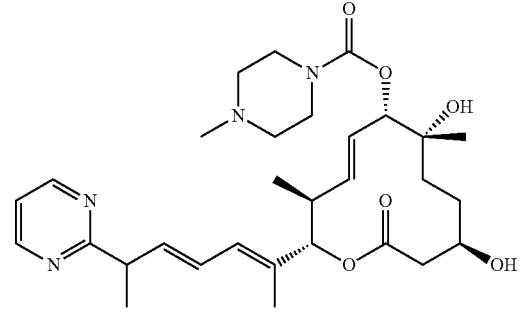 42 | −22.224 | 155.424 | 60.103 | >1000 | 38.444 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 43 | −90.107 | 26.610 | 31.754 | >1000 | 6.373 |
| 44 | −78.056 | 65.979 | 76.010 | >1000 | 13.057 |
| 45 | −89.491 | 27.891 | 19.587 | >1000 | 8.756 |
| 46 | −87.701 | 37.193 | 53.113 | >1000 | 8.560 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 47 | −41.858 | 114.631 | 129.855 | >1000 | 71.254 |
| 48 | −60.371 | 126.216 | 132.822 | >1000 | |
| 49 | −83.573 | 38.919 | 36.709 | >1000 | 7.230 |

TABLE 13-continued
Biological Activity of Example Compounds
| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 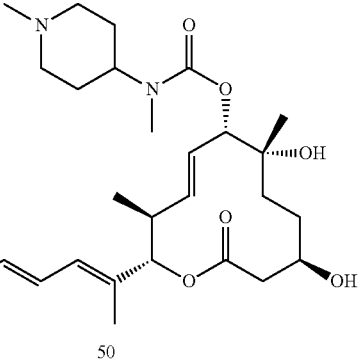 50 | −60.16 | 25.08 | 16.250 | >1000 | |
| 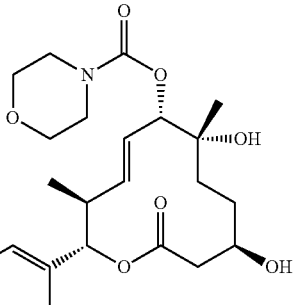 51 | 35.309 | 2545.788 | >1000.000 | >1000 | 479.605 |
| 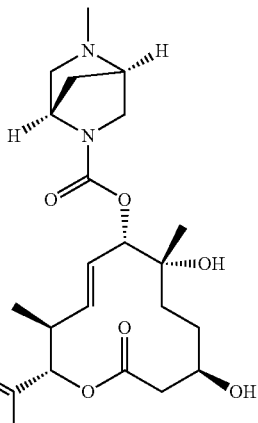 52 | −29.357 | 56.386 | 41.521 | >1000 | 12.258 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 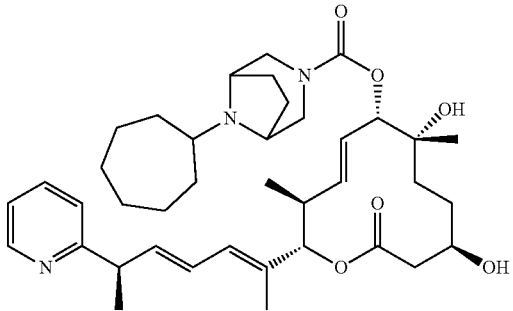 53 | −95.714 | 64.987 | 51.978 | >1000 | |
| 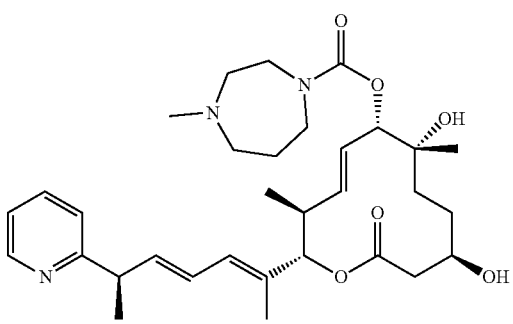 54 | −23.122 | 84.867 | 33.109 | >1000 | 6.869 |
| 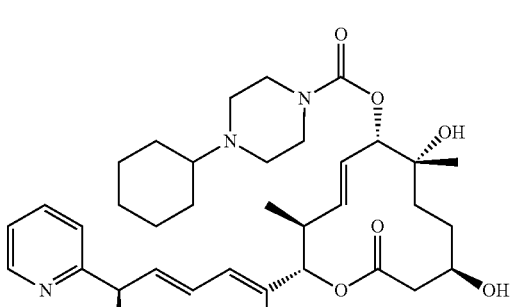 55 | −94.348 | 21.406 | 21.202 | >1000 | 3.325 |
| 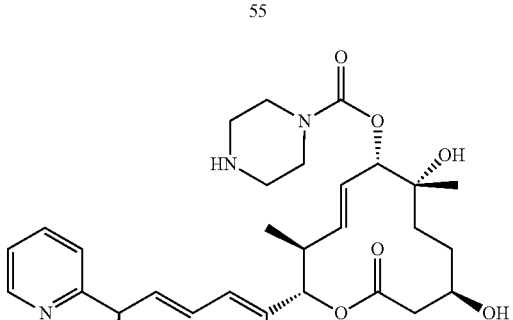 56 | −76.515 | 39.538 | 15.971 | >1000 | 26.868 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 57 | −12.670 | 103.826 | 74.907 | >1000 | 7.317 |
| 58 | 35.115 | 1389.178 | 1145.992 | >10000 | |
| 59 | −93.786 | 13.556 | 7.178 | >1000 | 2.347 |
| 60 | −90.314 | 76.078 | | | 47.340 |

TABLE 13-continued
| | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| Structure and Compound # 61 | −86.908 | 3.254 | 12.669 | >1000 | 5.114 |
| Structure and Compound # 62 | −92.429 | 278.544 | 43.378 | >1000 | |
| Structure and Compound # 63 | −87.256 | 1.658 | 2.545 | >1000 | 2.825 |
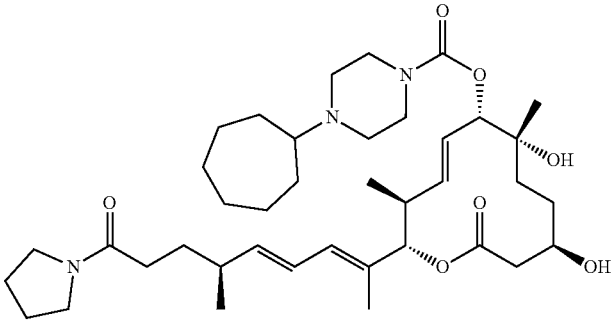
61
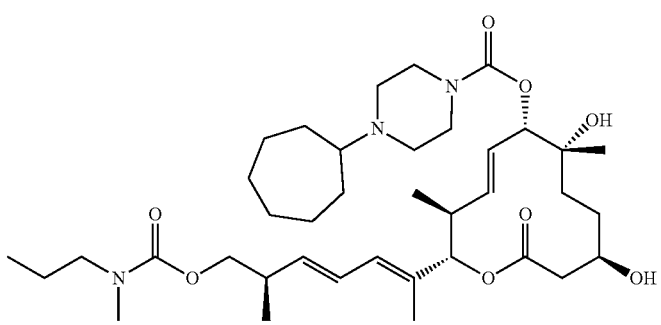
62
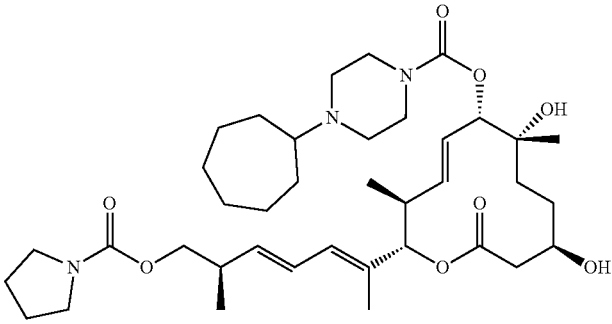
63

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 64 | −84.513 | 5.509 | 5.562 | >1000 | 7.661 |
| 65 | −70.370 | 2.394 | 2.735 | 40.140 | 7.033 |
| 66 | 80.11 | 77.26 | >1000 | | |
| 67 | 2.52 | 1.424 | 21.764 | | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
| --- | --- | --- | --- | --- | --- |
| 68 | −86.642 | 1.198 | 3.934 | >1000 | |
| 69 | −93.599 | 2.593 | 6.204 | >1000 | |
| 70 | −92.870 | 40.226 | 32.782 | >1000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
| --- | --- | --- | --- | --- | --- |
| 71 | −89.146 | 11.933 | 29.094 | >1000 | 16.761 |
| 72 | −68.88 | 4.52 | 2.392 | | 14.819 |
| 73 | −92.218 | 22.502 | 7.641 | >1000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 74 | −79.385 | 1.764 | 4.297 | >1000 | 1.929 |
| 75 | −92.980 | 10.383 | 28.938 | >1000 | |
| 76 | −79.728 | 4.434 | 3.462 | 221.390 | 5.142 |
| 77 | −92.417 | 86.299 | 41.399 | 1879.784 | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 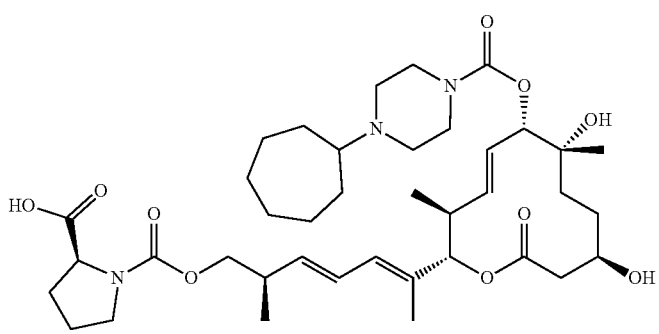 78 | 35.028 | 2635.026 | >1000.000 | >1000 | 36.054 |
| 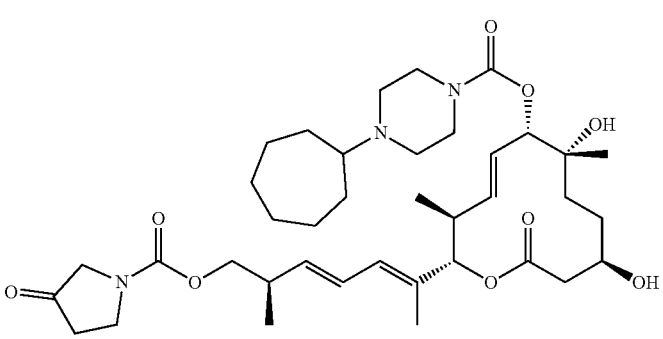 79 | −93.610 | 2.845 | 4.774 | | 449.450 |
| 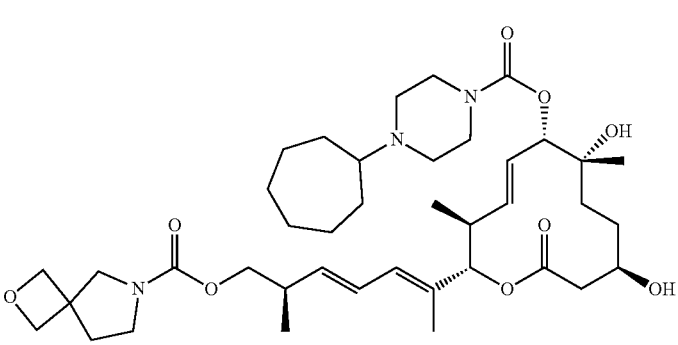 80 | −76.42 | 7.98 | 6.393 | | 602.820 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 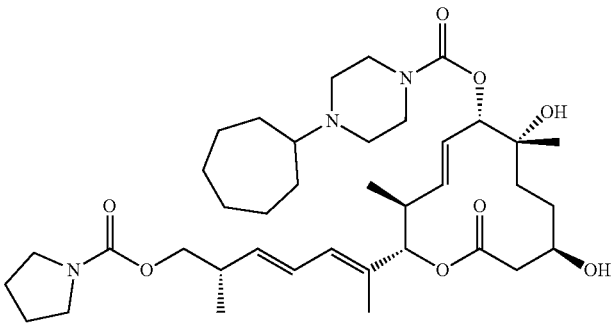 81 | −93.540 | 11.681 | 11.789 | 861.860 | 11.552 |
| 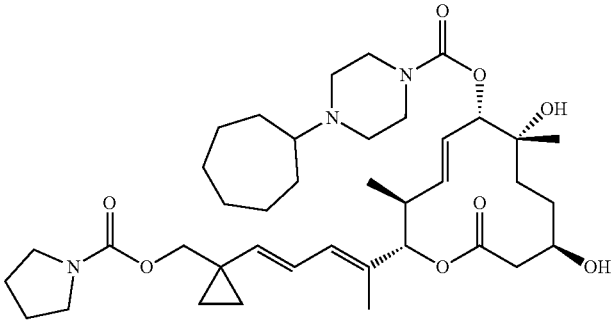 82 | −24.659 | 302.087 | 137.820 | >1000 | |
| 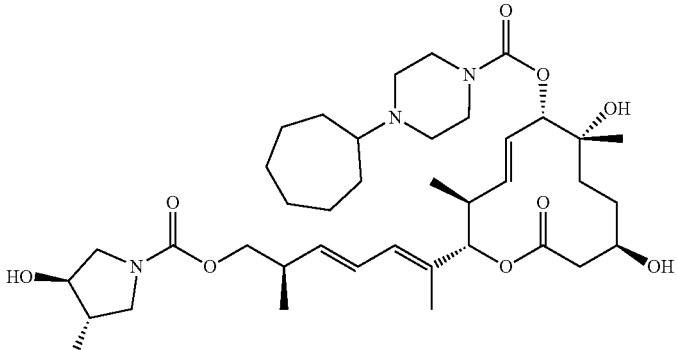 [SMILES: C/C(=C\C=C\[C@@H](C)COC(=O)N1CC[C@@H](O)C1)[C@H]1OC(=O)C[C@H](O)CC[C@@](C)(O)[C@@H](OC(=O)N2CCN(C3CCCCCC3)CC2)/C=C/[C@@H]1C] 83 | −95.353 | 74.626 | 294.340 | >1000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 84 | −58.256 | 108.430 | 691.610 | >1000 | 2.255 |
| 85 | −85.429 | 33.049 | 30.233 | 3992.400 | 9.701 |
| 86 | −89.812 | 3.676 | 22.230 | >1000 | 3.679 |
| 87 | −72.713 | 1.745 | 1.235 | >1000 | 4.234 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 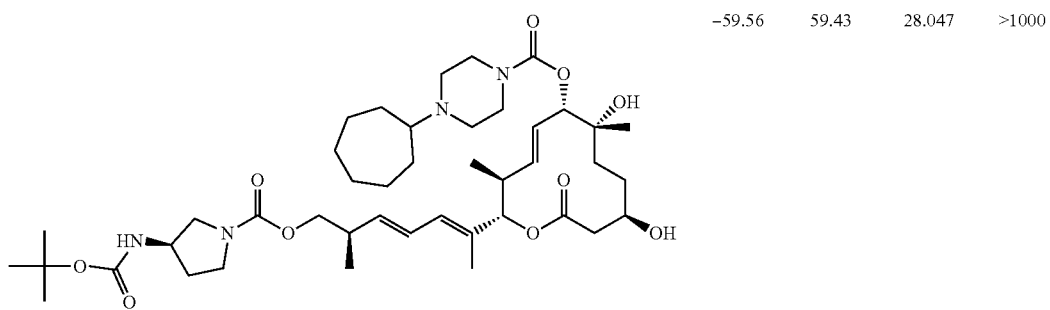 88 | −59.56 | 59.43 | 28.047 | >1000 | |
| 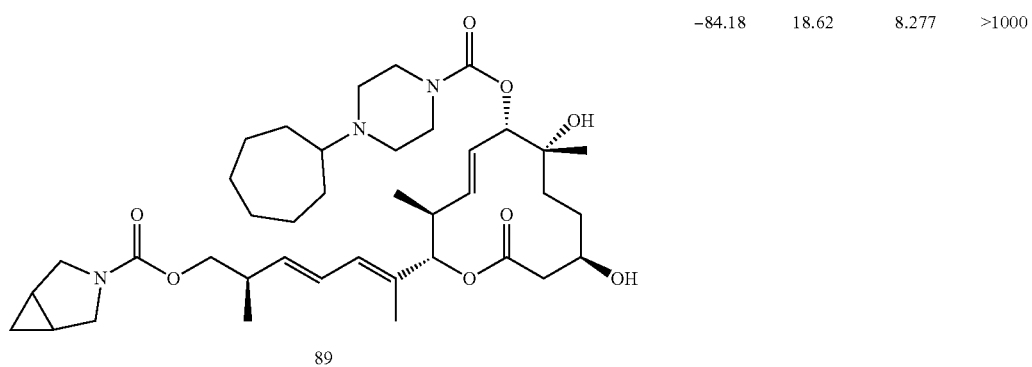 89 | −84.18 | 18.62 | 8.277 | >1000 | |
| 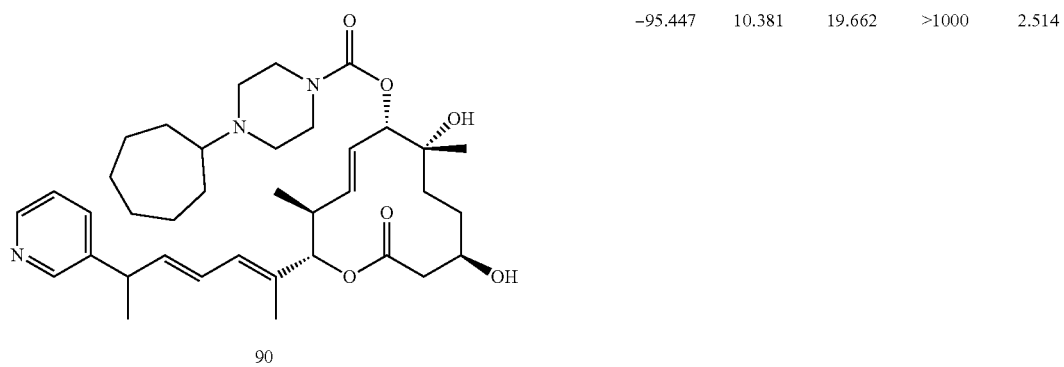 90 | −95.447 | 10.381 | 19.662 | >1000 | 2.514 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 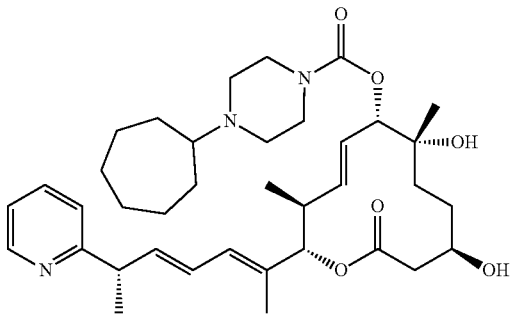 91 | −90.025 | 71.754 | 65.037 | >1000 | 5.952 |
| 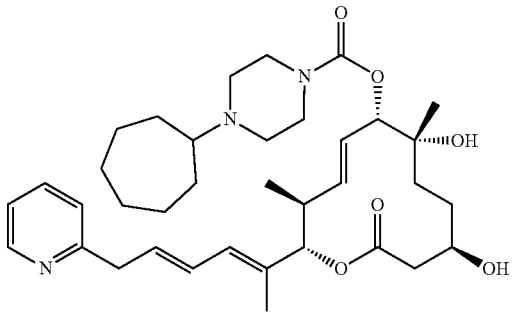 92 | 63.471 | >4000.000 | 148.414 | >1000 | |
| 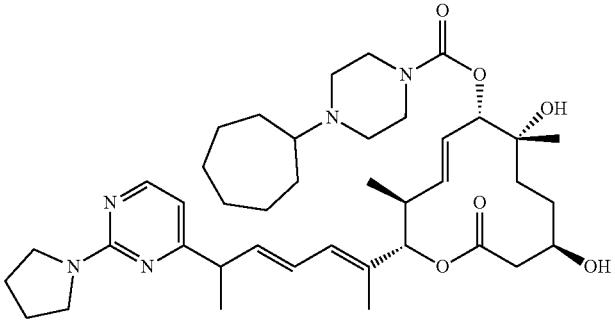 93 | −96.595 | 147.043 | 22.977 | 4310.192 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 94 | −93.732 | 22.057 | 31.918 | >10000 | 6.375 |
| 95 | −94.489 | 98.272 | 40.135 | >10000 | 16.134 |
| 96 | −92.260 | 21.238 | 15.850 | >1000 | 6.265 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 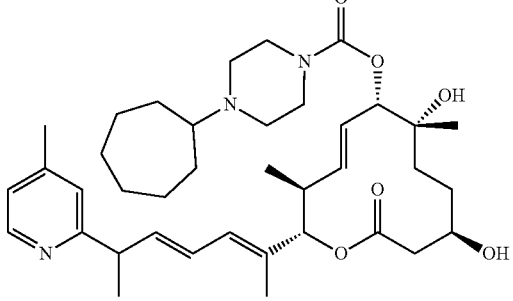 97 | −92.395 | 59.861 | 58.701 | >1000 | 6.791 |
| 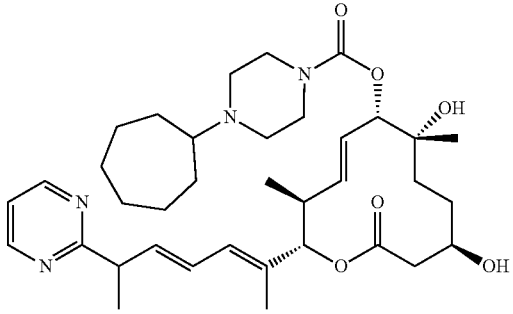 98 | −91.588 | 30.954 | 45.936 | >1000 | 11.891 |
| 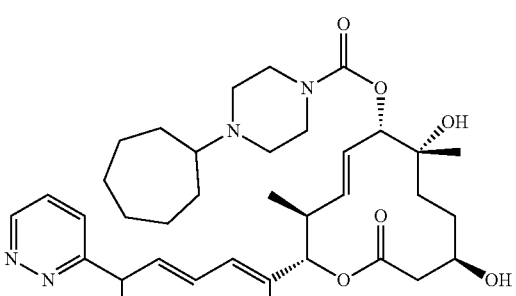 99 | −94.716 | 22.005 | 15.089 | >1000 | 3.382 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 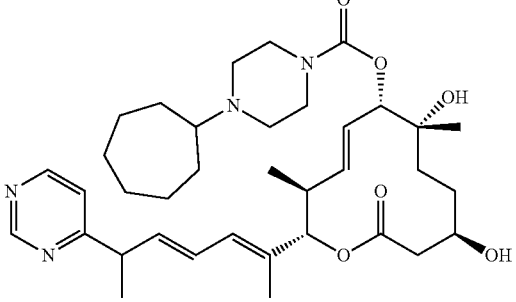<br>100 | −26.648 | 955.710 | 531.915 | >1000 | 503.624 |
| 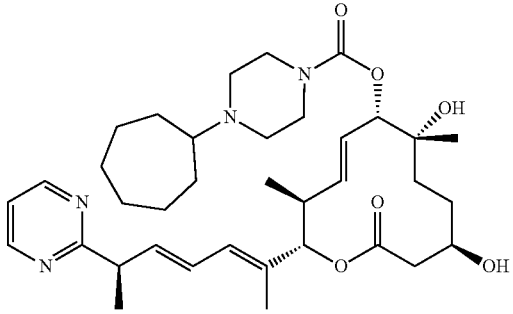<br>101 | −92.893 | 29.505 | 33.604 | >1000 | 8.103 |
| 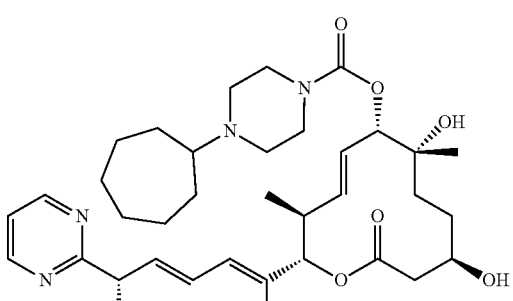<br>102 | −93.100 | 34.531 | 38.061 | >1000 | 6.573 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 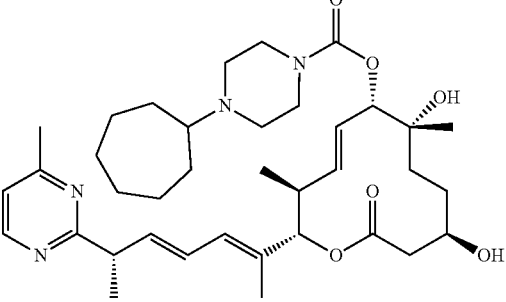 103 | −76.743 | 100.995 | 124.520 | >1000 | 9.698 |
| 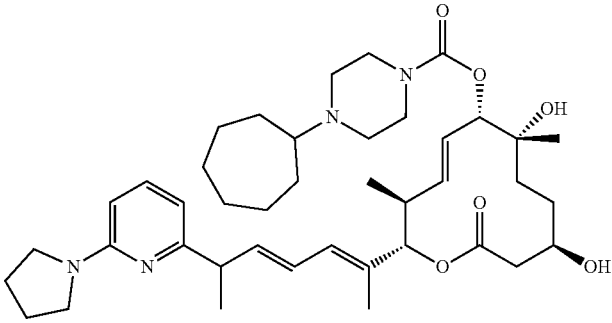 104 | −95.264 | 121.789 | 320.244 | >1000 | 21.857 |
| 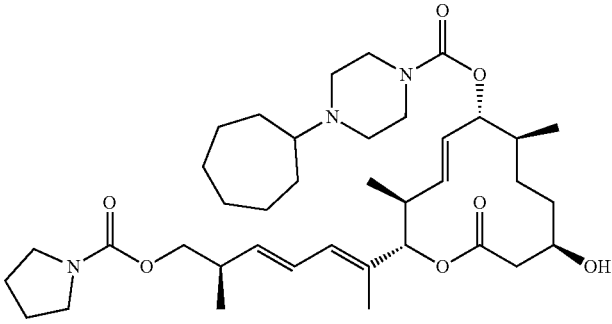 105 | −90.949 | 10.781 | 8.393 | >1000 | |

TABLE 13-continued
| | Biological Activity of Example Compounds | | | | |
|---|---|---|---|---|---|
| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
| 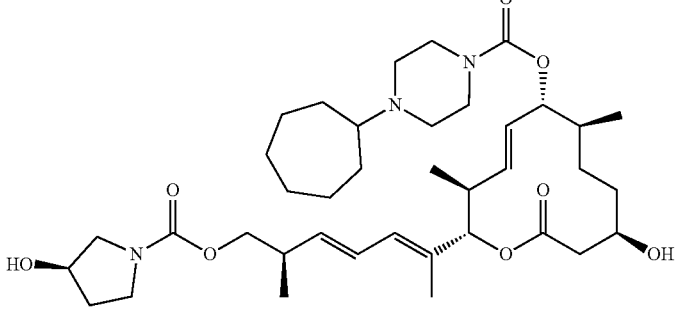 106 | −77.841 | 10.825 | 8.272 | >1000 | 5.670 |
| 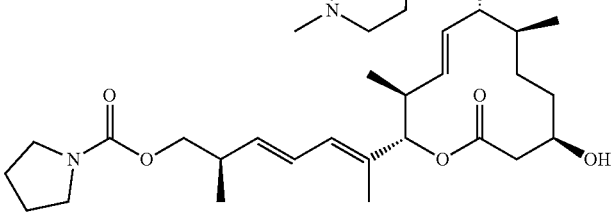 107 | −86.024 | 1.364 | 3.805 | >1000 | 2.961 |
| 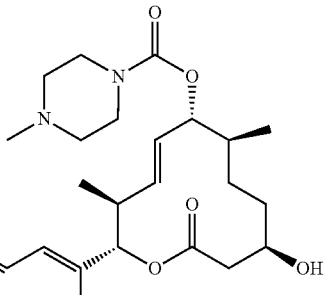 108 | −83.342 | 3.374 | 4.863 | >1000 | 5.435 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 109 | −78.99 | 4.36 | 2.656 | >1000 | |
| 110 | −77.71 | 6.76 | 5.055 | >1000 | |
| 111 | −79.107 | 0.339 | 2.198 | >1000 | |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 112 | 28.067 | 2890.203 | 420.641 | >10000 | 538.320 |
| 113 | −96.287 | 43.969 | 33.240 | 2428.955 | 10.560 |
| 114 | −94.255 | 8.070 | 15.318 | >10000 | 3.784 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 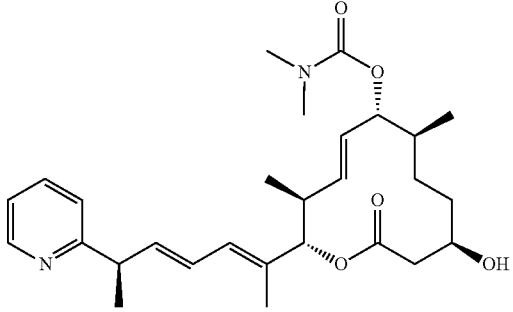 115 | 23.951 | 1717.435 | 478.606 | >10000 | 142.021 |
| 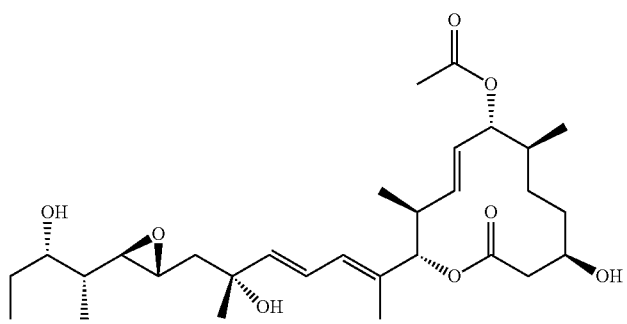 116 | −65.323 | 4.885 | 2.140 | 821.510 | 5.281 |
| 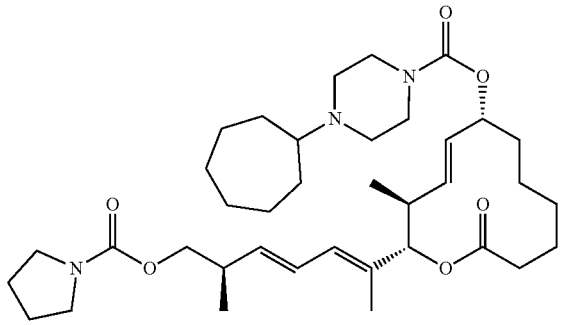 117 | −93.253 | 170.176 | 74.629 | 929.153 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 118 | −90.468 | 6.738 | 7.836 | 2443.625 | 3.712 |
| 119 | −94.777 | 155.862 | 135.293 | 6382.117 | 71.129 |
| 120 | −83.689 | 139.143 | 154.043 | −10000 | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 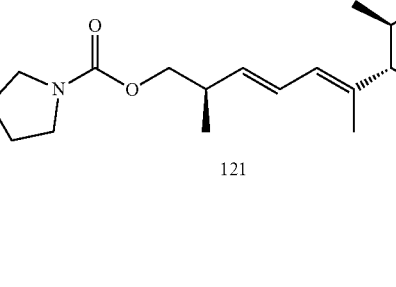 121 | −87.001 | 6.480 | 8.588 | 2835.605 | 5.422 |
| 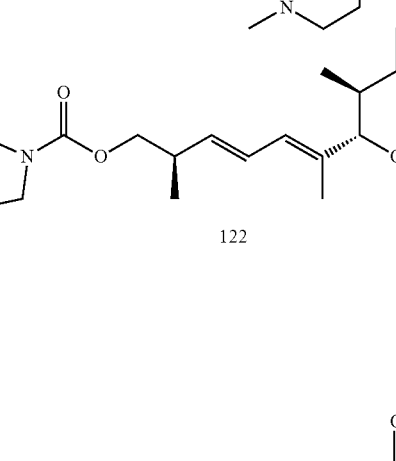 122 | −65.34 | 7.73 | 3.440 | 680.844 | |
| 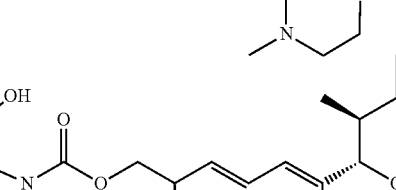 123 | −62.754 | 2.897 | 2.519 | 422.835 | 3.608 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 124 | −81.612 | 35.234 | 45.539 | >1000 | 40.193 |
| 125 | −85.578 | 54.749 | 65.541 | >1000 | 113.381 |
| 126 | >10000 | >10000 | >10000 | | |
| 127 | −40.649 | 882.501 | 258.063 | 3819.588 | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 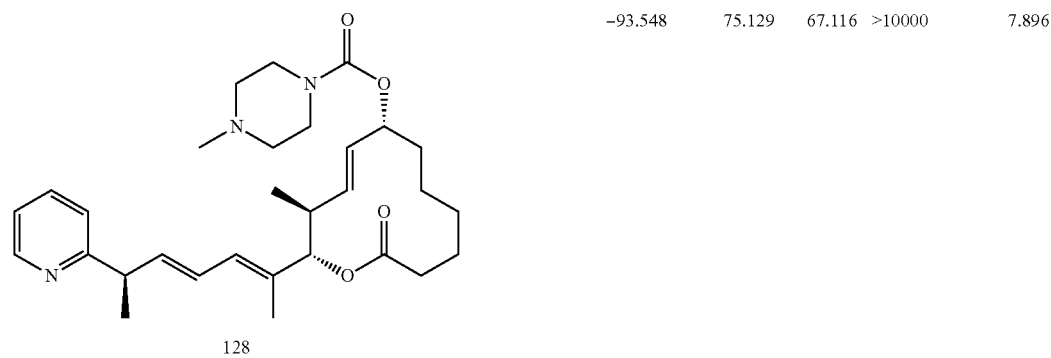 128 | −93.548 | 75.129 | 67.116 | >10000 | 7.896 |
| 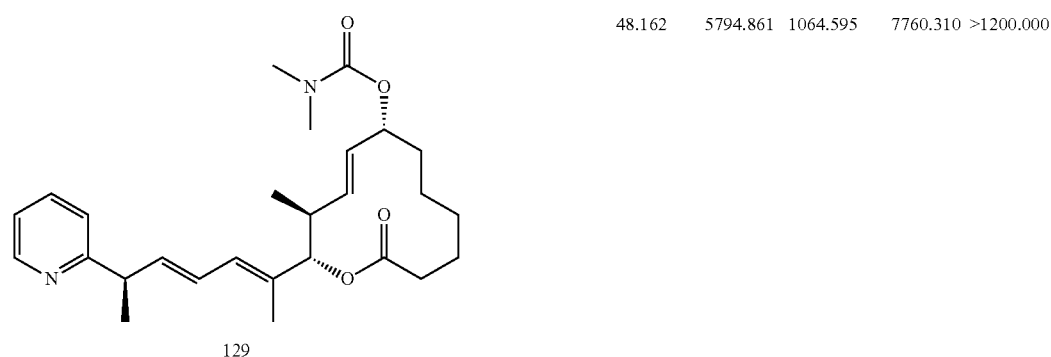 129 | 48.162 | 5794.861 | 1064.595 | 7760.310 | >1200.000 |
| 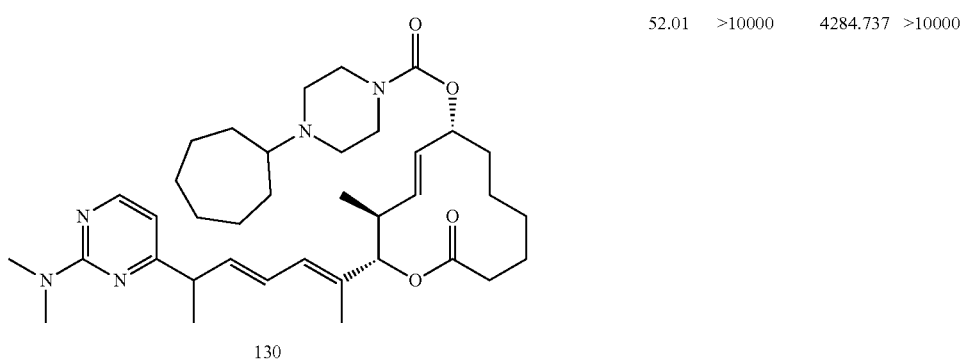 130 | 52.01 | >10000 | 4284.737 | >10000 | |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 131 | 51.96 | >10000 | 810.247 | 4077.331 | |
| 132 | | | >1000.000 | >10000 | |
| 133 | −94.806 | 474.937 | 454.567 | >10000 | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 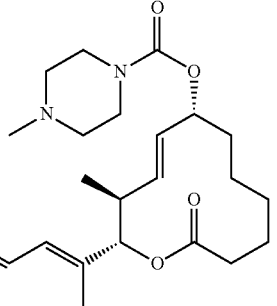 134 | −72.647 | 40.380 | 45.671 | >1000 | |
| 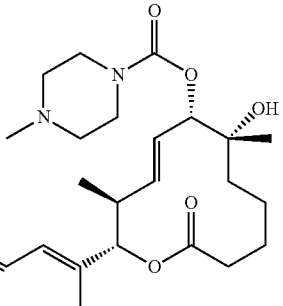 135 | −91.386 | 2.385 | 4.925 | >1000 | 1.667 |
| 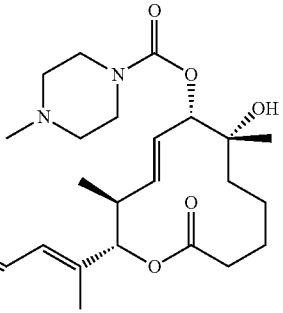 136 | −72.301 | 2.068 | 1.742 | >1000 | 2.543 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 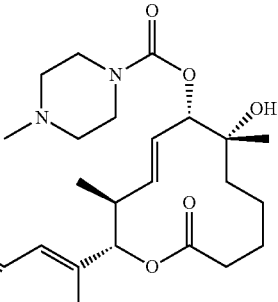 137 | −94.561 | 4.443 | 11.236 | >1000 | |
| 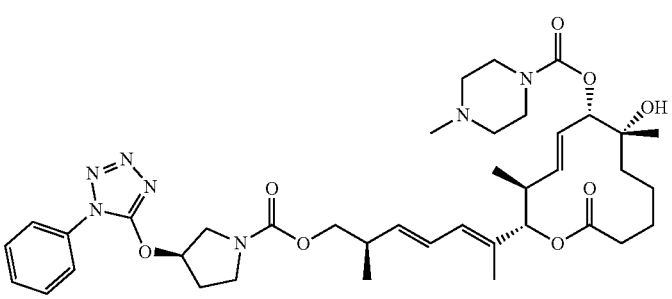 138 | −94.92 | 37.27 | 31.612 | >1000 | |
| 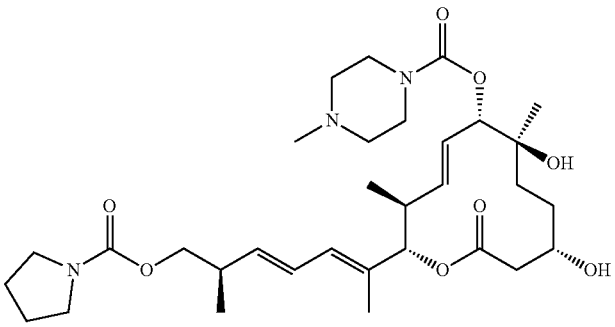 139 | −90.189 | 6.549 | 15.226 | >1000 | 47.804 |
| 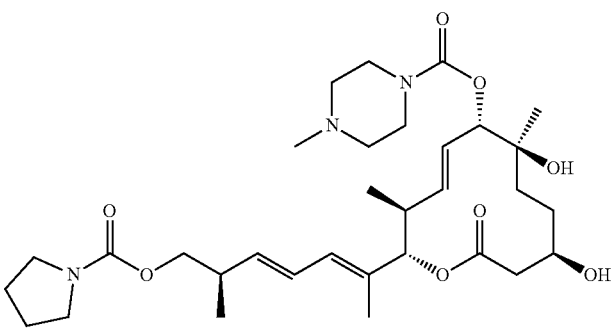 140 | −83.721 | 3.139 | 7.117 | >1000 | 5.692 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 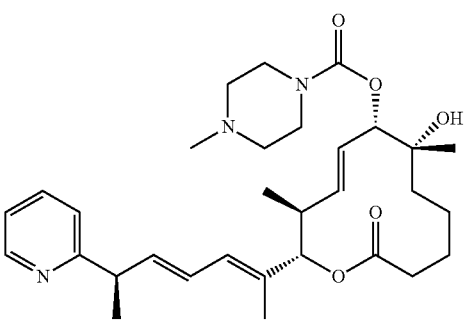 141 | −75.710 | 33.924 | 31.569 | >1000 | |
| 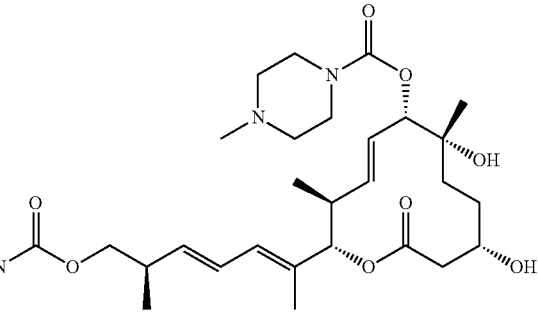 142 | −95.426 | 12.251 | 24.983 | >1000 | |
| 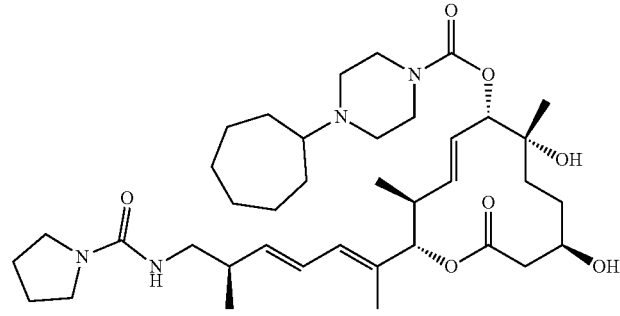 143 | −90.892 | 19.831 | 27.644 | >1000 | 5.244 |

TABLE 13-continued
| | Biological Activity of Example Compounds | | | | |
|---|---|---|---|---|---|
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
| 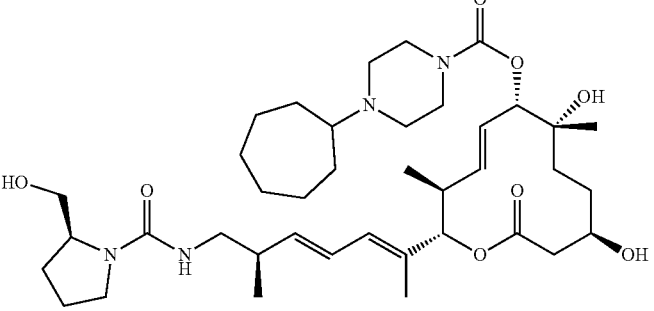 144 | −85.001 | 77.295 | 95.904 | >1000 | 40.798 |
| 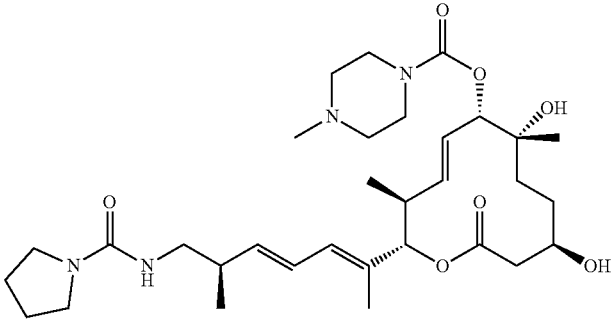 145 | −90.365 | 54.083 | 76.622 | >1000 | 7.619 |
| 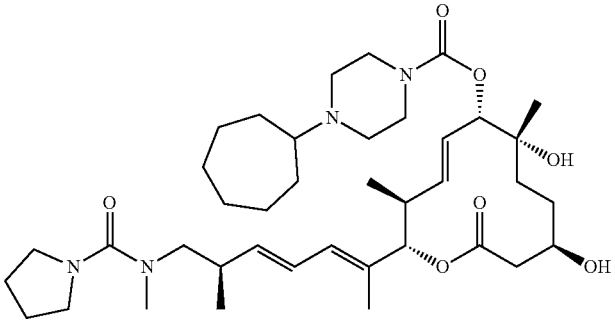 146 | −94.475 | 23.520 | 145.219 | >1000 | |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
| --- | --- | --- | --- | --- | --- |
| 147 | −94.521 | 38.566 | 51.840 | >1000 | 14.147 |
| 148 | −95.852 | 5.109 | 14.700 | >1000 | |
| 149 | −96.911 | 51.275 | 103.451 | >1000 | 4.542 |
| 150 | −88.360 | 53.333 | 72.976 | >1000 | 11.236 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 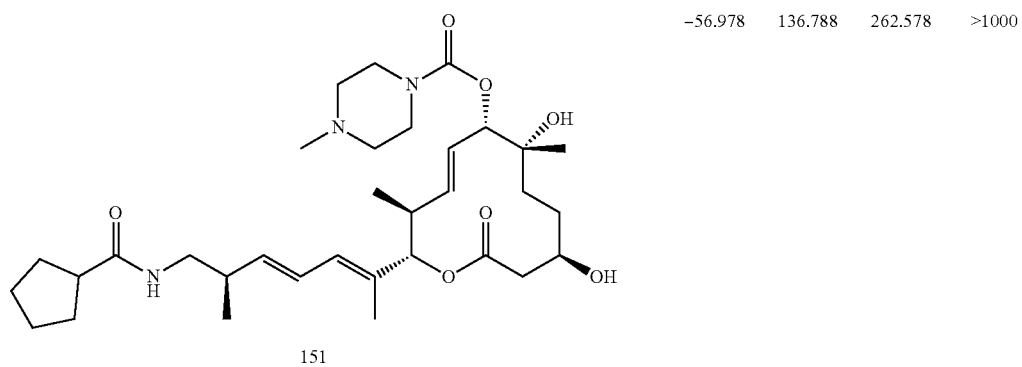 151 | −56.978 | 136.788 | 262.578 | >1000 | |
| 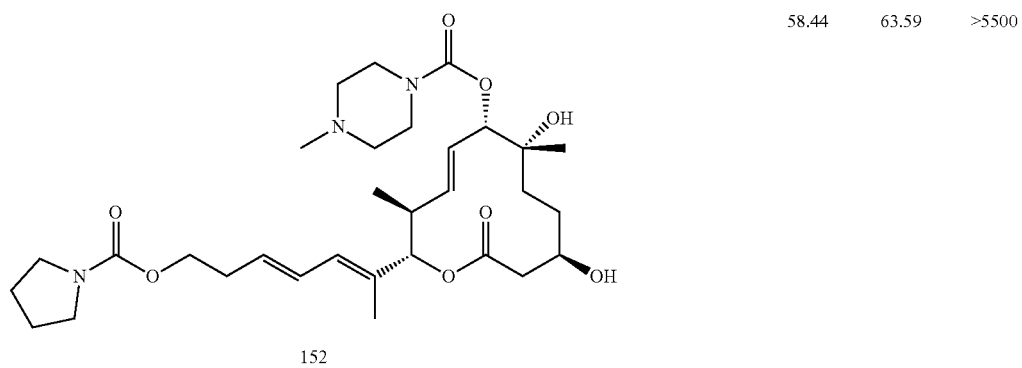 152 | | 58.44 | 63.59 | >5500 | |
| 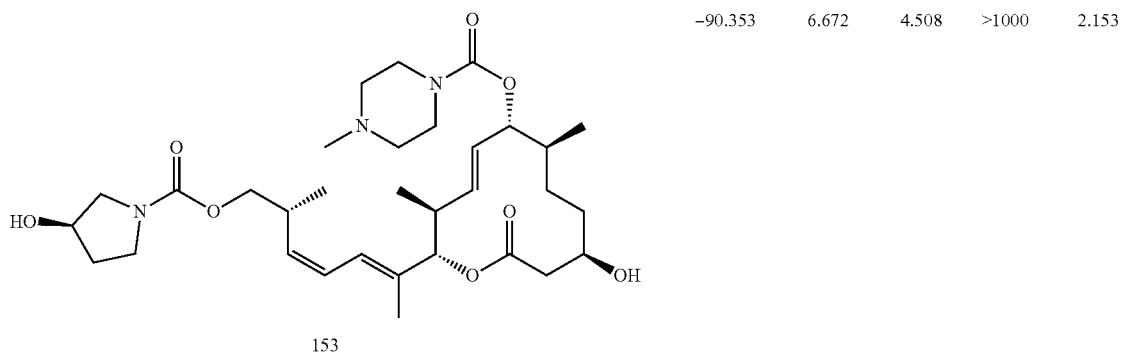 153 | −90.353 | 6.672 | 4.508 | >1000 | 2.153 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 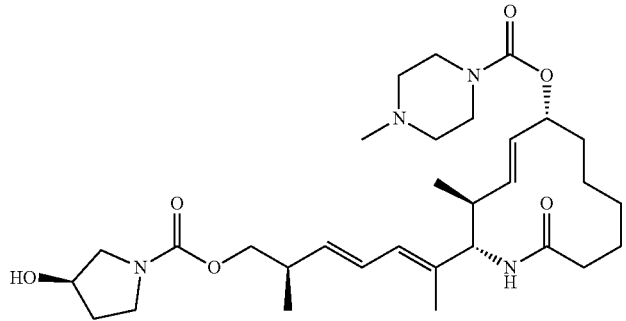 154 | 19.145 | 1179.770 | 375.699 | >10000 | 267.299 |
| 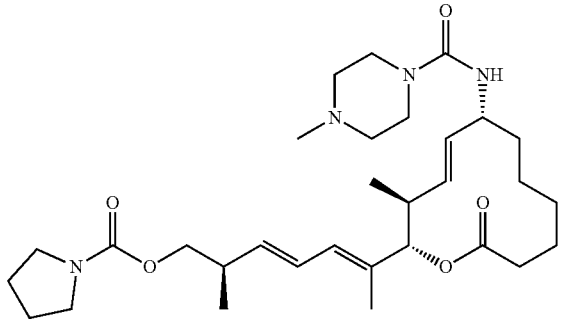 155 | −93.574 | 18.961 | 18.526 | >1000 | 14.419 |
| 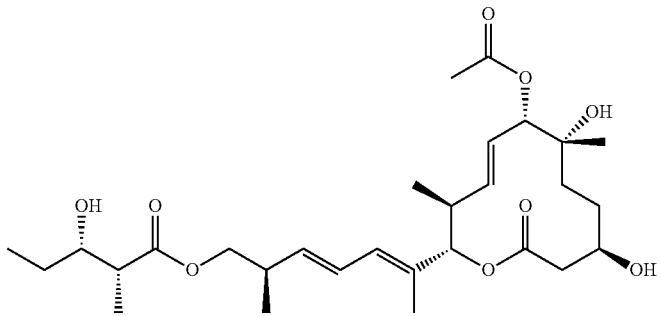 156 | −90.53 | 31.10 | 42.835 | >10000 | |
| 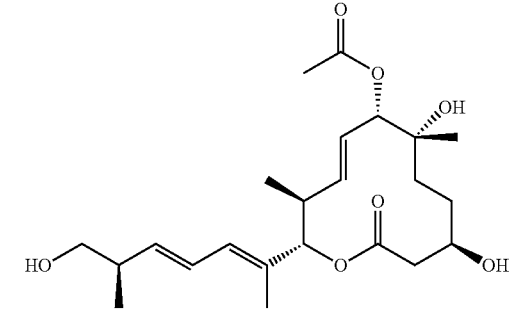 157 | 47.525 | 6919.552 | 4039.541 | >10000 | 326.162 |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 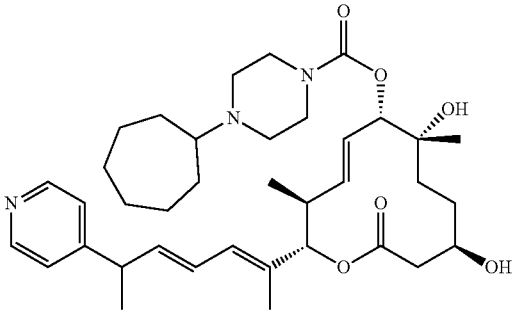 158 | −95.148 | 6.627 | 13.974 | >1000 | 2.744 |
| 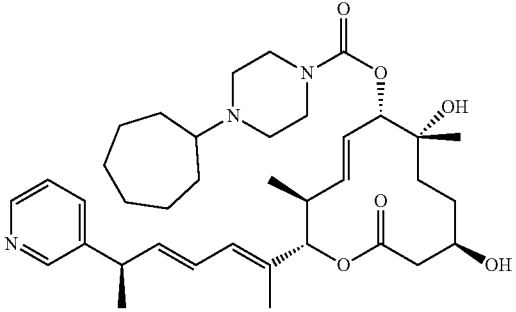 159 | −95.570 | 10.952 | 13.246 | >1000 | 2.342 |
| 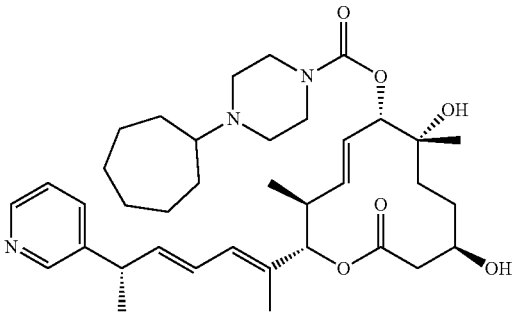 160 | −94.237 | 20.415 | 29.403 | >1000 | 2.562 |

TABLE 13-continued
Biological Activity of Example Compounds
| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 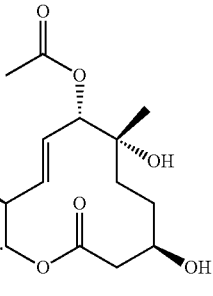 161 | | | | | 20.875 |
| 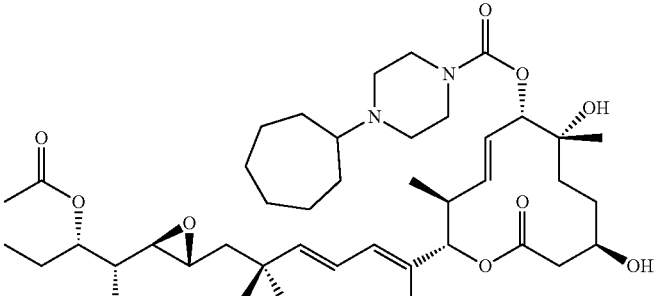 162 | −78.560 | 2.407 | 2.000 | 132.081 | 5.851 |
| 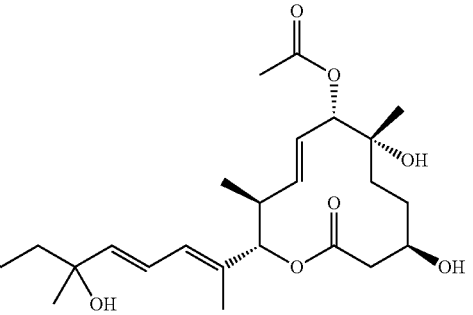 163 | −41.520 | 353.724 | 194 | >10000 | |
| 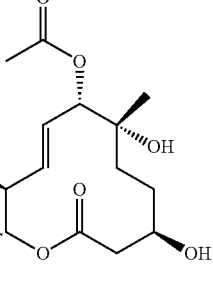 164 | 13.281 | 1501.265 | 657 | >10000 | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 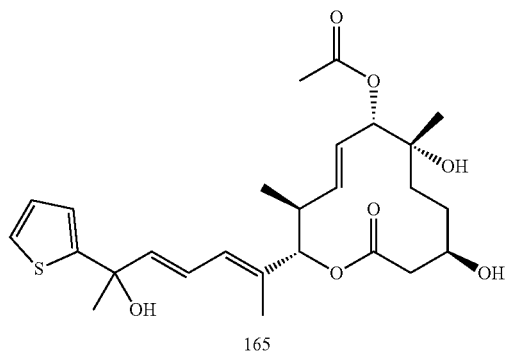 [SMILES: CC(=O)O[C@H]1/C=C/[C@H](C)[C@@H](/C(C)=C/C=C/C(C)(O)c2cccs2)OC(=O)C[C@H](O)CC[C@@]1(C)O]<br>165 | 32.802 | 3786.286 | 473 | >10000 | |
| 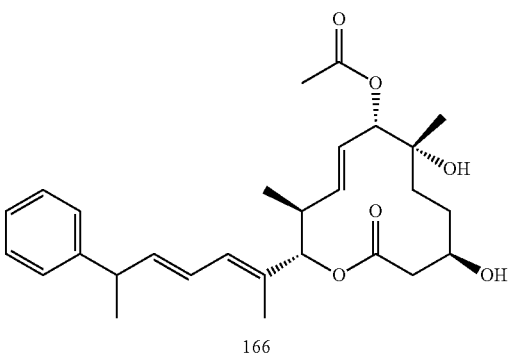 [SMILES: CC(=O)O[C@H]1/C=C/[C@H](C)[C@@H](/C(C)=C/C=C/C(C)c2ccccc2)OC(=O)C[C@H](O)CC[C@@]1(C)O]<br>166 | 12.322 | 932.044 | 382 | >10000 | |
| 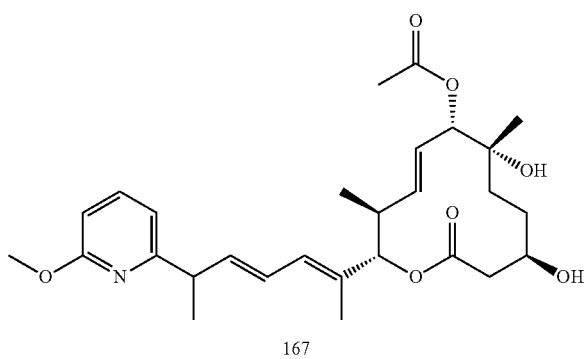 [SMILES: COc1cccc(C(C)/C=C/C=C(\C)[C@H]2OC(=O)C[C@H](O)CC[C@@](C)(O)[C@@H](OC(C)=O)/C=C/[C@@H]2C)n1]<br>167 | −12.662 | 554.116 | 282 | >10000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 168 | −27.091 | 841.978 | 440 | >10000 | |
| 169 | 0.954 | 971.633 | 593 | >10000 | |
| 170 | 20.264 | 1667.412 | 911 | >10000 | |
| 171 | −55.378 | 313.799 | 167 | >10000 | |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 172 | 87.197 | >10000 | 559 | >10000 | >1200 |
| 173 | 76.538 | >6400 | 610 | >10000 | |
| 174 | 84.545 | >6400 | 538 | >10000 | |
| 175 | −70.521 | 248.761 | | | |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 176 | −26.377 | 827.322 | | | |
| 177 | −39.524 | 427.157 | | | |
| 178 | −67.307 | 320.764 | | | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 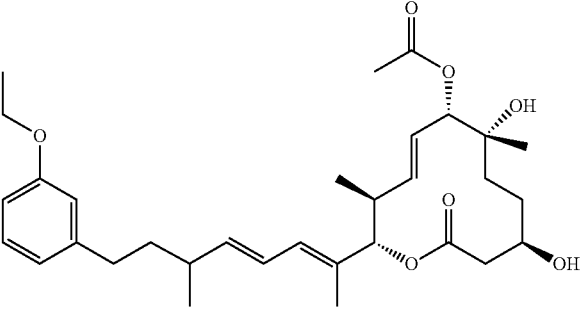 179 | −32.036 | 508.411 | | | |
| 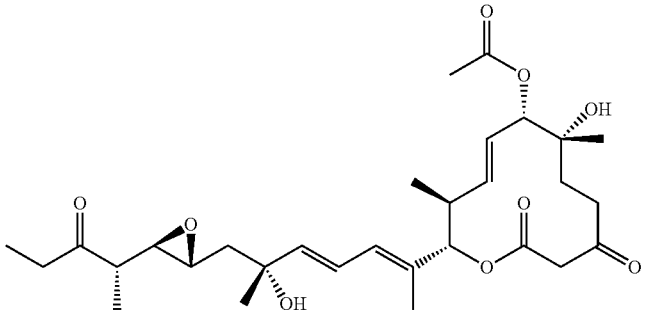 180 | −81.709 | 97.681 | | | |
| 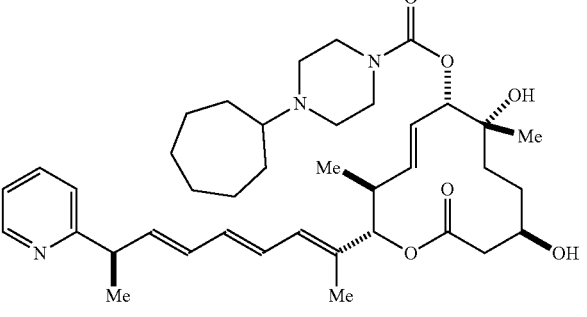 181 | 11.003 | 720.201 | | | 119.866 |
| 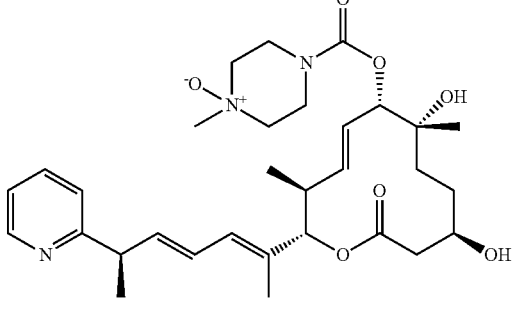 182 | −81.172 | 45.423 | | | 5.891 |

TABLE 13-continued
Biological Activity of Example Compounds
| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
|  183 | 12.455 | 861.913 | | | |
|  184 | −2.901 | 94.839 | | | 30.921 |
|  185 | 49.481 | 3980.021 | | | >1200 |
|  186 | −73.192 | 26.834 | | | 8.778 |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 187 | −74.150 | 23.547 | | | 5.921 |
| 188 | −47.060 | 2.051 | | | 2.117 |
| 189 | −75.410 | 1.759 | | | 9.228 |
| 190 | −78.918 | 0.860 | | | 2.085 |

TABLE 13-continued

Biological Activity of Example Compounds

| Structure and Compound # | Panc 05.04 (mt SF3B1 cells) E$_{max}$ (%) | Panc 05.04 (mt SF3B1 cells), GI$_{50}$ (nM) | WiDr GI$_{50}$ (nM) | WiDr-R GI$_{50}$ (nM) | SPA (wt SF3B1 cells) IC$_{50}$ (nM) |
|---|---|---|---|---|---|
| 191 | | | | | 0.990 |
| 192 | | | | | 1.521 |
| 193 | | | | | 18.251 |
| 194 | −64.413 | 3.485 | | | |

TABLE 13-continued
Biological Activity of Example Compounds
| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 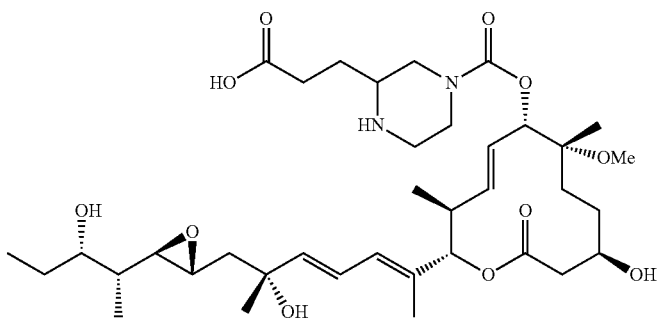 195 | | | | | 29.188 |
| 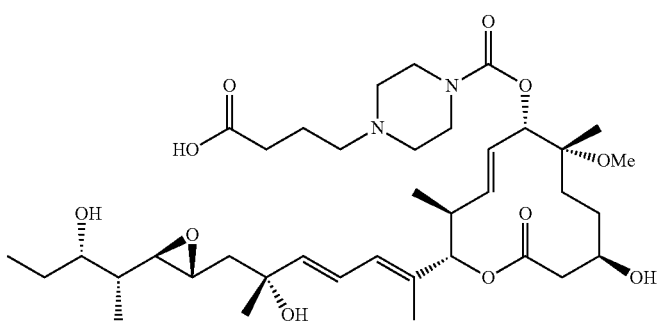 196 | | | | | 14.557 |
| 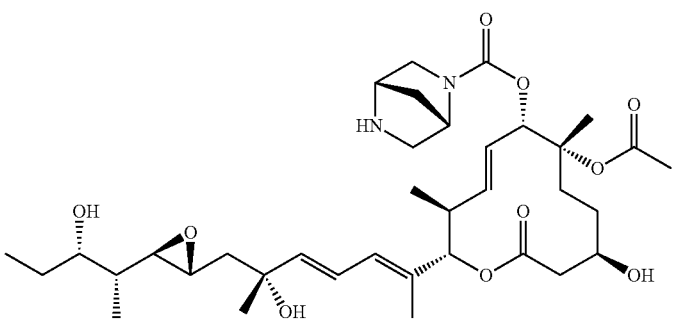 197 | | | | | 16.0 |

TABLE 13-continued

Biological Activity of Example Compounds

| Structure and Compound # | Panc 05.04 (mt SF3B1 cells) $E_{max}$ (%) | Panc 05.04 (mt SF3B1 cells), $GI_{50}$ (nM) | WiDr $GI_{50}$ (nM) | WiDr-R $GI_{50}$ (nM) | SPA (wt SF3B1 cells) $IC_{50}$ (nM) |
|---|---|---|---|---|---|
| 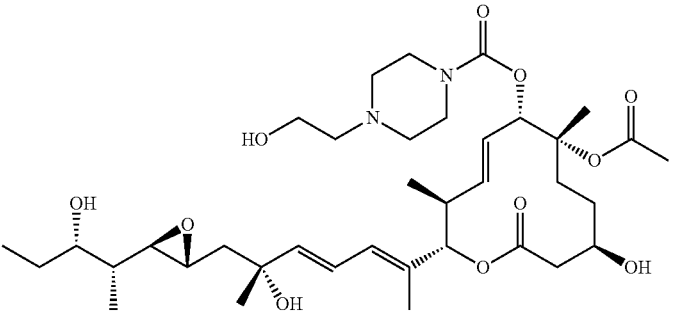 199 | | | | | 24.3 |

Administration of at least one compound chosen from compounds of Formula I, compounds of Formula II, compounds of Formula III, and pharmaceutically acceptable salts of any of the foregoing CT26 colon cancer cells (0.25×10⁶; ATCC Cat. #CRL-2638) are implanted subcutaneously into the right flank of eight-week old female Balb/c mice (Envigo) in 100 µL of PVS lacking Matrigel. CT26 tumors are allowed to grow to an average of ~100 mm³ before animals are enrolled into the efficacy study. Each treatment group contains 12 mice. Mice are treated with at least one compound chosen from compounds of Formula I, compounds of Formula II, compounds of Formula III, and pharmaceutically acceptable salts of any of the foregoing, an anti-CTLA4 antibody, or a combination thereof, at various doses and via various routes of administration. The at least one compound chosen from compounds of Formula I, compounds of Formula II, compounds of Formula III, and pharmaceutically acceptable salts of any of the foregoing is formulated in a composition containing 5% ethanol and 95% methylcellulose solution (0.5% methylcellulose). The anti-CTLA4 antibody is formulated in PBS at pH 7. Tumors are measured 3 times per week for up to 19 days. Tumor volumes are calculated using the ellipsoid formula: Tumor Volume=(length×width²)/2.

We claim:

1. A compound of Formula

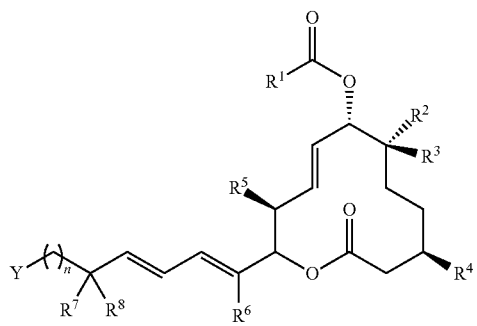

or a pharmaceutically acceptable salt thereof,
wherein:

n is chosen from 0, 1, 2 or 3;

$R^1$ is chosen from $C_1$-$C_6$ alkyl groups, $C_3$-$C_8$ cycloalkyl groups, —$NR^9R^{10}$,

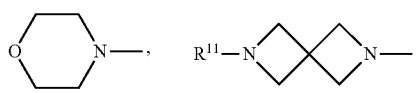

groups,

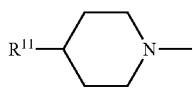

groups,

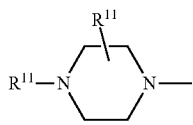

groups,

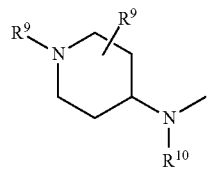

groups,

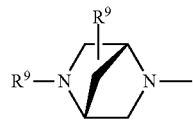

groups,

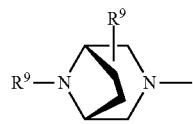

groups,

groups, and

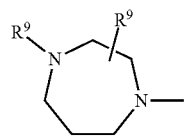

groups;

$R^9$ is chosen from hydrogen, —$NR^{11}R^{12}$ groups, $C_1$-$C_8$ alkyl groups, —($C_1$-$C_6$ alkyl)-$CO_2H$ groups, $C_3$-$C_8$ cycloalkyl groups, and heterocyclyl groups, wherein the —$NR^{11}R^{12}$ groups, $C_1$-$C_8$ alkyl groups, $C_3$-$C_8$ cycloalkyl groups, and heterocyclyl groups may be unsubstituted or substituted from 1-3 times with a group independently chosen from $C_1$-$C_8$ alkyl groups, —($C_1$-$C_8$ alkyl)-$CO_2H$ groups, hydroxy, halogen groups, and $C_1$-$C_8$ alkoxy groups, and wherein the heterocyclyl group is a 3-, 4-, 5-, 6-, 7-, or 8-membered ring containing at least one heteroatom independently chosen from O, N, and S or a bicyclic heterocycle;

$R^{10}$ is chosen from hydrogen and $C_1$-$C_8$ alkyl groups;
one of either $R^2$ or $R^3$ is chosen from hydrogen and $C_1$-$C_8$ alkyl groups, and the other is chosen from hydrogen, —$OR^{10}$, —$OC(O)R^{10}$, —$OC(O)R^{10}$, and $C_1$-$C_8$ alkyl groups;
$R^4$ is chosen from hydrogen and hydroxy;
$R^5$ and $R^6$ are each independently chosen from $C_1$-$C_8$ alkyl groups;
$R^7$ and $R^8$ are each independently chosen from hydrogen, hydroxy, $C_1$-$C_8$ alkoxy groups, and $C_1$-$C_8$ alkyl groups; and
Y is chosen from phenyl, thiophenyl, triazolyl, pyridinyl, pyrimidinyl, pyridazinyl, and pyrazinyl, wherein Y may be unsubstituted or substituted from 1-3 times with groups independently chosen from oxo groups, $C_1$-$C_8$ alkyl groups, $C_3$-$C_5$ cycloalkyl groups, hydroxy $C_1$-$C_8$ alkyl groups, $C_1$-$C_8$ alkoxy groups, methoxy $C_1$-$C_8$ alkyl groups, —$NR^{11}R^{12}$ groups,

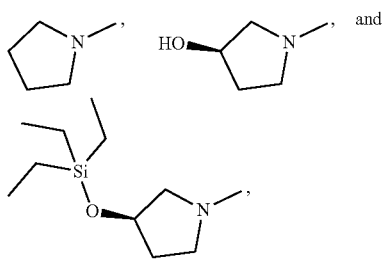

wherein $R^{11}$ and $R^{12}$ are each independently chosen from hydrogen and $C_1$-$C_6$ alkyl groups;
wherein if:
Y is

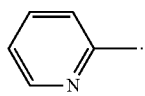

$R^1$ is a

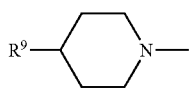

group,
$R^2$ is $OR^{10}$ and $R^{10}$ is hydrogen,
$R^3$ is a $C_1$-$C_6$ alkyl group,
$R^4$ is hydroxy,
$R^5$ and $R^6$ are each a $C_1$-$C_6$ alkyl group, and
one of $R^7$ and $R^8$ is hydrogen and the other is a $C_1$-$C_6$ alkyl group,
then $R^9$ is not a 3-, 4-, 5-, 6-, 7-, or 8-membered ring containing one N; and
wherein if:
Y is

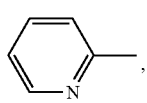

$R^1$ is a

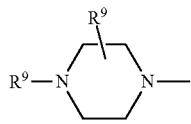

group,
$R^2$ is $OR^{10}$ and $R^{10}$ is hydrogen,
$R^3$ is a $C_1$-$C_6$ alkyl group,
$R^4$ is hydroxy,
$R^5$ and $R^6$ are each a $C_1$-$C_6$ alkyl group, and
one of $R^7$ and $R^8$ is hydrogen and the other is a $C_1$-$C_6$ alkyl group,
then $R^9$ is not a $C_1$-$C_6$ alkyl group or a $C_3$-$C_8$ cycloalkyl group.

2. The compound of claim 1 or a pharmaceutically acceptable salt thereof, wherein Y is

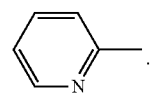

3. The compound of claim 1 or a pharmaceutically acceptable salt thereof, wherein Y is optionally substituted phenyl.

4. The compound of claim 1 or a pharmaceutically acceptable salt thereof, wherein $R^1$ is chosen from methyl,

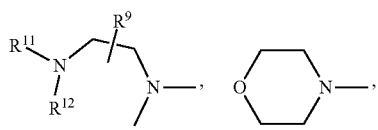

groups,

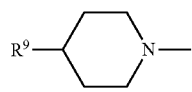

groups,

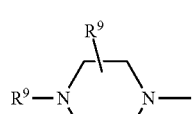

groups,

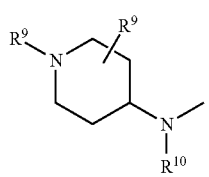

groups,

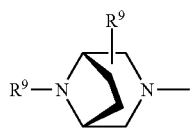

groups,

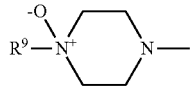

groups,

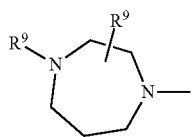

groups, and

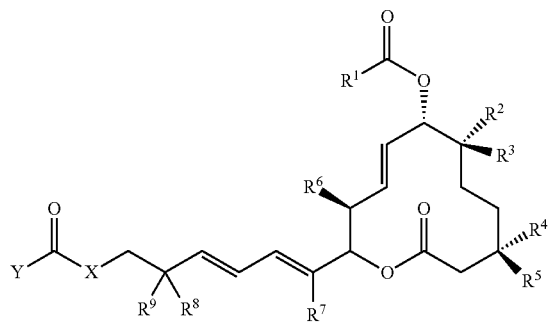

groups.

5. A compound of Formula II:

or a pharmaceutically acceptable salt thereof, wherein:

X is chosen from O, NR' groups, and $CH_2$, wherein R' is chosen from hydrogen and $C_1$-$C_8$ alkyl groups;

$R^1$ is chosen from methyl, groups,

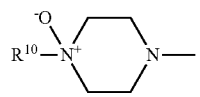

groups, and

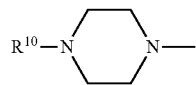

groups, $R^{10}$ is chosen from $C_1$-$C_8$ alkyl groups, $C_3$-$C_8$ cycloalkyl groups, and halo $C_1$-$C_8$ alkyl groups, wherein the $C_3$-$C_8$ cycloalkyl groups may be unsubstituted or substituted from 1-3 times with a group independently chosen from $C_1$-$C_8$ alkyl groups, hydroxy, halogen groups, and $C_1$-$C_8$ alkoxy groups;

$R^{11}$ and $R^{12}$ are each independently chosen from $C_1$-$C_8$ alkyl groups;

one of either $R^2$ or $R^3$ is chosen from hydrogen and $C_1$-$C_8$ alkyl groups, and the other is chosen from hydrogen, hydroxy and $C_1$-$C_6$ alkyl groups;

one of either $R^4$ or $R^5$ is hydrogen, and the other is chosen from hydrogen, hydroxy, and

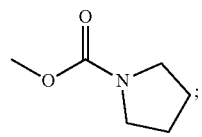

$R^6$ and $R^7$ are each independently chosen from $C_1$-$C_8$ alkyl groups;

$R^8$ and $R^9$ are each independently chosen from hydrogen and $C_1$-$C_8$ alkyl groups; or Fe and $R^9$ are taken together to form a cyclopropyl ring; and Y is chosen from $C_1$-$C_8$ alkyl groups, $C_3$-$C_8$ cycloalkyl groups, methoxy, and —$NR^{13}R^{14}$ groups, wherein $R^{13}$ and $R^{14}$ are each independently chosen from hydrogen, $C_1$-$C_8$ alkyl groups, and methoxy $C_1$-$C_8$ alkyl groups; or $R^{13}$ and $R^{14}$ may be taken together with the N to form a group chosen from

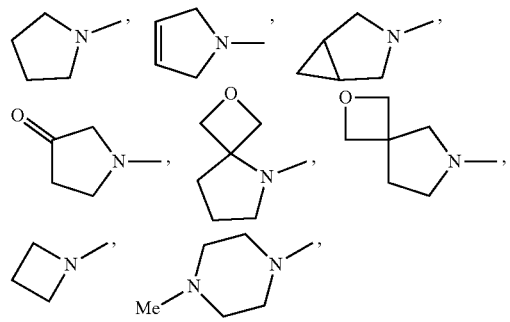

a morpholine, a piperidine, a thiazolidine, an indole, an indoline, and an isoindoline ring;

wherein Y may be unsubstituted or substituted from 1-3 times with a group independently chosen from $C_1$-$C_8$ alkyl groups, hydroxy, hydroxy $C_1$-$C_8$ alkyl groups, methoxy, methoxy $C_1$-$C_8$ alkyl groups, halo, halo $C_1$-$C_8$ alkyl groups, —C(O)NH$_2$, —NHCOO—$C_1$-$C_8$ alkyl groups, —COOH,

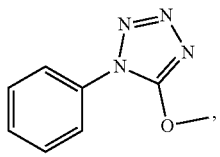

and —NR$^{15}$R$^{16}$ groups, wherein R$^{15}$ and R$^{16}$ are each independently chosen from hydrogen and $C_1$-$C_8$ alkyl groups.

6. A compound of Formula III:

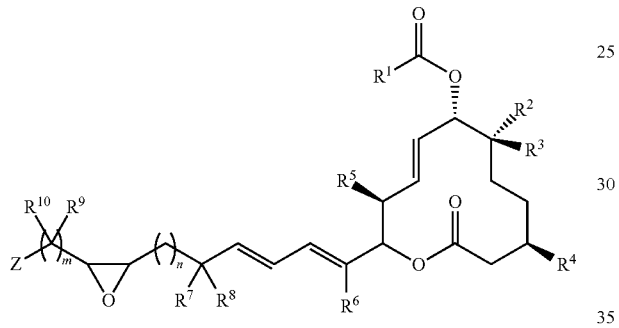

or a pharmaceutically acceptable salt thereof,
wherein:
n is chosen from 0, 1 and 2;
m is chosen from 1, 2, and 3;
R$^1$ is chosen from $C_1$-$C_8$ alkyl groups, $C_3$-$C_8$ cycloalkyl groups, —NR$^{11}$R$^{12}$ groups,

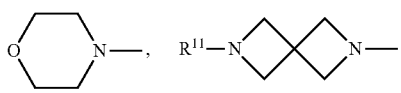

groups,

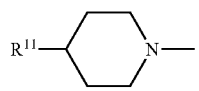

groups,

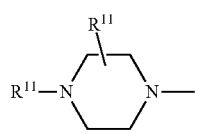

groups,

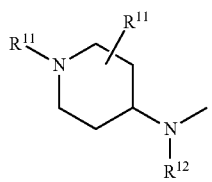

groups,

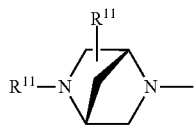

groups,

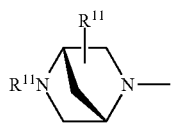

groups,

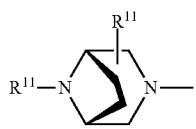

groups,

groups, and

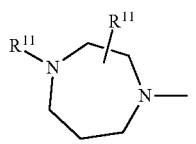

groups,
R$^{11}$ is chosen from hydrogen, —NR$^{16}$R$^{17}$ groups, $C_1$-$C_8$ alkyl groups, alkyl)-CO$_2$H groups, —($C_1$-$C_8$ alkyl)-CO$_2$R$^{12}$ groups, —($C_1$-$C_8$ alkyl)-NR$^{16}$R$^{17}$ groups, $C_3$-$C_8$ cycloalkyl groups, and heterocyclyl groups, wherein the —NR$^{11}$R$^{12}$ groups, $C_1$-$C_8$ alkyl groups, $C_3$-$C_8$ cycloalkyl groups and heterocyclyl groups may be unsubstituted or substituted from 1-3 times with a group independently chosen from $C_1$-$C_6$ alkyl groups, —($C_1$-$C_6$ alkyl)-CO$_2$H groups, hydroxy, halogen groups, and $C_1$-$C_6$ alkoxy groups, and wherein the heterocyclyl group is a 3-, 4-, 5-, 6-, 7-, or 8-membered ring containing at least one heteroatom independently chosen from O, N, and S or a bicyclic heterocycle;

$R^{12}$ is chosen from hydrogen and $C_1$-$C_6$ alkyl groups;

one of either $R^2$ or $R^3$ is chosen from hydrogen and $C_1$-$C_6$ alkyl groups, and the other is chosen from hydrogen, —$OR^{10}$, —$OC(O)R^{10}$, —$OC(O)R^1$, and $C_1$-$C_6$ alkyl groups;

$R^4$ is hydrogen or hydroxy;

$R^5$ and $R^6$ are each independently chosen from $C_1$-$C_6$ alkyl groups;

$R_7$ and $R_8$ are each independently chosen from hydrogen, hydroxy, $C_1$-$C_6$ alkoxy groups, and $C_1$-$C_6$ alkyl groups; and $R^9$ and $R^{10}$ are each independently chosen from hydrogen, $C_1$-$C_6$ alkyl groups, hydroxy, and $C_1$-$C_6$ alkoxy groups; or, one of $R^9$ or $R^{10}$ is oxo and the other is absent;

Z is chosen from $C_1$-$C_6$ alkyl groups, —C(O)—$C_1$-$C_6$ alkyl groups, —$OR^{13}$, and —$NR^{14}R^{15}$ groups, wherein $R^{13}$ is chosen from hydrogen, $C_1$-$C_6$ alkyl groups, and —C(O)—$C_1$-$C_6$ alkyl groups, wherein $R^{14}$ and $R^{15}$ are each independently chosen from hydrogen, $C_1$-$C_6$ alkyl groups, and methoxy $C_1$-$C_6$ alkyl groups; or $R^{14}$ and $R^{15}$ may be taken together with the N to form a group chosen from

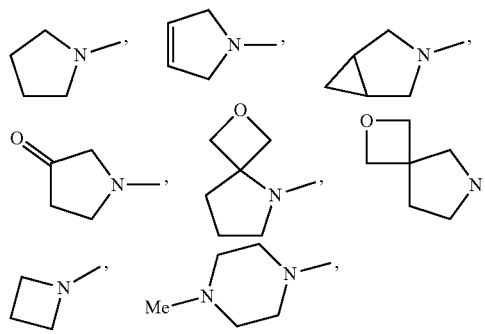

a morpholine, a piperidine, a thiazolidine, an indole, an indoline, and an isoindoline ring;

wherein Z may be unsubstituted or substituted from 1-3 times with a group independently chosen from $C_1$-$C_6$ alkyl groups, $C_3$-$C_5$ cycloalkyl groups, hydroxy $C_1$-$C_6$ alkyl groups, $C_1$-$C_6$ alkoxy groups, methoxy $C_1$-$C_6$ alkyl groups, —$NR^{16}R^{17}$ groups,

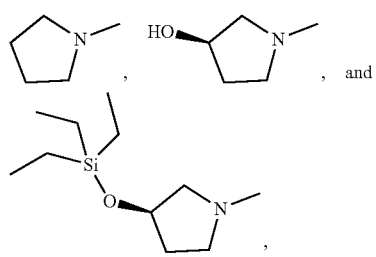

wherein $R^{16}$ and $R^{17}$ are each independently chosen from hydrogen and $C_1$-$C_6$ alkyl groups;

wherein if:

$R^9$ and $R^{10}$ are each independently chosen from hydrogen, hydroxy, and a $C_1$-$C_6$ alkyl group, Z is a $C_1$-$C_6$ alkyl group, $R^2$ is $OR^{10}$ and $R^{10}$ is hydrogen, $R^3$ is a $C_1$-$C_6$ alkyl group, $R^4$ is hydroxy, $R^5$ and $R^6$ are each a $C_1$-$C_6$ alkyl group, and one of $R^7$ and $R^8$ is hydrogen and the other is a $C_1$-$C_6$ alkyl group or hydroxy, then $R^1$ is not a $C_1$-$C_6$ alkyl group.

7. The compound of claim 6 or a pharmaceutically acceptable salt thereof, wherein $R^1$ is chosen from methyl,

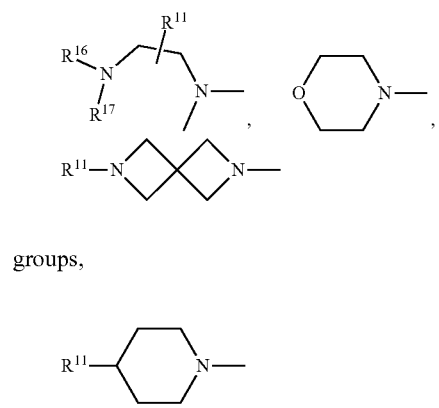

groups,

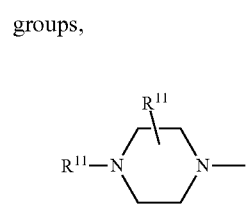

groups,

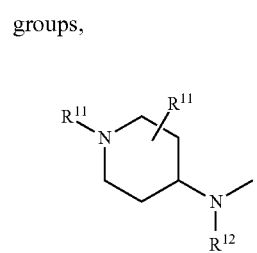

groups,

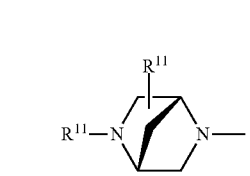

groups,

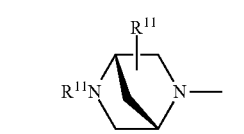

groups,

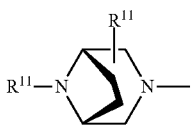

groups,

groups, and

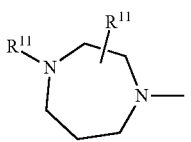

groups.

8. The compound of claim 1 chosen from:

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] acetate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] acetate;

[(2S,3S,4E,6S,7S,10S)-7,10-dihydroxy-2-[(2E,4E)-6-[6-[(2R)-1-hydroxypropan-2-yl]pyridin-2-yl]hepta-2,4-dien-2-yl]-3,7-dimethyl-12-oxo-1-oxacyclododec-4-en-6-yl] acetate;

[(2S,3S,4E,6S,7S,10S)-2-[(2E,4E)-6-[2-(dimethylamino)pyrimidin-4-yl]hepta-2,4-dien-2-yl]-7,10-dihydroxy-3,7-dimethyl-12-oxo-1-oxacyclododec-4-en-6-yl] 4-methylpiperazine-1-carboxylate;

[(2S,3S,4E,6S,7S,10S)-7,10-dihydroxy-3,7-dimethyl-12-oxo-2-[(2E,4E)-6-pyridazin-3-ylhepta-2,4-dien-2-yl]-1-oxacyclododec-4-en-6-yl] 4-methylpiperazine-1-carboxylate;

[(2S,3S,4E,6S,7S,10S)-7,10-dihydroxy-3,7-dimethyl-12-oxo-2-[(2E,4E)-6-pyrimidin-2-ylhepta-2,4-dien-2-yl]-1-oxacyclododec-4-en-6-yl] 4-methylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(oxan-4-yl)piperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 6-cycloheptyl-2,6-diazaspiro[3.3]heptane-2-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] N-methyl-N-(1-methylpiperidin-4-yl)carbamate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] morpholine-4-carboxylate;

[(2R,3R,4E,6S,7R,10S)-7,10-dihydroxy-3,7-dimethyl-12-oxo-2-[(2E,4E,6R)-6-pyridin-2-ylhepta-2,4-dien-2-yl]-1-oxacyclododec-4-en-6-yl] (1S,4R)-5-methyl-2,5-diazabicyclo[2.2.1]heptane-2-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 8-cycloheptyl-3,8-diazabicyclo[3.2.1]octane-3-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methyl-1,4-diazepane-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] piperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptyl-1,4-diazepane-1-carboxylate;

[(2S,3S,4E,6S,7S,10S)-7,10-dihydroxy-2-[(2E,4E,6R)-7-hydroxy-6-methylhepta-2,4-dien-2-yl]-3,7-dimethyl-12-oxo-1-oxacyclododec-4-en-6-yl] 4-m ethylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-(8,8-difluoro-3-azabicyclo[3.2.1]octan-3-yl)piperidine-1-carboxylate;

[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-cycloheptylpiperazine-1-carboxylate;

[(2S,3S,4E,6R,7R,10R)-7,10-dihydroxy-3,7-dimethyl-12-oxo-2-[(2E,4E)-6-pyridin-2-ylhexa-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-(2-pyrrolidin-1-ylpyrimidin-4-yl)hepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyrazin-2-ylhepta-2,4-dien-2-yl]-1-oxacyclododec-4-en-6-yl] 4-cycloheptylpiperazine-1-carboxylate;

[(2S,3S,4E,6S,7S,10S)-2-[(2E,4E)-6-[2-(dimethylamino)pyrimidin-4-yl]hepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(3-methylpyridin-2-yl)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(4-methylpyridin-2-yl)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyrimidin-2-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyridazin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E)-6-pyrimidin-4-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyrimidin-2-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyrimidin-2-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(4-methylpyrimidin-2-yl)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-6-(6-pyrrolidin-1-ylpyridin-2-yl)hepta-2,4-dien-2-yl]-1-oxacyclododec-4-en-6-yl] 4-cycloheptylpiperazine-1-carboxylate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] acetate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate;

[(2S,3S,4E,6R,7R,10S)-10-hydroxy-3,7-dimethyl-12-oxo-2-[(2E,4E,6S)-6-pyridin-2-ylhepta-2,4-dien-2-yl]-1-oxacyclododec-4-en-6-yl] N,N-dimethylcarbamate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] acetate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] 4-cycloheptylpiperazine-1-carboxylate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] 4-methylpiperazine-1-carboxylate;

[(2S,3S,4E,6R)-3-methyl-12-oxo-2-[(2E,4E,6S)-6-pyridin-2-ylhepta-2,4-dien-2-yl]-1-oxacyclododec-4-en-6-yl] N, N-dimethylcarbamate;

[(2S,3S,4E,6R)-2-[(2E,4E)-6-[2-(dimethylamino)pyrimidin-4-yl]hepta-2,4-dien-2-yl]-3-methyl-12-oxo-1-oxacyclododec-4-en-6-yl] 4-cycloheptylpiperazine-1-carboxylate;

[(2S,3S,4E,6R)-3-methyl-12-oxo-2-[(2E,4E)-6-(2-pyrrolidin-1-ylpyrimidin-4-yl)hepta-2,4-dien-2-yl]-1-oxacyclododec-4-en-6-yl] 4-cycloheptylpiperazine-1-carboxylate;

[(2S,3S,4E,6R)-2-[(2E,4E)-6-[2-[(3S)-3-triethylsilyloxypyrrolidin-1-yl]pyrimidin-4-yl]hepta-2,4-dien-2-yl]-1-oxacyclododec-4-en-6-yl] 4-cycloheptylpiperazine-1-carboxylate;

[(2S,3S,4E,6R)-2-[(2E,4E)-6-[2-[(3R)-3-hydroxypyrrolidin-1-yl]pyrimidin-4-yl]hepta-2,4-dien-2-yl]-3-methyl-12-oxo-1-oxacyclododec-4-en-6-yl] 4-cycloheptylpiperazine-1-carboxylate;

[(2S,3S,4E,6R)-3-methyl-12-oxo-2-[(2E,4E)-6-pyrimidin-2-ylhepta-2,4-dien-2-yl]-1-oxacyclododec-4-en-6-yl] 4-methylpiperazine-1-carboxylate;

[(2S,3S,4E,6S,7S)-7-hydroxy-3,7-dimethyl-12-oxo-2-[(2E,4E,6S)-6-pyridin-2-ylhepta-2,4-dien-2-yl]-1-oxacyclododec-4-en-6-yl] 4-methylpiperazine-1-carboxylate;

[(2S,3S,4E,6S,7S,10S)-2-[(2E,4E,6R)-7-(4-cyclopropyltriazol-1-yl)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-hydroxy-6-methylhepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-12-oxo-2-[(2E,4E)-6-pyridin-4-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-3-ylhepta-2,4-dien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E)-7-methyl-6-pyridin-2-ylocta-2,4-dien-2-yl]-12-oxo-1-oxacyclododec-4-en-6-yl] acetate;

[(2S,3S,4E,6R,7R,10R)-7,10-dihydroxy-2-[(2E,4E)-6-hydroxy-6-methyl-8-phenylocta-2,4-dien-2-yl]-3,7-dimethyl-12-oxo-1-oxacyclododec-4-en-6-yl] acetate;

[(2S,3S,4E,6R,7R,10R)-7,10-dihydroxy-2-[(2E,4E)-6-hydroxy-6-phenylhepta-2,4-dien-2-yl]-3,7-dimethyl-12-oxo-1-oxacyclododec-4-en-6-yl] acetate;

[(2S,3S,4E,6R,7R,10R)-7,10-dihydroxy-2-[(2E,4E)-6-hydroxy-6-thiophen-2-ylhepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-12-oxo-2-[(2E,4E)-6-phenylhepta-2,4-dien-2-yl]-1-oxacyclododec-4-en-6-yl] acetate;

[(2S,3S,4E,6S,7S,10S)-7,10-dihydroxy-2-[(2E,4E)-6-(6-methoxypyridin-2-yl)hepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E)-6-[6-(2-methylpropoxy)pyridin-2-yl]hepta-2,4-dien-2-yl]-12-oxo-1-oxacyclododec-4-en-6-yl] acetate;

[(2S,3S,4E,6S,7S,10S)-7,10-dihydroxy-3,7-dimethyl-2-[(2E,4E)-6-methyl-8-pyridin-2-ylocta-2,4-dien-2-yl]-12-oxo-1-oxacyclododec-4-en-6-yl] acetate;

[(2S,3S,4E,6S,7S,10S)-7,10-dihydroxy-3,7-dimethyl-2-[(2E,4E)-6-methyl-7-pyridin-2-ylhepta-2,4-dien-2-yl]-12-oxo-1-oxacyclododec-4-en-6-yl] acetate;

[(2S,3S,4E,6R,7R,10R)-7,10-dihydroxy-2-[(2E,4E,6R)-6-hydroxy-6-methyl-8-phenylocta-2,4-dien-2-yl]-3,7-dimethyl-12-oxo-1-oxacyclododec-4-en-6-yl] acetate;

[(2S,3S,4E,6R,7R,10R)-7,10-dihydroxy-3,7-dimethyl-12-oxo-2-[(2E,4E)-6-pyridin-2-ylhexa-2,4-dien-2-yl]-1-oxacyclododec-4-en-6-yl] acetate;

[(2S,3S,4E,6R,7R,10R)-7,10-dihydroxy-3,7-dimethyl-12-oxo-2-[(2E,4E)-6-pyridin-3-ylhexa-2,4-dien-2-yl]-1-oxacyclododec-4-en-6-yl] acetate;

[(2S,3S,4E,6R,7R,10R)-7,10-dihydroxy-3,7-dimethyl-12-oxo-2-[(2E,4E)-6-pyridin-4-ylhexa-2,4-dien-2-yl]-1-oxacyclododec-4-en-6-yl] acetate;

[(2S,3S,4E,6R,7R,10R)-7,10-dihydroxy-2-[(2E,4E)-6-hydroxy-8-(4-hydroxyphenyl)-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E)-6-methyl-8-phenylocta-2,4-dien-2-yl]-12-oxo-1-oxacyclododec-4-en-6-yl] acetate;

[(2S,3S,4E,6S,7S,10S)-7,10-dihydroxy-2-[(2E,4E)-8-[2-(methoxymethyl)phenyl]-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-2-[(2E,4E)-8-[4-(methoxymethyl)phenyl]-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-2-[(2E,4E)-8-[3-(methoxymethyl)phenyl]-6-methylocta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-12-oxo-2-[(2E,4E,6E,8S)-8-pyridin-2-ylnona-2,4,6-trien-2-yl]-1-oxacyclododec-4-en-6-yl] 4-cycloheptylpiperazine-1-carboxylate;

[(2S,3S,4E,6S,7S,10S)-7,10-dihydroxy-3,7-dimethyl-12-oxo-2-[(2E,4E,6S)-6-pyridin-2-ylhepta-2,4-dien-2-yl]-1-oxacyclododec-4-en-6-yl] 4-methyl-4-oxidopiperazin-4-ium-1-carboxylate;

[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-(4-fluoropiperidin-1-yl)piperidine-1-carboxylate;

[(2S,3S,4E,6S,7S,10S)-7,10-dihydroxy-3,7-dimethyl-12-oxo-2-[(2E,4E)-6-pyridin-3-ylhepta-2,4-dien-2-yl]-1-oxacyclododec-4-en-6-yl] 4-(4,4-difluoropiperidin-1-yl)piperidine-1-carboxylate;

and pharmaceutically acceptable salts thereof.

9. The compound of claim 5 chosen from:

[(2S,3S,4E,6S,7S,10S)-7,10-dihydroxy-3,7-dimethyl-2-[(2E,4E,6S)-6-methyl-9-oxo-9-pyrrol id in-1-ylnona-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-2-[(2E,4E,6S)-7-[[(2R,3R)-3-hydroxypentan-2-yl]carbamoyloxy]-6-methylhepta-2,4-dien-2-yl]-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E,6S)-6-methyl-7-(propylcarbamoyloxy)hepta-2,4-dien-2-yl]-12-oxo-1-oxacyclododec-4-en-6-yl] acetate;

[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] acetate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] pyrrolidine-1-carboxylate;

[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] 4-cycloheptyl-4-oxidopiperazin-4-ium-1-carboxylate;

[(2S,3S,4E,6S,7S,10S)-2-[(2E,4E,6R)-7-(dimethylcarbamoyloxy)-6-methylhepta-2,4-dien-2-yl]-7,10-dihydroxy-3,7-di methyl-12-oxo-1-oxacyclododec-4-en-6-yl] acetate;

[(2S,3S,4E,6S,7S,10S)-2-[(2E,4E,6S)-7-(diethylcarbamoyloxy)-6-methylhepta-2,4-dien-2-yl]-7,10-dihydroxy-3,7-dimethyl-12-oxo-1-oxacyclododec-4-en-6-yl] acetate;

[(2S,3S,4E,6S,7S,10S)-7,10-dihydroxy-3,7-dimethyl-2-[(2E,4E,6S)-6-methyl-7-[methyl(propan-2-yl)carbamoyl]oxyhepta-2,4-dien-2-yl]-12-oxo-1-oxacyclododec-4-en-6-yl] acetate;

[(2S,3S,4E,6S,7S,10S)-2-[(2E,4E,6S)-7-[butyl(methyl)carbamoyl]oxy-6-methylhepta-2,4-dien-2-yl]-7,10-dihydroxy-3,7-dimethyl-12-oxo-1-oxacyclododec-4-en-6-yl] acetate;

[(2S,3S,4E,6S,7S,10S)-2-[(2E,4E,6S)-7-[butan-2-yl(methyl)carbamoyl]oxy-6-methylhepta-2,4-dien-2-yl]-7,10-dihydroxy-3,7-dimethyl-12-oxo-1-oxacyclododec-4-en-6-yl] acetate;

[(2S,3S,4E,6S,7S,10S)-2-[(2E,4E,6R)-7-carbamoyloxy-6-methylhepta-2,4-dien-2-yl]-7,10-dihydroxy-3,7-dimethyl-12-oxo-1-oxacyclododec-4-en-6-yl] acetate;

[(2S,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R)-2-(methoxymethyl)pyrrolidine-1-carboxylate;

[(2S,3S,4E,6S,7S,10S)-7,10-dihydroxy-2-[(2E,4E,6S)-7-[2-methoxyethyl(methyl)carbamoyl]oxy-6-methylhepta-2,4-dien-2-yl]-3,7-dimethyl-12-oxo-1-oxacyclododec-4-en-6-yl] acetate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] azetidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2S)-2-methylpyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2S)-2-methylpyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] piperidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R)-2-(hydroxymethyl)pyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (3R)-3-hydroxypyrrolidine-1-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] morpholine-4-carboxylate;

[(2R,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] 4-methylpiperazine-1-carboxylate;

3-thiazolidinecarboxylic acid [(2R,3E,5E)-6-[(2R,3S,4E,6R,7R,1 OR)-6-acetyloxy-7,10-dihydroxy-3,7-dimethyl-12-oxo-1-oxacyclodec-4-en-2-yl]-2-methylhepta-3,5-dienyl] ester;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-7,10-dihydroxy-2-[(2E,4E,6R)-7-[(2R)-2-(hydroxymethyl)pyrrolidine-1-carbonyl]oxy- 6-methyl hepta-2,4-dien-2-yl]-3,7-dimethyl-12-oxo-1-oxacyclododec-4-en-6-yl] 4-methylpiperazine-1-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclododec-4-en-2-yl]-2-methylhepta-3,5-dienyl] 1,3-dihydroisoindole-2-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclododec-4-en-2-yl]-2-methylhepta-3,5-dienyl] indole-1-carboxylate;

[(2S,3S,4E,6S,7S,10S)-7,10-dihydroxy-2-[(2E,4E,6S)-7-[2-(1-hydroxyethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-2-[(2E,4E,6R)-7-(2,2-dimethylpyrrolidine-1-carbonyl)oxy-6-methylhepta-2,4-dien-2-yl]-7,10-dihydroxy-3,7-dimethyl-12-oxo-1-oxacyclododec-4-en-6-yl] 4-methylpiperazine-1-carboxylate;

[(2S,3S,4E,6S,7S,10S)-2-[(2E,4E,6R)-7-[(2S,5S)-2,5-dimethylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-methylpiperazine-1-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclododec-4-en-2-yl]-2-methylhepta-3,5-dienyl] 2,3-dihydroindole-1-carboxylate;

[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-methylpiperazine-1-carboxylate;

[(2S,3S,4E,6S,7S,10S)-2-[(2E,4E,6R)-7-[(2R)-2-(fluoromethyl)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-methylpiperazine-1-carboxylate;

[(2R,3E,5E)-6-[(2S,3S,4E,6S,7S,10S)-7,10-dihydroxy-3,7-dimethyl-6-(4-methylpiperazine-1-carbonyl)oxy-12-oxo-1-oxacyclododec-4-en-2-yl]-2-methylhepta-3,5-dienyl] 2-oxa-5-azaspiro[3.4]octane-5-carboxylate;

[(2S,3S,4E,6S,7S,10S)-7,10-dihydroxy-3,7-dimethyl-2-[(2E,4E,6S)-6-methyl-9-oxo-9-pyrrolidin-1-ylnona-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6S)-6-methyl-7-[methyl(propyl)carbamoyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10R)-7-hydroxy-3,7-dimethyl-2-[(2E,4E,6R)-6-methyl-7-(pyrrolidine-1-carbonyloxy)hepta-2,4-dien-2-yl]-12-oxo-10-(pyrrolidine-1-carbonyloxy)-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(2S)-2-methylpyrrolidine-1-carbonyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(3R)-3-methylpyrrolidine-1-carbonyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(3R)-3-methylpyrrolidine-1-carbonyl]oxyhepta-2,4-dien-2-yl]-12-oxo-1-oxacyclododec-4-en-6-yl] 4-cycloheptylpiperazine-1-carboxylate;

[(2S,3S,4E,6S,7S,10S)-2-[(2E,4E,6R)-7-[(2R)-2-carbamoylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6S)-7-[(2R)-2-(methoxymethyl)pyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(2S,5S)-2,5-dimethylpyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(3R)-3-fluoropyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(2,2-dimethylpyrrolidine-1-carbonyl)oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6R,7R,10R)-2-[(2E,4E)-6,6-dimethyl-7-(pyrrolidine-1-carbonyloxy)hepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6R,7R,10S)-2-[(2E,4E)-6,6-dimethyl-7-(pyrrolidine-1-carbonyloxy)hepta-2,4-dien-2-yl]-7-hydroxy-3,7-dimethyl-12-oxo-10-(pyrrolidine-1-carbonyloxy)-1-oxacyclododec-4-en-6-yl] 4-cycloheptylpiperazine-1-carboxylate;

(2R)-1-[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienoxy]carbonylpyrrolidine-2-carboxylic acid;

[(2S,3S,4E,6S,7S,10S)-7,10-dihydroxy-3,7-dimethyl-2-[(2E,4E,6R)-6-methyl-7-(3-oxopyrrolidine-1-carbonyl)oxyhepta-2,4-dien-2-yl]-12-oxo-1-oxacyclododec-4-en-6-yl] 4-cycloheptylpiperazine-1-carboxylate;

[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienyl] 2-oxa-7-azaspiro[3.4]octane-7-carboxylate;

[(2S,3S,4E,6S,7S,10S)-7,10-dihydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6R,7R,10R)-7,10-dihydroxy-3,7-dimethyl-12-oxo-2-[(2E,4E)-5-[1-(pyrrolidine-1-carbonyloxymethyl)cyclopropyl]penta-2,4-dien-2-yl]-1-oxacyclododec-4-en-6-yl] 4-cycloheptylpiperazine-1-carboxylate;

[(2S,3S,4E,6S,7S,10S)-2-[(2E,4E,6R)-7-[(3S,4R)-3,4-dihydroxypyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

(3S)-1-[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienoxy]carbonylpyrrolidine-3-carboxylic acid;

[(2S,3S,4E,6S,7S,10S)-2-[(2E,4E,6R)-7-[(3S)-3-(dimethylamino)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(2,5-dihydropyrrole-1-carbonyloxy)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-[(2R)-2-(fluoromethyl)pyrrolidine-1-carbonyl]oxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-[(3S)-3-[(2-methylpropan-2-yl)oxycarbonylamino]pyrrolidine-1-carbonyl]oxyhepta-2,4-dien-2-yl]-12-oxo-1-oxacyclododec-4-en-6-yl] 4-cycloheptylpiperazine-1-carboxylate;

[(2R,3E,5E)-6-[(2S,3S,4E,6S,7S,10S)-6-(4-cycloheptylpiperazine-1-carbonyl)oxy-7,10-dihydroxy-3,7-dimethyl-12-oxo-1-oxacyclododec-4-en-2-yl]-2-methylhepta-3,5-dienyl] 3-azabicyclo[3.1.0]hexane-3-carboxylate;

[(2S,3S,4E,6R,7R,10S)-10-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6R,7R,10S)-10-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6R,7R,10S)-10-hydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6R,7R,10S)-2-[(2E,4E,6R)-7-[(2R)-2-(fluoromethyl)pyrrolidine-1-carbonyl]oxy-6-methylhepta-2,4-dien-2-yl]-10-hydroxy-3,7-dimethyl-12-oxo-1-oxacyclododec-4-en-6-yl] 4-cycloheptylpiperazine-1-carboxylate;

[(2S,3S,4E,6R,7R,10S)-2-[(2E,4E,6R)-7-[(2R)-2-(fluoromethyl)pyrrolidine-1-carbonyl]oxy-6-methylhepta-2,4-dien-2-yl]-10-hydroxy-3,7-dimethyl-12-oxo-1-oxacyclododec-4-en-6-yl] 4-methylpiperazine-1-carboxylate;

[(2S,3S,4E,6R)-3-methyl-2-[(2E,4E,6R)-6-methyl-7-(pyrrolidine-1-carbonyloxy)hepta-2,4-dien-2-yl]-12-oxo-1-oxacyclododec-4-en-6-yl] 4-cycloheptylpiperazine-1-carboxylate;

[(2S,3S,4E,6R)-3-methyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2R,3E,5E)-6-[(2S,3S,4E,6R)-6-(dimethylcarbamoyloxy)-3-methyl-12-oxo-1-oxacyclododec-4-en-2-yl]-2-methylhepta-3,5-dienyl] pyrrolidine-1-carboxylate;

[(2R,3E,5E)-6-[(2S,3S,4E,6R)-6-(dimethylcarbamoyloxy)-3-methyl-12-oxo-1-oxacyclododec-4-en-2-yl]-2-methylhepta-3,5-dienyl] (3R)-3-hydroxypyrrolidine-1-carboxylate;

[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-oxacyclododec-4-en-6-yl] 4-methylpiperazine-1-carboxylate;

[(2S,3S,4E,6R)-3-methyl-2-[(2E,4E,6R)-6-methyl-7-[(2S)-2-methylpyrrolidine-1-carbonyl]oxyhepta-2,4-dien-2-yl]-12-oxo-1-oxacyclododec-4-en-6-yl] 4-methylpiperazine-1-carboxylate;

[(2S,3S,4E,6R)-2-[(2E,4E,6R)-7-[(2R)-2-(hydroxymethyl)pyrrolidine-1-carbonyl]oxy-6-methylhepta-2,4-dien-2-yl]-3-methyl-12-oxo-1-oxacyclododec-4-en-6-yl] 4-methylpiperazine-1-carboxylate;

[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-oxacyclododec-4-en-6-yl] 4-cycloheptylpiperazine-1-carboxylate;

[(2S,3S,4E,6R)-2-[(2E,4E,6R)-7-[(2R)-2-(hydroxymethyl)pyrrolidine-1-carbonyl]oxy-6-methylhepta-2,4-dien-2-yl]-3-methyl-12-oxo-1-oxacyclododec-4-en-6-yl] 4-(2,2,2-trifluoroethyl)piperazine-1-carboxylate;

[(2S,3S,4E,6S,7S)-7-hydroxy-3,7-dimethyl-2-[(2E,4E,6R)-6-methyl-7-(pyrrolidine-1-carbonyloxy)hepta-2,4-dien-2-yl]-12-oxo-1-oxacyclododec-4-en-6-yl] 4-methylpiperazine-1-carboxylate;

[(2S,3S,4E,6S,7S)-7-hydroxy-2-[(2E,4E,6R)-7-[(2R)-2-(hydroxymethyl)pyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S)-7-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S)-7-hydroxy-3,7-dimethyl-2-[(2E,4E,6R)-6-methyl-7-[(3S)-3-(1-phenyltetrazol-5-yl)oxypyrrolidine-1-carbonyl]oxyhepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonylamino)hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6R)-7-[[(2R)-2-(hydroxymethyl)pyrrolidine-1-carbonyl]amino]-6-methylhepta-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-7,10-dihydroxy-3,7-dimethyl-2-[(2E,4E,6R)-6-methyl-7-(pyrrolidine-1-carbonylamino)hepta-2,4-dien-2-yl]-12-oxo-1-oxacyclododec-4-en-6-yl] 4-methylpiperazine-1-carboxylate;

[(2S,3S,4E,6S,7S,10S)-7,10-dihydroxy-3,7-dimethyl-2-[(2E,4E,6R)-6-methyl-7-[methyl(pyrrolidine-1-carbonyl)amino]hepta-2,4-dien-2-yl]-12-oxo-1-oxacyclododec-4-en-6-yl] 4-cycloheptylpiperazine-1-carboxylate;

[(2S,3S,4E,6S,7S,10S)-7,10-dihydroxy-2-[(2E,4E,6S)-7-methoxycarbonyloxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-7,10-dihydroxy-2-[(2E,4E,6R)-9-methoxy-6-methyl-9-oxonona-2,4-dien-2-yl]-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(cyclopentanecarbonylamino)-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-2-[(2E,4E,6R)-7-(cyclopentanecarbonylamino)-6-methylhepta-2,4-dien-2-yl]-7,10-dihydroxy-3,7-dimethyl-12-oxo-1-oxacyclododec-4-en-6-yl] 4-methylpiperazine-1-carboxylate;

4-cycloheptyl-1-piperazinecarboxylic acid [(2R,3S,4E,6R,7R,10R)-7,10-dihydroxy-3,7-dimethyl-12-oxo-2-[(2E,4E)-7-[oxo(1-pyrrolidinyl)methoxy]hepta-2,4-dien-2-yl]-1-oxacyclododec-4-en-6-yl] ester;

[(2S,3S,4E,6R,7R,10S)-10-hydroxy-2-[(2E,4E,6R)-7-[(3R)-3-hydroxypyrrolidine-1-carbonyl]oxy-6-methylhepta-2,4-dien-2-yl]-3,7-dimethyl-12-oxo-1-oxacyclododec-4-en-6-yl] 4-methylpiperazine-1-carboxylate;

[(2S,3S,4E,6R)-2-[(2E,4E,6R)-7-[(3R)-3-hydroxypyrrolidine-1-carbonyl]oxy-6-methylhepta-2,4-dien-2-yl]-3-methyl-12-oxo-1-azacyclododec-4-en-6-yl] 4-methylpiperazine-1-carboxylate;

[(2R,3E,5E)-2-methyl-6-[(2S,3S,4E,6R)-3-methyl-6-[(4-methylpiperazine-1-carbonyl)amino]-12-oxo-1-oxacyclododec-4-en-2-yl]hepta-3,5-dienyl] pyrrolidine-1-carboxylate;

[(2S,3E,5E)-6-[(2S,3S,4E,6S,7S,10S)-6-acetyloxy-7,10-dihydroxy-3,7-dimethyl-12-oxo-1-oxacyclododec-4-en-2-yl]-2-methylhepta-3,5-dienyl] (2R,3R)-3-hydroxy-2-methylpentanoate;

and pharmaceutically acceptable salts thereof.

10. The compound of claim 6 chosen from:

[(2S,3S,4E,6R,7R,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] acetate;

[(2S,3S,4E,6S,7S,10S)-2-[(2E,4E,6S)-7-[(2R,3R)-3-[(2R,3R)-3-acetyloxypentan-2-yl]oxiran-2-yl]-6-hydroxy-6-methylhepta-2,4-dien-2-yl]-7,10-dihydroxy-3,7-dimethyl-12-oxo-1-oxacyclododec-4-en-6-yl] 4-cycloheptylpiperazine-1-carboxylate;

[(2S,3S,4E,6S,7S,10S)-7-acetyloxy-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] piperazine-1-carboxylate;

[(2S,3S,4E,6S,7S,10S)-6-acetyloxy-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-7-yl] piperazine-1-carboxylate;

[(2S,3S,4E,6S,7S,10S)-7-acetyloxy-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-6-yl] piperazine-1-carboxylate;

[(2S,3S,4E,6S,7R,10R)-7-ethoxy-10-hydroxy-2-[(2E,4E,6R)-6-hydroxy-7-[(2R,3R)-3-[(2S,3S)-3-hydroxypentan-2-yl]oxiran-2-yl]-6-methylhepta-2,4-dien-2-yl]-3,7-dimethyl-12-oxo-1-oxacyclododec-4-en-6-yl] 4-methylpiperazine-1-carboxylate;

[(2S,3S,4E,6S,7S,10S)-6-acetyloxy-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-3,7-dimethyl-12-oxo-1-oxacyclododec-4-en-7-yl] piperazine-1-carboxylate;

[(2S,3S,4E,6S,7S,10S)-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-7-m ethoxy-3,7-dimethyl-12-oxo-1-oxacyclododec-4-en-6-yl] piperazine-1-carboxylate;

[(2S,3S,4E,6S,7S,10S)-10-hydroxy-2-[(2E,4E,6R)-7-[(2R,3R)-3-[(2R,3R)-3-hydroxypentan-2-yl]oxiran-2-yl]-6-methylhepta-2,4-dien-2-yl]-7-m ethoxy-3,7-dimethyl-12-oxo-1-oxacyclododec-4-en-6-yl] 4-methylpiperazine-1-carboxylate;

[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-m ethoxy-3,7-dimethyl-12-oxo-1-oxacyclododec-4-en-6-yl] N-methyl-N-[2-(methylamino)ethyl]carbamate;

[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-m ethoxy-3,7-dimethyl-12-oxo-1-oxacyclododec-4-en-6-yl] N-methyl-N-[2-(dimethylamino)ethyl]carbamate;

3-[4-[[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-m ethoxy-3,7-dimethyl-12-oxo-1-oxacyclododec-4-en-6-yl]oxycarbonyl]piperazin-2-yl]propanoic acid;

4-[4-[[(2S,3S,4E,6S,7S,10S)-10-hydroxy-2-[(2E,4E,6S)-6-hydroxy-7-[(2R,3R)-3-[(2R,3R)-3-hydroxypentan-2-yl]oxiran-2-yl]-6-methylhepta-2,4-dien-2-yl]-7-methoxy-3,7-dimethyl-12-oxo-1-oxacyclododec-4-en-6-yl]oxycarbonyl]piperazin-1-yl]butanoic acid;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl (1 S,4S)-2,5-diazabicyclo[2.2.1]heptane-2-carboxylate;

(2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl 2,5-diazabicyclo[2.2.1]heptane-2-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-propylpiperazine-1-carboxylate;

(2R,3S,6S,7R,10R,E)-6-acetoxy-10-hydroxy-2-((2S,6R,E)-6-hydroxy-7-((2R,3R)-3-((2R,3S)-3-hydroxypentan-2-yl)oxiran-2-yl)-6-methylhept-4-en-2-yl)-3,7-dimethyl-12-oxooxacyclododec-4-en-7-yl 4-(2-hydroxyethyl)piperazine-1-carboxylate;

(2S,3S,6S,7R,10R,E)-6-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-7-yl 4-methylpiperazine-1-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-aminoethyl)piperazine-1-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl 4-(2-ethoxy-2-oxoethyl)piperazine-1-carboxylate;

(2S,3S,6S,7R,10R,E)-7,10-dihydroxy-2-((R,2E,4E)-6-hydroxy-74(2R,3R)-34(2R,3S)-3-hydroxypentan-2-yl)oxiran-2-yl)-6-methylhepta-2,4-dien-2-yl)-3,7-dimethyl-12-oxooxacyclododec-4-en-6-yl 4-methylpiperazine-1-carboxylate;

(2S,3S,6S,7R,10R,E)-7,10-dihydroxy-2-((R,2E,4E)-6-hydroxy-74(2R,3R)-34(2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate;

(2S,3S,6S,7R,10R,E)-7-acetoxy-10-hydroxy-2-((R,2E,4E)-6-hydroxy-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate;

(2S,3S,6S,7R,10R,E)-7-acetoxy-10-hydroxy-2-((S,2E,4E)-7-((2R,3R)-3-((2R,3S)-3-hydroxypentan-2-yl)oxiran-2-yl)-6-methylhepta-2,4-dien-2-yl)-3,7-dimethyl-12-oxooxacyclododec-4-en-6-yl piperazine-1-carboxylate;

and pharmaceutically acceptable salts thereof.

11. The compound of any one of claims 1, 5, 6, 8, 9, and 10 or a pharmaceutically acceptable salt thereof, wherein said compound is stereomerically pure.

12. A pharmaceutical composition comprising a compound and/or pharmaceutically acceptable salt according to any one of claims 1, 5, 6, 8, 9, and 10.

13. The pharmaceutical composition of claim 12, wherein said composition is formulated for intravenous, oral, subcutaneous, or intramuscular administration.

14. A method of treating cancer in a subject in need thereof, comprising administering to said subject a therapeutically effective amount of a compound and/or pharmaceutically acceptable salt according to any one of claims 1, 5, 6, 8, 9, and 10, or a pharmaceutical composition comprising a compound and/or pharmaceutically acceptable salt according to any one of claims 1, 5, 6, 8, 9, and 10; wherein the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

15. A method of treating cancer in a subject in need thereof, comprising administering to said subject a therapeutically effective amount of a compound and/or pharmaceutically acceptable salt according to any one of claims 1, 5, 6, 8, 9, and 10, or a pharmaceutical composition comprising a compound and/or pharmaceutically acceptable salt according to any one of claims 1, 5, 6, 8, 9, and 10; and at least one additional therapy; wherein the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

16. A method of inducing at least one neoantigen, comprising contacting a neoplastic cell with a therapeutically effective amount of a compound and/or pharmaceutically acceptable salt according to any one of claims 1, 5, 6, 8, 9, and 10, or a pharmaceutical composition comprising a compound and/or pharmaceutically acceptable salt according to any one of claims 1, 5, 6, 8, 9, and 10, thereby inducing production of at least one neoantigen; wherein the neoplastic cell is derived from a cancer and the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

17. A method of inducing at least one neoantigen and/or a T-cell response in a subject having or suspected of having a neoplastic disorder, comprising administering to the subject a therapeutically effective amount of a compound and/or pharmaceutically acceptable salt according to any one of claims 1, 5, 6, 8, 9, and 10, or a pharmaceutical composition comprising a compound and/or pharmaceutically acceptable salt according to any one of claims 1, 5, 6, 8, 9, and 10; wherein the neoplastic cell is derived from a cancer and the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

18. A method of treating a subject having or suspected of having a neoplastic disorder, comprising administering to the subject a therapeutically effective amount of a compound and/or pharmaceutically acceptable salt according to any one of claims 1, 5, 6, 8, 9, and 10, or a pharmaceutical composition comprising a compound and/or pharmaceutically acceptable salt according to any one of claims 1, 5, 6, 8, 9, and 10, wherein administration of the compound and/or pharmaceutically acceptable salt, or pharmaceutical composition, induces at least one neoantigen and/or a T-cell response; wherein the neoplastic cell is derived from a cancer and the cancer is chosen from myelodysplastic syndrome, chronic lymphocytic leukemia, acute lymphoblastic leukemia, chronic myelomonocytic leukemia, acute myeloid leukemia, colon cancer, pancreatic cancer, endometrial cancer, ovarian cancer, breast cancer, uveal melanoma, gastric cancer, cholangiocarcinoma, and lung cancer.

* * * * *